United States Patent
Jung et al.

(10) Patent No.: US 12,414,463 B2
(45) Date of Patent: Sep. 9, 2025

(54) CONDENSED CYCLIC COMPOUND AND ORGANIC LIGHT-EMITTING DEVICE INCLUDING THE SAME

(71) Applicants: Samsung Electronics Co., Ltd., Suwon-si (KR); SAMSUNG SDI CO., LTD., Yongin-si (KR)

(72) Inventors: Yongsik Jung, Seoul (KR); Wataru Sotoyama, Kanagawa (JP); Eunsuk Kwon, Suwon-si (KR); Sungho Nam, Daegu (KR); Jhunmo Son, Yongin-si (KR); Hasup Lee, Seoul (KR)

(73) Assignee: SAMSUNG SDI CO., LTD., Gyeonggi-Do (KR)

( * ) Notice: Subject to any disclaimer, the term of this patent is extended or adjusted under 35 U.S.C. 154(b) by 475 days.

(21) Appl. No.: 16/457,037

(22) Filed: Jun. 28, 2019

(65) Prior Publication Data
US 2020/0203625 A1   Jun. 25, 2020

(30) Foreign Application Priority Data
Dec. 21, 2018  (KR) .......... 10-2018-0167896

(51) Int. Cl.
| | |
|---|---|
| H10K 85/60 | (2023.01) |
| C07D 209/88 | (2006.01) |
| C09K 11/06 | (2006.01) |
| H10K 50/11 | (2023.01) |
| H10K 101/10 | (2023.01) |

(52) U.S. Cl.
CPC ....... H10K 85/6572 (2023.02); C07D 209/88 (2013.01); C09K 11/06 (2013.01); *C09K 2211/1018* (2013.01); *H10K 50/11* (2023.02); *H10K 2101/10* (2023.02)

(58) Field of Classification Search
CPC . H01L 51/0072; C07D 209/88; C07D 403/14; H10K 85/6572
See application file for complete search history.

(56) References Cited

U.S. PATENT DOCUMENTS

| | | |
|---|---|---|
| 6,562,982 B1 | 5/2003 | Hu et al. |
| 10,062,853 B2 | 8/2018 | Jung et al. |
| 10,707,423 B2 | 7/2020 | Zeng et al. |
| 2015/0243894 A1 | 8/2015 | Zeng et al. |
| 2016/0248026 A1 | 8/2016 | Wolleb et al. |
| 2017/0358755 A1* | 12/2017 | Jung .................... C07D 209/86 |
| 2018/0198075 A1 | 7/2018 | Danz et al. |
| 2020/0031812 A1 | 1/2020 | Jung et al. |

FOREIGN PATENT DOCUMENTS

| | | |
|---|---|---|
| JP | 2011153276 A | 8/2011 |
| JP | 201494935 A | 5/2014 |
| KR | 20150099395 A | 8/2015 |
| KR | 1020170088822 A | 8/2017 |
| KR | 20170139339 A | 12/2017 |
| WO | 2018001820 A1 | 1/2018 |
| WO | 2018001821 A1 | 1/2018 |
| WO | 2018001822 A1 | 1/2018 |

OTHER PUBLICATIONS

Office Action dated Aug. 2, 2023, issued in corresponding KR Patent Application No. 10-2018-0167896, 9 pp.

* cited by examiner

*Primary Examiner* — Jenna N Chandhok
(74) *Attorney, Agent, or Firm* — CANTOR COLBURN LLP

(57) ABSTRACT

A condensed cyclic compound and an organic light-emitting device including the same.

6 Claims, 1 Drawing Sheet

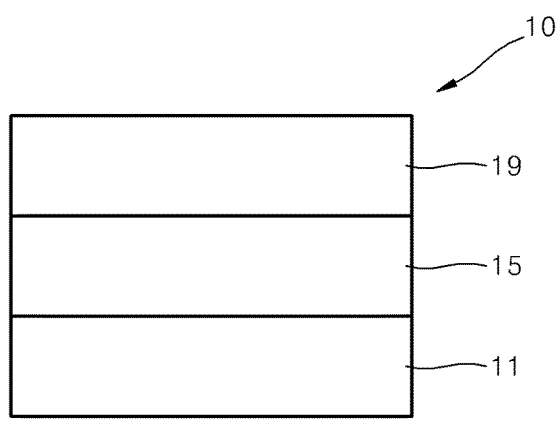

CONDENSED CYCLIC COMPOUND AND ORGANIC LIGHT-EMITTING DEVICE INCLUDING THE SAME

CROSS-REFERENCE TO RELATED APPLICATION

This application claims the priority to and benefit of Korean Patent Application No. 10-2018-0167896, filed on Dec. 21, 2018, in the Korean Intellectual Property Office, and all the benefits accruing therefrom under 35 U.S.C. § 119, the contents of which in their entirety are herein incorporated by reference.

BACKGROUND

1. Field

One or more embodiments relate to a condensed cyclic compound and an organic light-emitting device including the same.

2. Description of the Related Art

Organic light-emitting devices are self-emission devices that produce full-color images, and also have wide viewing angles, high contrast ratios, short response times, and excellent characteristics in terms of brightness, driving voltage, and response speed, compared to devices in the art.

In an example, an organic light-emitting device includes an anode, a cathode, and an organic layer that is disposed between the anode and the cathode and includes an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

SUMMARY

Aspects of the present disclosure provide a condensed cyclic compound and an organic light-emitting device including the same.

Additional aspects will be set forth in part in the description which follows and, in part, will be apparent from the description, or may be learned by practice of the presented embodiments.

An aspect provides a condensed cyclic compound represented by Formula 1 below:

$$A_{11}\text{-}L_{11}\text{-}L_{12}\text{-}A_{12}.$$  Formula 1

In Formula 1, $A_{11}$ may be a group represented by Formula 1-1, $L_{11}$ may be a group represented by Formulae 2-1 to 2-3, $L_{12}$ may be a group represented by Formulae 3-1 to 3-3, and $A_{12}$ may be a group represented by Formula 1-2:

Formula 1-1

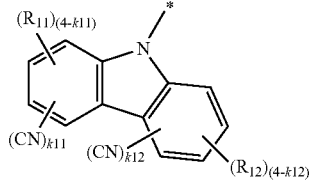

Formula 1-2

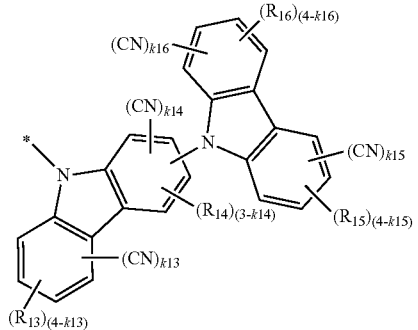

Formula 2-1

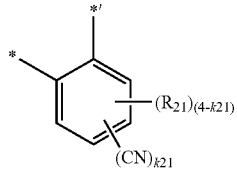

Formula 2-2

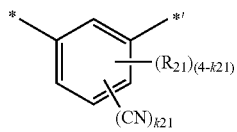

Formula 2-3

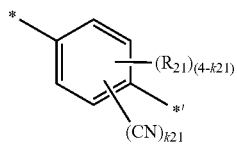

Formula 3-1

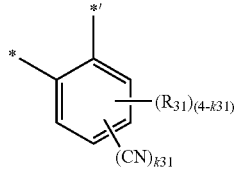

Formula 3-2

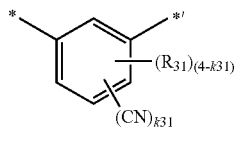

Formula 3-3

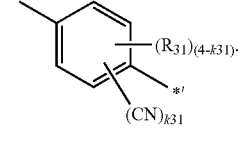

In Formulae 1-1 and 1-2, k11 to k13, k15, and k16 may each independently be 0, 1, 2, 3, or 4, k14 may be 0, 1, 2, or 3, the sum of k11 to k16 may be 1 or more, $R_{11}$ to $R_{16}$ may each independently be hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), wherein $R_{11}$ and $R_{12}$ are not a substituted or unsubstituted carbazolyl group, in Formulae 2-1 to 2-3 and 3-1 to 3-3, k21 and k31 may each independently be 0, 1, 2, 3, or 4, the sum of k21 and k31 may be 1 or more, $R_{21}$ and $R_{31}$ may each independently be hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), $Q_1$ to $Q_7$ may each independently be hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group, and and *' each indicate a binding site to a neighboring atom.

Another aspect provides an organic light-emitting device including: a first electrode; a second electrode; and an organic layer disposed between the first electrode and the second electrode and including an emission layer, wherein the organic layer includes a condensed cyclic compound described above.

BRIEF DESCRIPTION OF THE DRAWING

These and/or other aspects will become apparent and more readily appreciated from the following description of the embodiments, taken in conjunction with FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, "a first element," "component," "region," "layer" or "section" discussed below could be termed a second element, component, region, layer, or section without departing from the teachings herein.

As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the FIGURES. It will be understood that relative terms are intended to encompass different orientations of the device in addition to the orientation depicted in the FIGURES. For example, if the device in one of the FIGURES is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the FIGURES is turned over, elements described as "below," or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A condensed cyclic compound according to an embodiment may be represented by Formula 1:

Formula 1

In Formula 1, $A_{11}$ may be a group represented by Formula 1-1, $L_{11}$ may be a group represented by Formulae 2-1 to 2-3, $L_{12}$ may be a group represented by Formulae 3-1 to 3-3, and $A_{12}$ is a group represented by Formula 1-2:

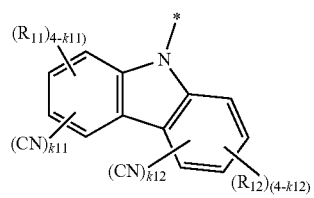

Formula 1-1

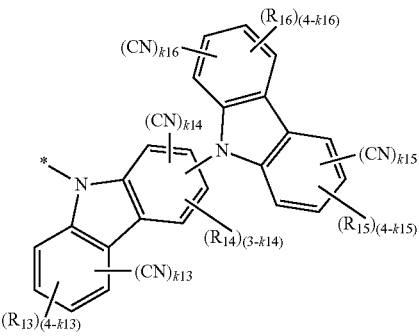

Formula 1-2

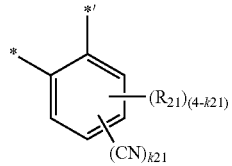

Formula 2-1

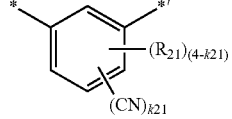

Formula 2-2

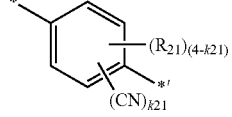

Formula 2-3

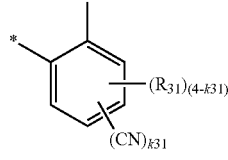

Formula 3-1

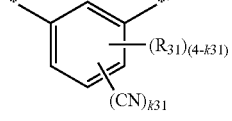

Formula 3-2

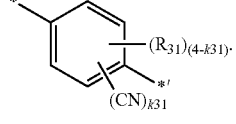

Formula 3-3

Formulae 1-1, 1-2, 2-1 to 2-3, and 3-1 to 3-3 are each independently the same as described herein, and * and *' each indicate a binding site to a neighboring atom.

In Formulae 1-1, 1-2, 2-1 to 2-3, and 3-1 to 3-3, k11 to k16, k21, and k31 each indicate the number of cyano groups.

In Formulae 1-1 and 1-2, k11 to k13, k15, and k16 may each independently be 0, 1, 2, 3, or 4, k14 may be 0, 1, 2, or 3, and the sum of k11 to k16 may be 1 or more.

In an exemplary embodiment, in Formulae 1-1 and 1-2, the sum of k11 to k16 may be 1, 2, 3, or 4, but embodiments of the present disclosure are not limited thereto.

In one embodiment, in Formulae 1-1 and 1-2, the sum of k11 and k12 may be 1, 2, 3, or 4, but embodiments of the present disclosure are not limited thereto.

In one embodiment, in Formulae 1-1 and 1-2, the sum of k11 to k16 may be 1, but embodiments of the present disclosure are not limited thereto.

In one embodiment, in Formulae 1-1 and 1-2, the sum of k11 and k12 may be 1, and the sum of k13 to k16 may be 0, but embodiments of the present disclosure are not limited thereto.

In one embodiment, in Formulae 1-1 and 1-2, the sum of k11 and k12 may be 0, and the sum of k13 to k16 may be 1, but embodiments of the present disclosure are not limited thereto.

In Formulae 2-1 to 2-3 and 3-1 to 3-3, k21 and k31 may each independently be 0, 1, 2, 3, or 4, and the sum of k21 and k31 may be 1 or more.

In an exemplary embodiment, in Formulae 2-1 to 2-3 and 3-1 to 3-3, the sum of k21 and k31 may be 1, 2, 3, or 4, but embodiments of the present disclosure are not limited thereto.

In one embodiment, in Formulae 2-1 to 2-3 and 3-1 to 3-3, the sum of k21 and k31 may be 1 or 2, but embodiments of the present disclosure are not limited thereto.

In one embodiment, in Formulae 1-1, 1-2, 2-1 to 2-3, and 3-1 to 3-3, the sum of k11 to k16 may be 1, 2, 3, or 4, and the sum of k21 and k31 may be 1, 2, 3, or 4, but embodiments of the present disclosure are not limited thereto.

In one or more embodiments, in Formulae 1-1, 1-2, 2-1 to 2-3, and 3-1 to 3-3, the sum of k11 and k12 may be 1, 2, 3, or 4, and the sum of k21 and k31 may be 1, 2, 3, or 4, but embodiments of the present disclosure are not limited thereto.

In one or more embodiments, in Formulae 1-1, 1-2, 2-1 to 2-3, and 3-1 to 3-3, the sum of k11 to k16 may be 1, and the sum of k21 and k31 may be 1 or 2, but embodiments of the present disclosure are not limited thereto.

In one or more embodiments, in Formulae 1-1, 1-2, 2-1 to 2-3, and 3-1 to 3-3, the sum of k11 and k12 may be 1, the sum of k13 to k16 may be 0, and the sum of k21 and k31 may be 1 or 2, but embodiments of the present disclosure are not limited thereto.

In one or more embodiments, in Formulae 1-1, 1-2, 2-1 to 2-3, and 3-1 to 3-3, the sum of k11 and k12 may be 0, the sum of k13 to k16 may be 1, and the sum of k21 and k31 may be 1 or 2, but embodiments of the present disclosure are not limited thereto.

In one or more embodiments, in Formula 1, $A_{11}$ may be a group represented by Formulae 4-1 to 4-4, but embodiments of the present disclosure are not limited thereto:

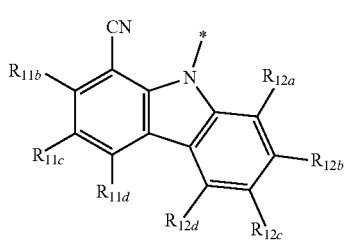

4-1

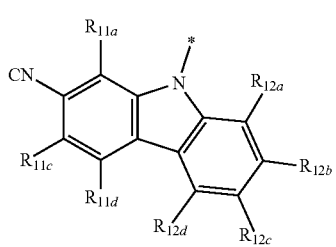

4-2

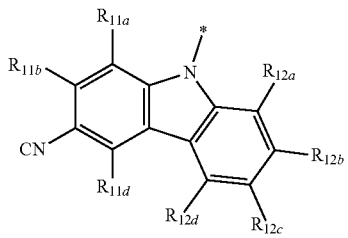

4-3

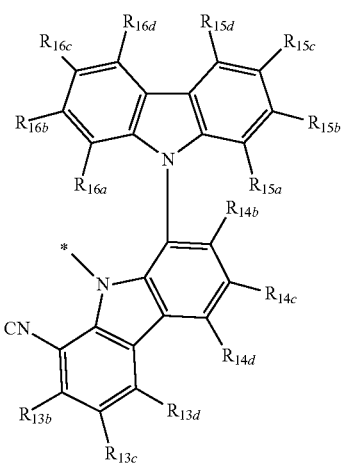

4-4

In Formulae 4-1 to 4-4, $R_{11a}$ to $R_{11d}$ and $R_{12a}$ to $R_{12d}$ may each independently be the same as defined in connection with $R_{11}$ in Formula 1-1, and * indicates a binding site to a neighboring atom.

In one embodiment, in Formula 1, $A_{12}$ may be a group represented by Formulae 5-1 to 5-44, but embodiments of the present disclosure are not limited thereto:

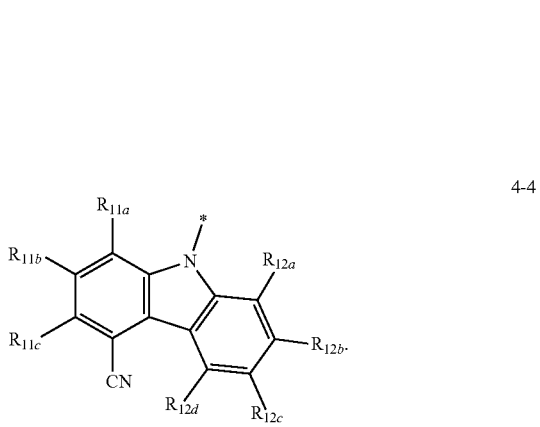

5-1

5-2 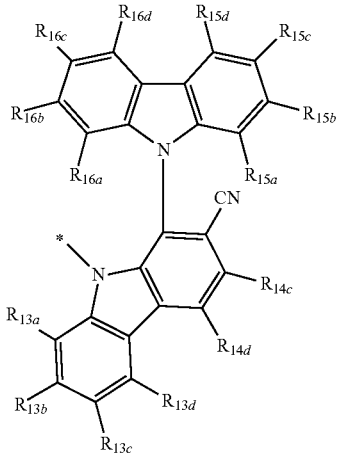
5-3 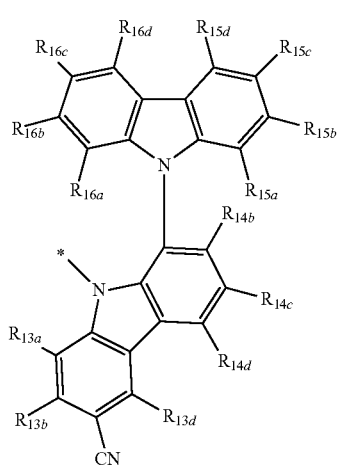
5-4 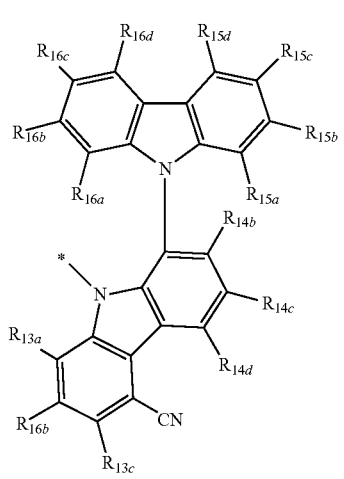
5-5 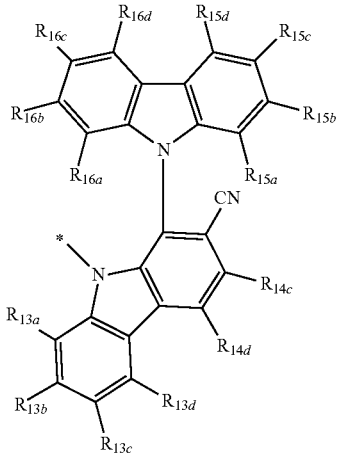
5-6 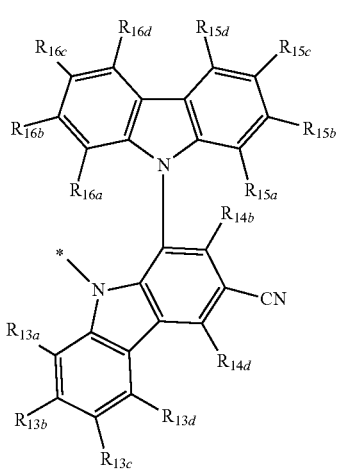
5-7 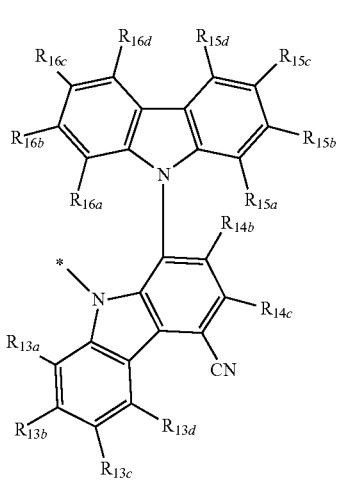

11
-continued
5
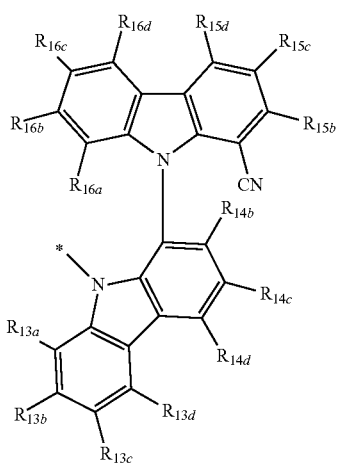
5-8
10
15
20
25
5-9
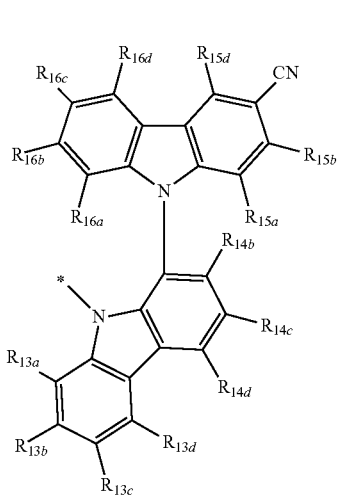
30
35
40
45
50
5-10
55
60
65
12
-continued
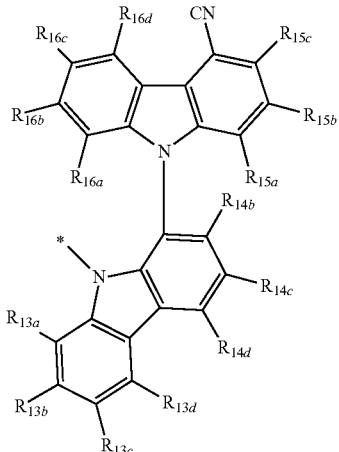
5-11
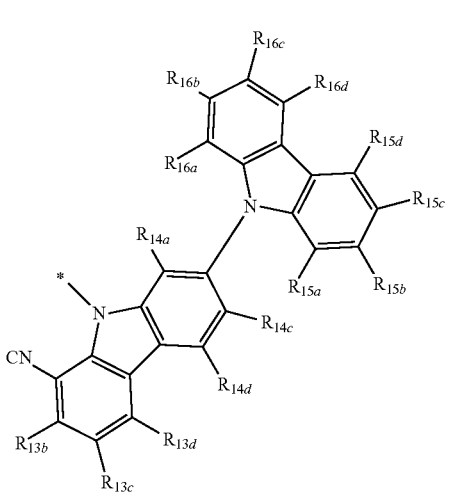
5-12
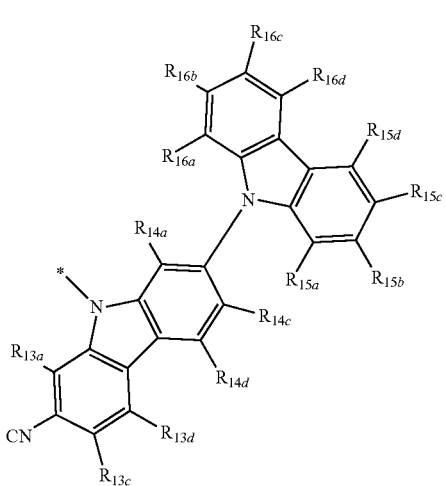
5-13

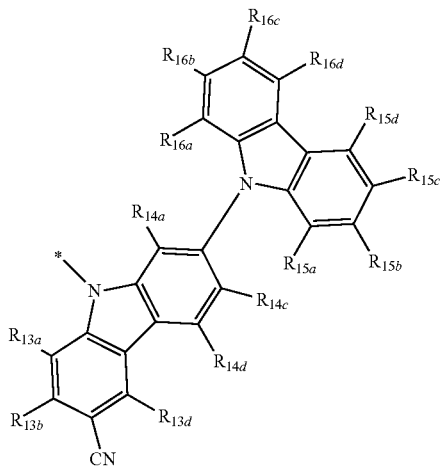
5-14
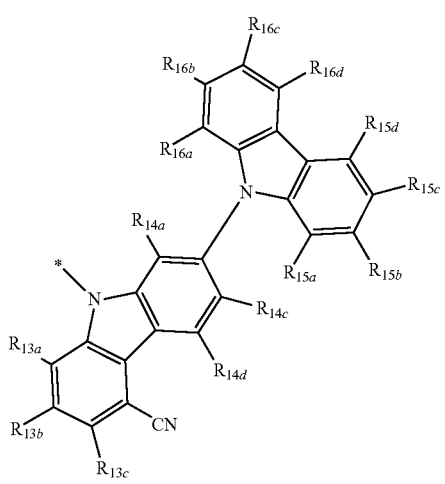
5-15
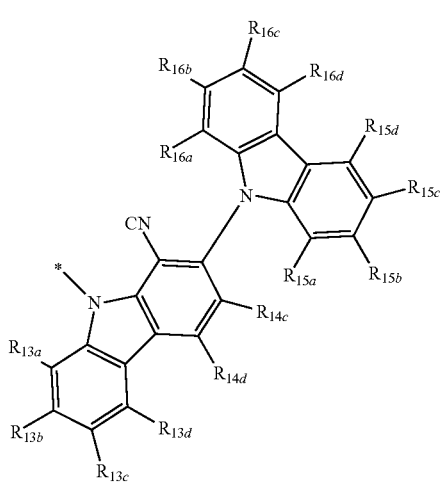
5-16
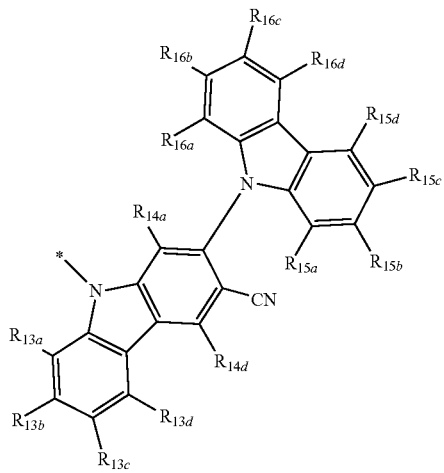
5-17
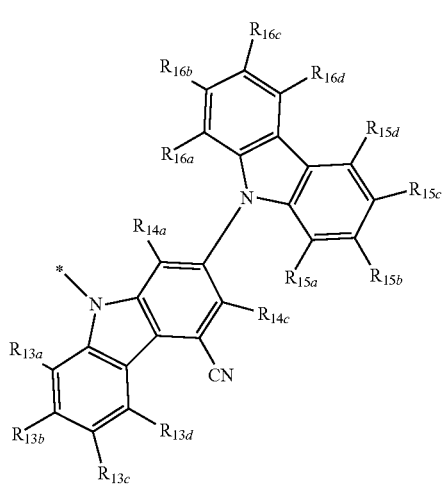
5-18
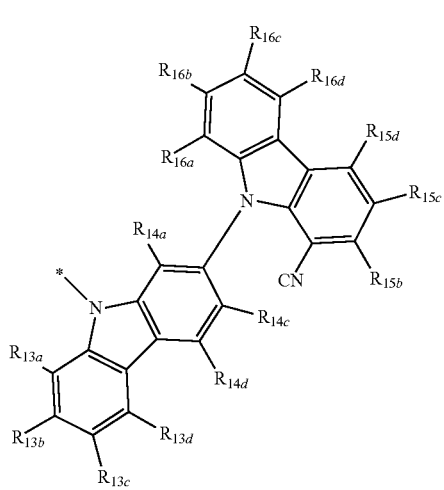
5-19

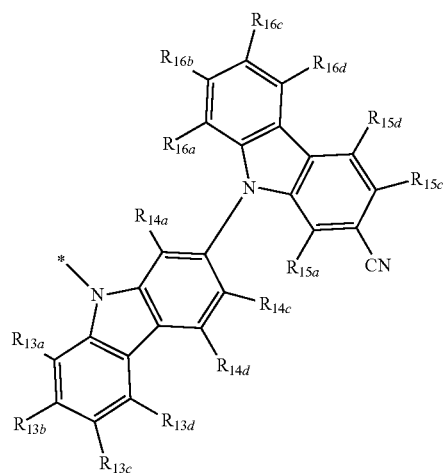
5-20
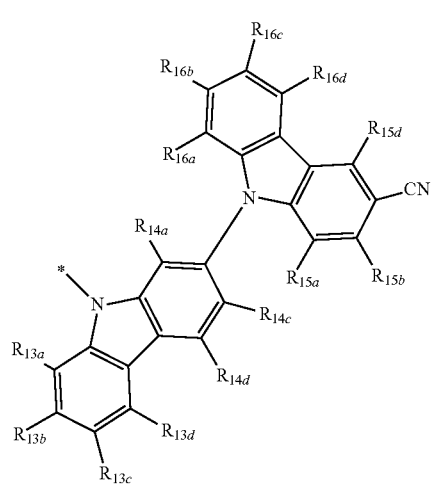
5-21
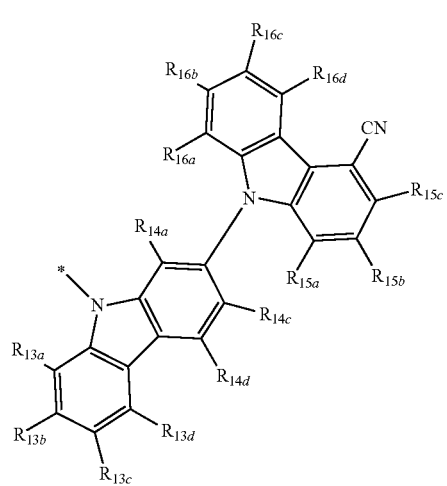
5-22
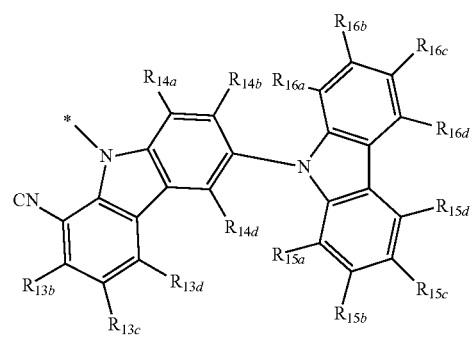
5-23
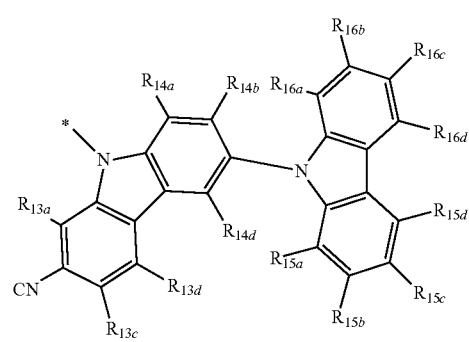
5-24
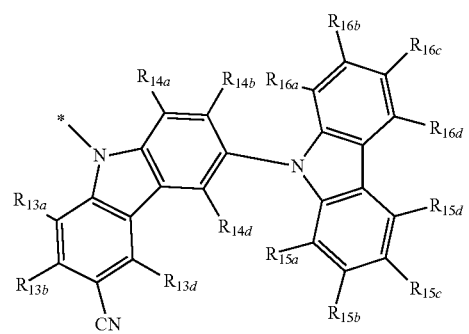
5-25
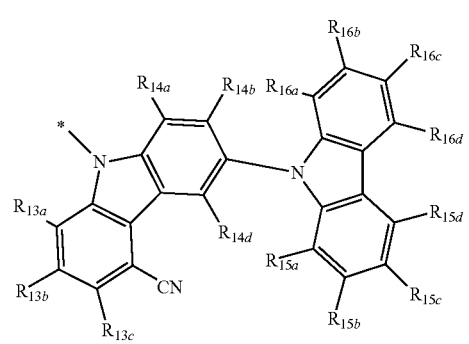
5-26

5-27 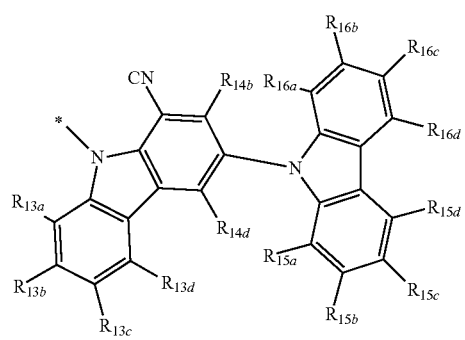
5-28 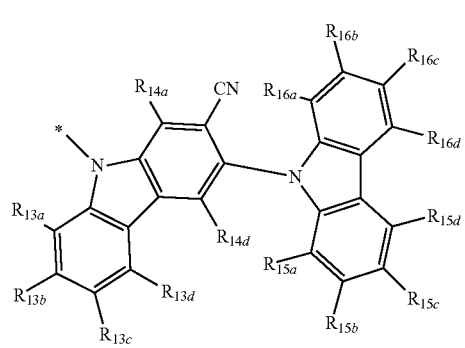
5-29 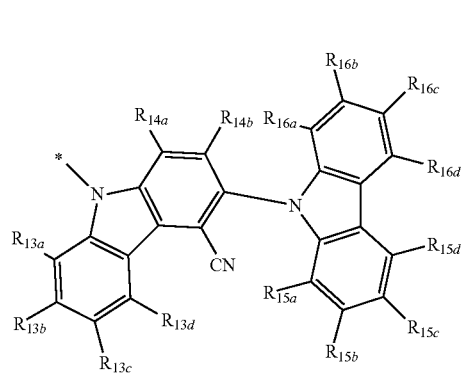
5-30 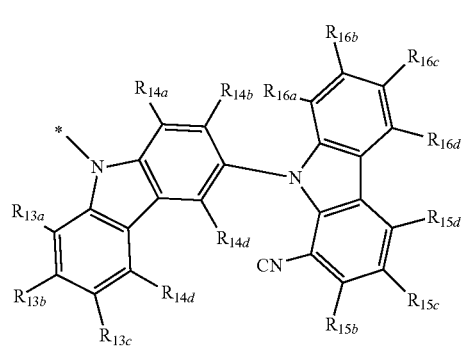
5-31 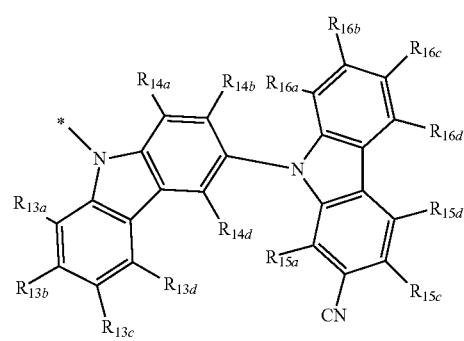
5-32 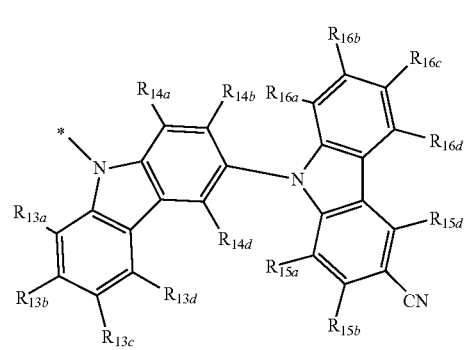
5-33 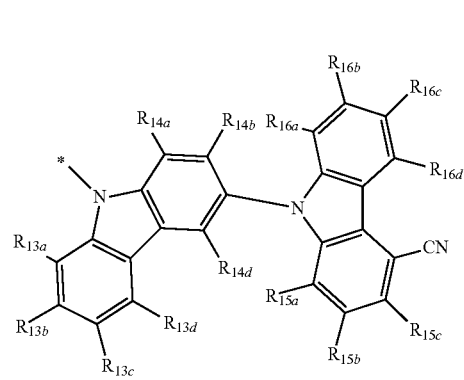
5-34 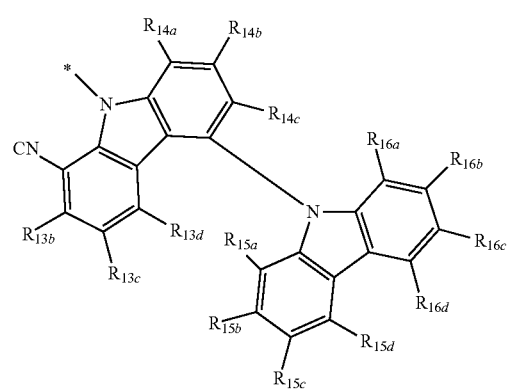

-continued
5-35
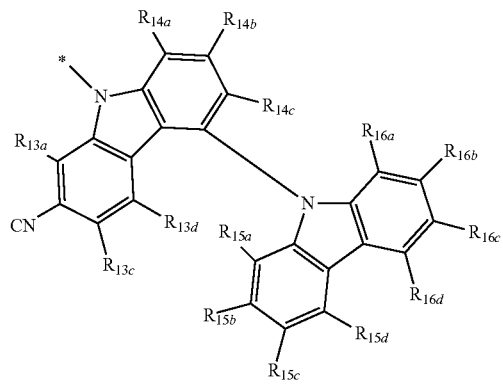
5-36
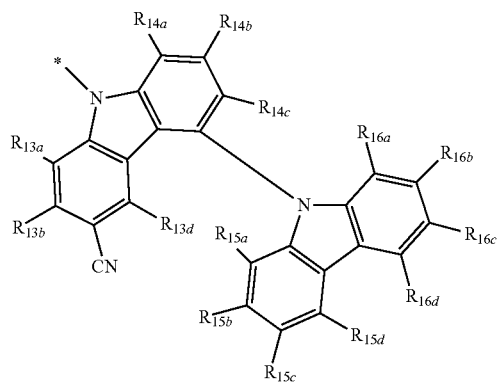
5-37
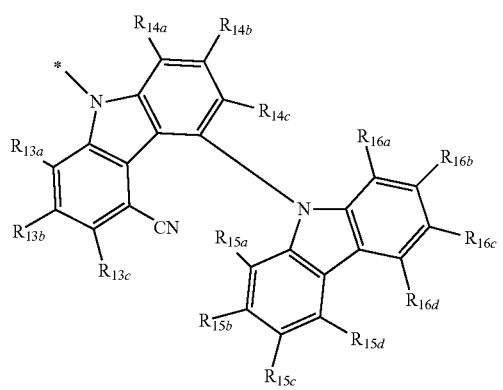
5-38
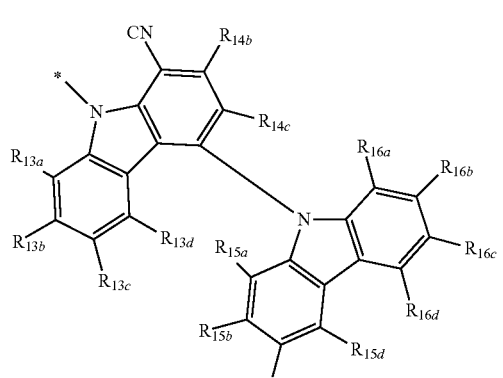
5-39
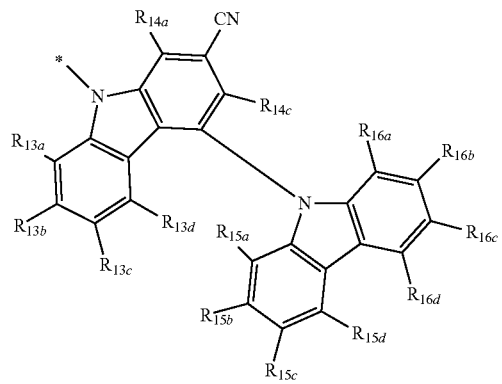
5-40
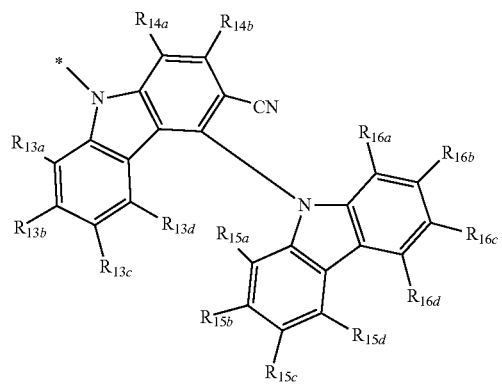
5-41
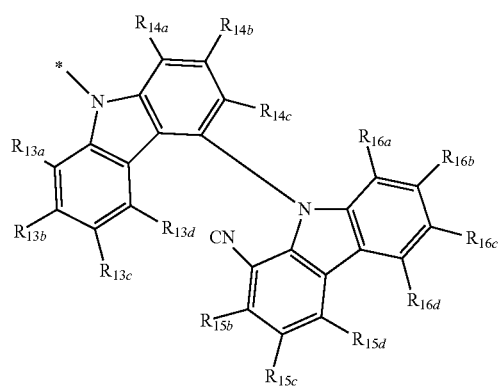
5-42
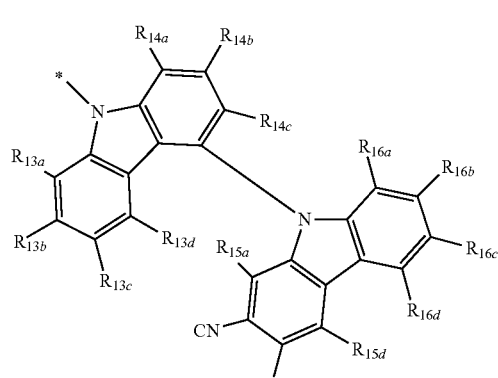

5-43

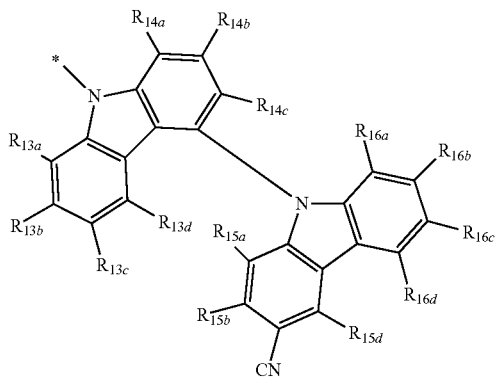

5-44

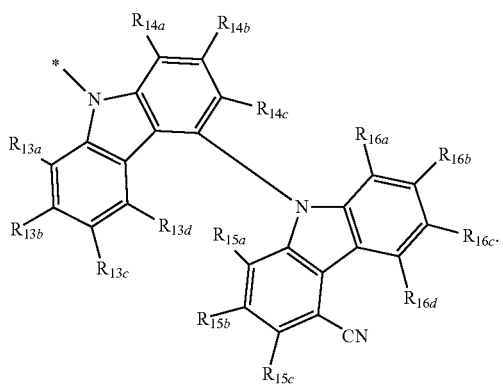

5-101

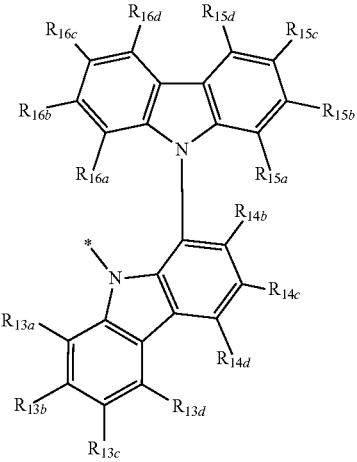

5-102

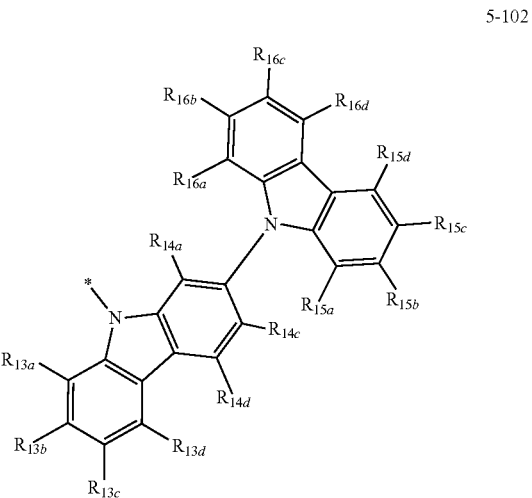

5-103

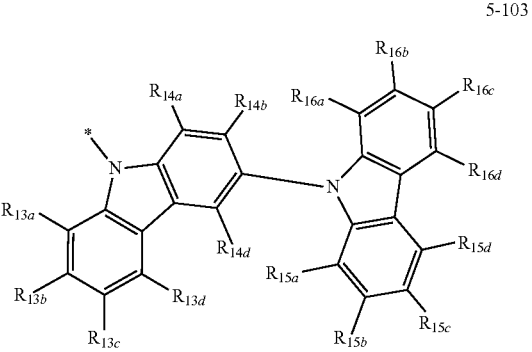

In Formulae 5-1 to 5-44, $R_{13a}$ to $R_{13d}$, $R_{14a}$ to $R_{14d}$, $R_{15a}$ to $R_{15d}$, and $R_{16a}$ to $R_{16d}$ may each independently be the same as defined in connection with $R_{11}$ in Formula 1-1, and * indicates a binding site to a neighboring atom.

In one embodiment, in Formula 1, $A_{11}$ may be a group represented by Formulae 4-1 to 4-4 or 4-101, and $A_{12}$ may be a group represented by Formulae 5-1 to 5-44, but embodiments of the present disclosure are not limited thereto:

4-101

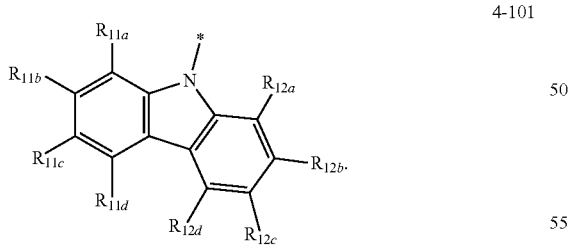

In Formula 4-101, $R_{11a}$ to $R_{11d}$ and $R_{12a}$ to $R_{12d}$ may each independently be the same as defined in connection with $R_{11}$ in Formula 1-1, and * indicates a binding site to a neighboring atom.

In one or more embodiments, in Formula 1, $A_{11}$ may be a group represented by Formulae 4-1 to 4-4, and $A_{12}$ may be a group represented by Formulae 5-1 to 5-44 and 5-101 to 5-104, but embodiments of the present disclosure are not limited thereto:

5-104

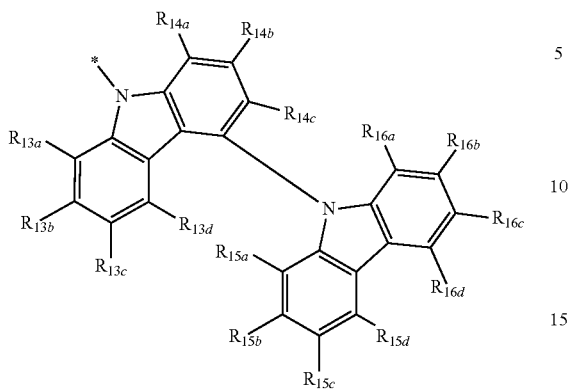

In Formulae 5-101 to 5-104, $R_{13a}$ to $R_{13d}$, $R_{14a}$ to $R_{14d}$, $R_{15a}$ to $R_{15d}$, and $R_{16a}$ to $R_{16d}$ may each independently be the same as defined in connection with $R_{11}$ in Formula 1-1, and * indicates a binding site to a neighboring atom.

In one embodiment, $A_{11}$ may be a group represented by Formulae 4-1 to 4-4, and $A_{12}$ may be a group represented by Formulae 5-101 to 5-104, but embodiments of the present disclosure are not limited thereto.

In one or more embodiments, $A_{11}$ may be a group represented by Formula 4-101, and $A_{12}$ may be a group represented by Formulae 5-1 to 5-44, but embodiments of the present disclosure are not limited thereto.

In one embodiment, in Formula 1, $L_{11}$ may be a group represented by Formulae 2-11 to 2-27, but embodiments of the present disclosure are not limited thereto:

2-11

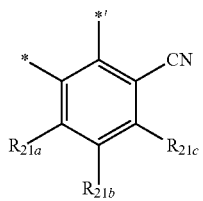

2-12

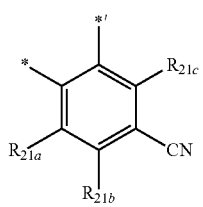

2-13

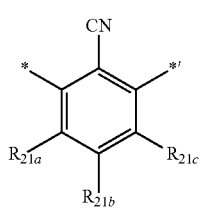

2-14

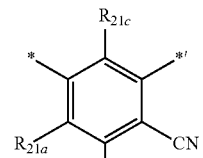

2-15

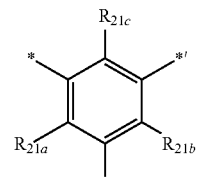

2-16

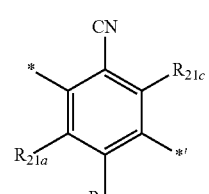

2-17

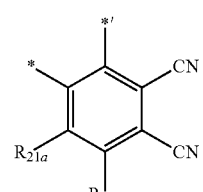

2-18

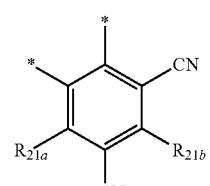

2-19

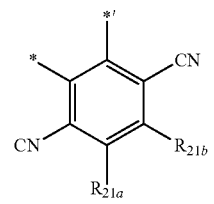

2-20

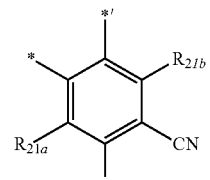

2-21

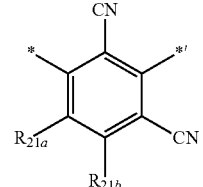

-continued
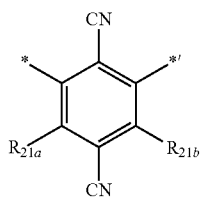
2-22
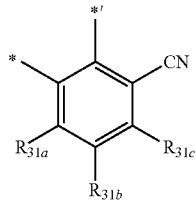
3-11
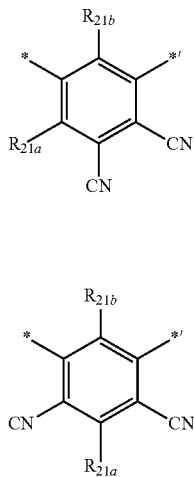
2-23
2-24
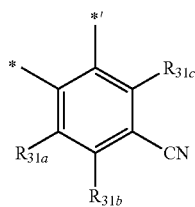
3-12
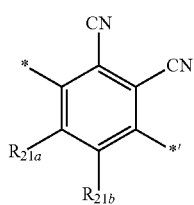
2-25
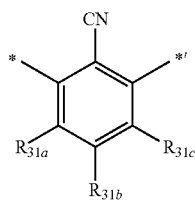
3-13
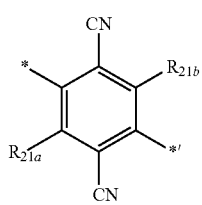
2-26
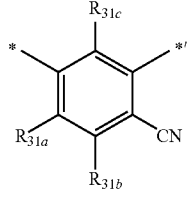
3-14
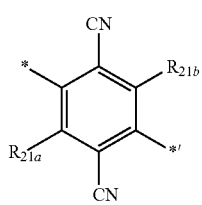
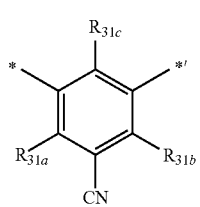
3-15
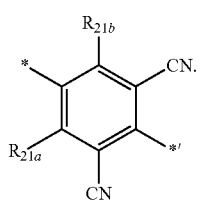
2-27
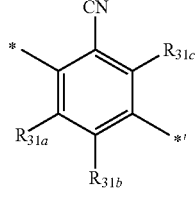
3-16
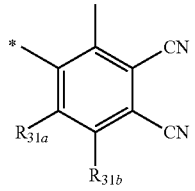
3-17
In Formulae 2-11 to 2-27, $R_{21a}$ to $R_{21c}$ may each independently be the same as defined in connection with $R_{21}$ in Formula 2-1, and * and *' each indicate a binding site to a neighboring atom.
In one embodiment, in Formula 1, $L_{12}$ may be a group represented by Formulae 3-11 to 3-27, but embodiments of the present disclosure are not limited thereto:

3-18 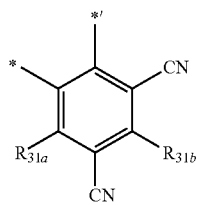

3-19 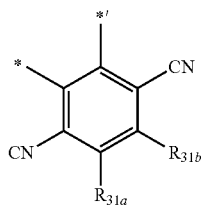

3-20 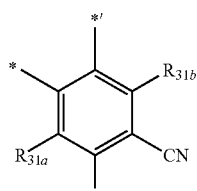

3-21 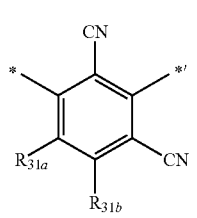

3-22 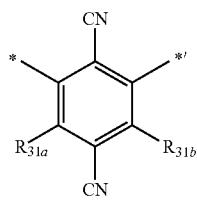

3-23 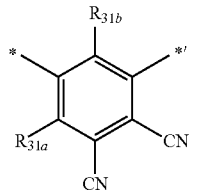

3-24 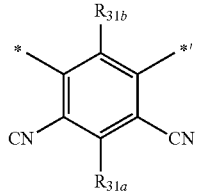

3-25 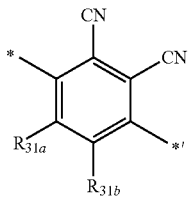

3-26 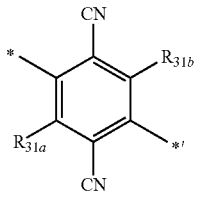

3-27 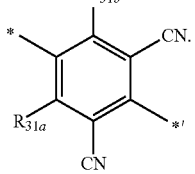

In Formulae 3-11 to 3-27, $R_{31a}$ to $R_{31c}$ may each independently be the same as defined in connection with $R_{31}$ in Formula 3-1, and * and *' each indicate a binding site to a neighboring atom.

In one embodiment, in Formula 1, $L_{11}$ may be a group represented by Formulae 2-11 to 2-27 or 2-101 to 2-103, and $L_{12}$ may be a group represented by Formulae 3-11 to 3-27, but embodiments of the present disclosure are not limited thereto:

2-101 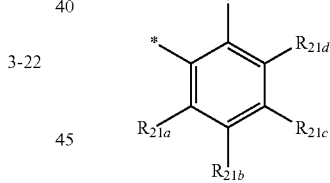

2-102 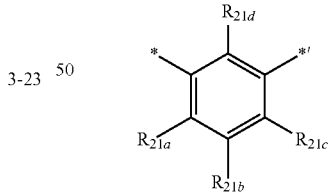

2-103 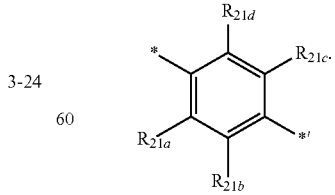

In Formulae 2-101 to 2-103,
$R_{21a}$ to $R_{21d}$ may each independently be the same as defined in connection with $R_{21}$ in Formula 2-1, and and *' each indicate a binding site to a neighboring atom.

In one or more embodiments, in Formula 1, $L_{11}$ may be a group represented by Formulae 2-11 to 2-27, and $L_{12}$ may be a group represented by Formulae 3-11 to 3-27 or 3-101 to 3-103, but embodiments of the present disclosure are not limited thereto:

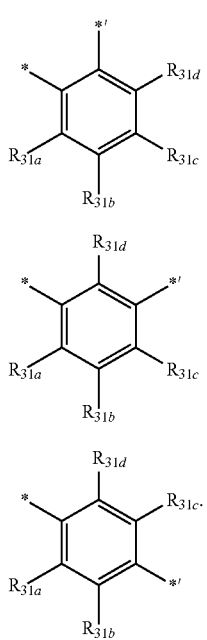

In Formulae 3-101 to 3-103, $R_{31a}$ to $R_{31d}$ may each independently be the same as defined in connection with $R_{31}$ in Formula 3-1, and * and *' each indicate a binding site to a neighboring atom.

In one embodiment,
i) $L_{11}$ may be a group represented by Formulae 2-11 to 2-16, and $L_{12}$ may be a group represented by Formulae 3-101 to 3-103;
ii) $L_{11}$ may be a group represented by Formulae 2-101 to 2-103, and $L_{12}$ may be a group represented by Formulae 3-11 to 3-16;
iii) $L_{11}$ may be a group represented by Formulae 2-11 to 2-16, and $L_{12}$ may be a group represented by Formulae 3-11 to 3-16;
iv) $L_{11}$ may be a group represented by Formulae 2-17 to 2-27, and $L_{12}$ may be a group represented by Formulae 3-101 to 3-103; or
v) $L_{11}$ may be a group represented by Formulae 2-101 to 2-103, and $L_{12}$ may be a group represented by Formulae 3-17 to 2-27, but embodiments of the present disclosure are not limited thereto.

In Formulae 1-1 and 1-2,
$R_{11}$ to $R_{16}$ may each independently be hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), wherein $R_{11}$ and $R_{12}$ may not each independently a substituted or unsubstituted carbazolyl group, and $Q_1$ to $Q_7$ may each independently be hydrogen, $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

In an exemplary embodiment, in Formulae 1-1 and 1-2, $R_{11}$ and $R_{12}$ may each independently be:
hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a pyridinyl group, a pyrimidinyl group, or a combination thereof;

a cyclopentyl group, a cyclohexyl group, a cycloheptyl group, a cyclooctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzosilolyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cycloctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cycloctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si(Q$_{11}$)(Q$_{12}$)(Q$_{13}$), —B(Q$_{11}$)(Q$_{12}$), —N(Q$_{11}$)(Q$_{12}$), or a combination thereof; or —Si(Q$_1$)(Q$_2$)(Q$_3$), —B(Q$_1$)(Q$_2$), or —N(Q$_1$)(Q$_2$), $R_{13}$ to $R_{16}$ may each independently be:

hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cycloctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a pyridinyl group, a pyrimidinyl group, or a combination thereof;

a cyclopentyl group, a cyclohexyl group, a cycloheptyl group, a cycloctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cycloctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si(Q$_{11}$)(Q$_{12}$)(Q$_{13}$), —B(Q$_{11}$)(Q$_{12}$), —N(Q$_{11}$)(Q$_{12}$), or a combination thereof; or —Si(Q$_1$)(Q$_2$)(Q$_3$), —B(Q$_1$)(Q$_2$), or —N(Q$_1$)(Q$_2$), and Q$_1$ to Q$_3$ and Q$_{11}$ to Q$_{13}$ may each independently be:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a $C_1$-$C_{20}$ alkylphenyl group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group, each substituted with deuterium, a phenyl group, or a combination thereof, but embodiments of the present disclosure are not limited thereto.

In one embodiment, in Formulae 1-1 and 1-2,

R$_{11}$ and R$_{12}$ may each independently be hydrogen, deuterium, —F, a nitro group, —CH$_3$, —CD$_3$, —CD$_2$H, —CDH$_2$, —CF$_3$, —CF$_2$H, —CFH$_2$, groups represented by Formulae 9-1 to 9-27, groups represented by Formulae 9-1 to 9-27 of which a hydrogen is substituted with deuterium, groups represented by Formulae 10-1 to 10-142, 10-148 to 10-195, or 10-220 to 10-226, —Si(Q$_1$)(Q$_2$)(Q$_3$), —B(Q$_1$)(Q$_2$), or —N(Q$_1$)(Q$_2$), R$_{13}$ to R$_{16}$ may each independently be hydrogen, deuterium, —F, a nitro group, —CH$_3$, —CD$_3$, —CD$_2$H, —CDH$_2$, —CF$_3$, —CF$_2$H, —CFH$_2$, groups represented by Formulae 9-1 to 9-27, groups represented by Formulae 9-1 to 9-27 of which a hydrogen is substituted with deuterium, groups represented by Formulae 10-1 to 10-226, —Si(Q$_1$)(Q$_2$)(Q$_3$), —B(Q$_1$)(Q$_2$), or —N(Q$_1$)(Q$_2$), but embodiments of the present disclosure are not limited thereto:

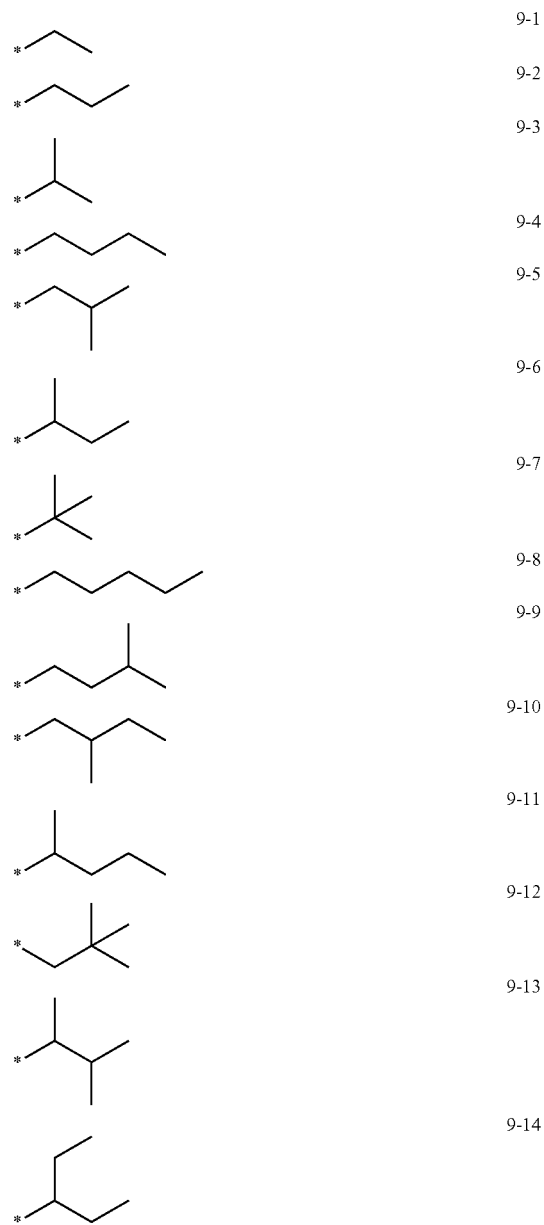

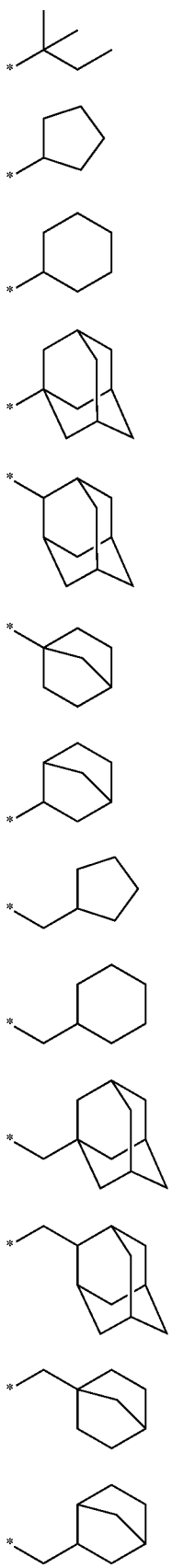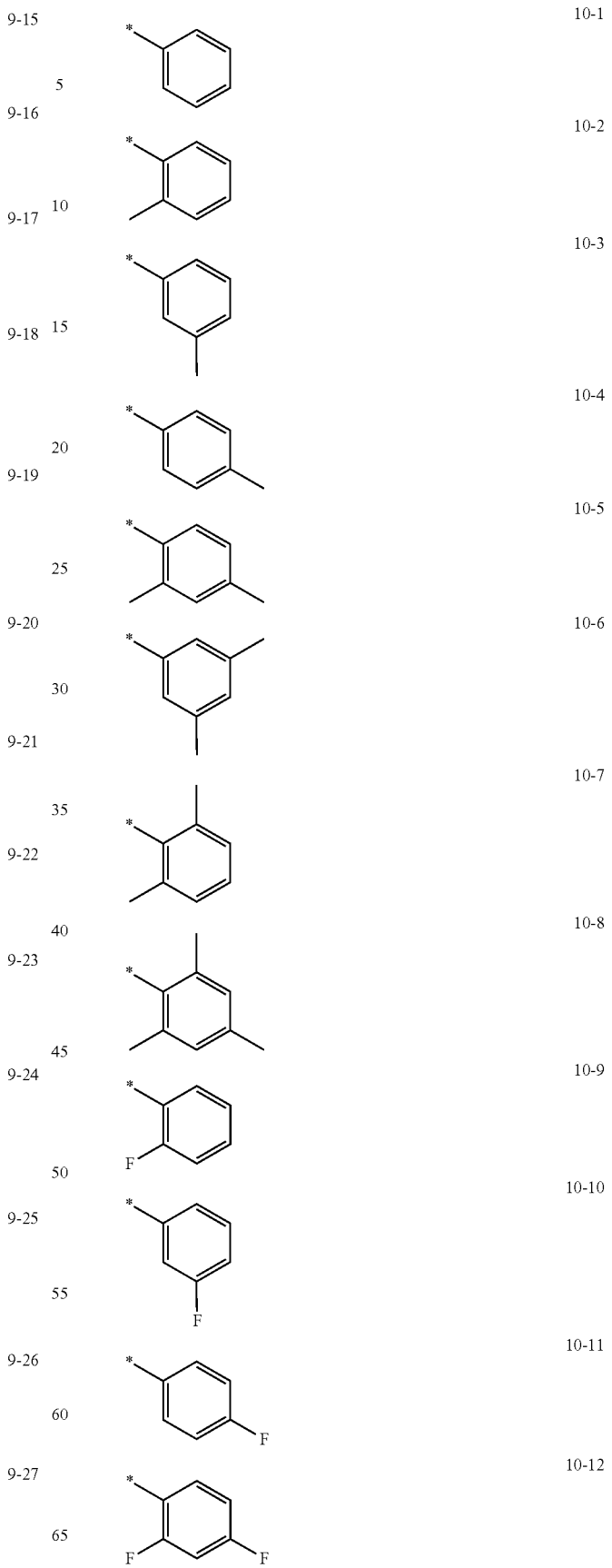

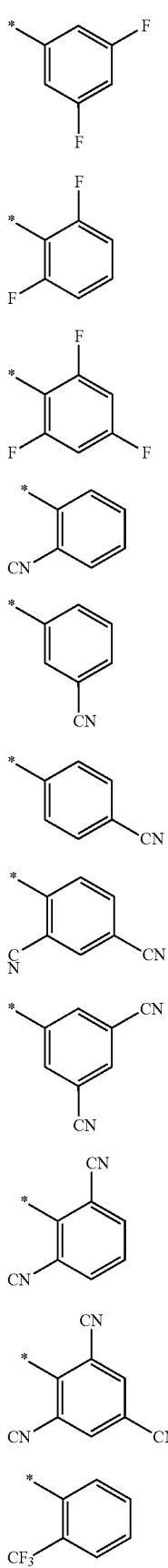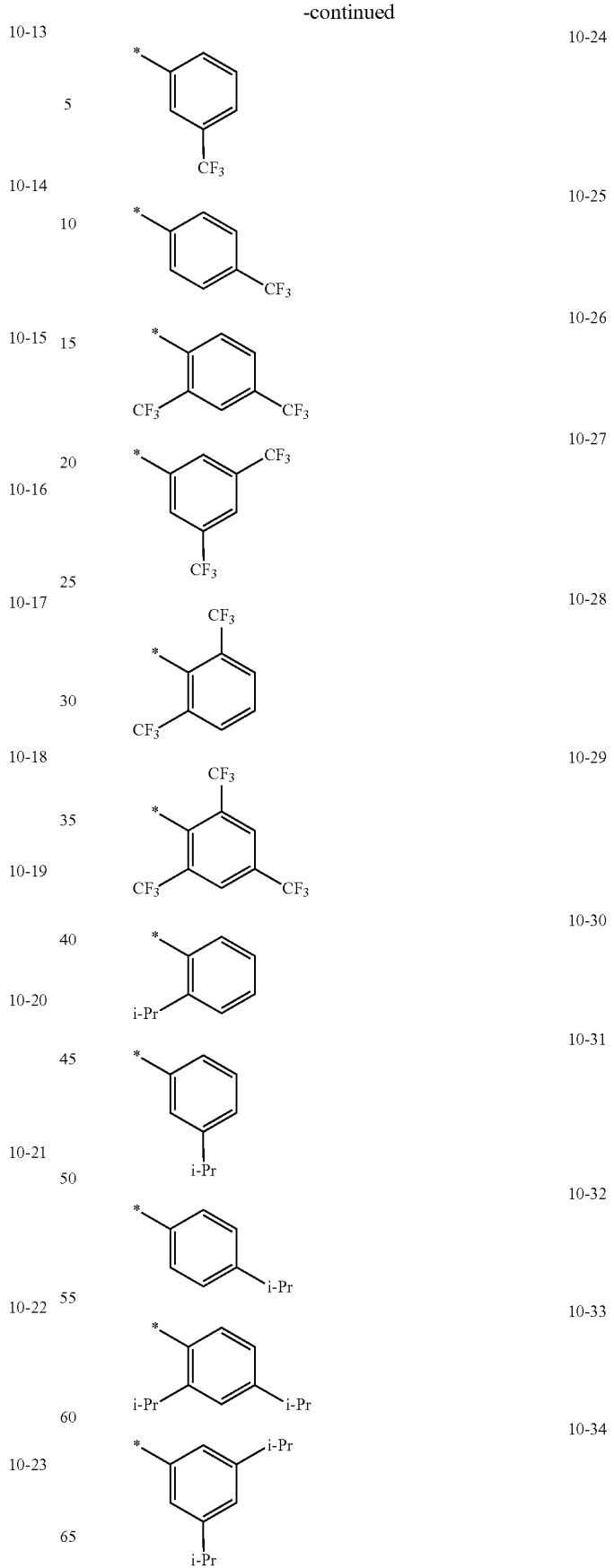

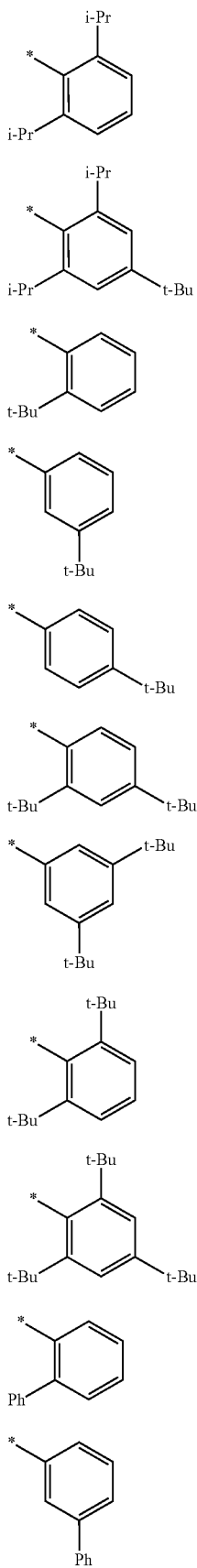
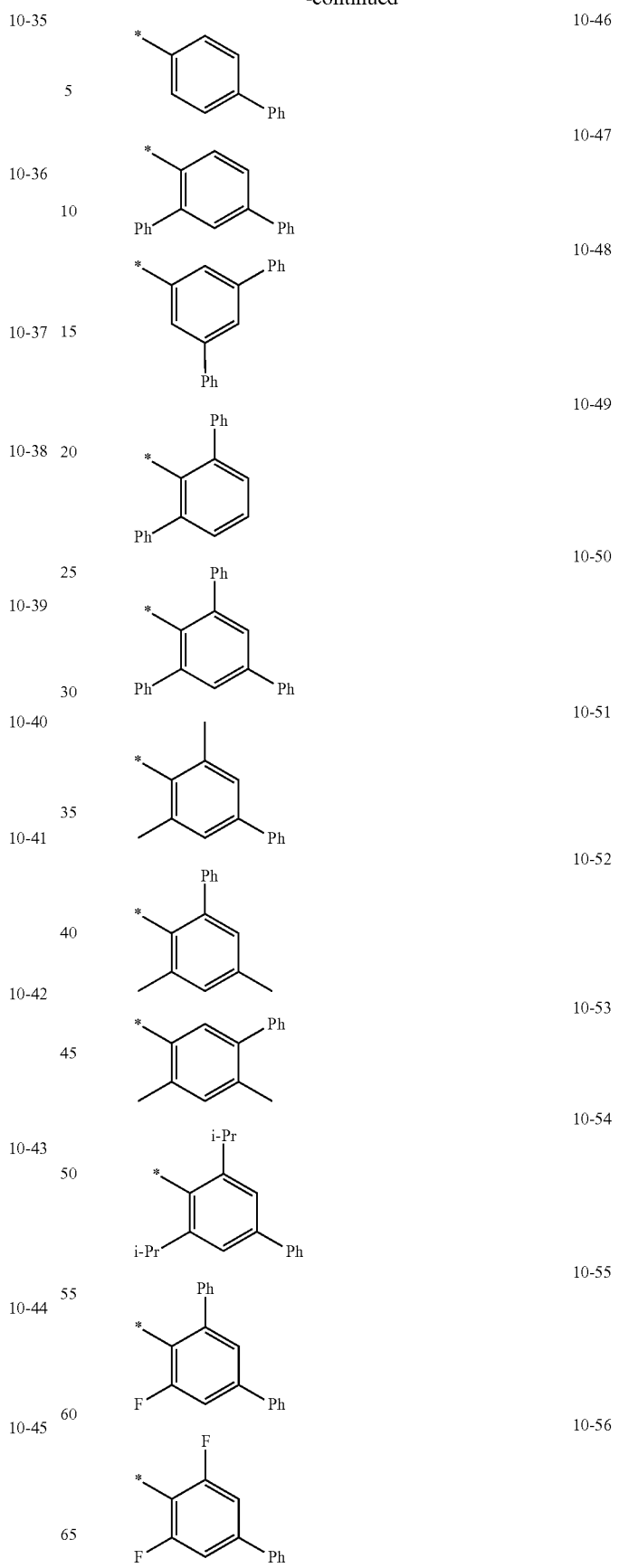

| | |
|---|---|
| 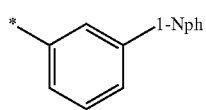 | 10-57 |
| 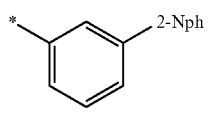 | 10-58 |
| 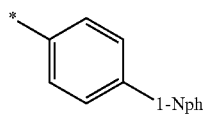 | 10-59 |
| 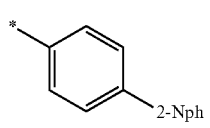 | 10-60 |
| 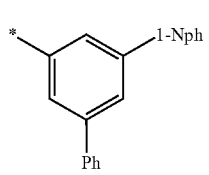 | 10-61 |
| 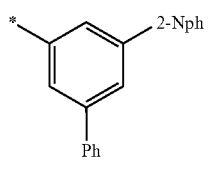 | 10-62 |
| 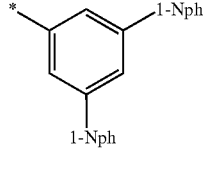 | 10-63 |
| 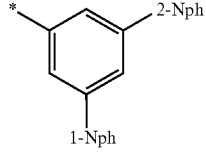 | 10-64 |
| 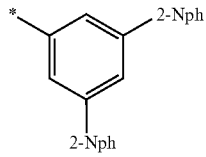 | 10-65 |
| 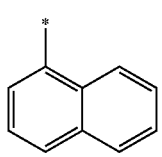 | 10-66 |
| 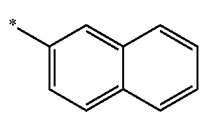 | 10-67 |
| 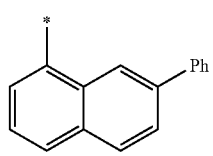 | 10-68 |
| 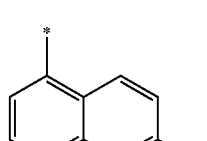 | 10-69 |
| 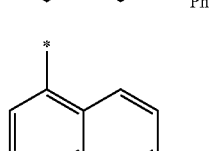 | 10-70 |
| 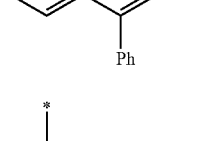 | 10-71 |
|  | 10-72 |
| 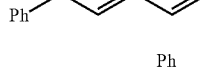 | 10-73 |
| 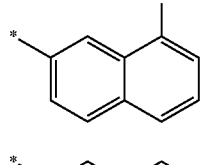 | |
| 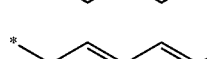 | 10-74 |
| 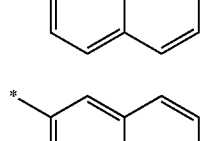 | 10-75 |
| 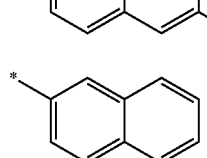 | 10-76 |
| 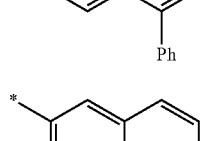 | 10-77 |
| 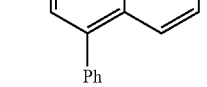 | |

-continued
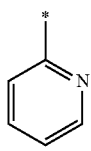 10-78
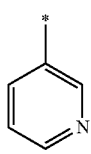 10-79
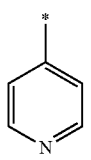 10-80
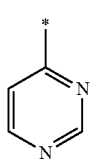 10-81
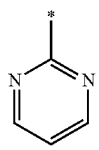 10-82
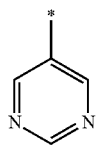 10-83
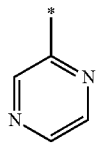 10-84
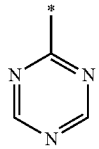 10-85
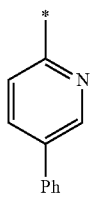 10-86
-continued
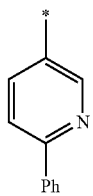 10-87
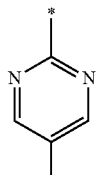 10-88
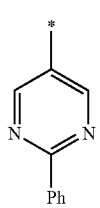 10-89
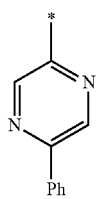 10-90
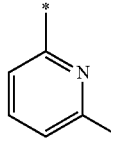 10-91
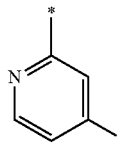 10-92
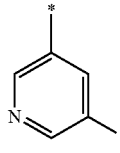 10-93
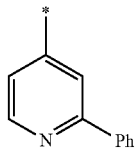 10-94
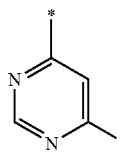 10-95

-continued
10-96 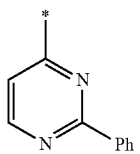
10-97 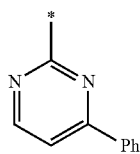
10-98 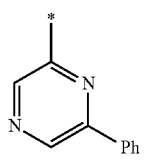
10-99 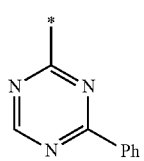
10-100 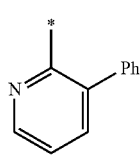
10-101 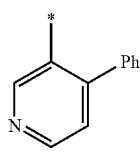
10-102 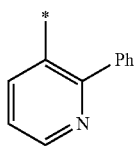
10-103 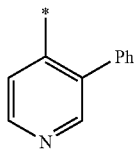
10-104 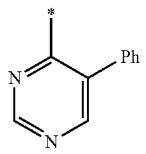
10-105 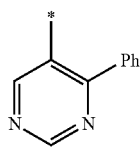
-continued
10-106 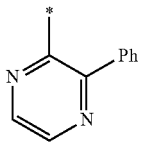
10-107 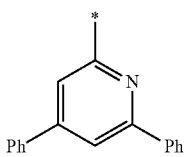
10-108 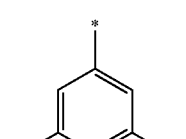
10-109 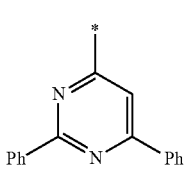
10-110 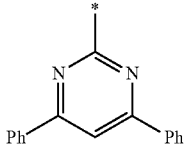
10-111 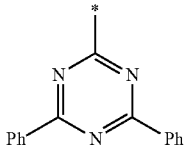
10-112 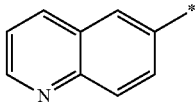
10-113 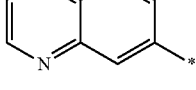
10-114 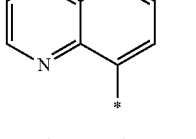
10-115 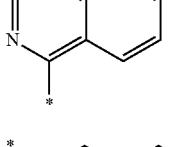
10-116 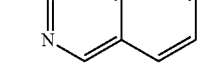

-continued
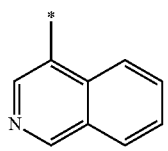
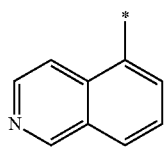
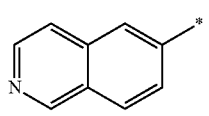
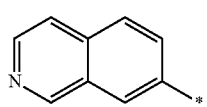
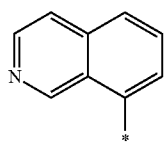
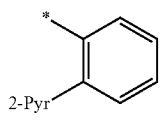
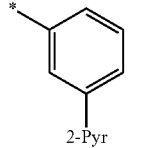
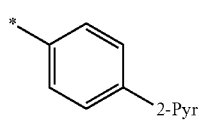
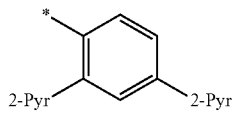
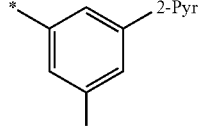
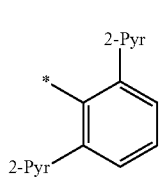
-continued
10-117
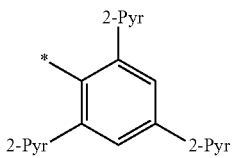
10-118
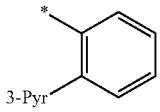
10-119
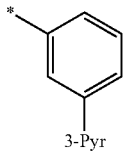
10-120
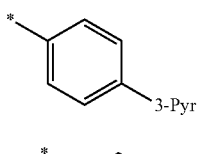
10-121
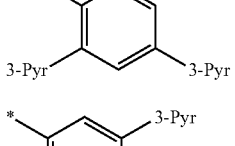
10-122
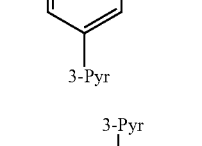
10-123

10-124

10-125
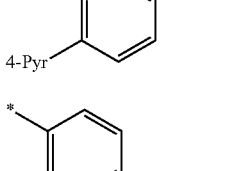
10-126
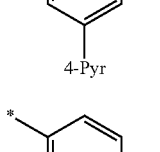
10-127
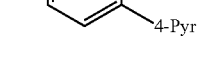
10-128
10-129
10-130
10-131
10-132
10-133
10-134
10-135
10-136
10-137
10-138

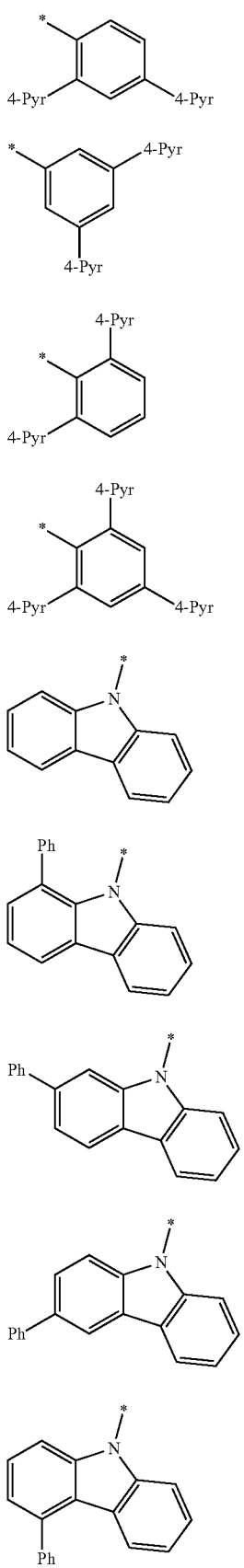
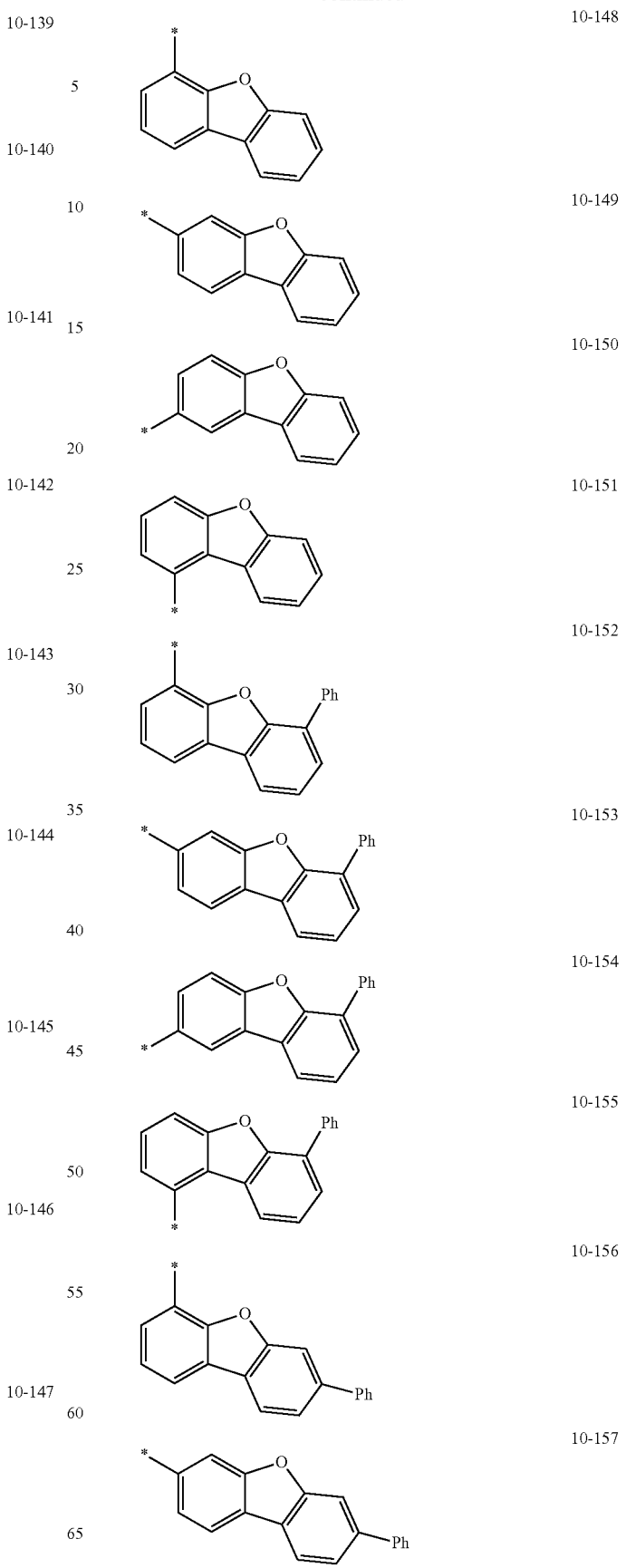

-continued
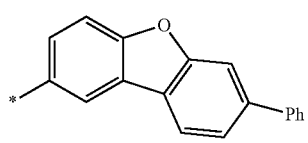
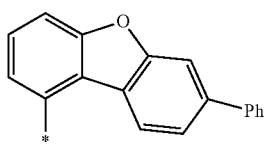
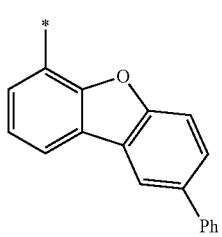
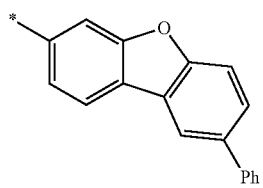
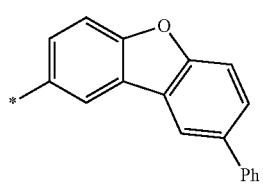
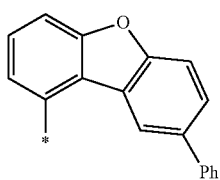
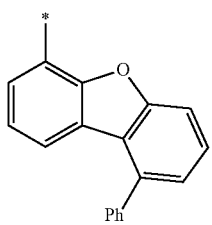
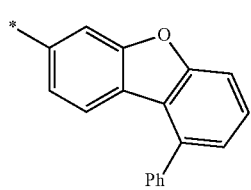
-continued
10-158 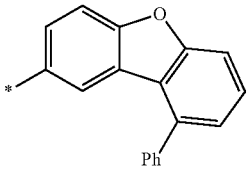
10-159 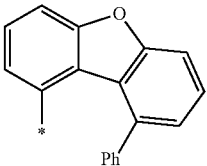
10-160 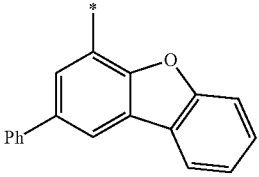
10-161 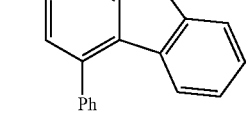
10-162 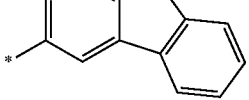
10-163 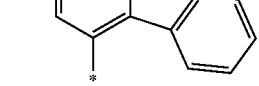
10-164 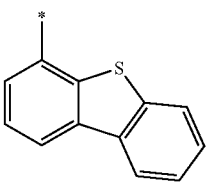
10-165 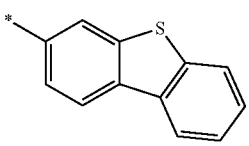
10-166
10-167
10-168
10-169
10-170
10-171
10-172
10-173
10-174 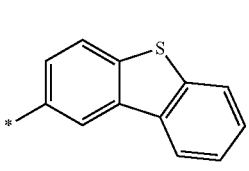

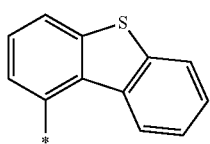
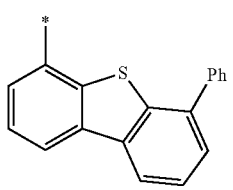
10-176
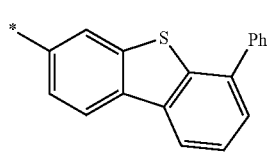
10-177
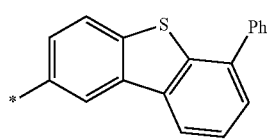
10-178
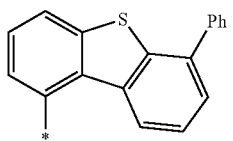
10-179
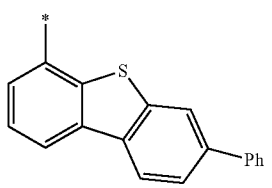
10-180
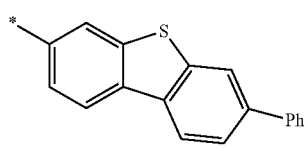
10-181
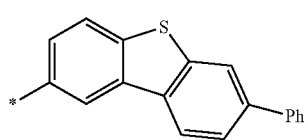
10-182
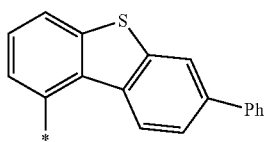
10-183
10-175
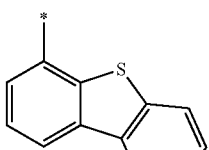
10-184
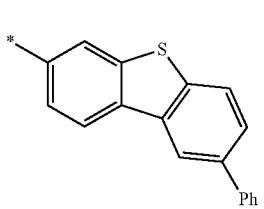
10-185
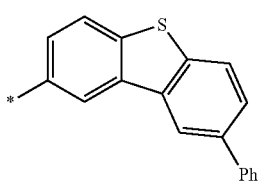
10-186
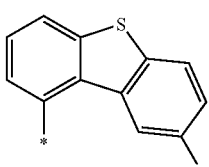
10-187
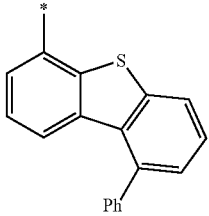
10-188
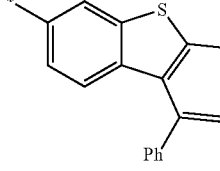
10-189
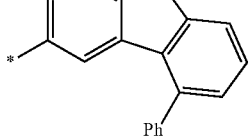
10-190
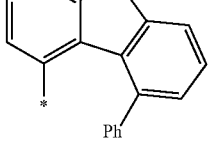
10-191

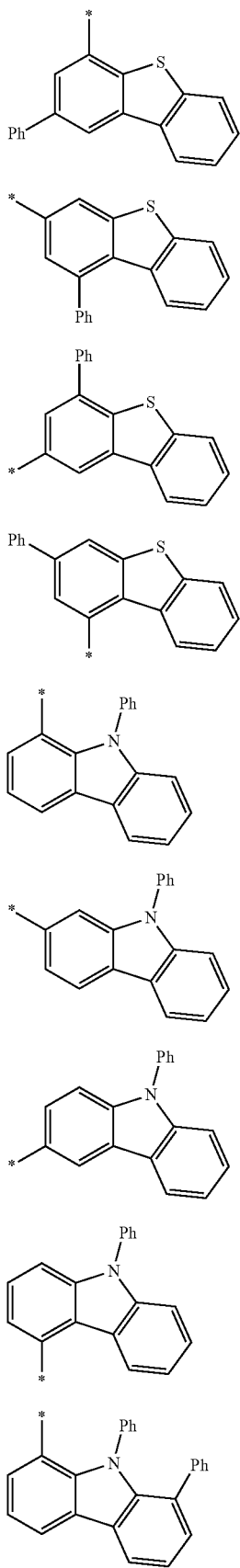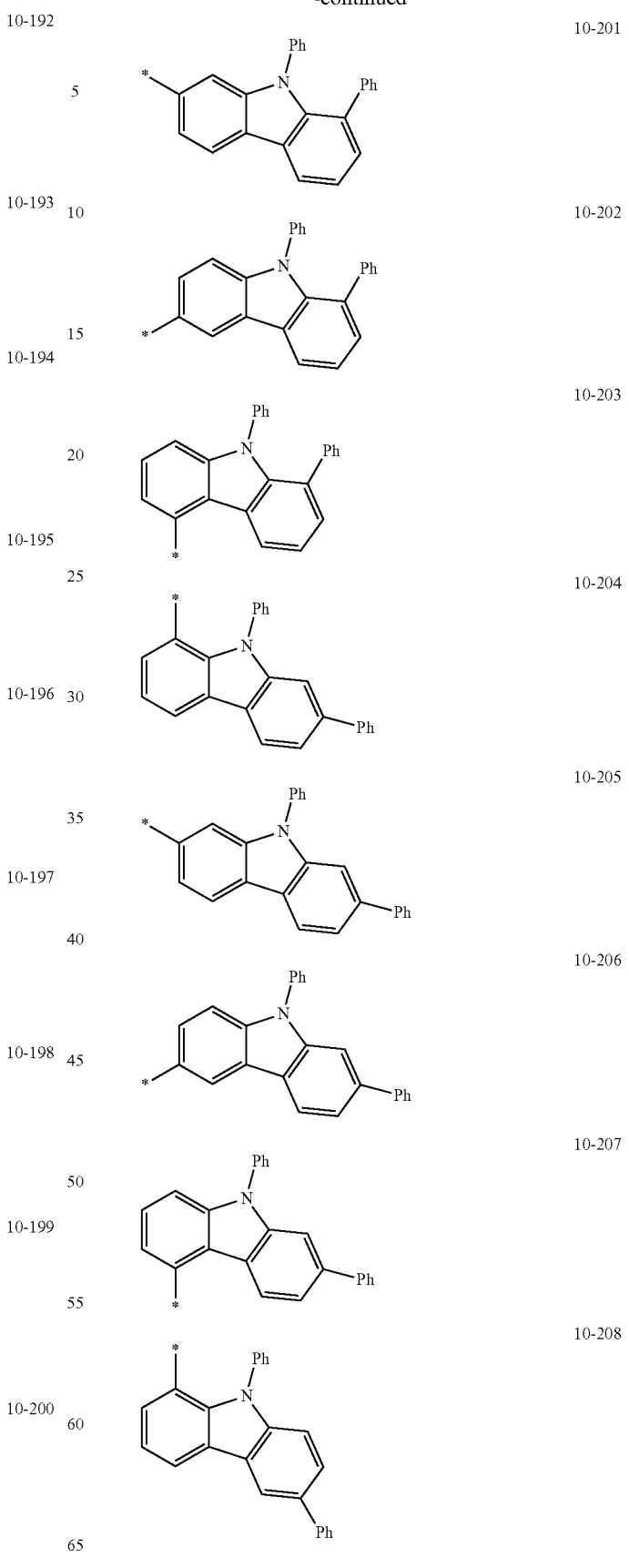

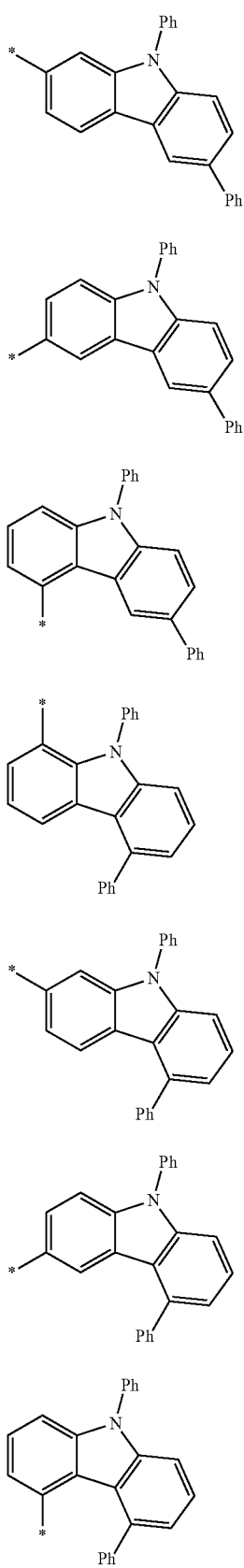
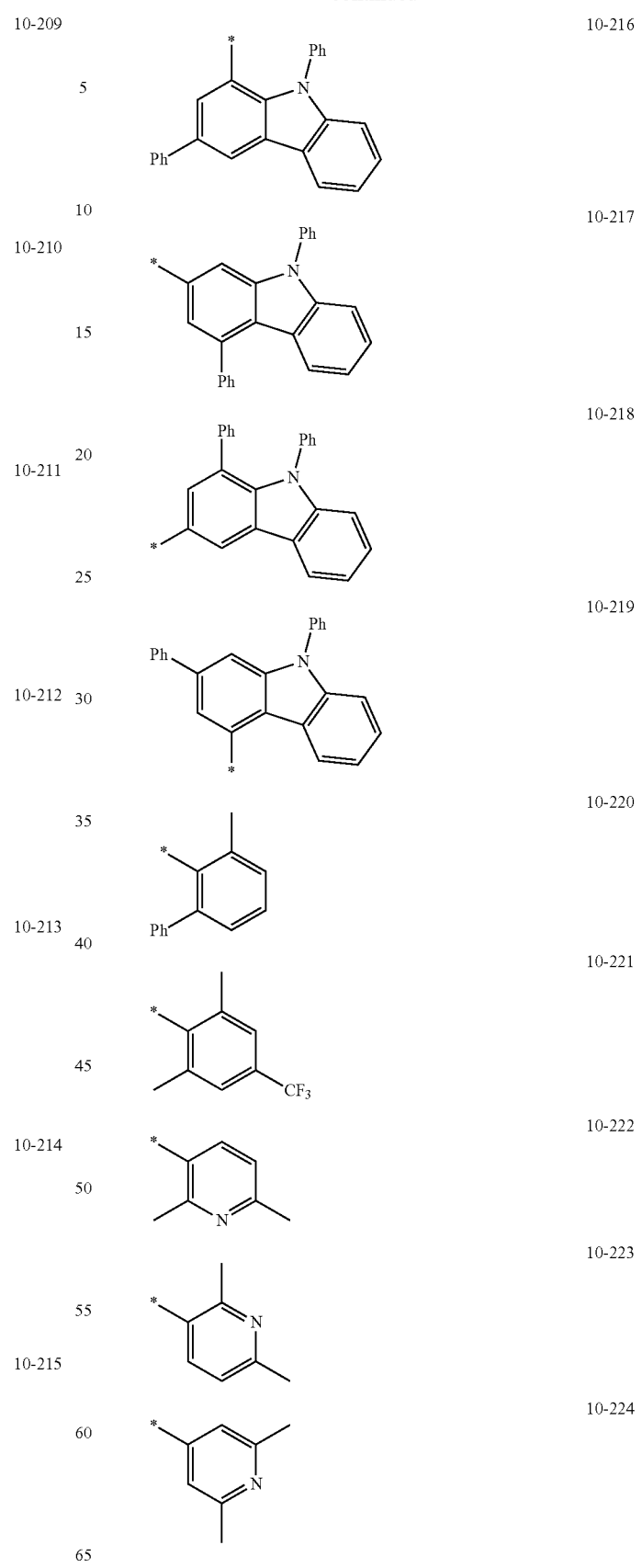

10-225

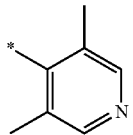

10-226

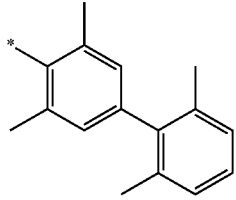

In Formulae 9-1 to 9-27 and 10-1 to 10-226,
* indicates a binding site to a neighboring atom,
i-Pr indicates an isopropyl group,
t-Bu indicates a tert-butyl group,
Ph indicates a phenyl group,
1-Nph indicates a 1-naphthyl group and 2-Nph indicates a 2-naphthyl group,
2-Pyr indicates a 2-pyridyl group, 3-Pyr indicates a 3-pyridyl group, and 4-Pyr indicates a 4-pyridyl group, and
$Q_1$ to $Q_3$ may each independently be:
a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a $C_1$-$C_{20}$ alkylphenyl group, or a naphthyl group; or
a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group, each substituted with deuterium, a phenyl group, or a combination thereof.

In one embodiment, $R_{11}$ to $R_{16}$ in Formulae 1-1 and 1-2 may each independently be hydrogen, deuterium, —F, a nitro group, —$CH_3$, —$CD_3$, —$CD_2H$, —$CDH_2$, —$CF_3$, —$CF_2H$, —$CFH_2$, groups represented by Formulae 9-1 to 9-15, or groups represented by Formulae 9-1 to 9-15 of which a hydrogen is substituted with deuterium, but embodiments of the present disclosure are not limited thereto.

In Formulae 2-1 to 2-3 and 3-1 to 3-3,
$R_{21}$ and $R_{31}$ may each independently be hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, or —$B(Q_6)(Q_7)$, and
$Q_1$ to $Q_7$ may each independently be hydrogen, $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

In an exemplary embodiment, in Formulae 2-1 to 2-3 and 3-1 to 3-3, $R_{21}$ and $R_{31}$ may each independently be:
hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;
a $C_1$-$C_{20}$ alkyl group or a $C_1$-$C_{20}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a pyridinyl group, a pyrimidinyl group, or a combination thereof;
a cyclopentyl group, a cyclohexyl group, a cycloheptyl group, a cyclooctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, a bicyclo[2.2.1]heptyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si(Q$_{11}$)(Q$_{12}$)(Q$_{13}$), —B(Q$_{11}$)(Q$_{12}$), —N(Q$_{11}$)(Q$_{12}$), or a combination thereof; or —Si(Q$_1$)(Q$_2$)(Q$_3$), —B(Q$_1$)(Q$_2$), or —N(Q$_1$)(Q$_2$), and Q$_1$ to Q$_3$ and Q$_{11}$ to Q$_{13}$ may each independently be:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a $C_1$-$C_{20}$ alkylphenyl group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group, each substituted with deuterium, a phenyl group, or a combination thereof, but embodiments of the present disclosure are not limited thereto.

In one embodiment, R$_{21}$ and R$_{31}$ in Formulae 2-1 to 2-3 and 3-1 to 3-3 may each independently be hydrogen, deuterium, —F, a nitro group, —CH$_3$, —CD$_3$, —CD$_2$H, —CDH$_2$, —CF$_3$, —CF$_2$H, —CFH$_2$, groups represented by Formulae 9-1 to 9-27, groups represented by Formulae 9-1 to 9-27 of which a hydrogen is substituted with deuterium, groups represented by Formulae 10-1 to 10-226, —Si(Q$_1$)(Q$_2$)(Q$_3$), —B(Q$_1$)(Q$_2$), or —N(Q$_1$)(Q$_2$), but embodiments of the present disclosure are not limited thereto.

In one embodiment, R$_{21}$ and R$_{31}$ in Formulae 2-1 to 2-3 and 3-1 to 3-3 may each independently be hydrogen, deuterium, —F, a nitro group, —CH$_3$, —CD$_3$, —CD$_2$H, —CDH$_2$, —CF$_3$, —CF$_2$H, —CFH$_2$, groups represented by Formulae 9-1 to 9-15, or groups represented by Formulae 9-1 to 9-15 of which a hydrogen is substituted with deuterium, but embodiments of the present disclosure are not limited thereto.

In one embodiment, the condensed cyclic compound may include one, two, or three cyano groups, but embodiments of the present disclosure are not limited thereto.

In one embodiment, the condensed cyclic compound may be of Group I, but embodiments of the present disclosure are not limited thereto:

Group I

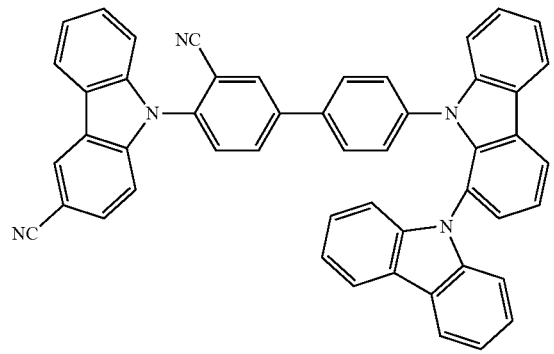

1

-continued
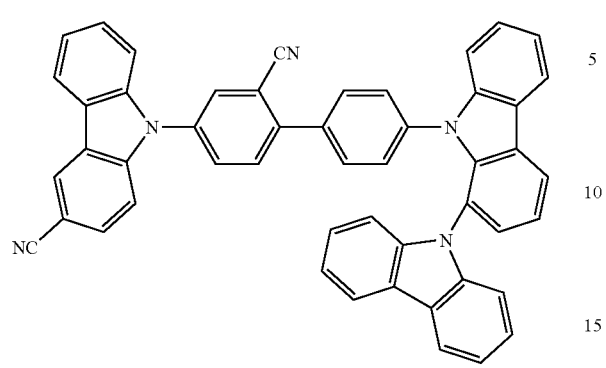
2
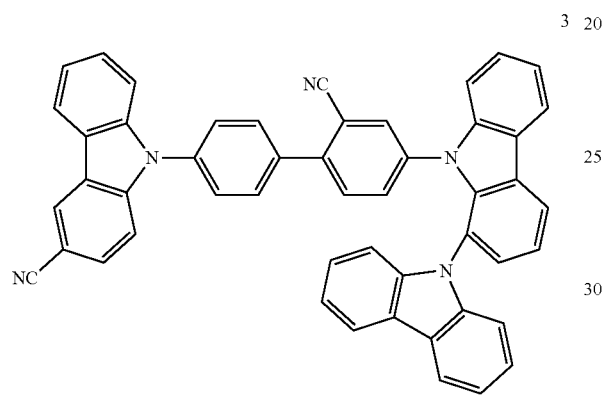
3
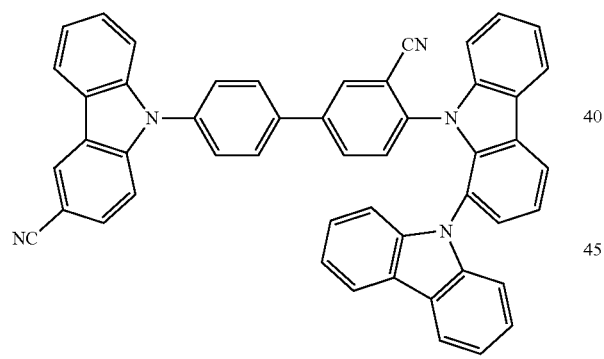
4
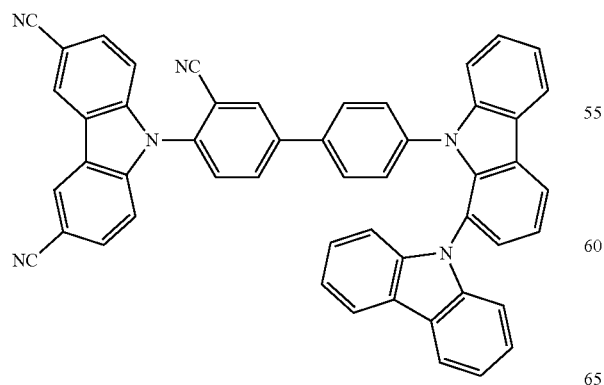
5
-continued
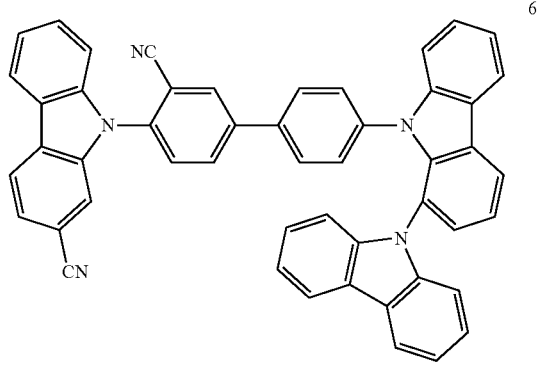
6
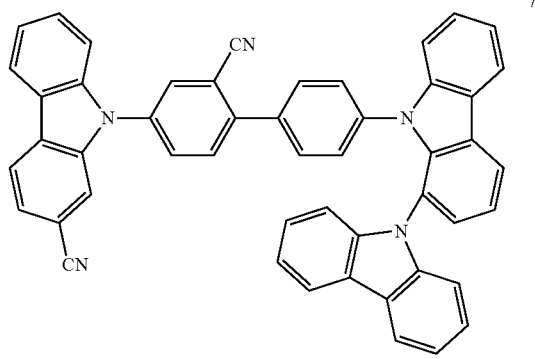
7
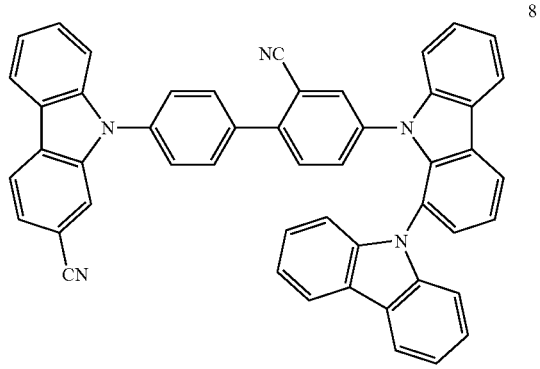
8
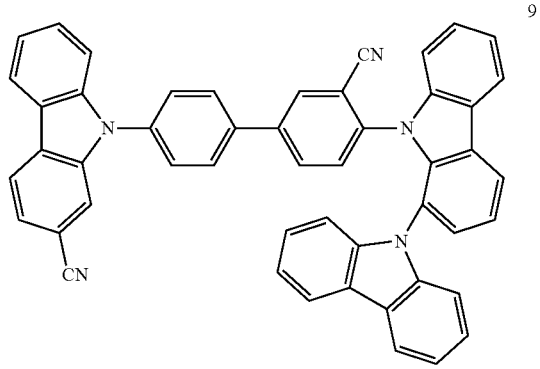
9

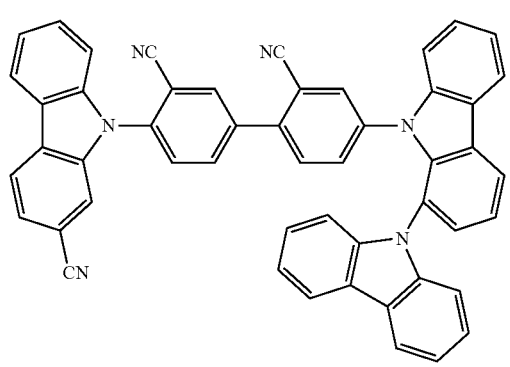
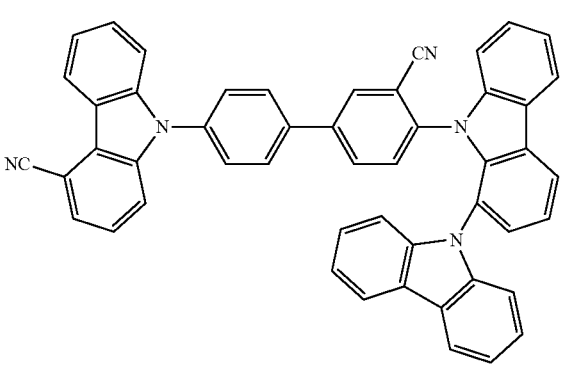

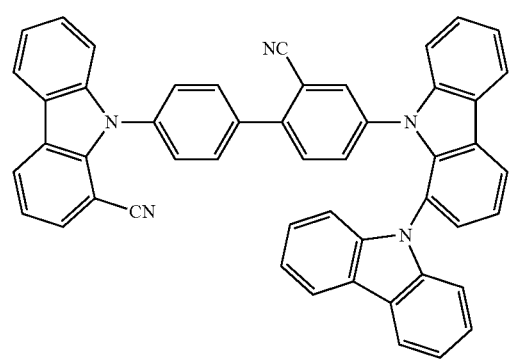
18
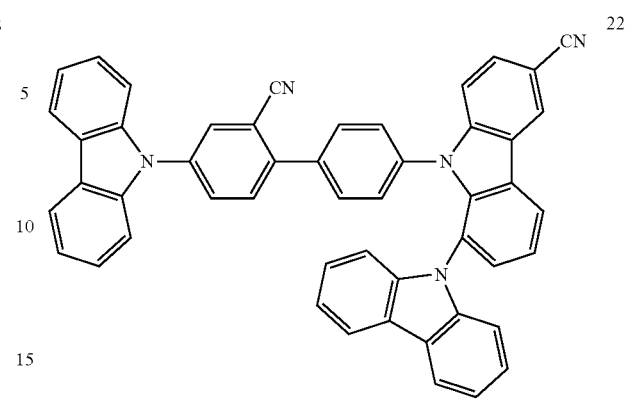
22
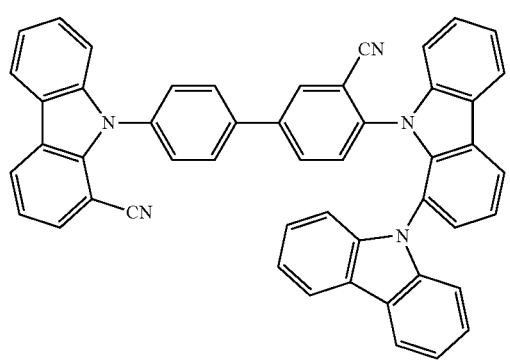
19
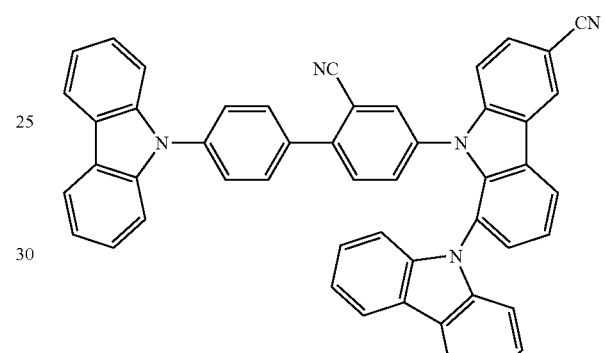
23
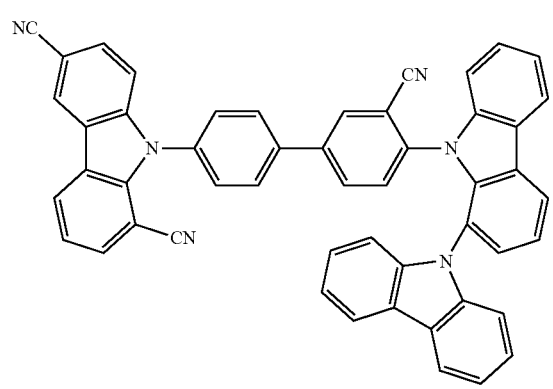
20
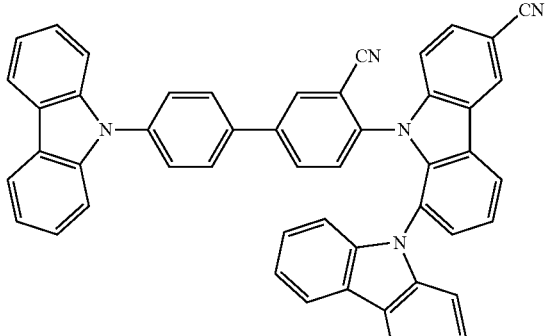
24
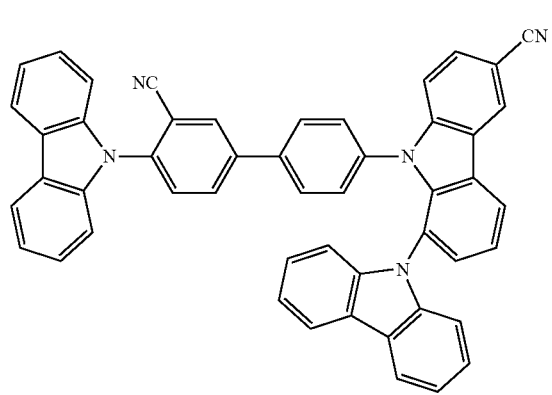
21
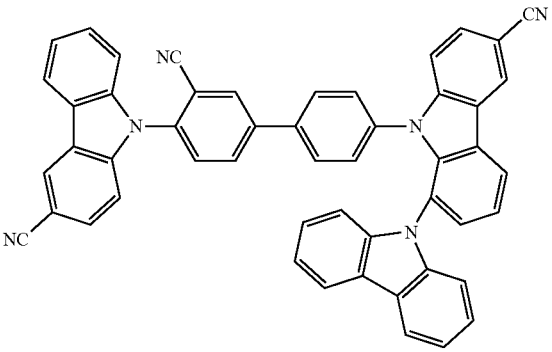
25

26
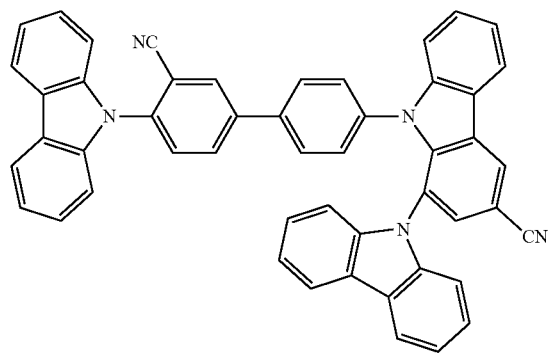
27
30
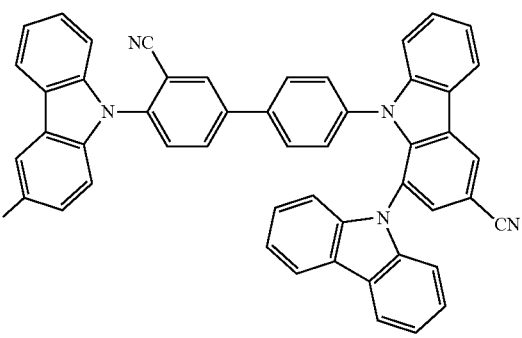
31
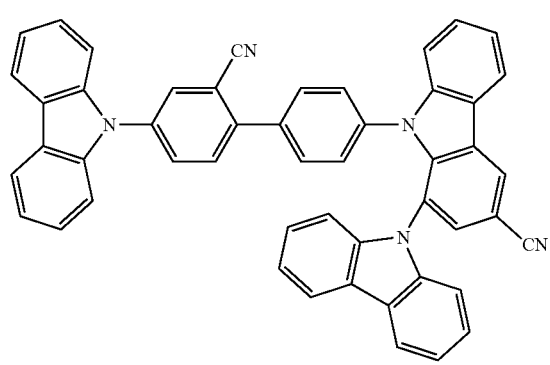
28
32
29
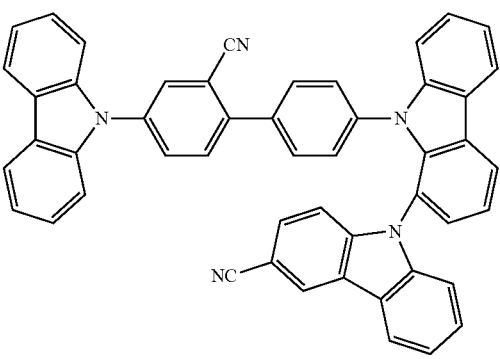
33
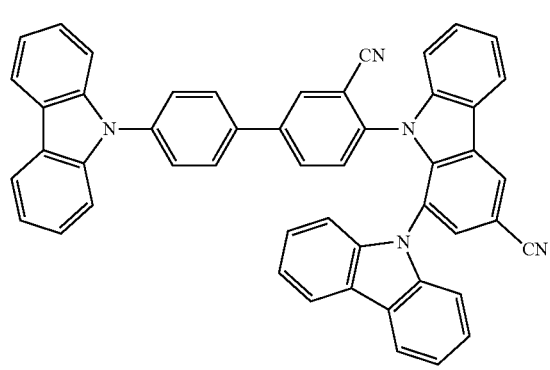
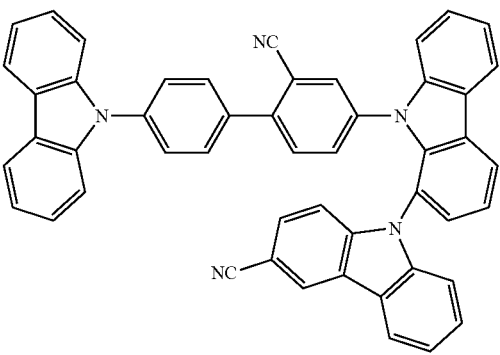

-continued
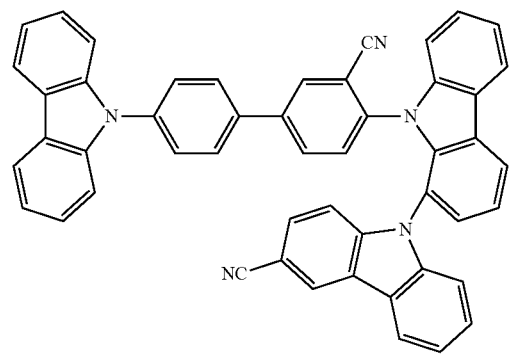
34
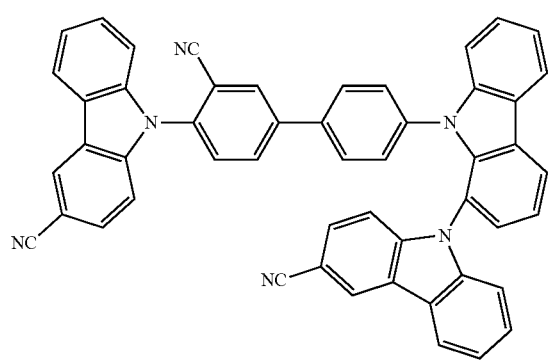
35
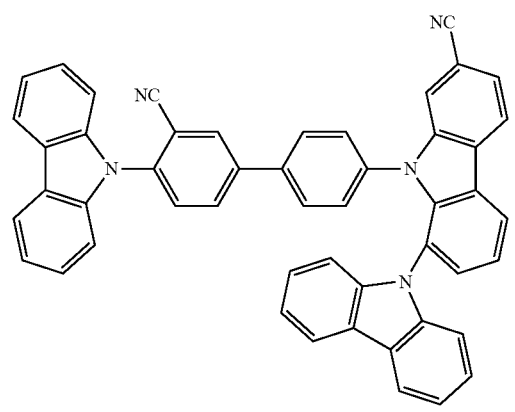
36
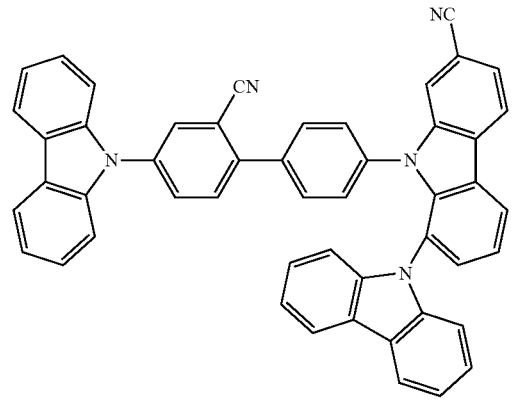
37
-continued
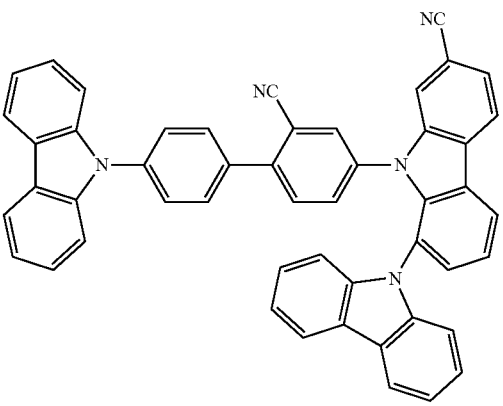
38
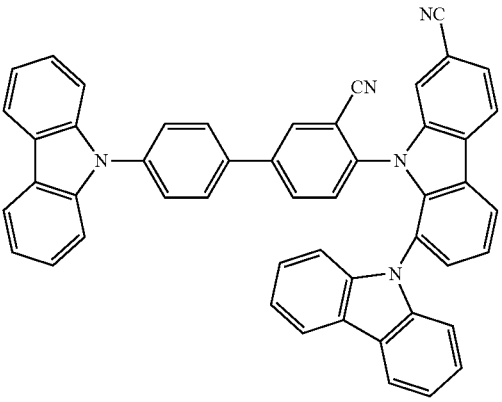
39
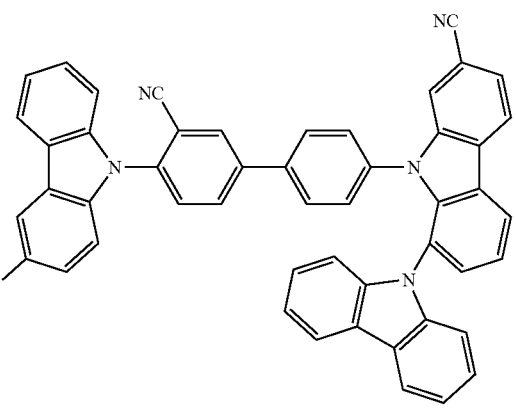
40
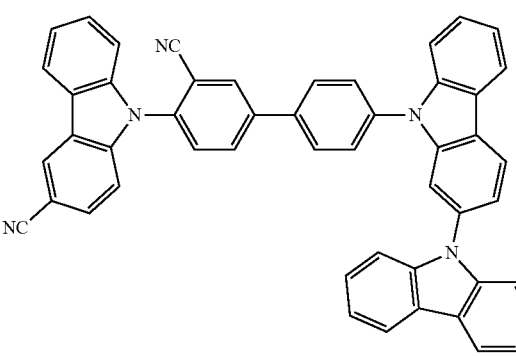
41

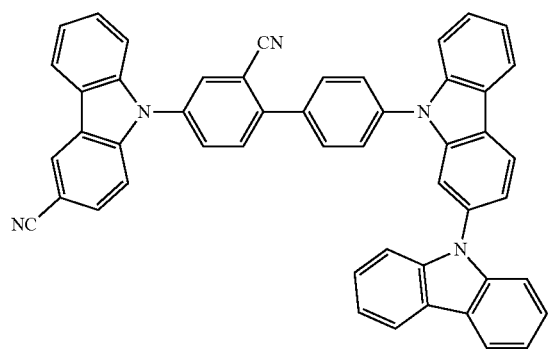
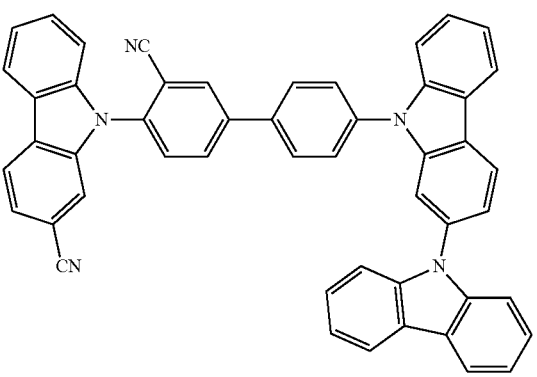
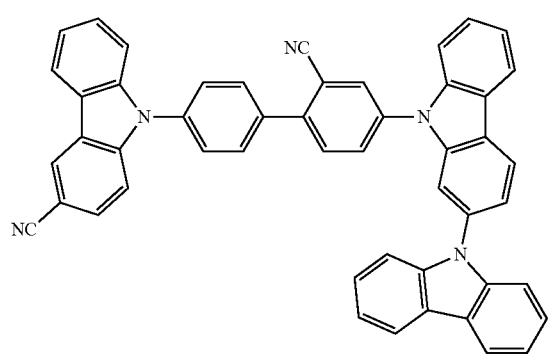

75
-continued
50
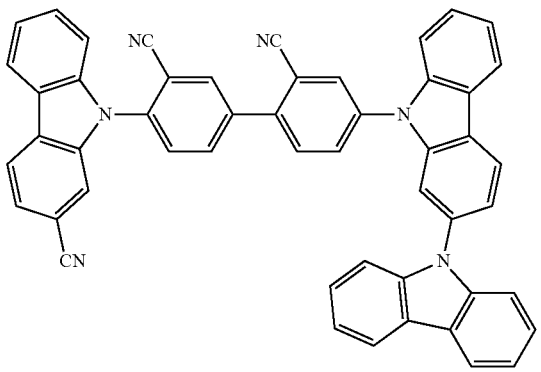
51
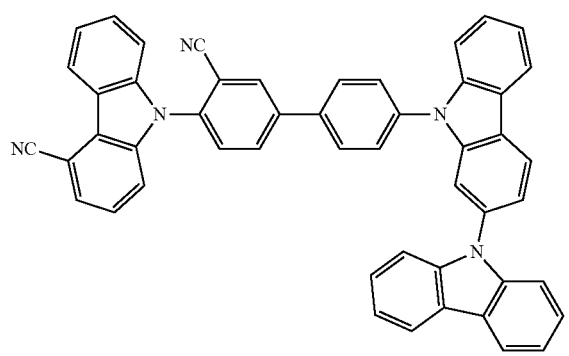
52
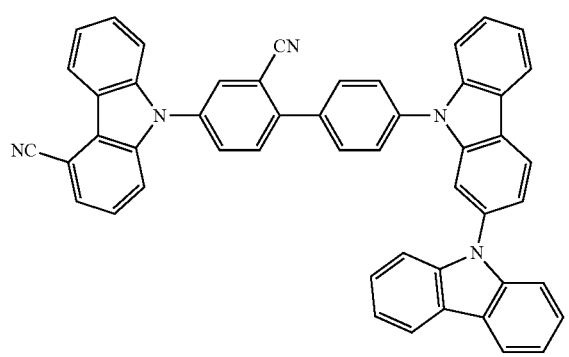
53
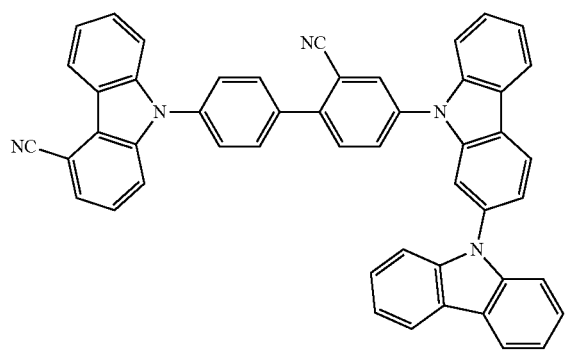
76
-continued
54
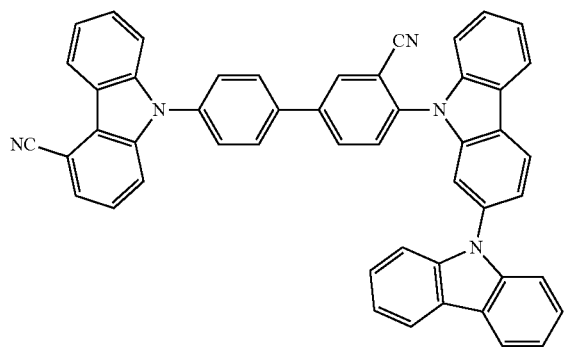
55
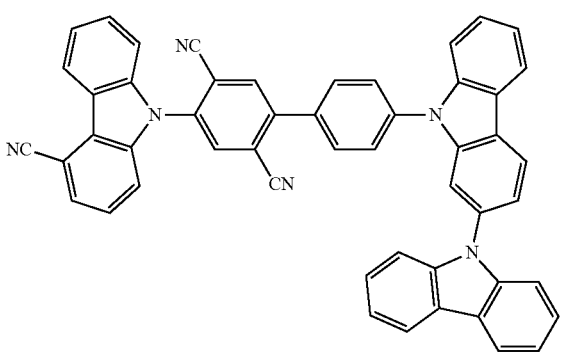
56
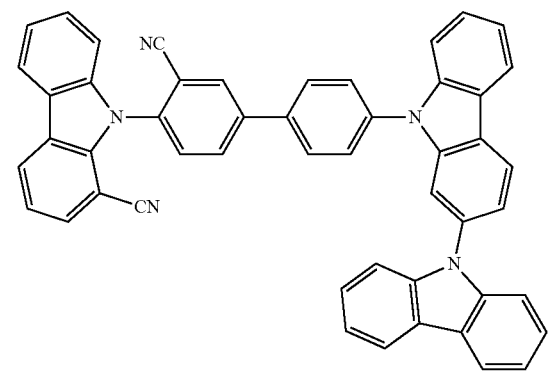
57
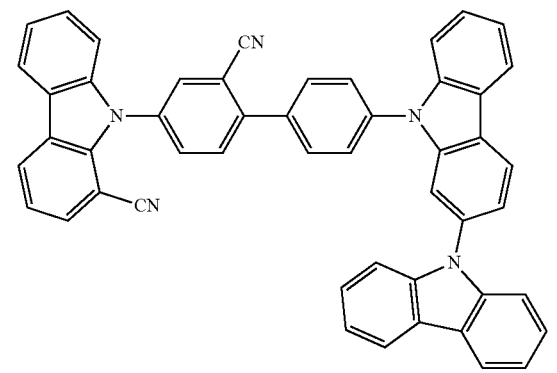

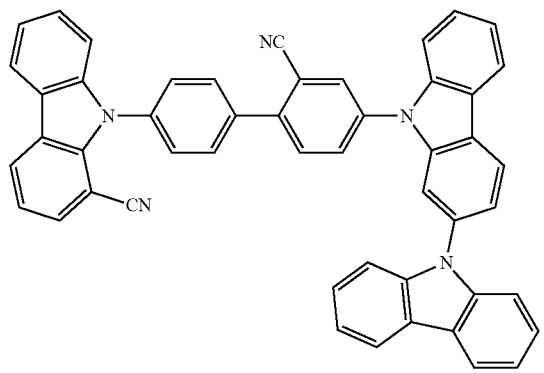
58
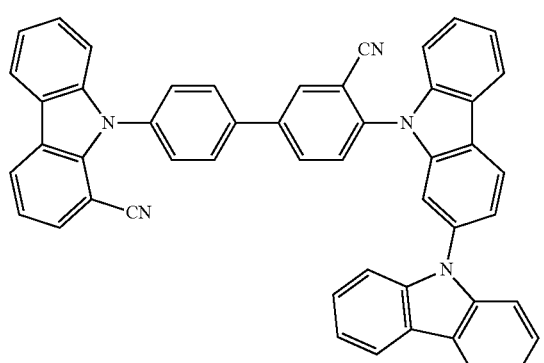
59
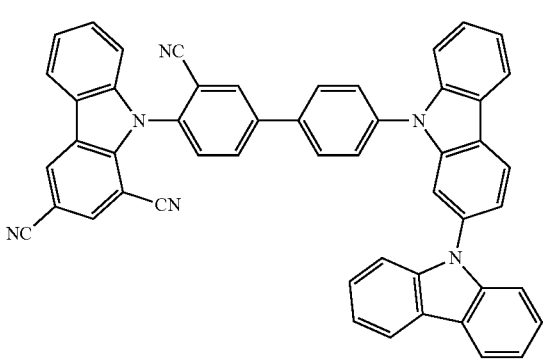
60
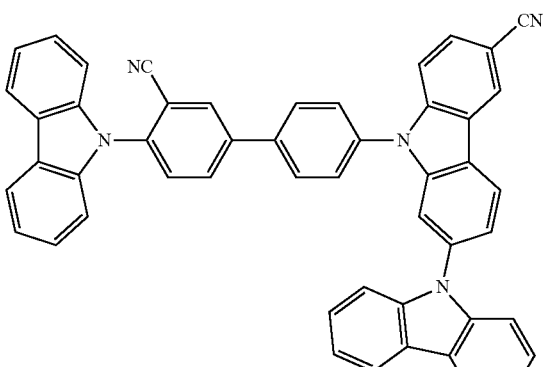
61
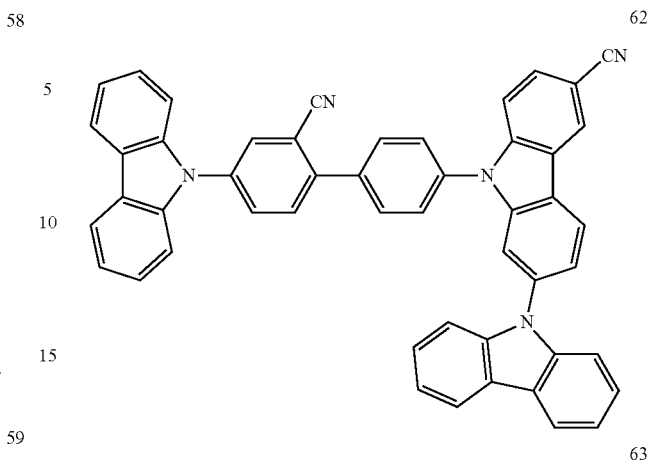

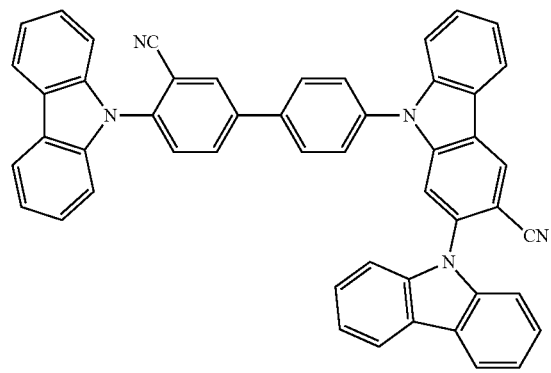
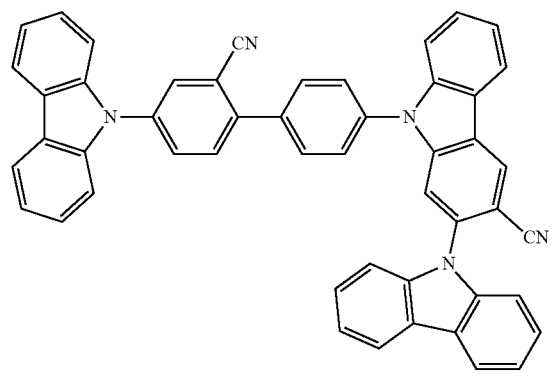
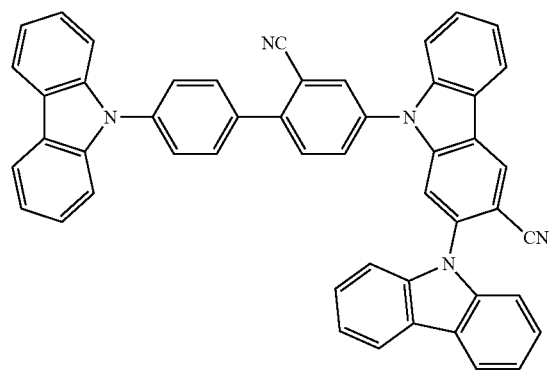
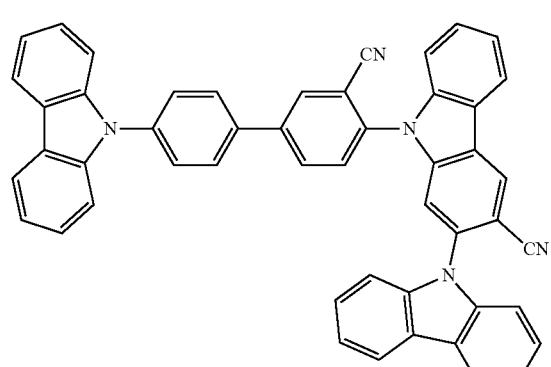
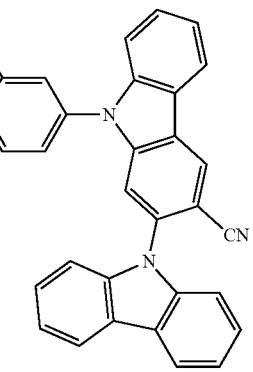
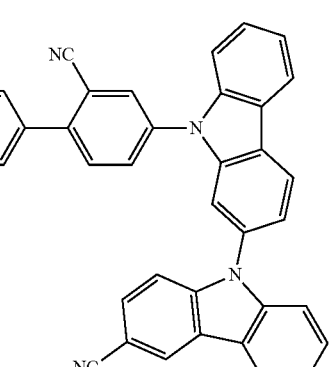

-continued
74
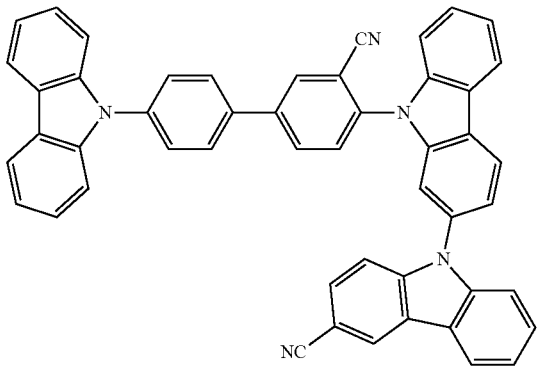
75
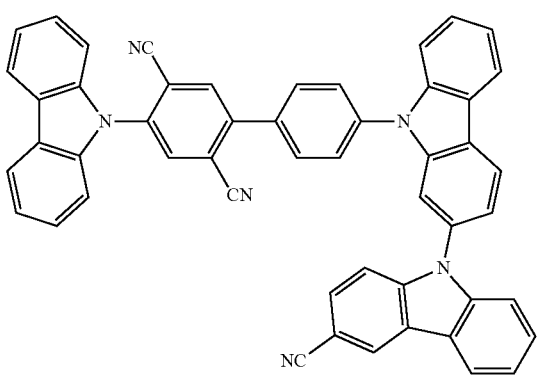
76
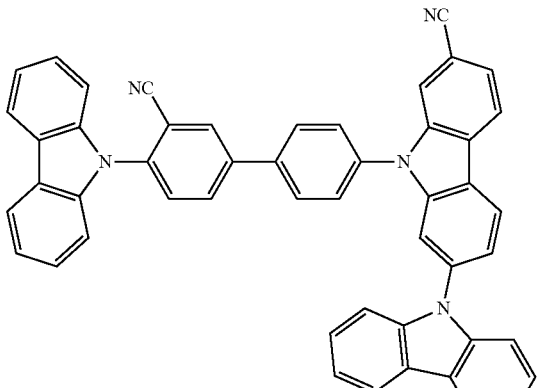
77
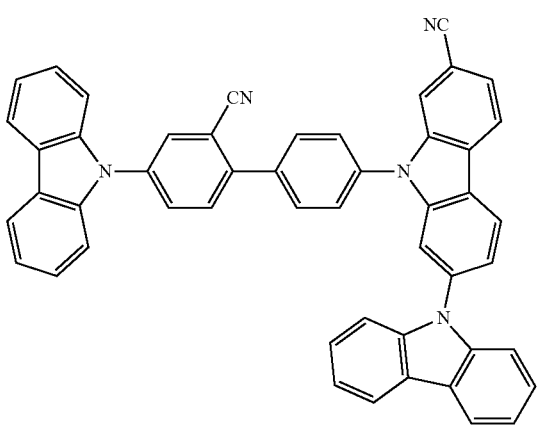
-continued
78
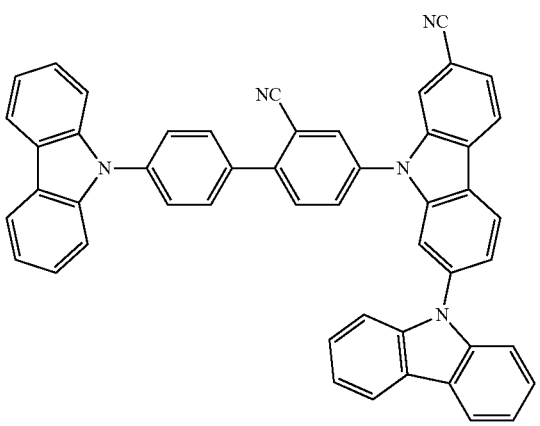
79
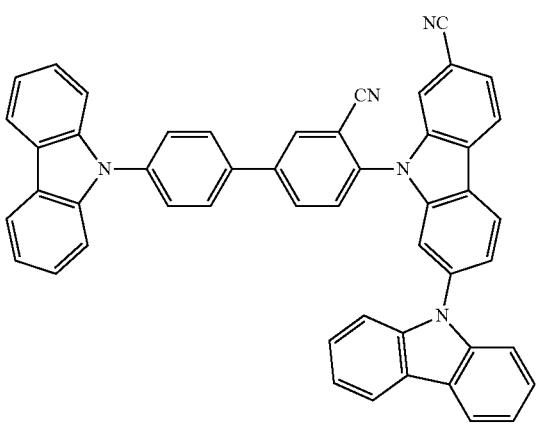
80
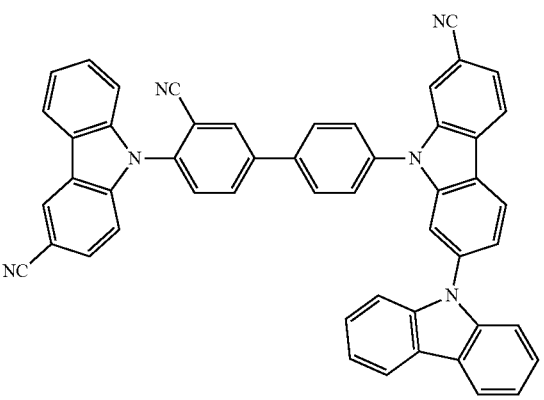
81
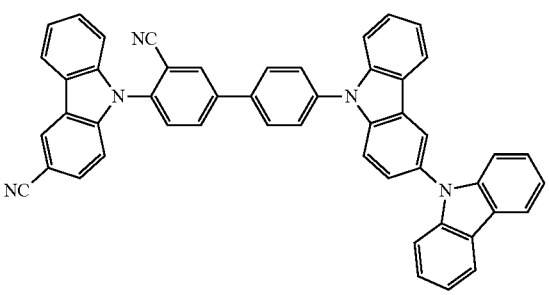

82
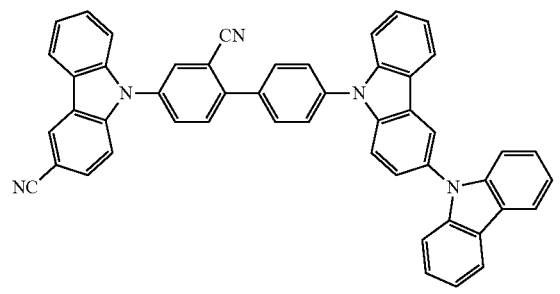
83
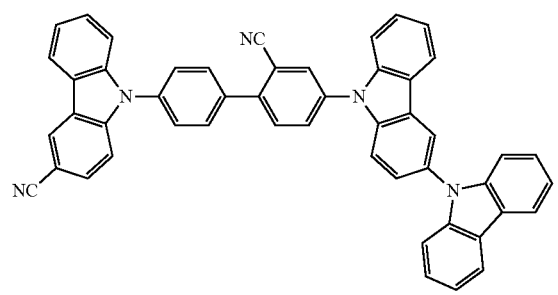
84
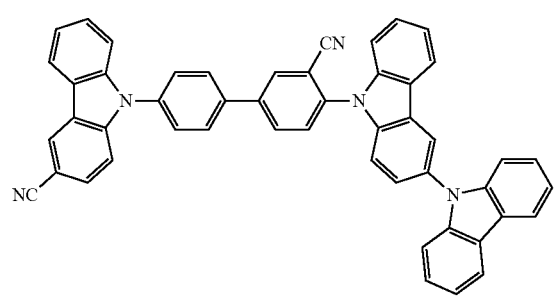
85
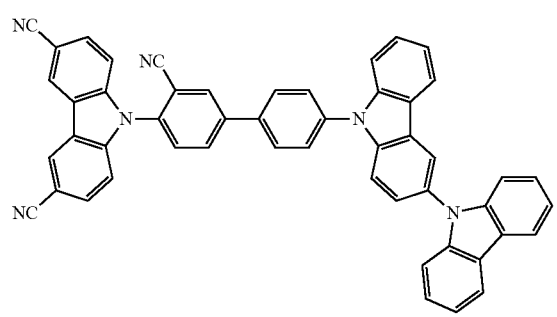
86
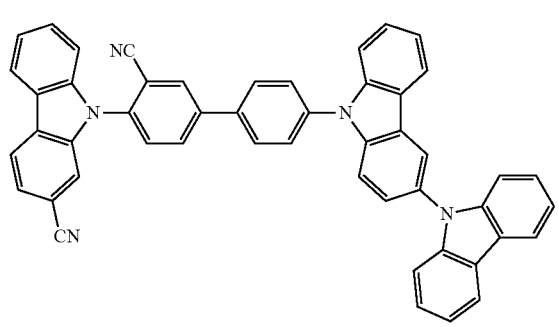
87
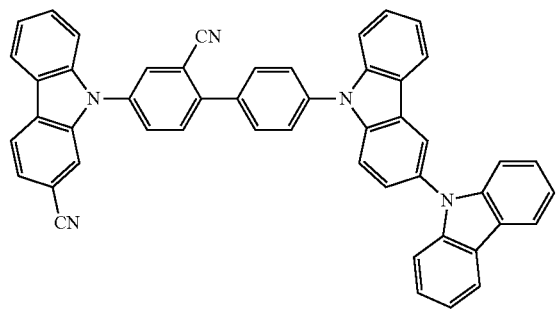
88
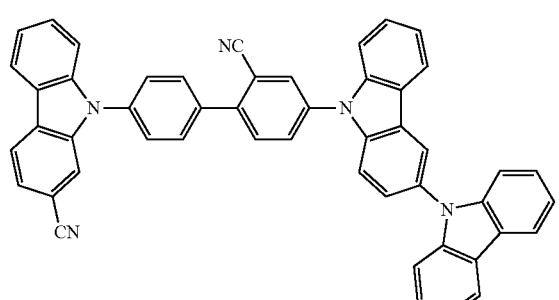
89
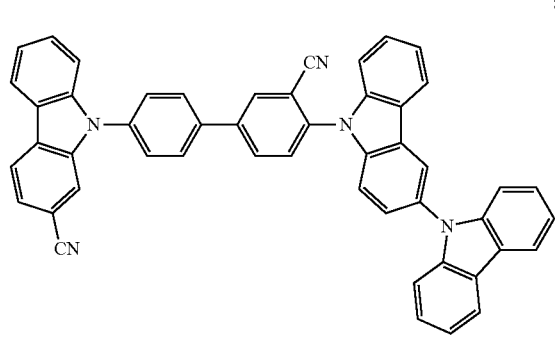
90
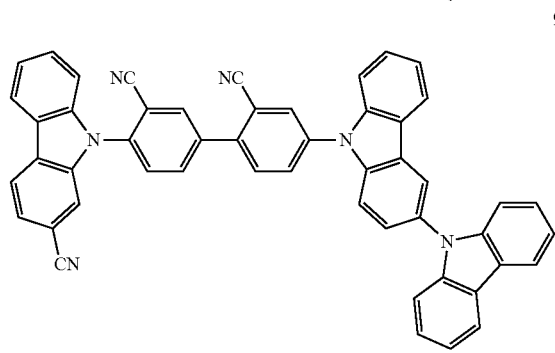
91
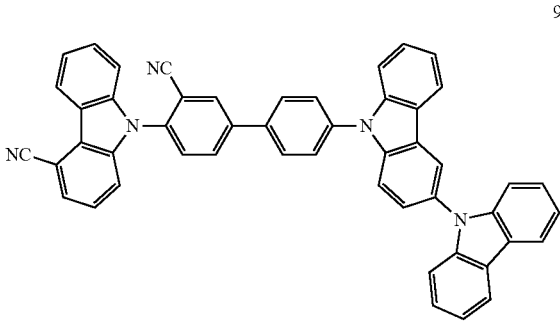

92
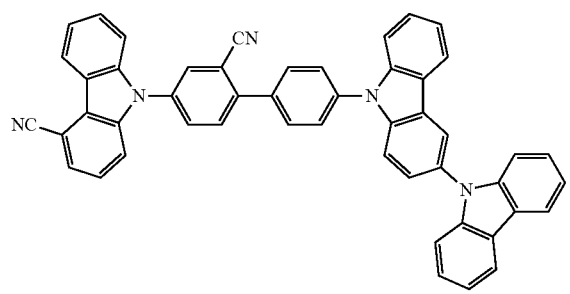
93
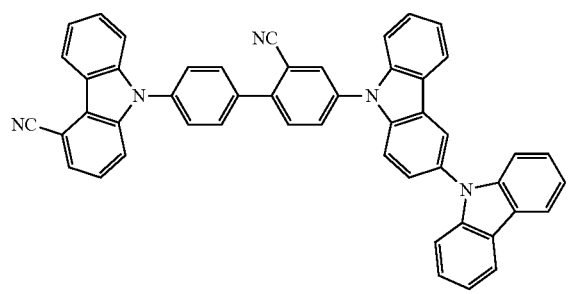
94
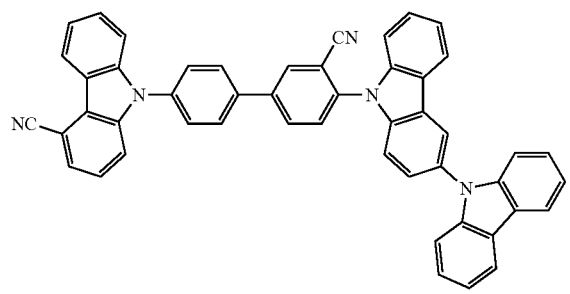
95
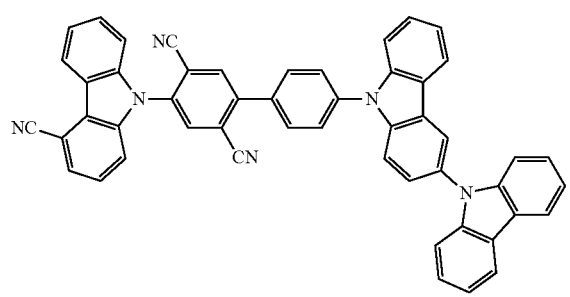
96
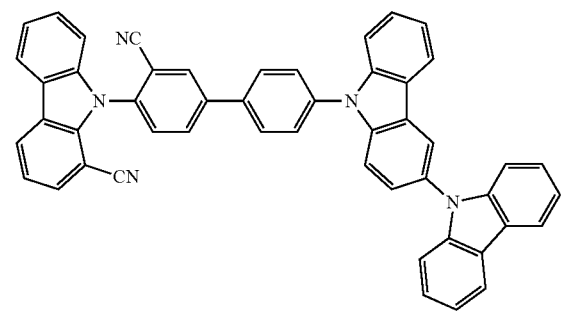
97
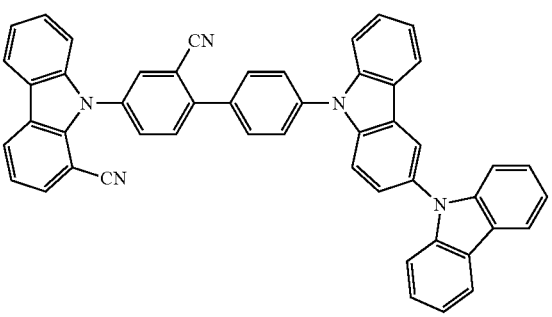
98
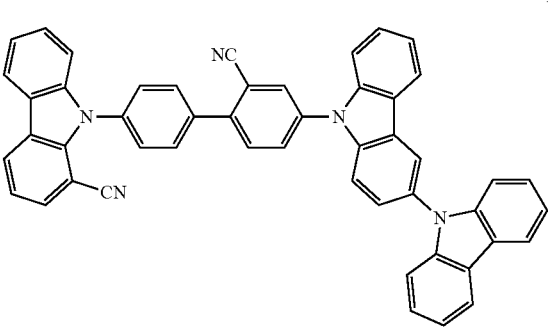
99
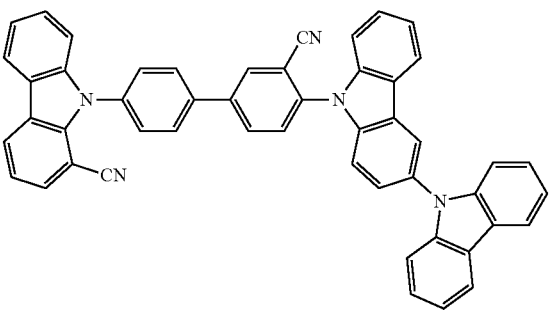
100
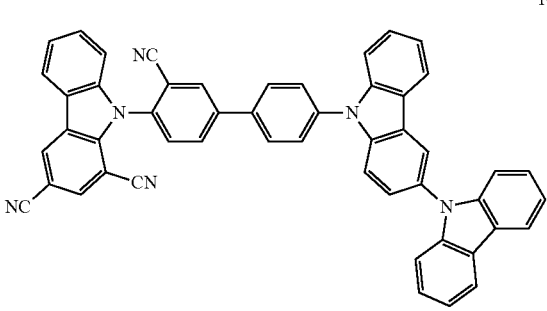

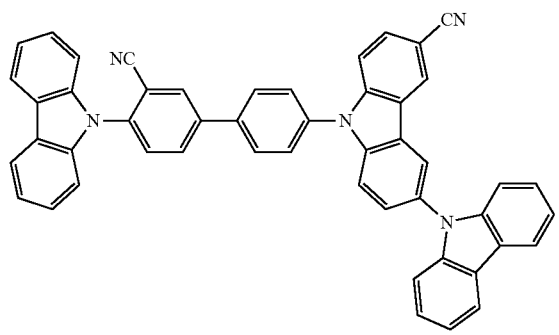
101
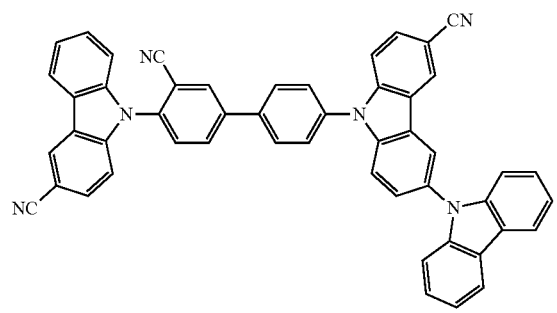
105
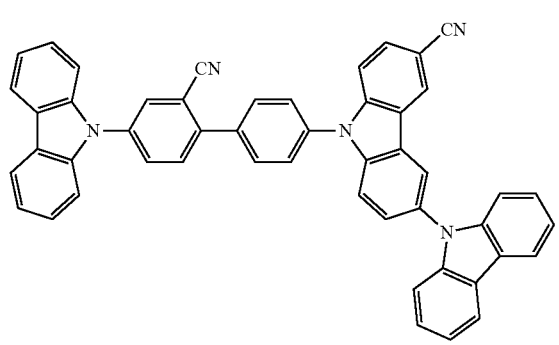
102
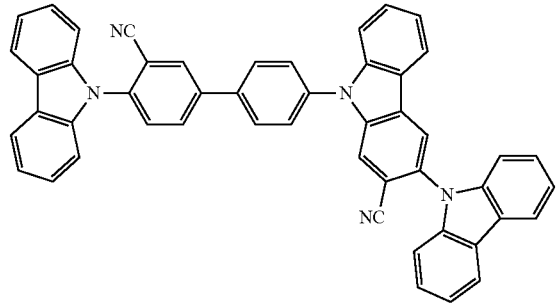
106
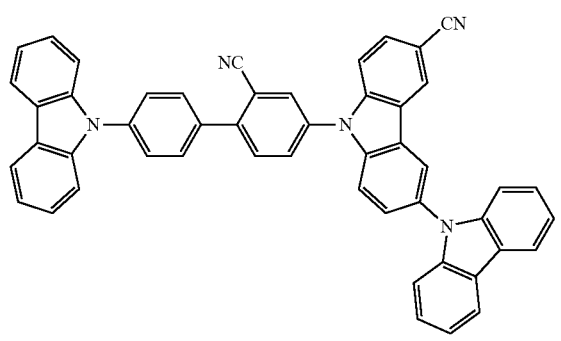
103
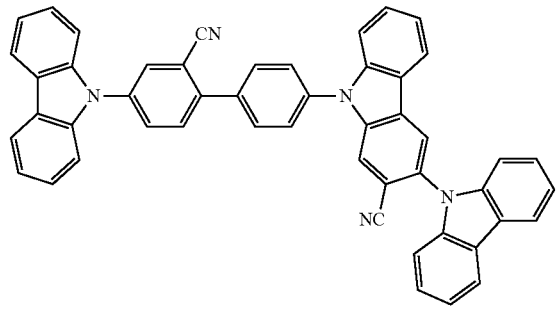
107
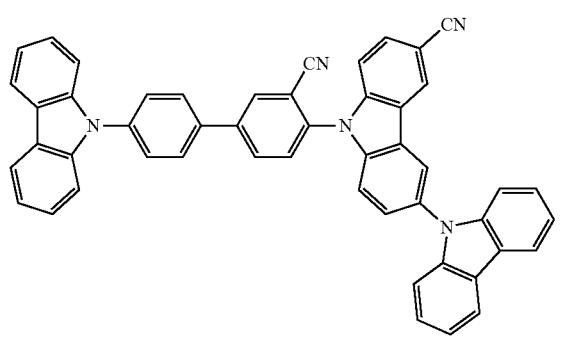
104
108

-continued
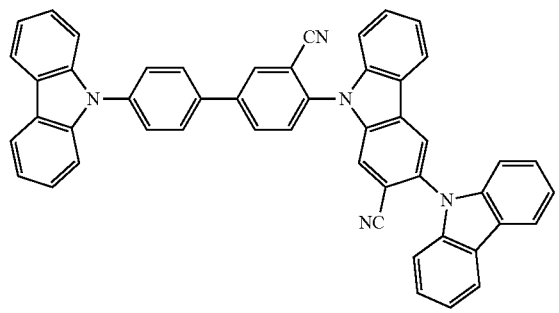
109
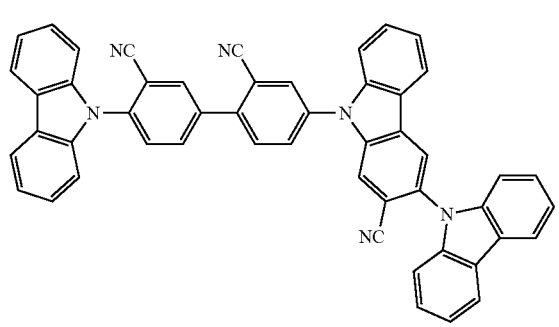
110
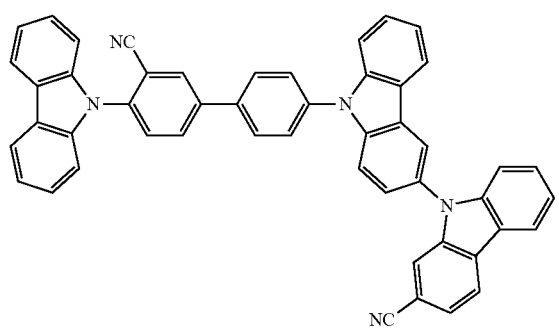
111
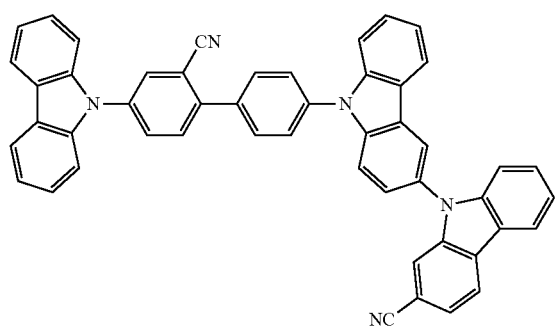
112
-continued
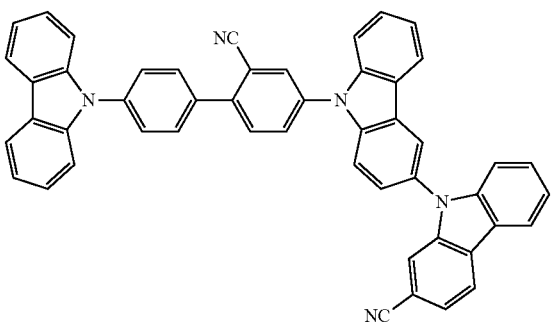
113
114
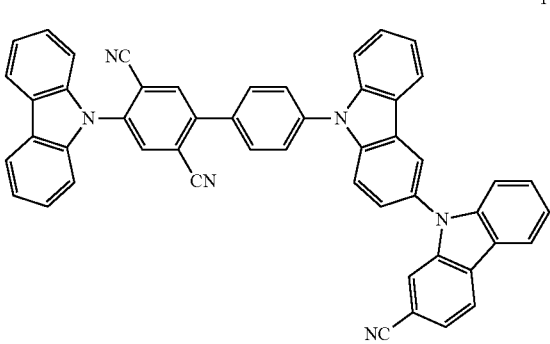
115
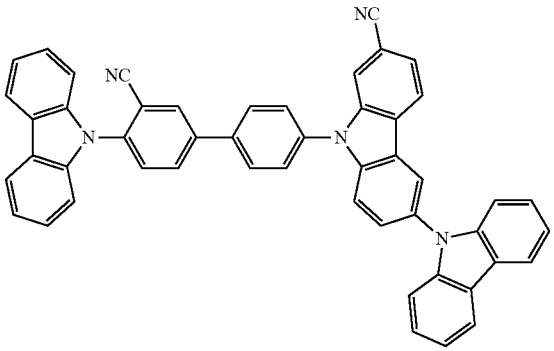
116

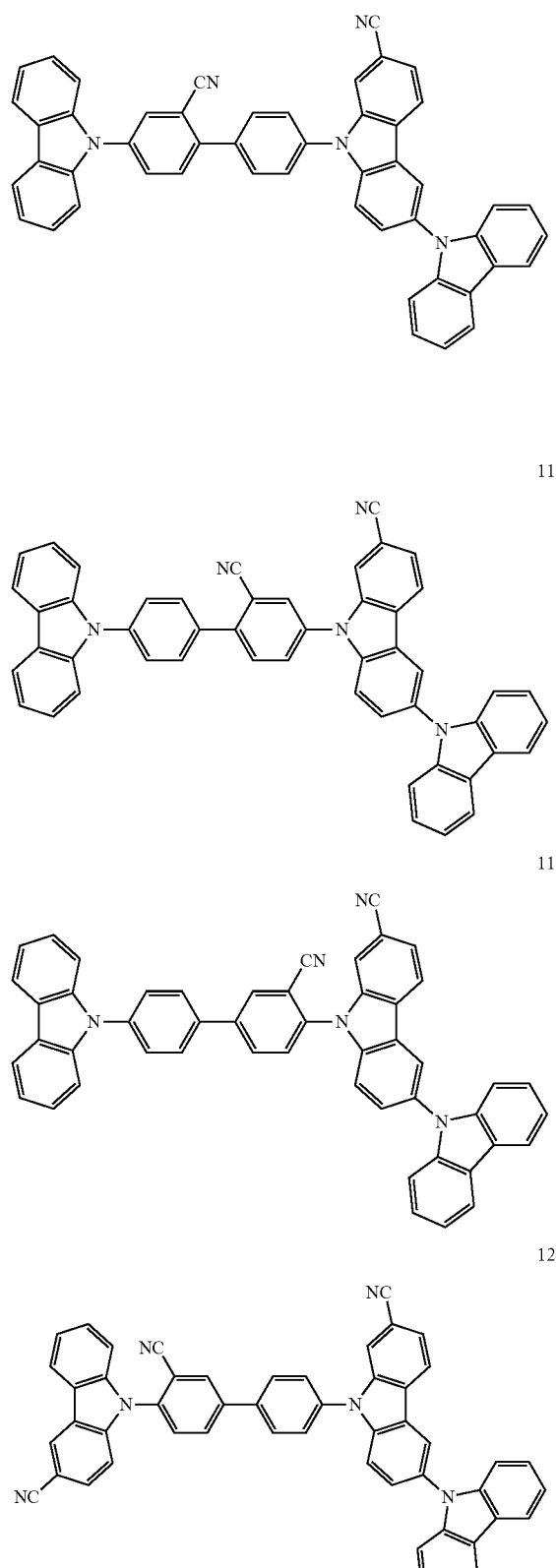
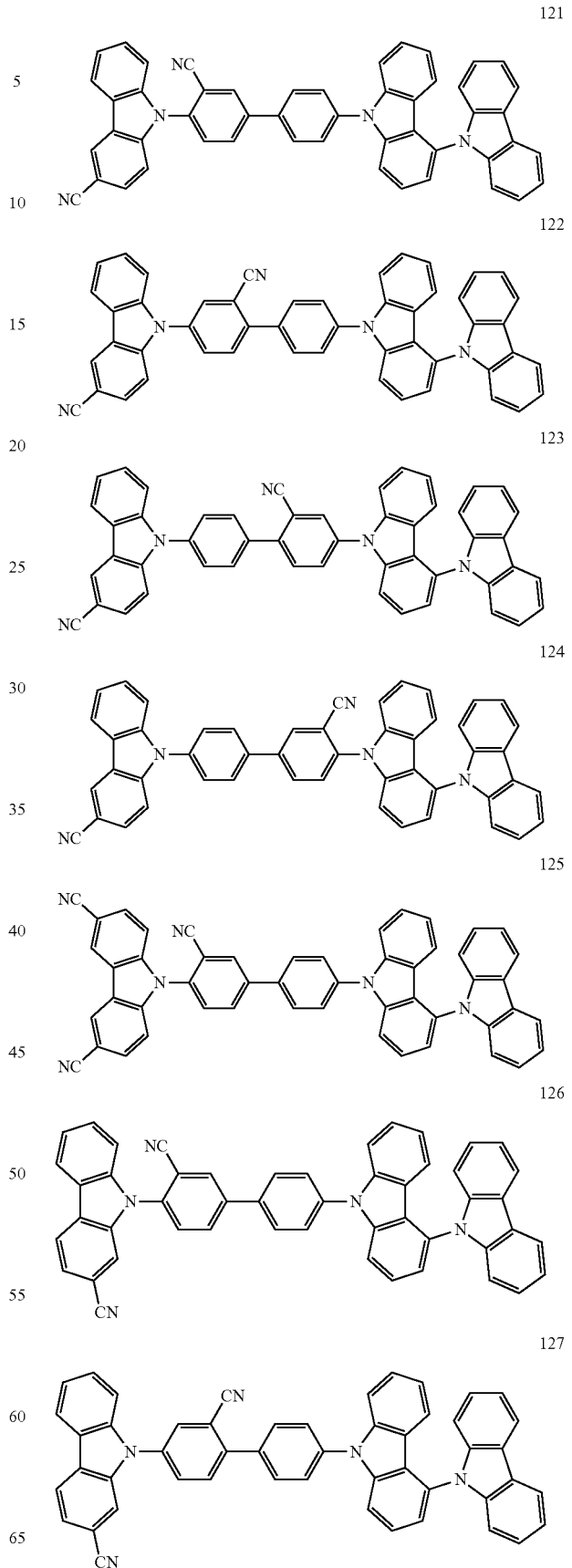

-continued
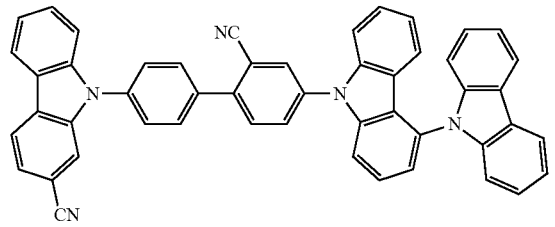
128
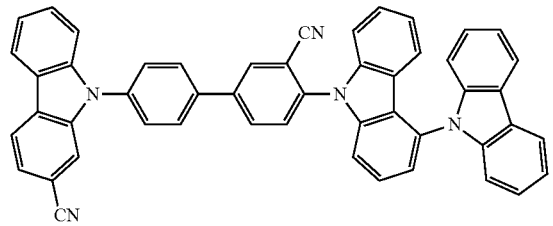
129
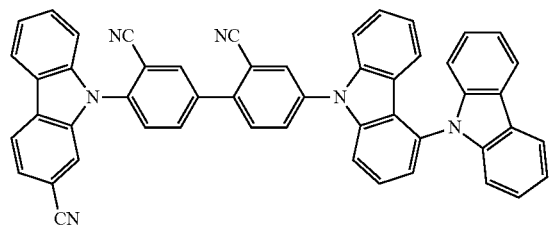
130
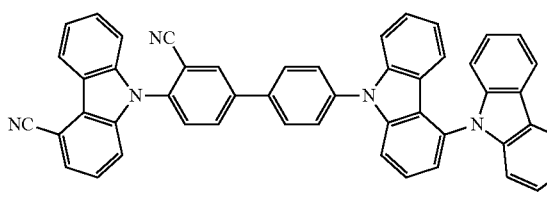
131
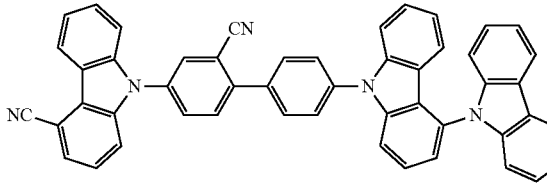
132
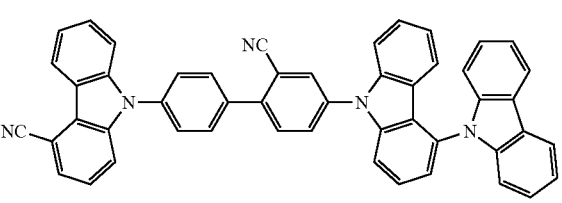
133
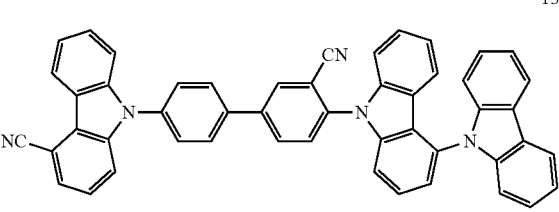
134
-continued
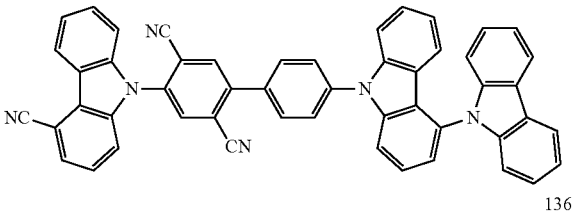
135
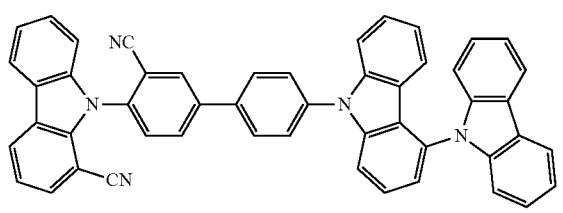
136
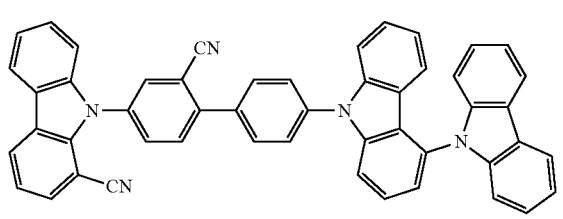
137
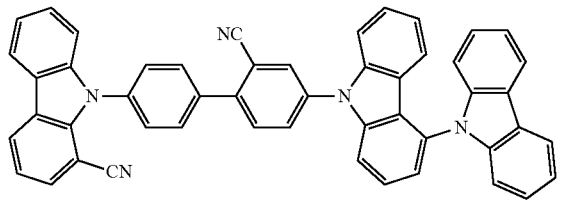
138
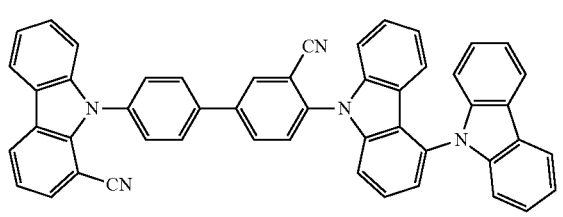
139
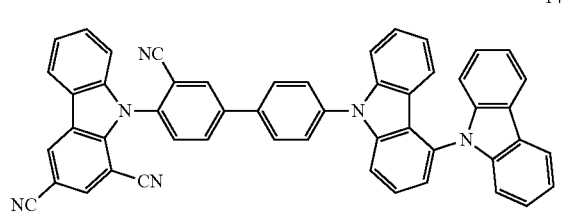
140
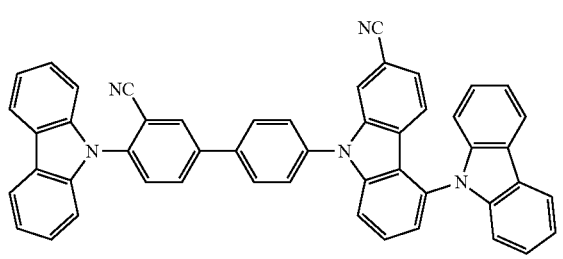
141

142
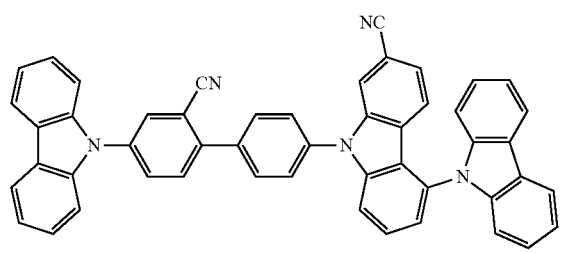
143
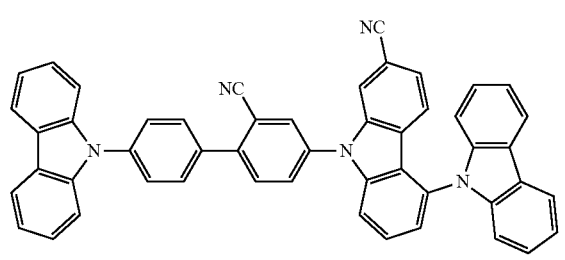
144
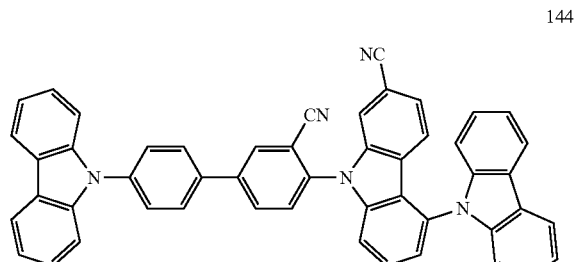
145
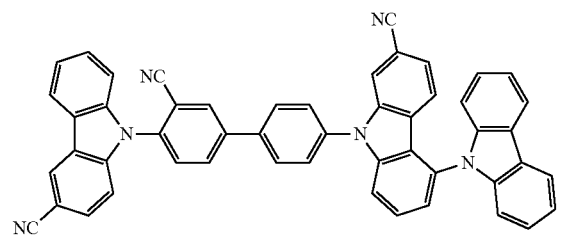
146
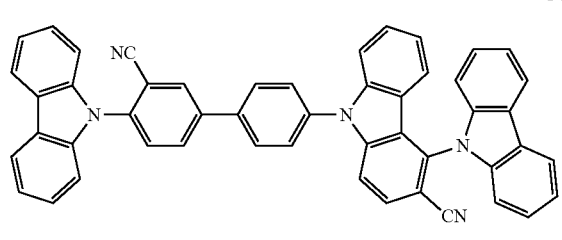
148
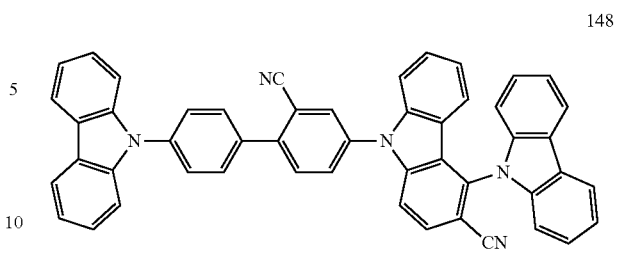
149
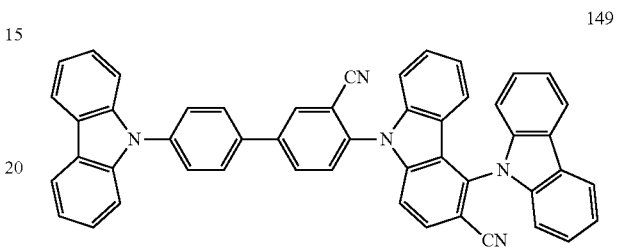
150
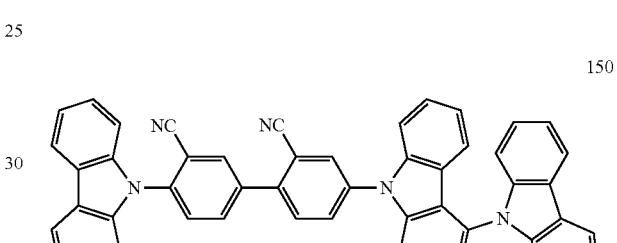
151
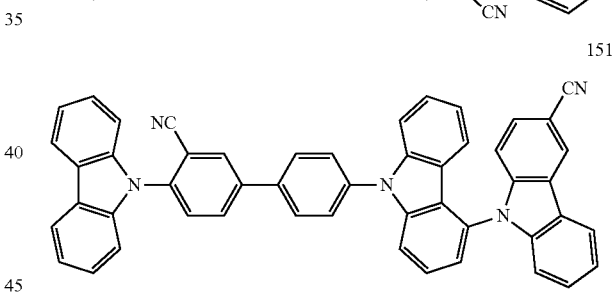
152
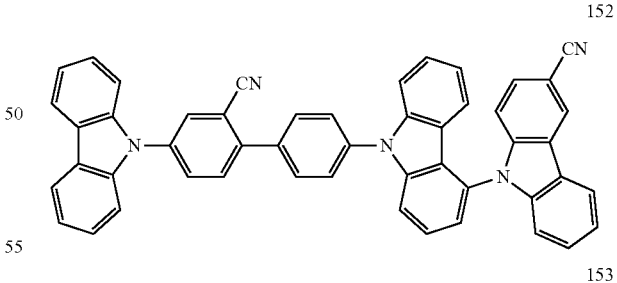
153
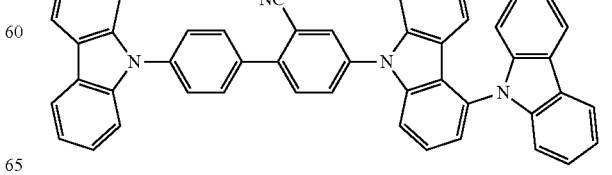

154
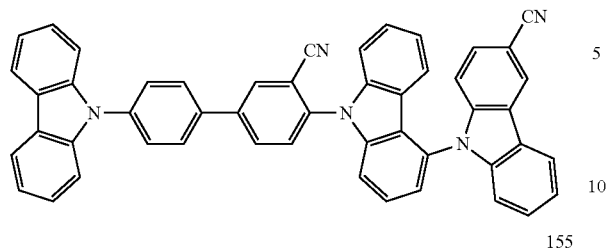
155
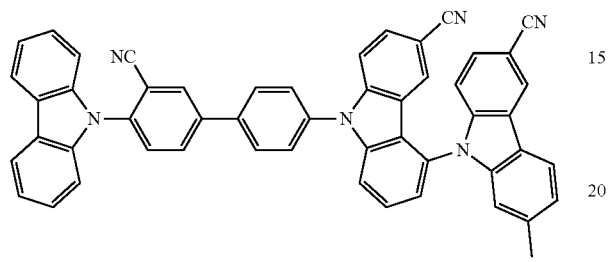
156
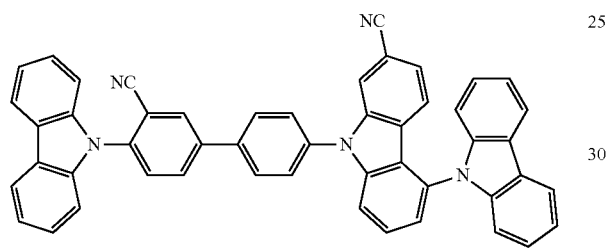
157
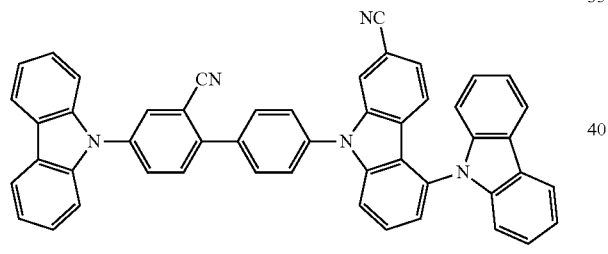
158
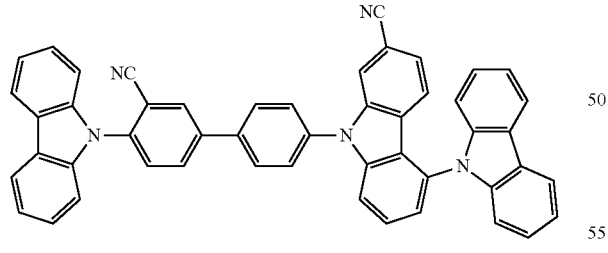
159
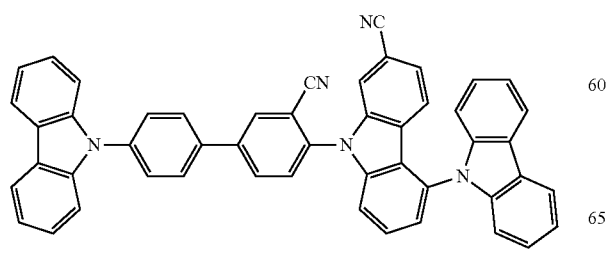
160
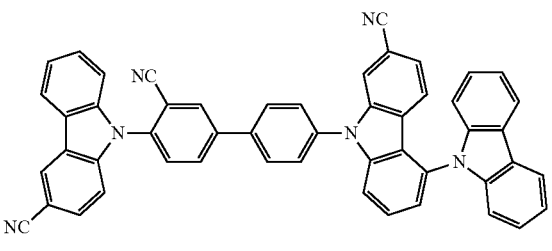
161
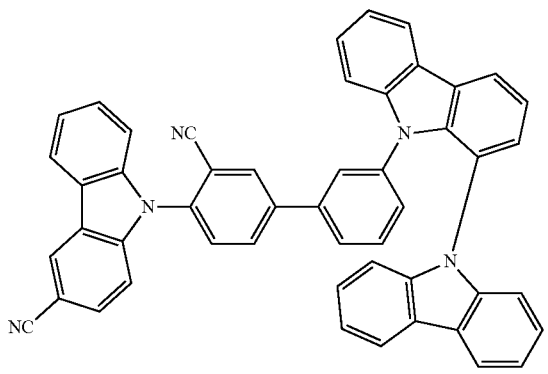
162
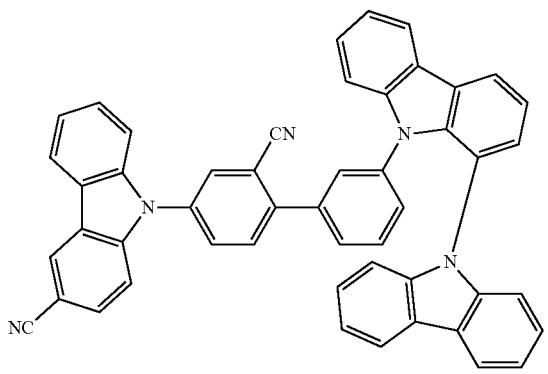
163
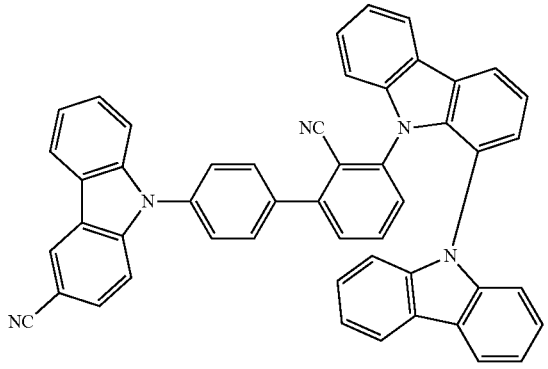

-continued
164
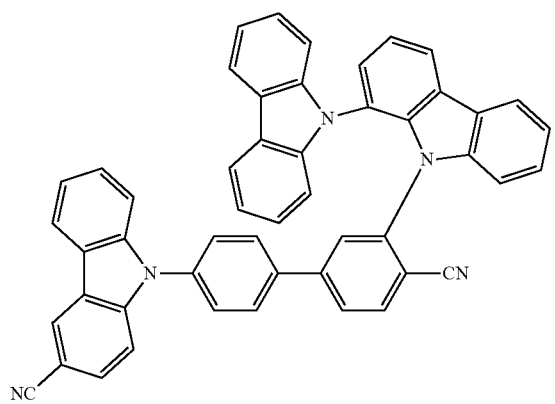
165
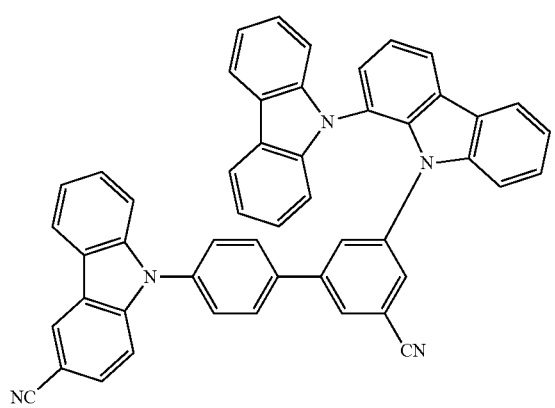
166
167
-continued
168
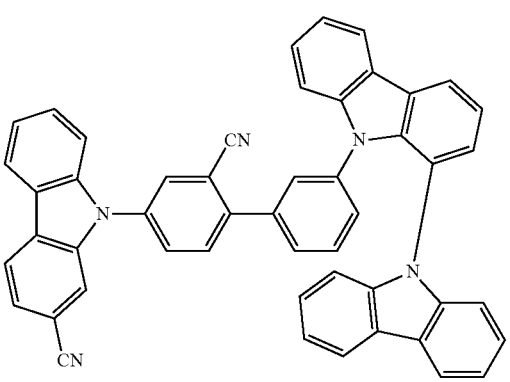
169
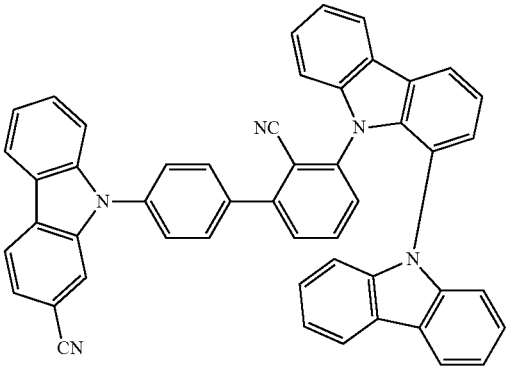
170
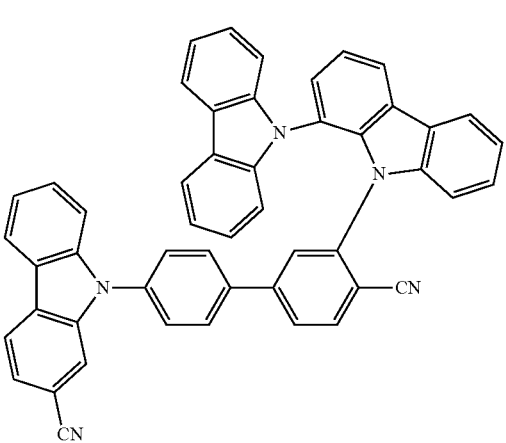

171
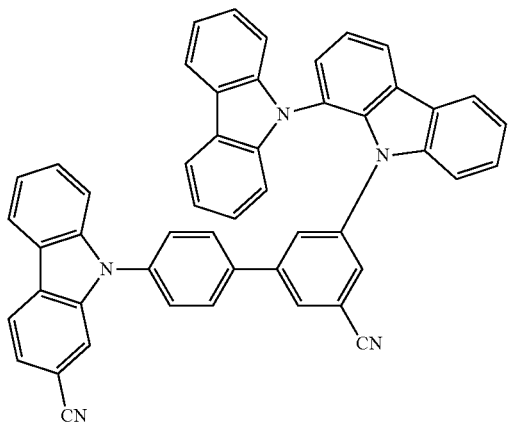
172
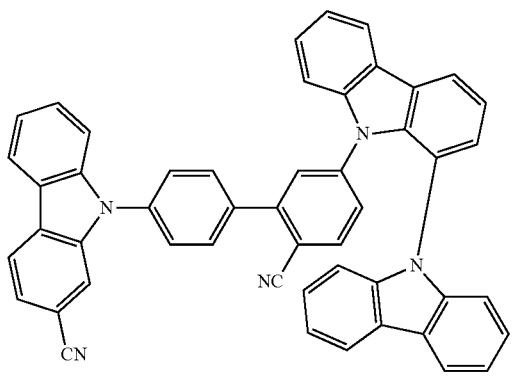
173
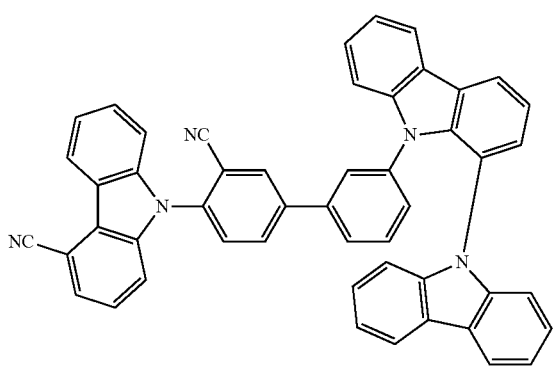
174
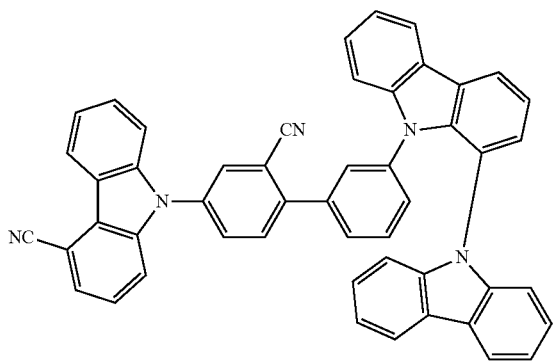
175
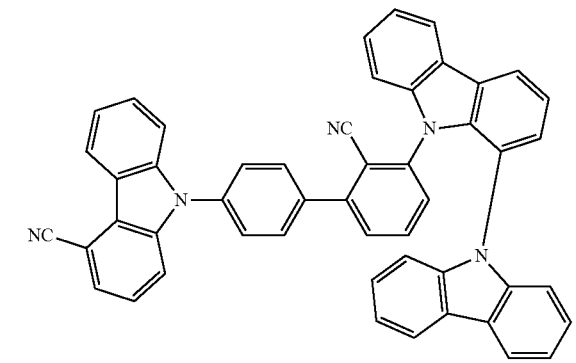
176
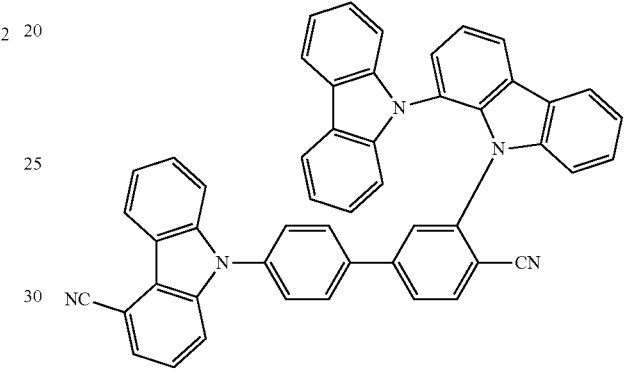
177
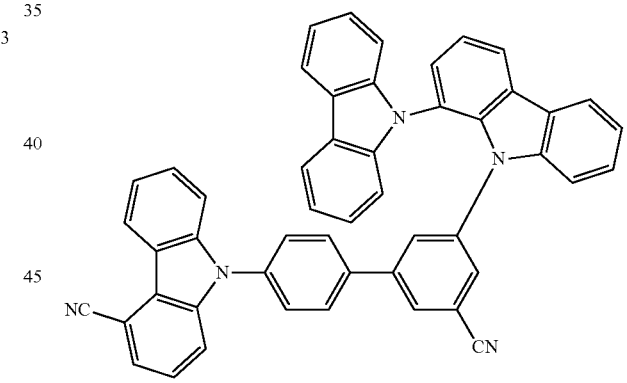
178
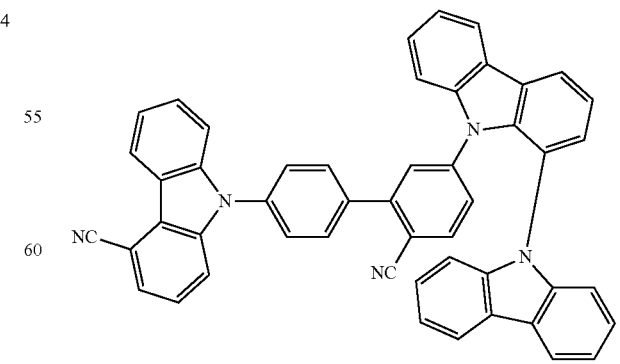

179
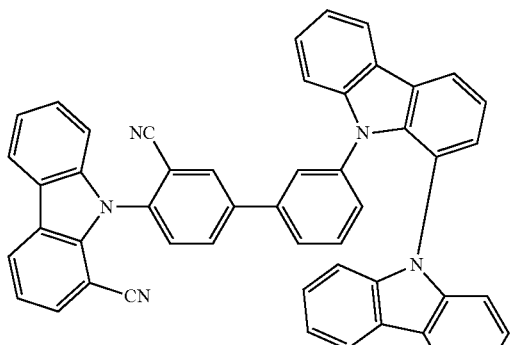
180
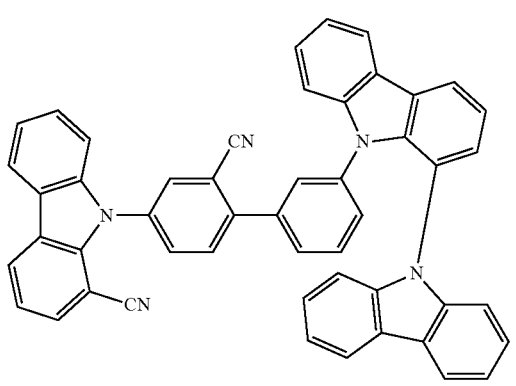
181
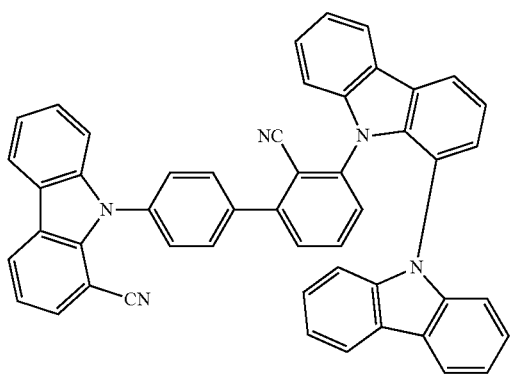
182
183
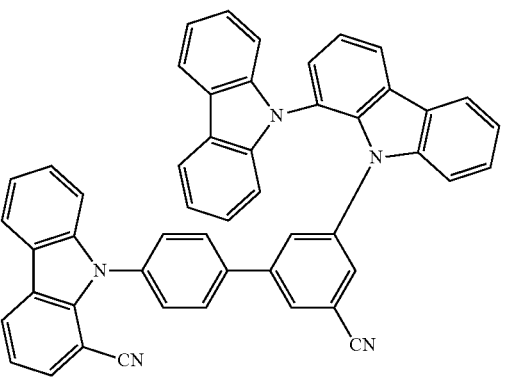
184
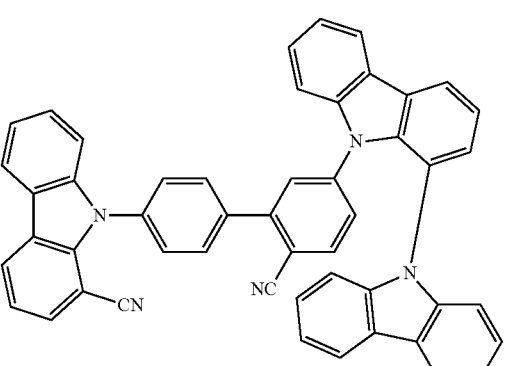
185
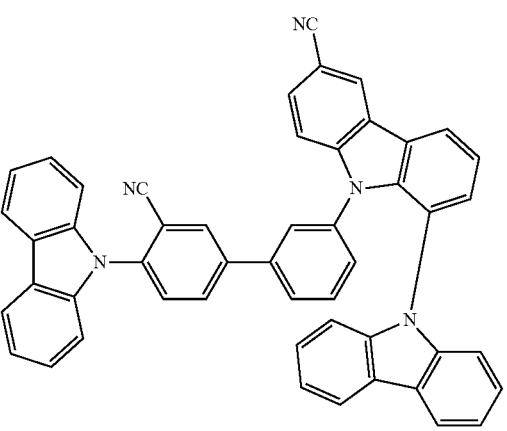

-continued
186
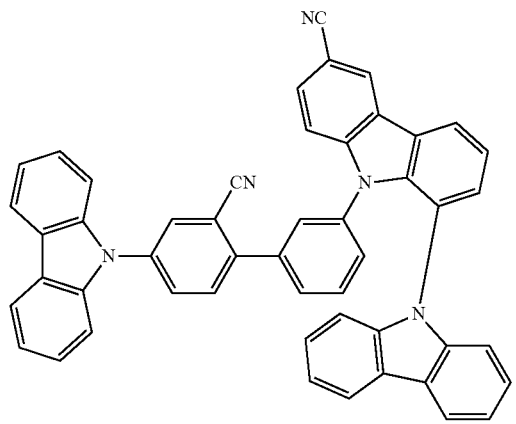
187
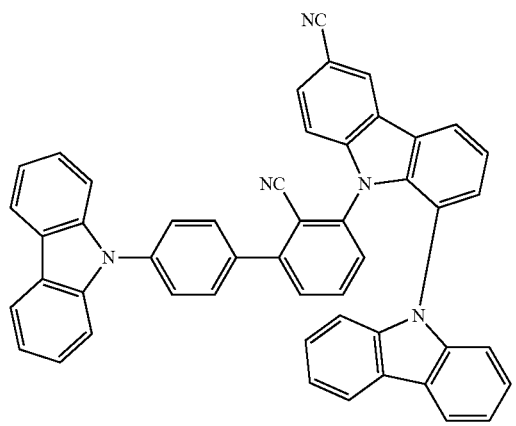
188
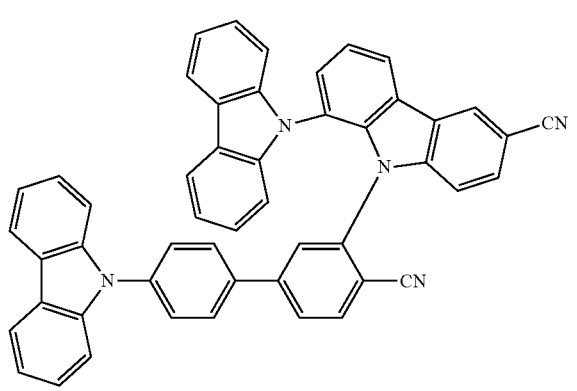
-continued
189
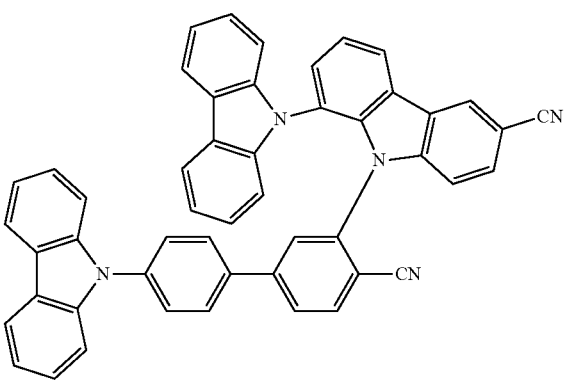
190
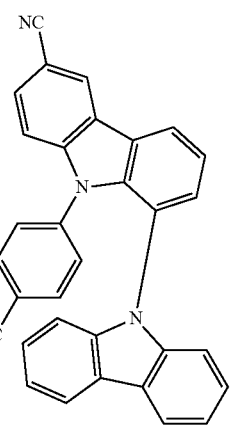
191
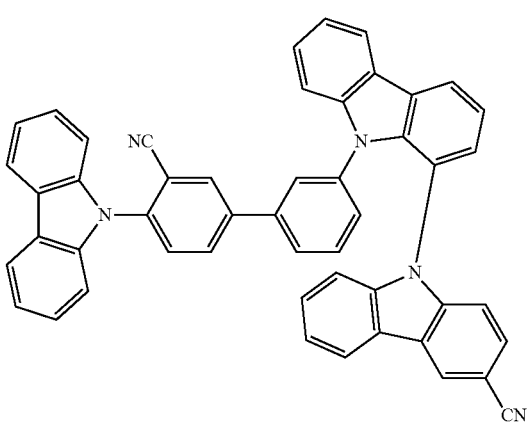

-continued
192
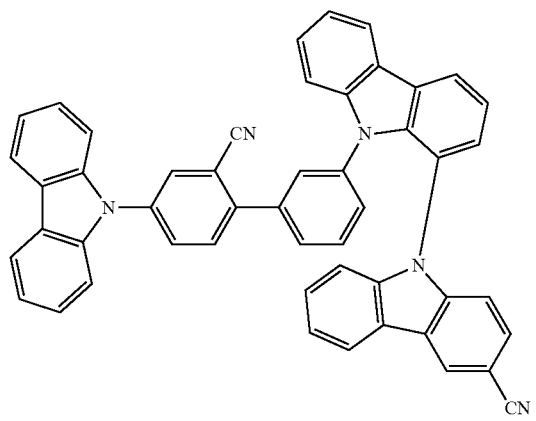
193
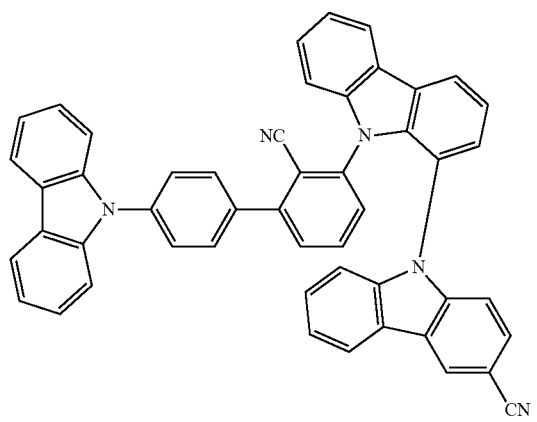
194
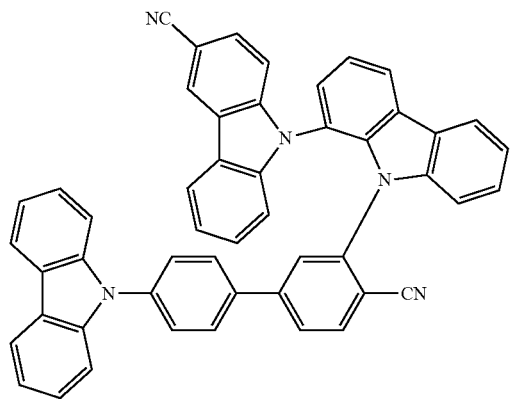
-continued
195
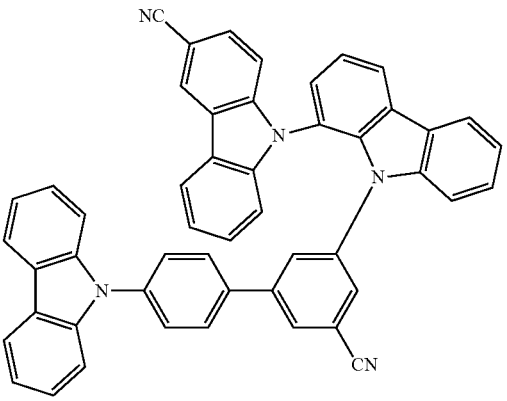
196
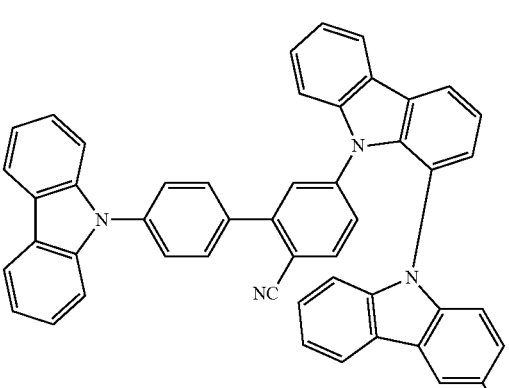
197
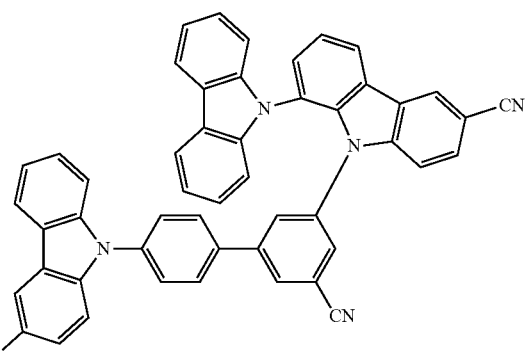
198
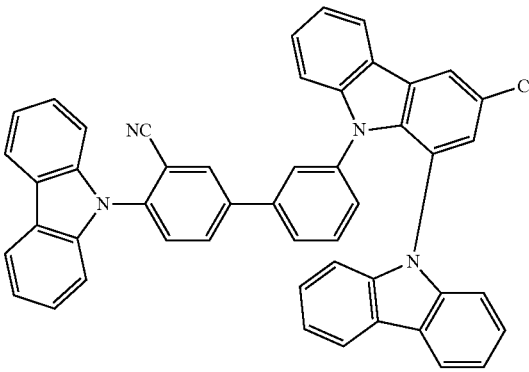

199
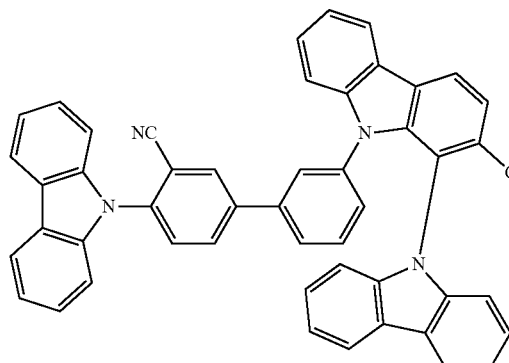
200
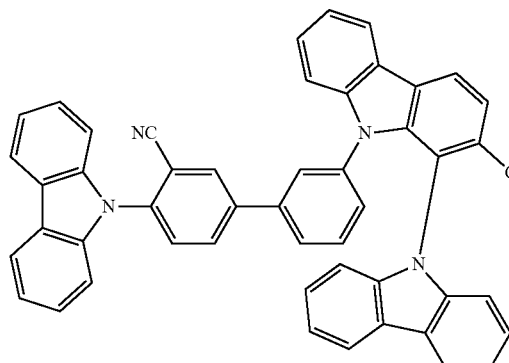
201
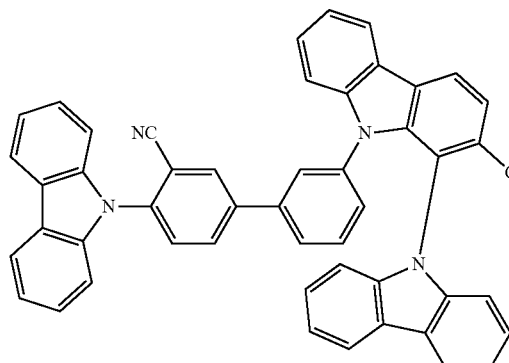
202
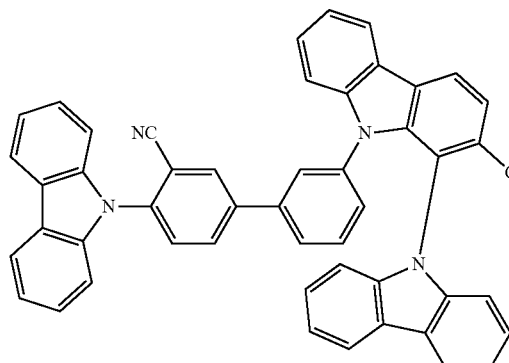
203
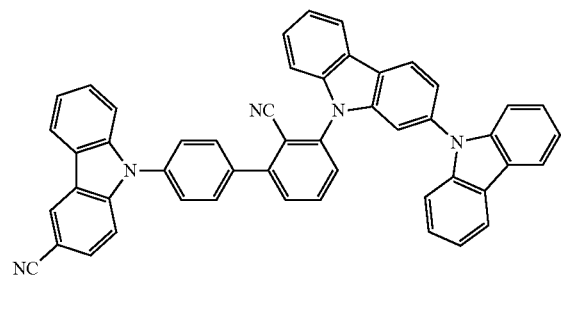
204
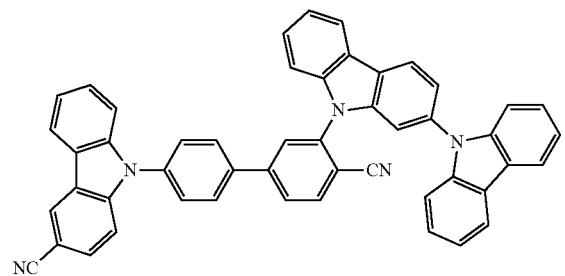
205
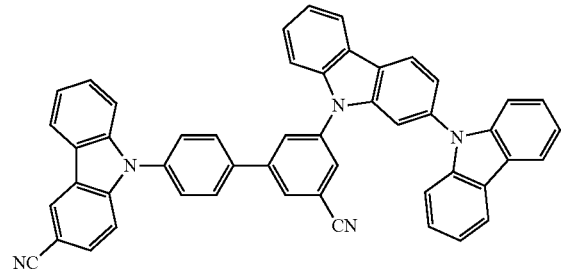
206
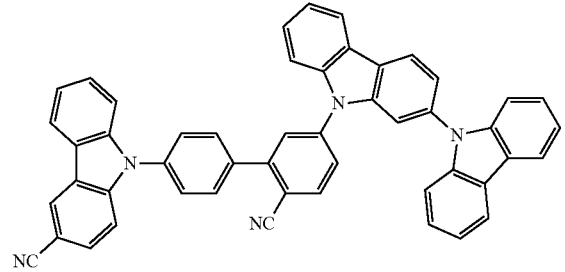
207
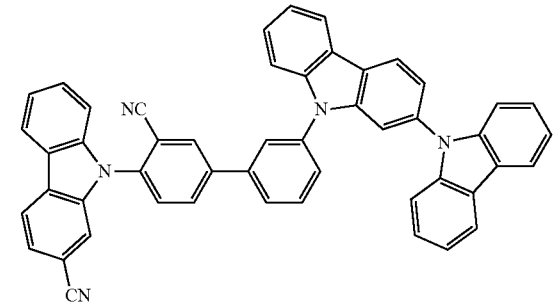

208
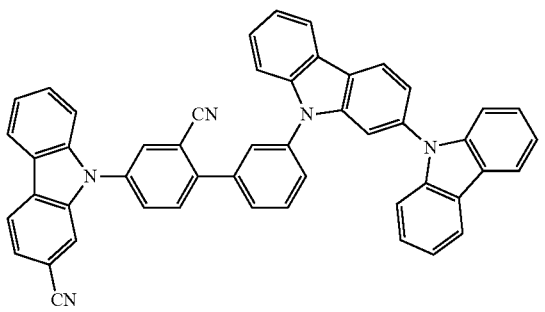
208
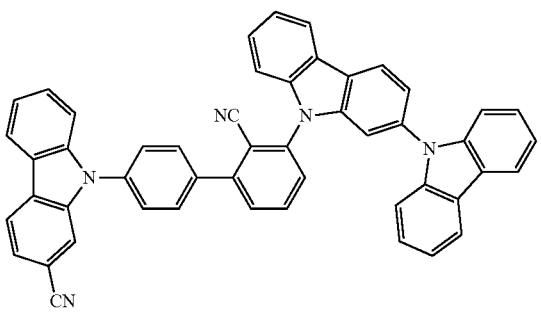
210
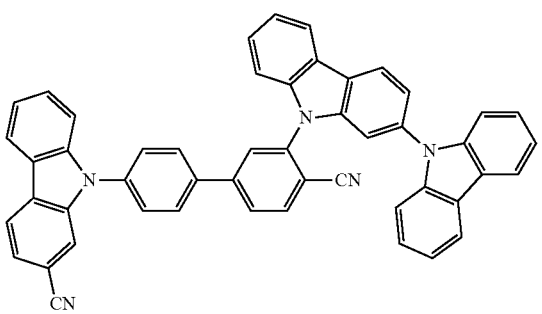
211
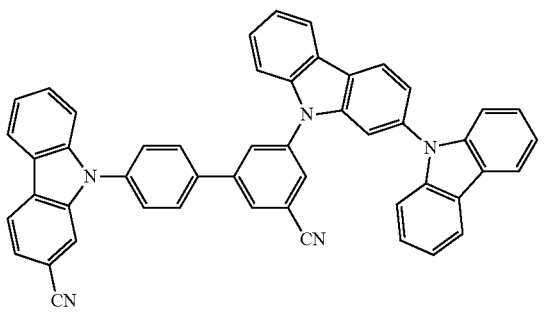
212
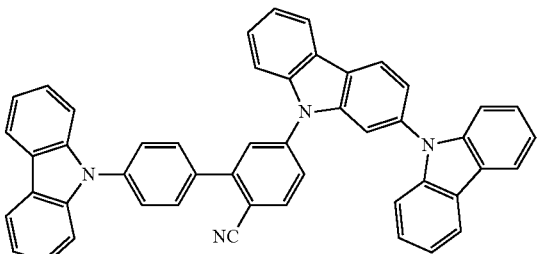
213
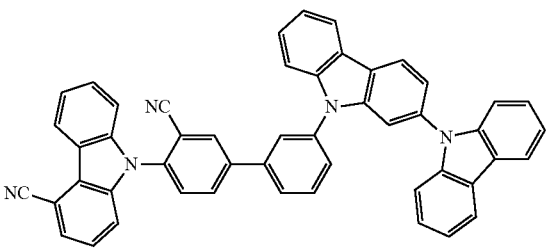
214
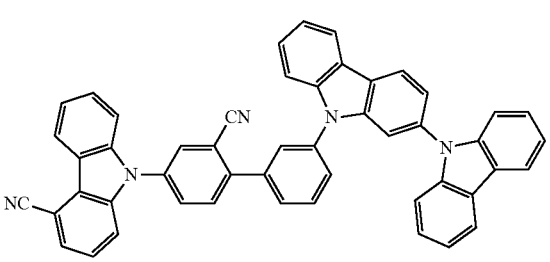
215
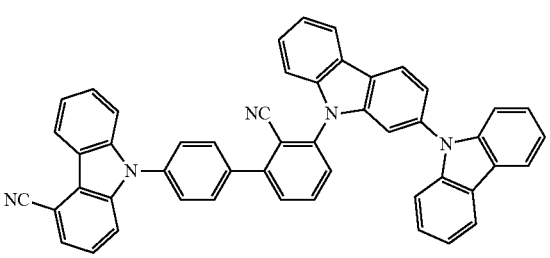
216
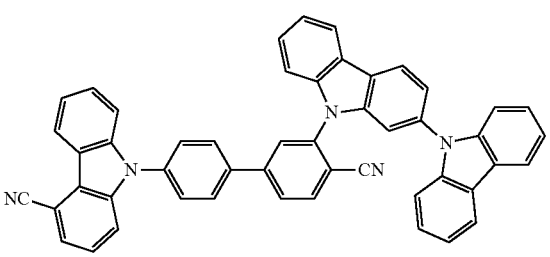

217
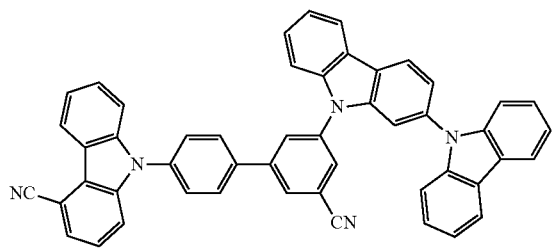
218
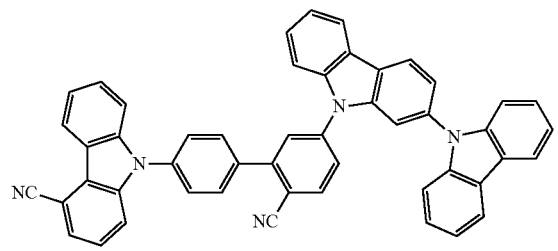
219
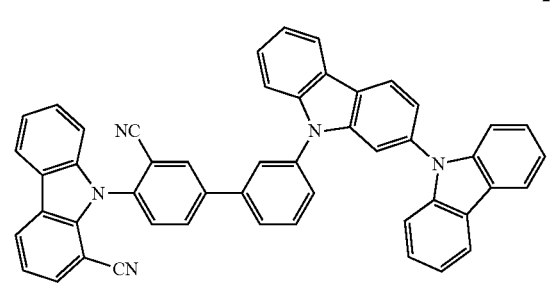
220
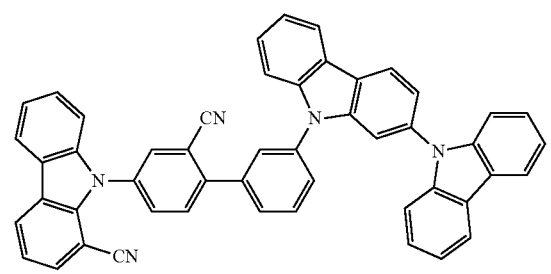
221
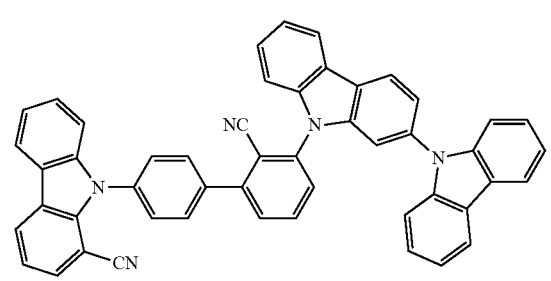
222
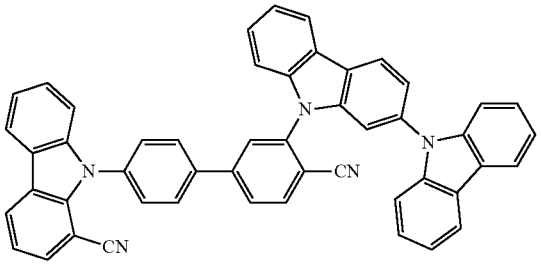
223
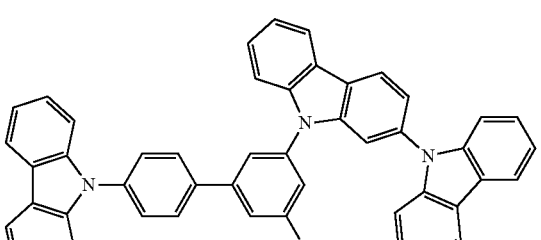
224
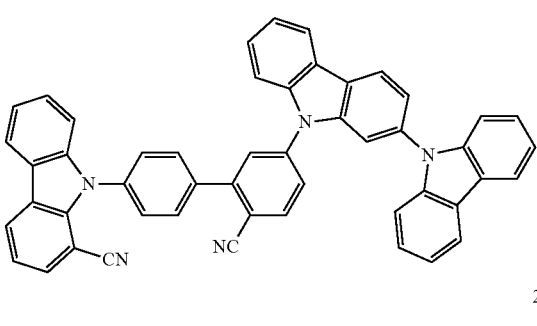
225
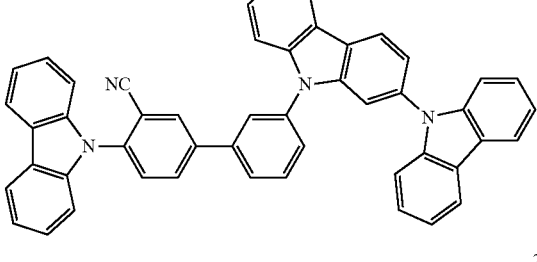
226
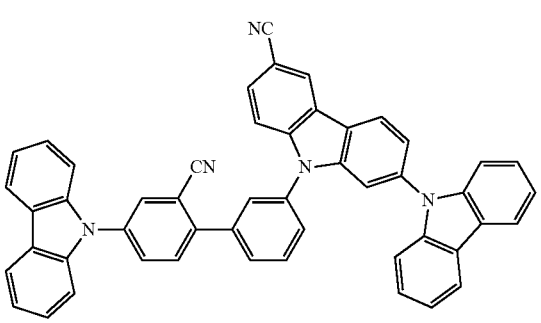

227
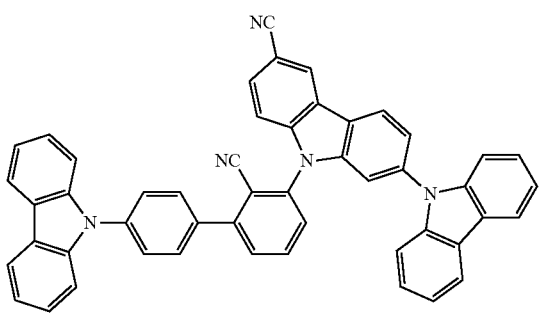
228
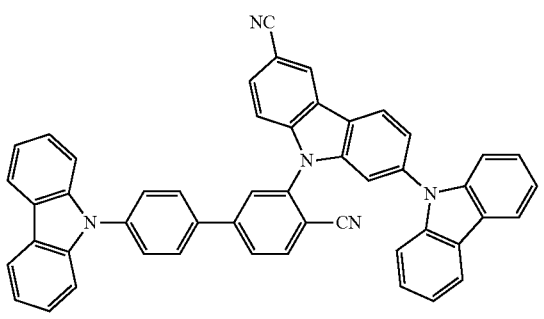
229
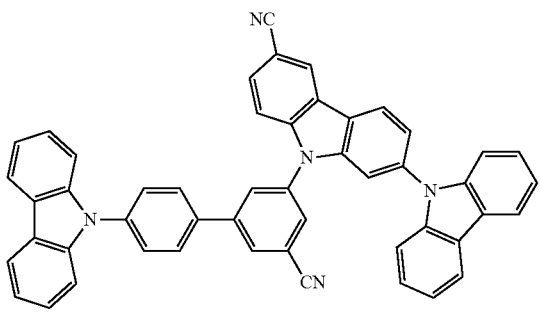
230
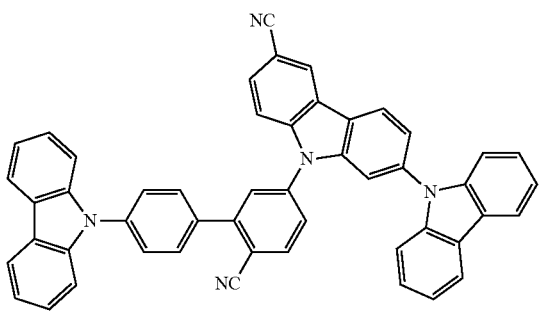
231
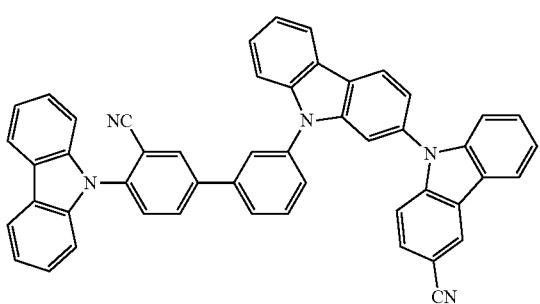
232
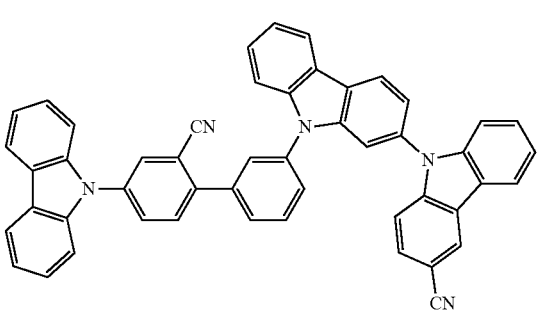
233
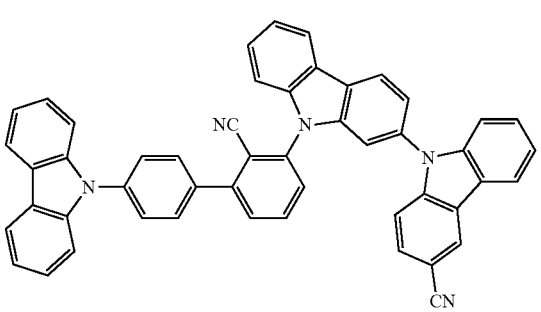
234
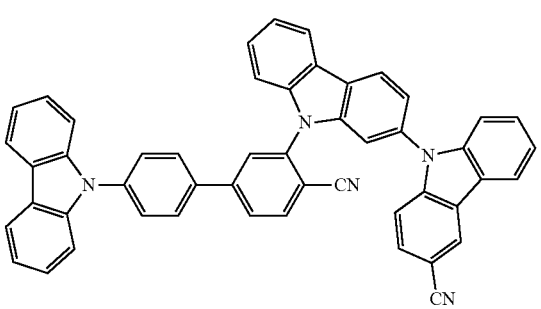
235
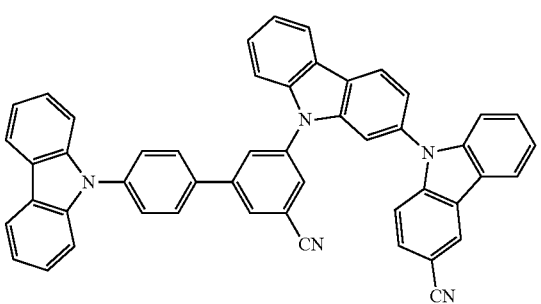
236
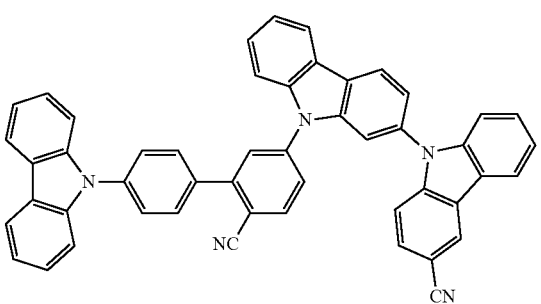

237
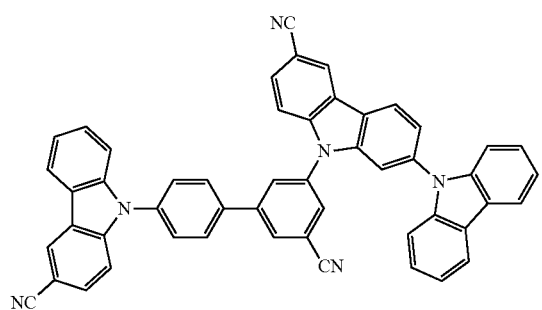
238
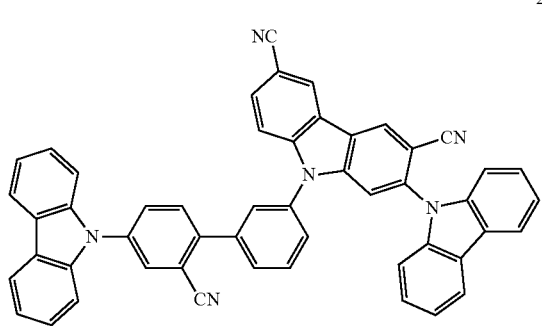
239
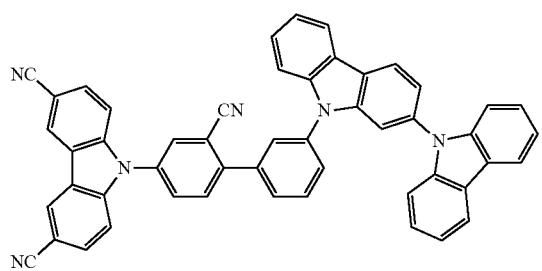
240
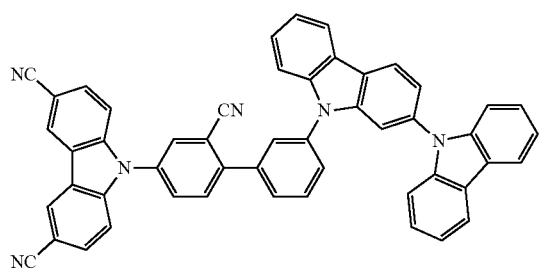
241
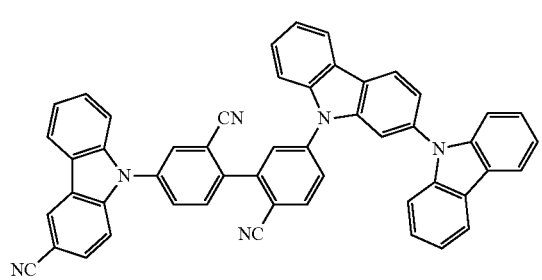
242
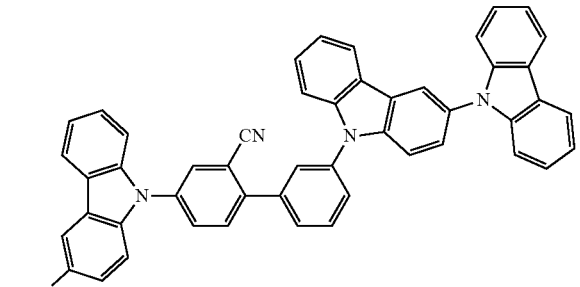
243
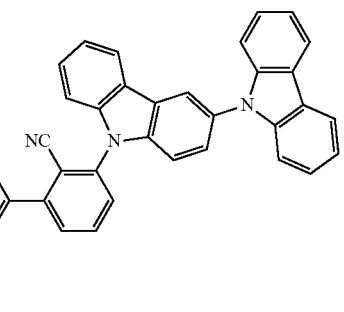
244
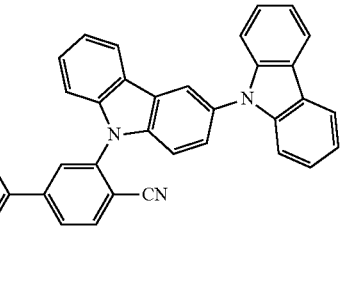
245
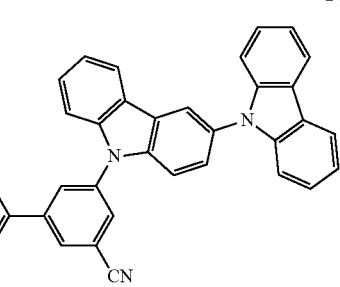
246
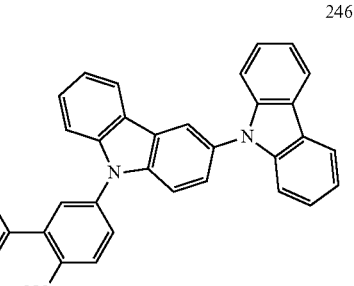

247
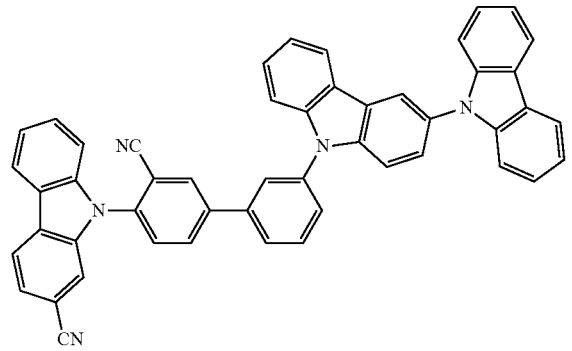
248
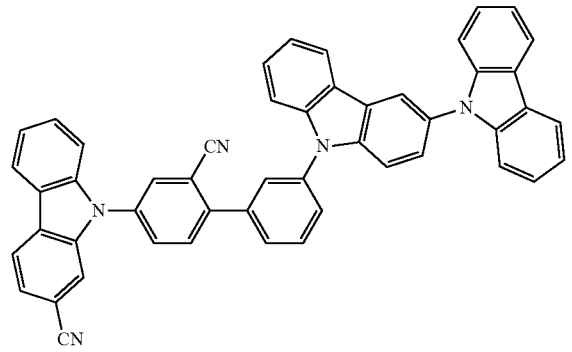
249
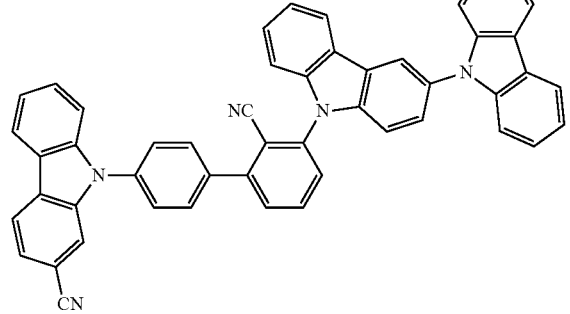
250
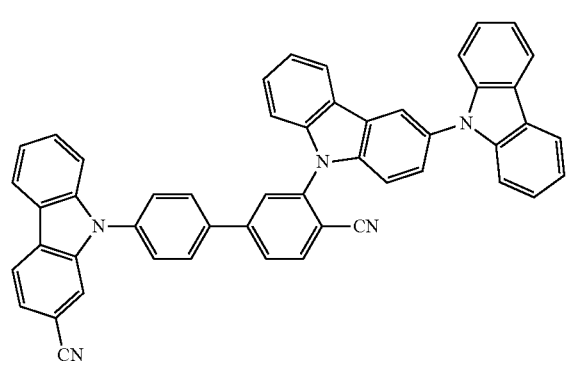
251
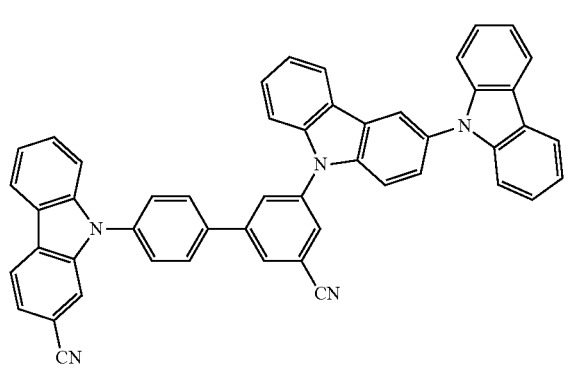
252
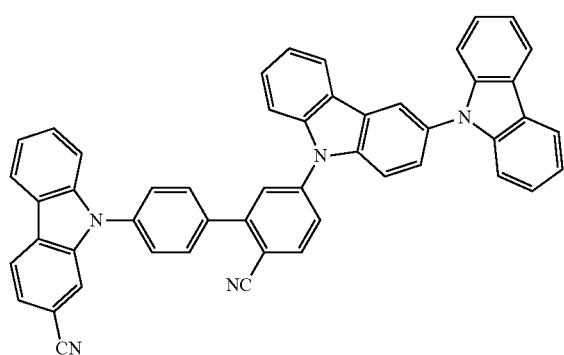
253
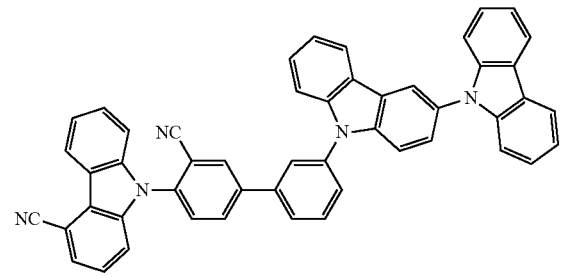
254
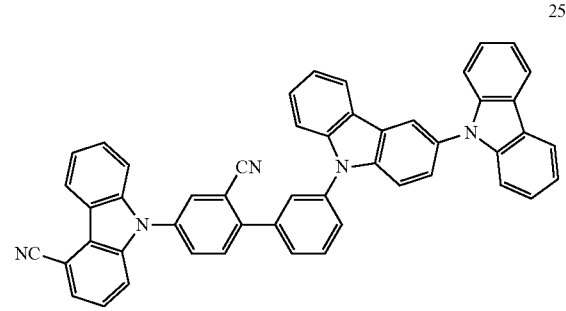
255
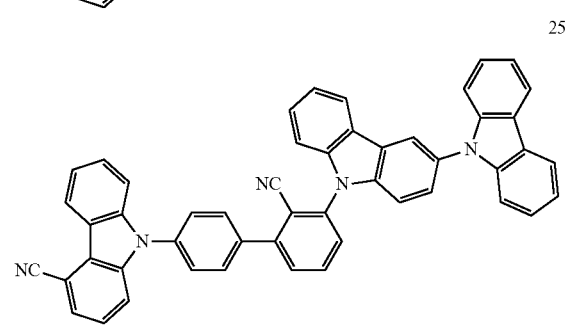

-continued
256
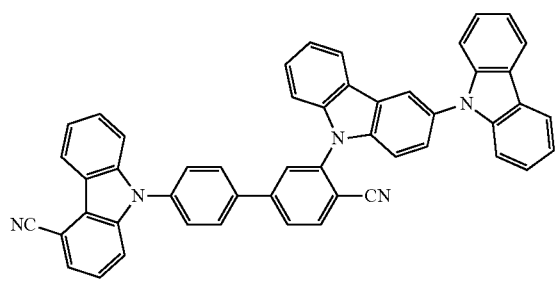
257
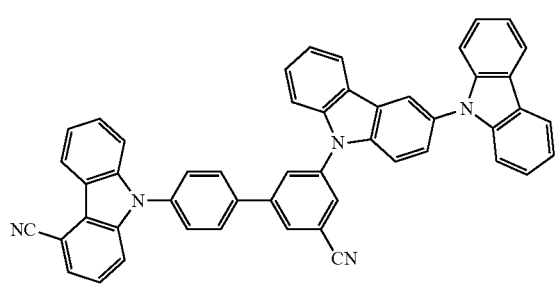
258
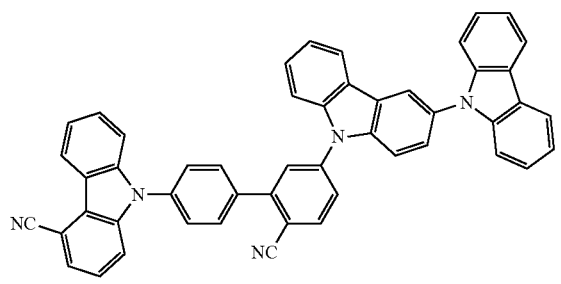
259
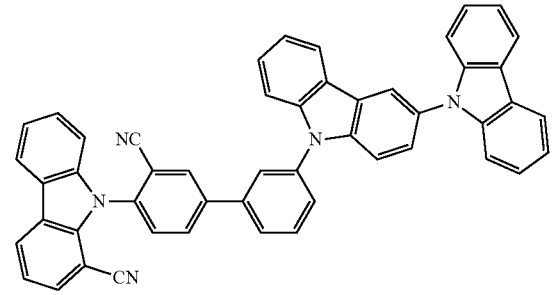
260
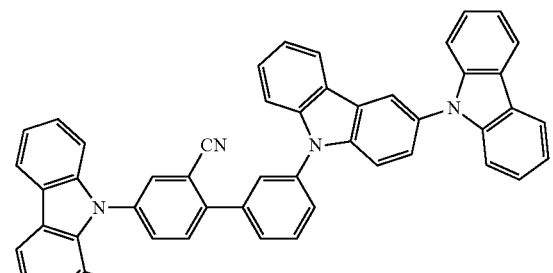
-continued
261
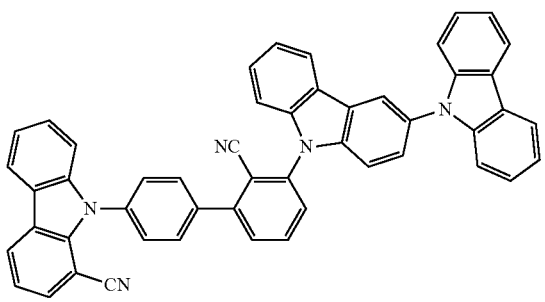
262
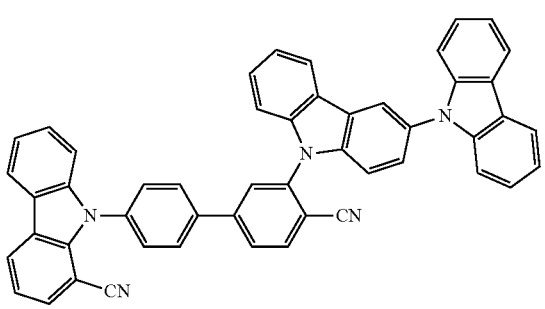
263
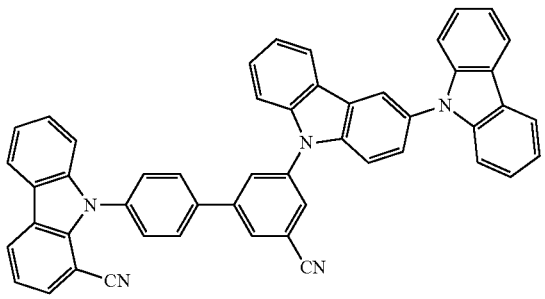
264
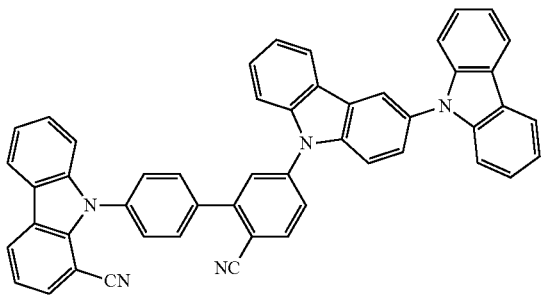
265
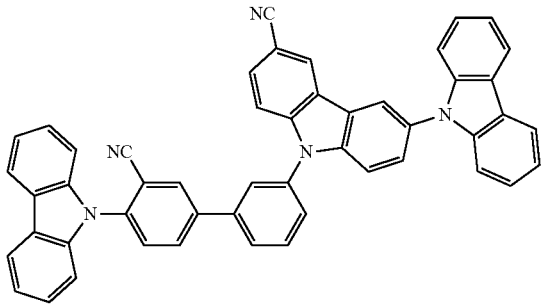

266
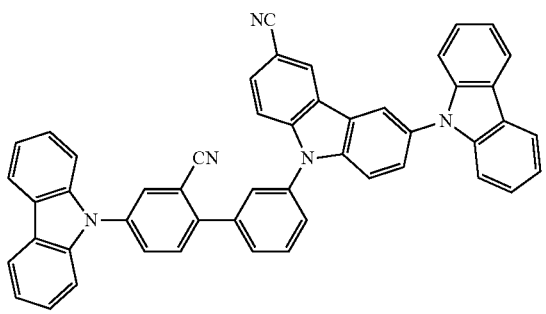
267
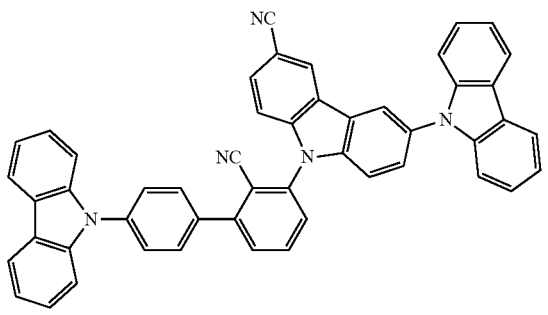
268
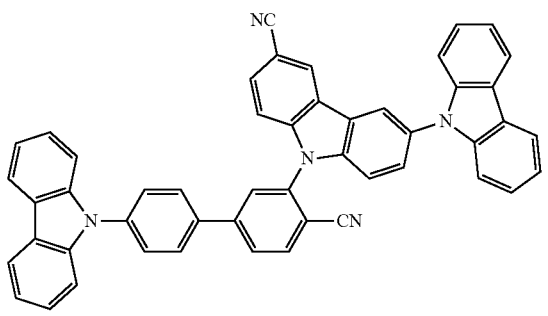
269
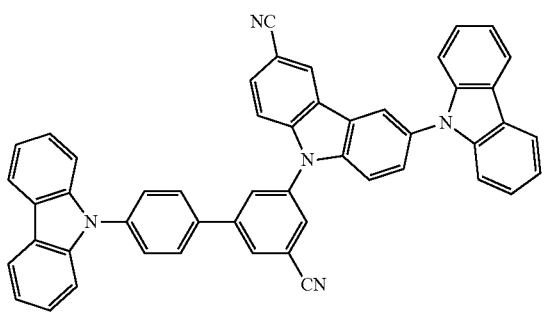
270
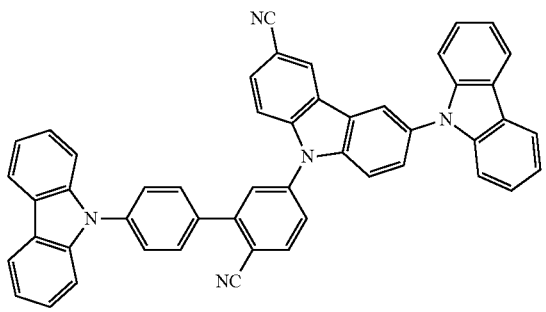
271
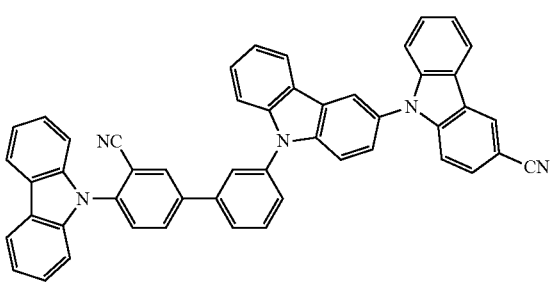
272
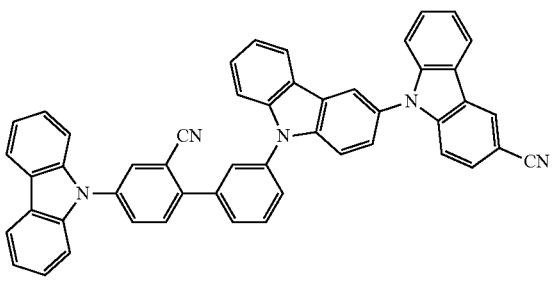
273
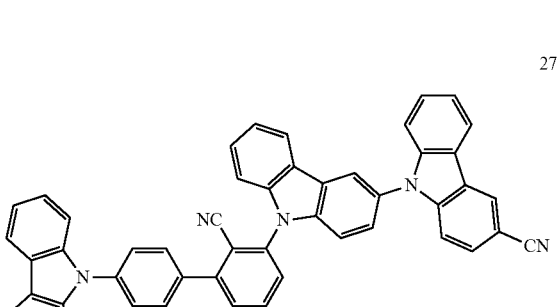
274
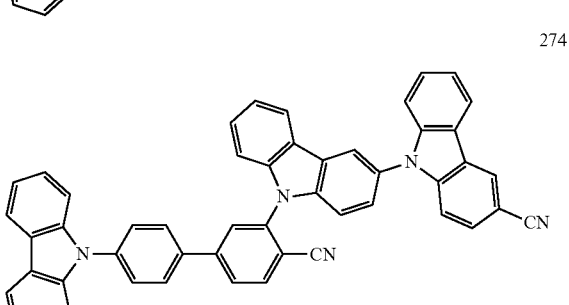
275
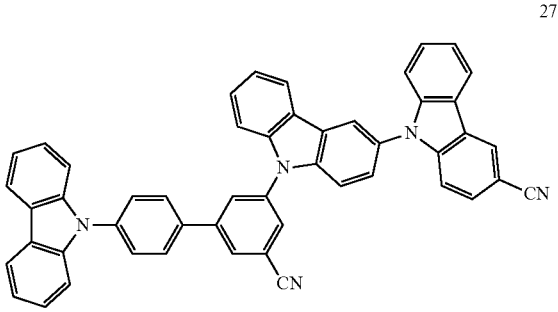

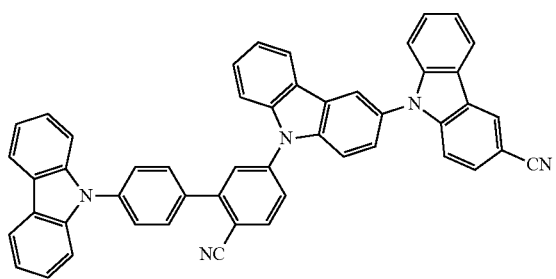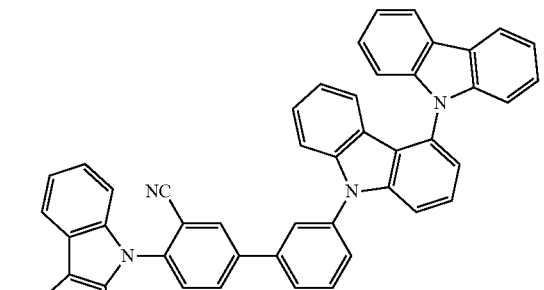

285
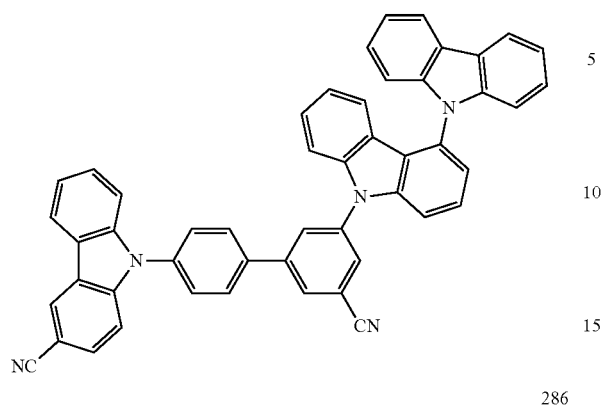
286
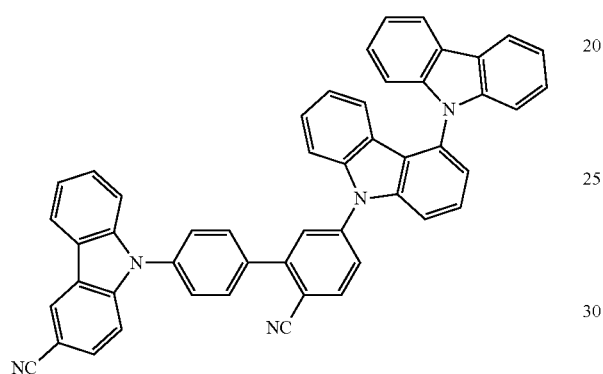
287
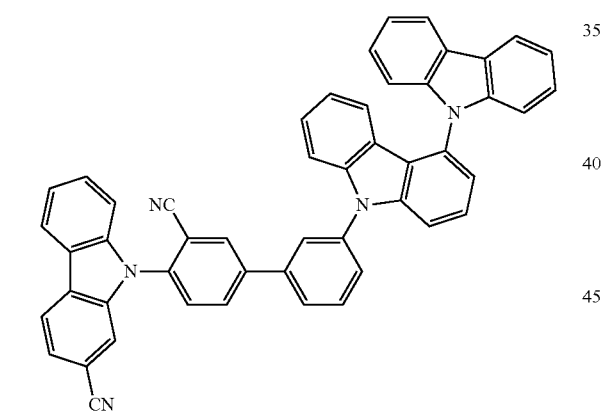
288
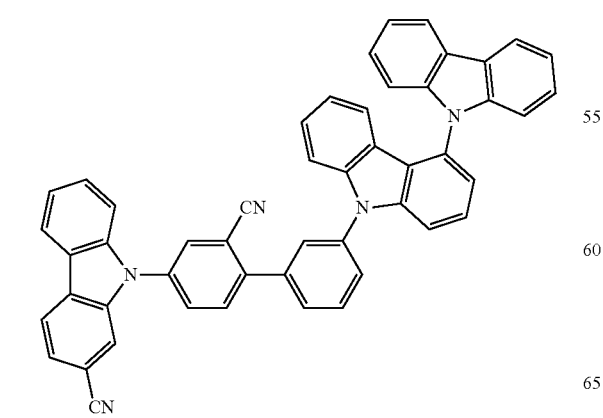
289
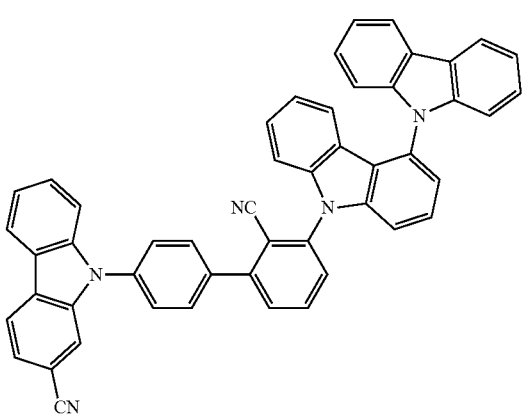
290
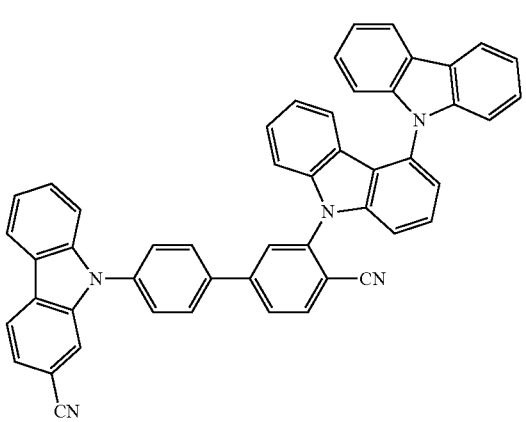
291
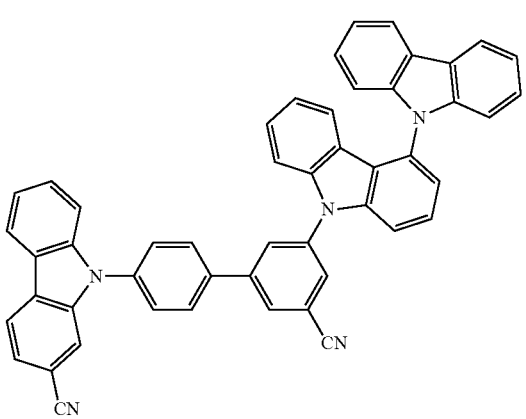

-continued
292
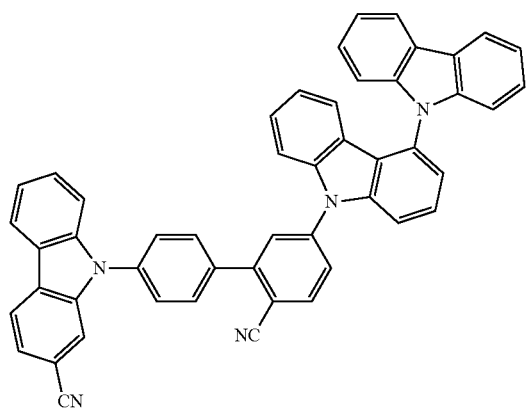
293
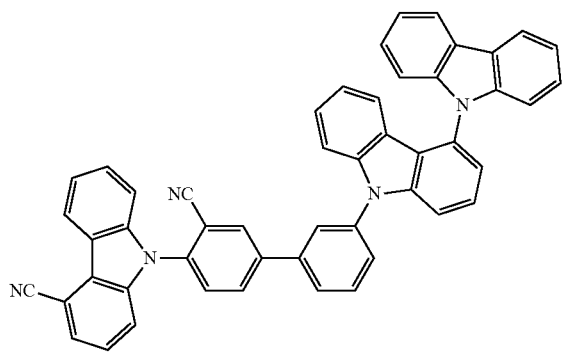
294
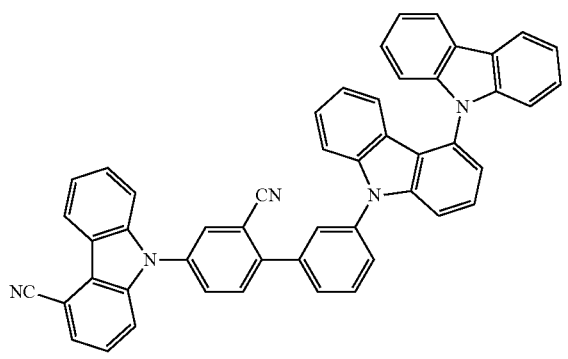
295
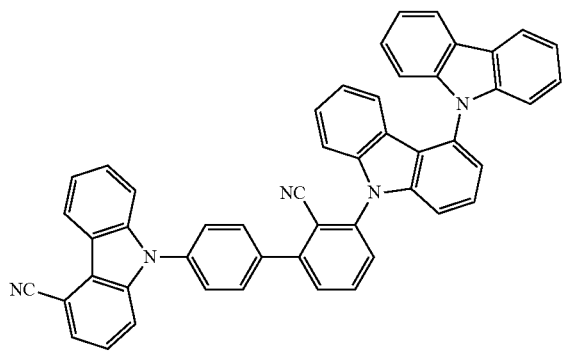
-continued
296
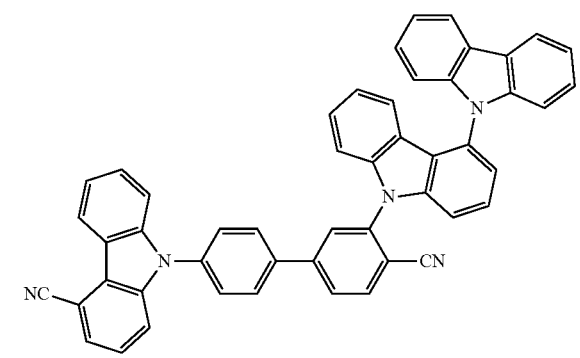
297
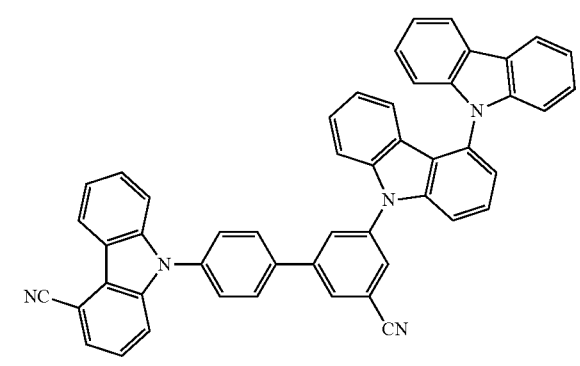
298
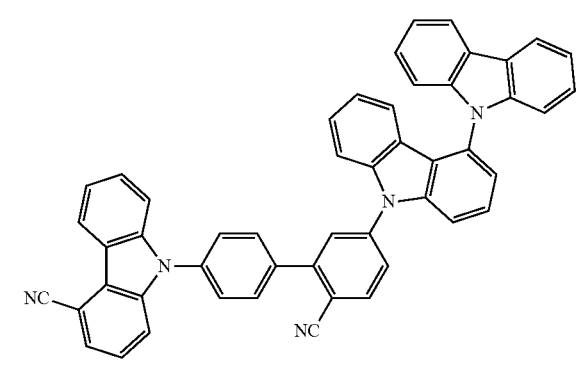
299
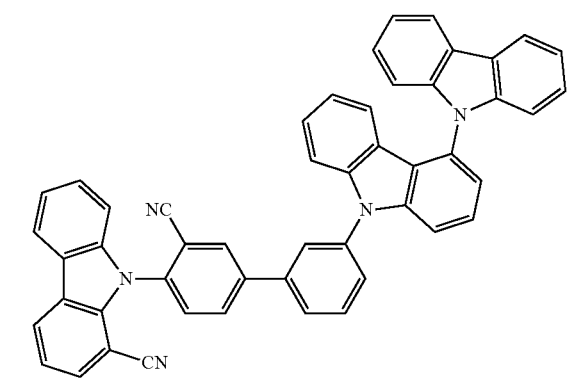

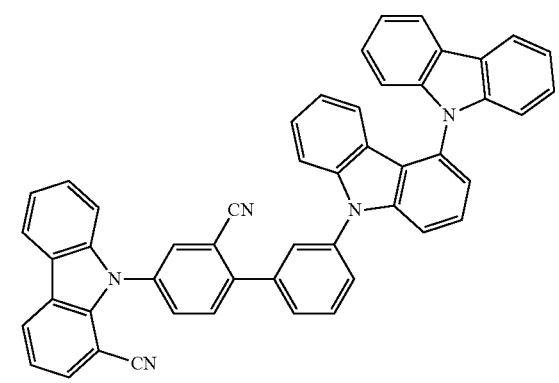
300
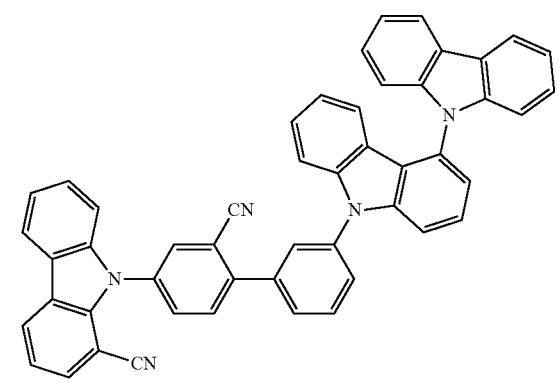
301
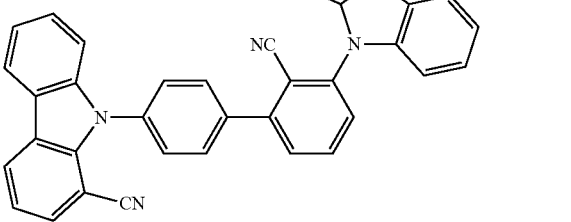
302
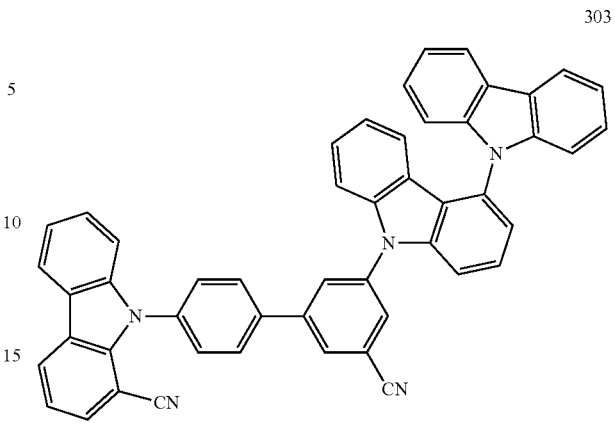
303
304
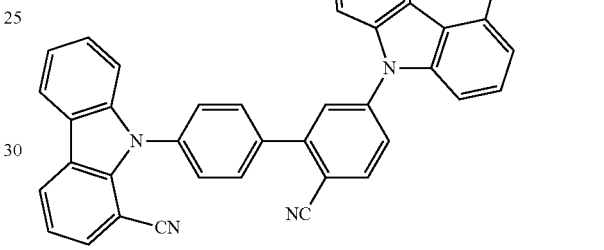
305
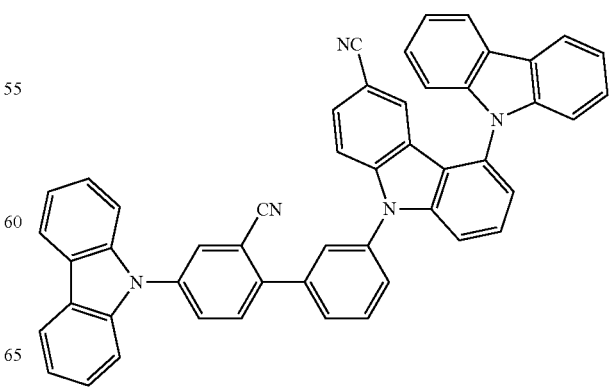
306

307
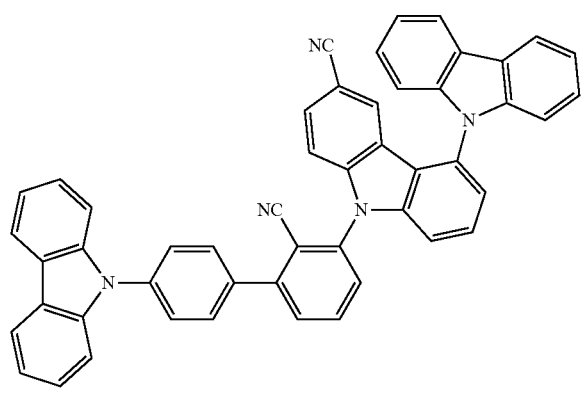
308
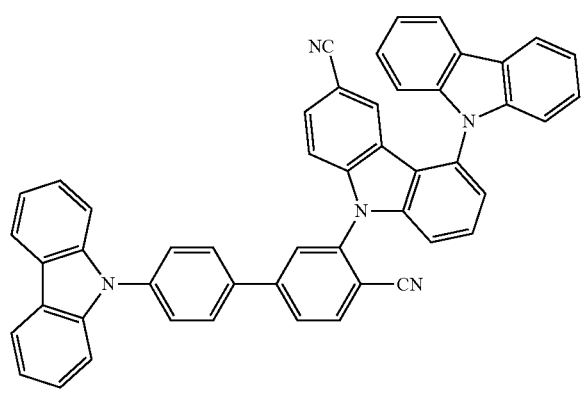
309
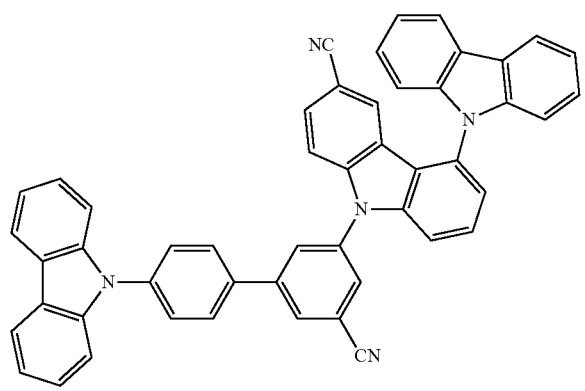
310
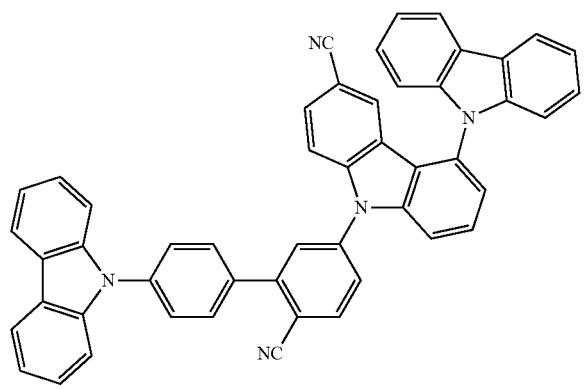
311
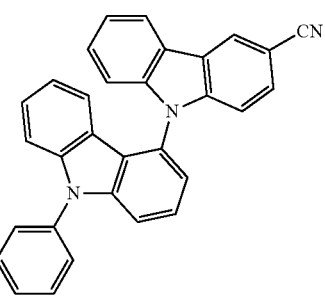
312
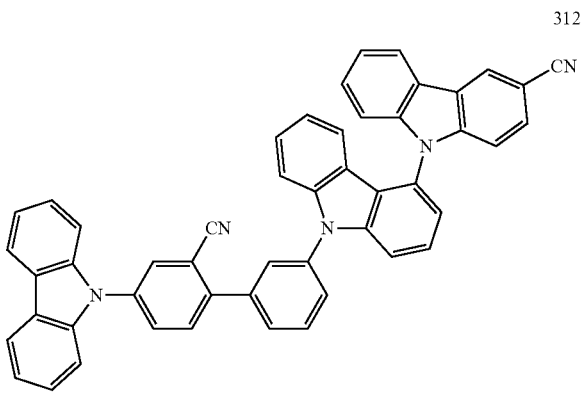
313
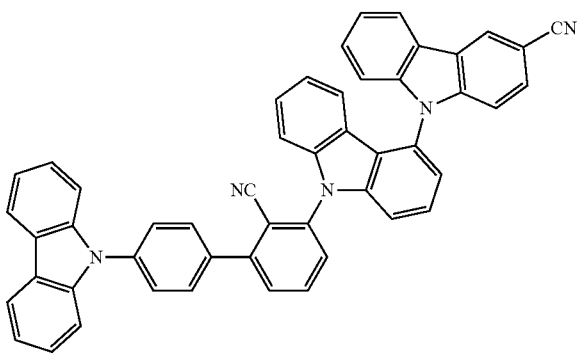
314
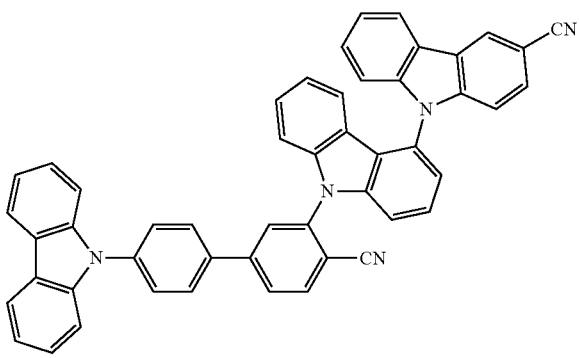

315
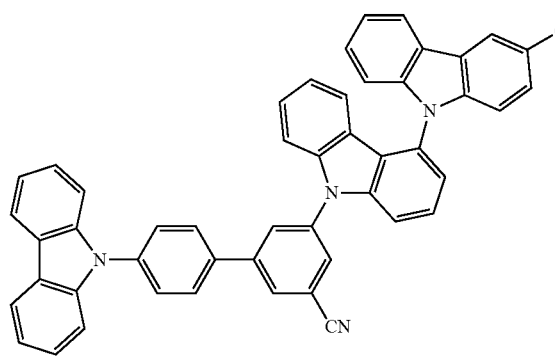
316
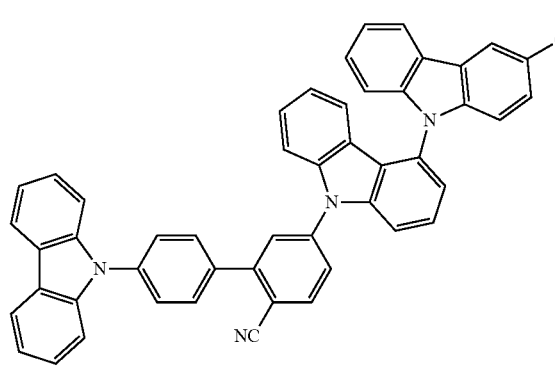
317

318
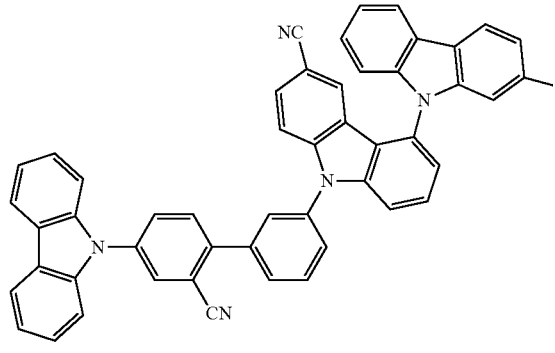
319
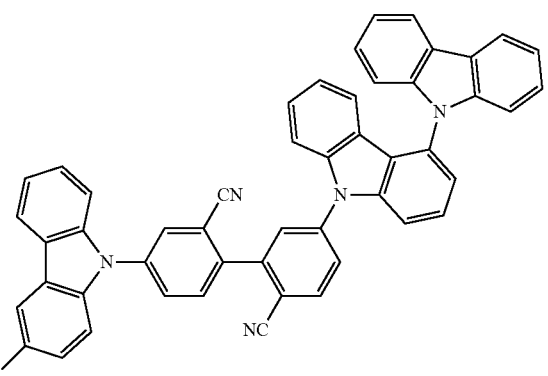
320
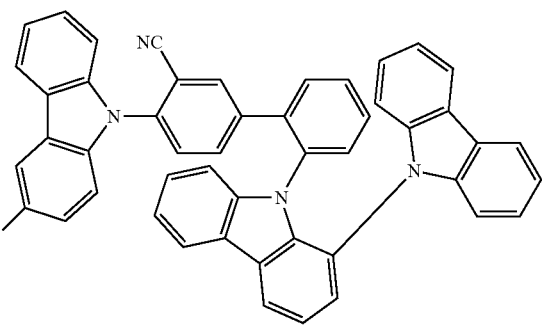
321
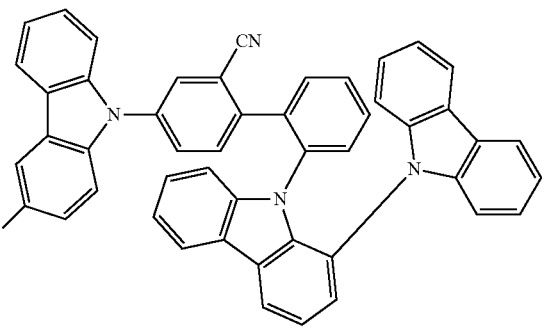
322
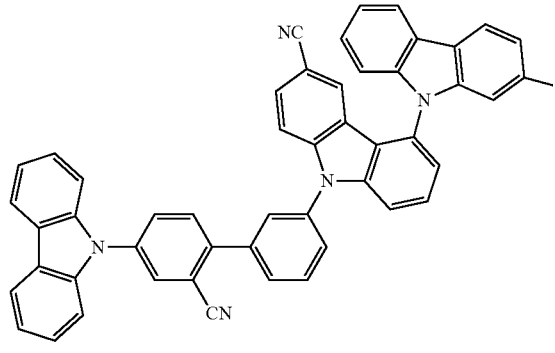

323
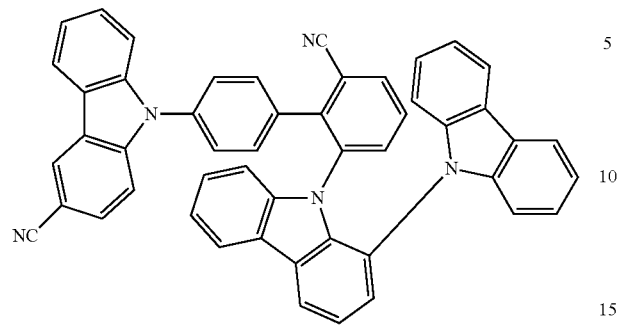
324
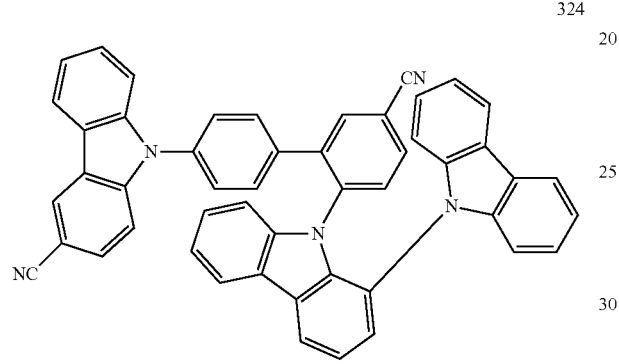
325
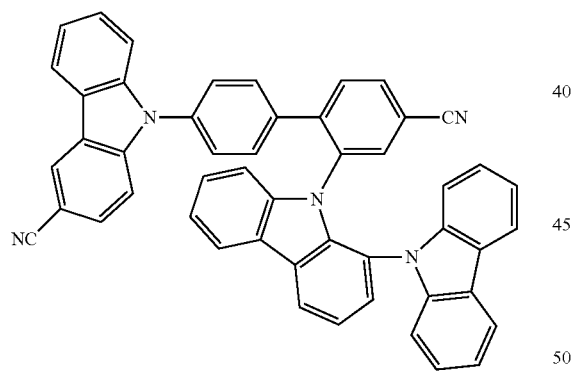
326
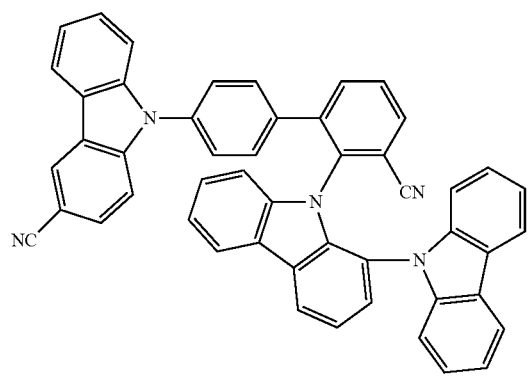
327
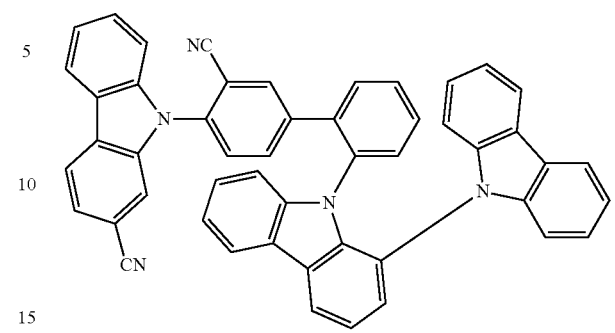
328
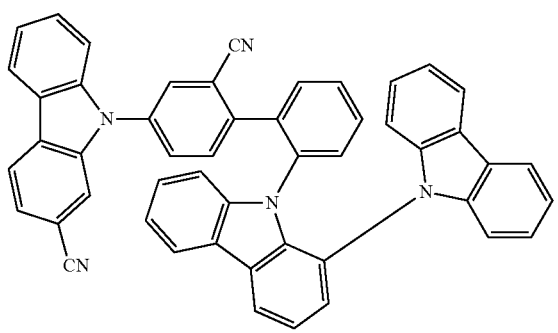
329
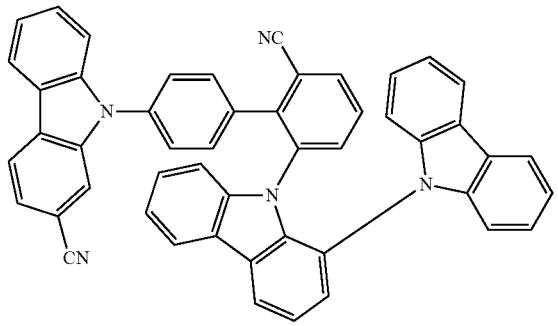
330
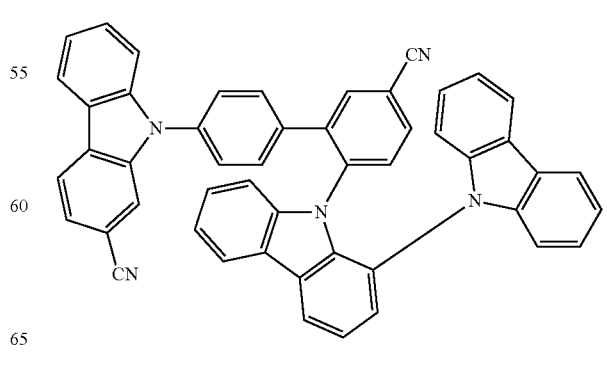

331
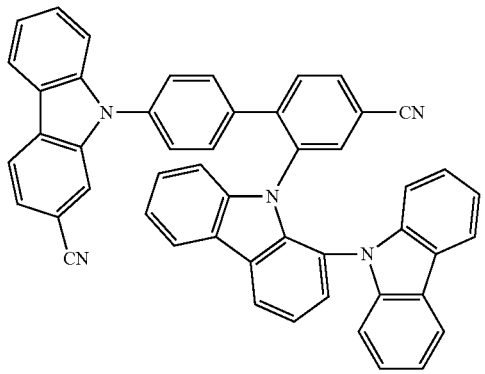
335
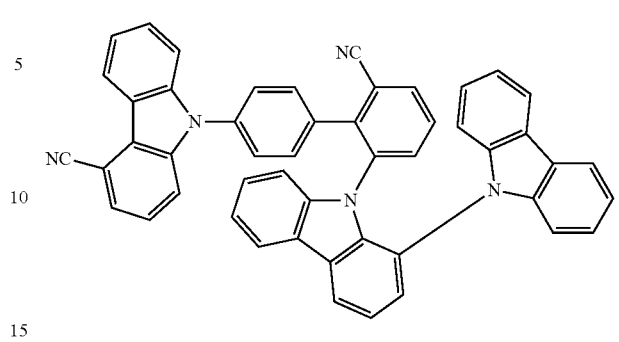
332
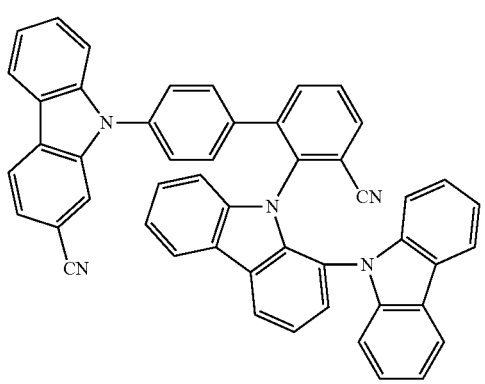
336
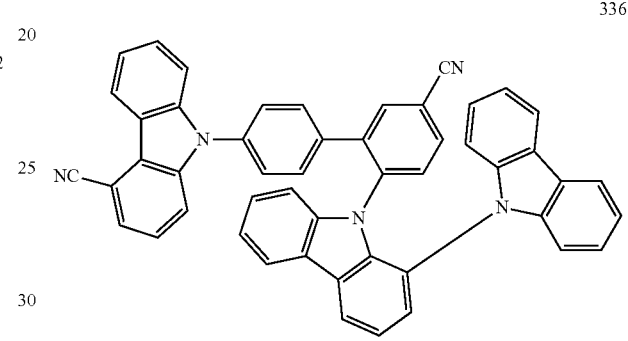
333
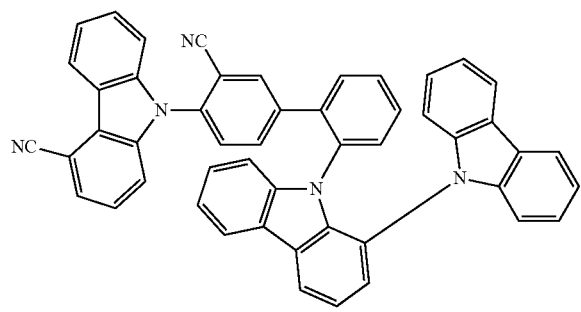
337
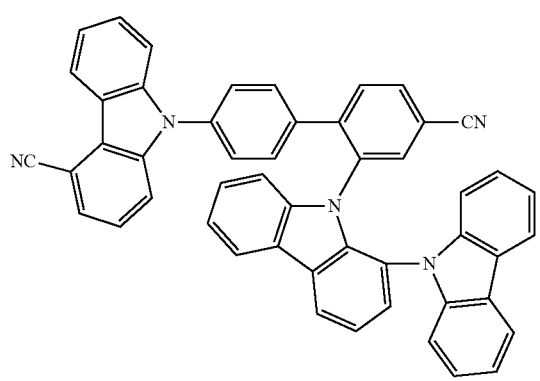
334
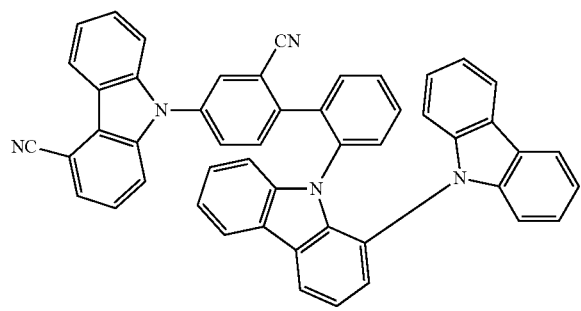
338
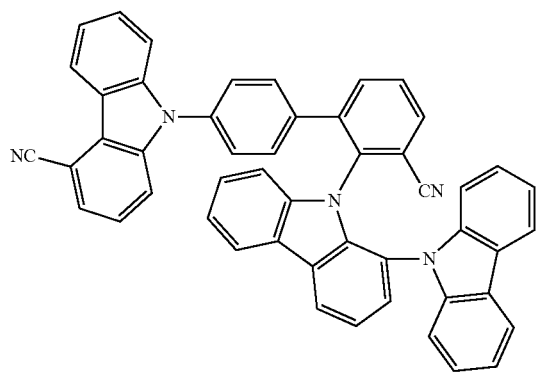

-continued
339
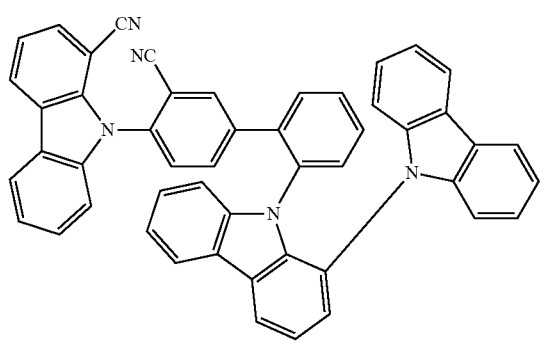
340
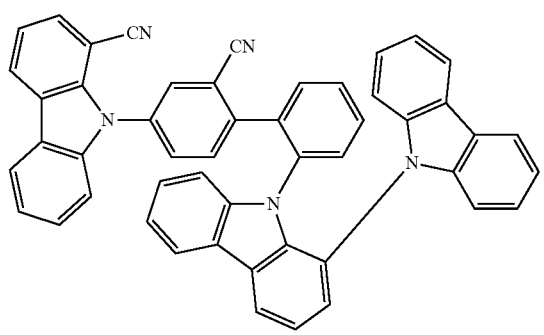
341
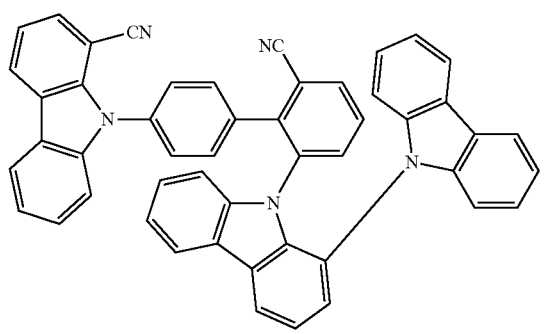
342
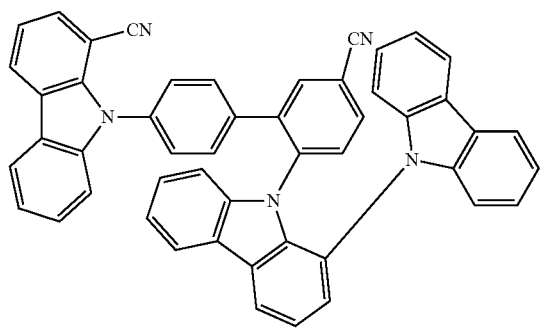
-continued
343
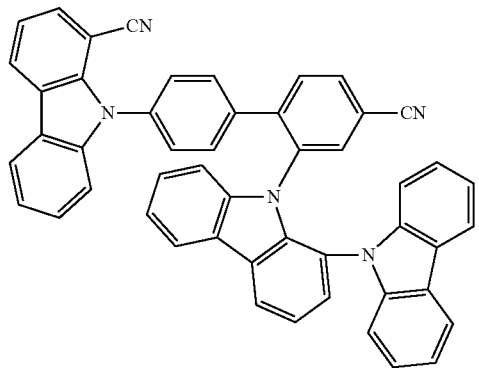
344
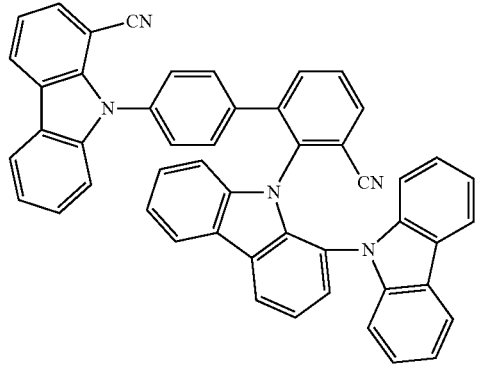
345
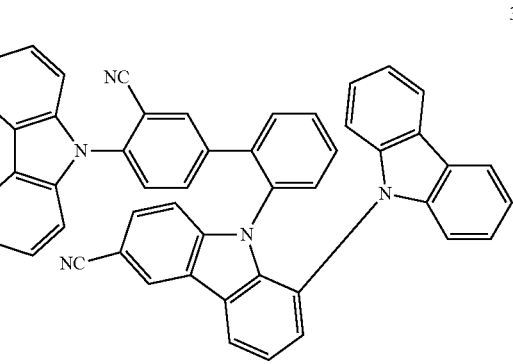
346
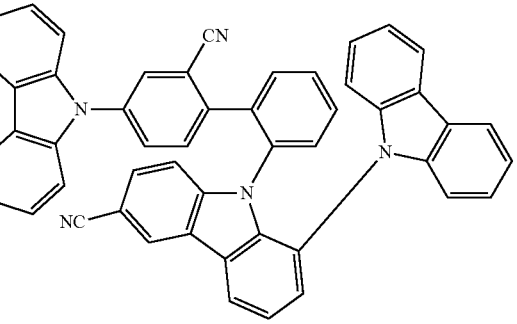

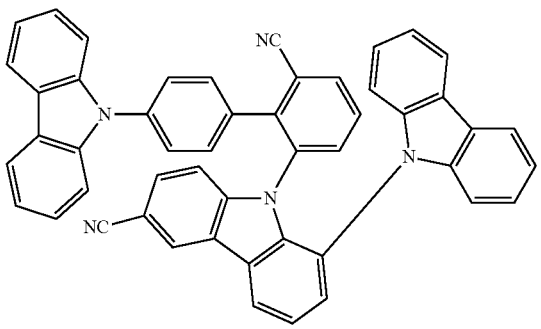
347
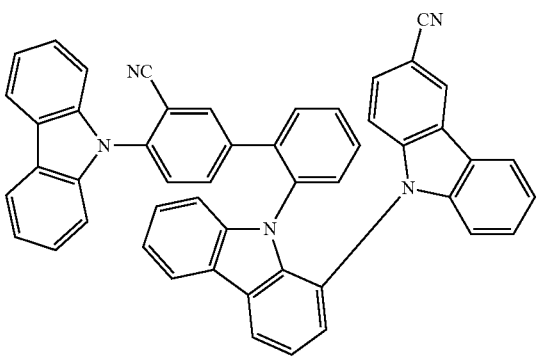
351
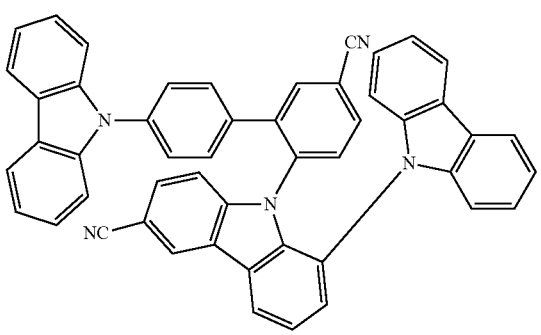
348
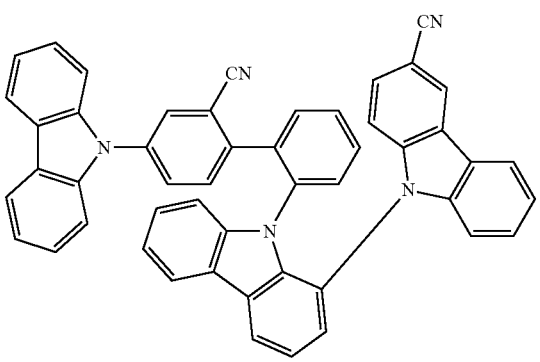
352
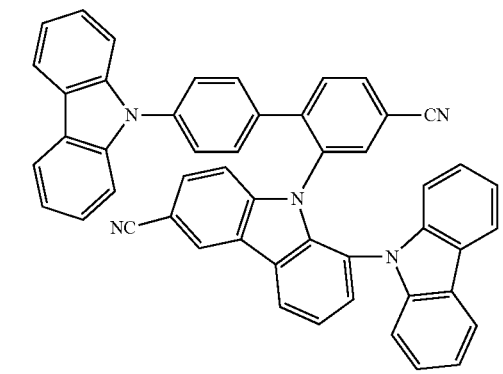
349
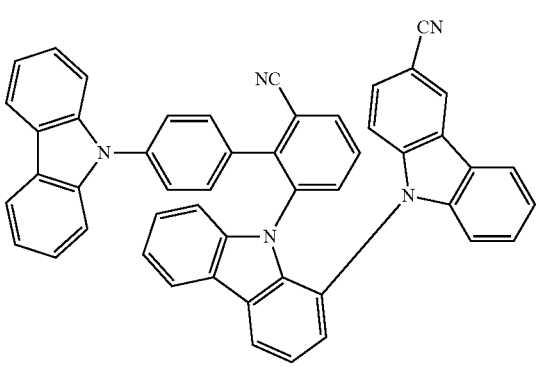
353
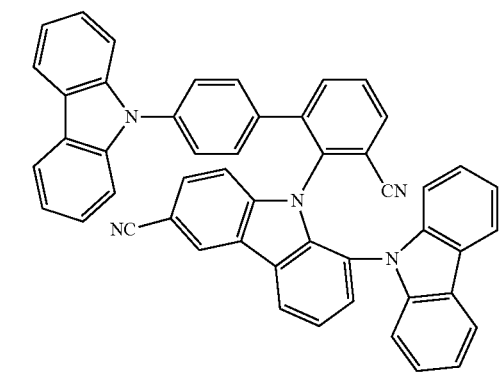
350

355
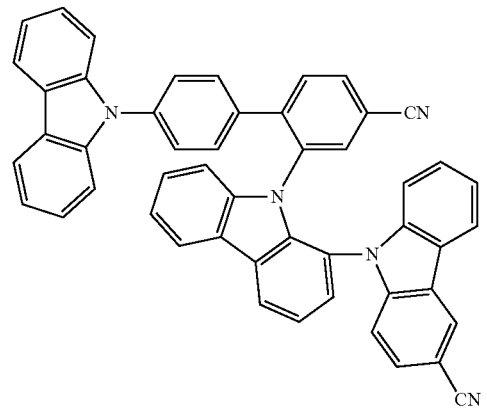
356
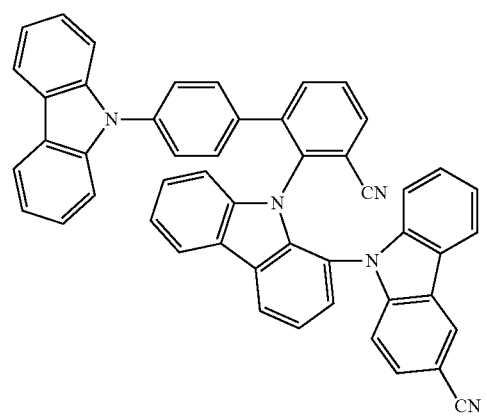
357
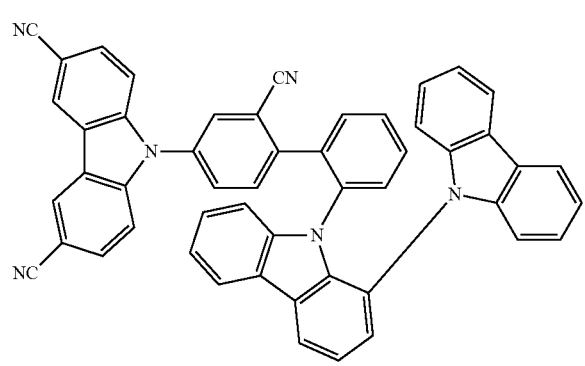
358
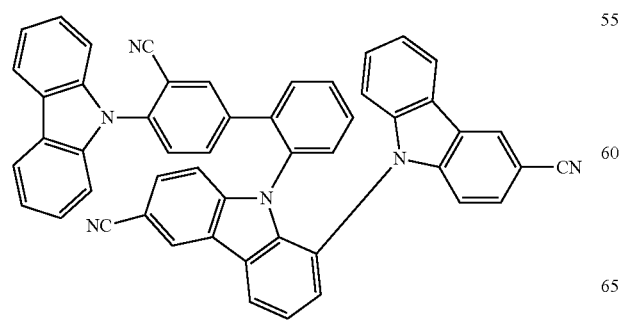
359
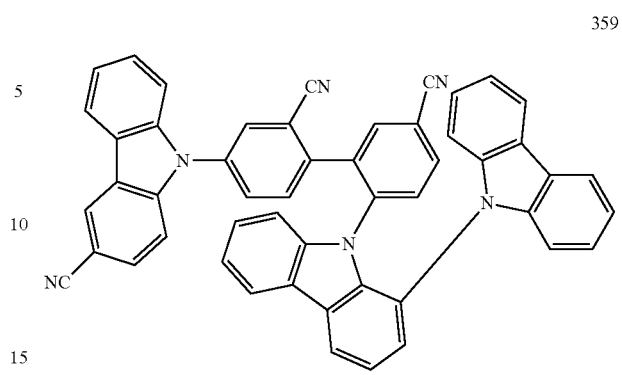
360
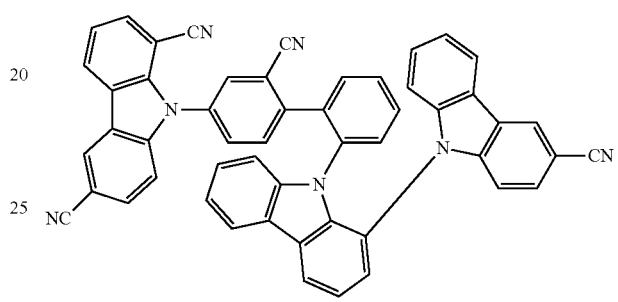
361
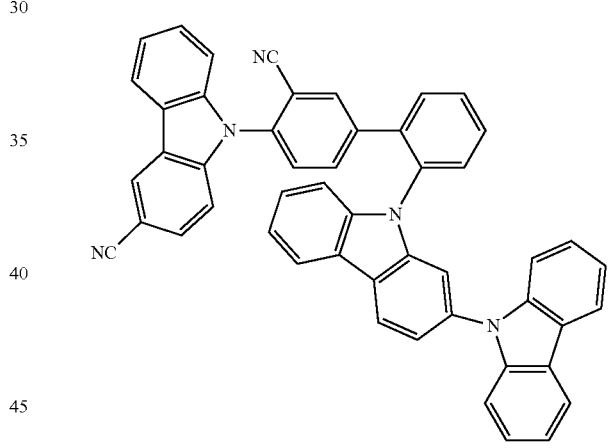
362
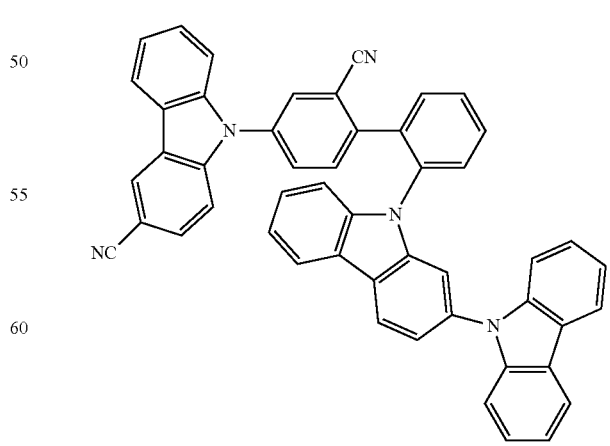

363
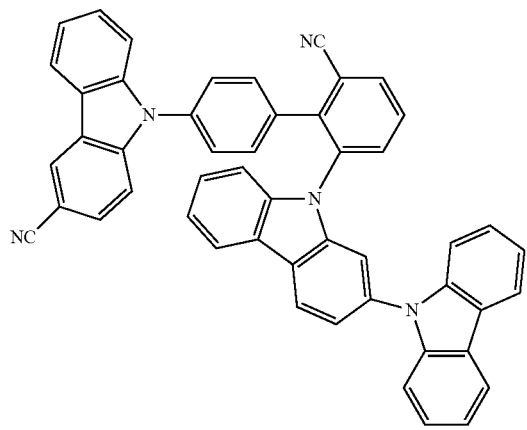
364
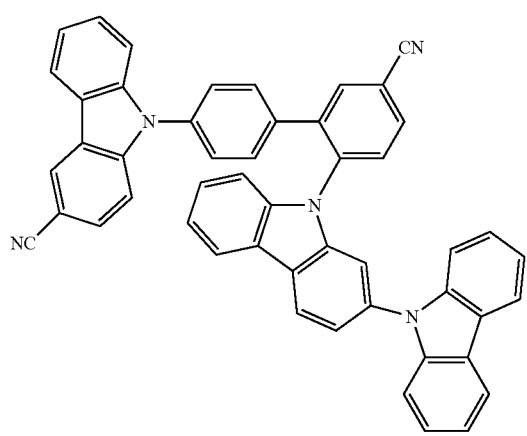
365
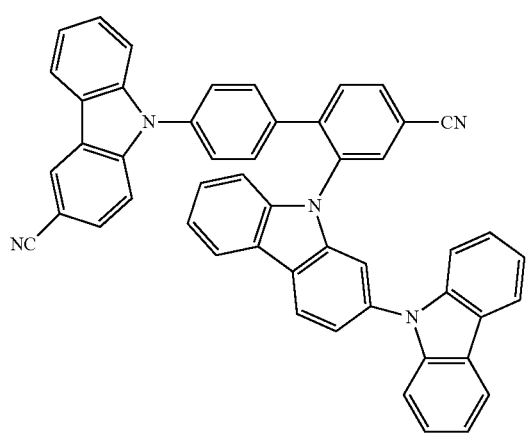
366
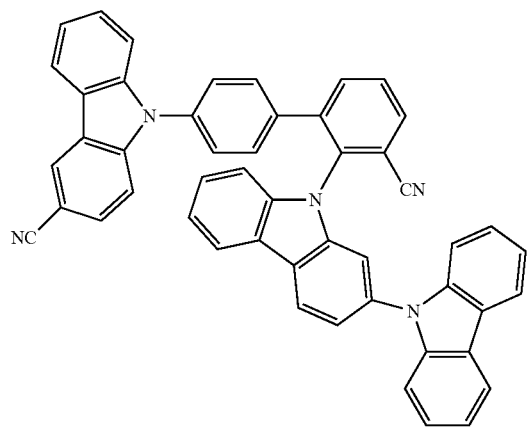
367
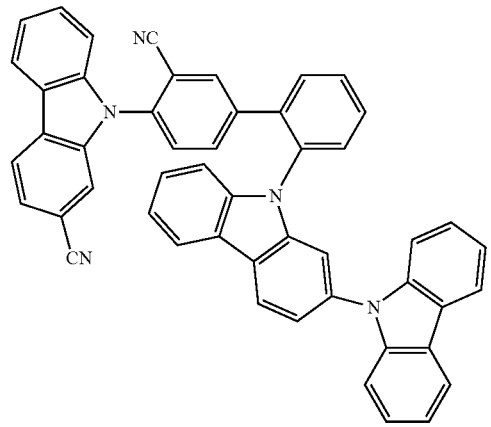
368
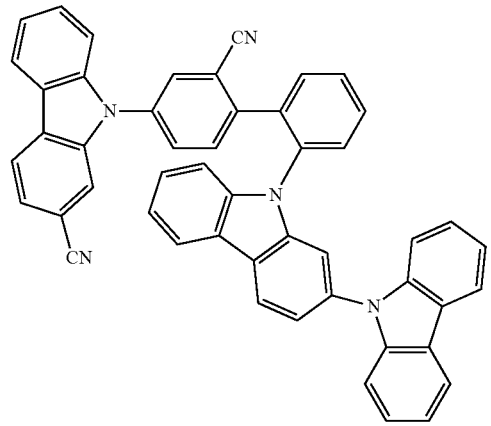

-continued
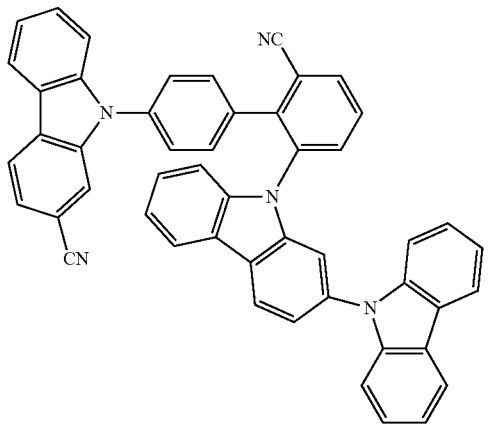
369
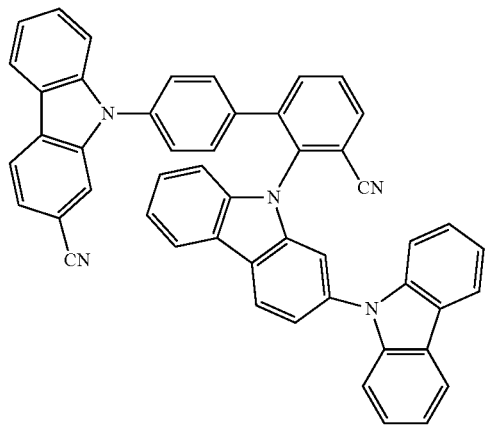
372
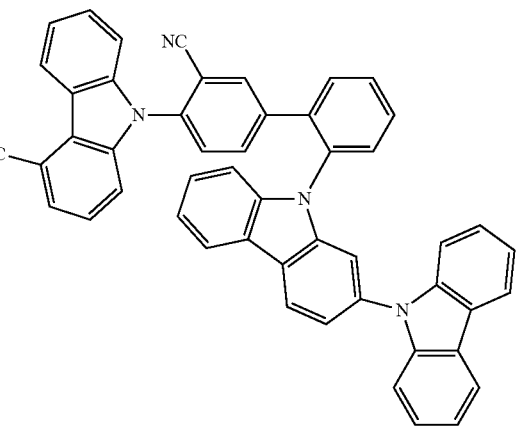
373
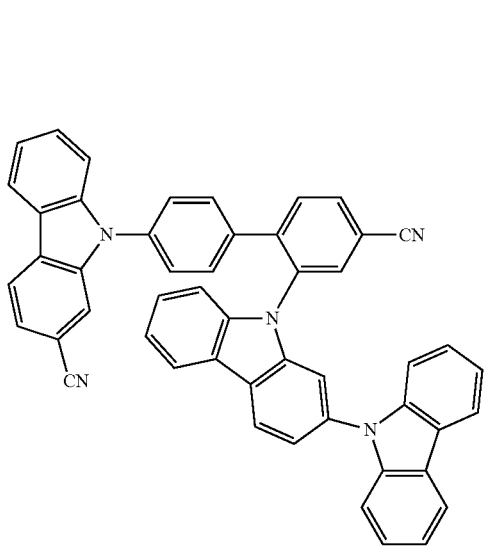
370
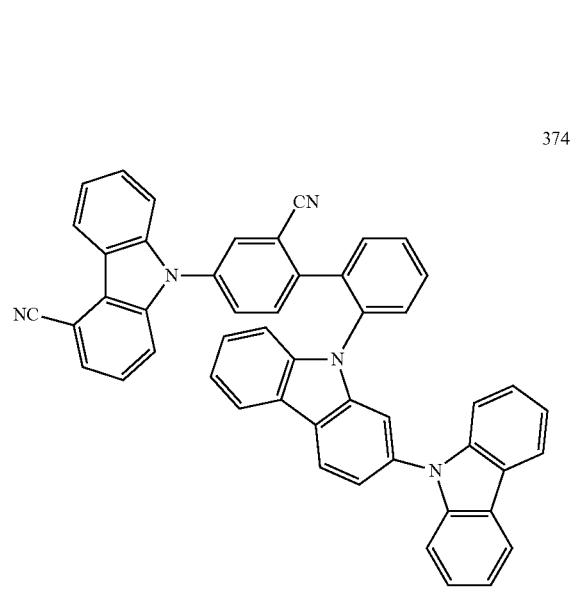
374
371

375
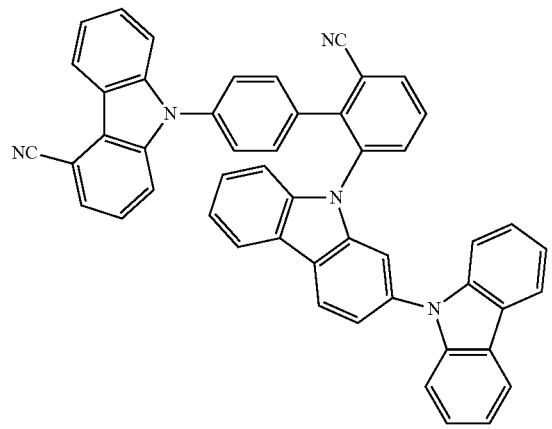
376
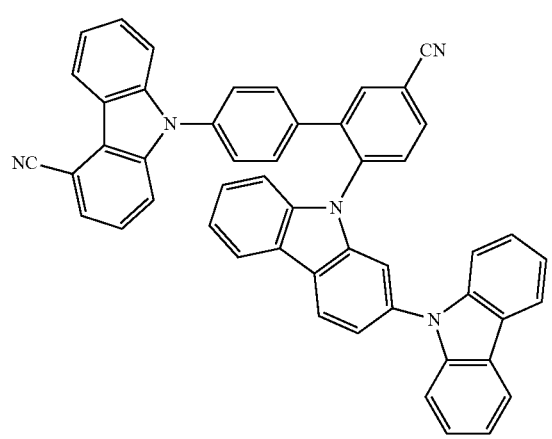
377
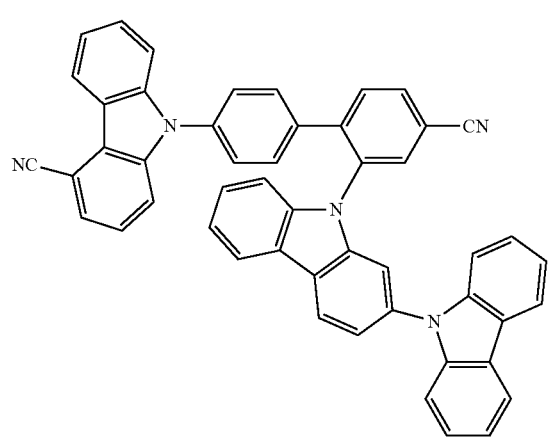
378
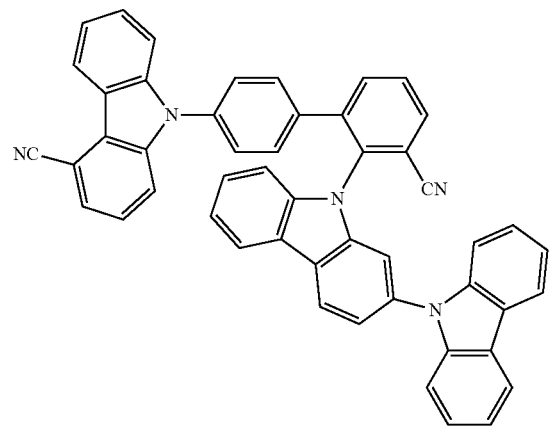
379
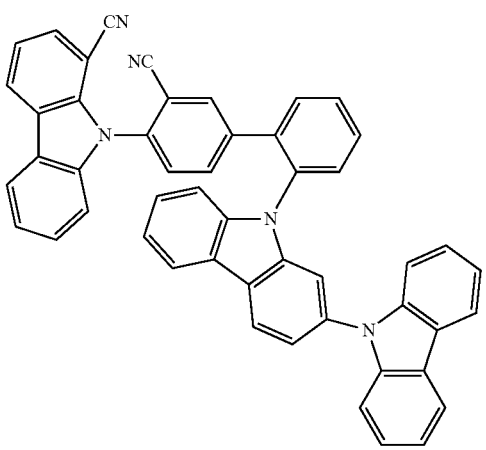
380
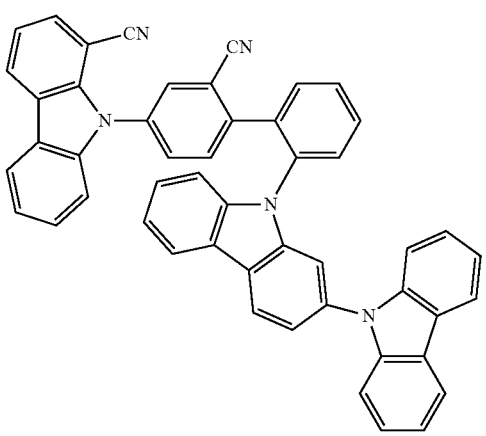

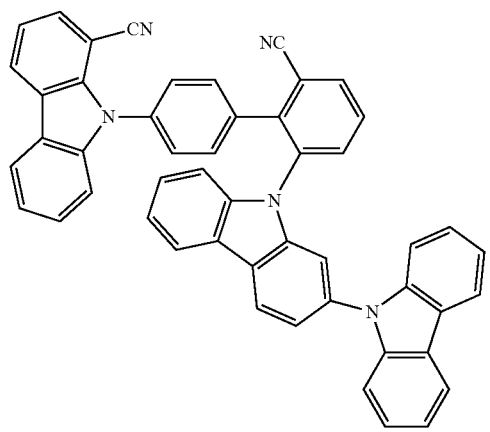
381
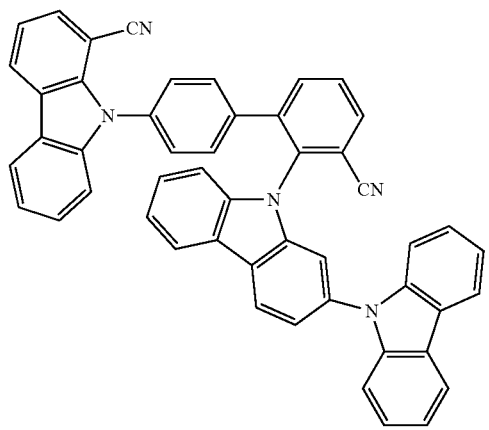
384
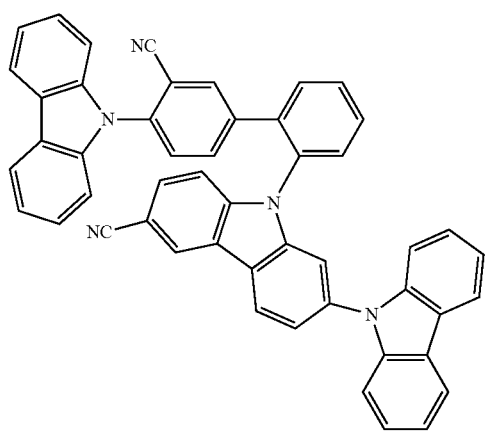
385
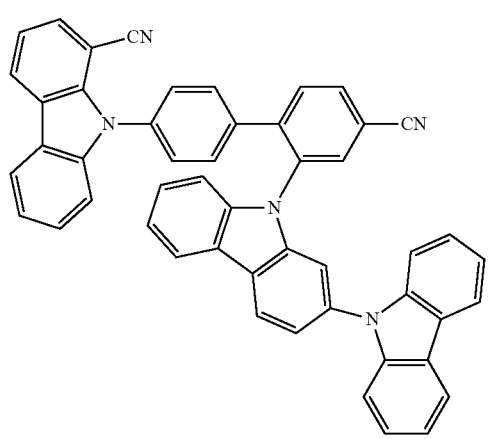
382
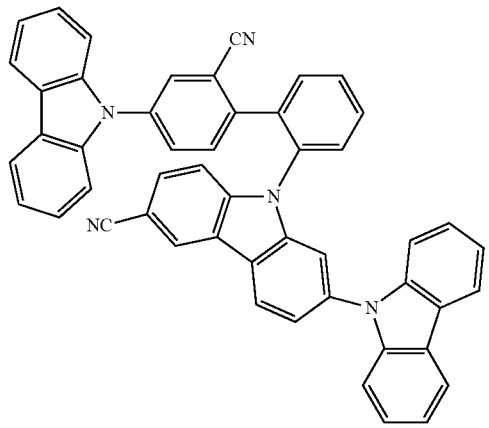
386
383

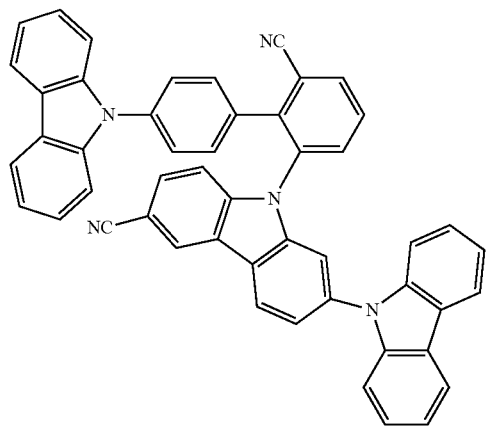
387
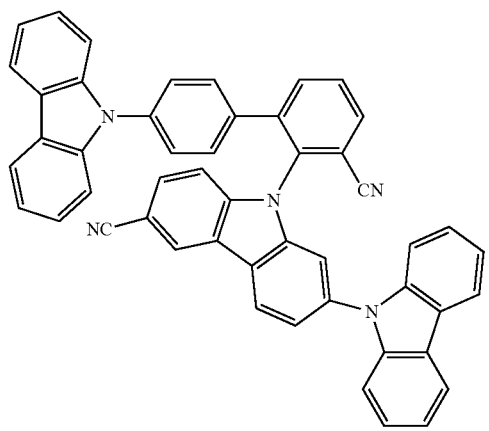
390
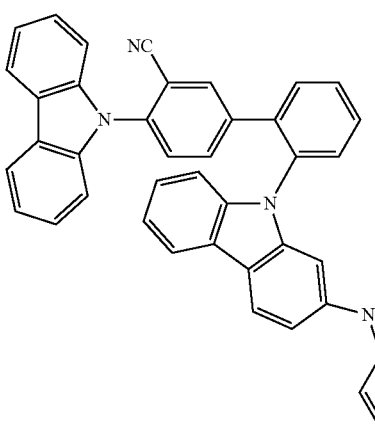
391
388
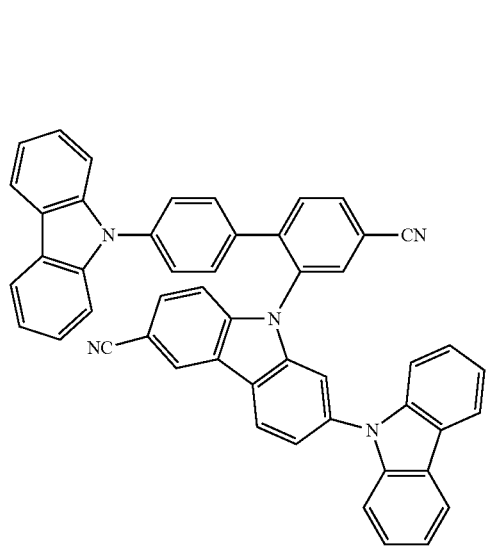
389
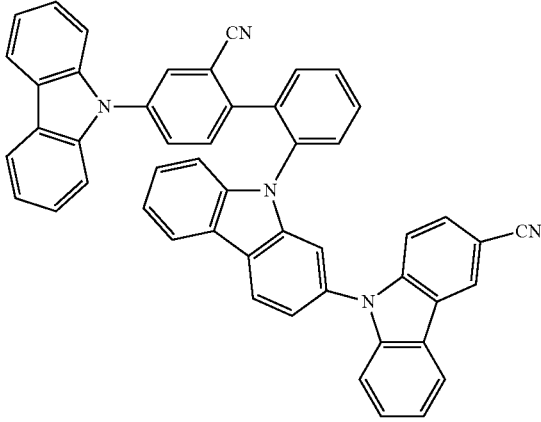
392

393
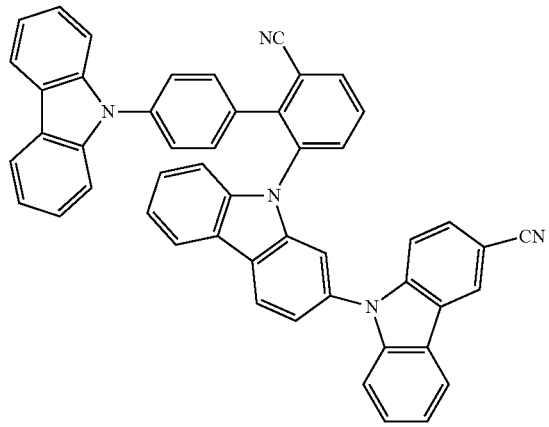
396
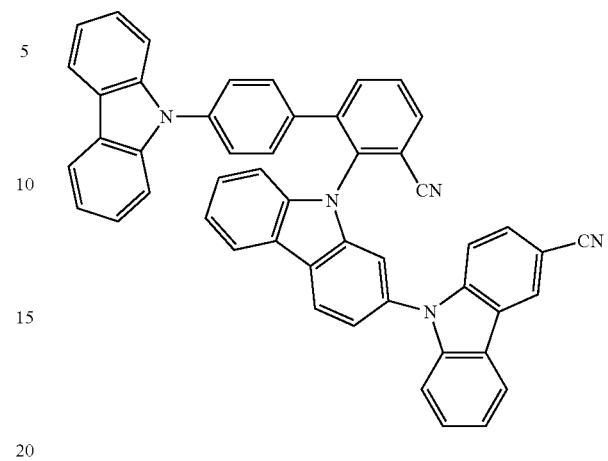
394
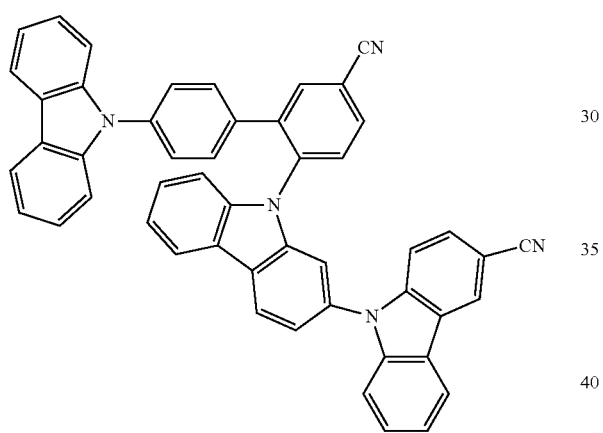
397
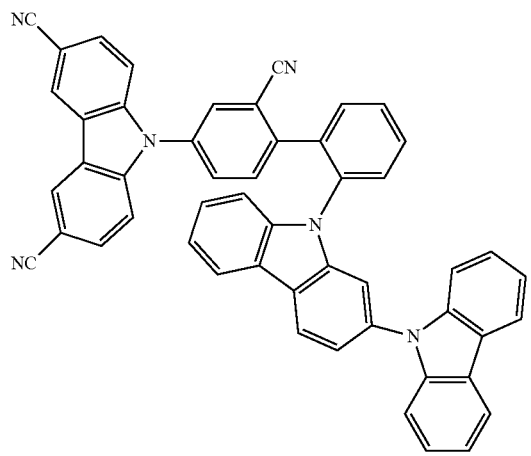
395
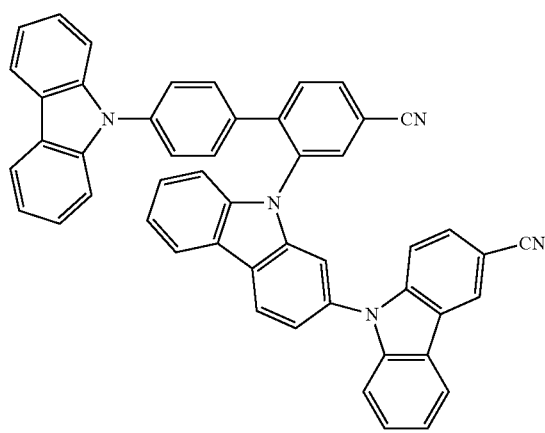
398
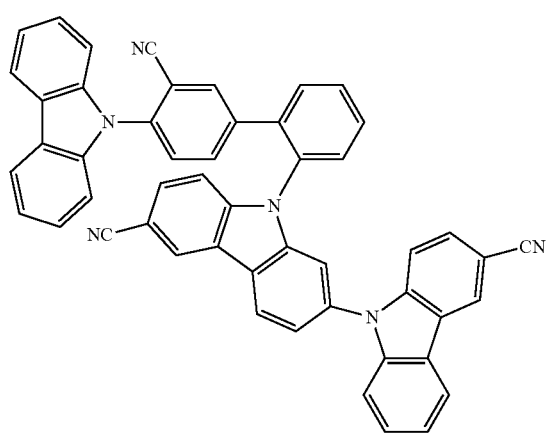

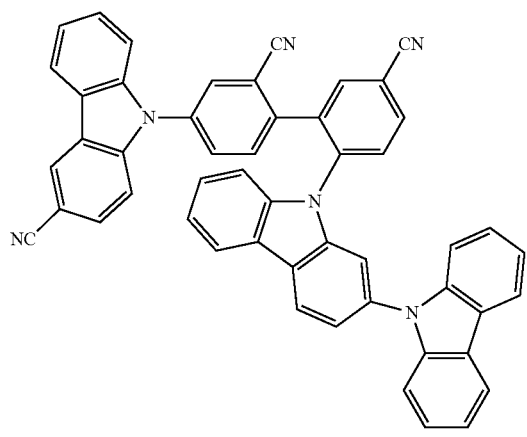
399
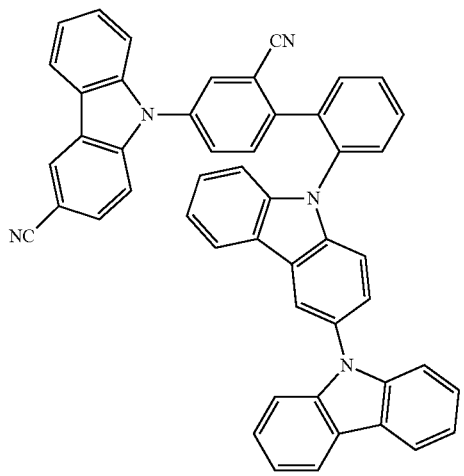
402
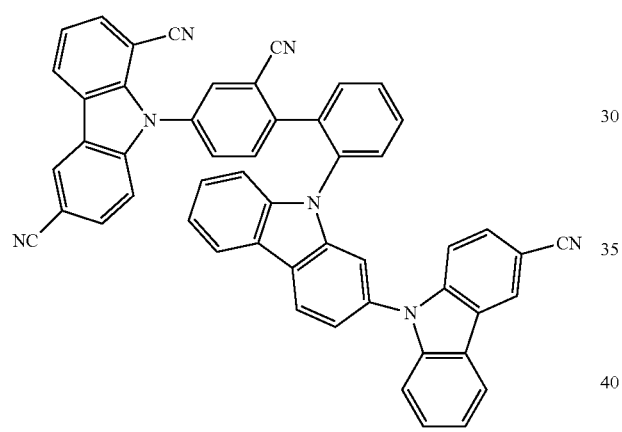
400
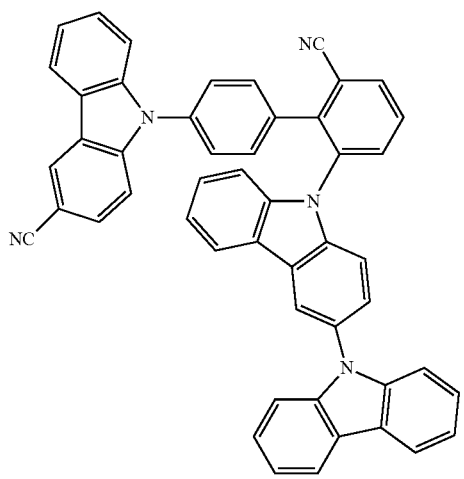
403
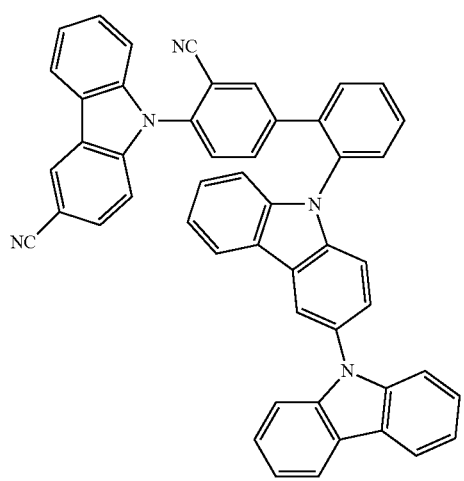
401
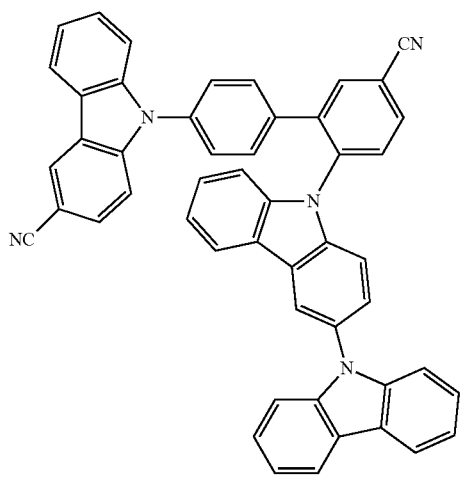
404

-continued
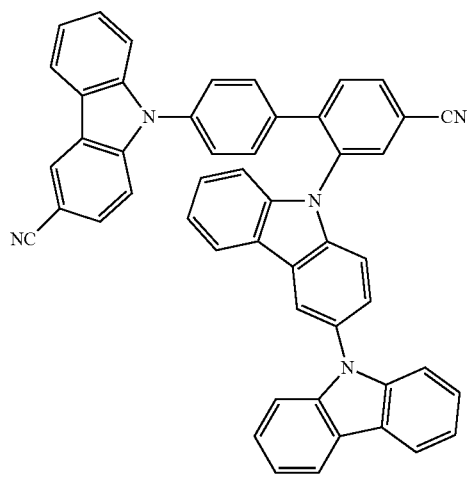
405
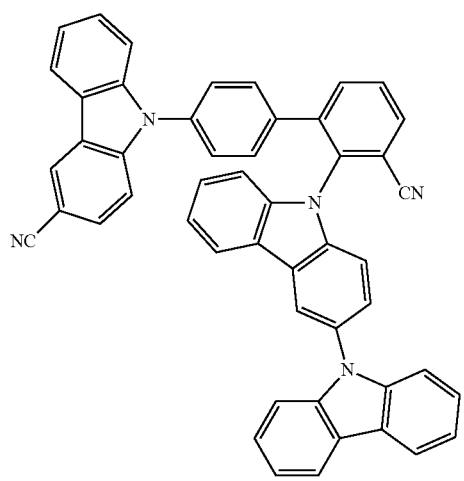
406
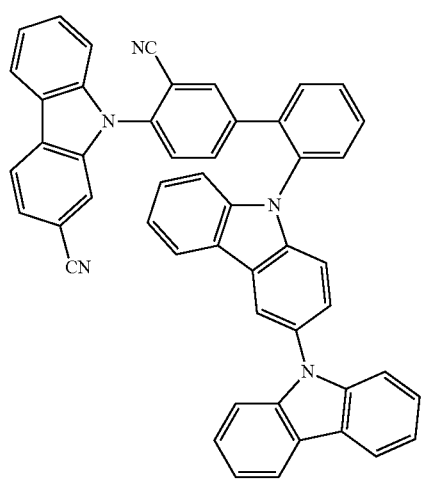
407
-continued
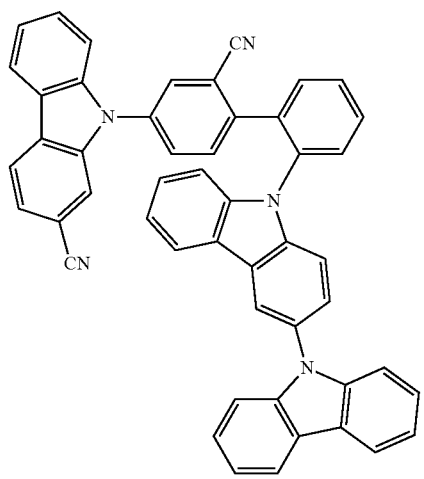
408
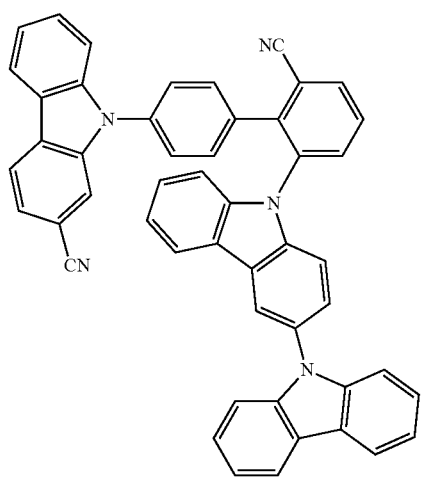
409
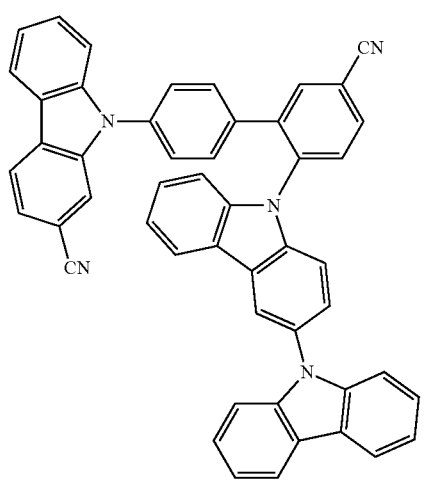
410

-continued
411
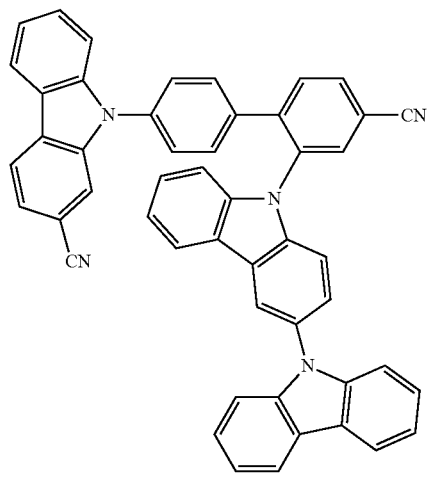
412
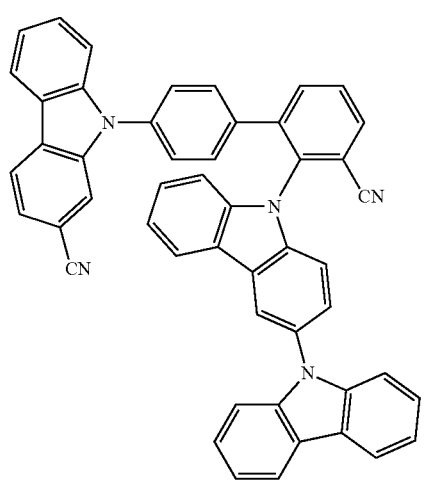
413
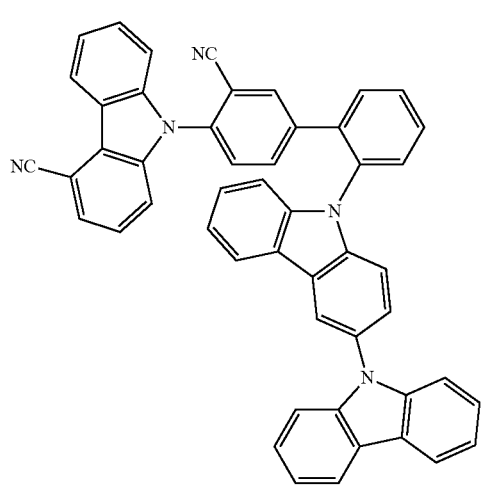
-continued
414
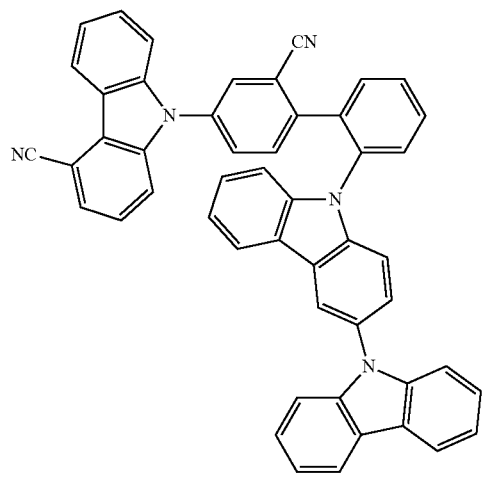
415
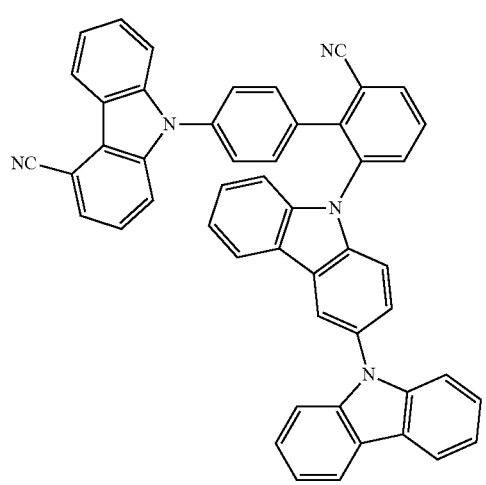
416
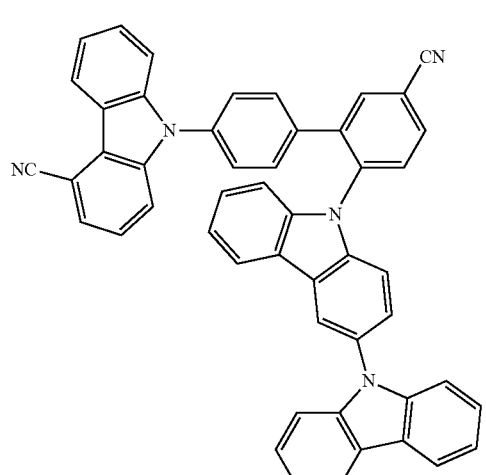

165
-continued
417
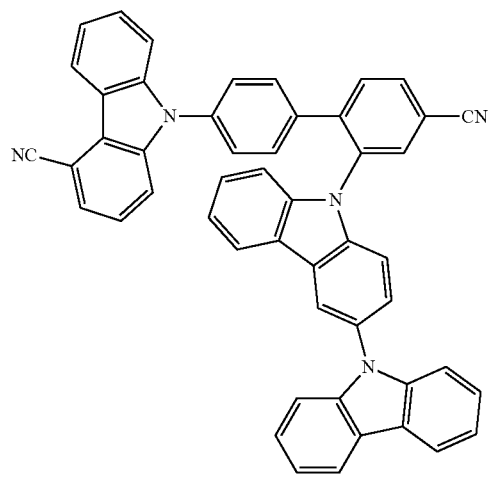
418
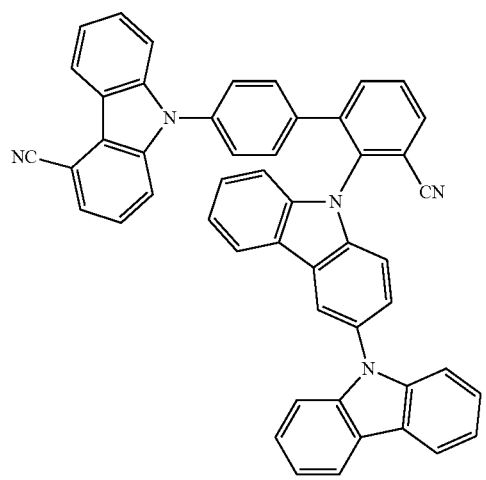
419
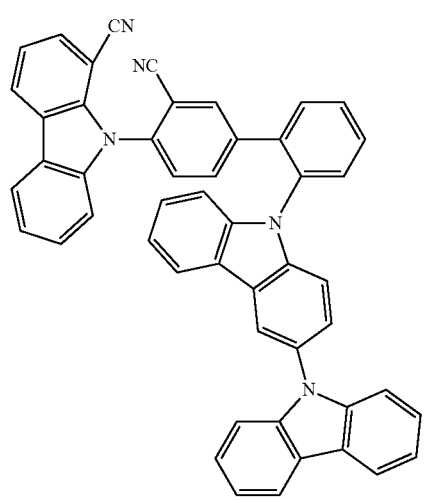
166
-continued
420
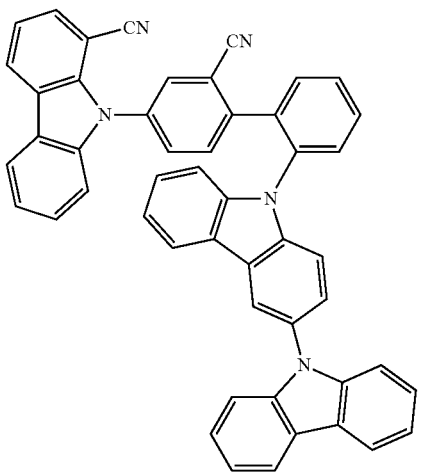
421
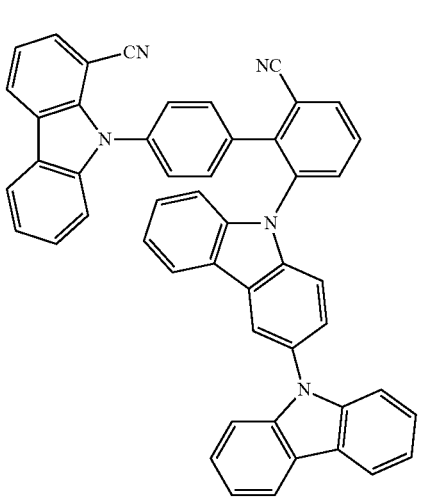
422
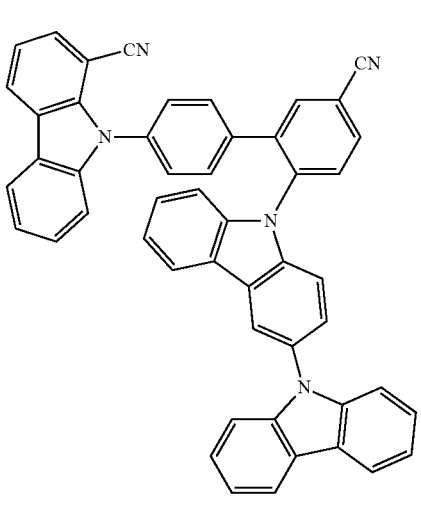

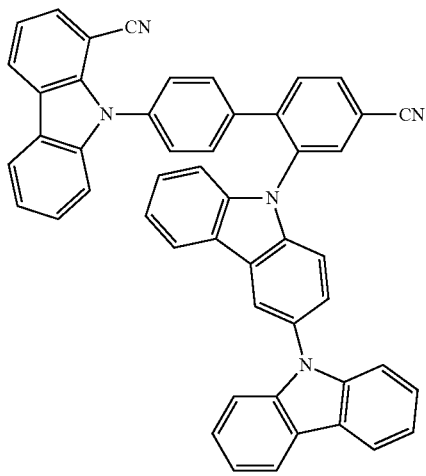
423
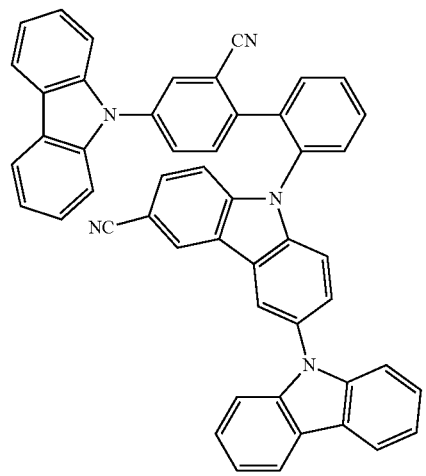
426
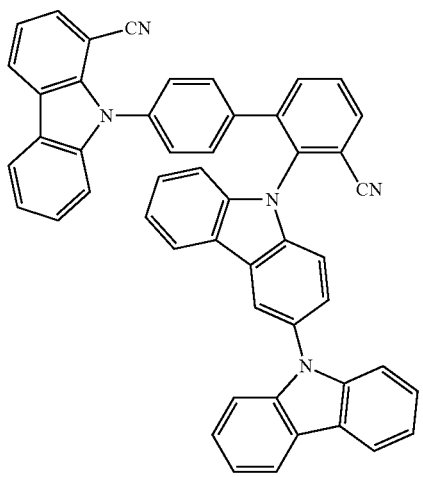
424
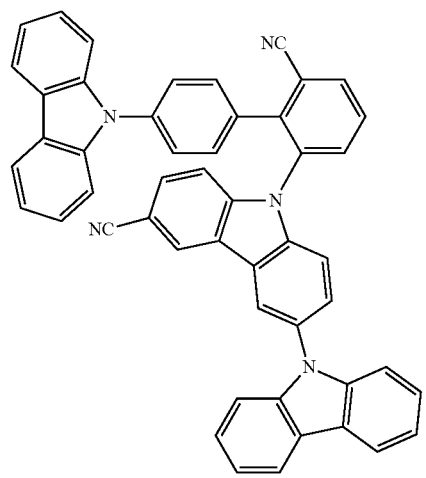
427
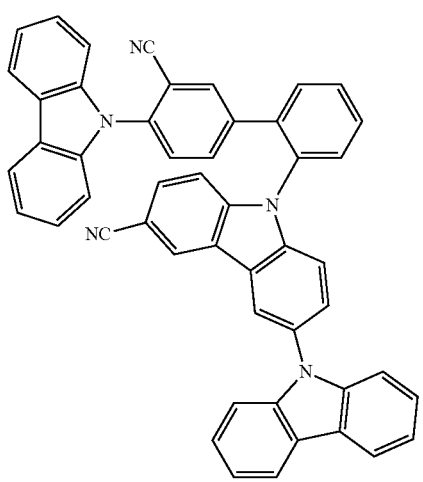
425
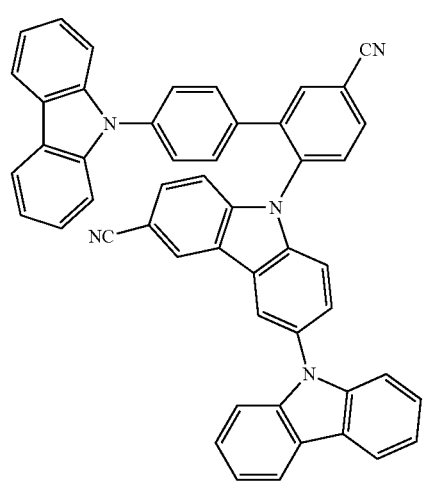
428

169
-continued
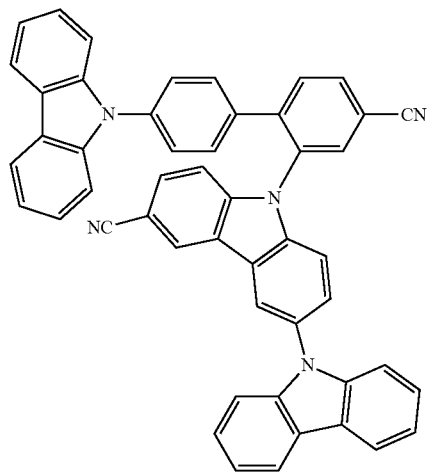
429
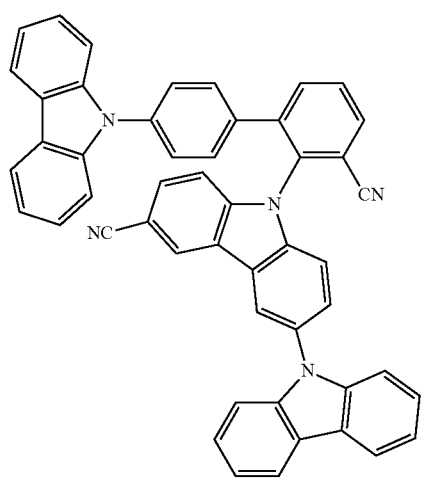
430
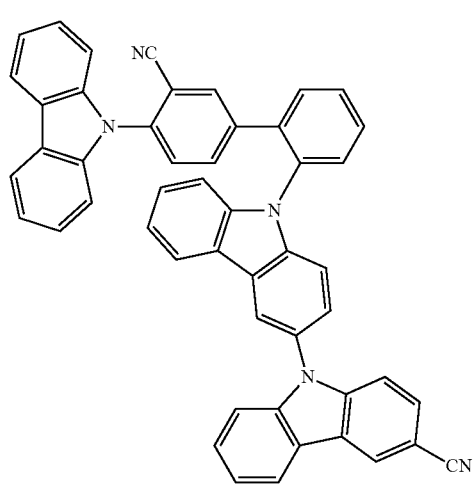
431
170
-continued
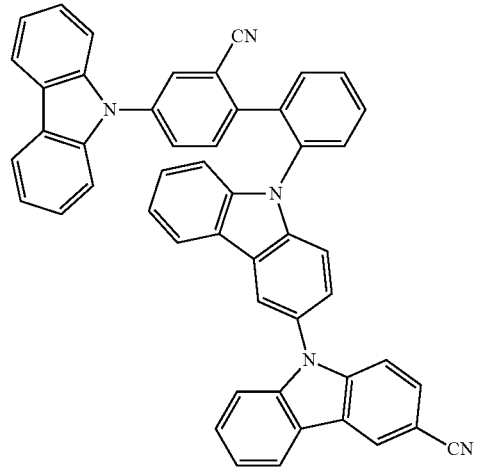
432
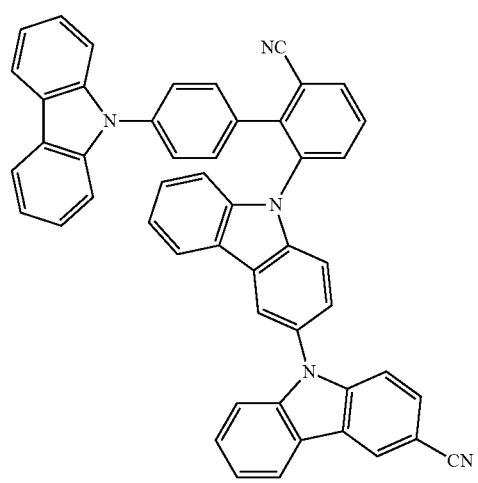
433
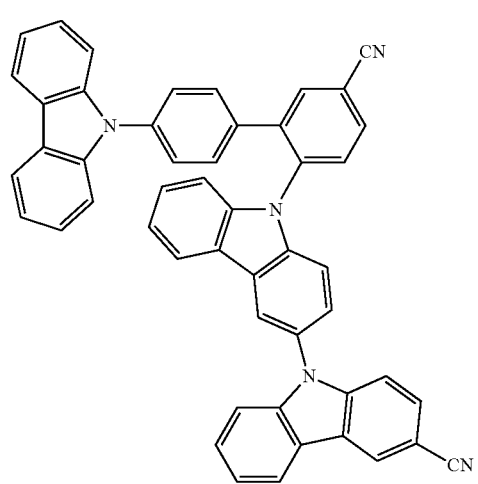
434

171
-continued
435
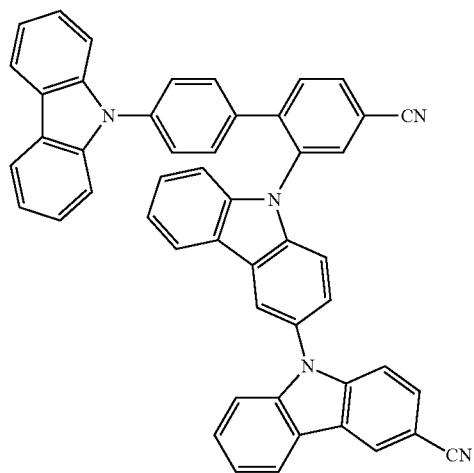
436
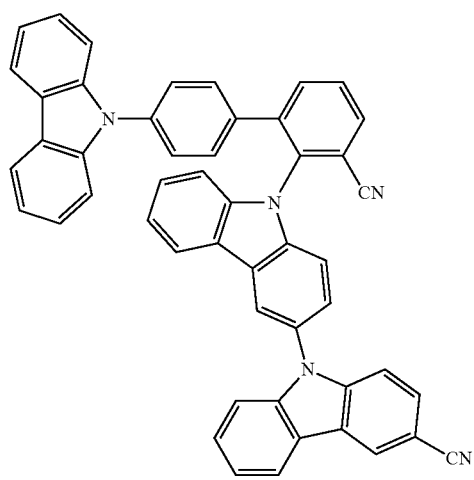
437
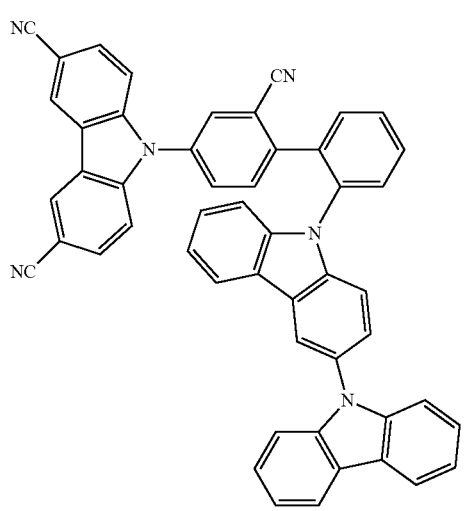
172
-continued
438
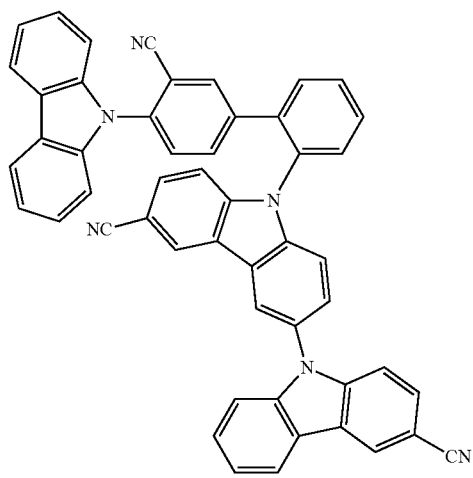
439
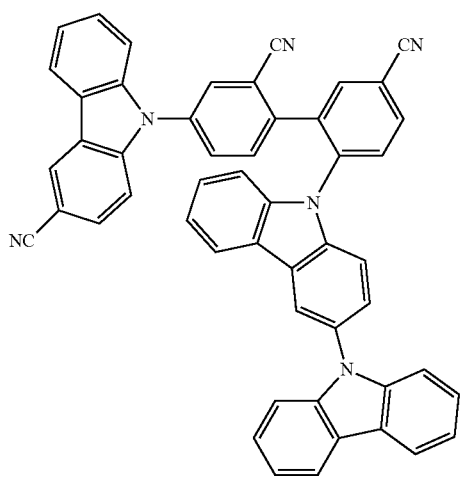
440
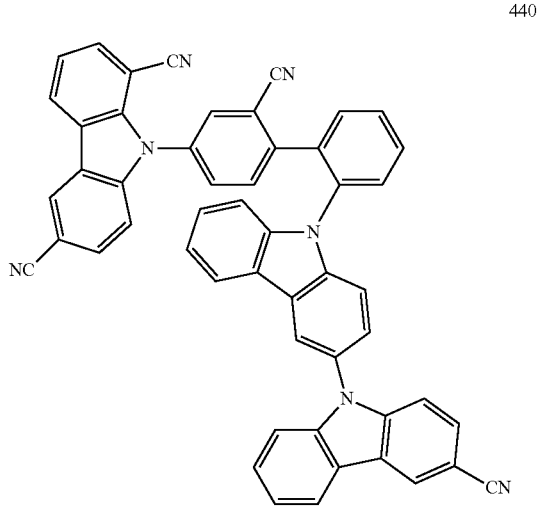

441
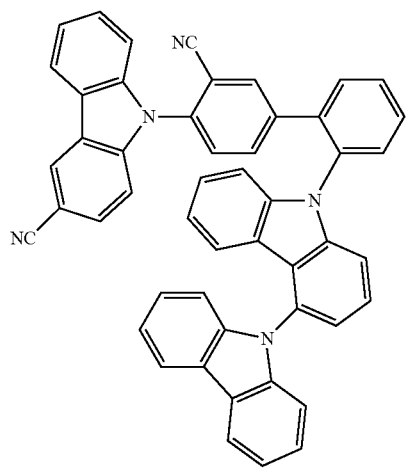
442
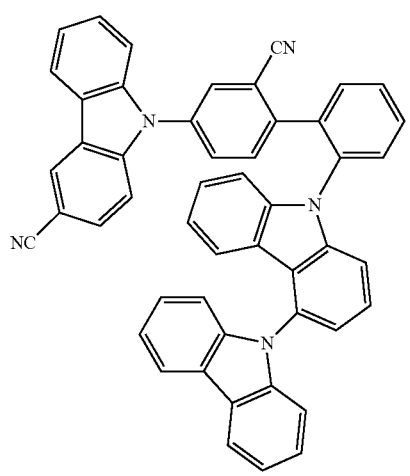
443
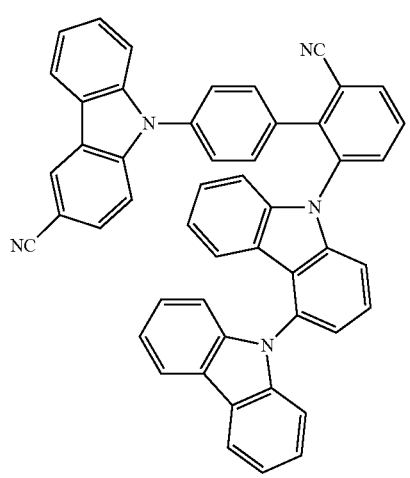
444
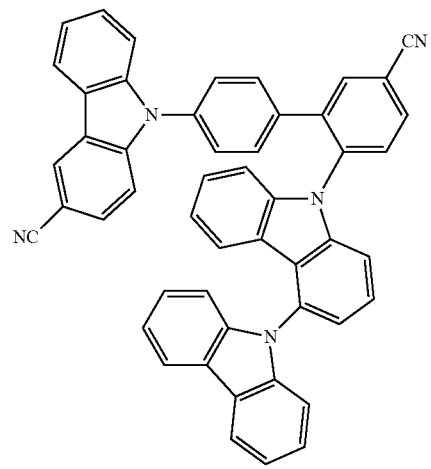
445
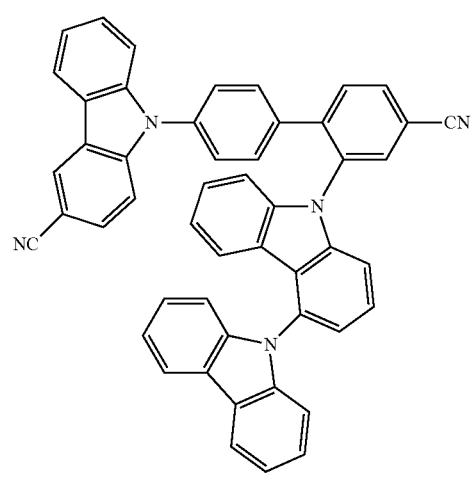
446
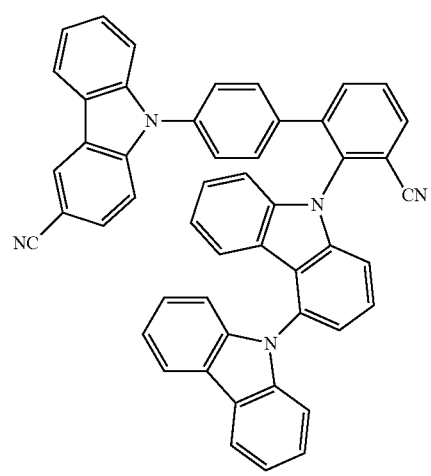

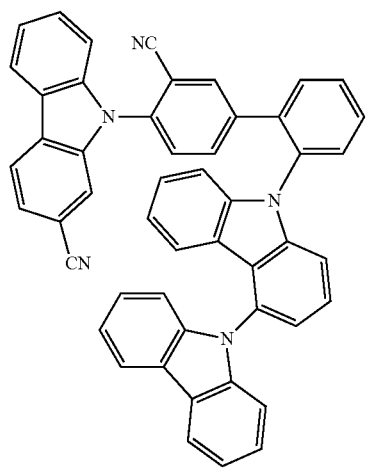
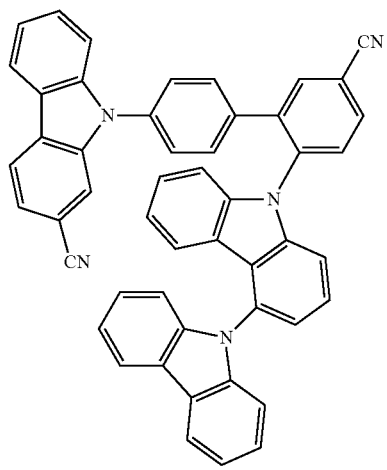

453
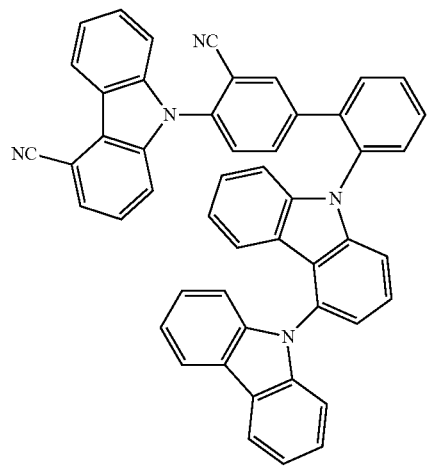
454
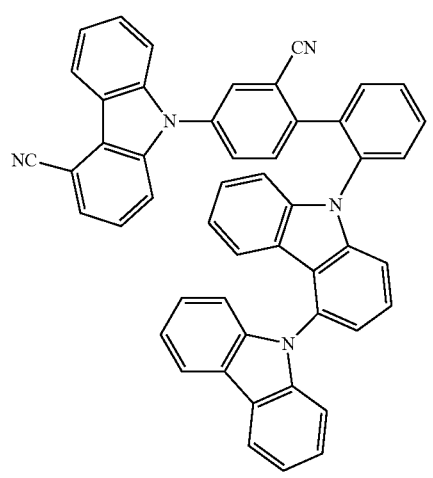
455
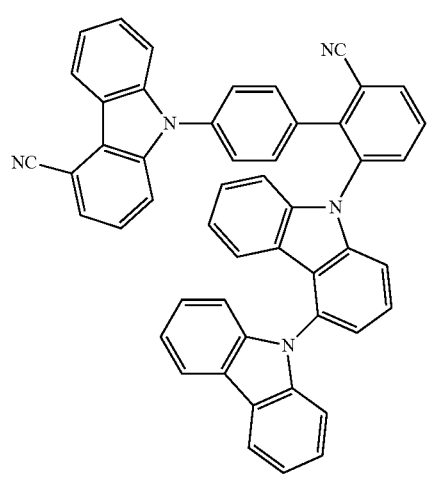
456
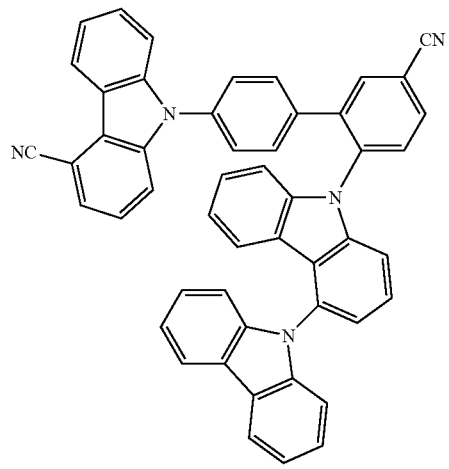
457
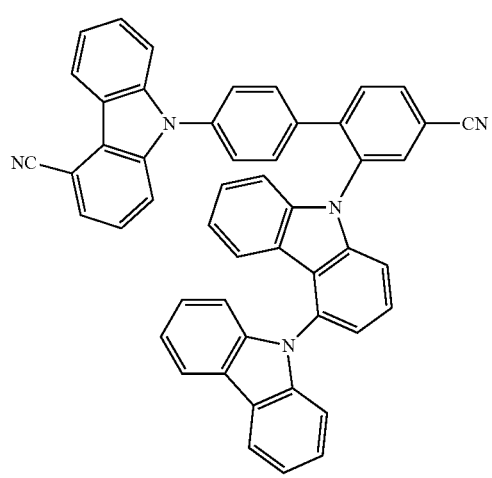
458
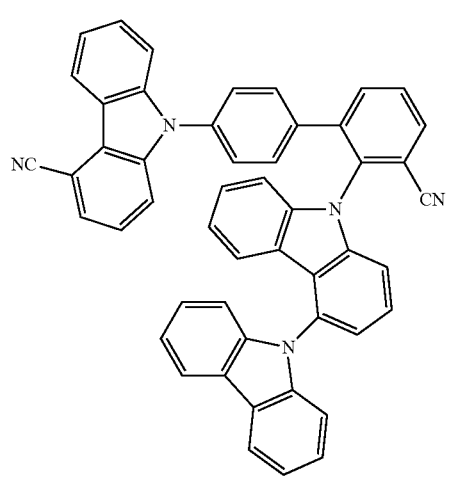

459
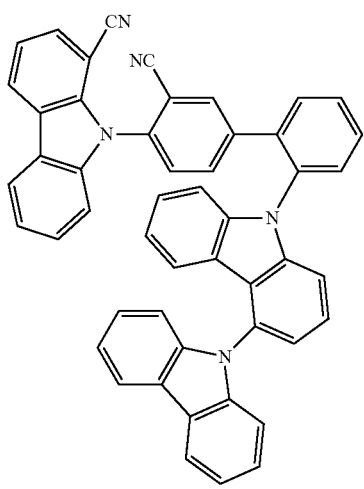
460
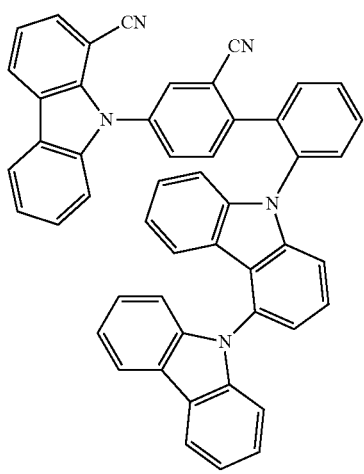
461
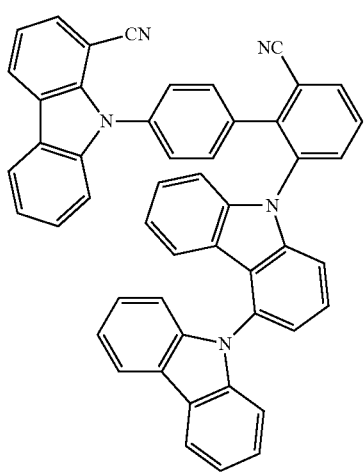
462
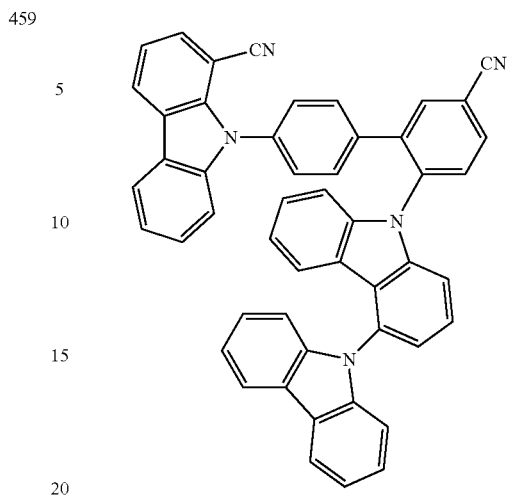
463
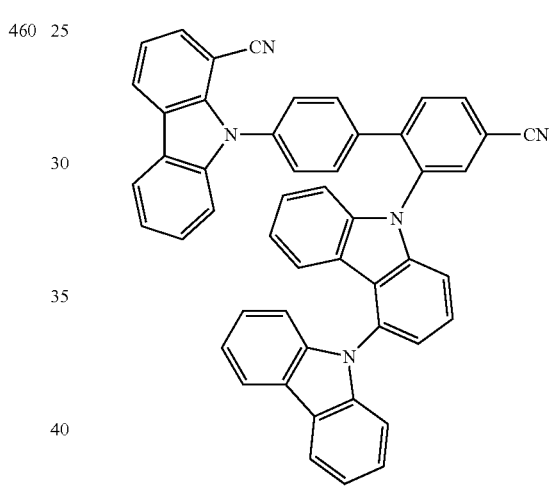
464
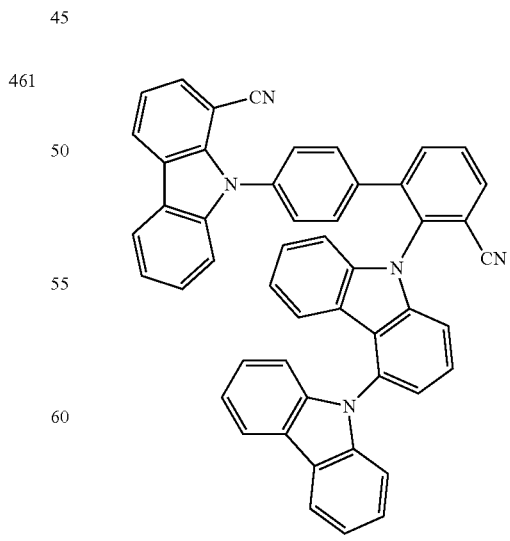

181
-continued
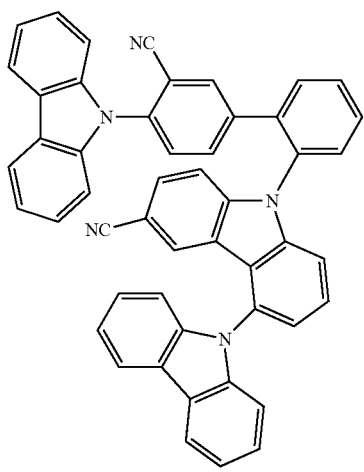
465
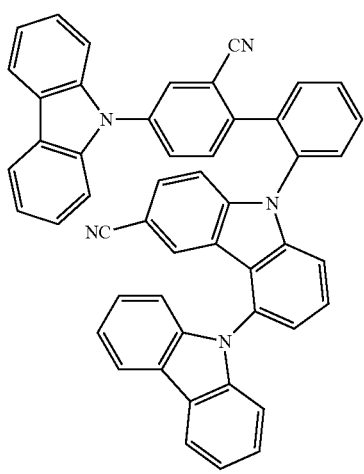
466
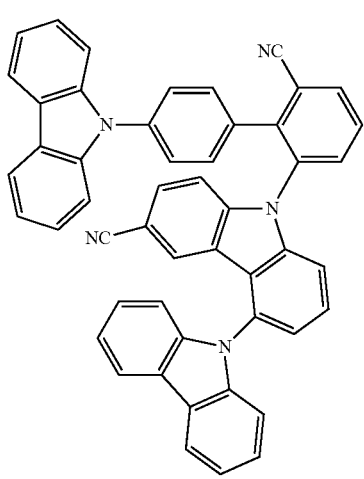
467
182
-continued
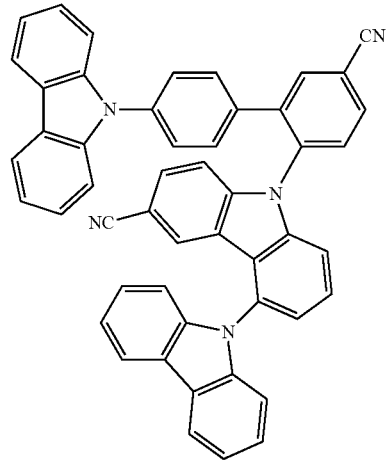
468
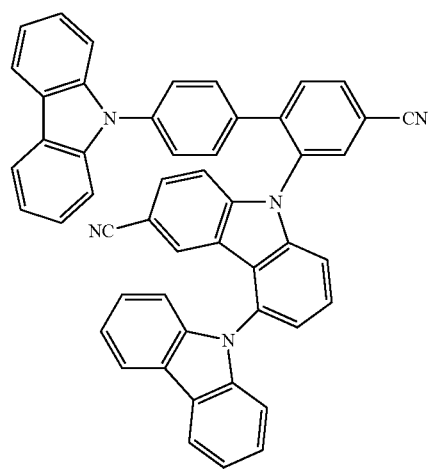
469
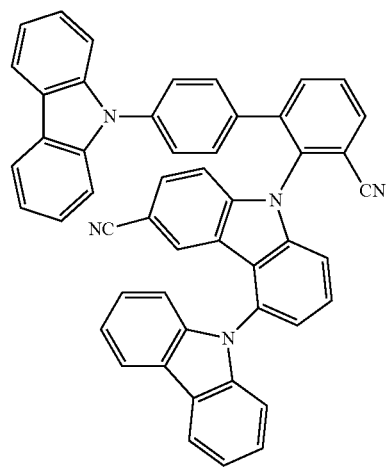
470

471
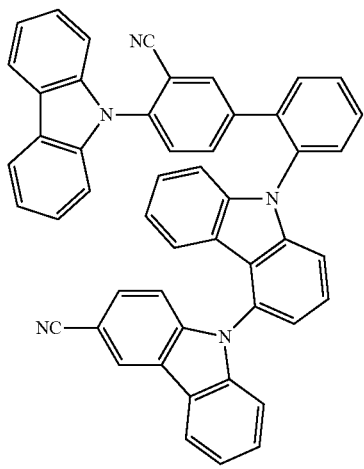
472
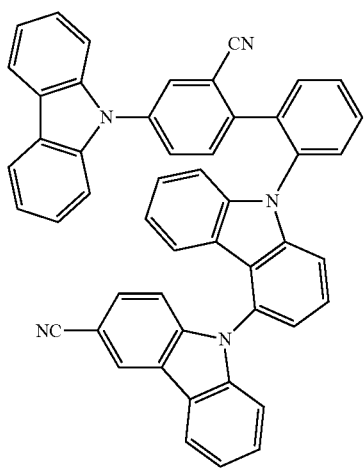
473
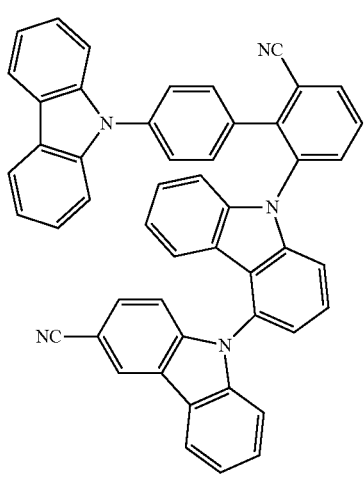
474
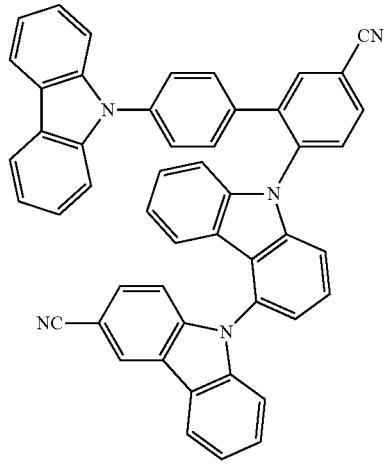
475
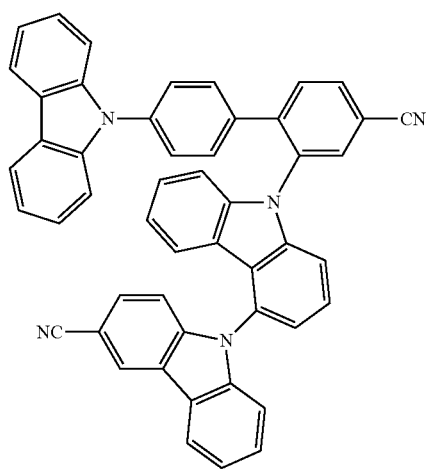
476
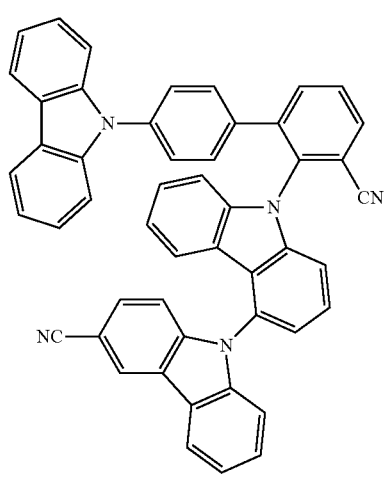

477
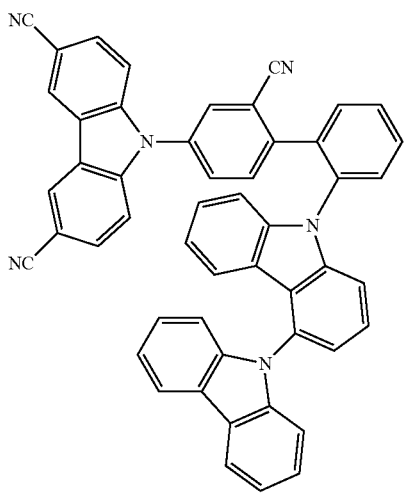
478
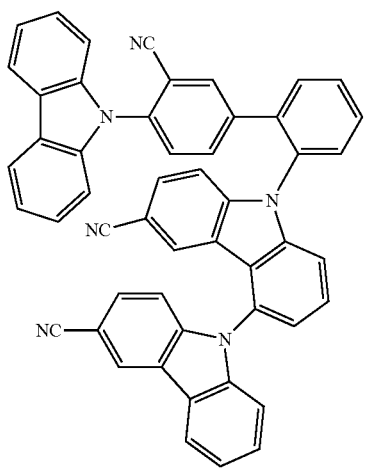
479
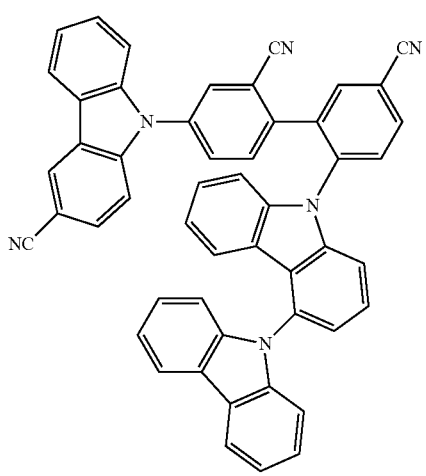
480
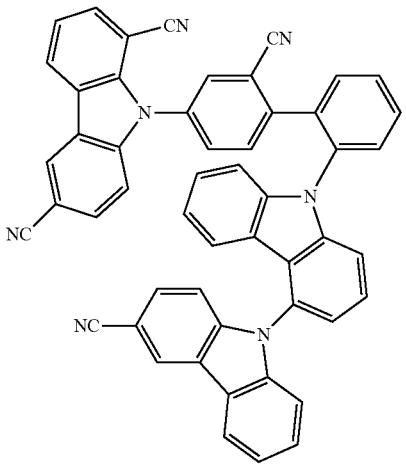
481
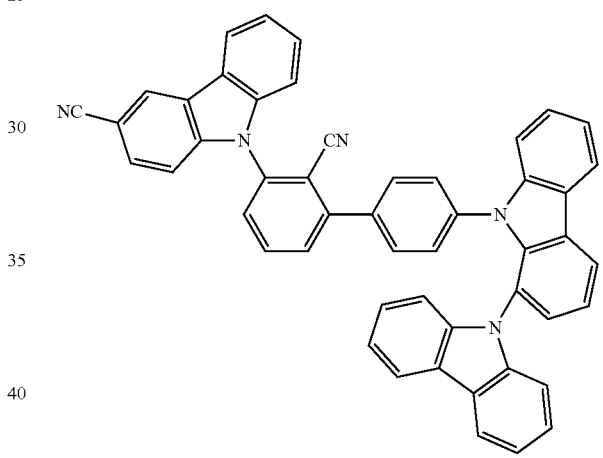
482
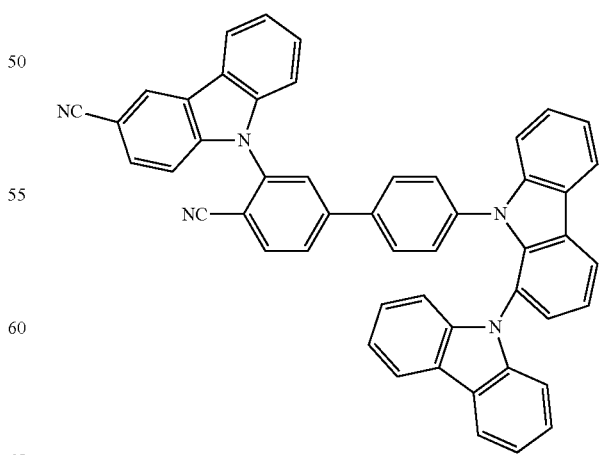

483
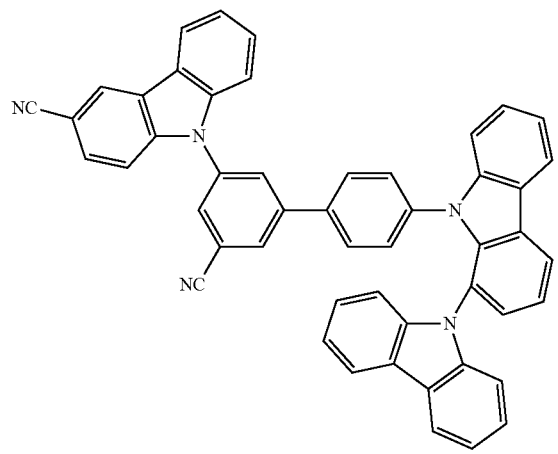
484
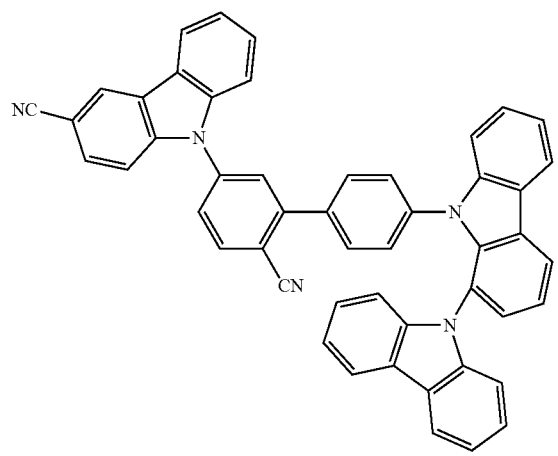
485
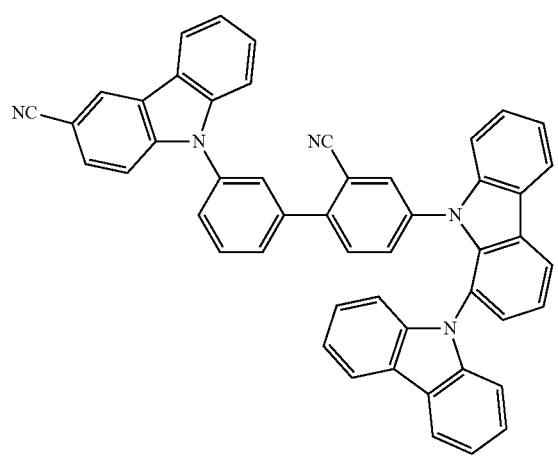
486
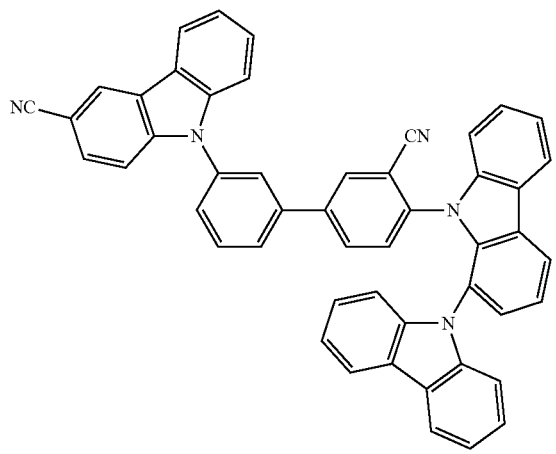
487
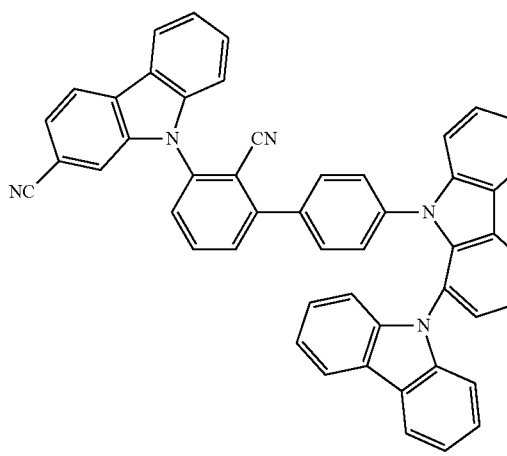
488
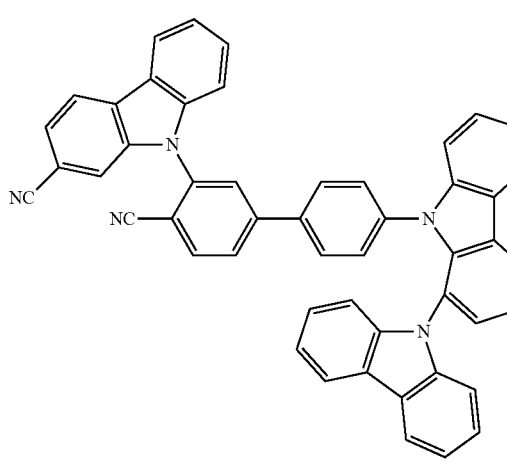

-continued
489
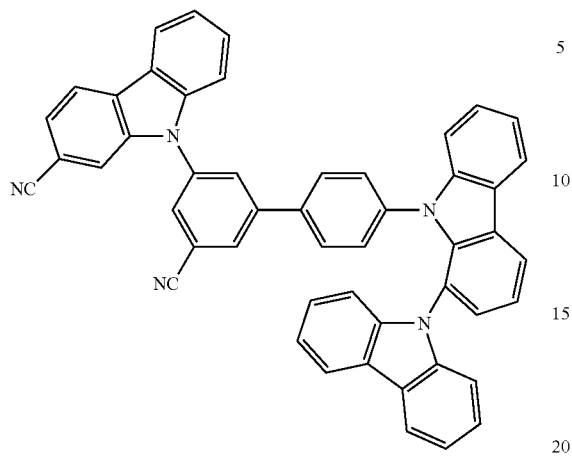
490
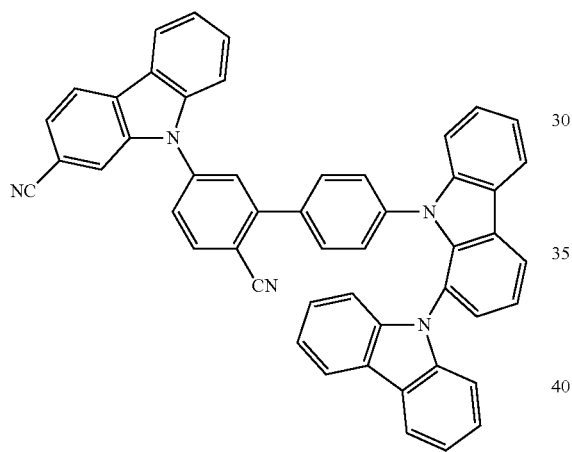
491
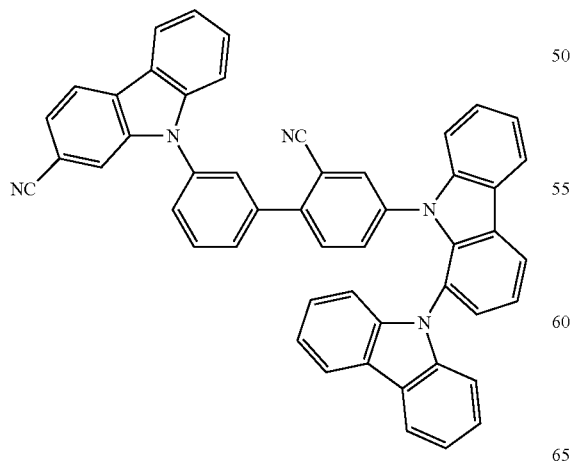
-continued
492
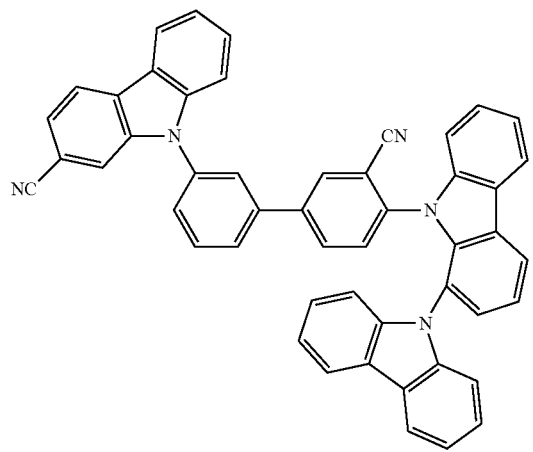
493
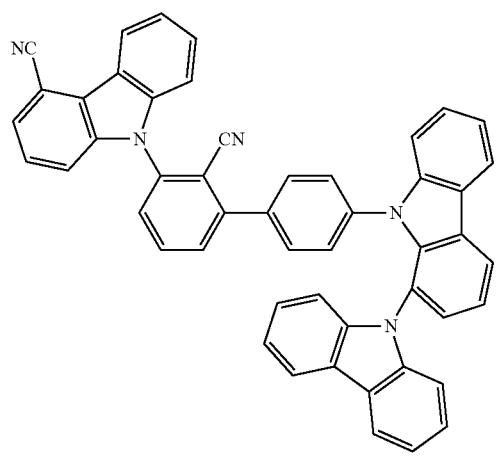
494
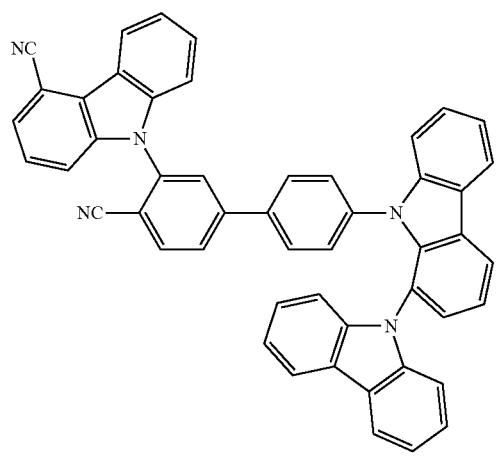

495
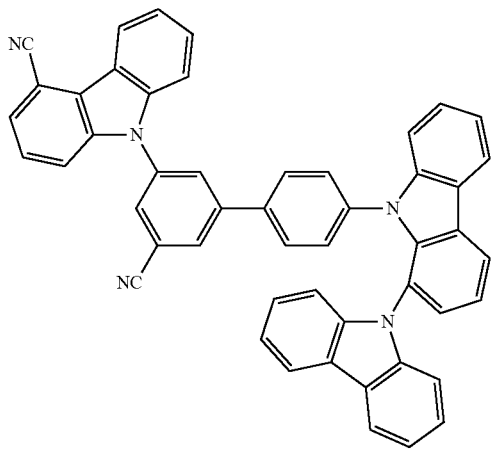
496
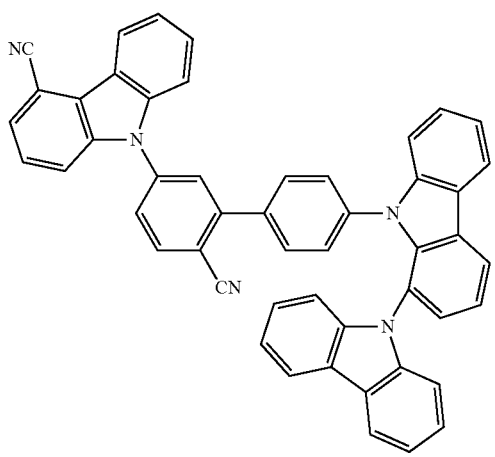
497
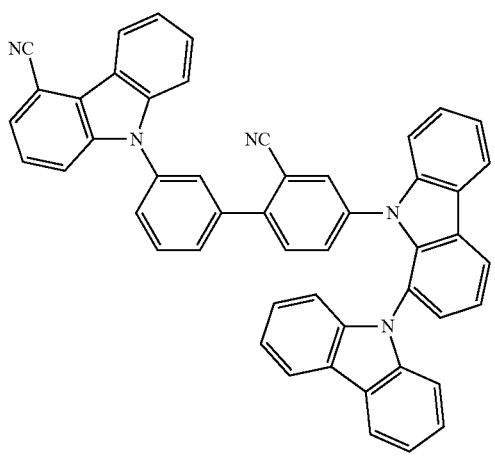
498
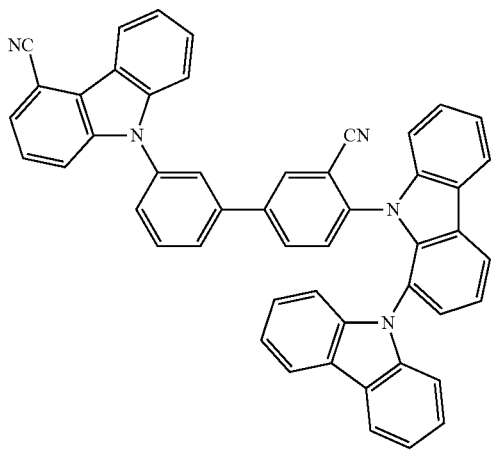
499
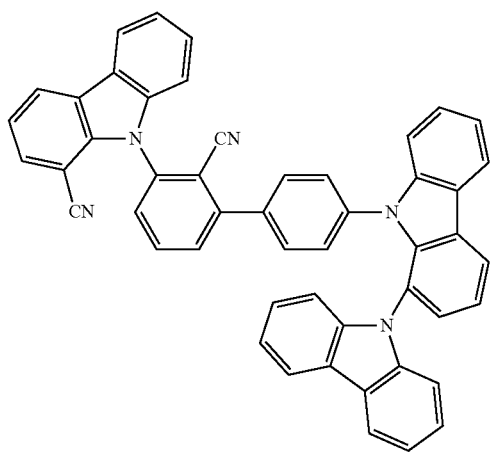
500
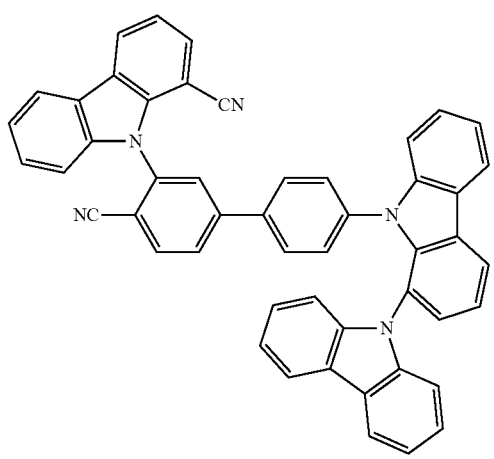

-continued
501
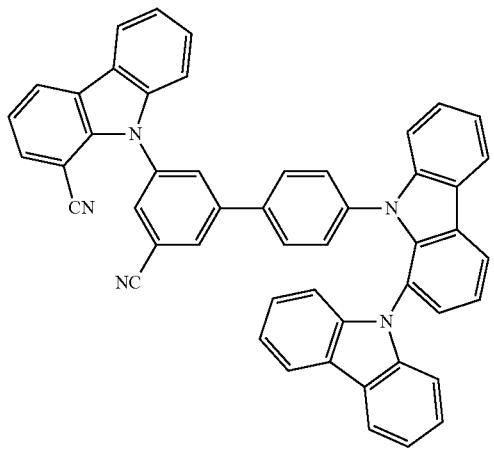
502
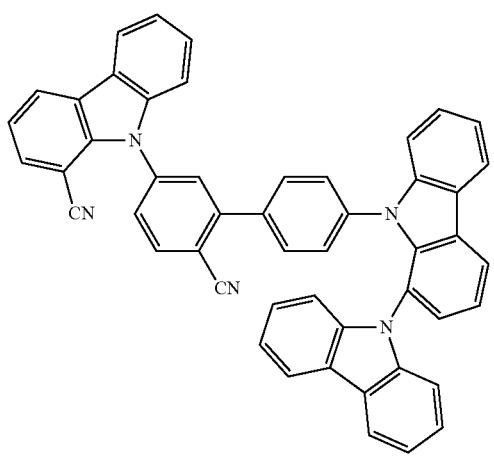
503
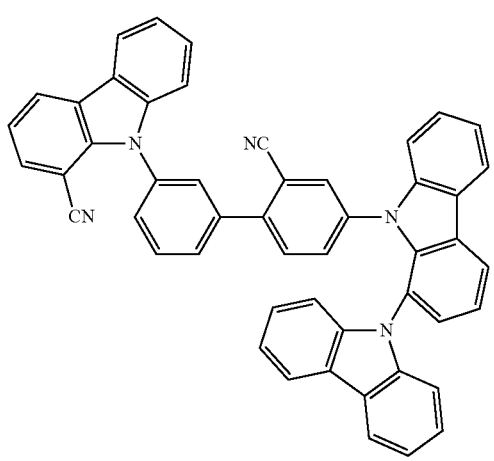
-continued
504
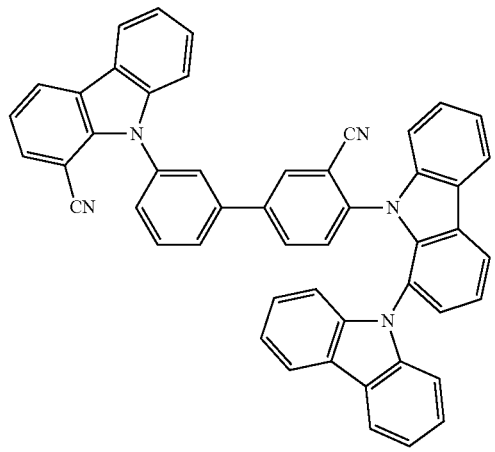
505
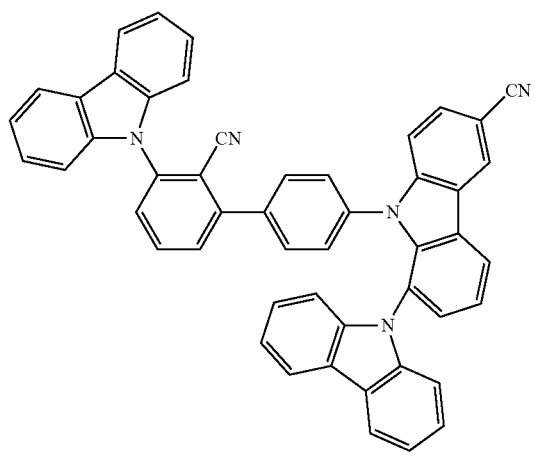
506
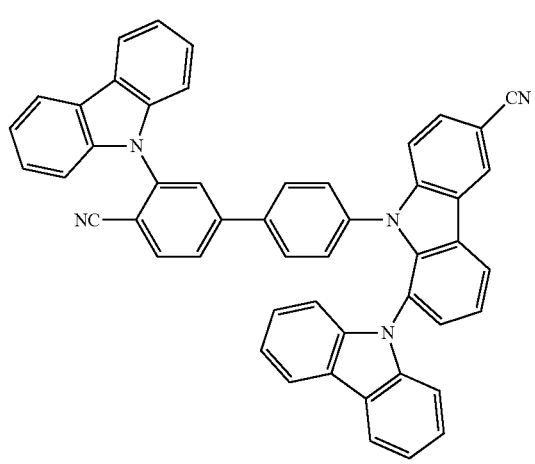

-continued
507
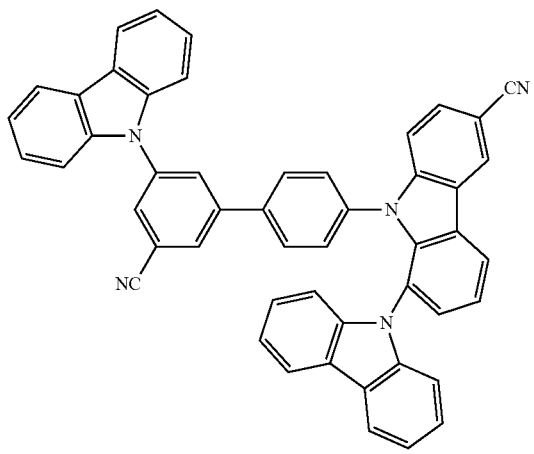
508
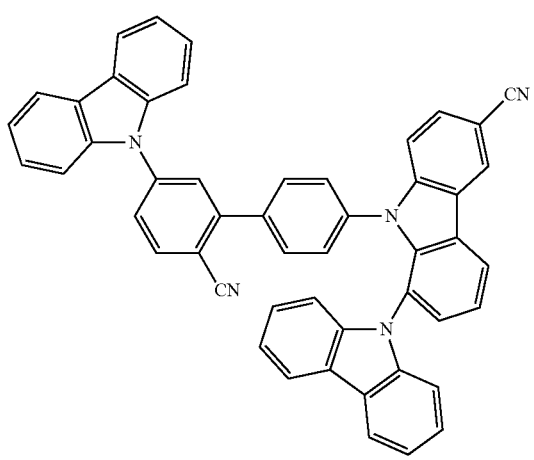
509
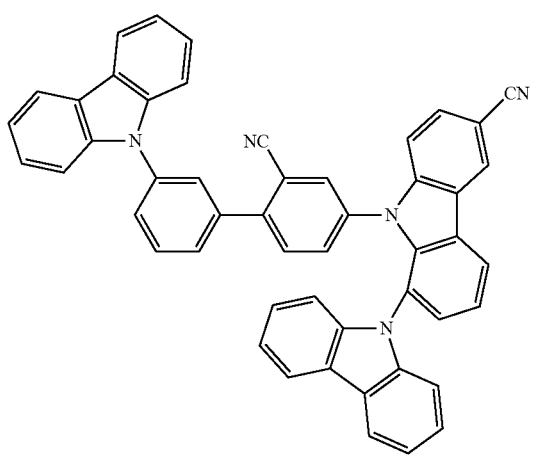
-continued
510
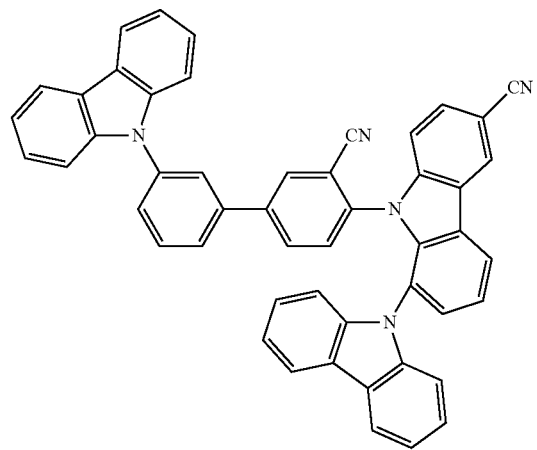
511
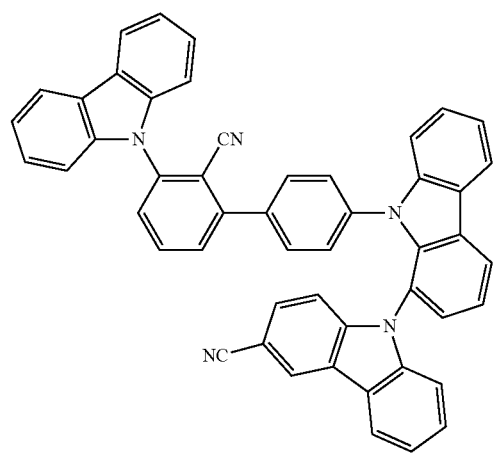
512
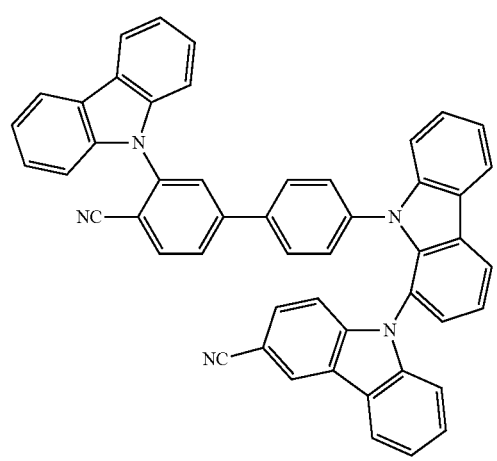

513
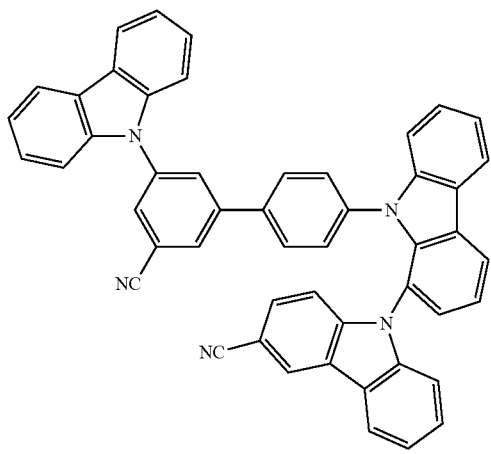
514
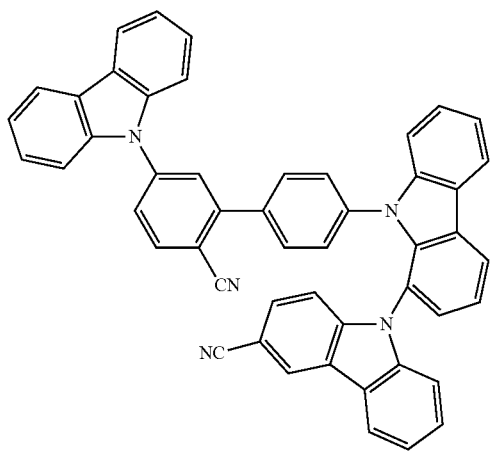
515
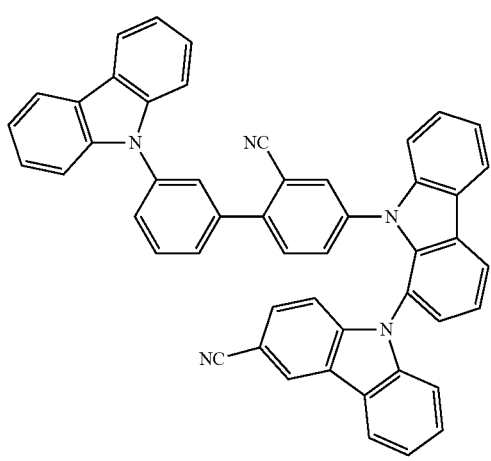
516
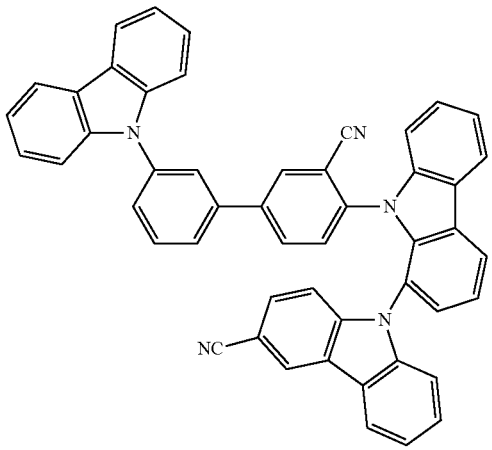
517
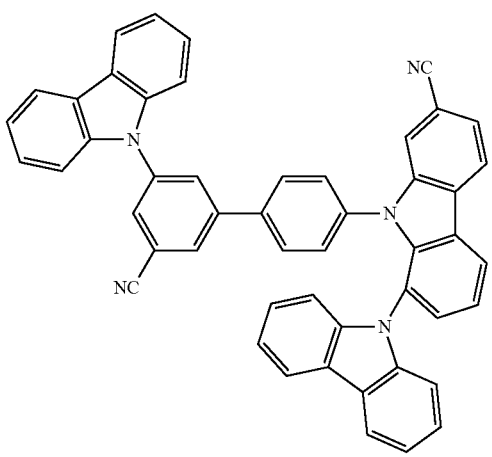
518
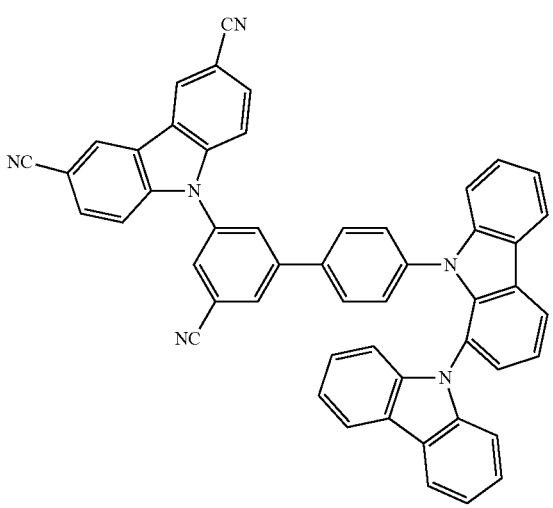

519
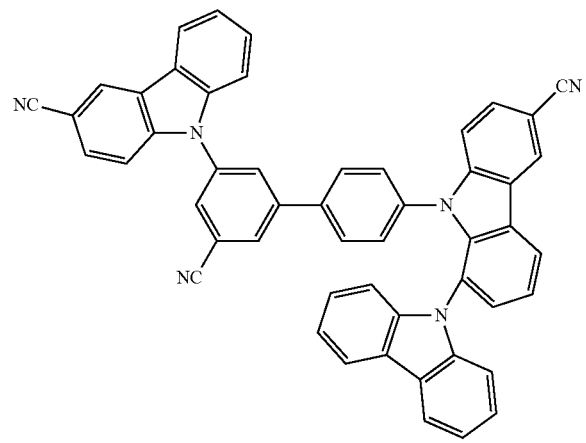
520
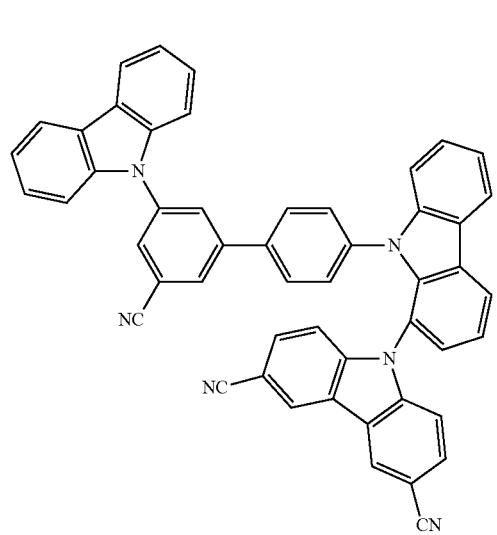
521
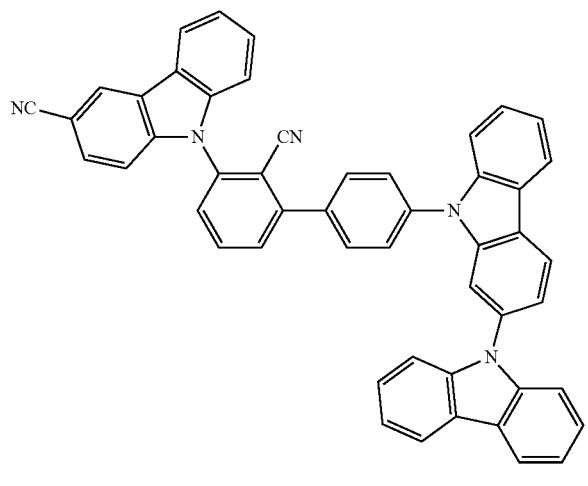
522
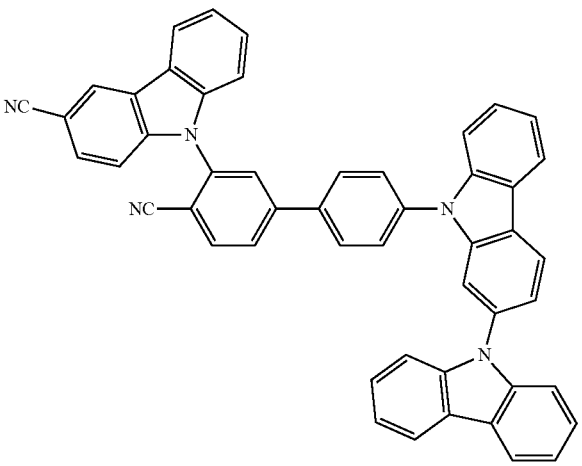
523
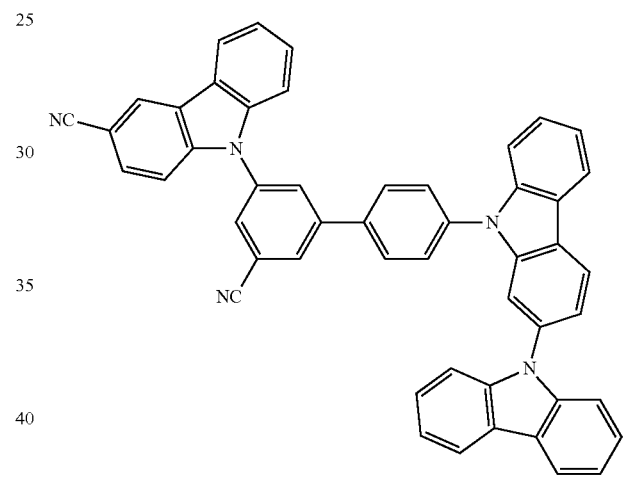
524
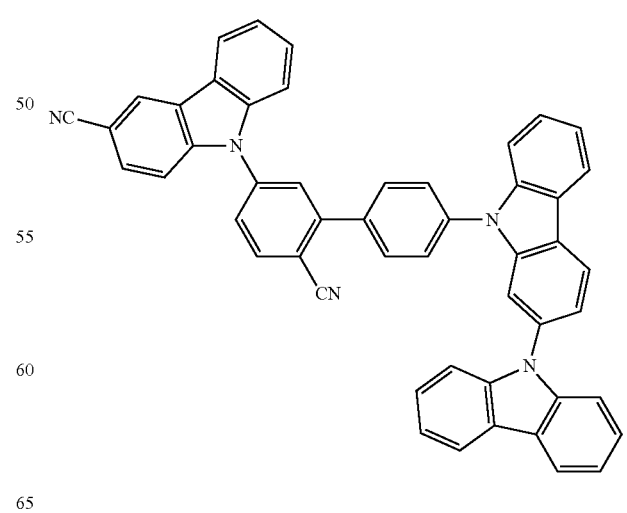

525
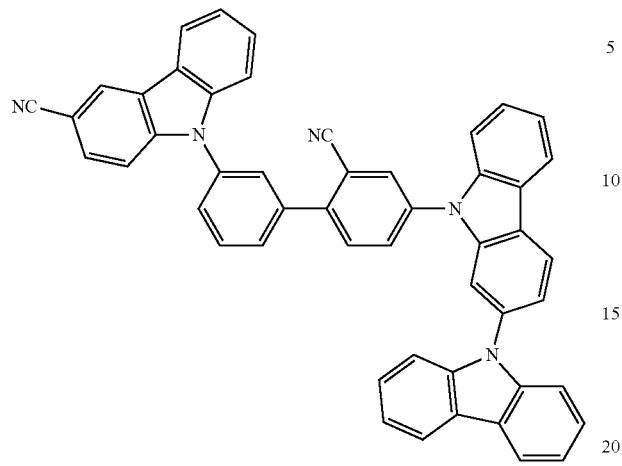
526
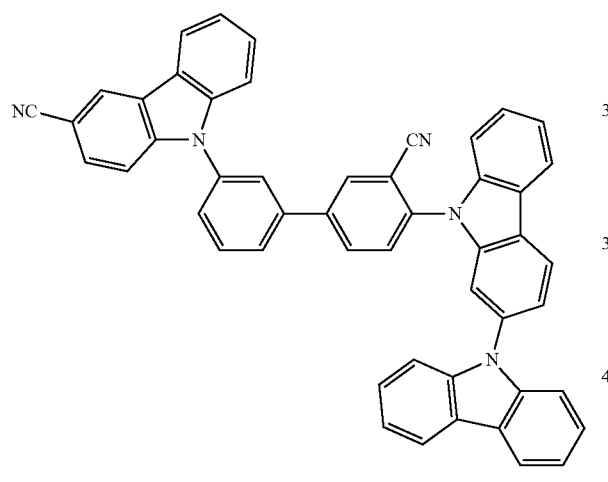
527
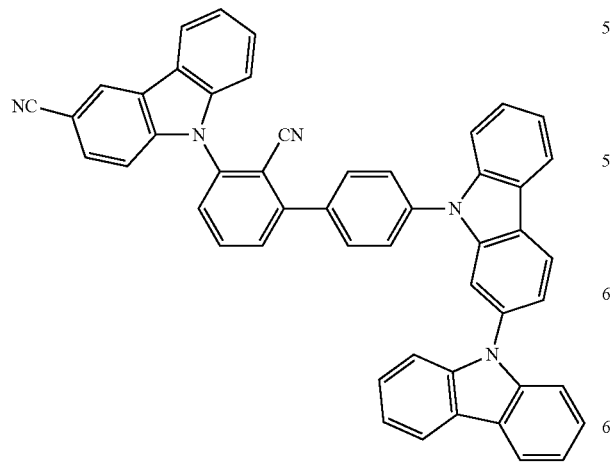
528
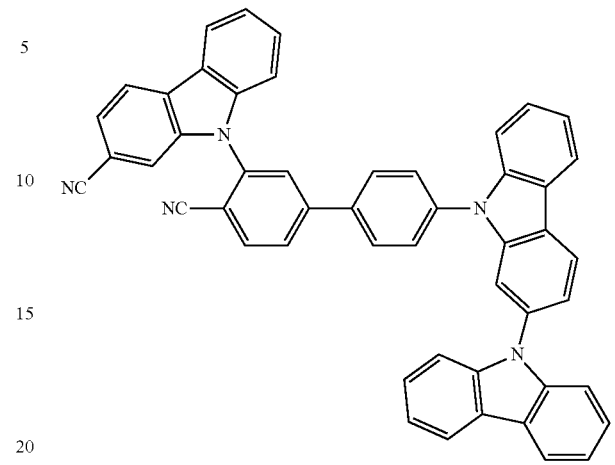
529
530
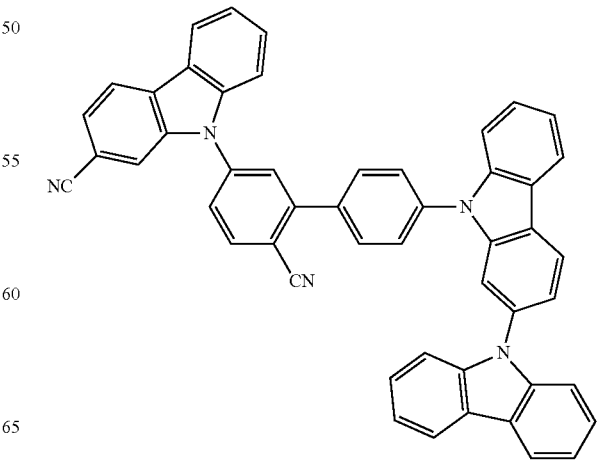

531
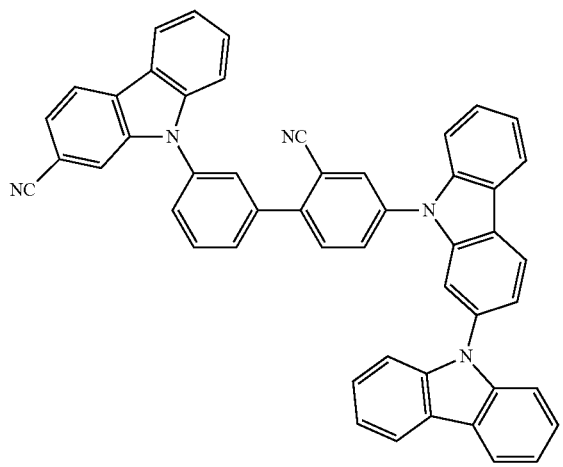
532
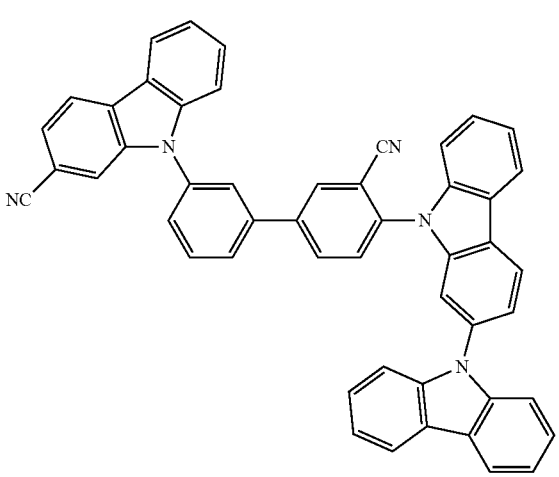
533
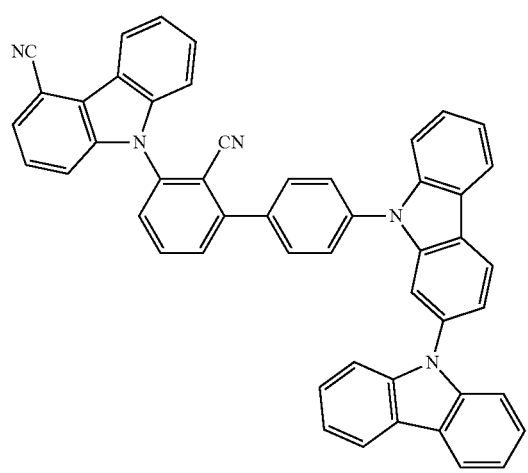
534
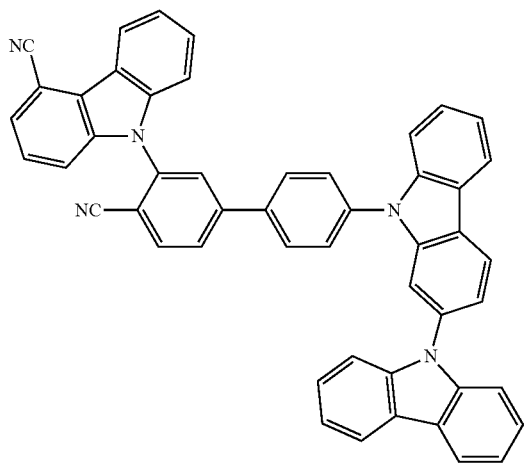
535
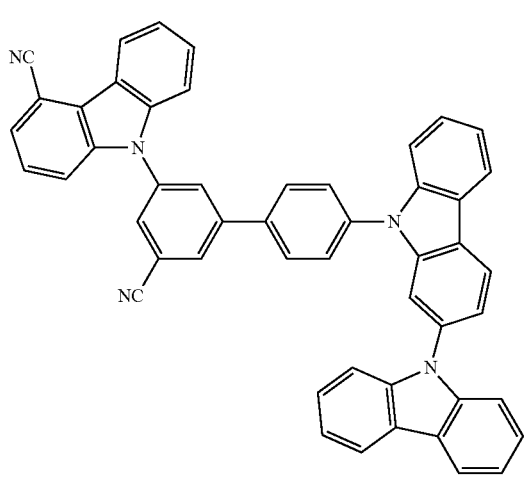
536
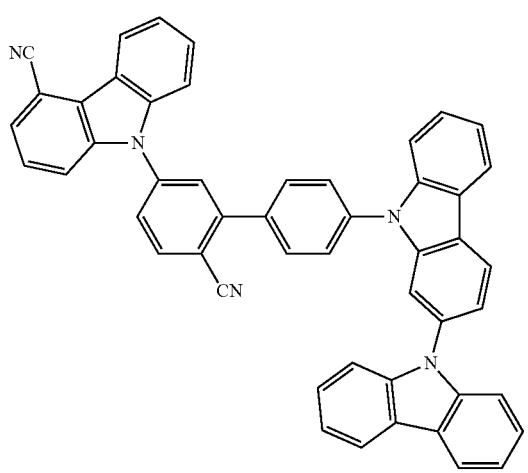

537
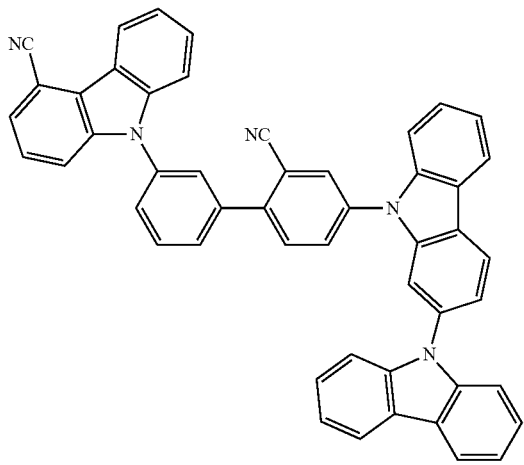
540
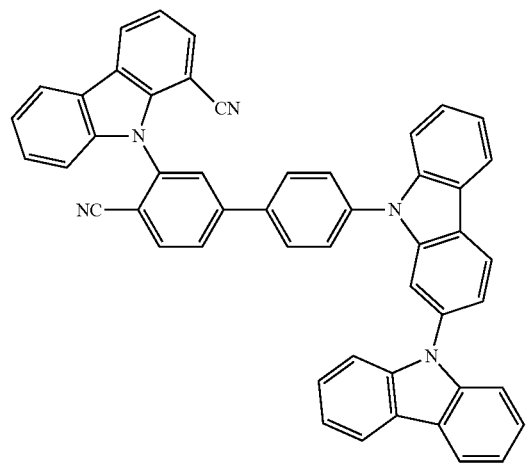
538
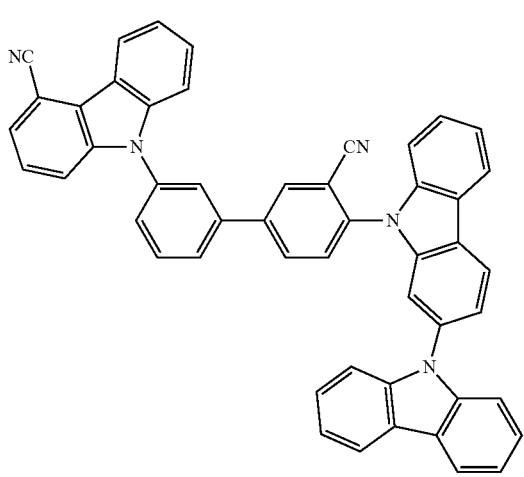
541
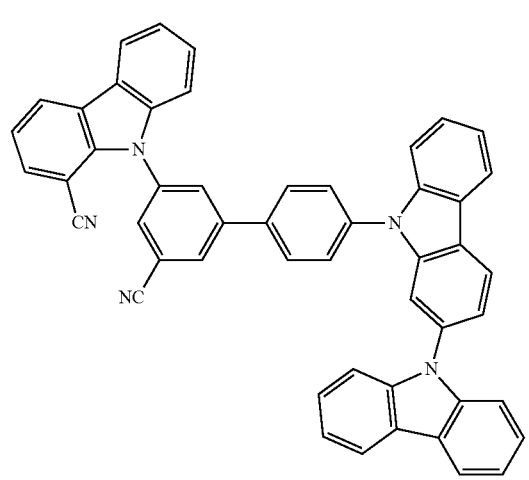
539
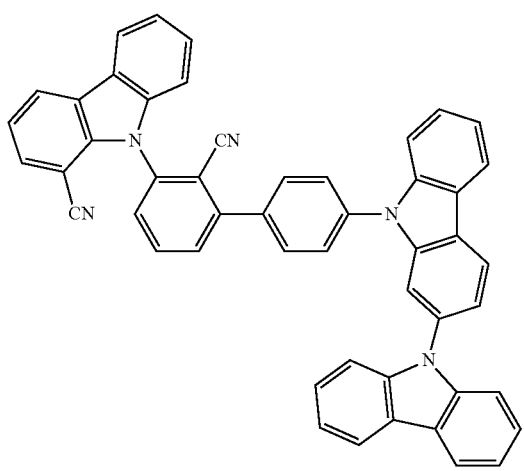
542
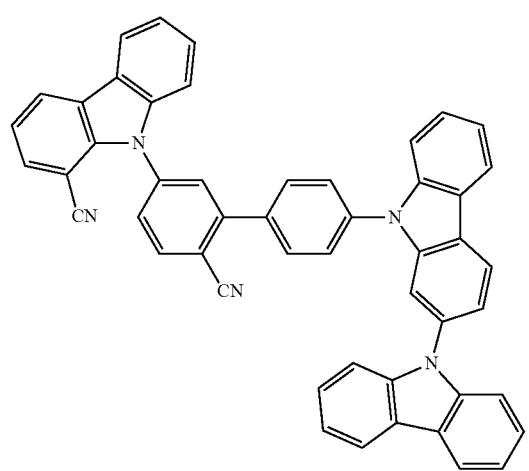

543
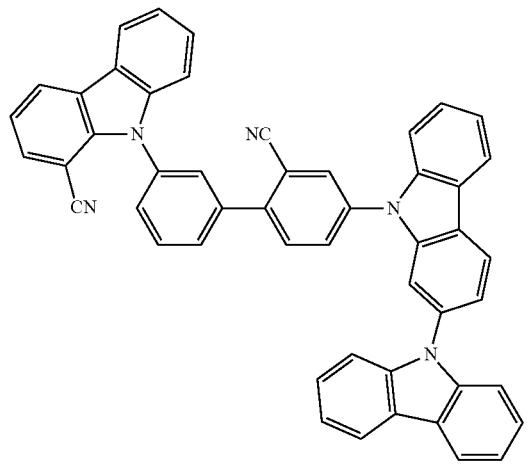
544
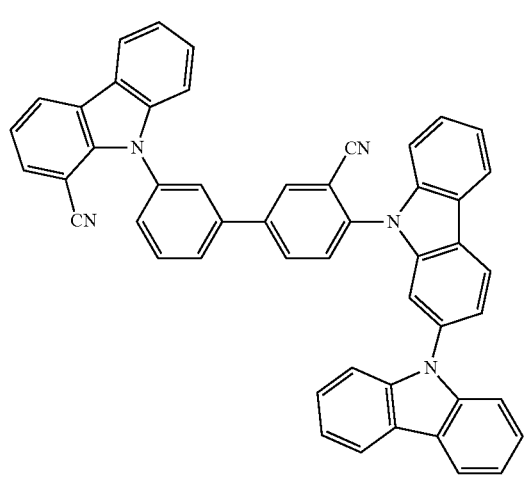
545
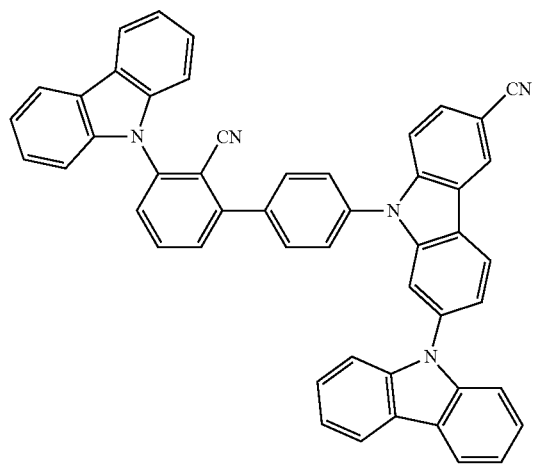
546
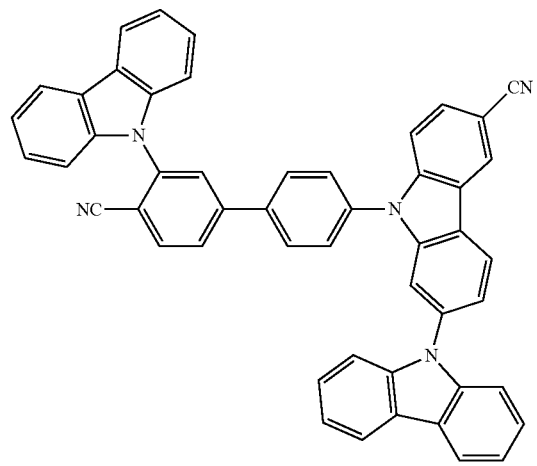
547
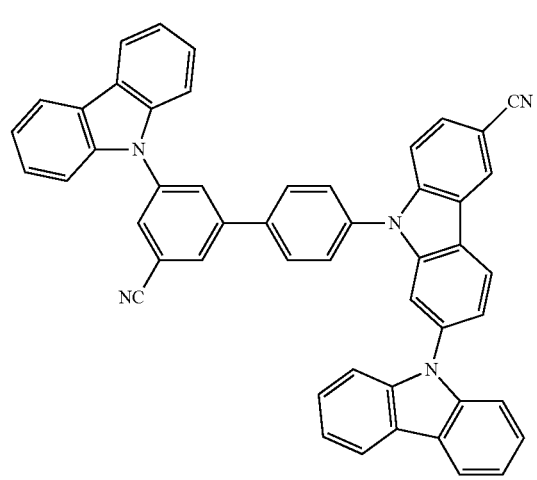
548
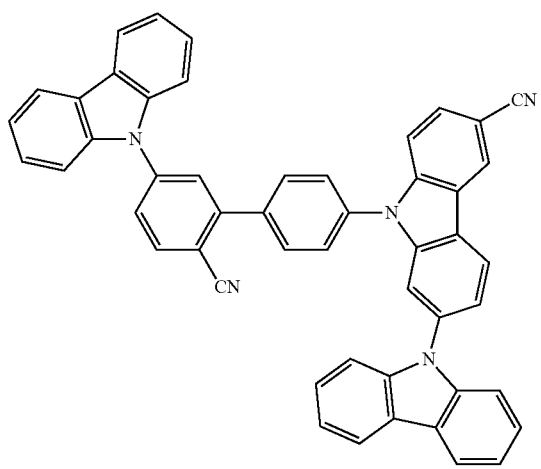

549
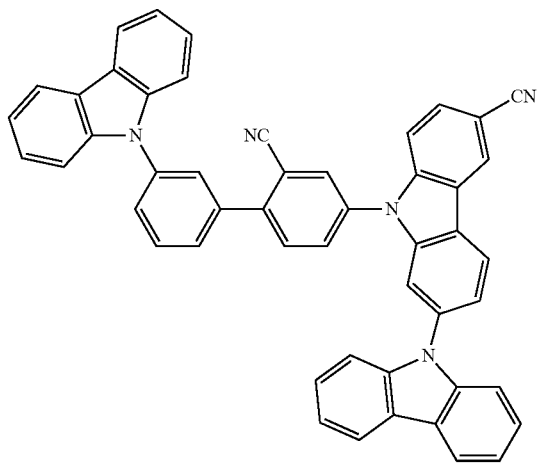
550
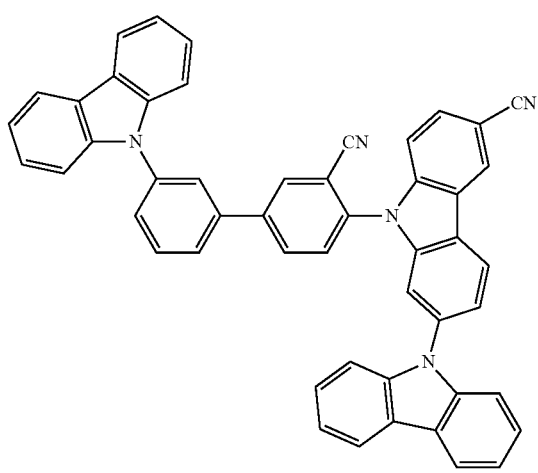
551
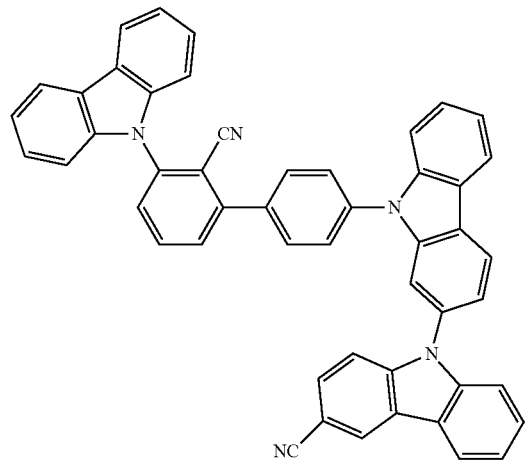
552
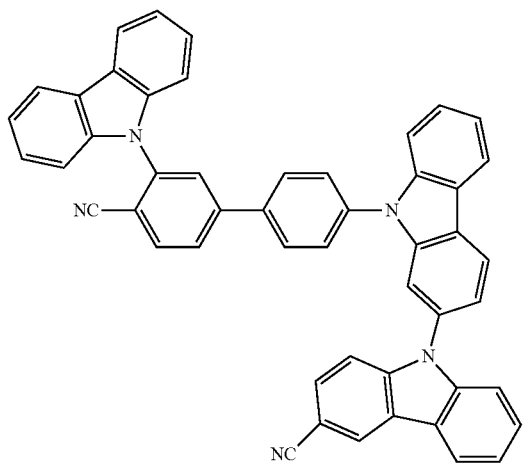
553
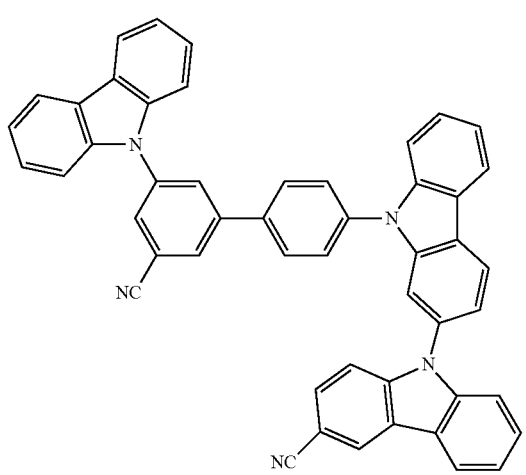
554
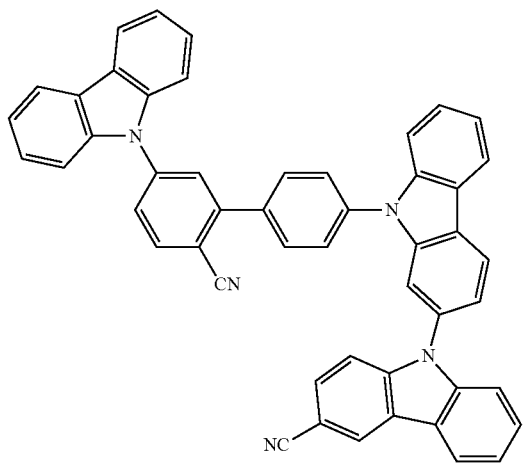

211
-continued
555
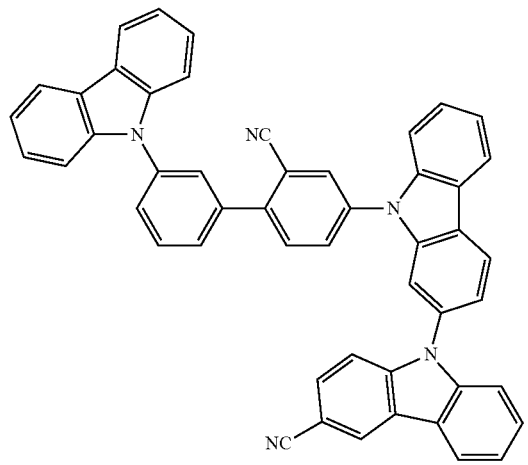
556
557
212
-continued
558
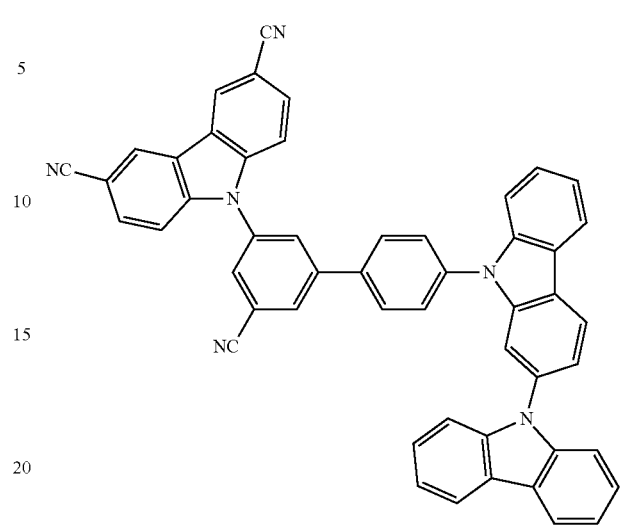
559
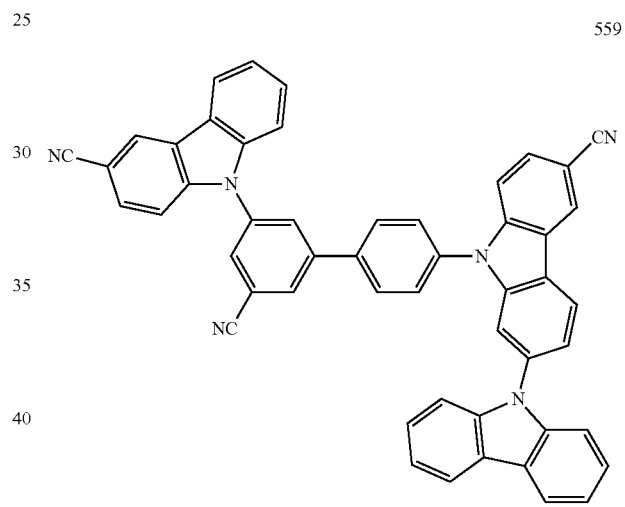
560
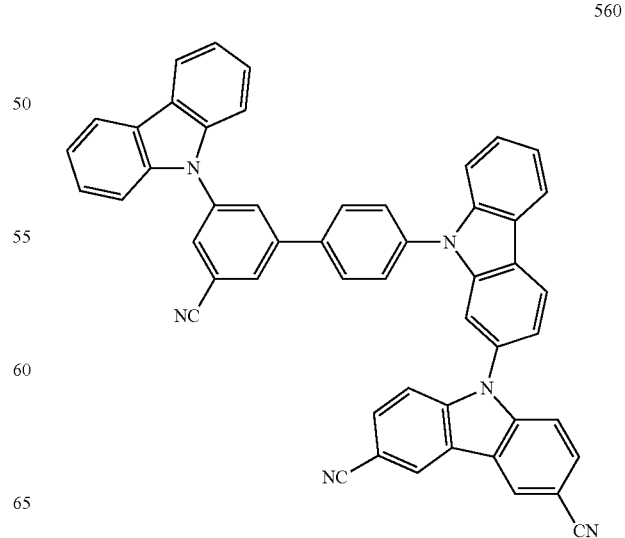

561
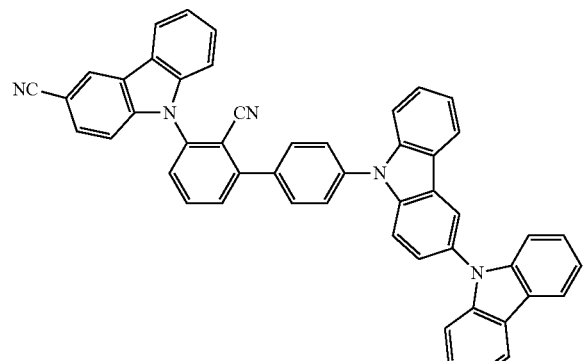
562
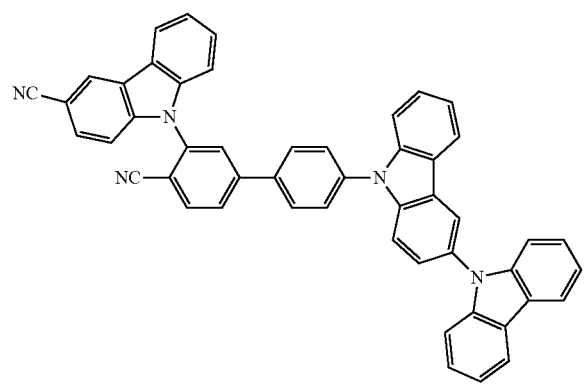
563
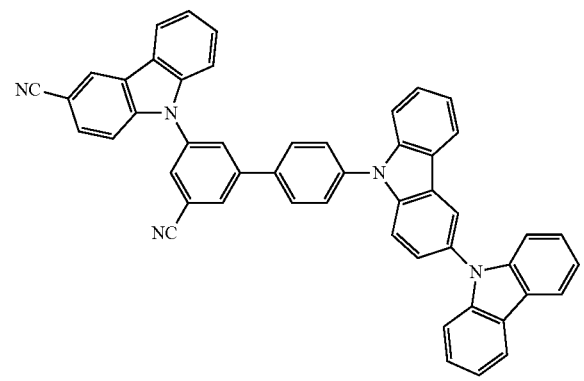
564
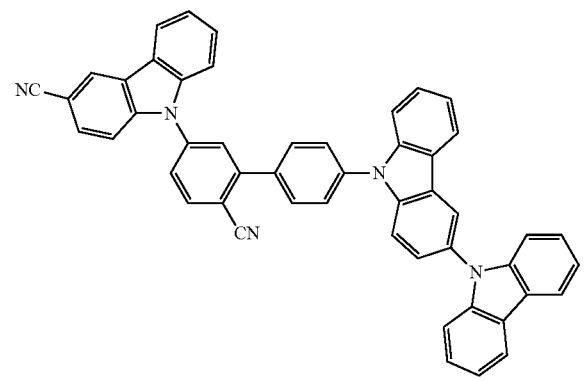
565
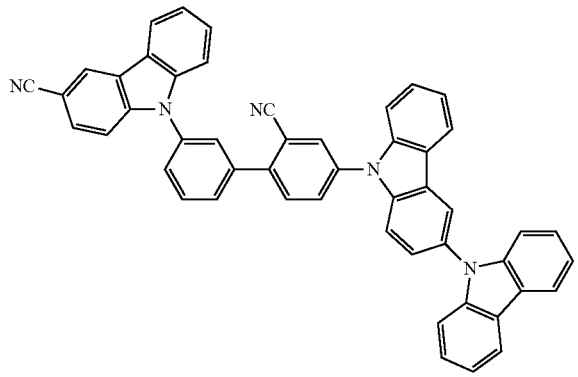
566
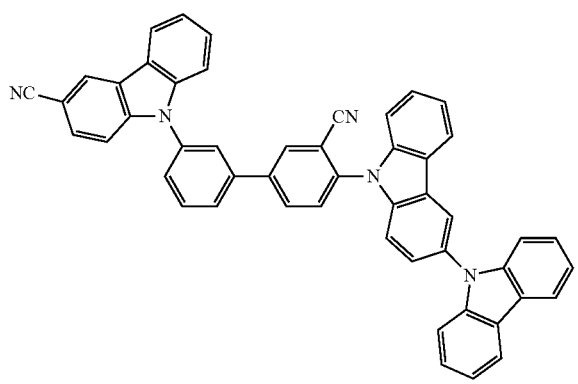
567
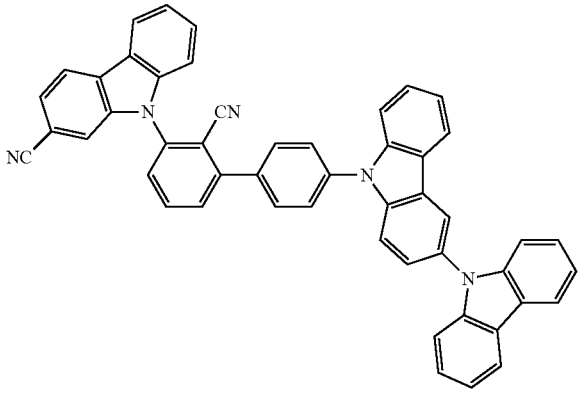
568
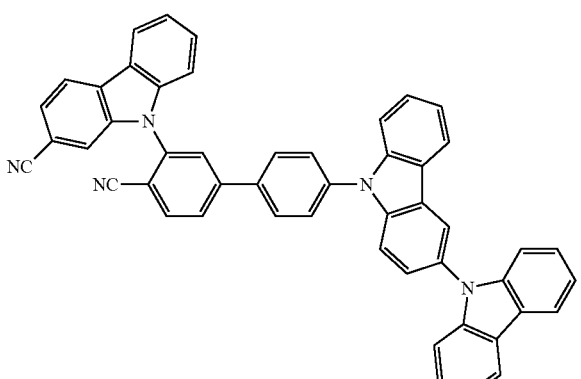

569
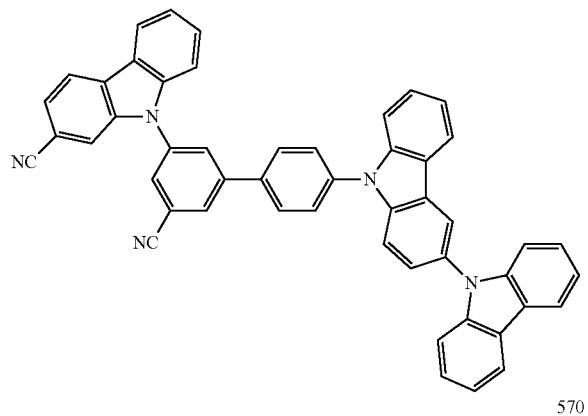
570
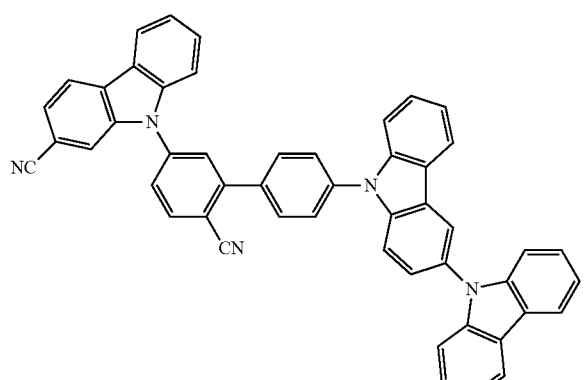
571
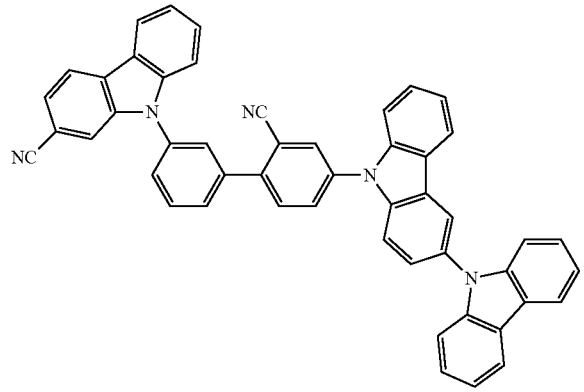
572
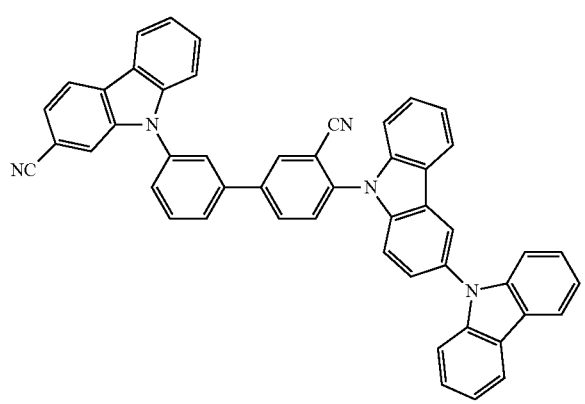
573
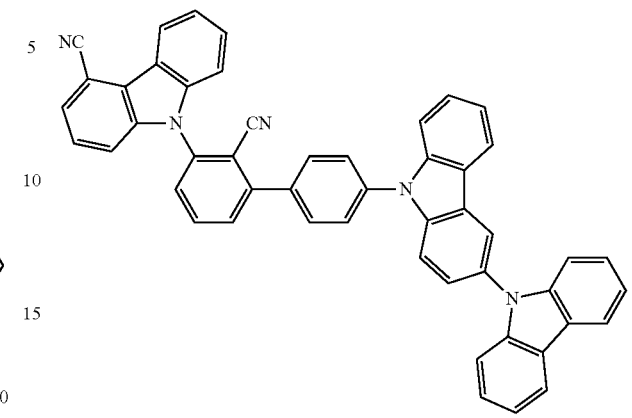
574
575

576
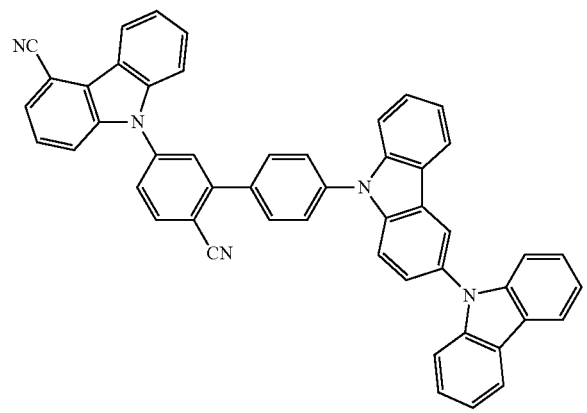
579
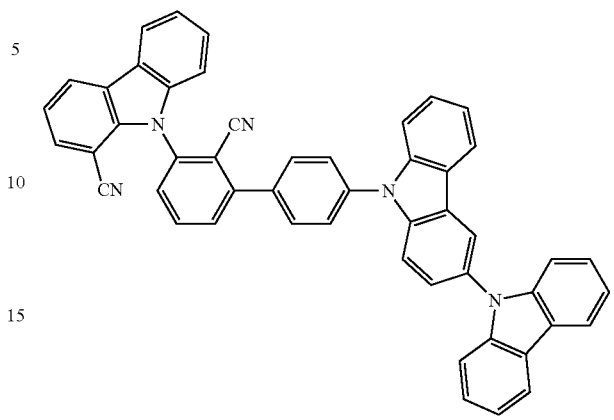
577
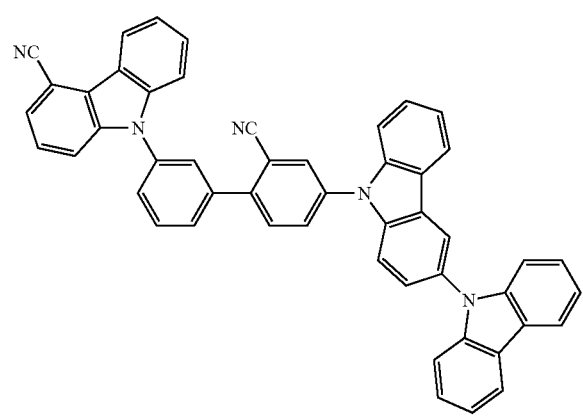
580
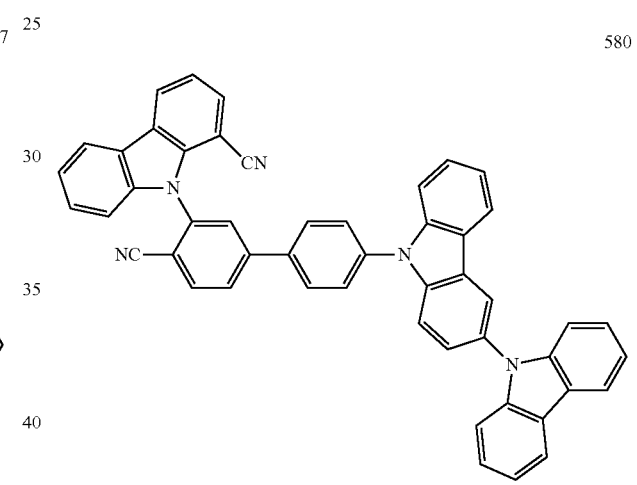
578
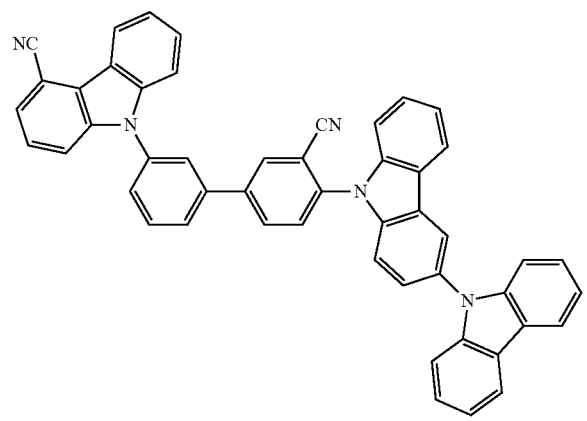
581
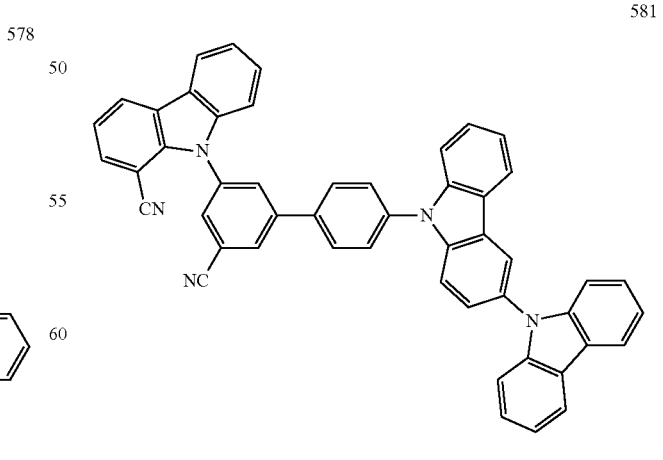

582
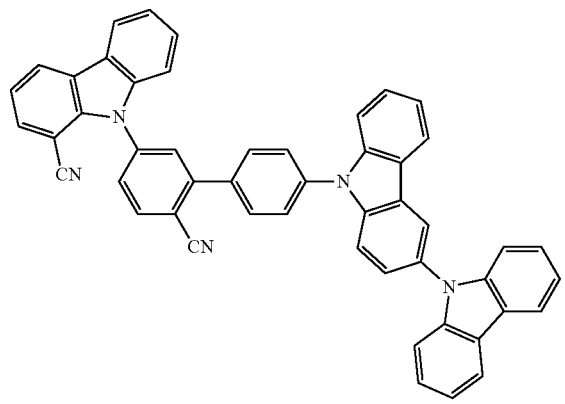
583
585

586
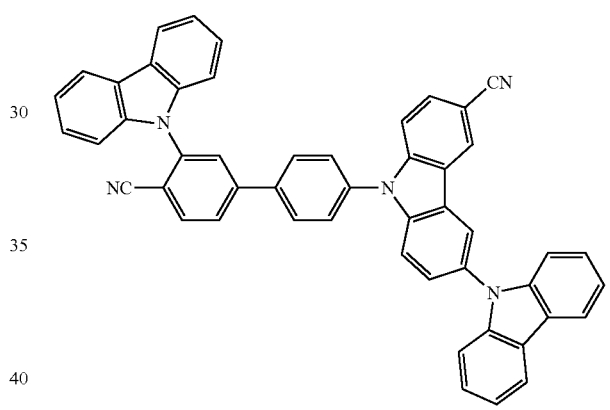
584
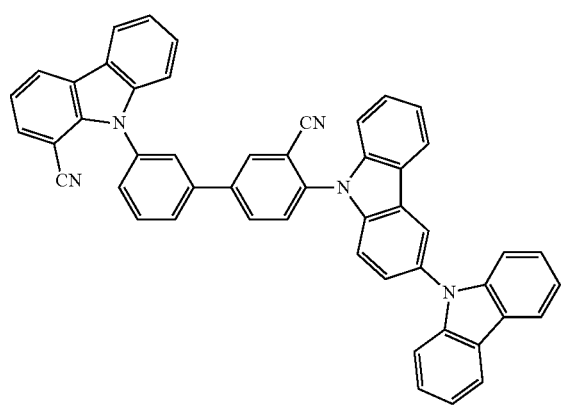
587
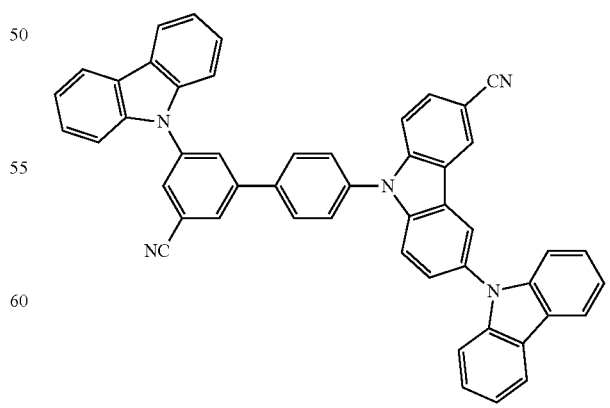

588
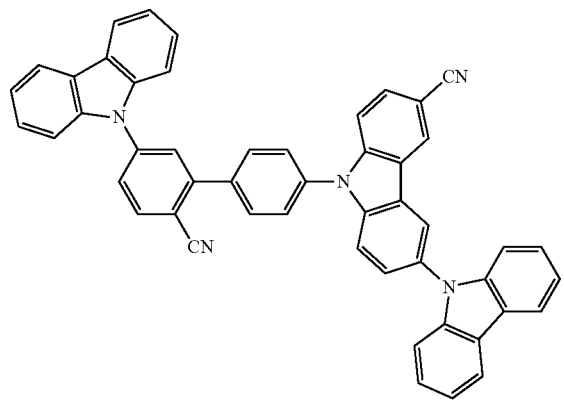
589
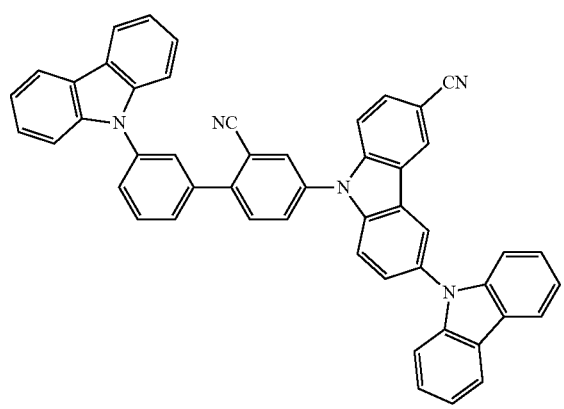
590
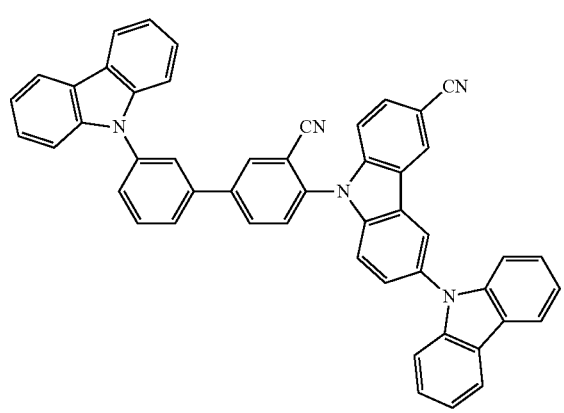
591
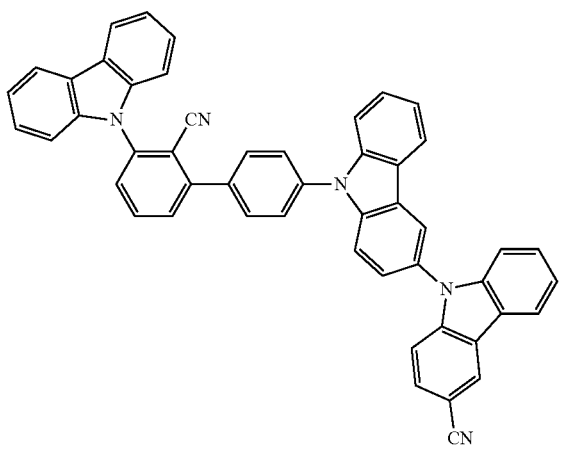
592
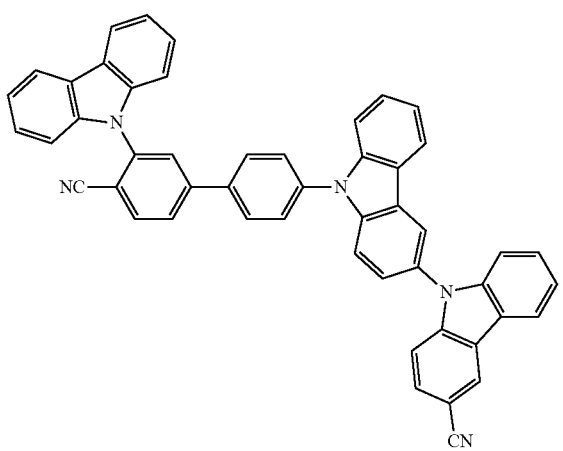
593
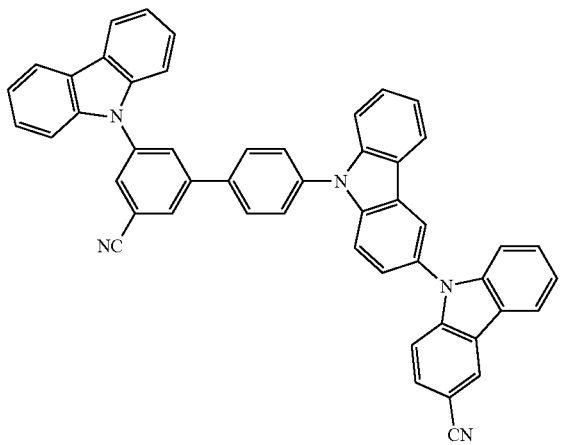

594
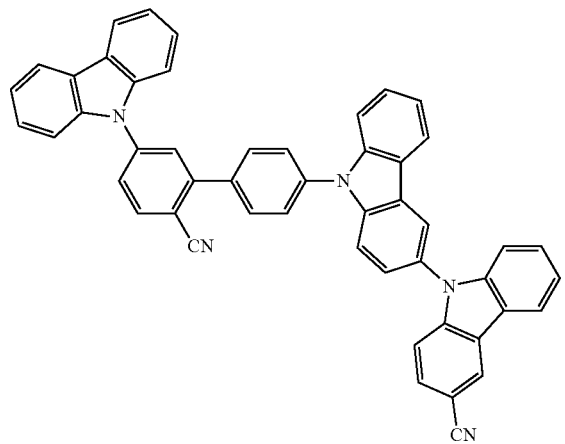
595
597
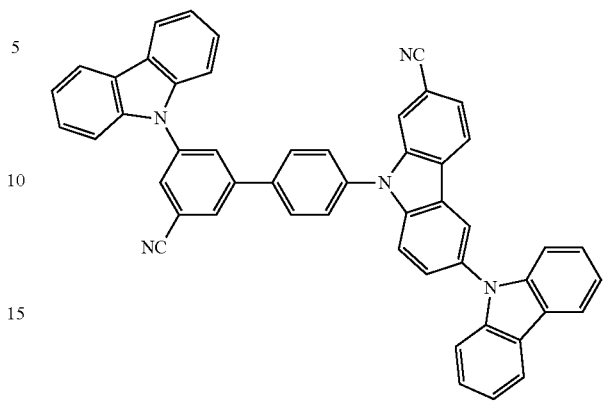
598
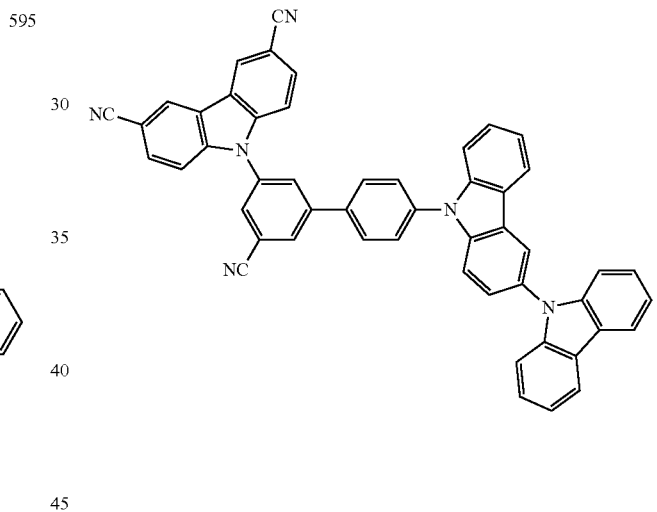
596
599
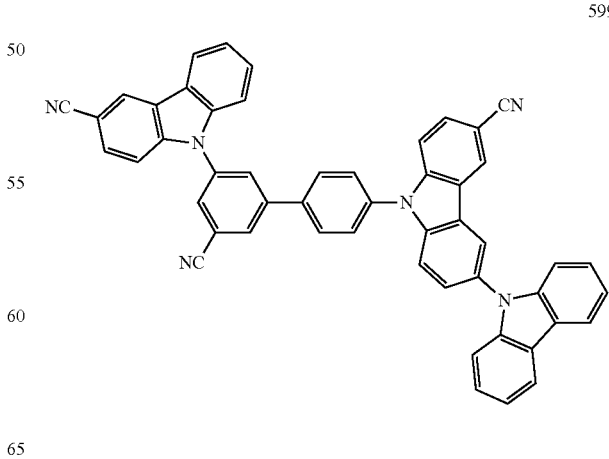

-continued
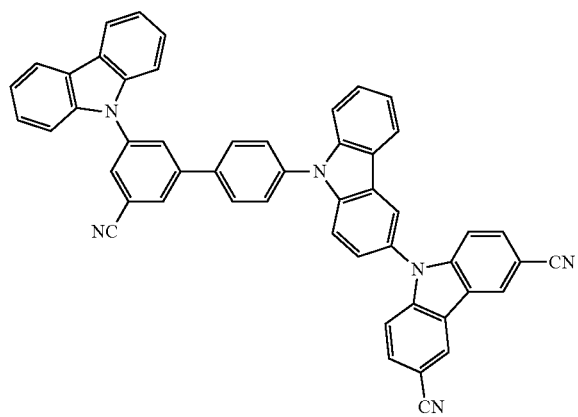
600

601
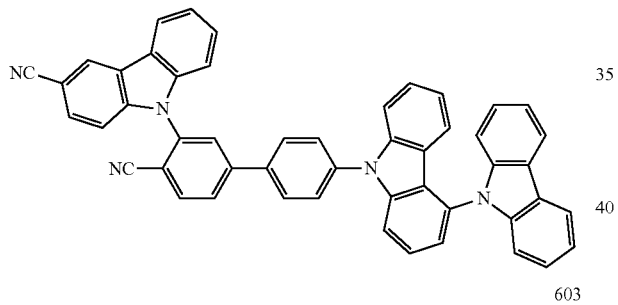
602
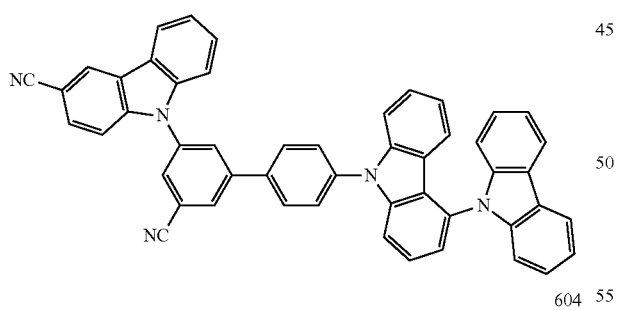
603
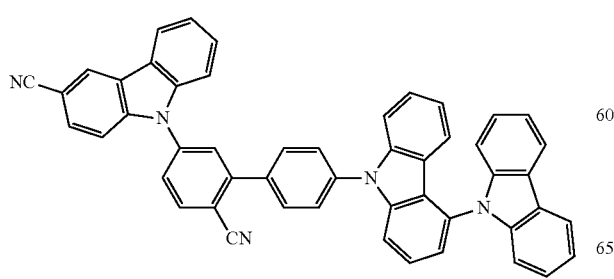
604
-continued
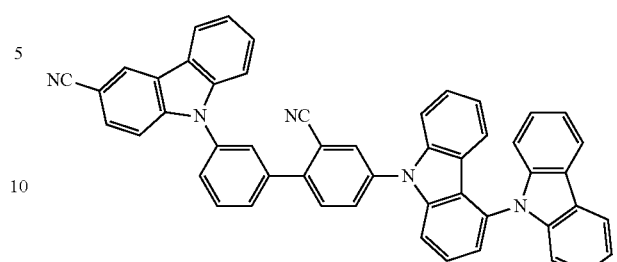
605
606
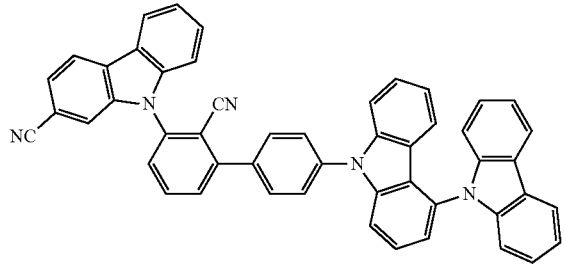
607
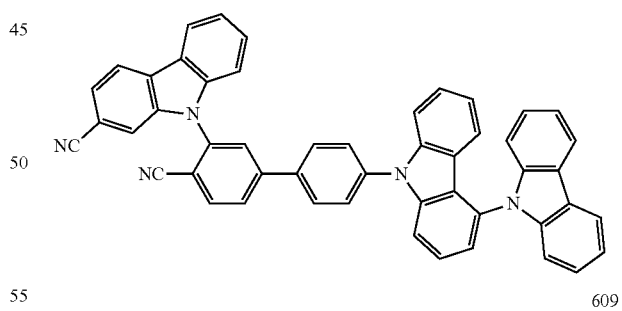
608
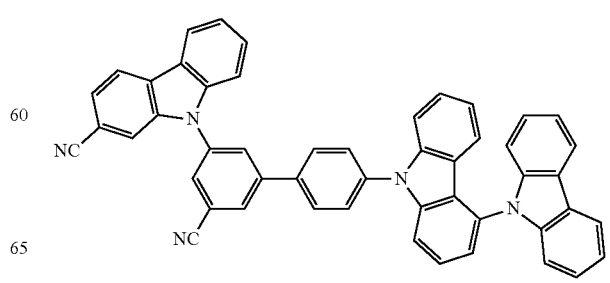
609

227
-continued
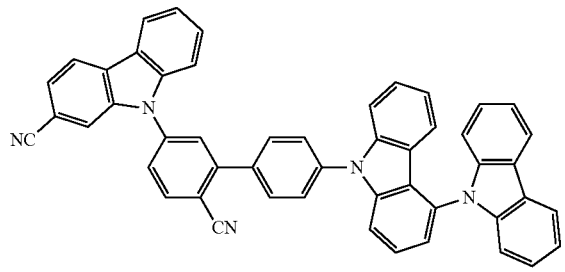
610
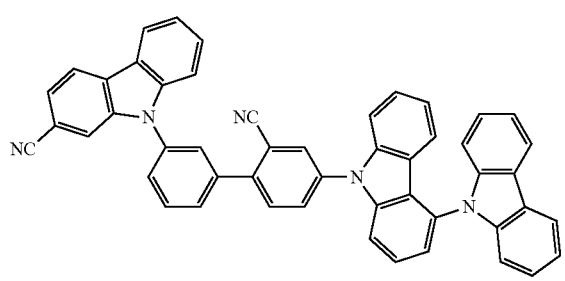
611
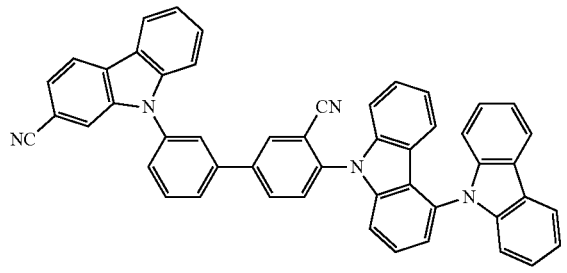
612
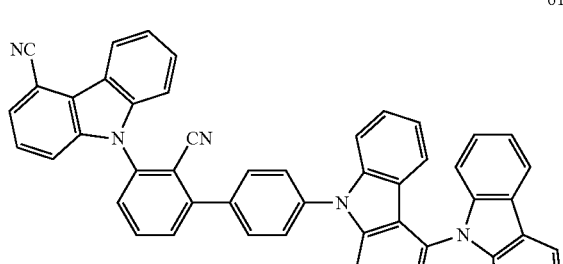
613
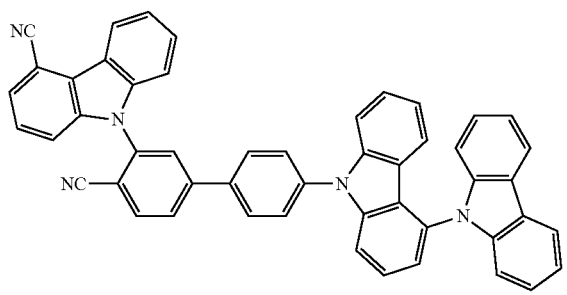
614
228
-continued
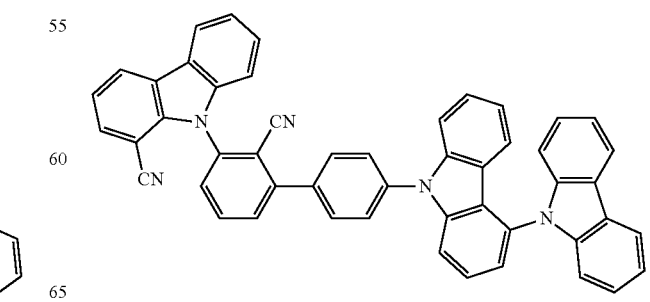
615
616
617
618
619

620
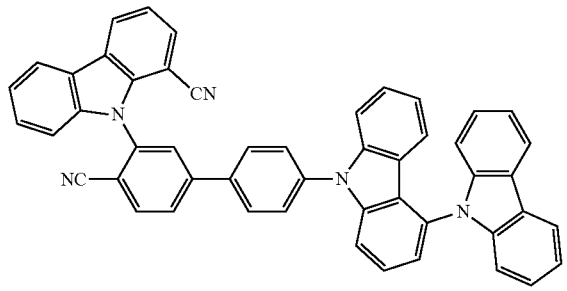
621
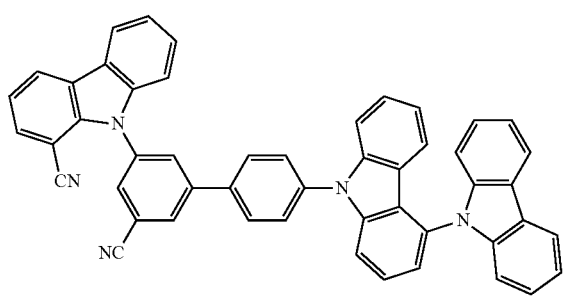
622
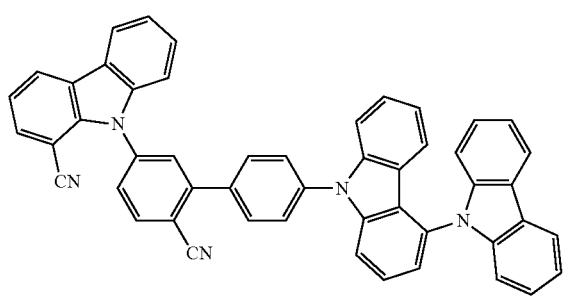
623
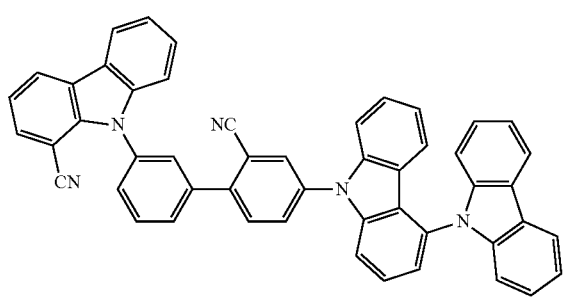
624
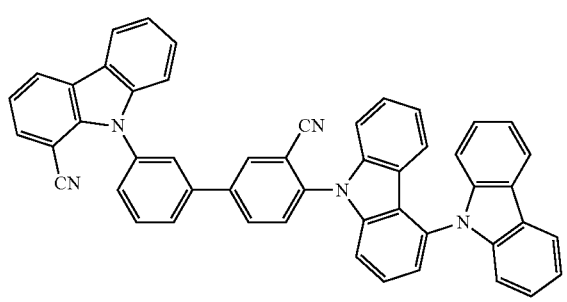
625
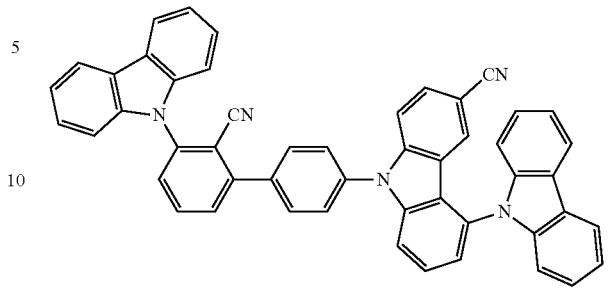
626
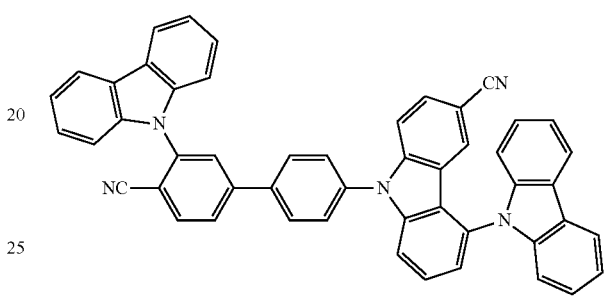
627
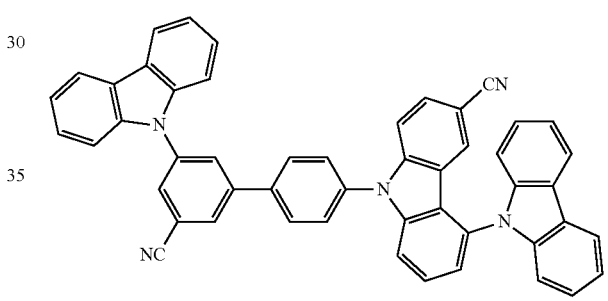
628
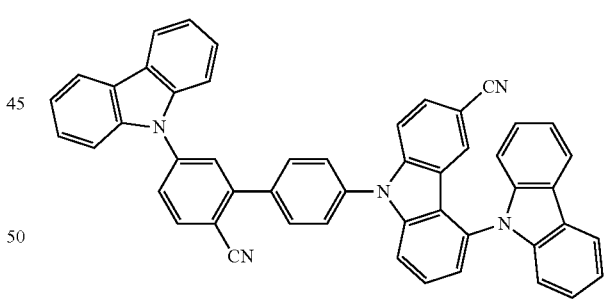
629
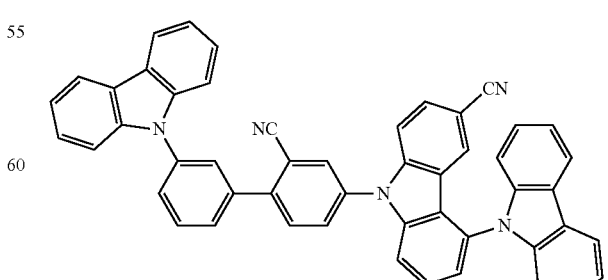

630
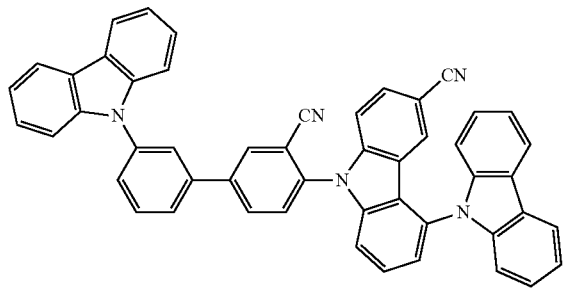
631
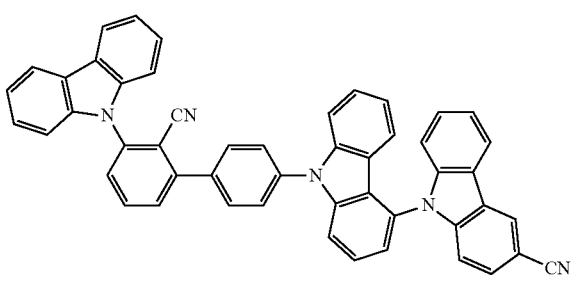
632
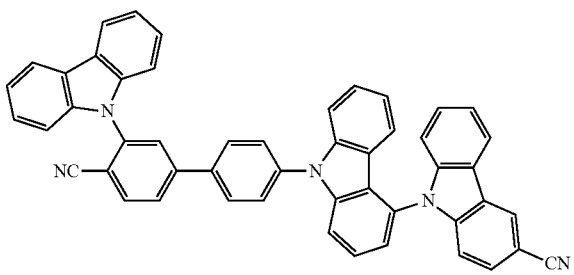
633
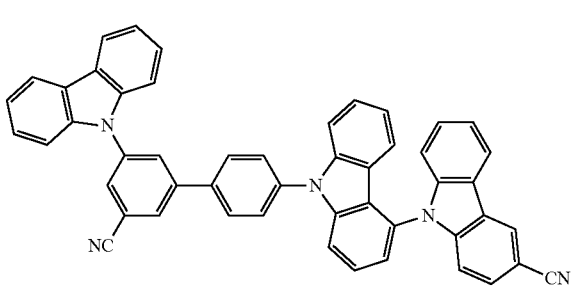
634
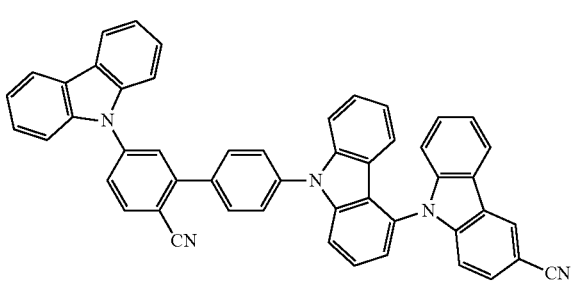
635
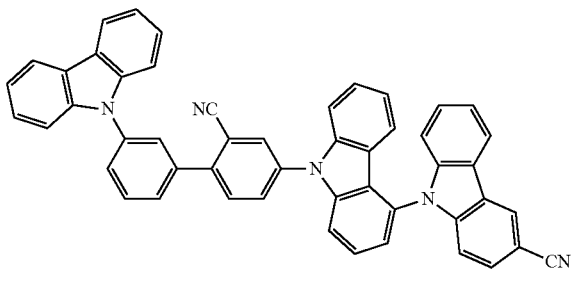
636
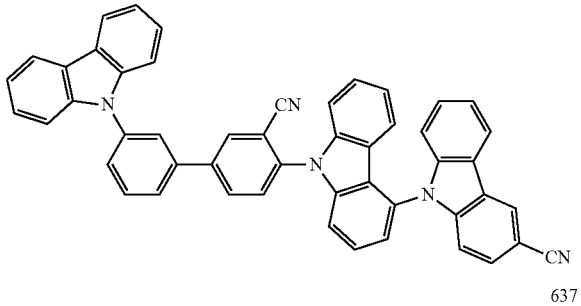
637
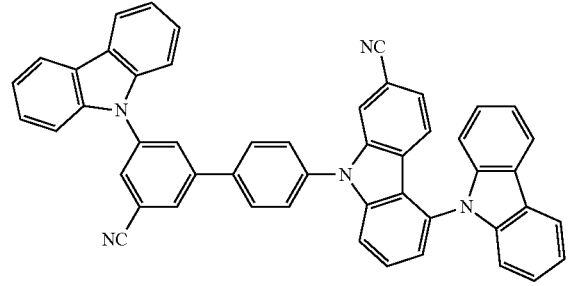
638
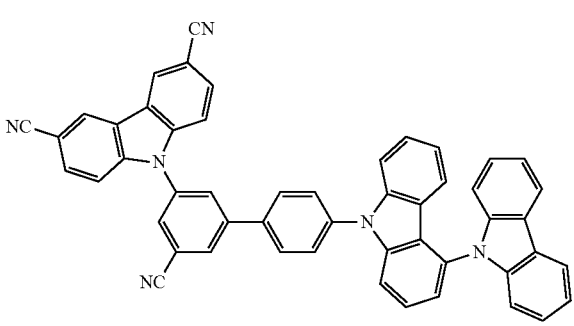
639
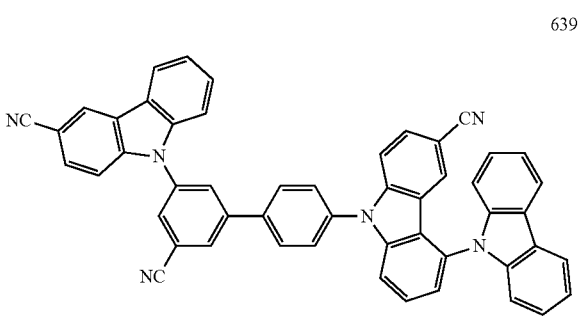

640
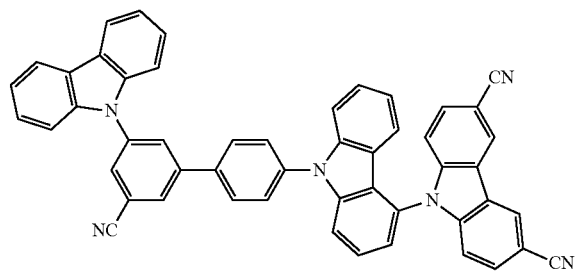
641
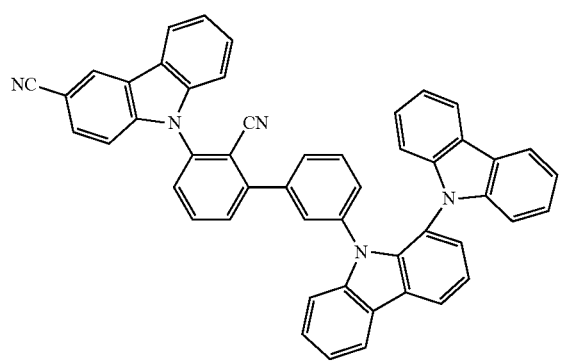
642
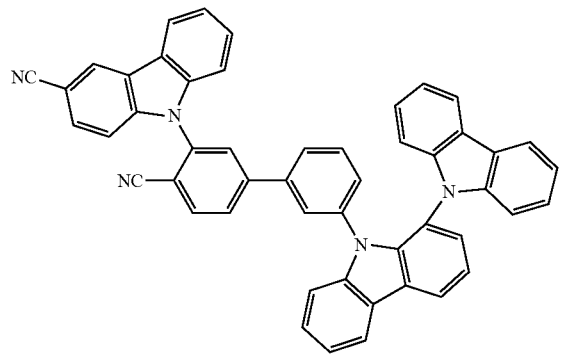
643
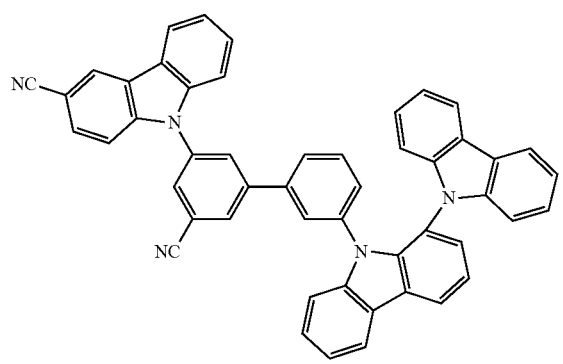
644
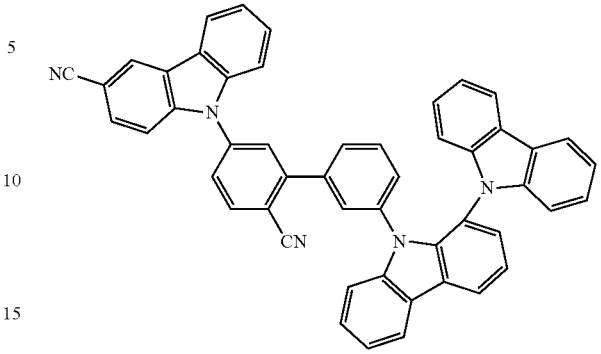
645
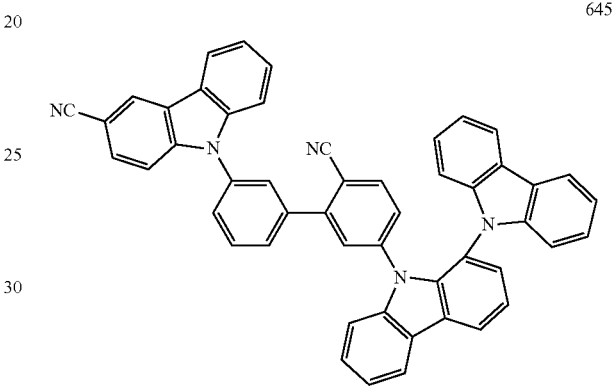
646
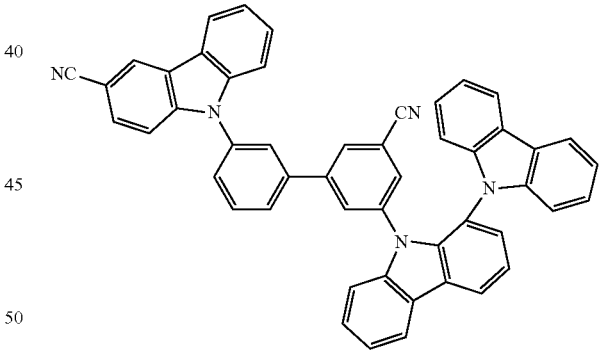
647
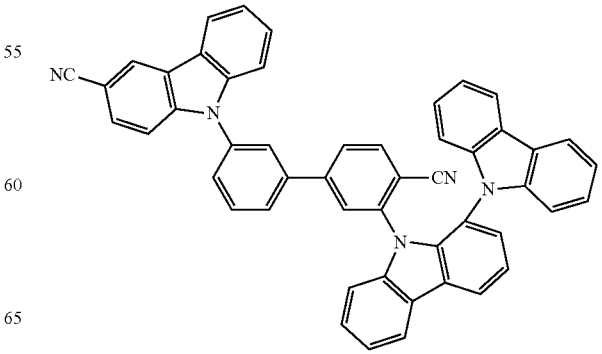

648
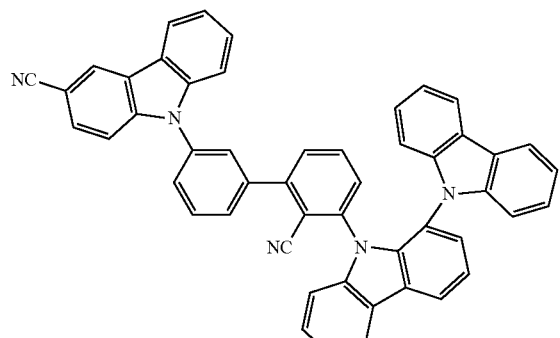
649
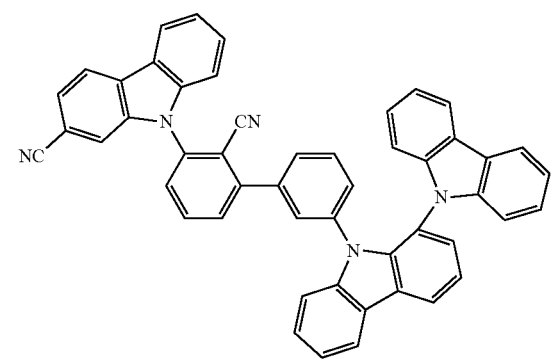
650
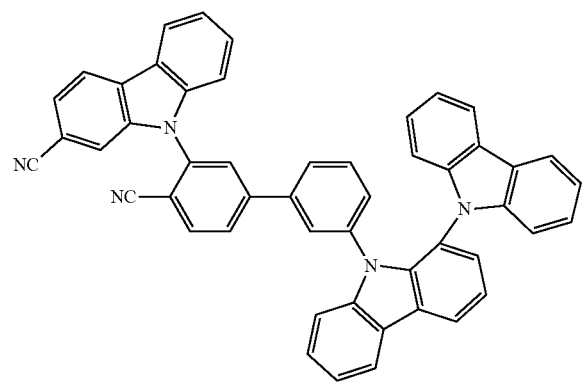
651
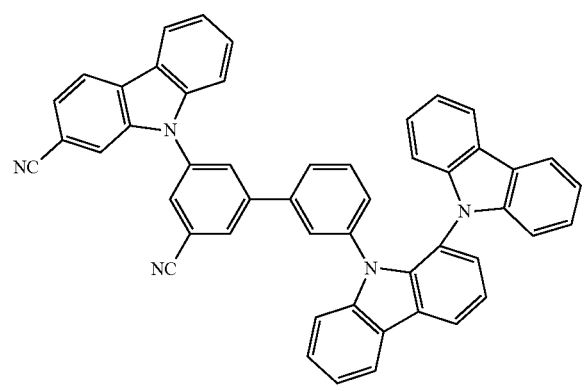
652
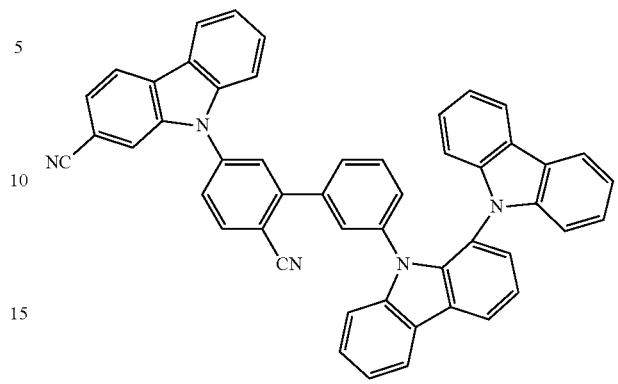
653
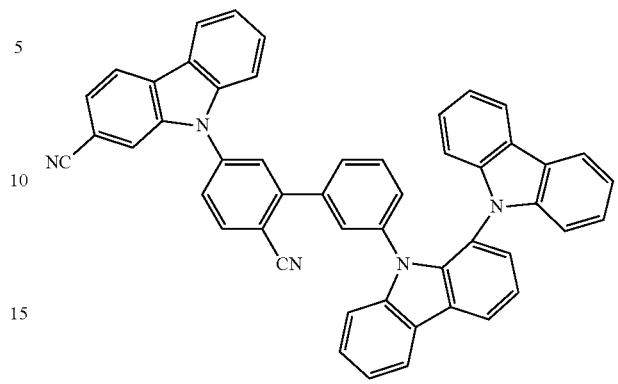
654
655
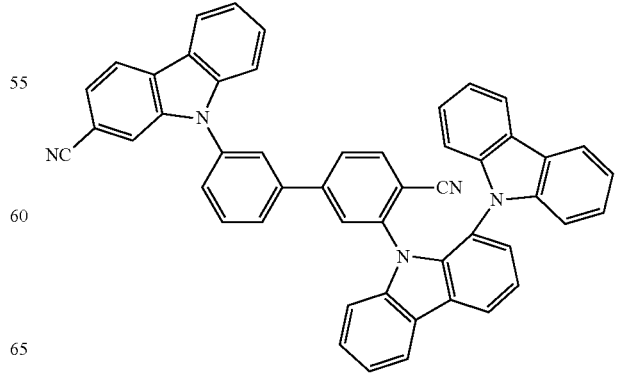

656
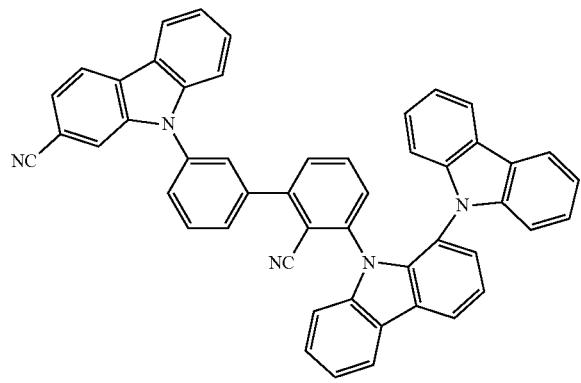
659
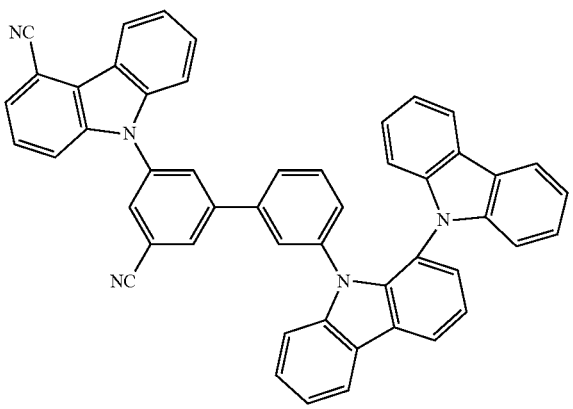
657
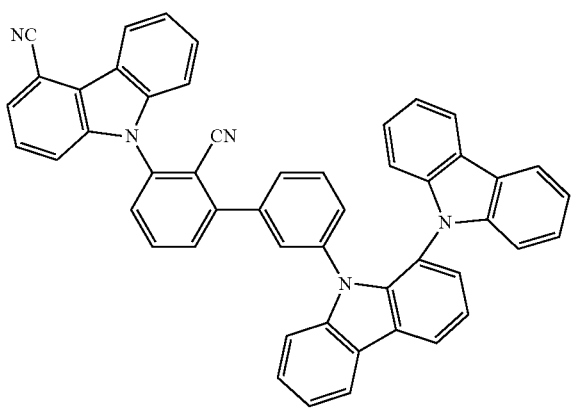
660
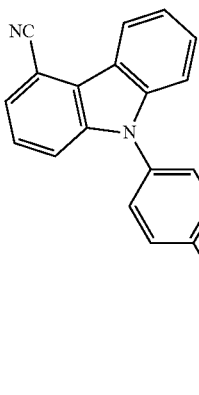
658
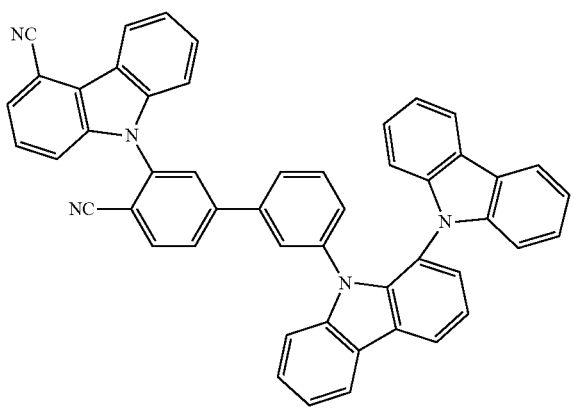
661
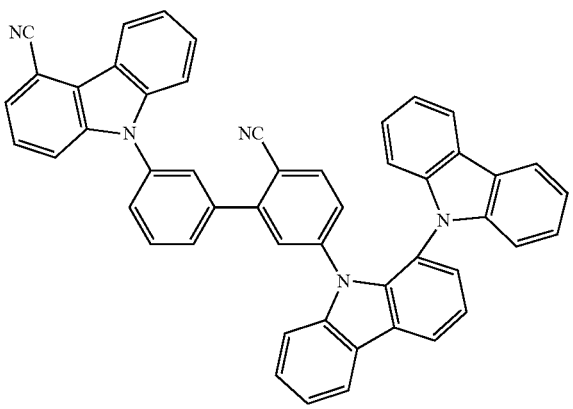

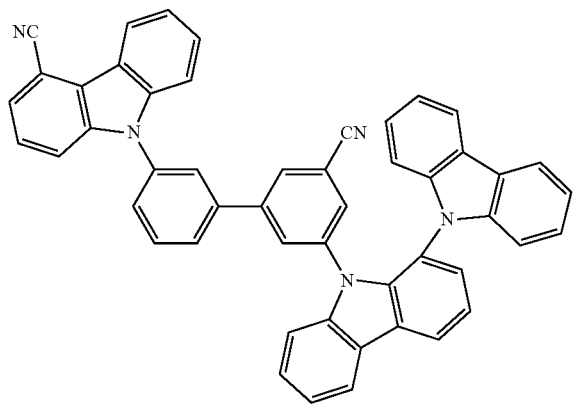
662
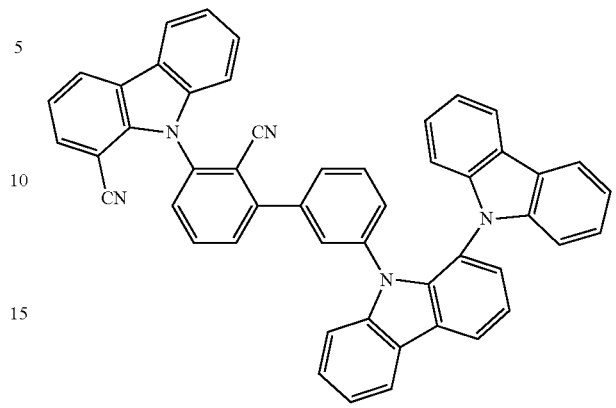
665
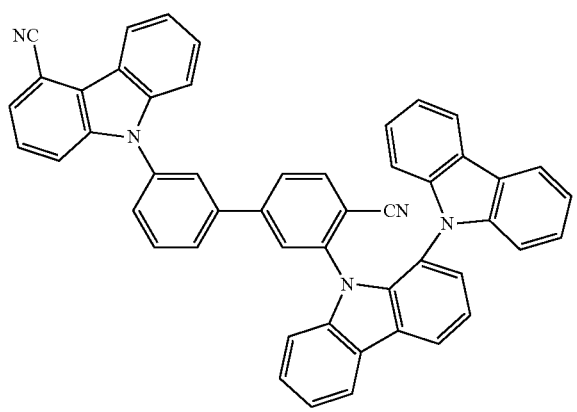
663
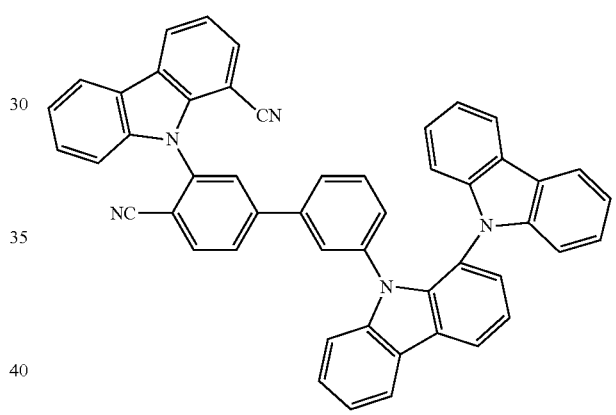
666
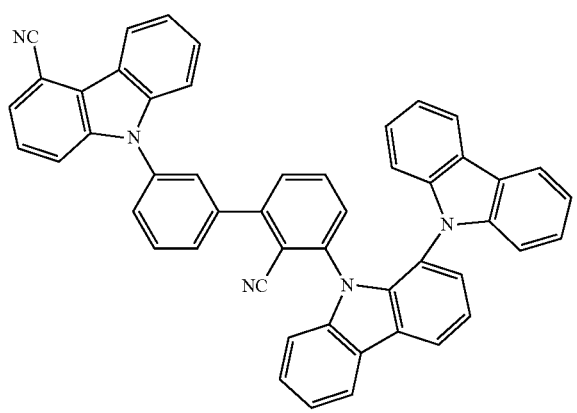
664
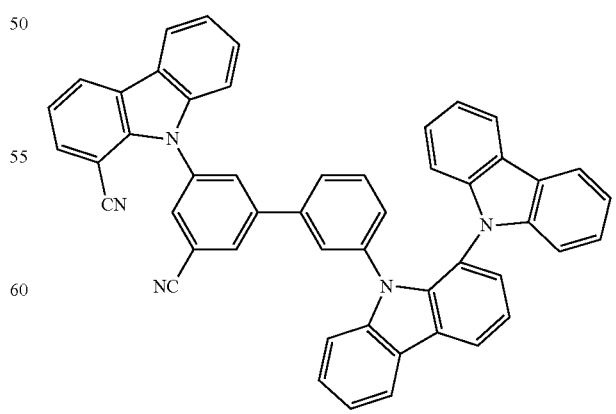
667

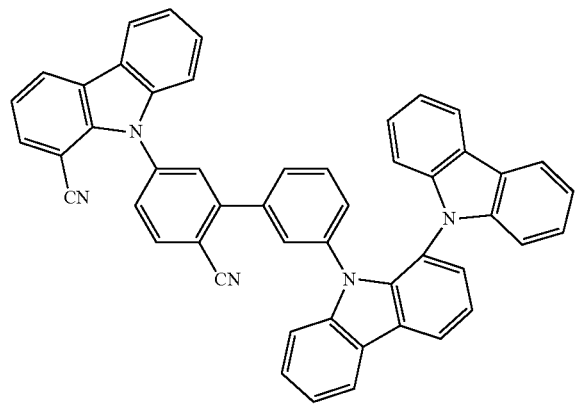
668
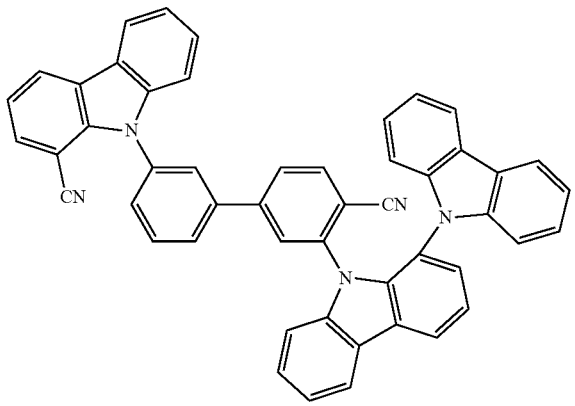
671
669
672
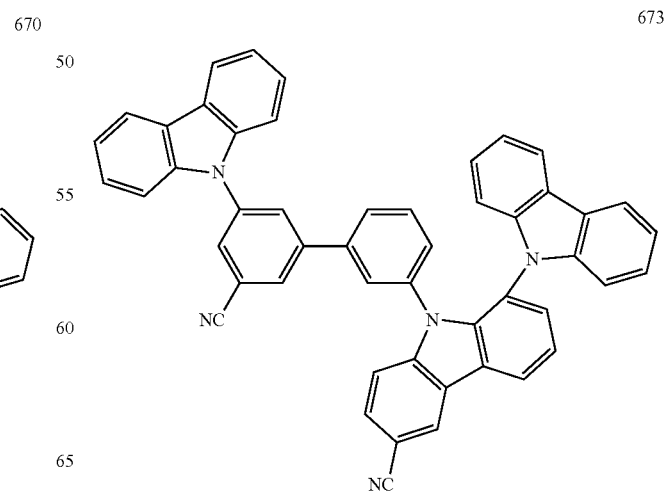
670
673

-continued
674
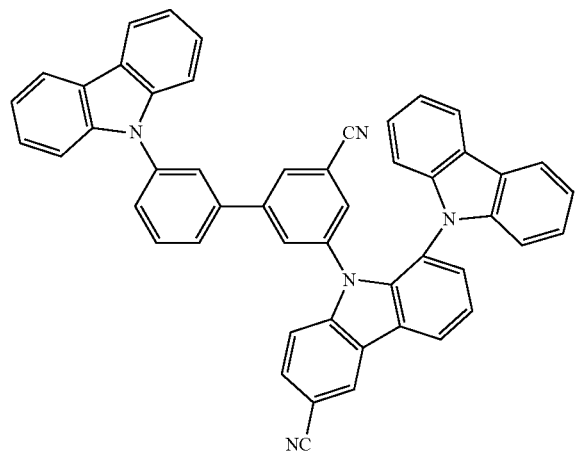
675
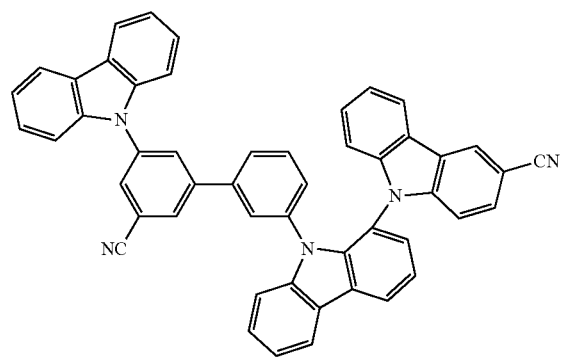
676
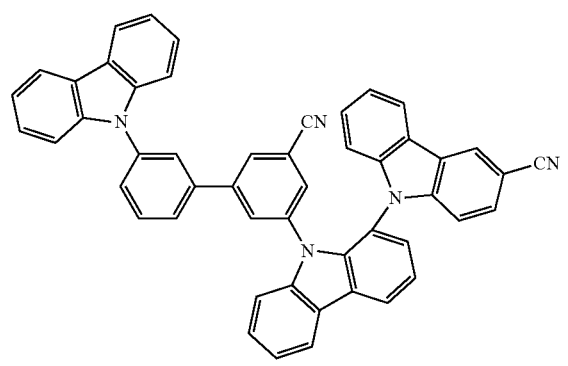
677
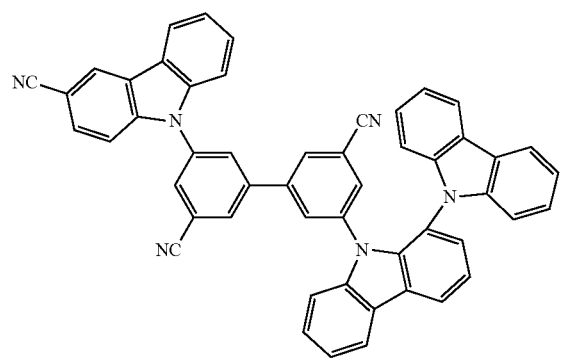
-continued
678
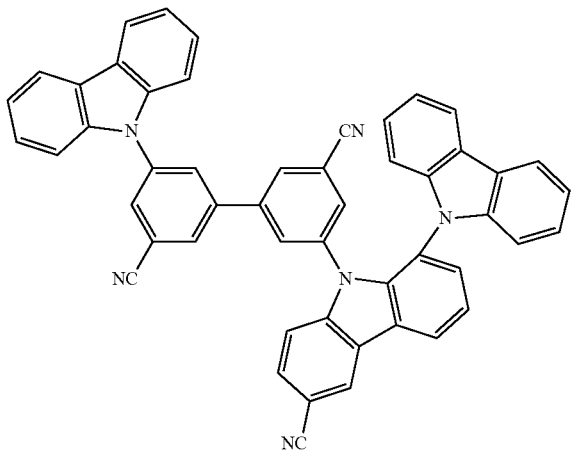
679
680
681
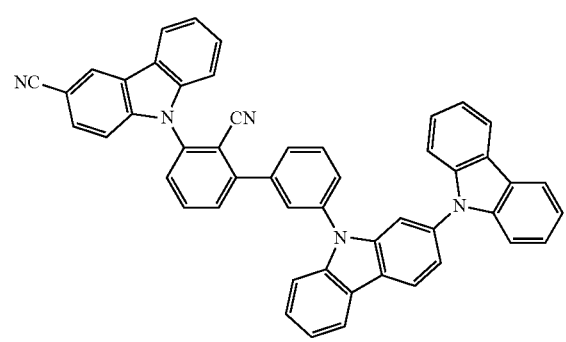

682
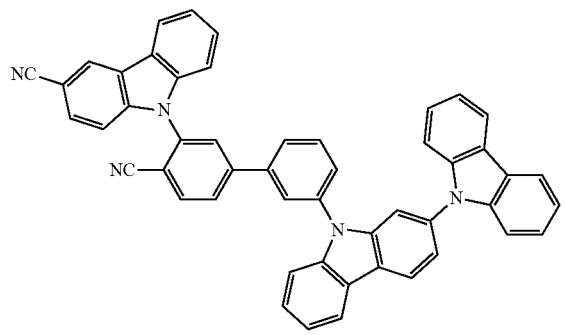
683
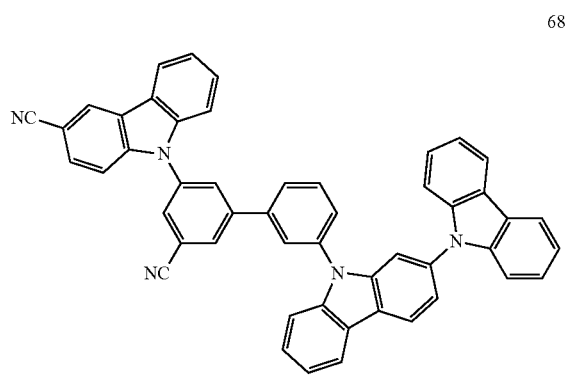
684
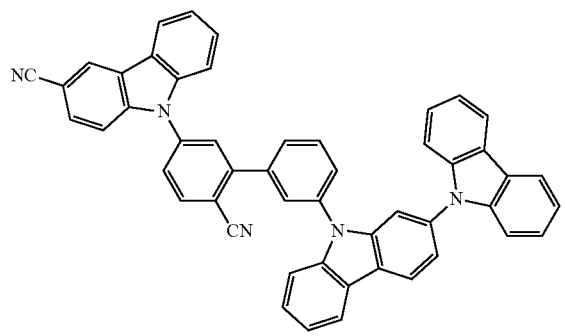
685
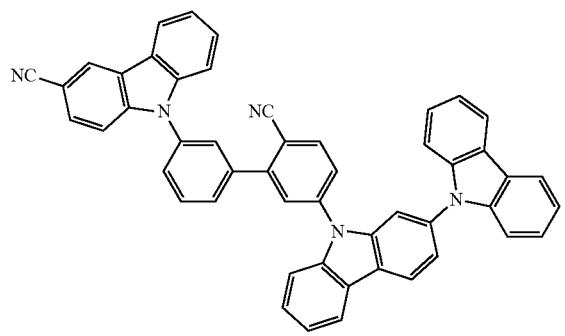
686
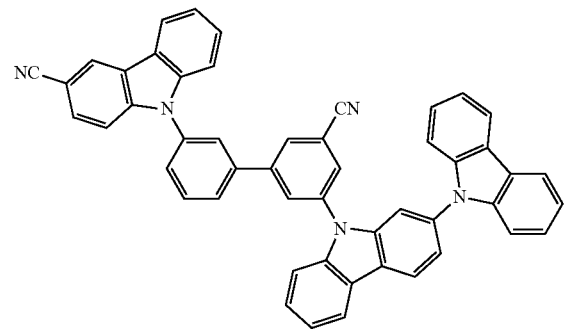
687
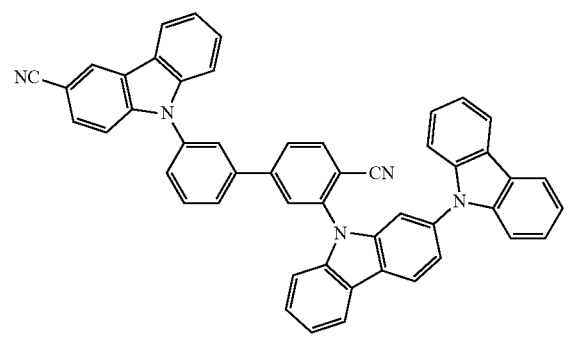
688
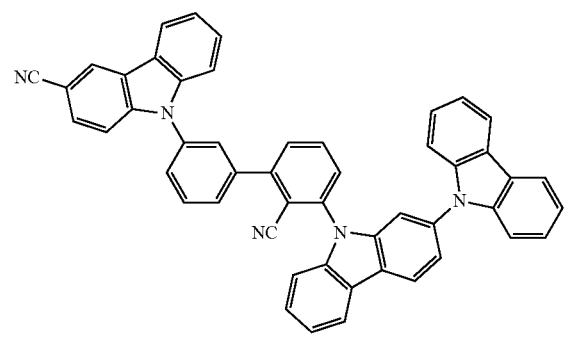
689
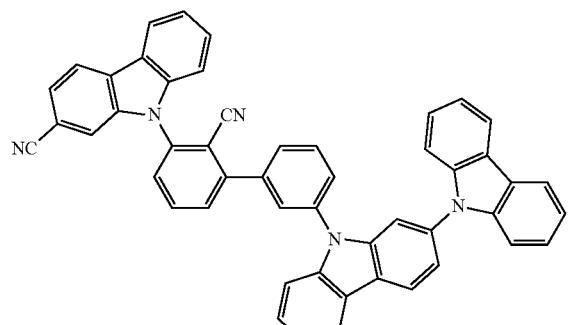

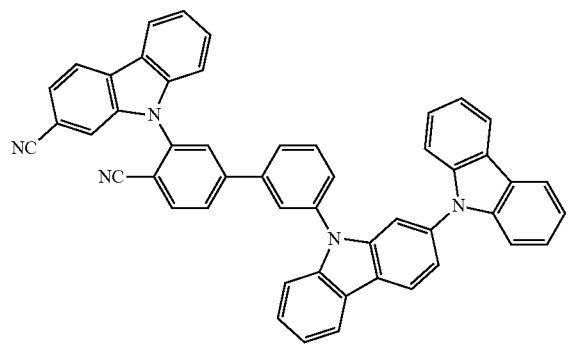
690
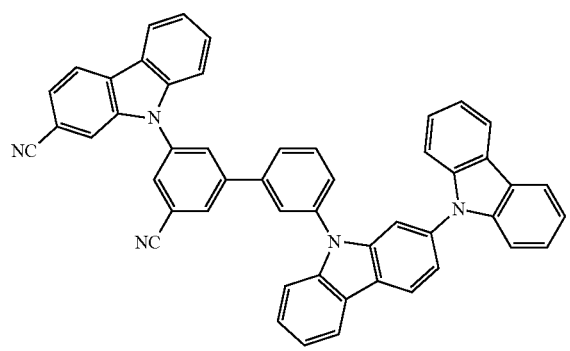
691
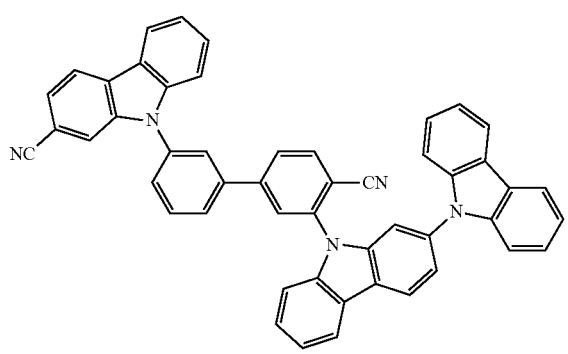
694
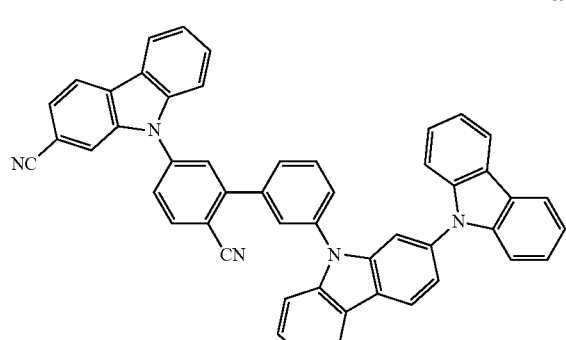
692
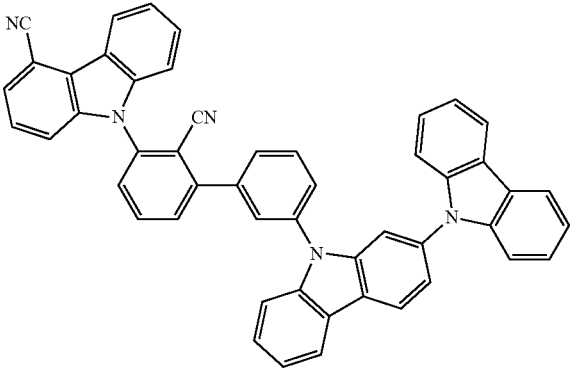
695
693
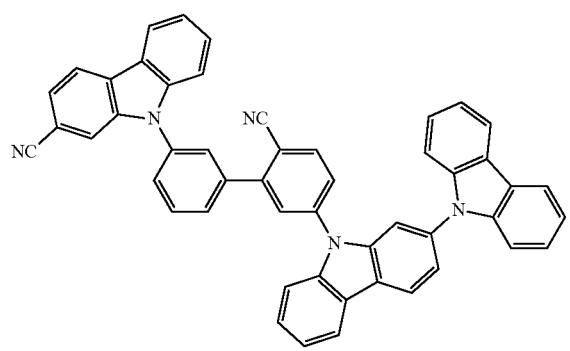
696
697

698
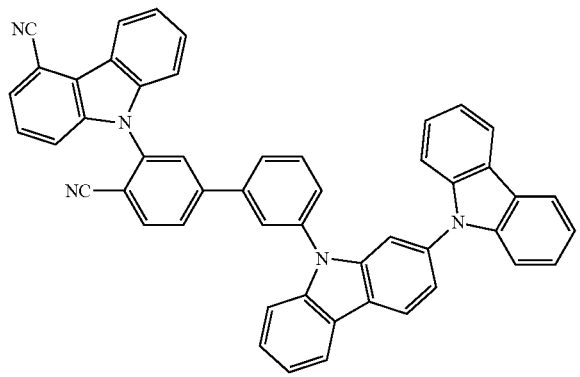
699
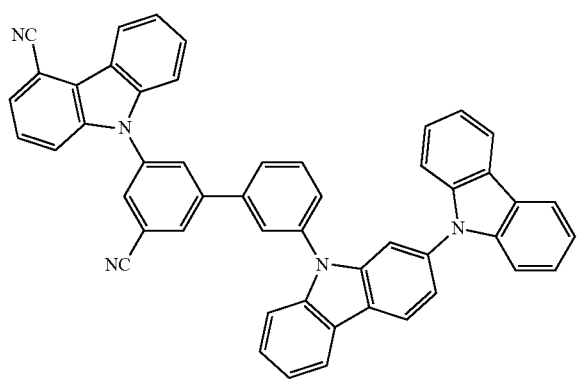
700
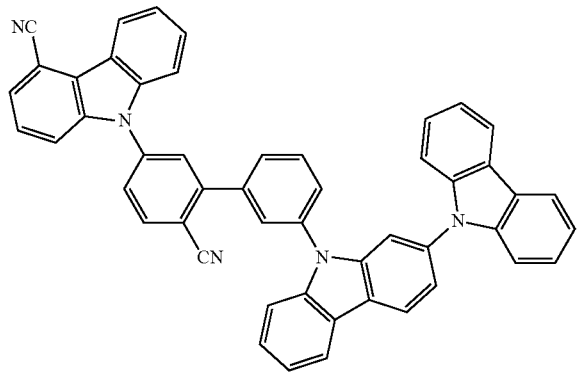
701
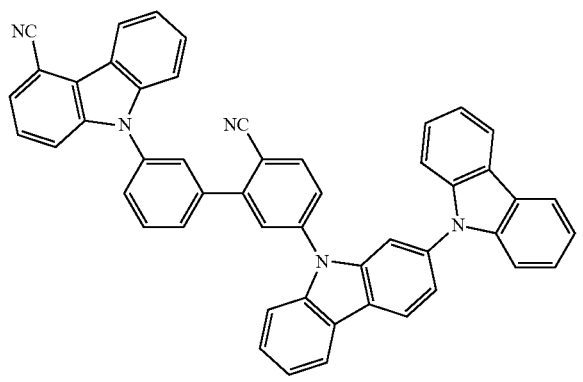
702
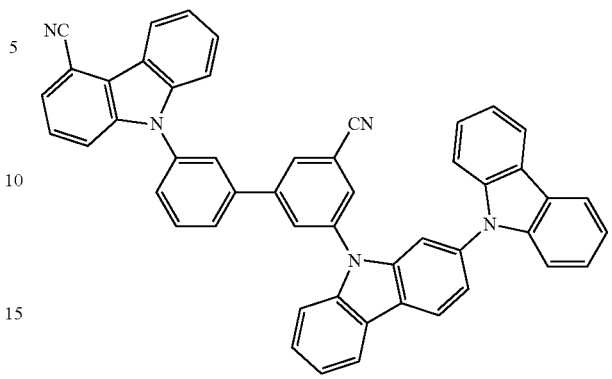
703
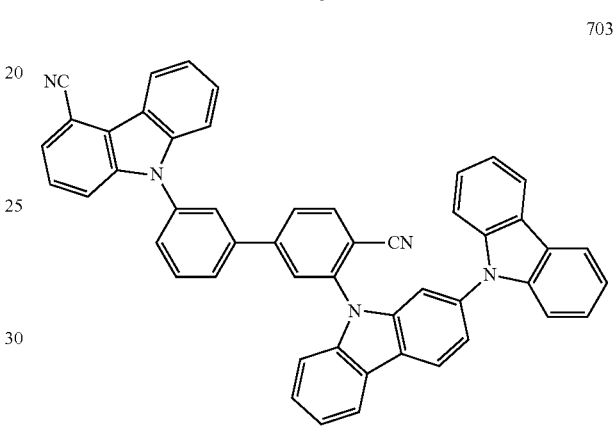
704

705
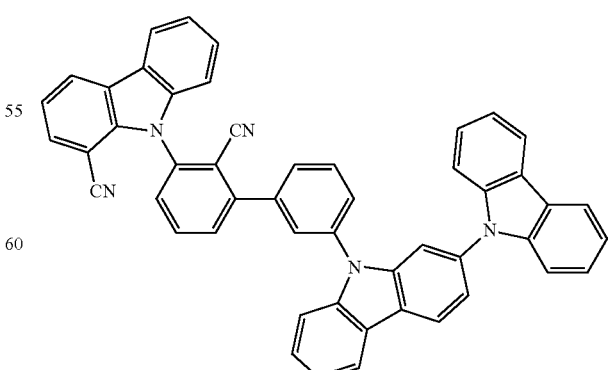

-continued
706
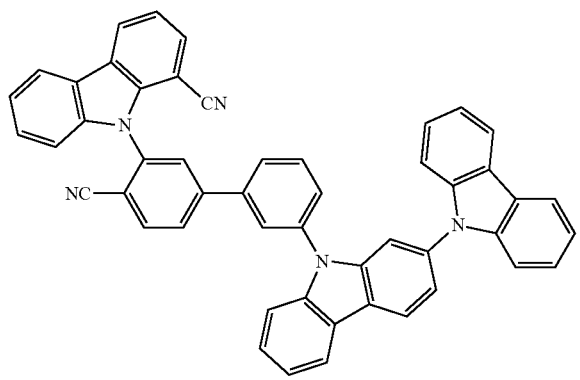
707
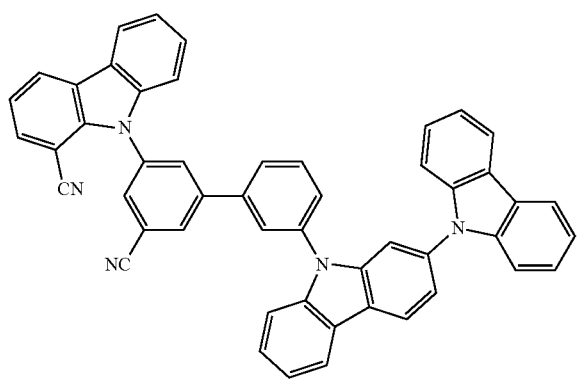
708
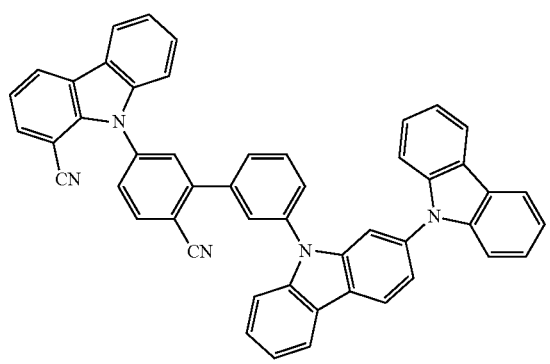
709
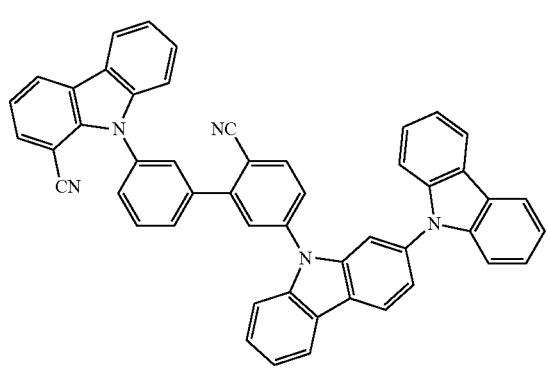
-continued
710
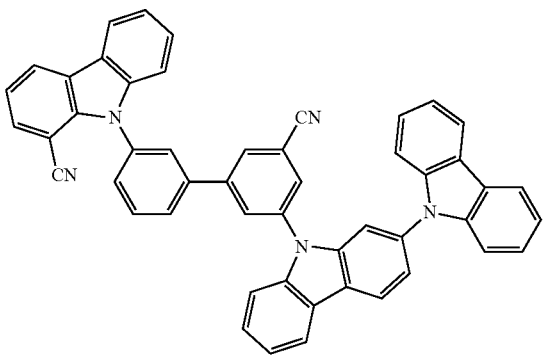
711
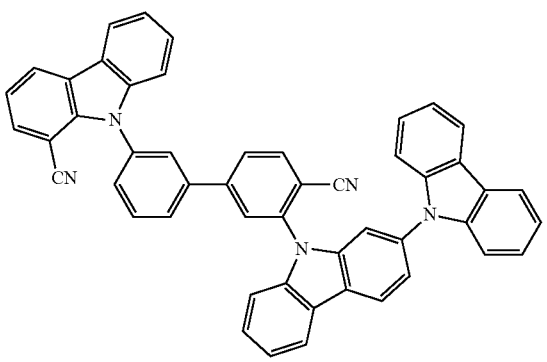
712
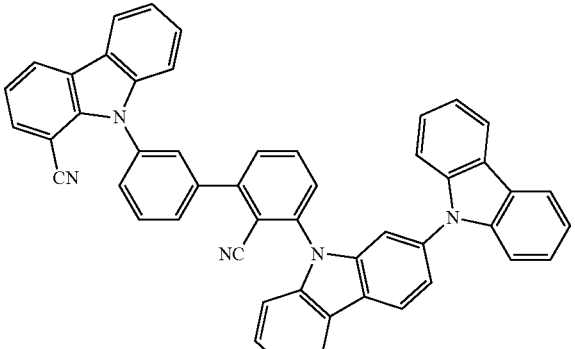
713
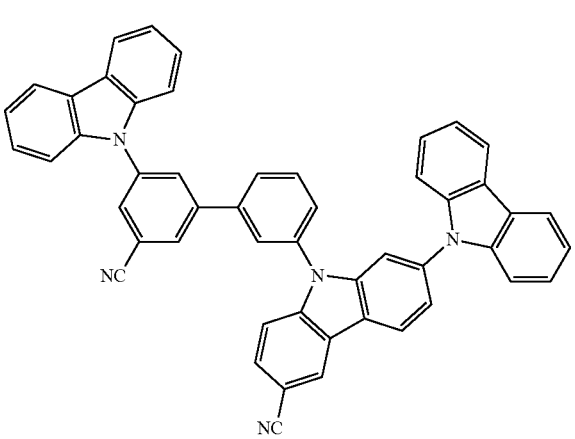

714
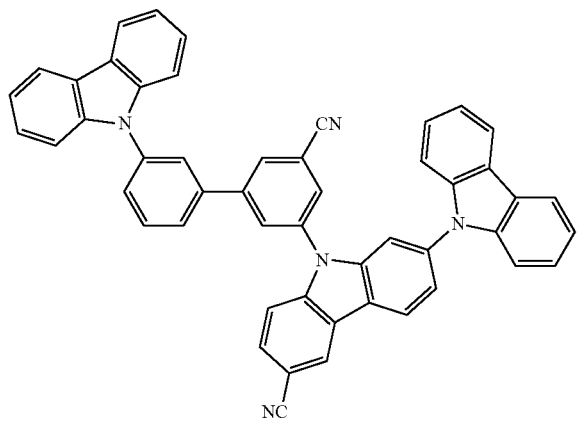
715
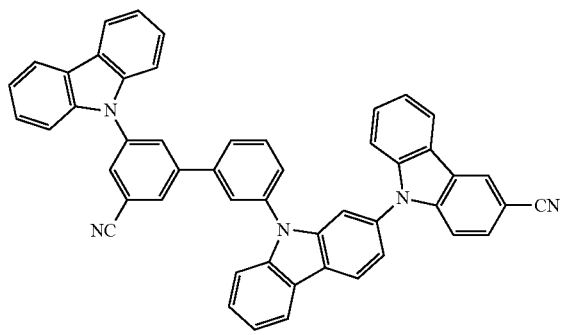
716
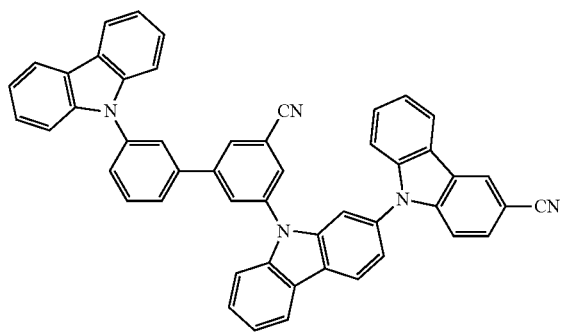
717
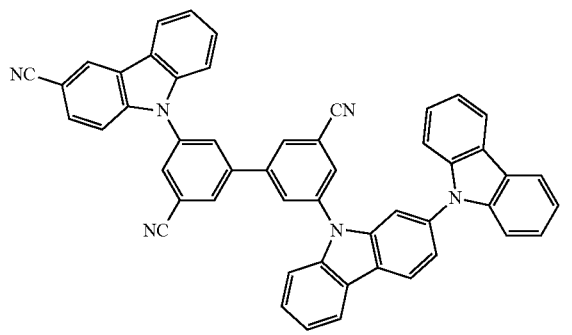
718
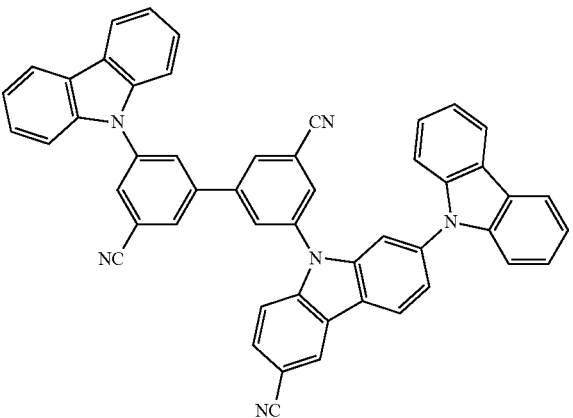
719
720
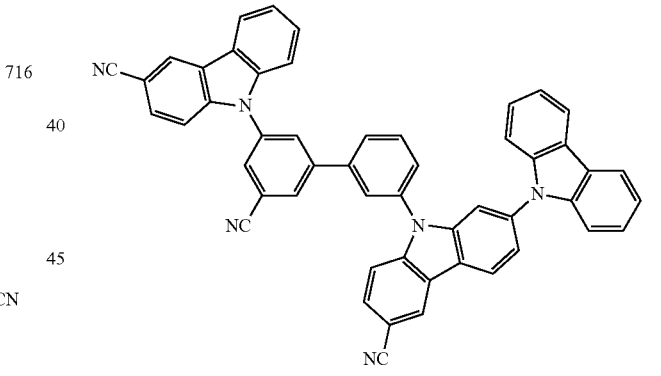
721

-continued
722
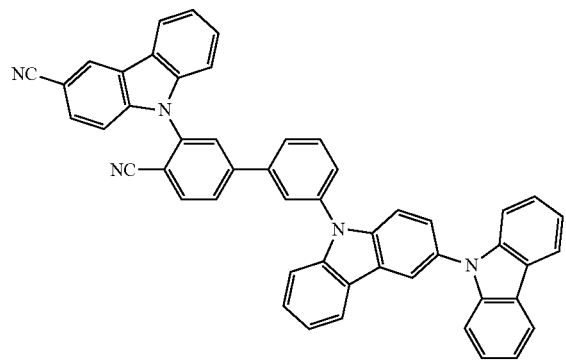
723
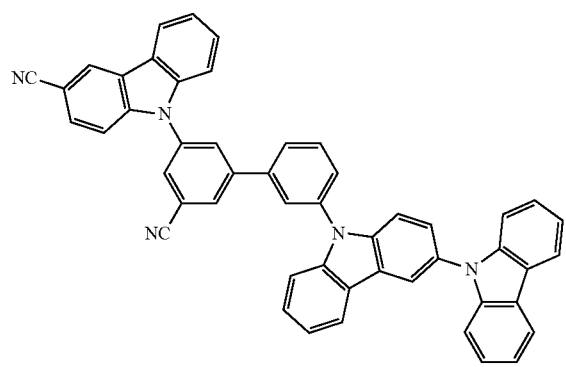
724
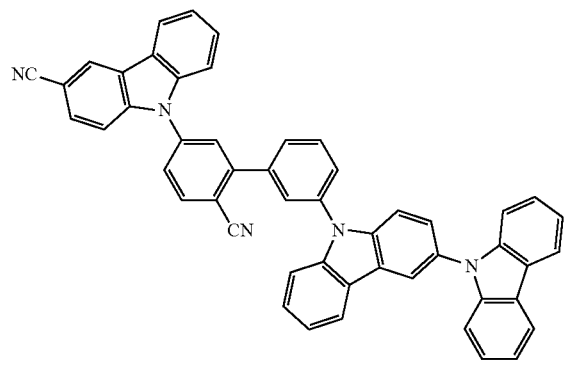
725
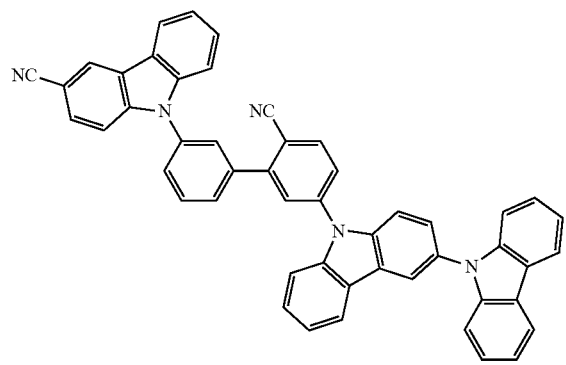
-continued
726
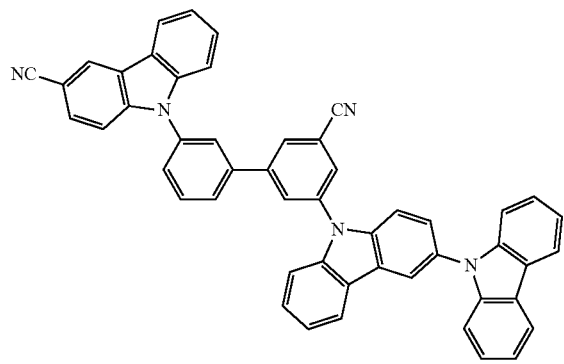
727
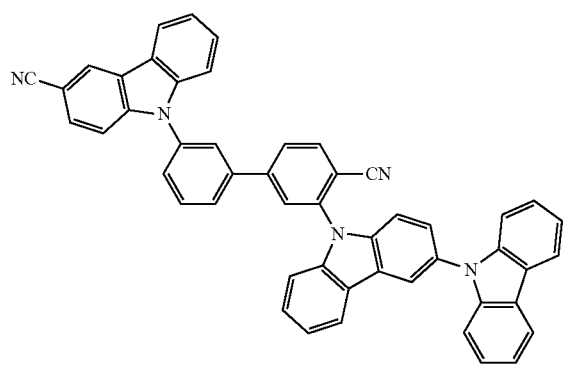
728
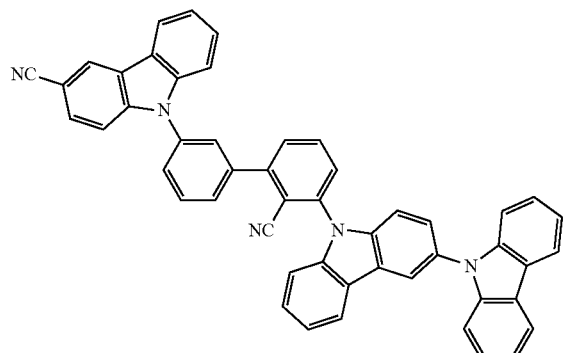
729
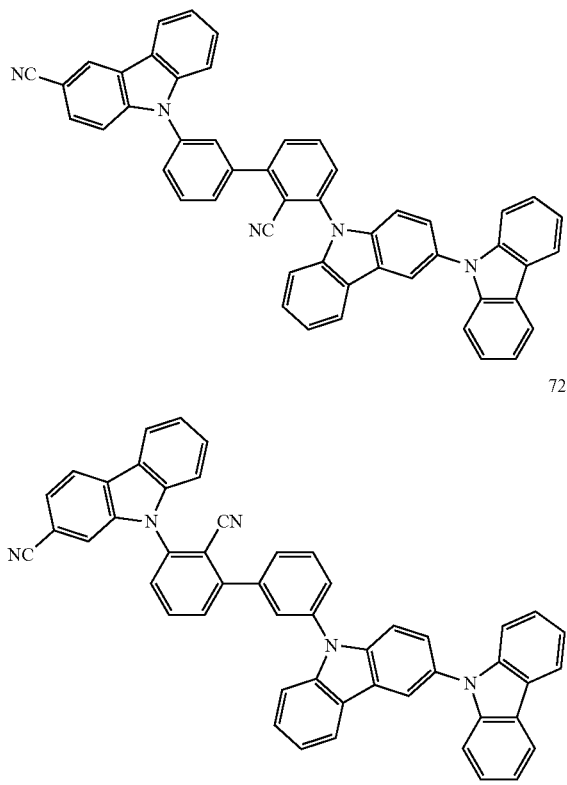

730
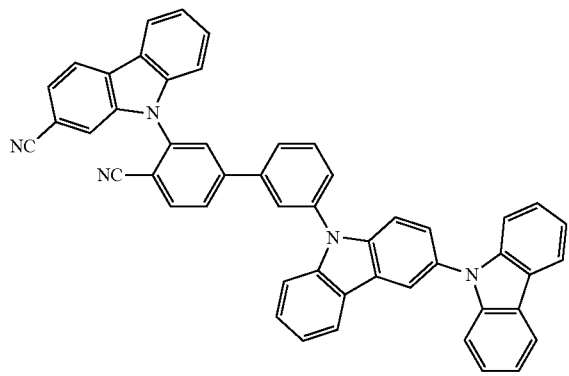
731
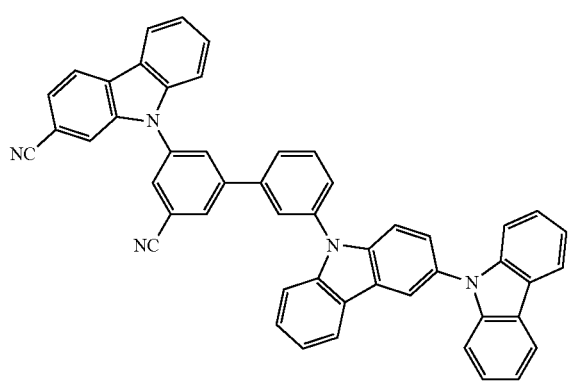
732
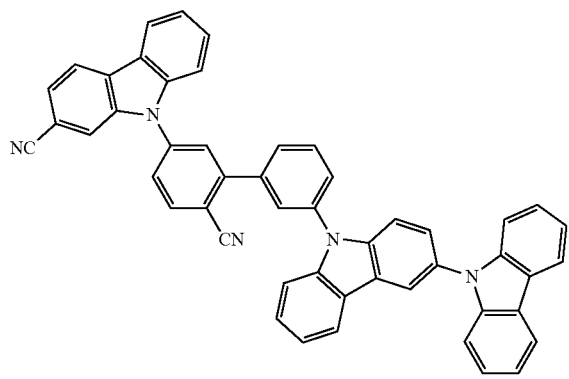
733
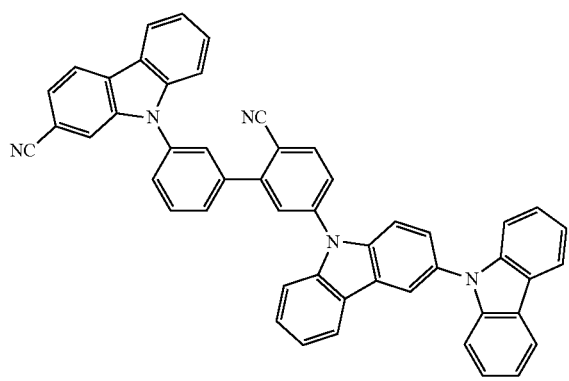
734
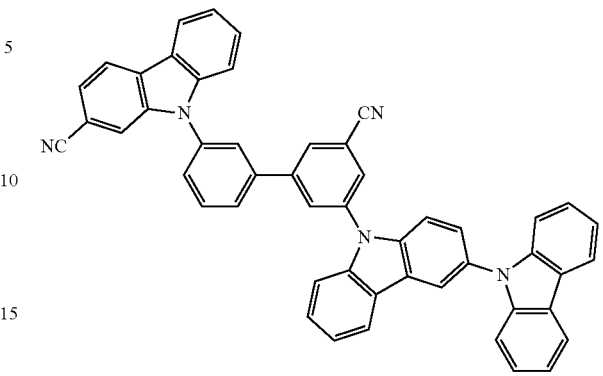
735
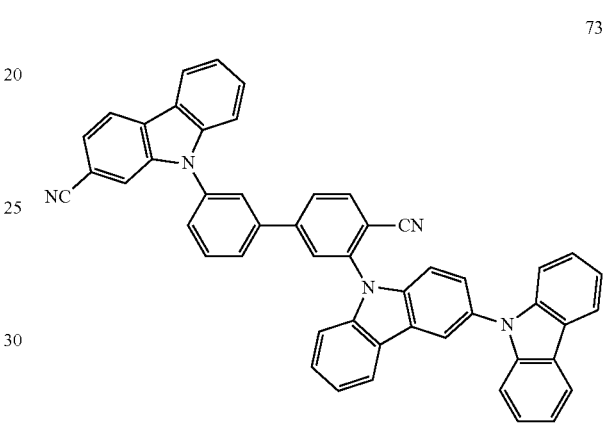
736
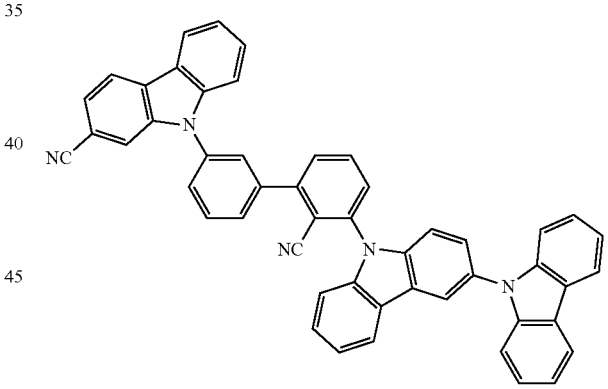
737
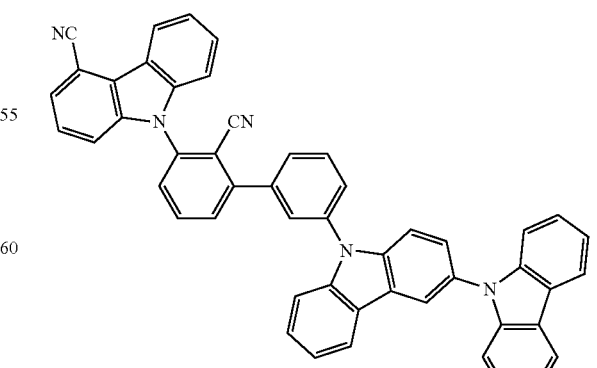

259
-continued
738
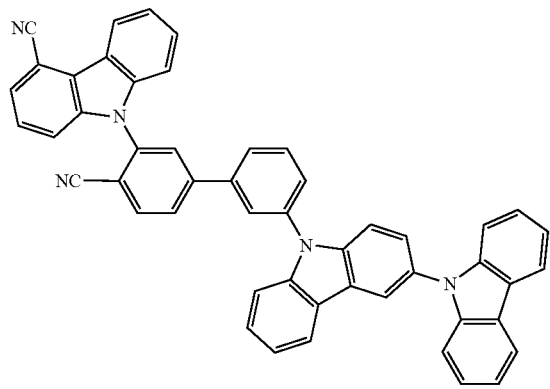
739
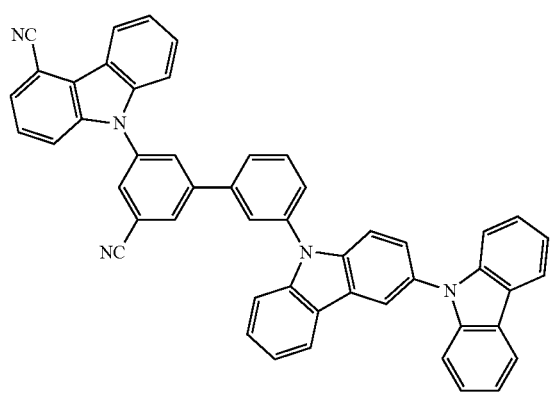
740
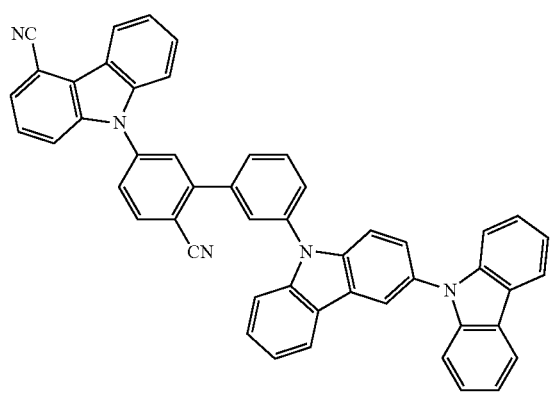
741
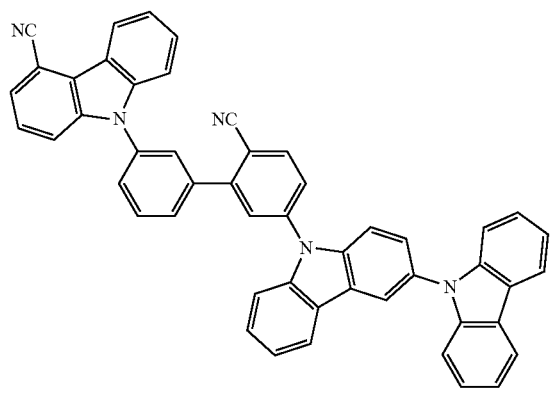
260
-continued
742
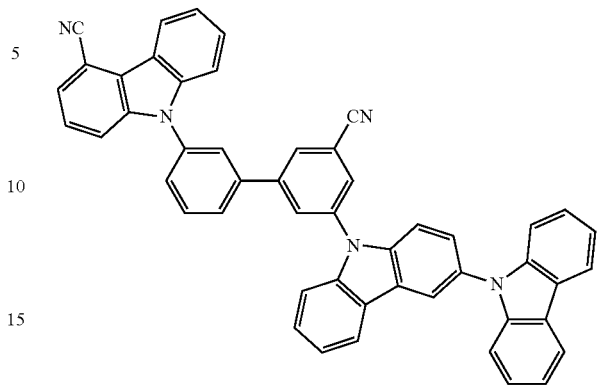
743

744

745

-continued
746
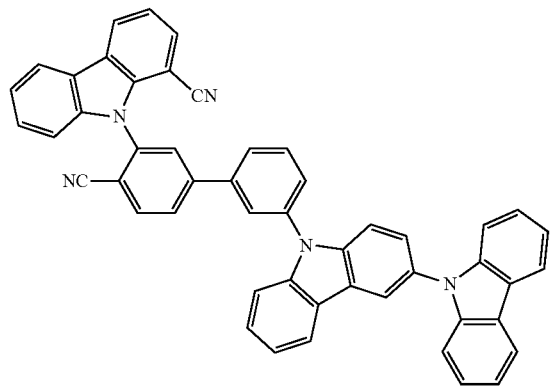
747
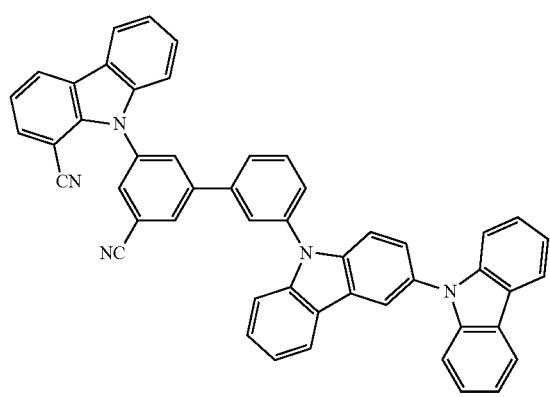
748
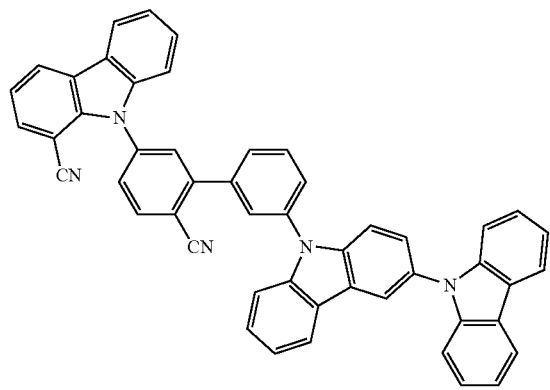
749
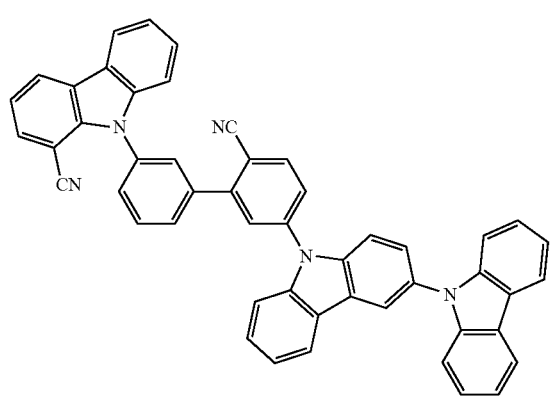
-continued
750
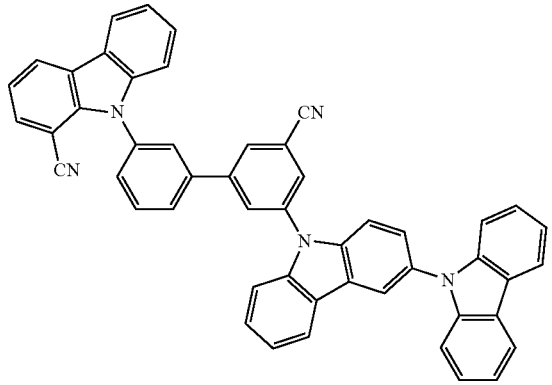
751
752
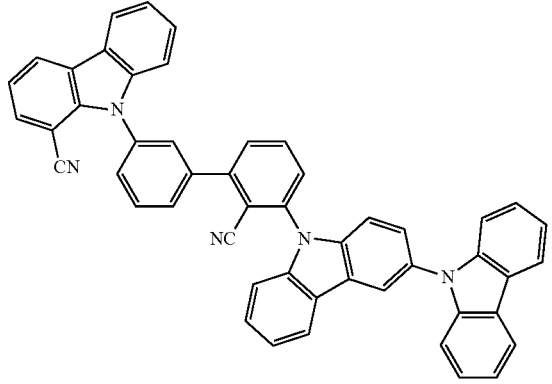
753
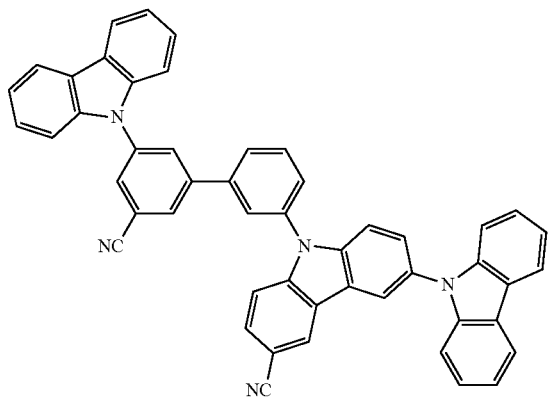

754
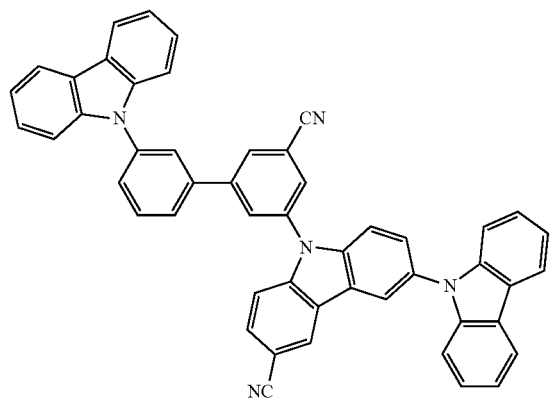
755
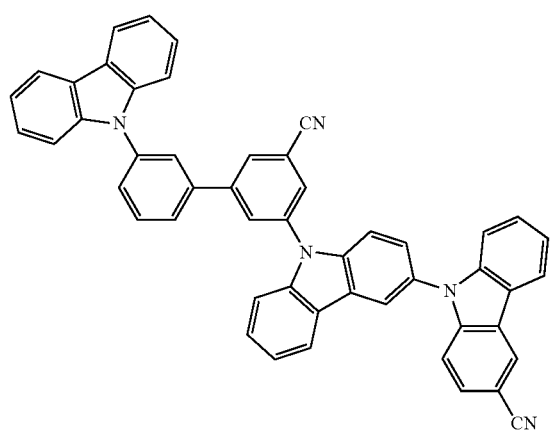
756
757
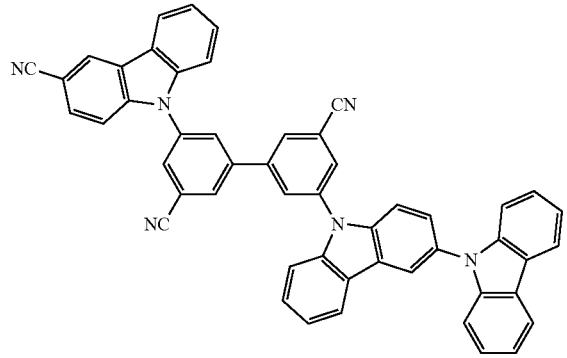
758
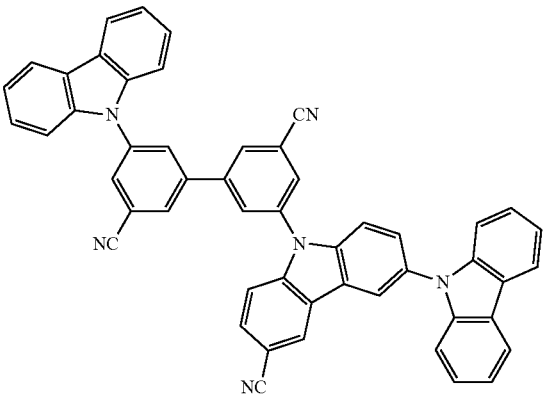
759
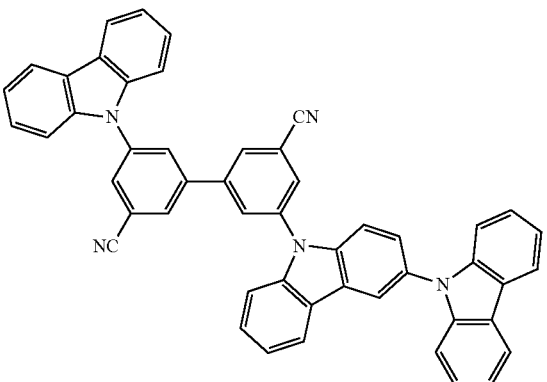
760

-continued
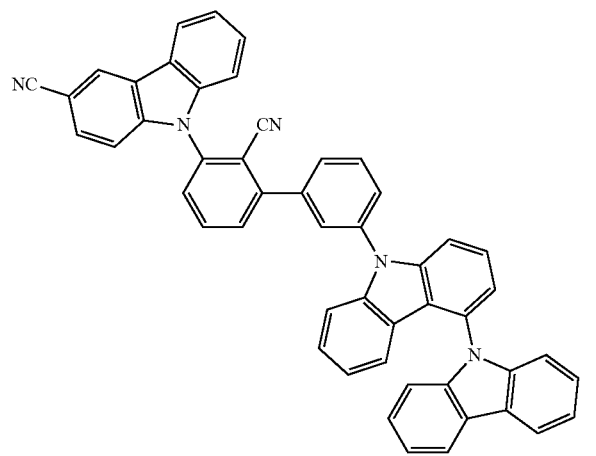
761
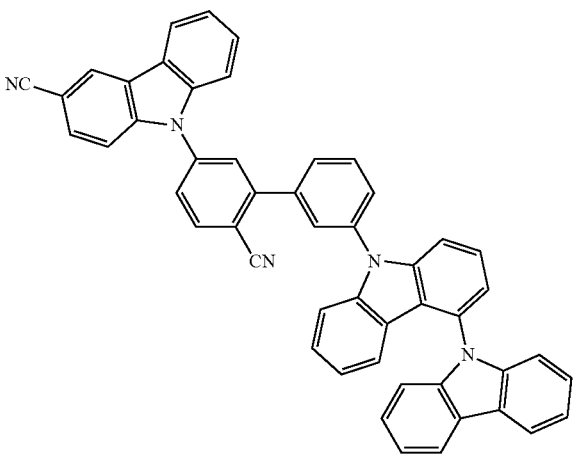
764
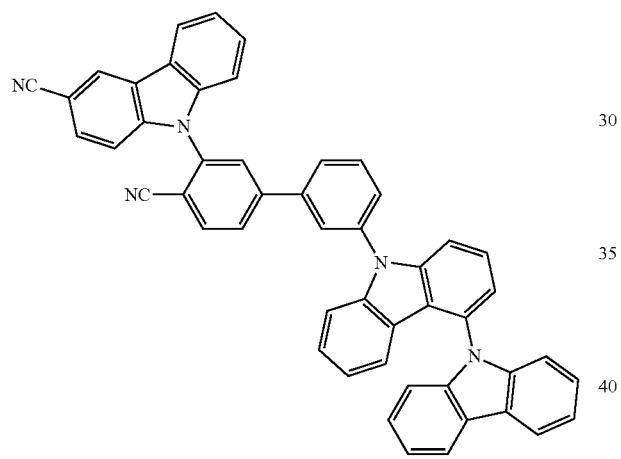
762
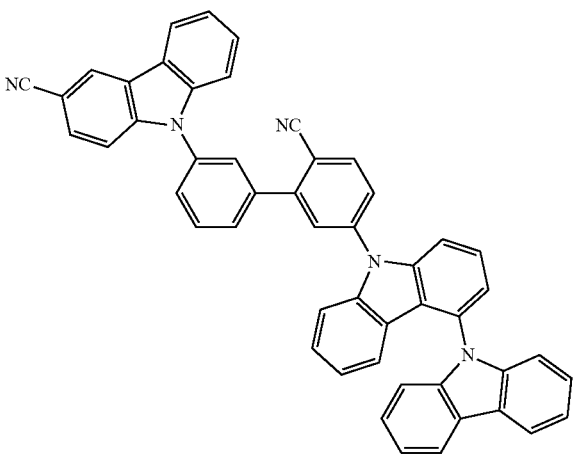
765
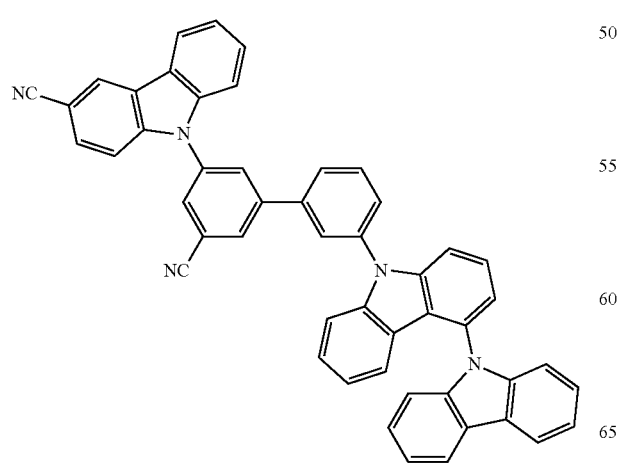
763
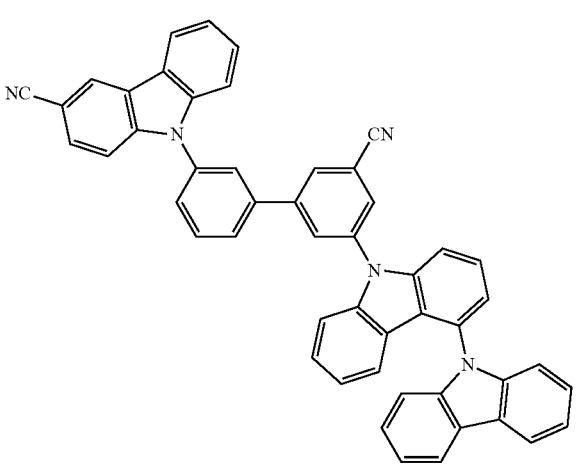
766

267
-continued
768

769
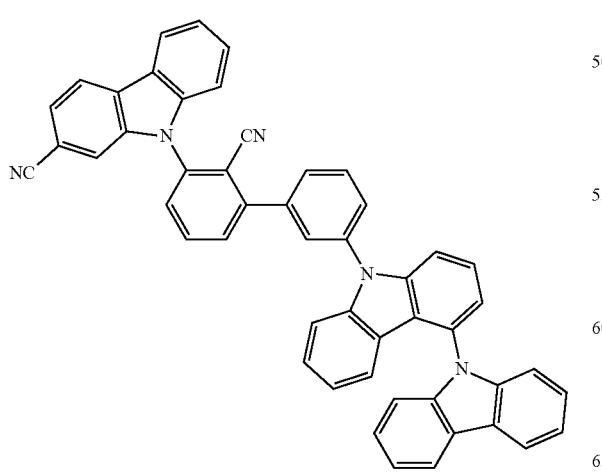
268
-continued
770

771
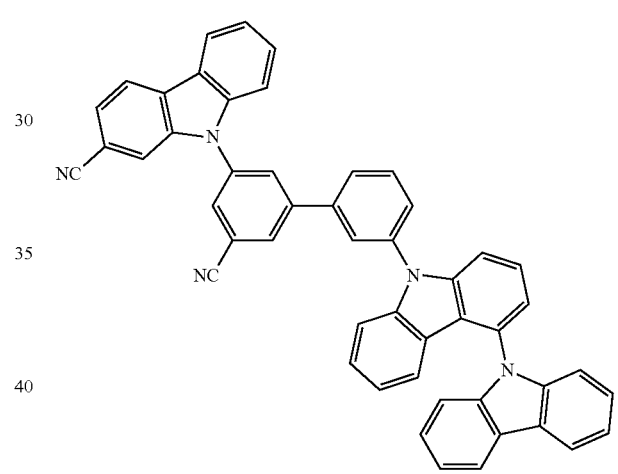
772
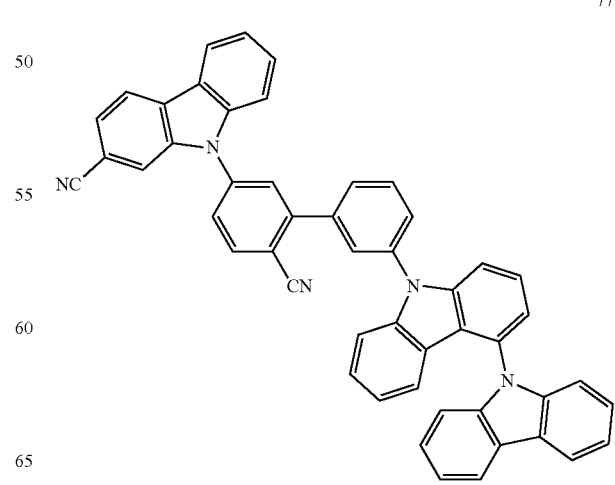

773
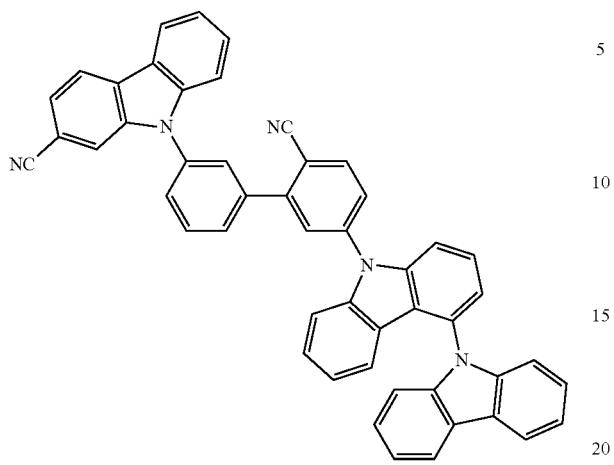
776
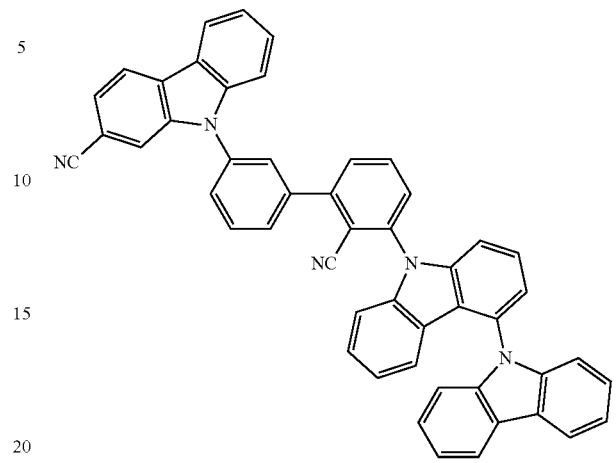
774
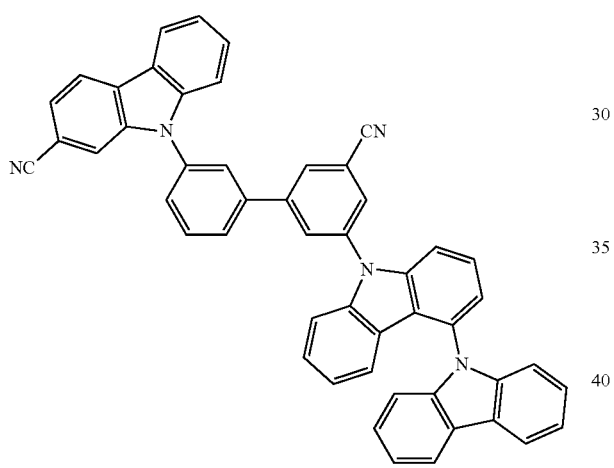
777
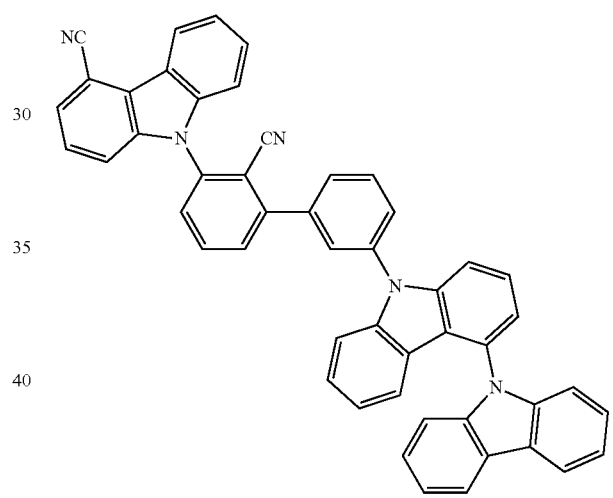
775
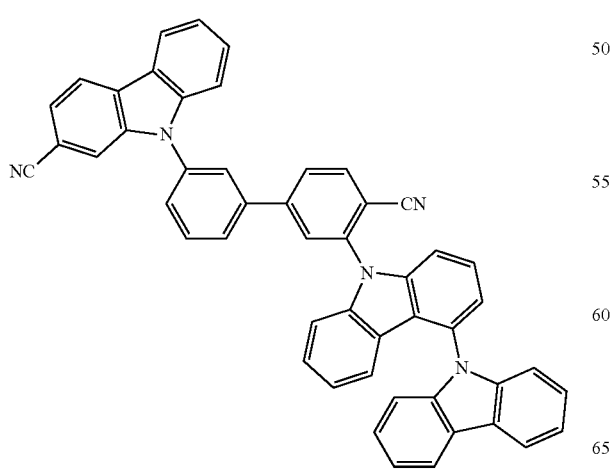
778
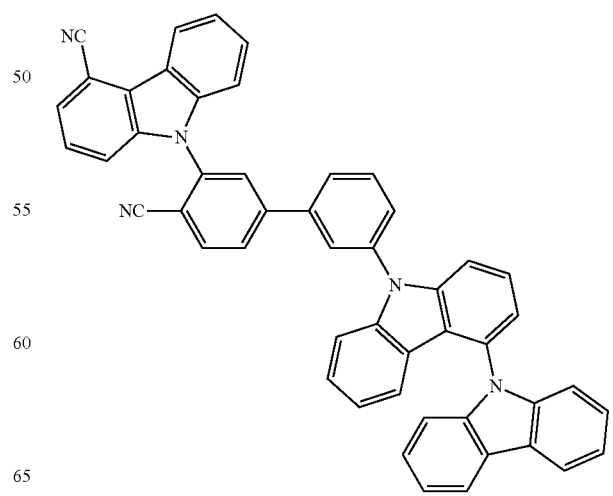

779
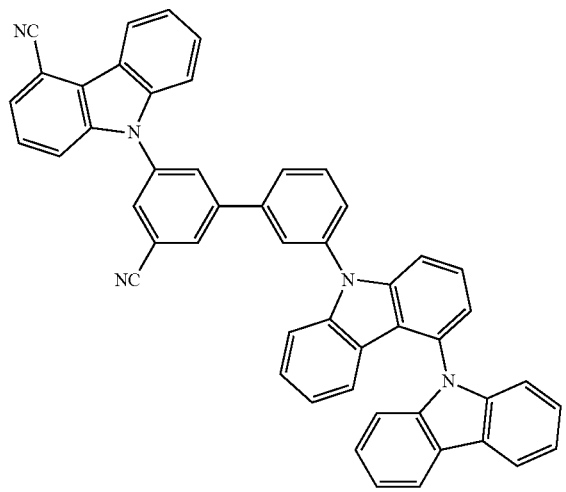
782
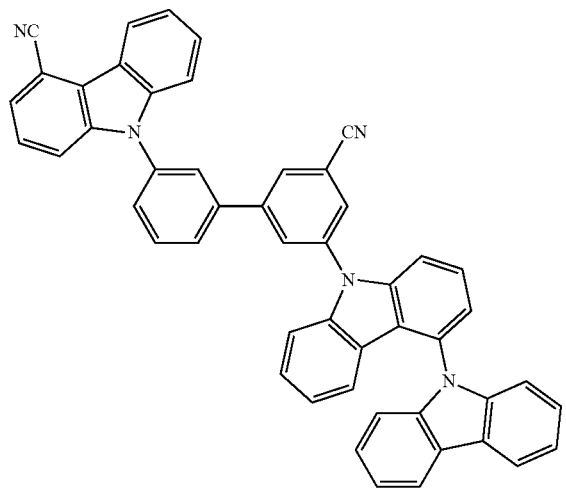
780
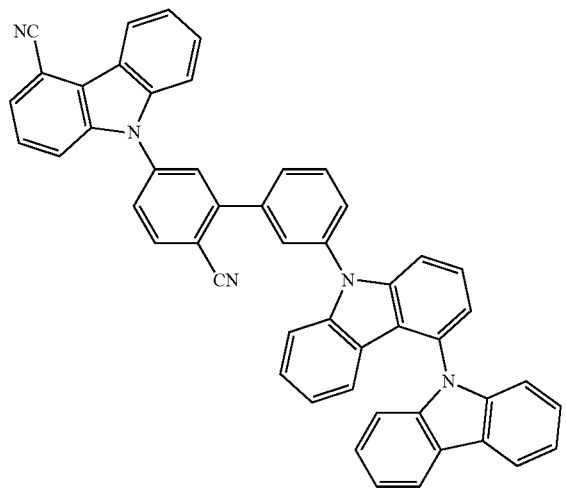
783
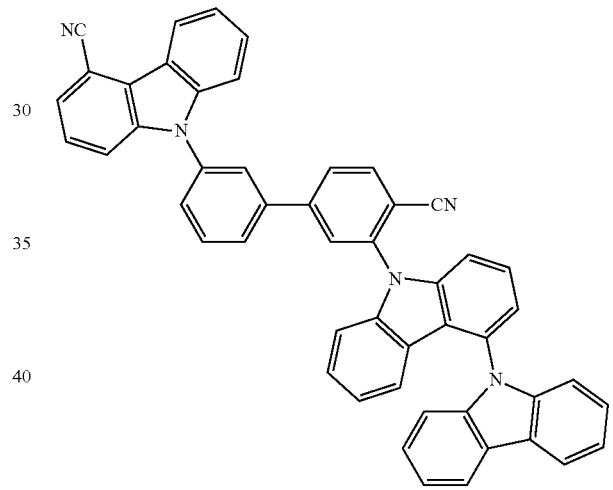
781
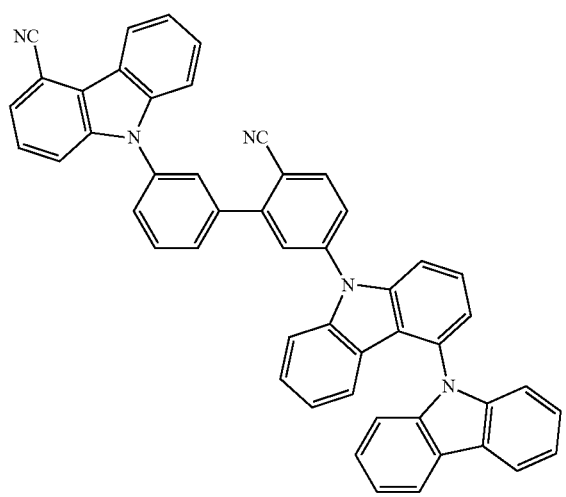
784
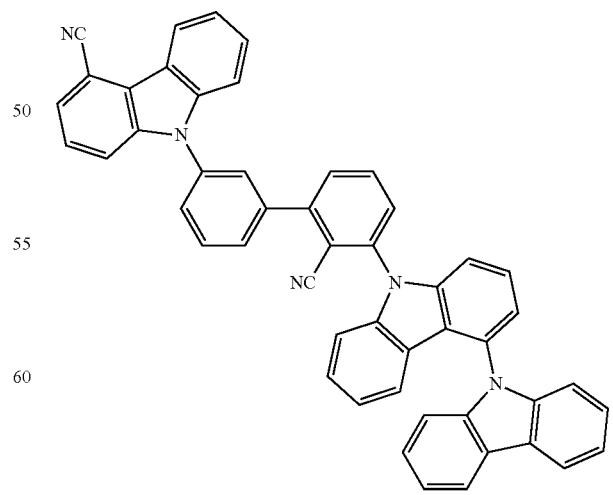

785
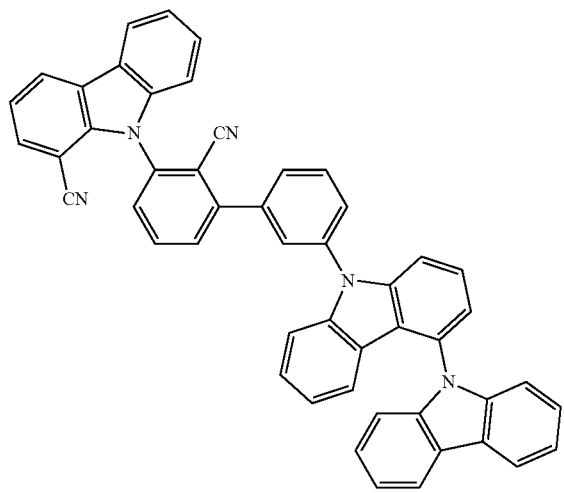
786
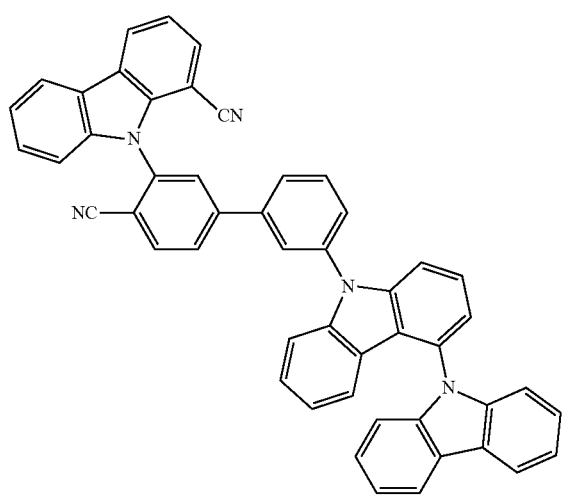
787
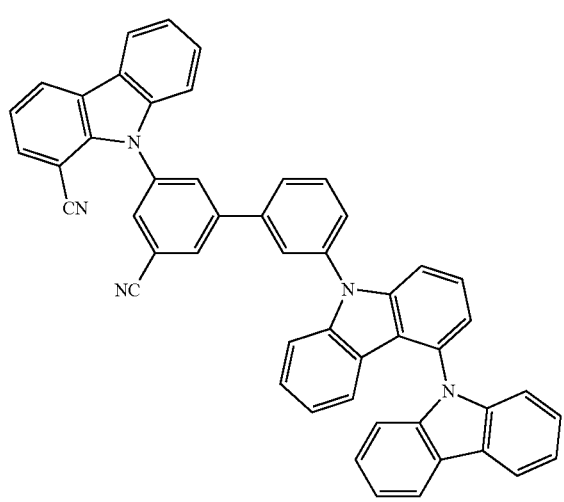
788
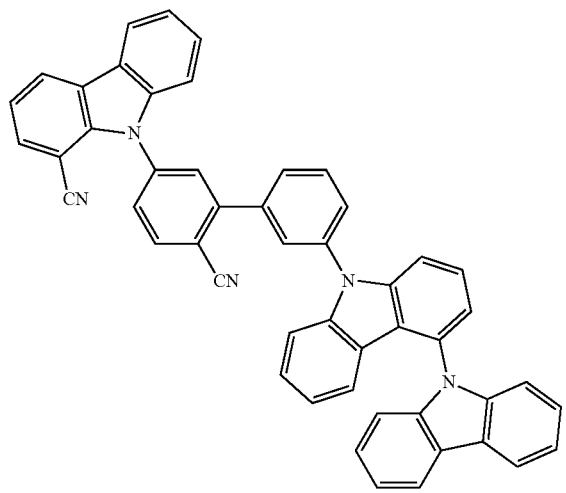
789
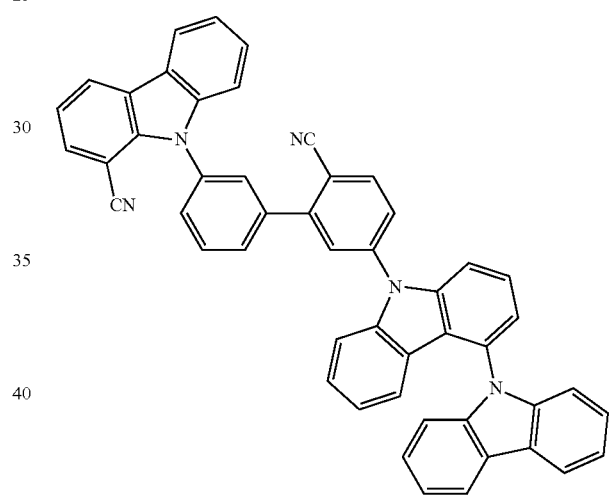
790
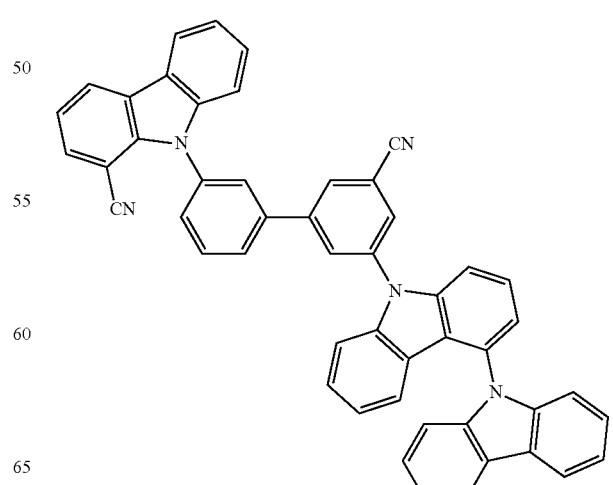

-continued
791
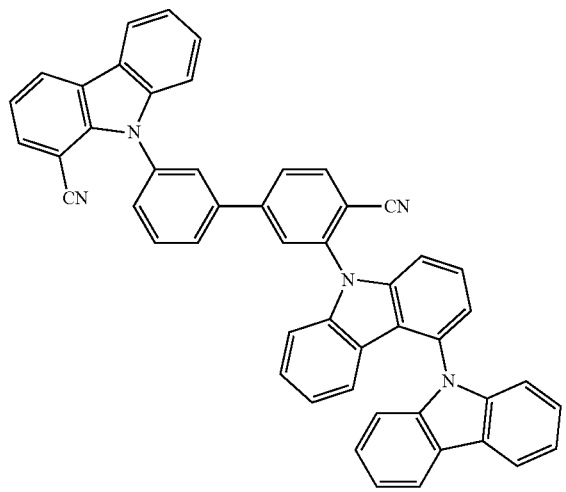
792
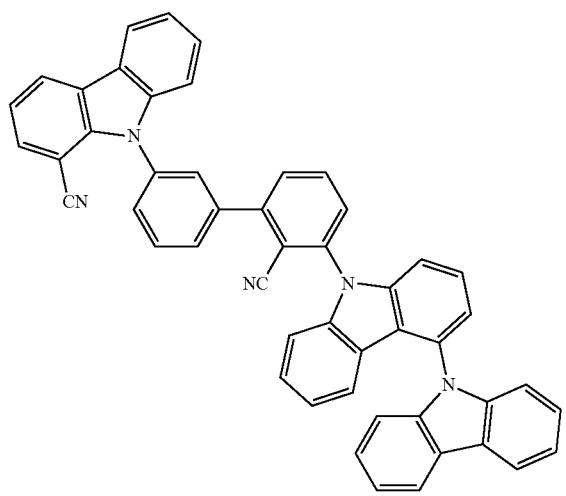
793
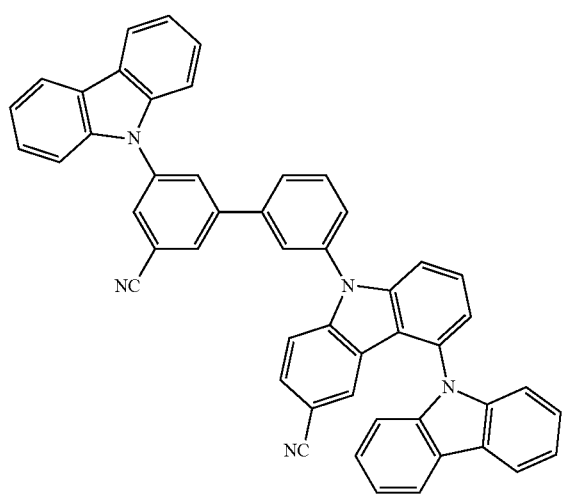
-continued
794
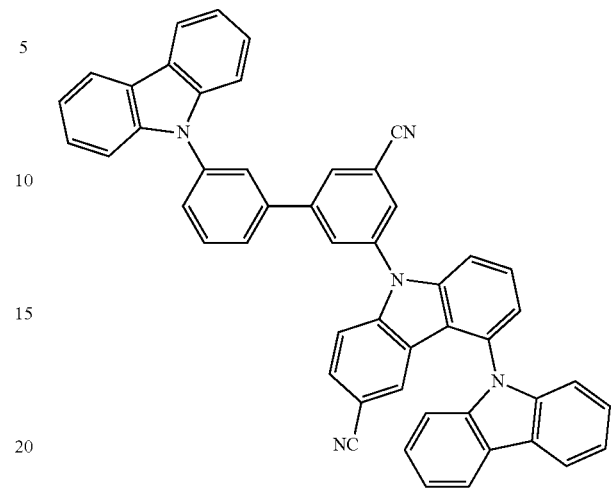
795
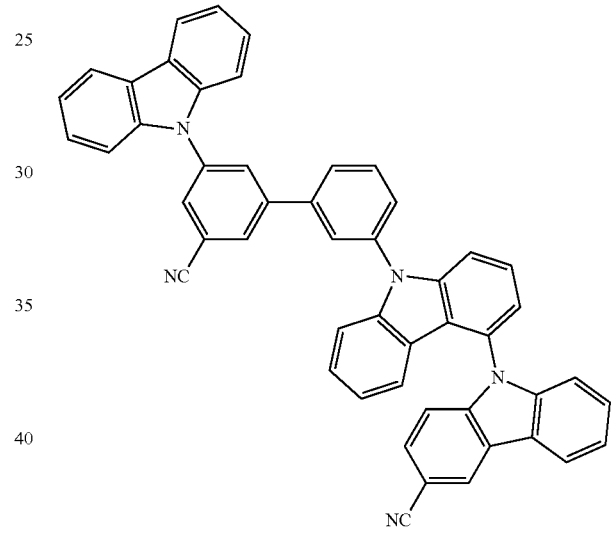
796
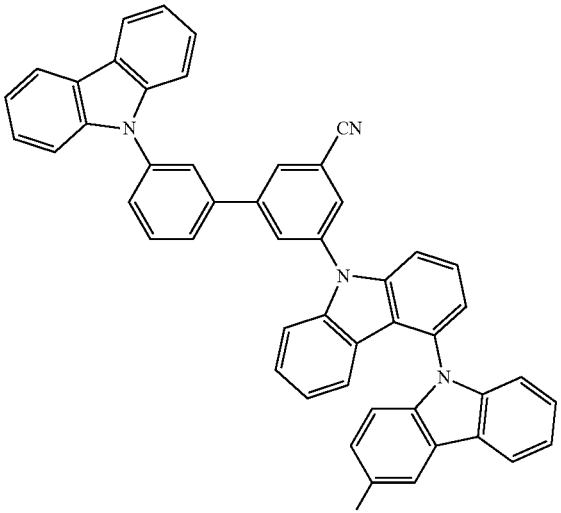

797
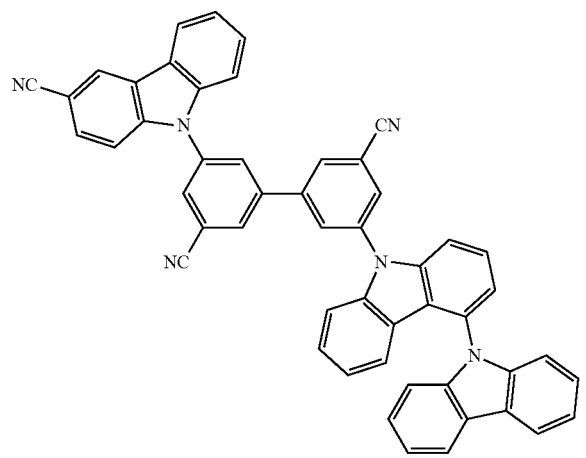
798
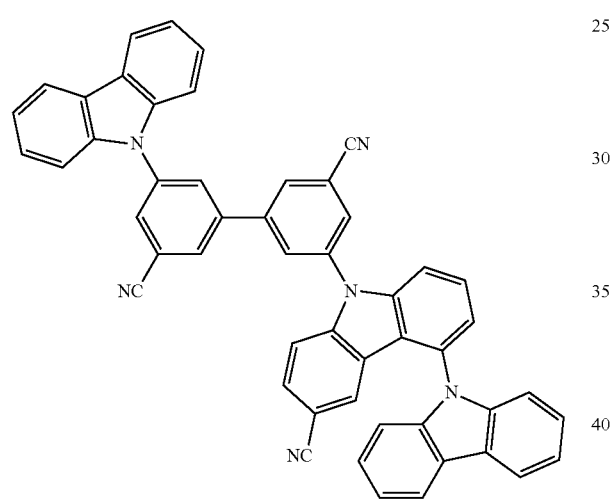
799
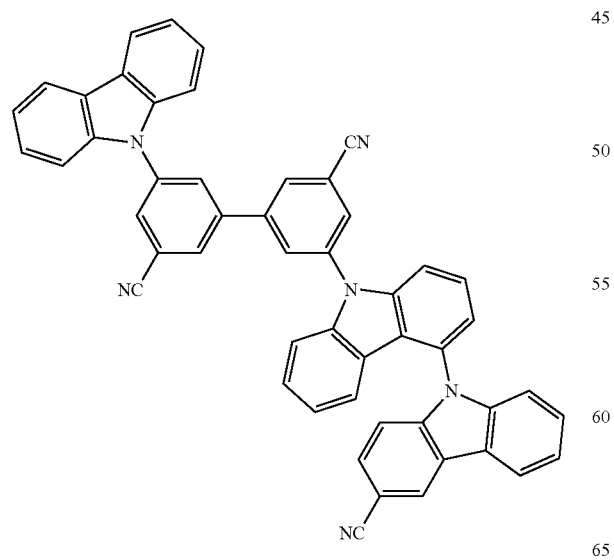
800
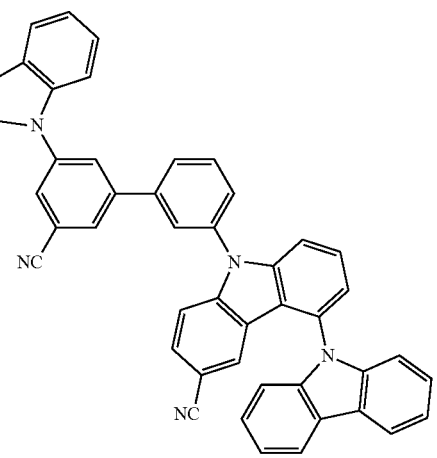
801
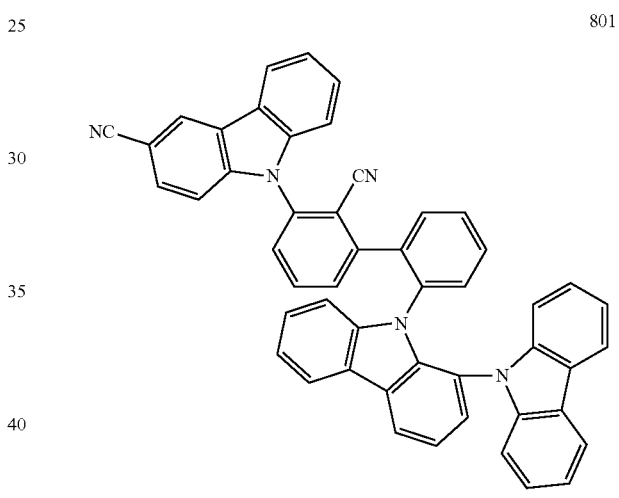
802
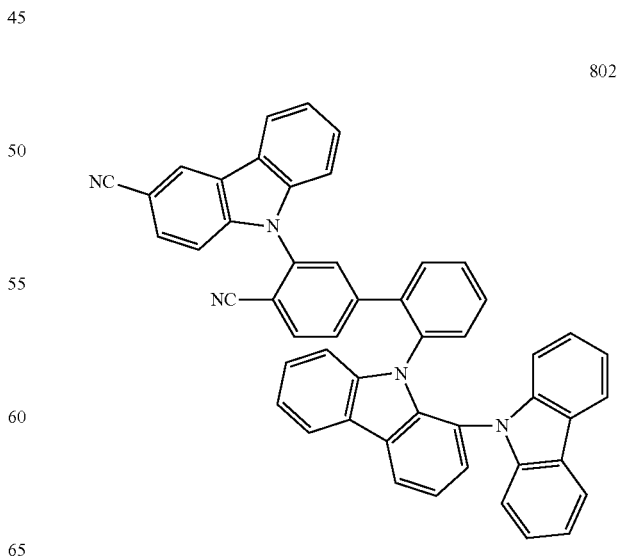

-continued
803
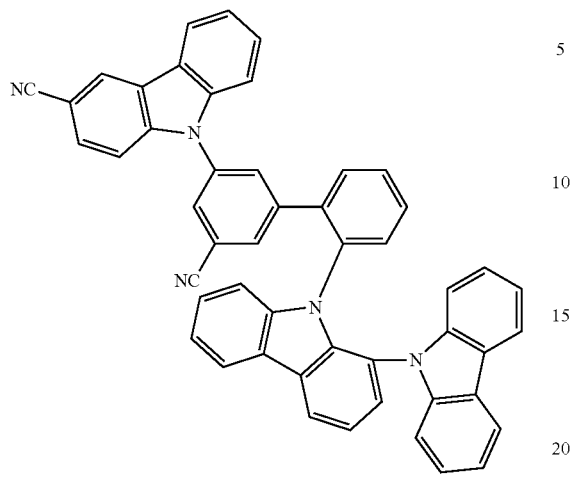
804
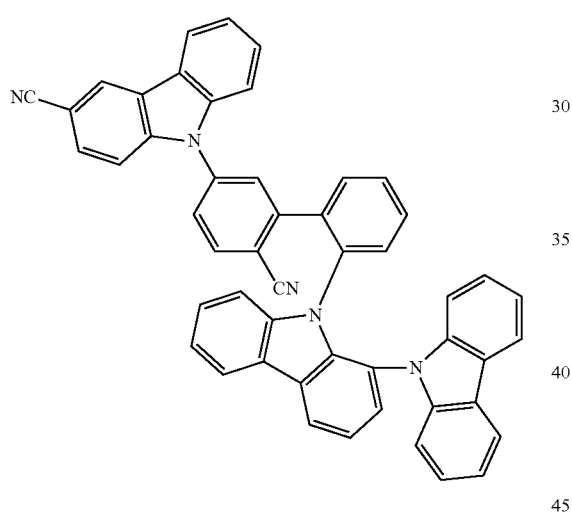
805
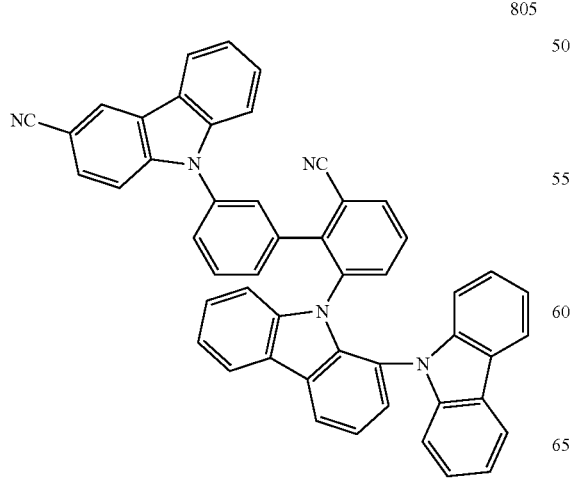
-continued
806
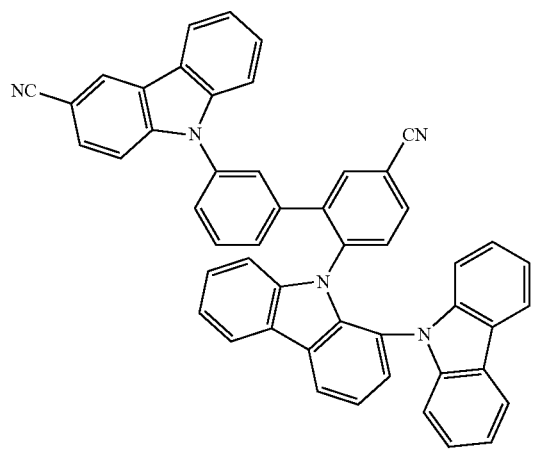
807
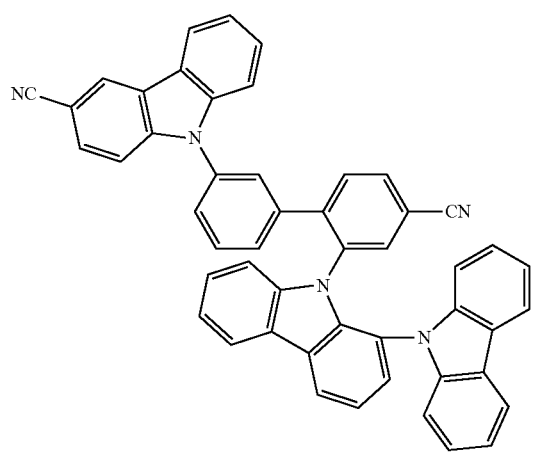
808
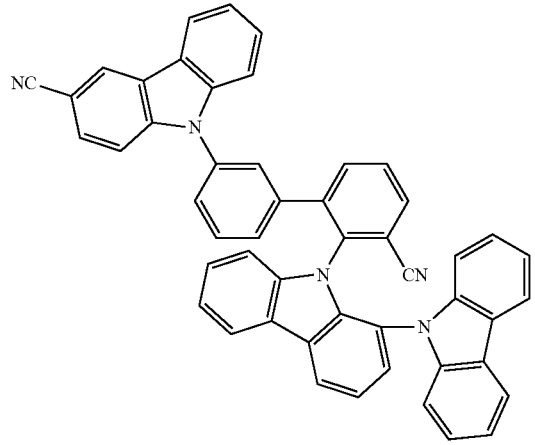

809
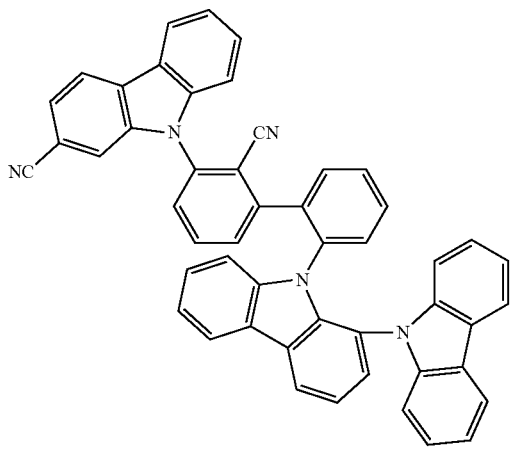
810
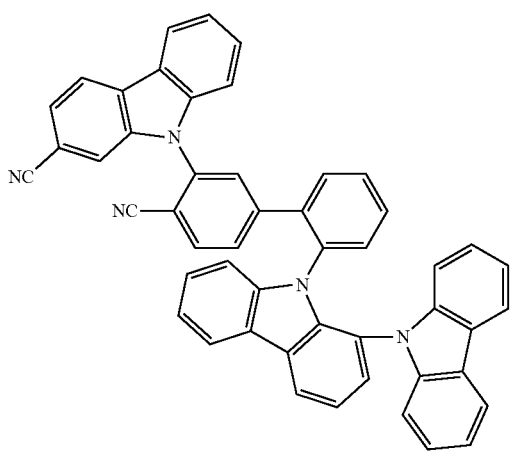
811
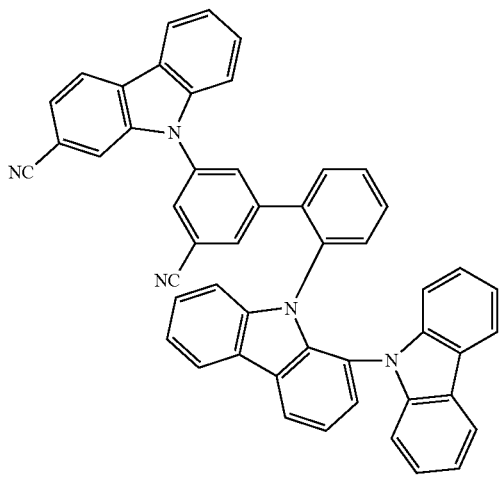
812
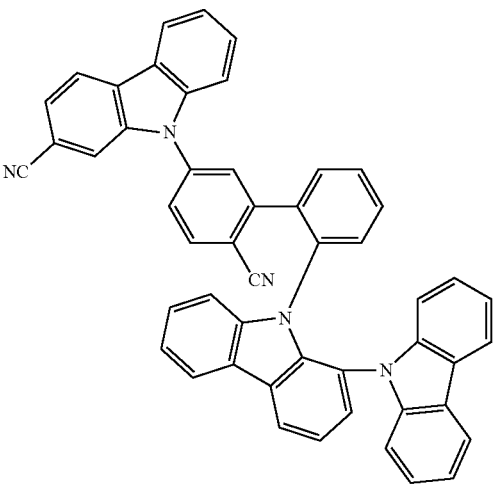
813
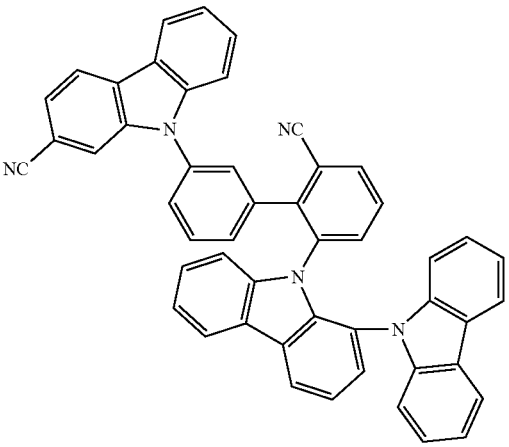
814
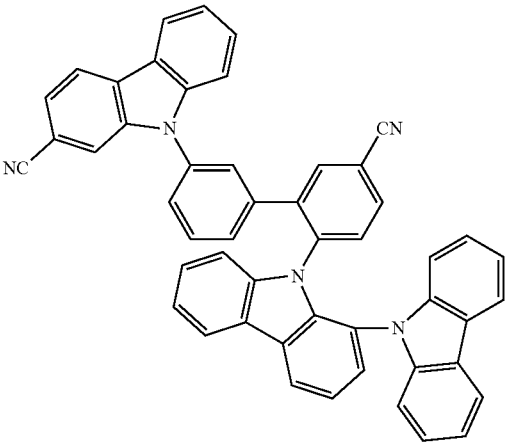

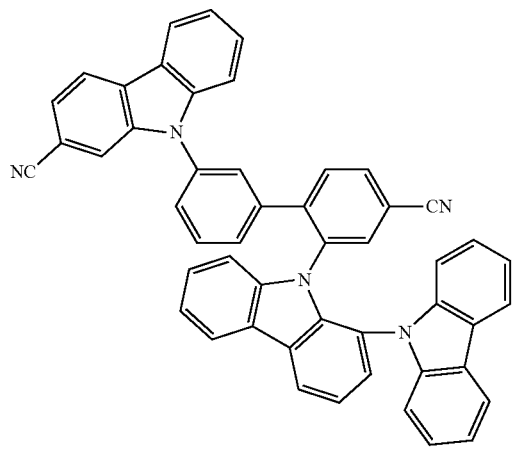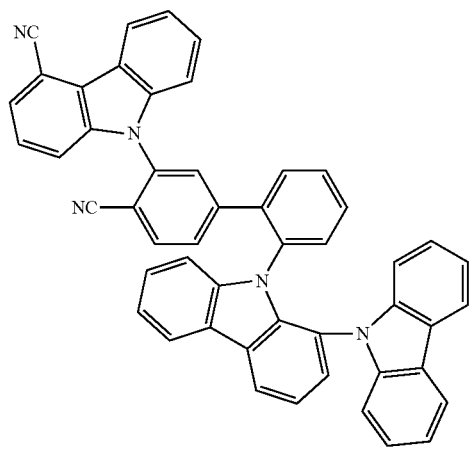

821
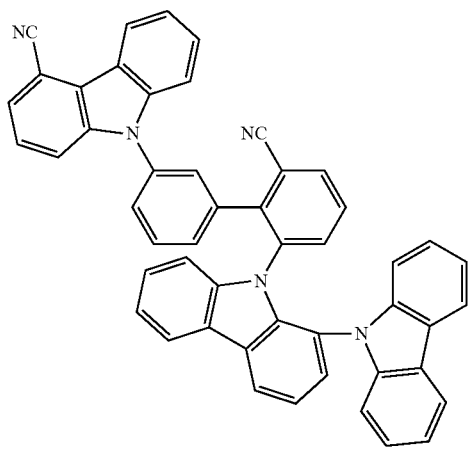
822
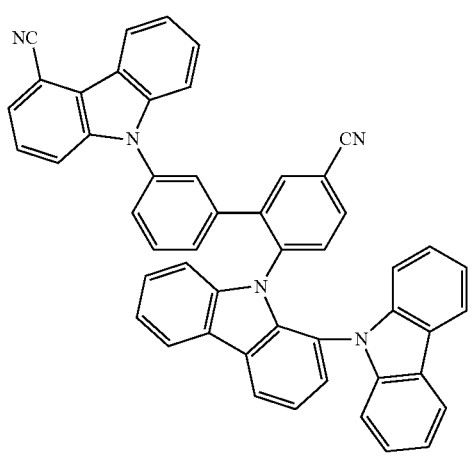
823
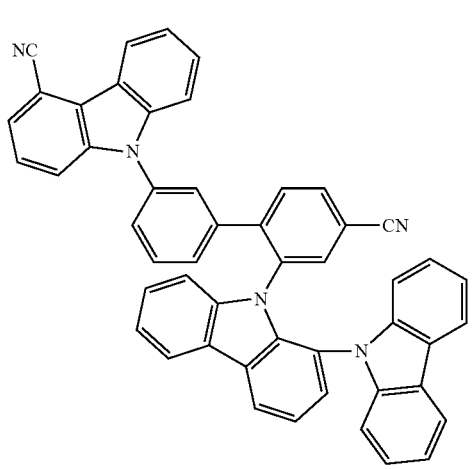
824
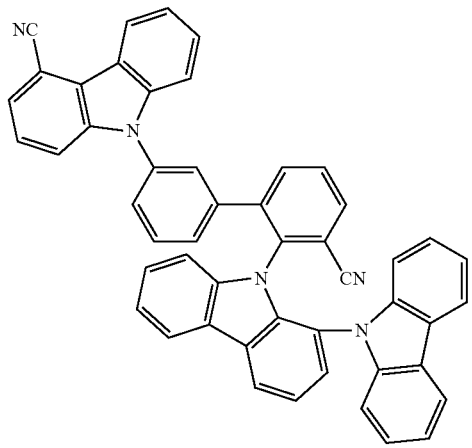
825
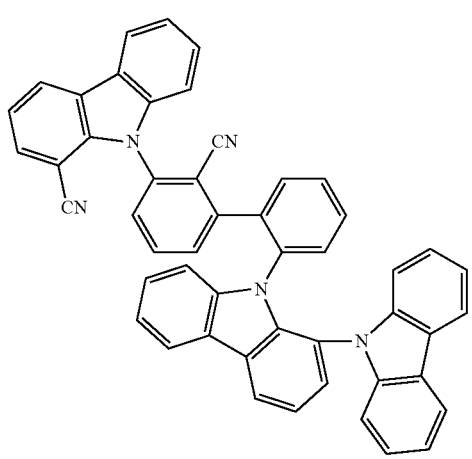
826
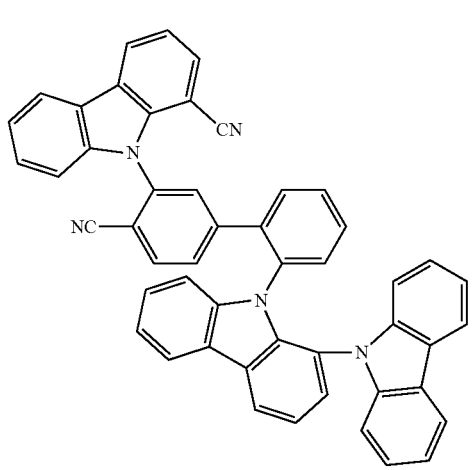

827
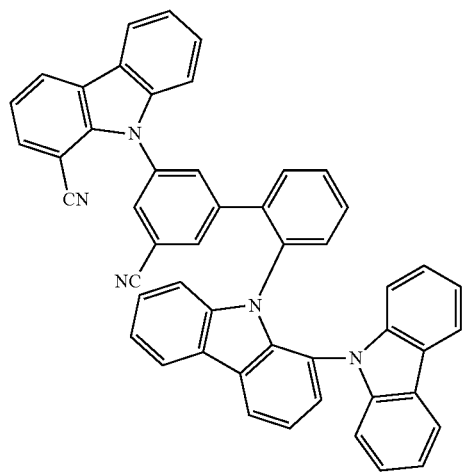
828
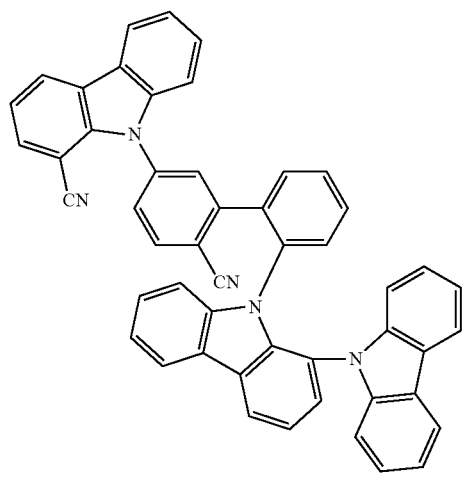
829
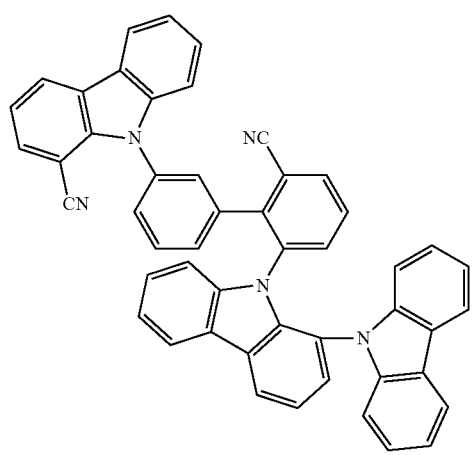
830
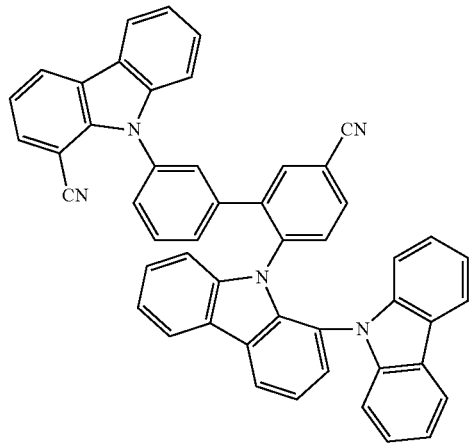
831
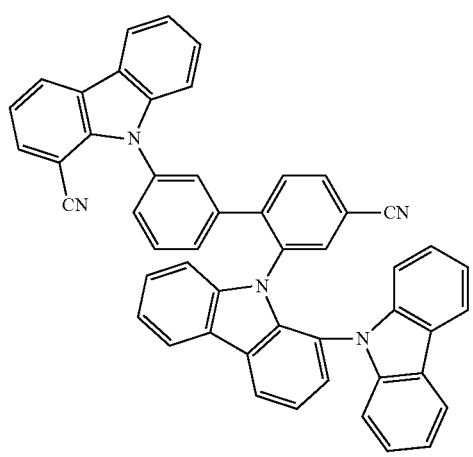
832
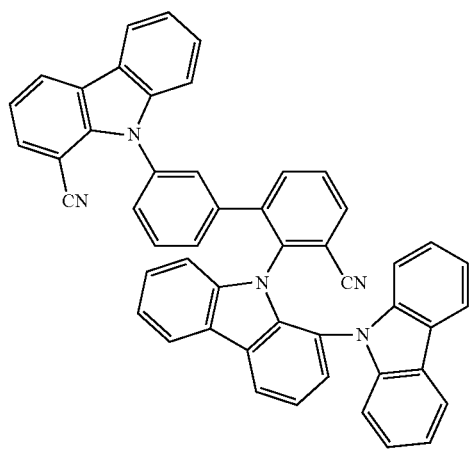

833
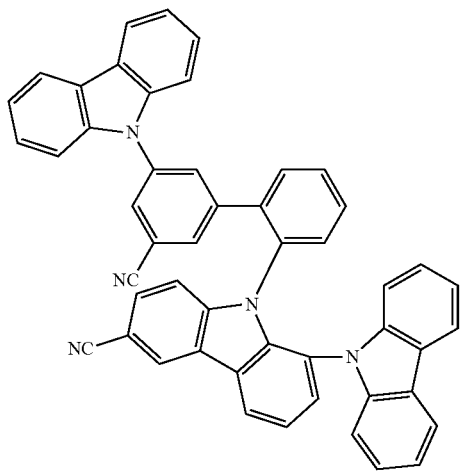
834
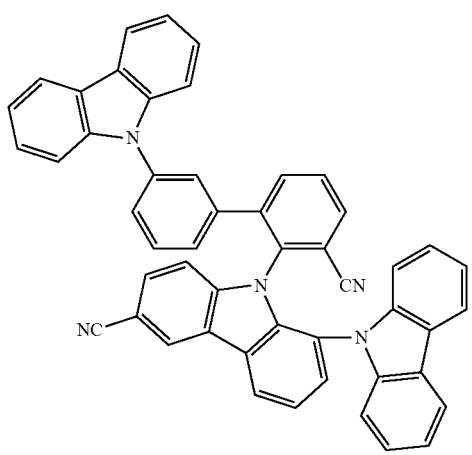
835
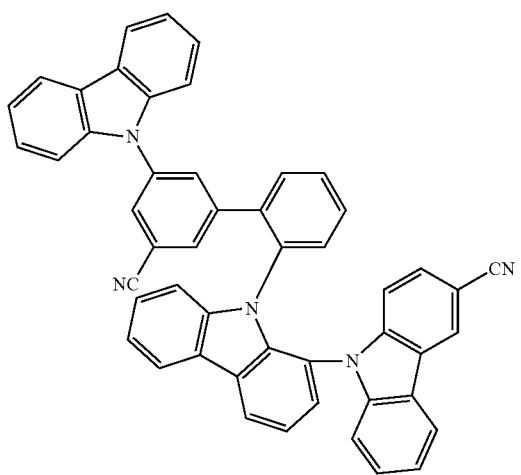
836
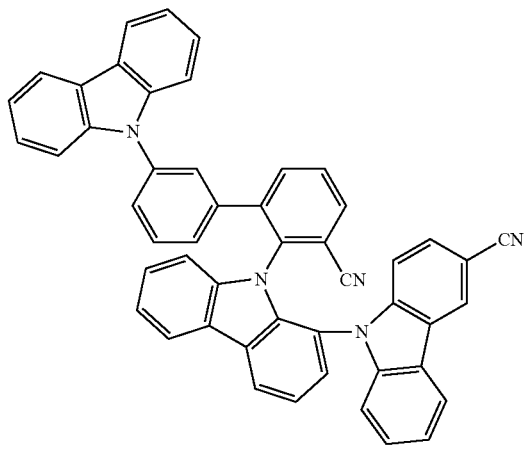
837
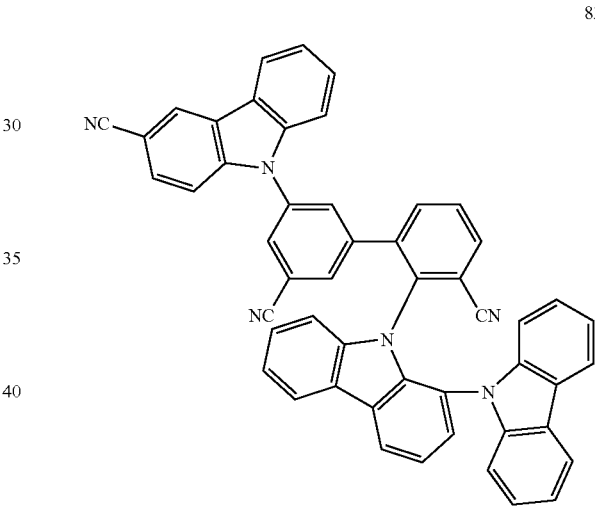
838
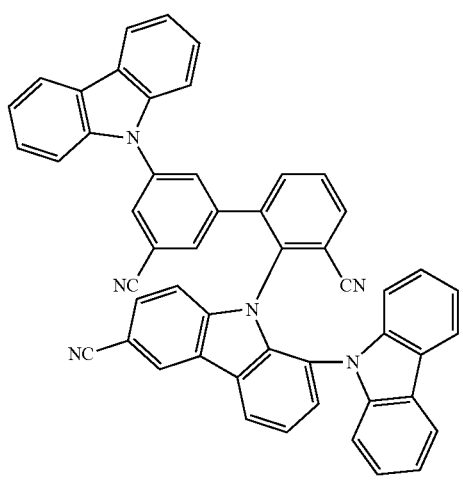

839
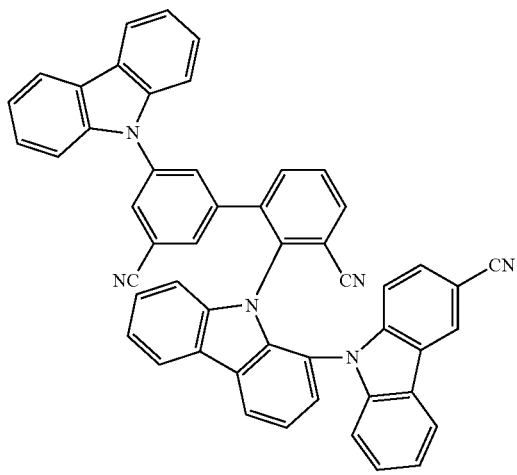
840
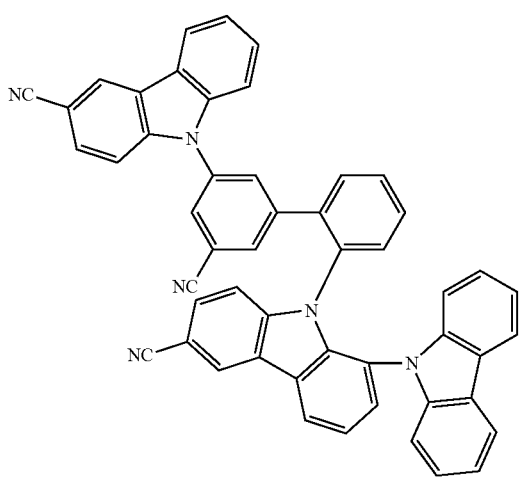
841
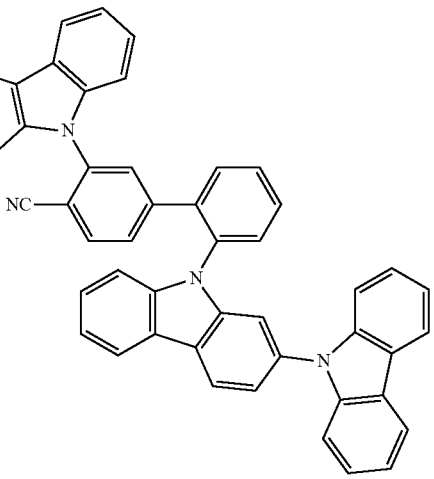
842
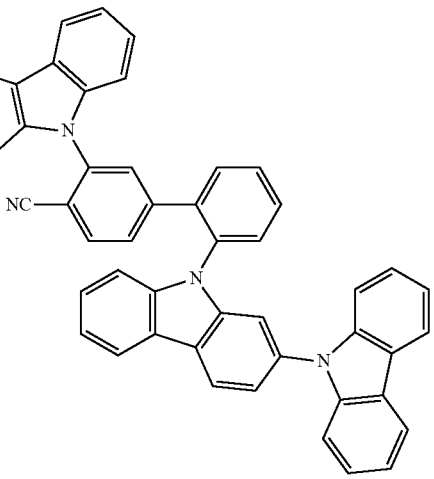
843
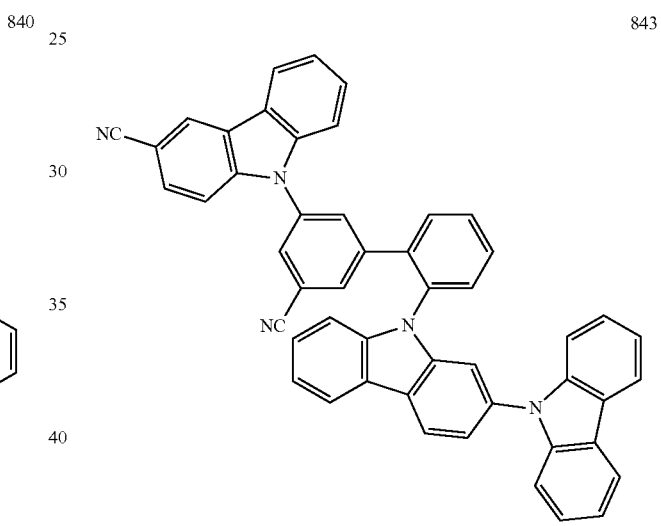
844
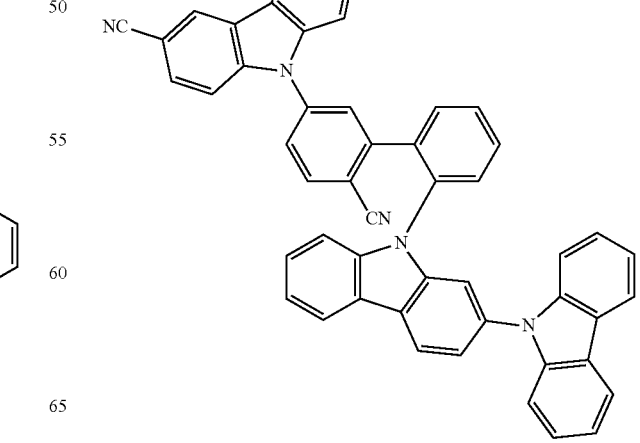

845
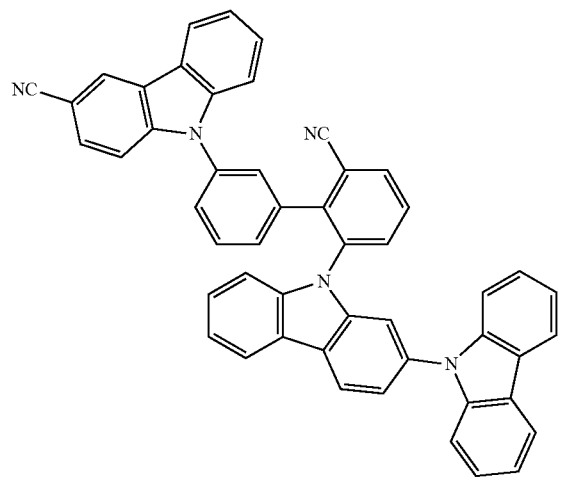
848
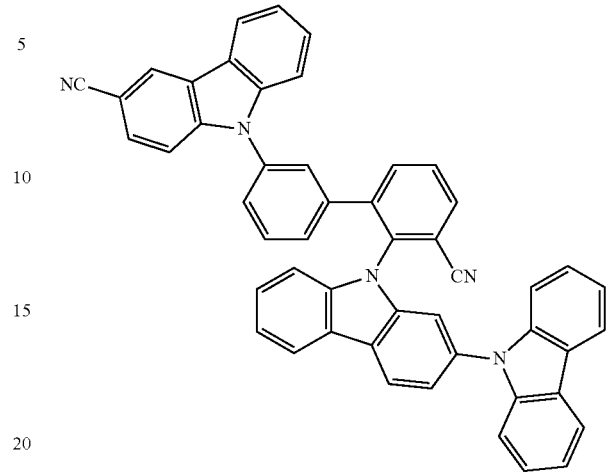
846
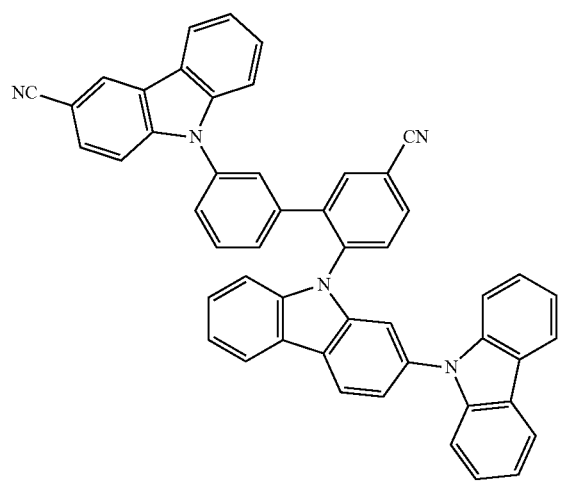
849
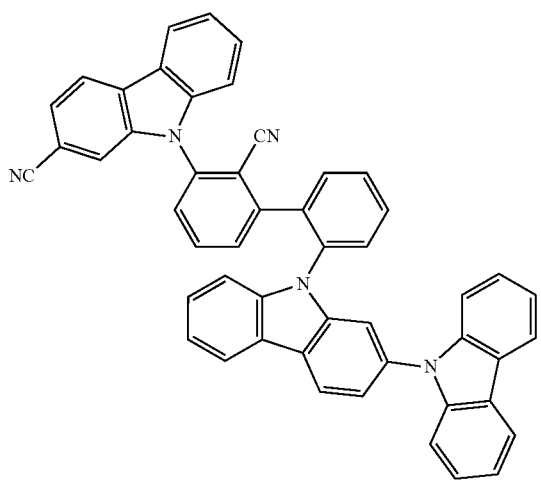
847
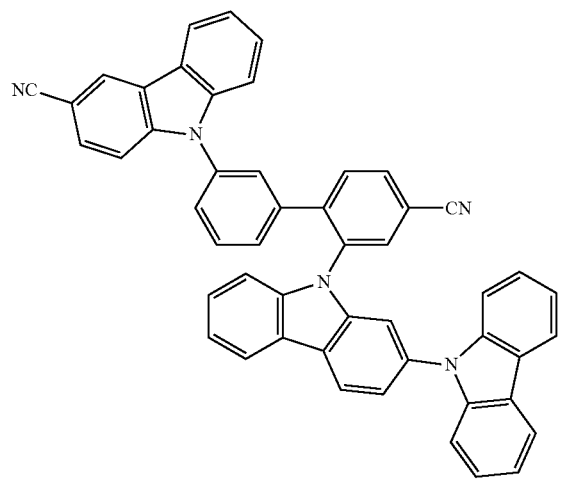
850
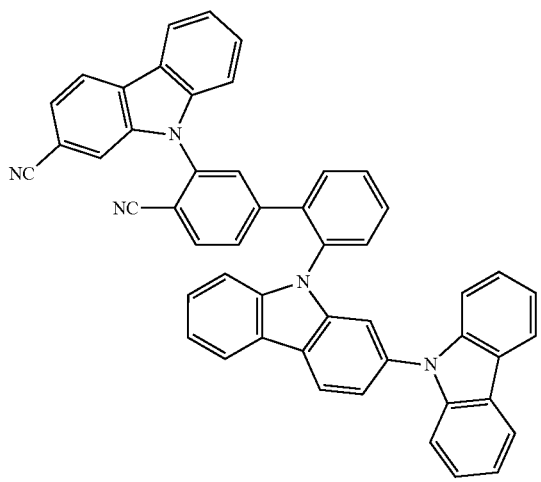

851
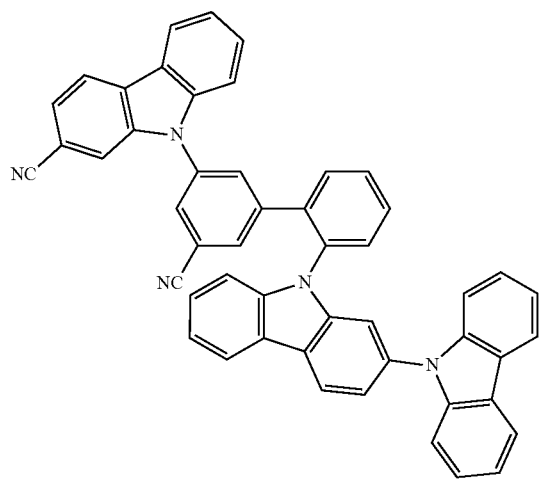
852
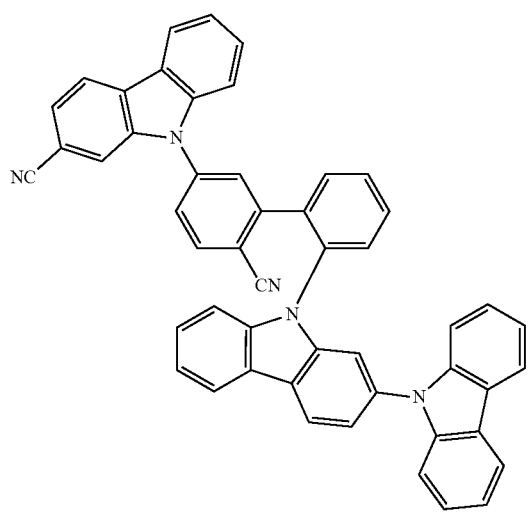
853
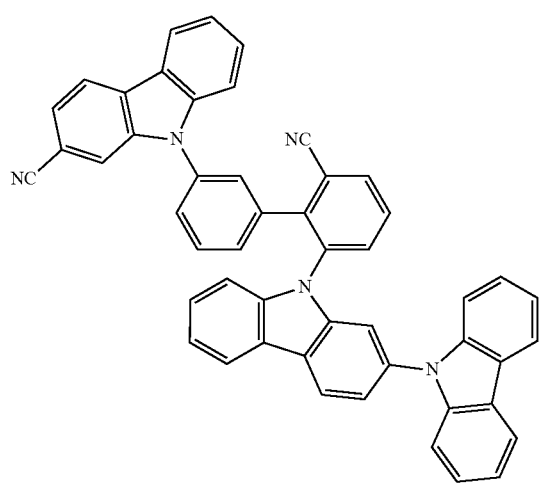
854
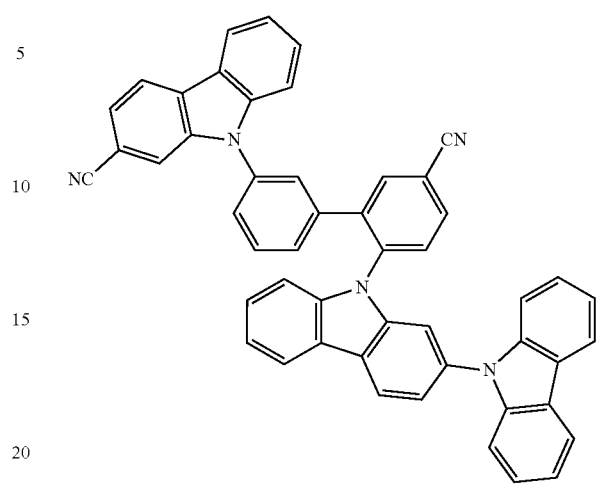
855
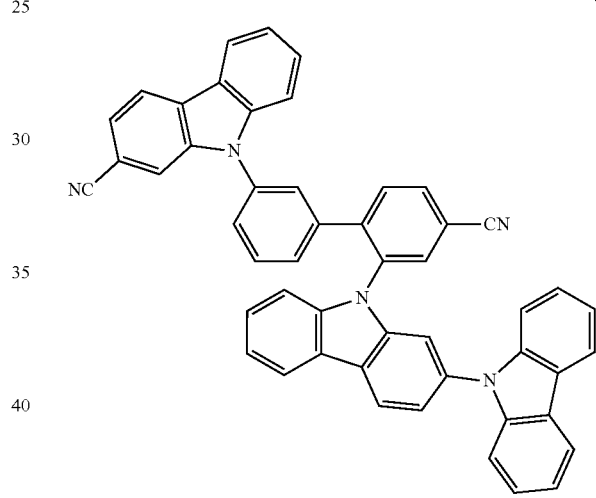
856
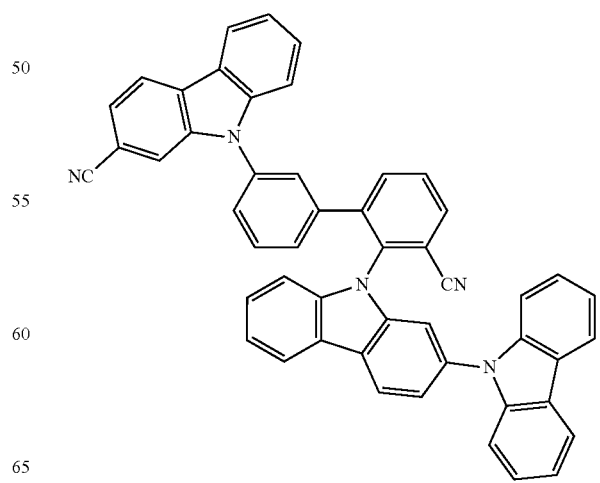

857
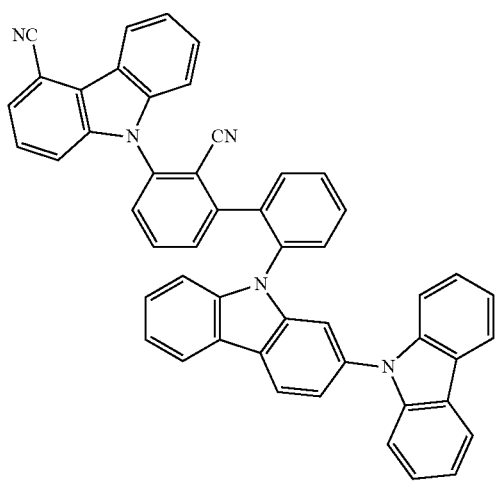
858
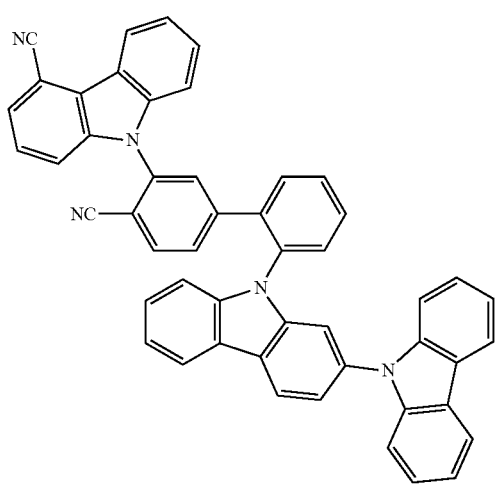
859
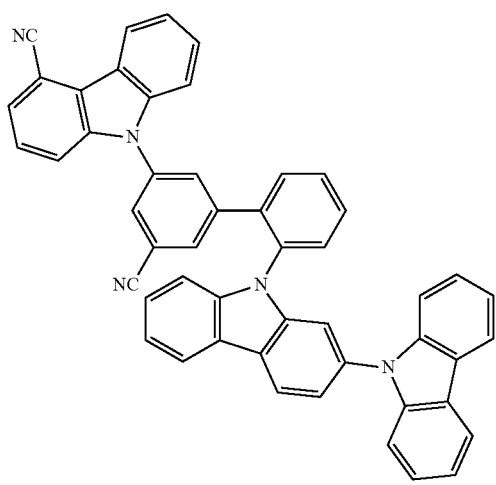
860
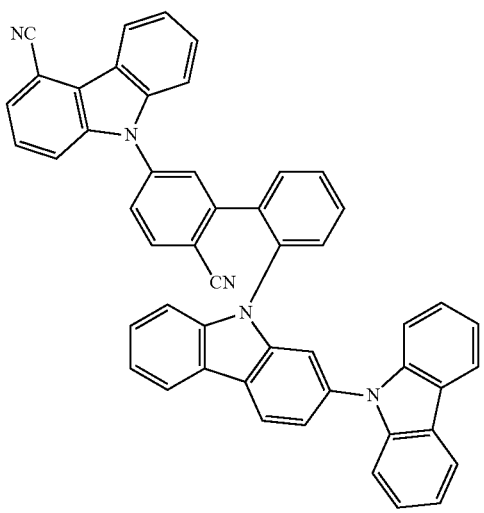
861
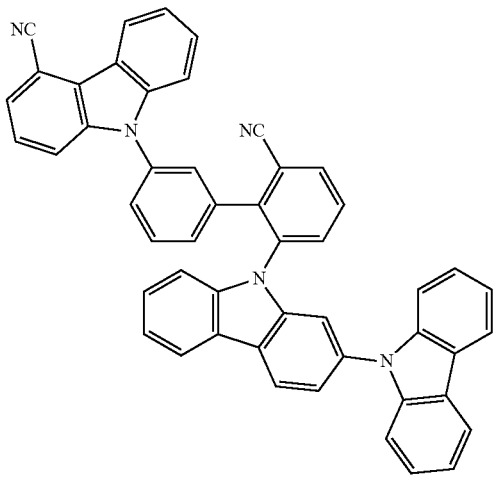
862
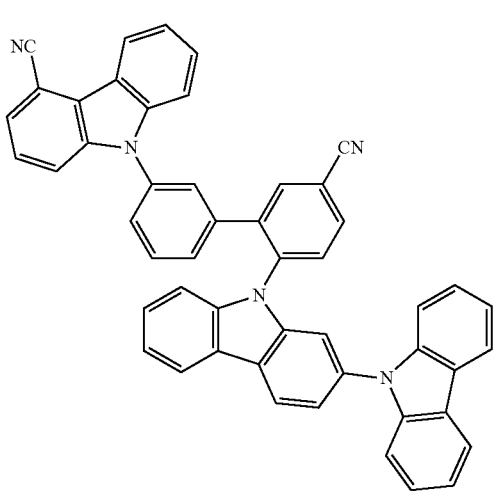

863
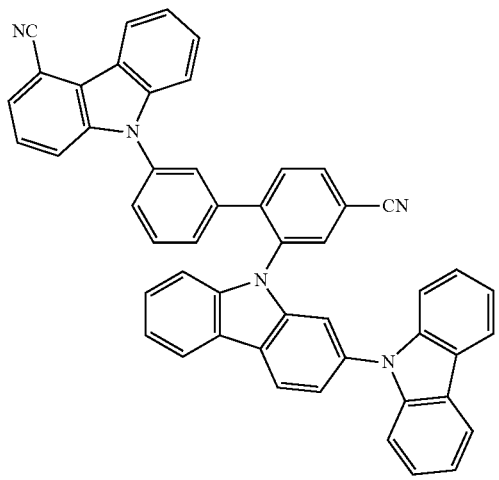
864
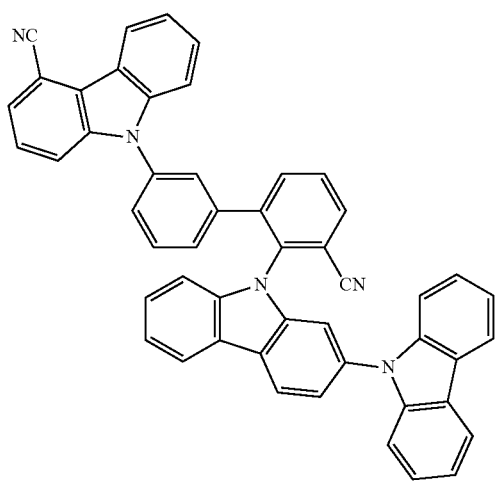
865
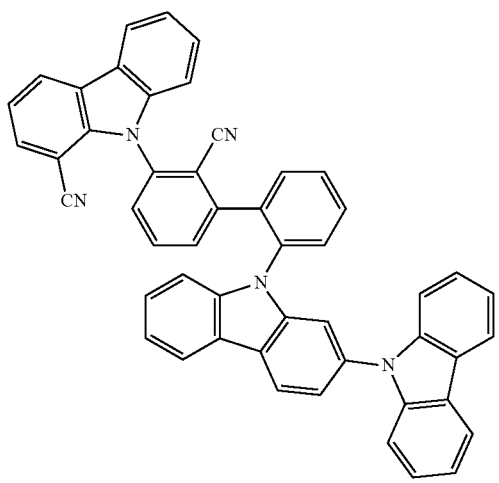
866
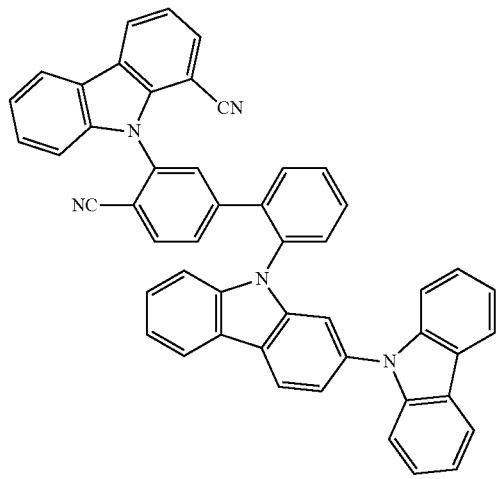
867
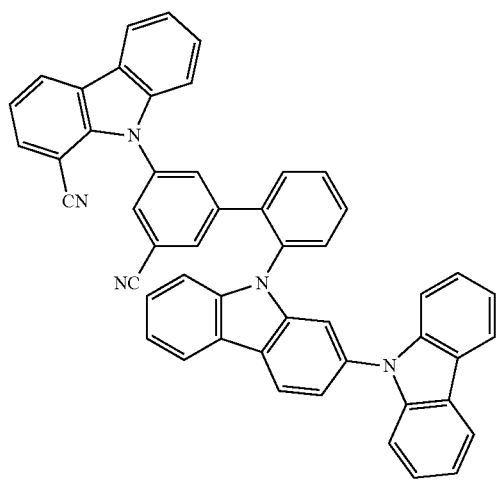
868
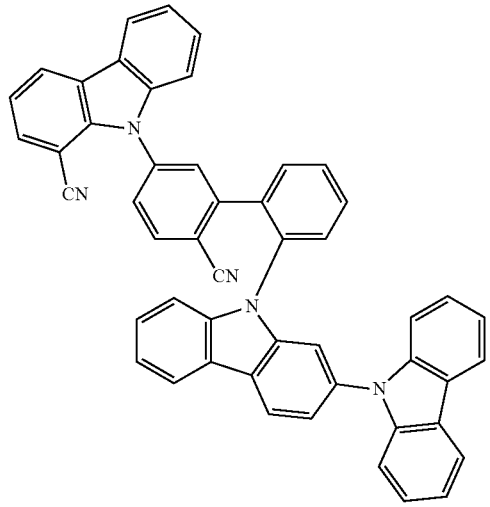

-continued
869
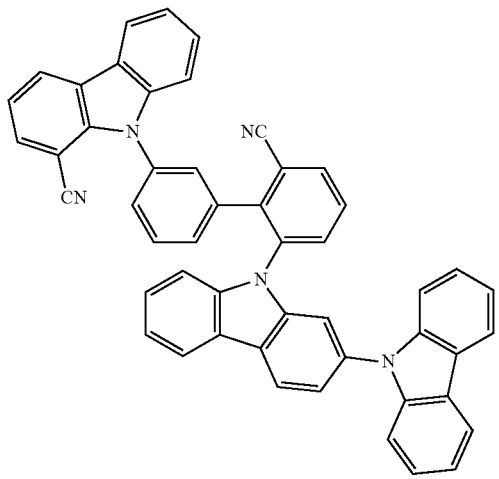
870
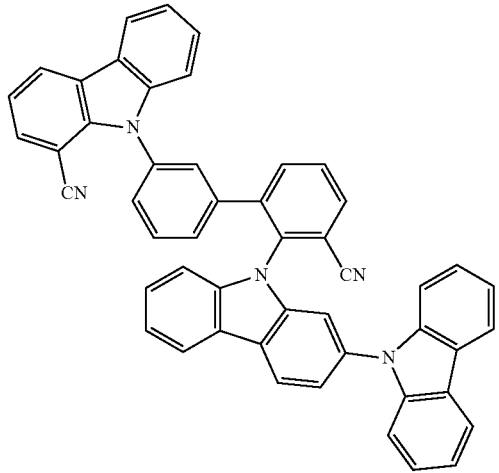
871
-continued
872
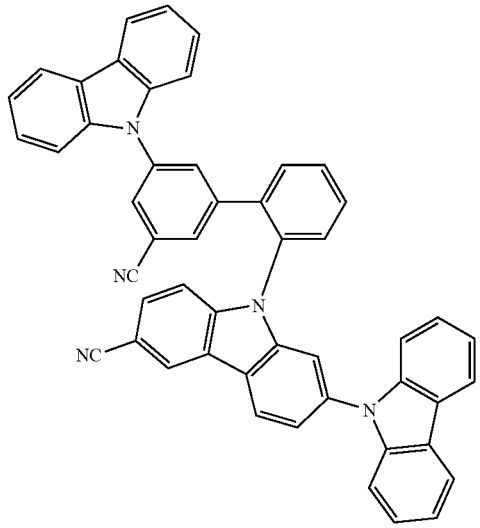
873
874
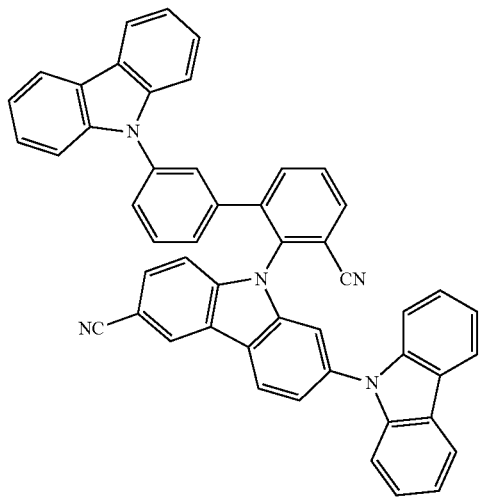

875
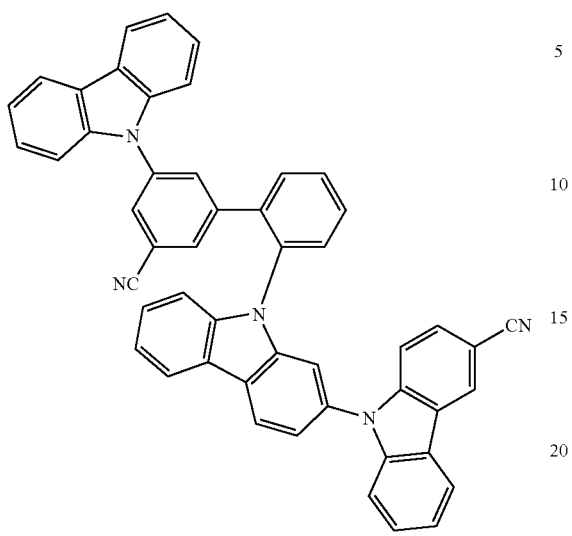
876
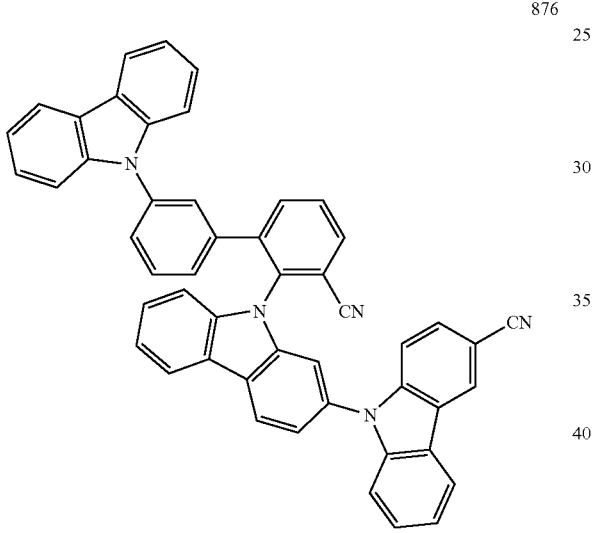
877
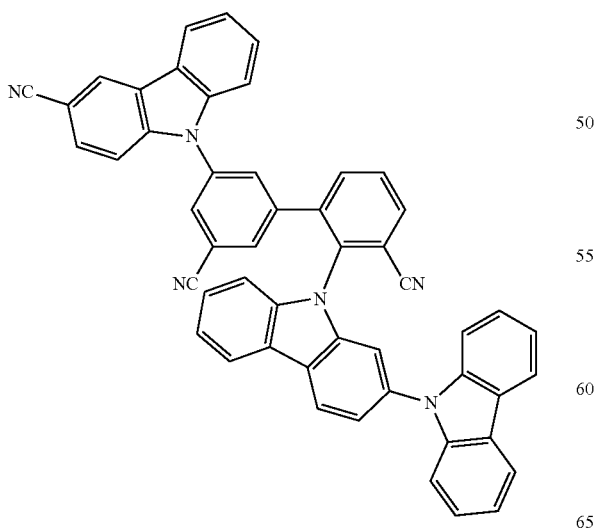
878
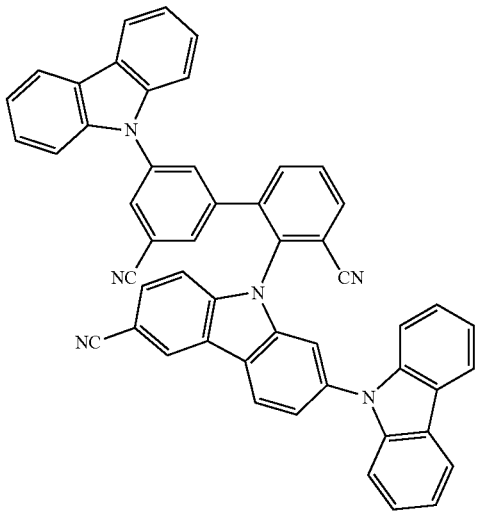
879
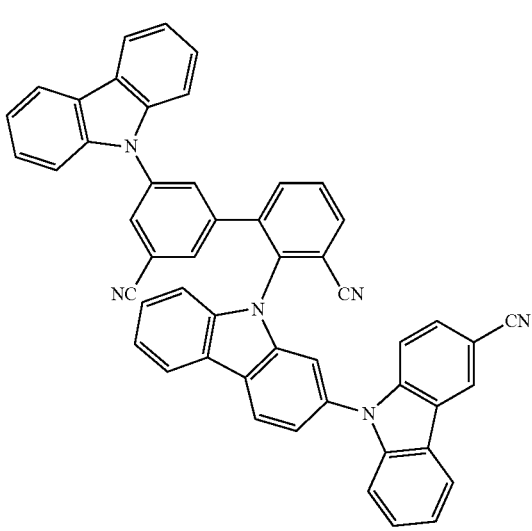
880

881
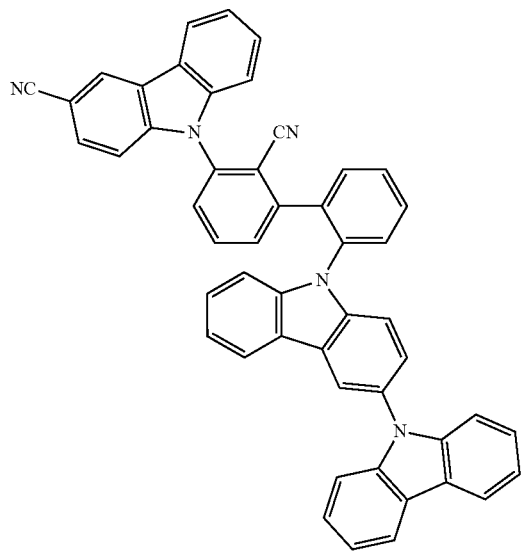
882
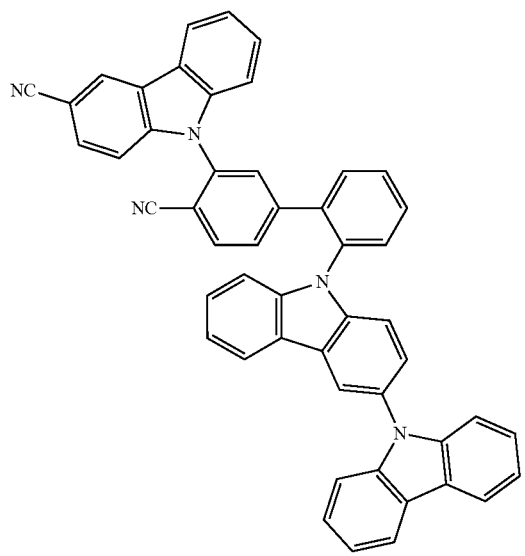
883
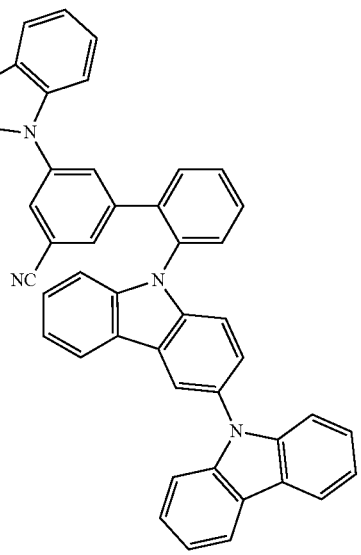
884
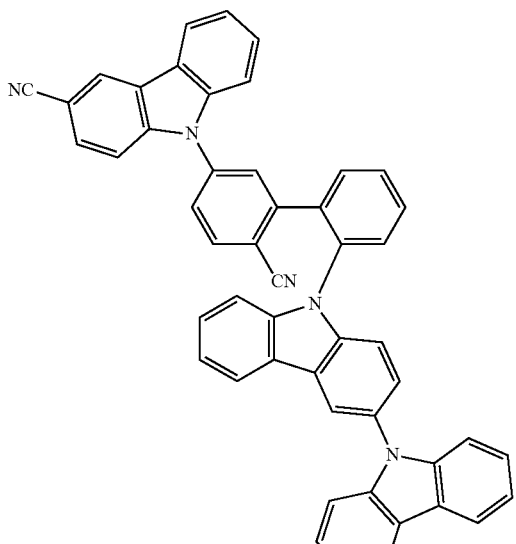

307
-continued
885
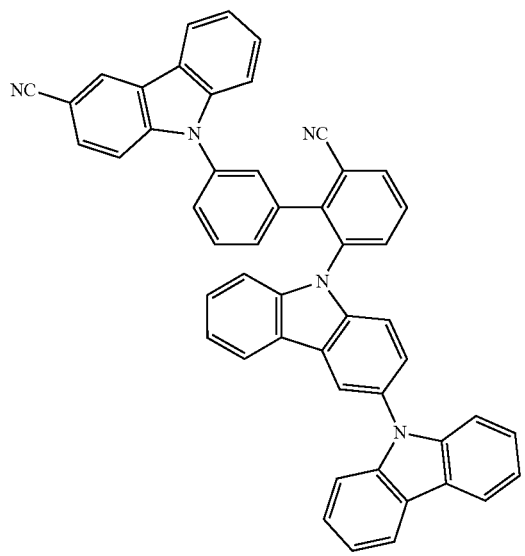
886
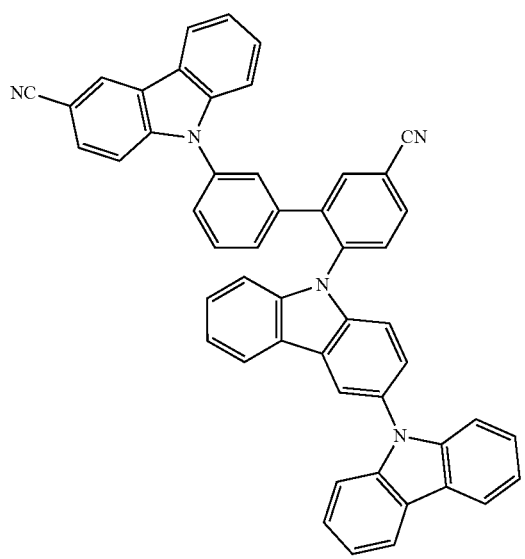
308
-continued
887
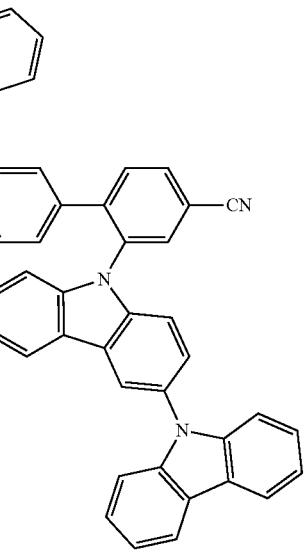
888

309
-continued
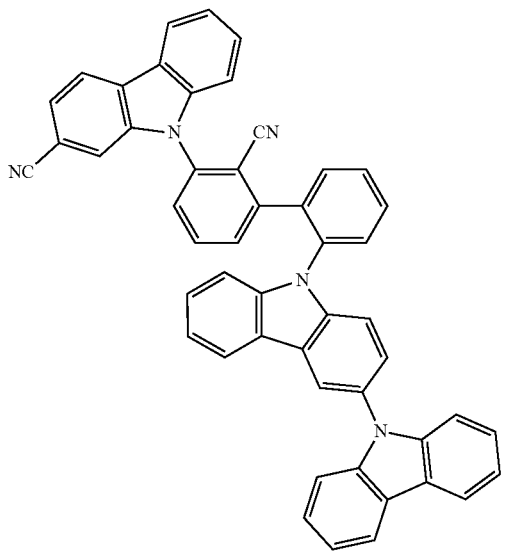
889
310
-continued
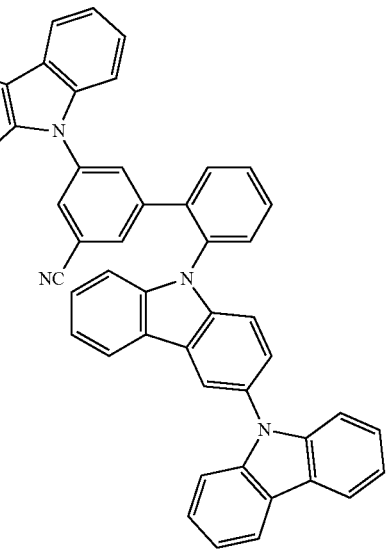
891
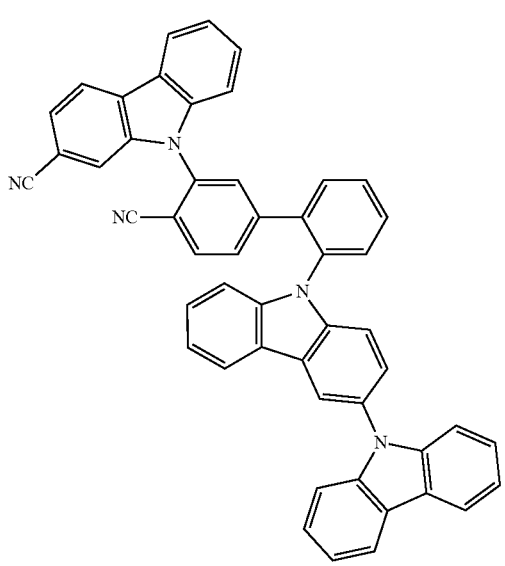
890
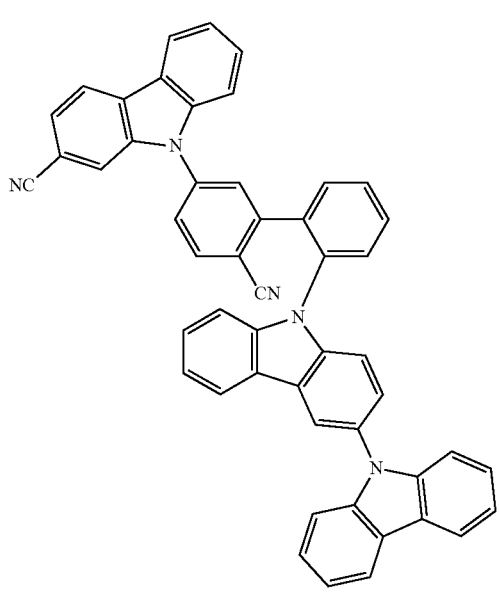
892

311
-continued
893
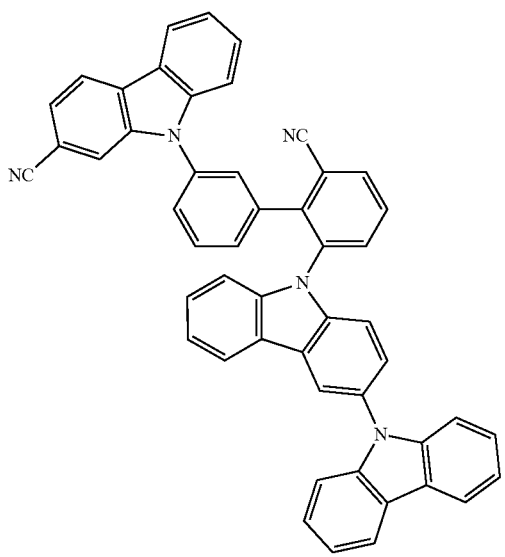
894
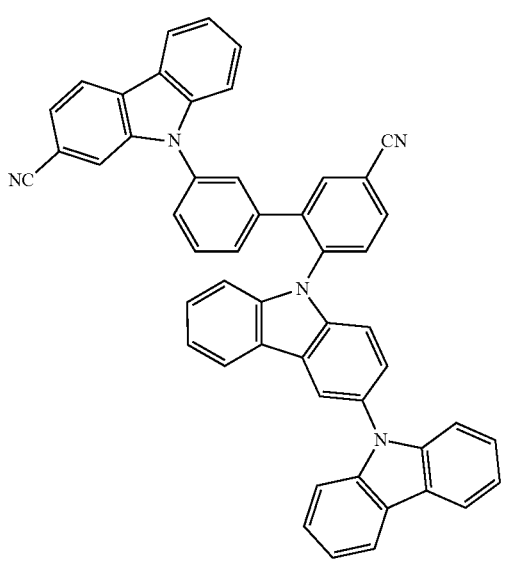
312
-continued
895
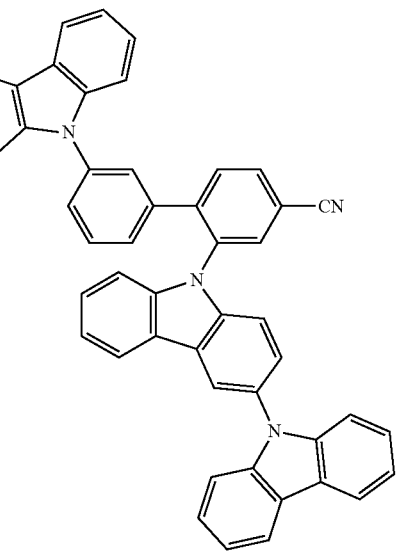
896
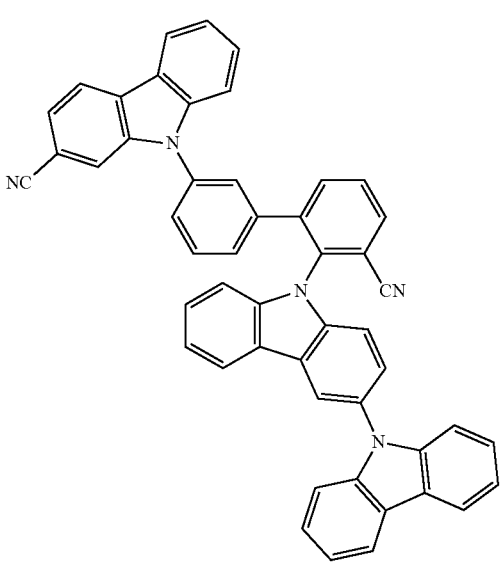

313
-continued
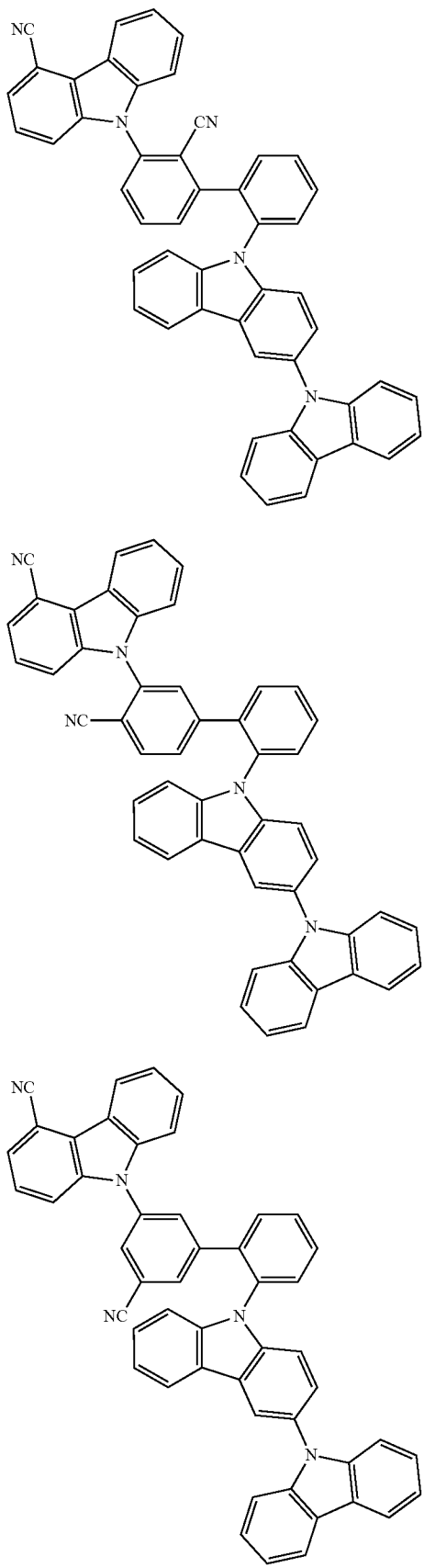
314
-continued
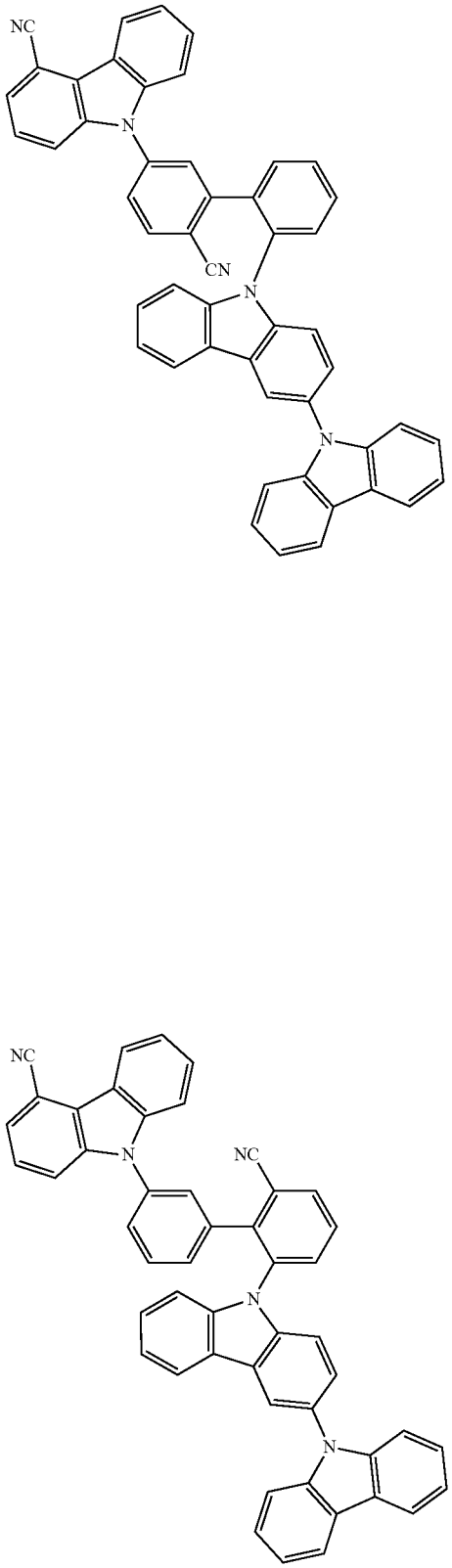

315
-continued
902
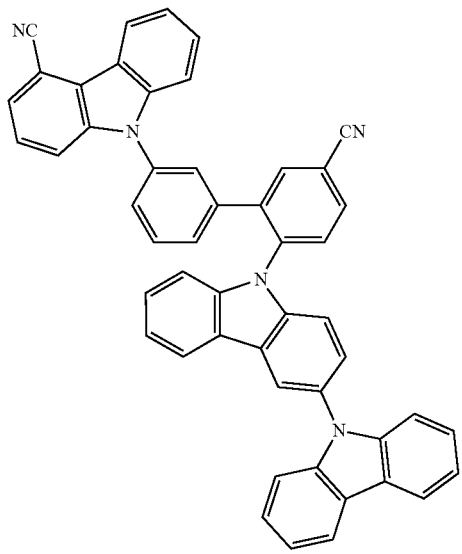
903
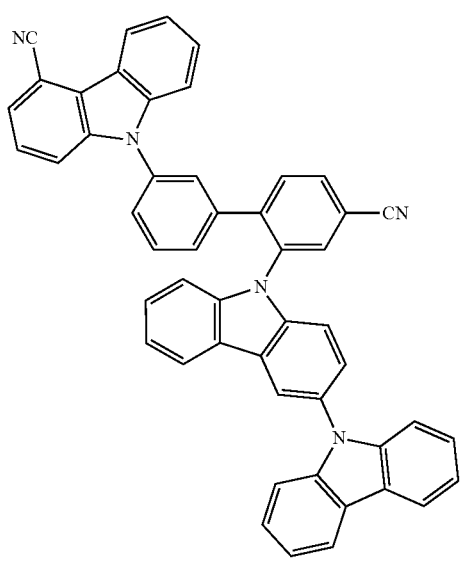
904
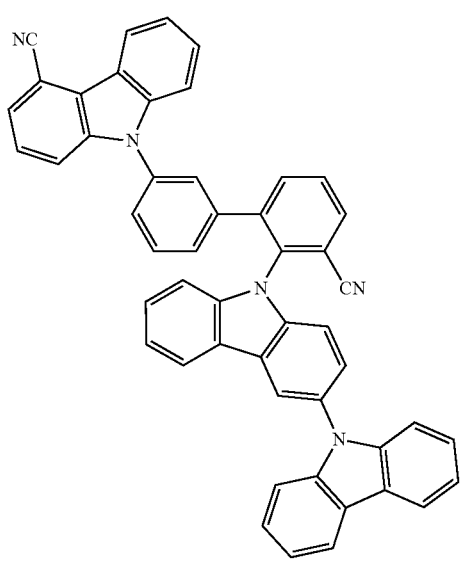
316
-continued
905
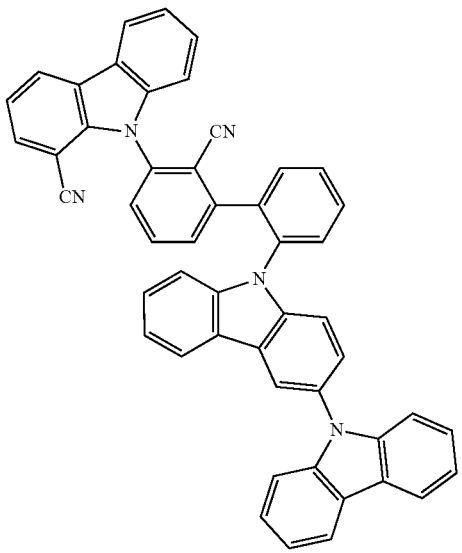
906
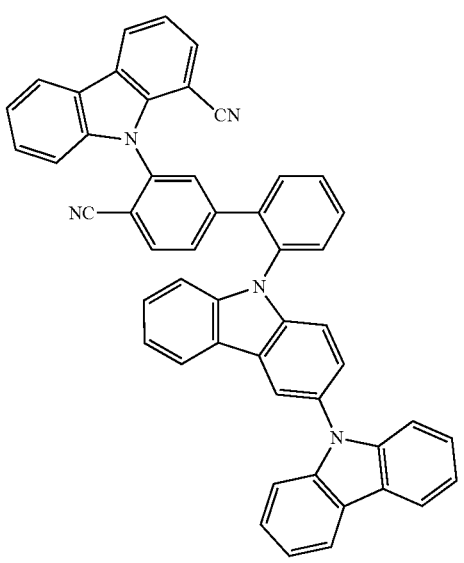
907
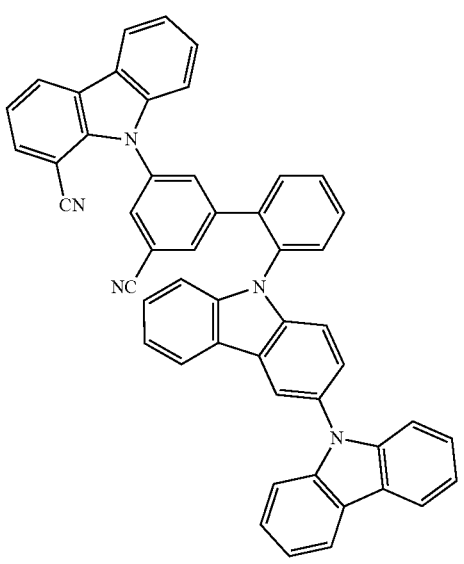

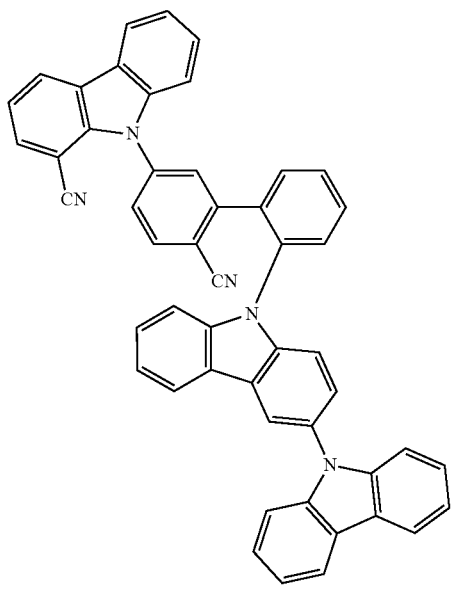
908
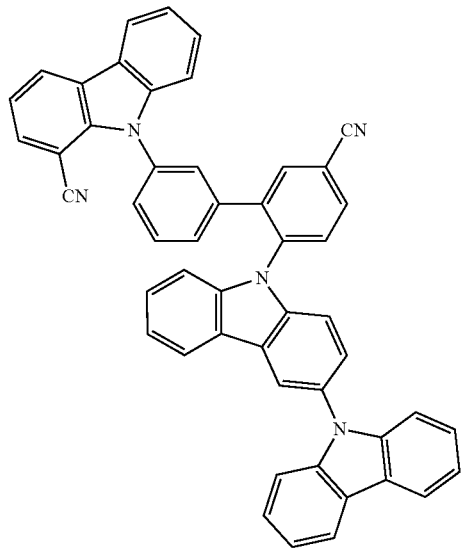
910
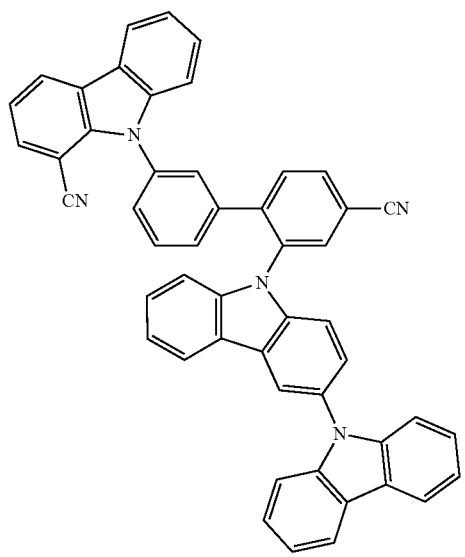
911
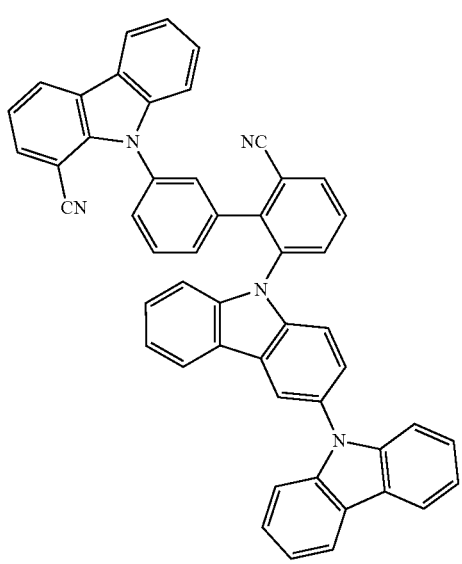
909
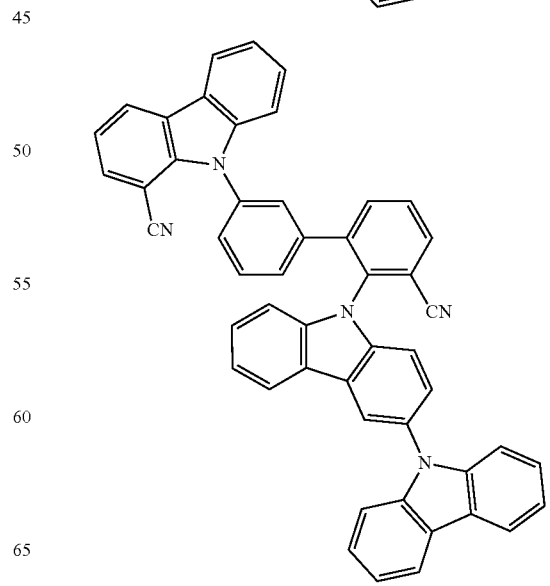
912

319
-continued
913
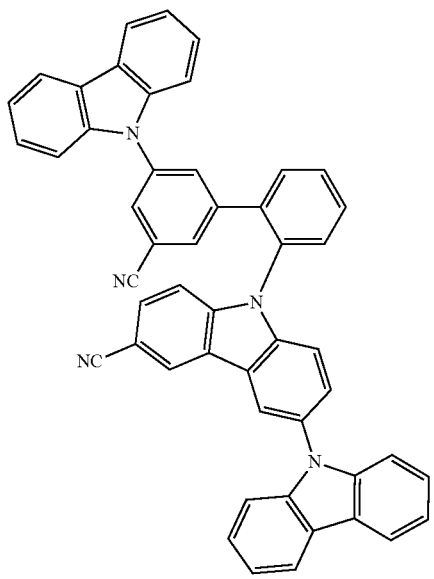
914
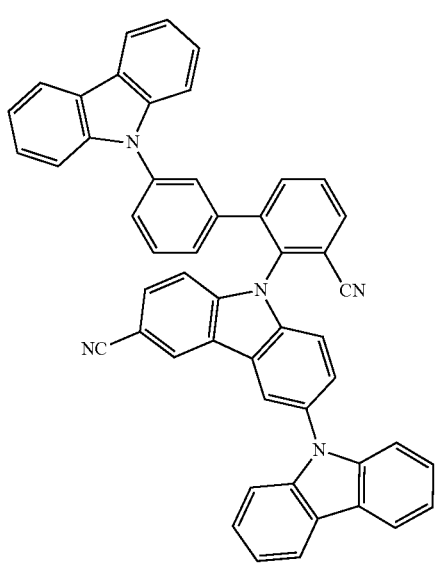
320
-continued
915
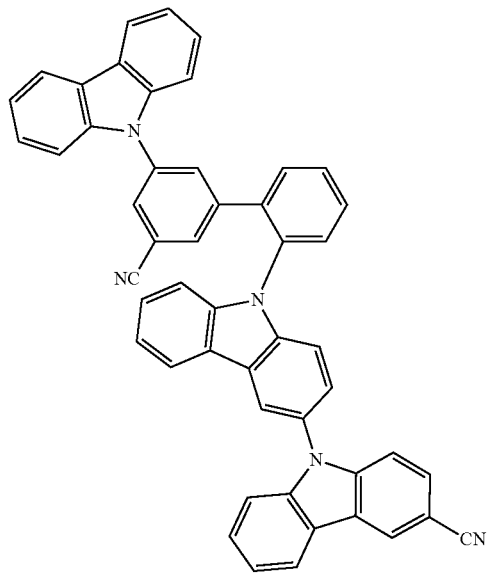
916
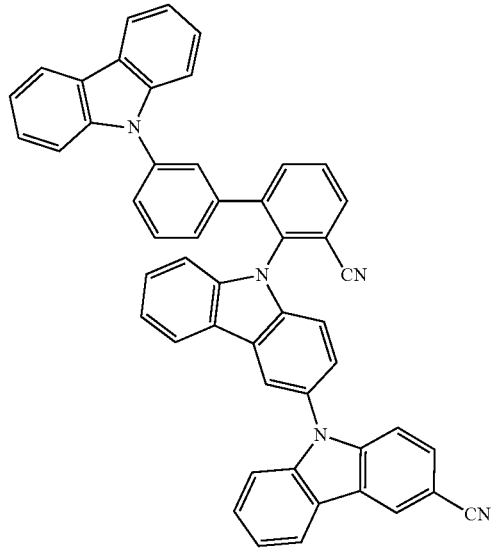

321
-continued
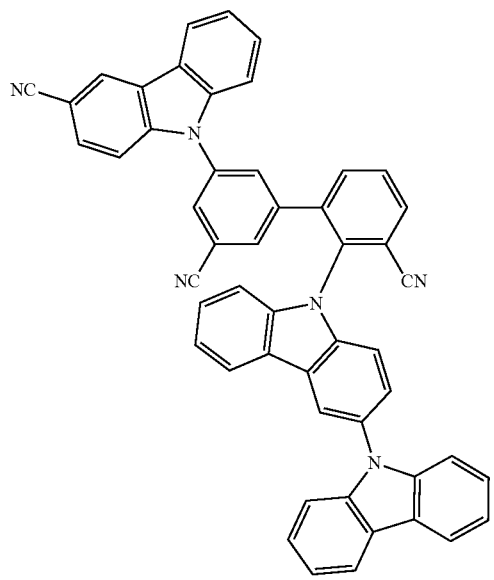
917
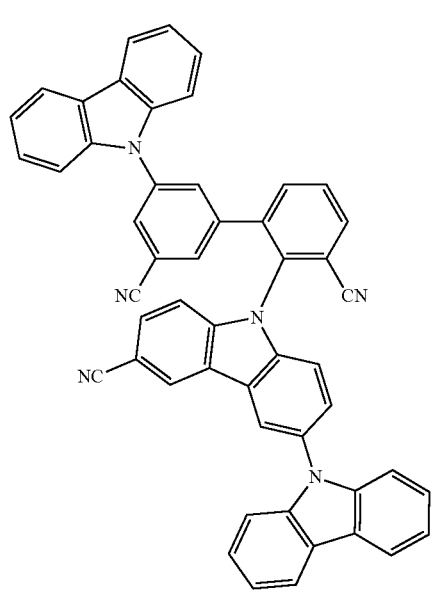
918
322
-continued
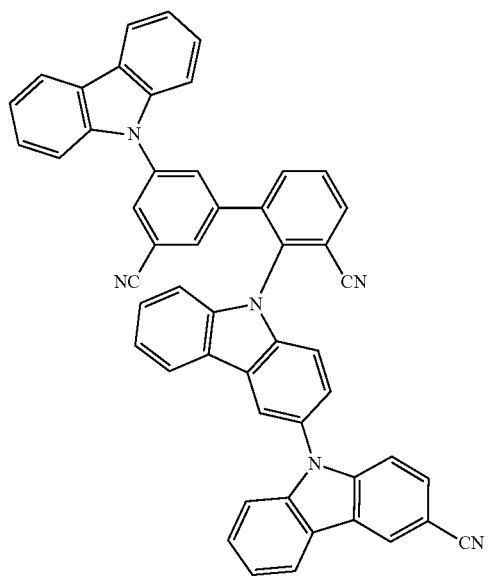
919
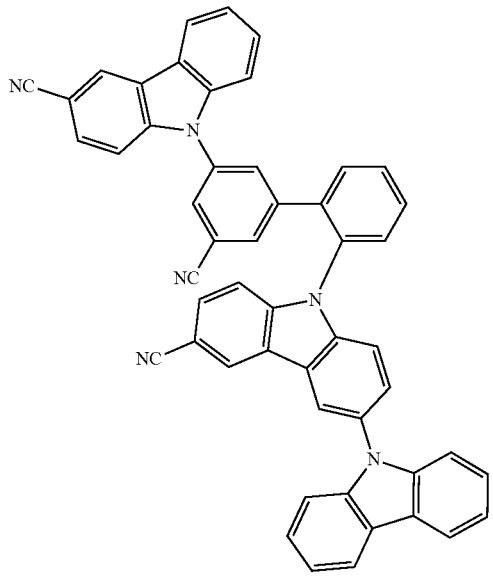
920

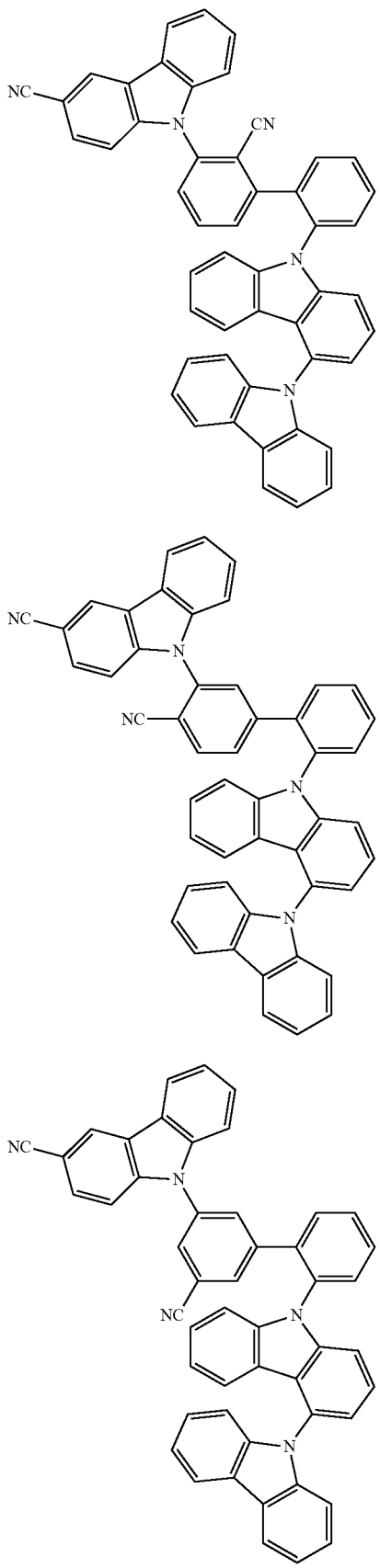
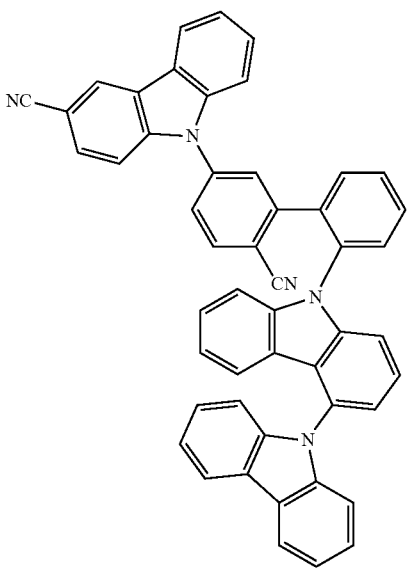
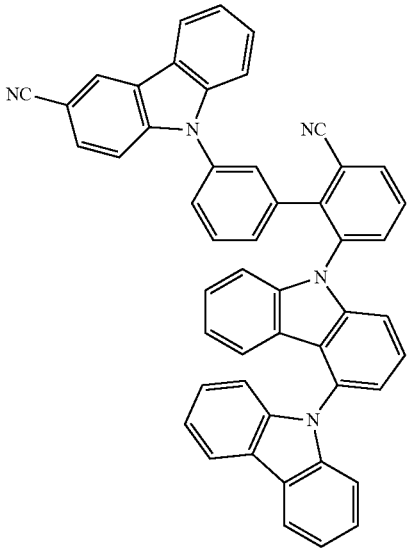

926
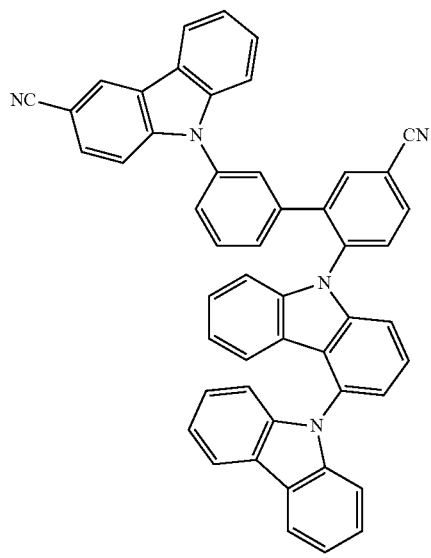
927
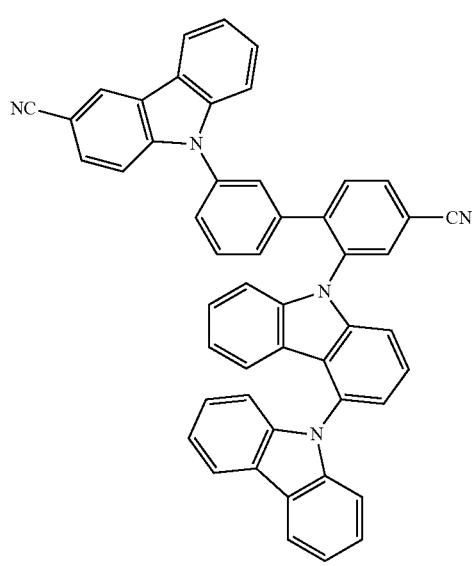
928
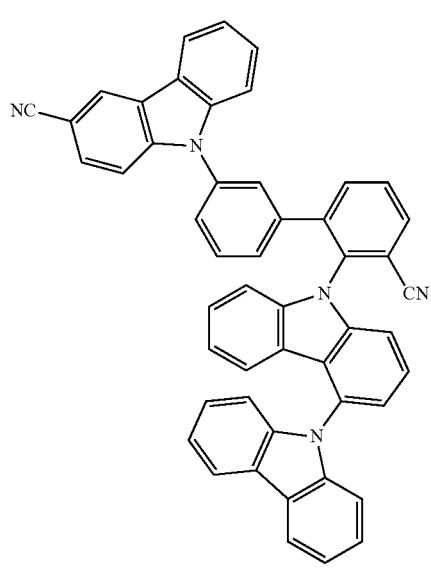
929
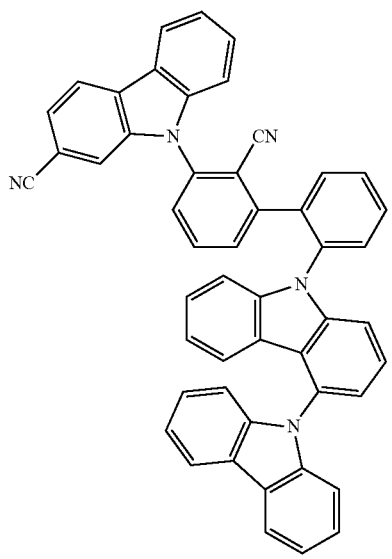
930
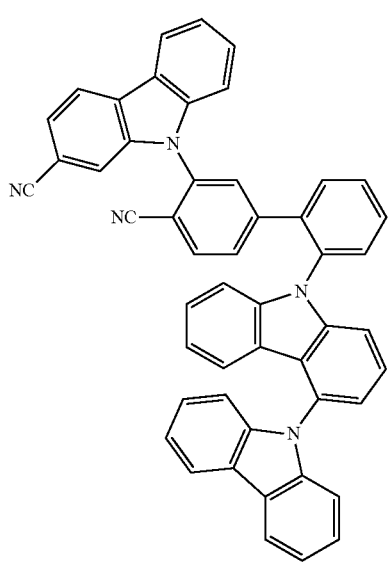
931
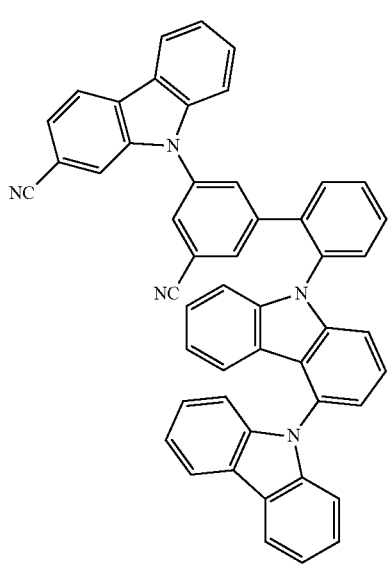

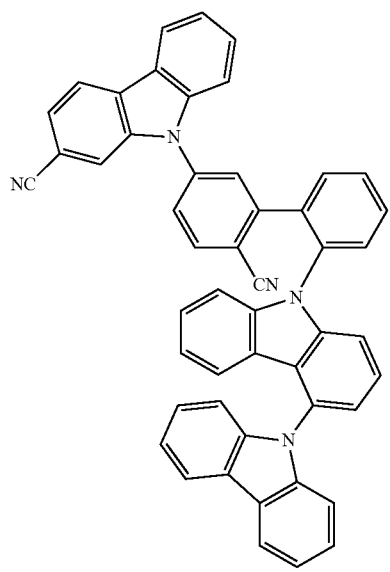
932
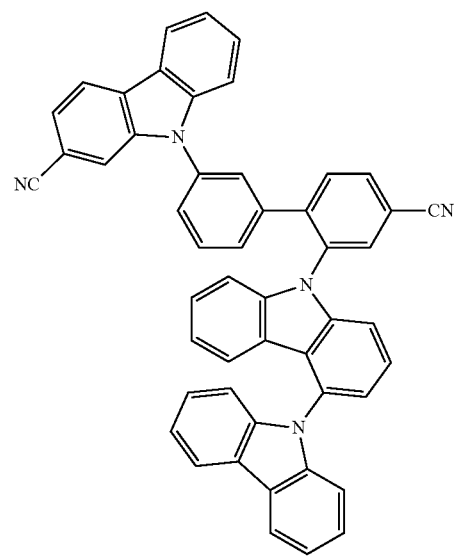
935
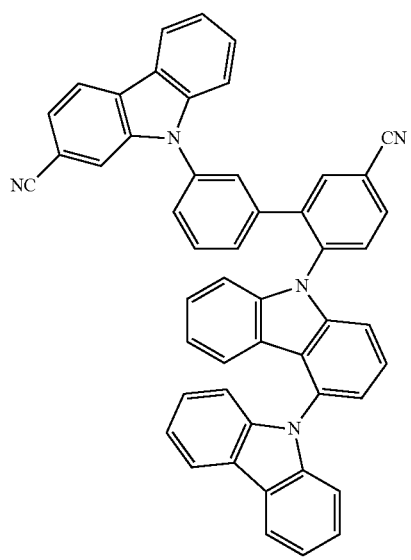
933
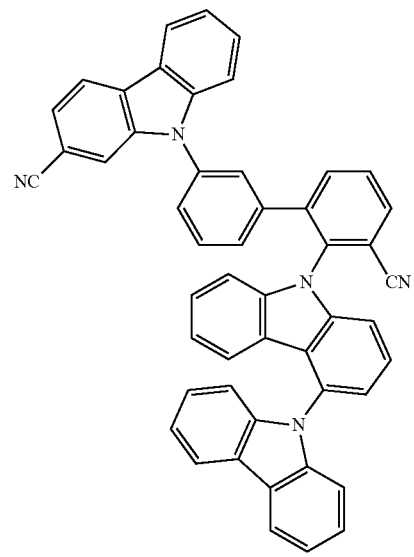
936
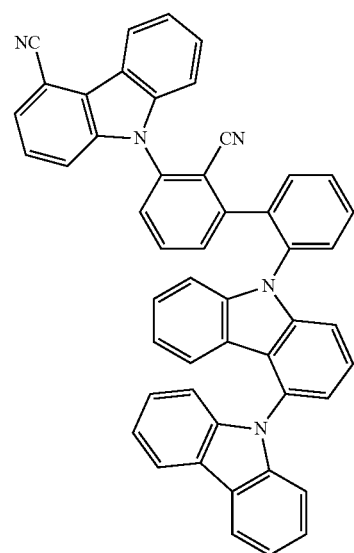
934
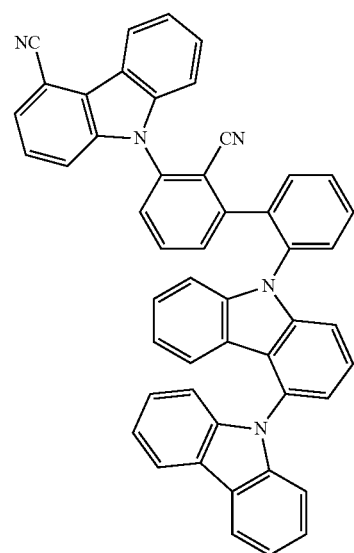
937

938
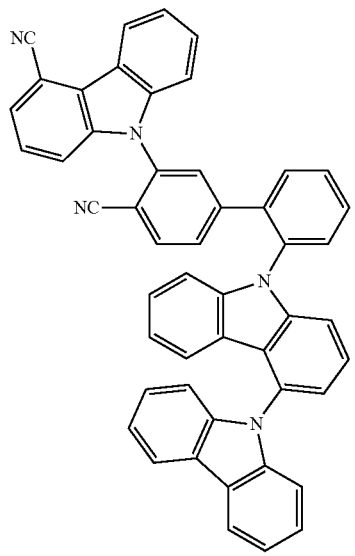
939
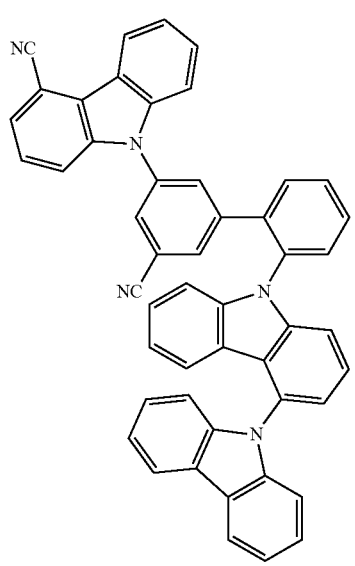
940
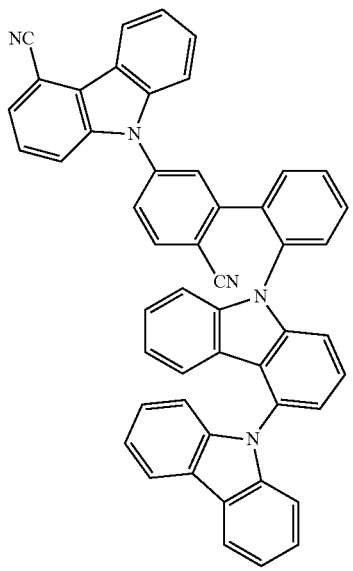
941
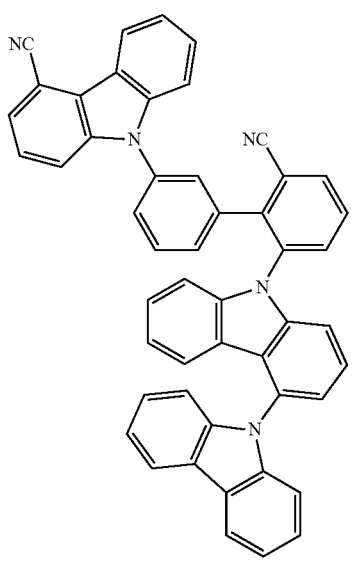
942
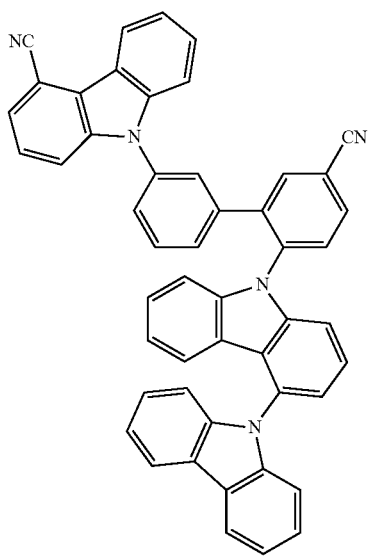

331
-continued
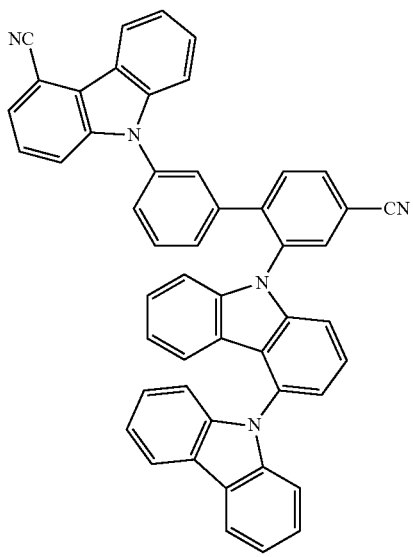
943
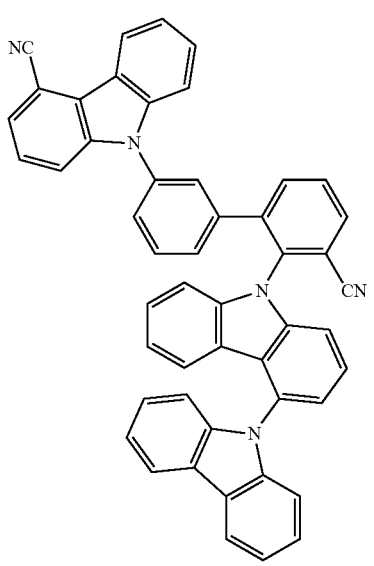
944
945
332
-continued
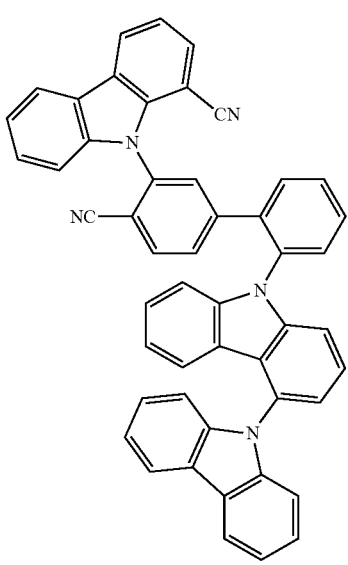
946
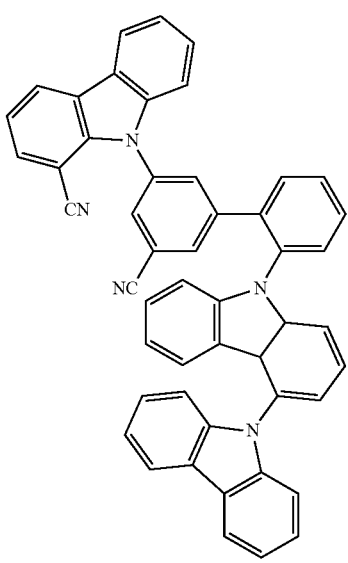
947

948
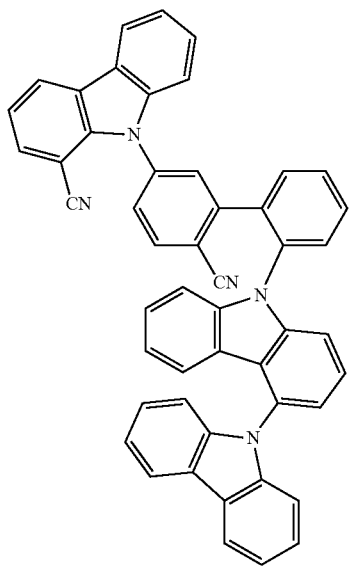
950
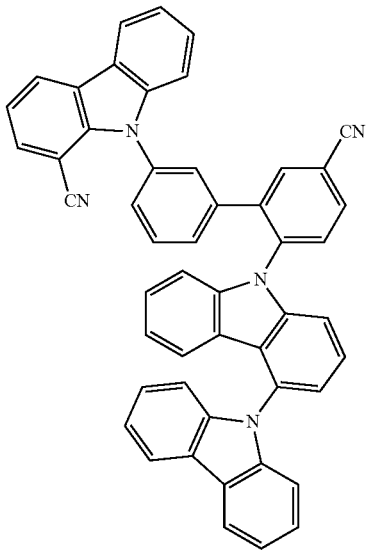
951
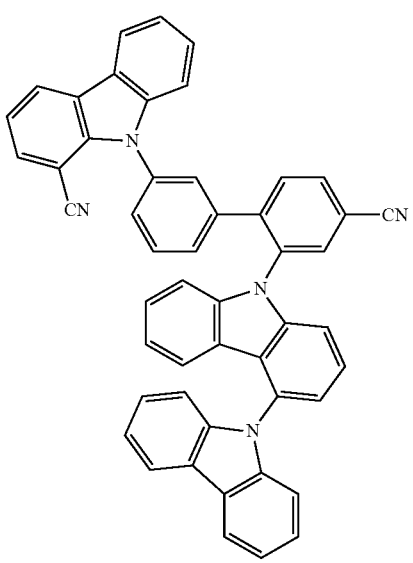
949
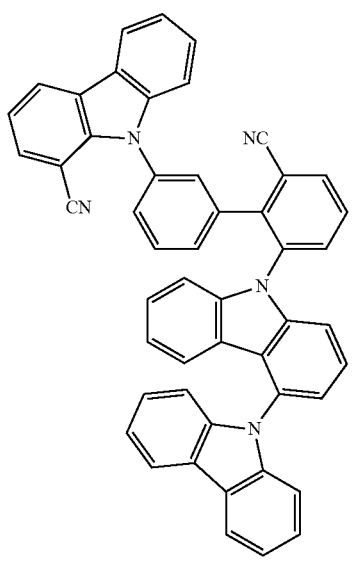
952
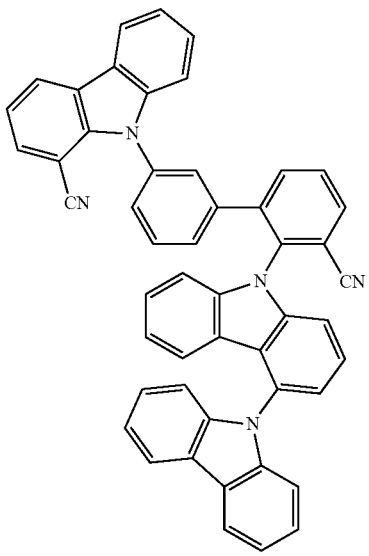

335
-continued
953
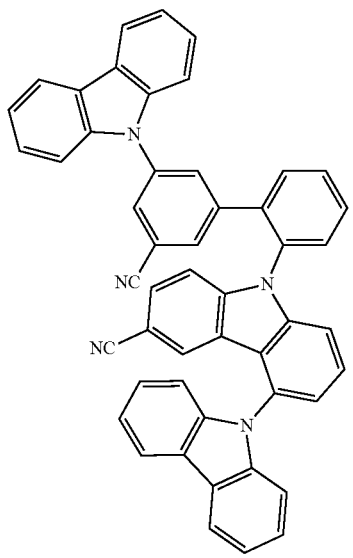
954
955
336
-continued
956
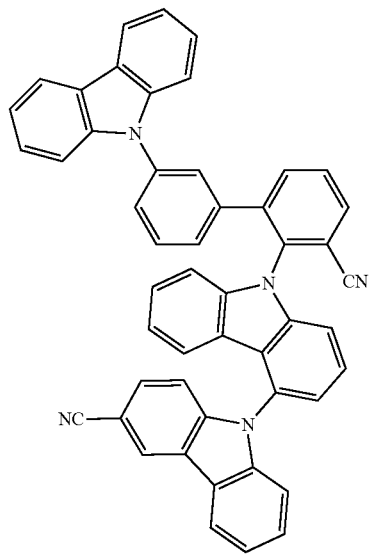
957
958

959
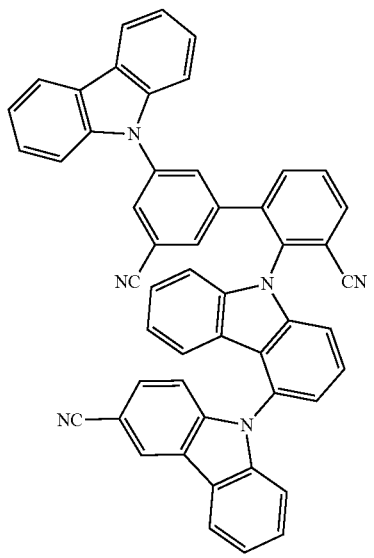
960
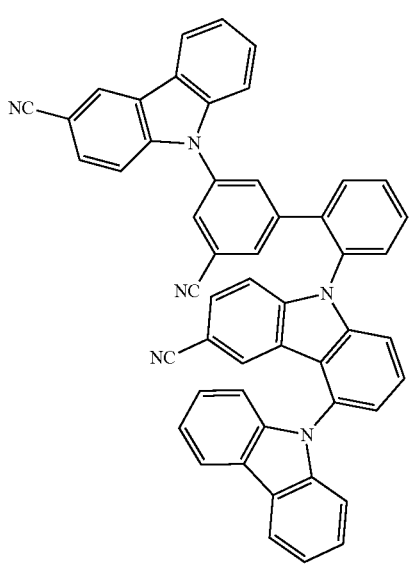
961
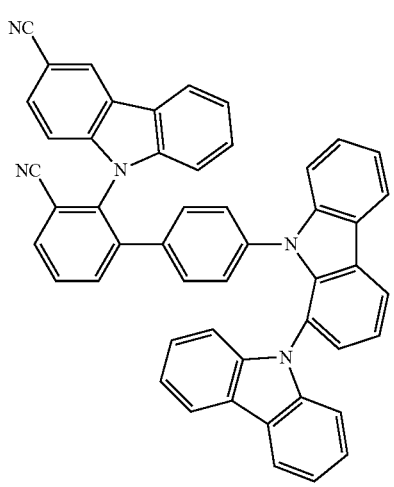
962
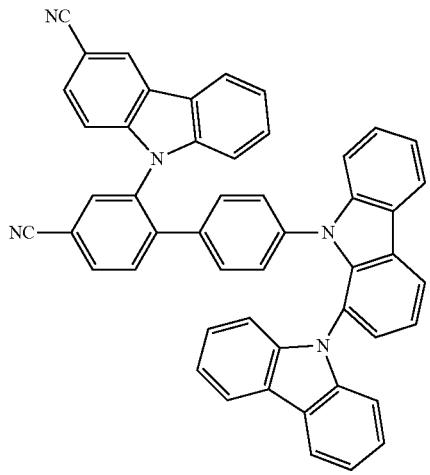
963
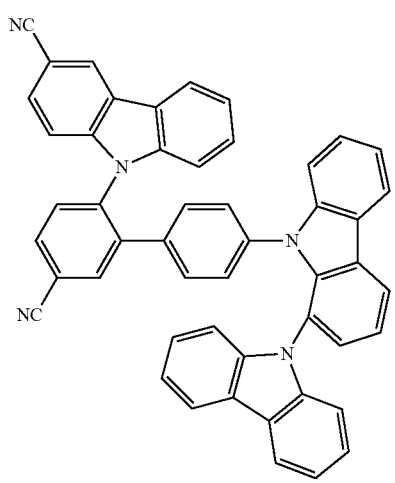
964
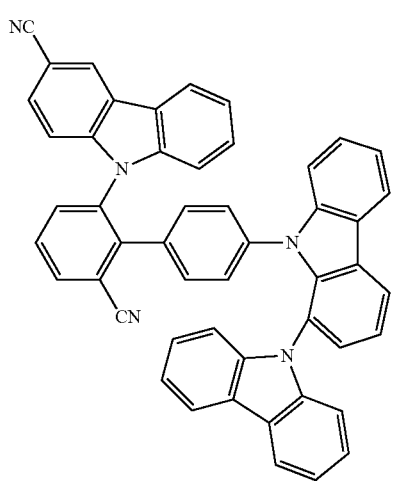

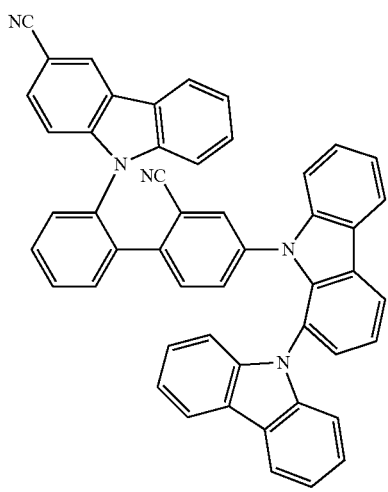
965
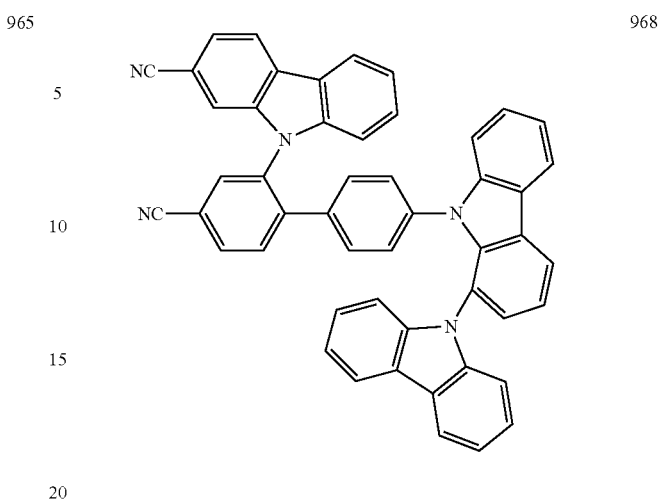
968
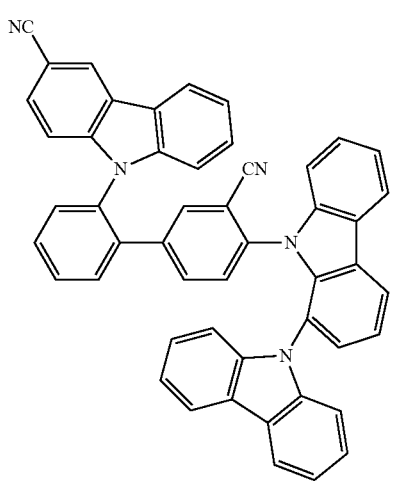
966
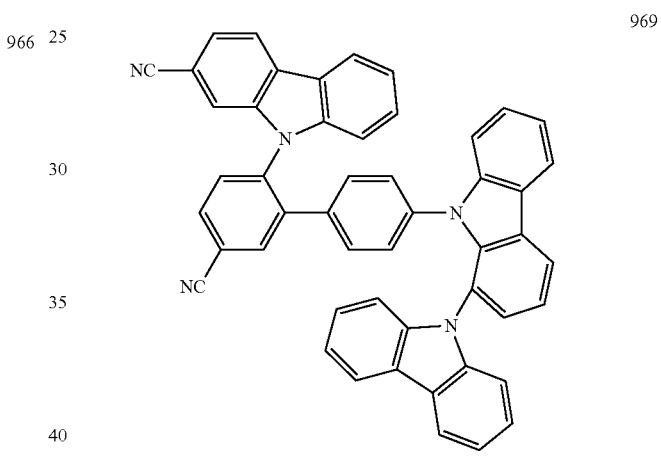
969
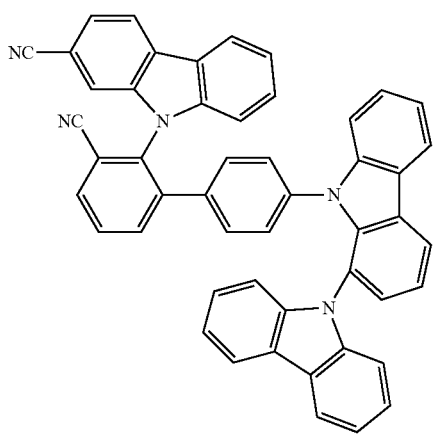
967
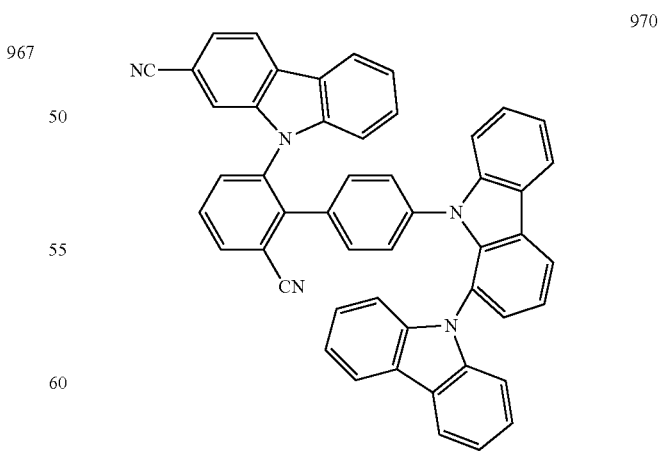
970

-continued
971
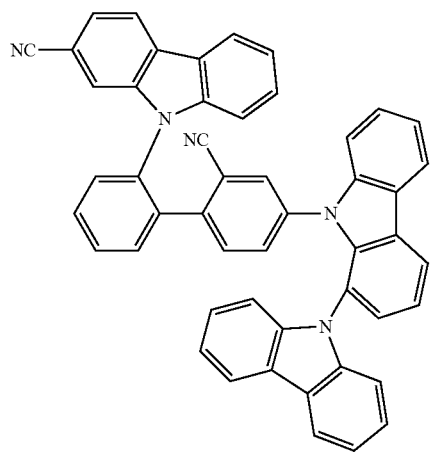
972
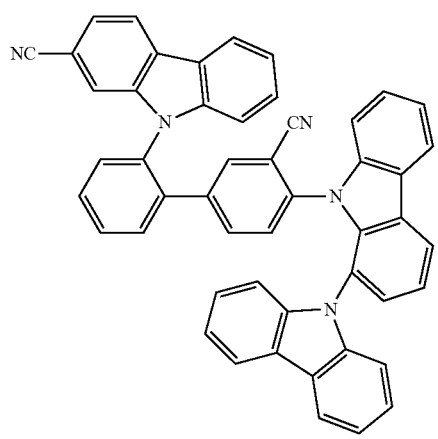
973
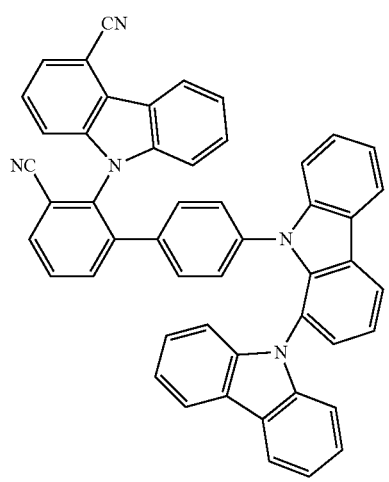
-continued
974
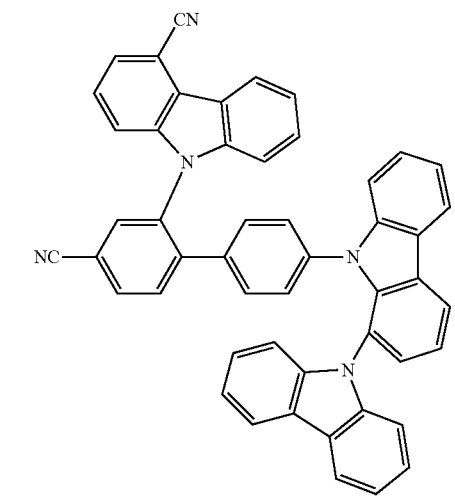
975
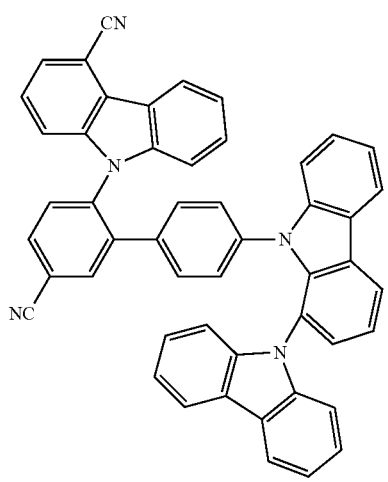
976
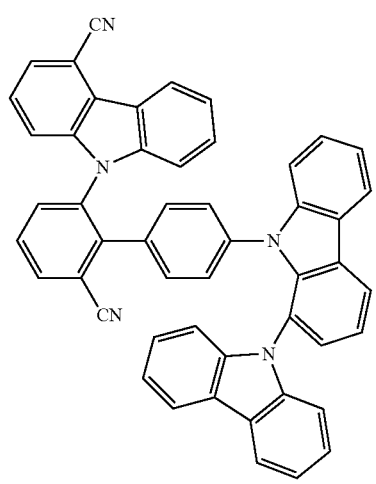

977
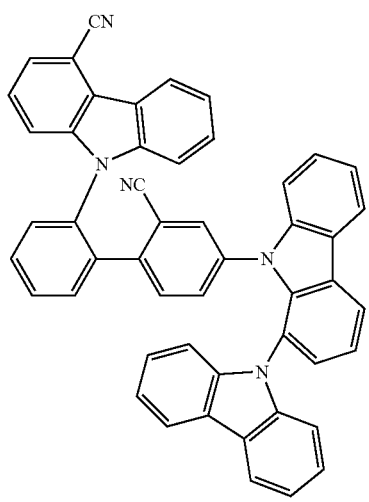
978
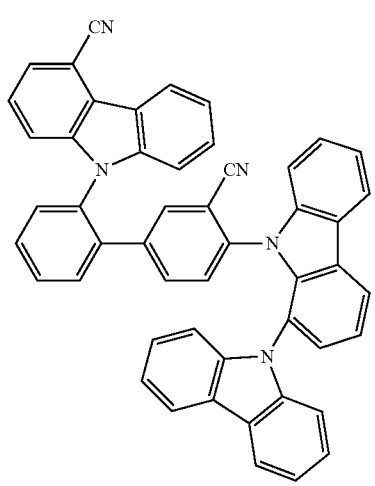
979
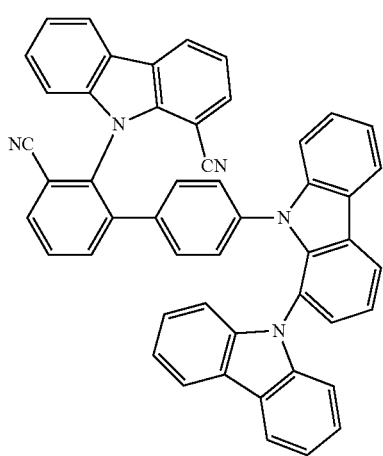
980
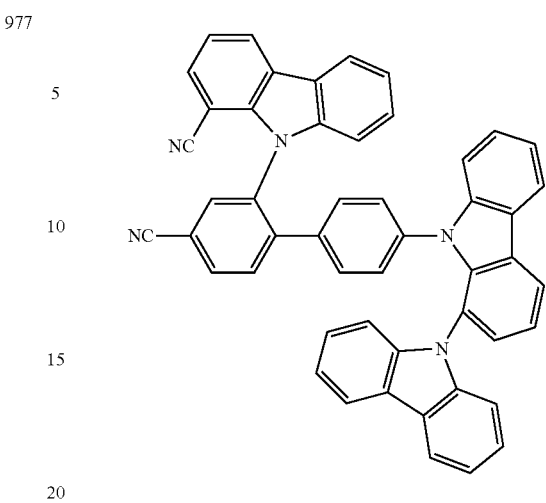
981
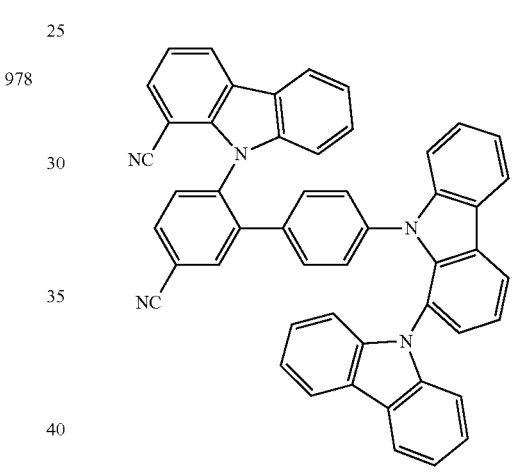
982
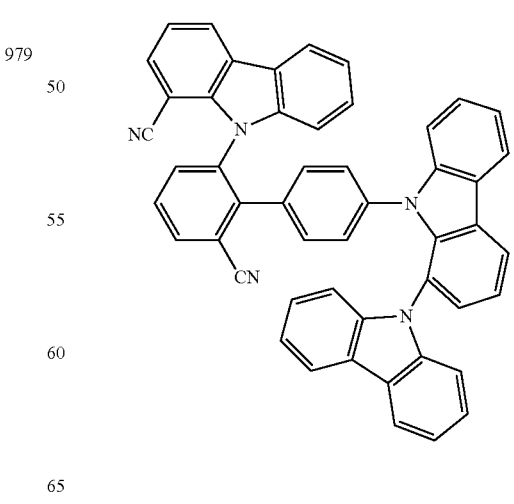

983
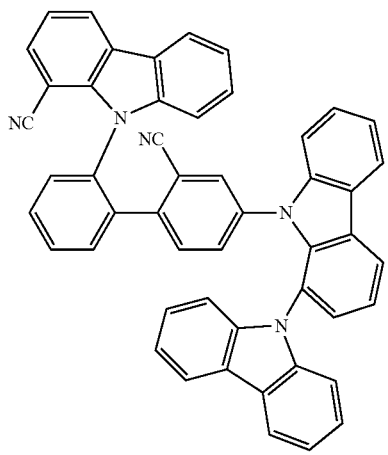
984
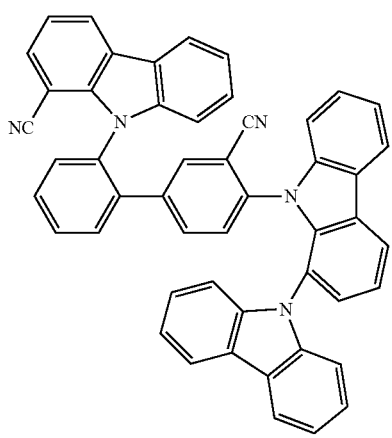
985
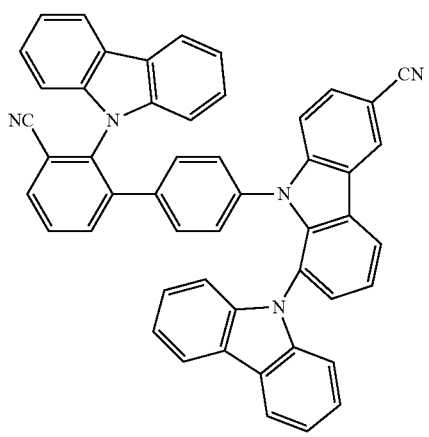
986
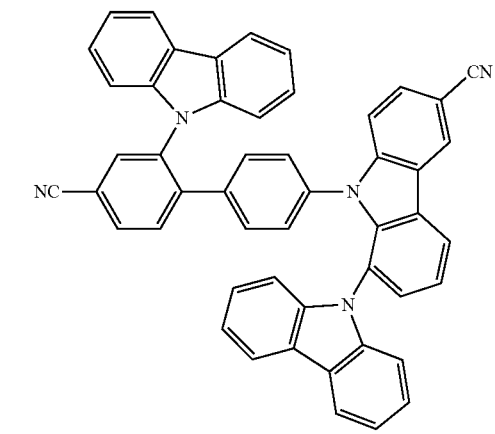
987
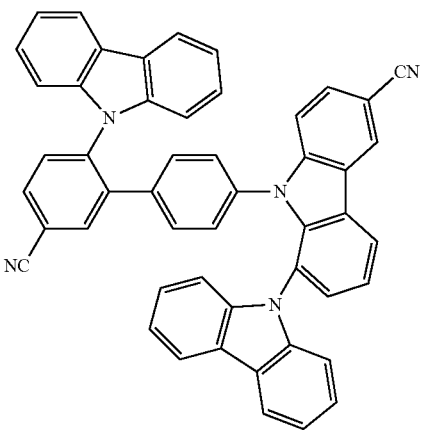
988
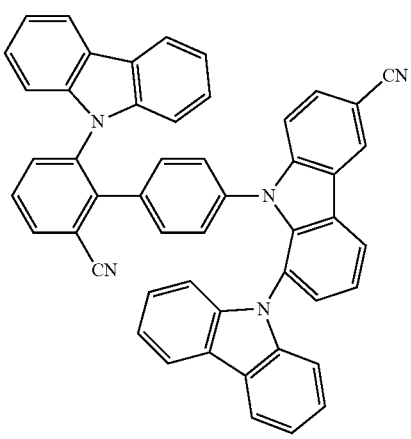

989
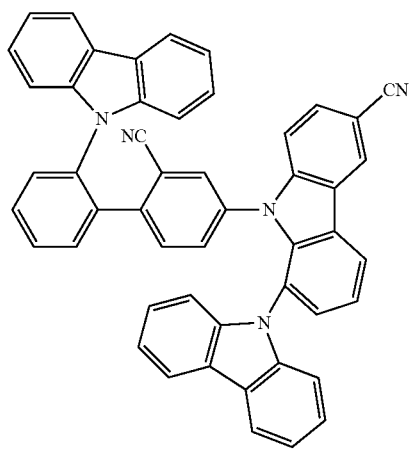
990
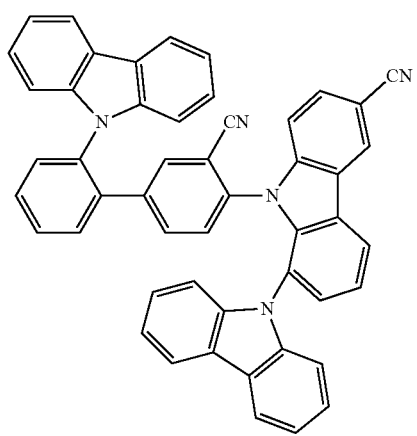
991
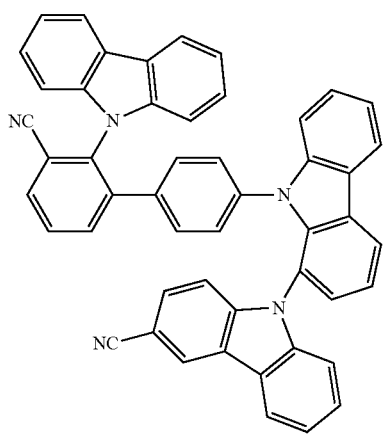
992
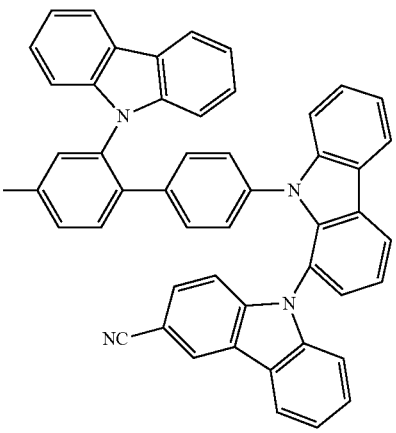
993
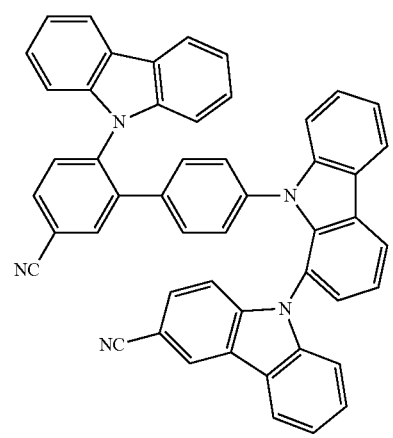
994
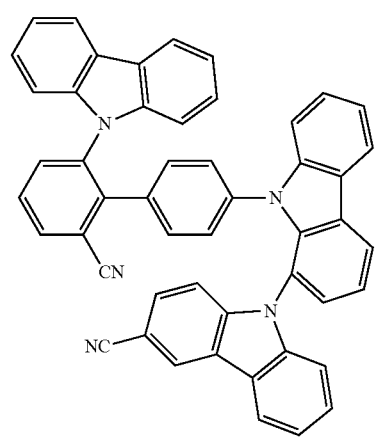

349
-continued
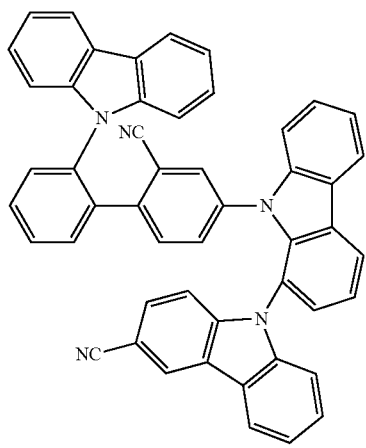
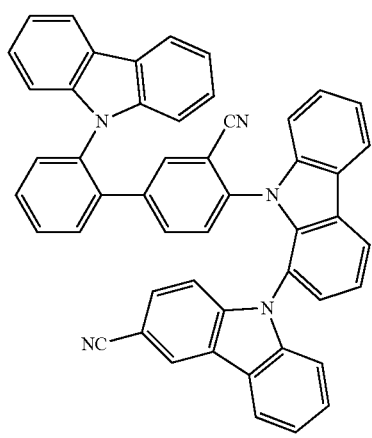
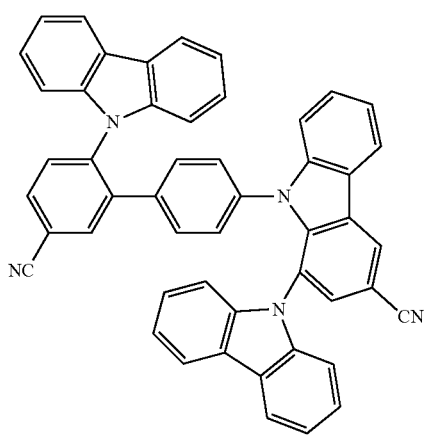
350
-continued
995
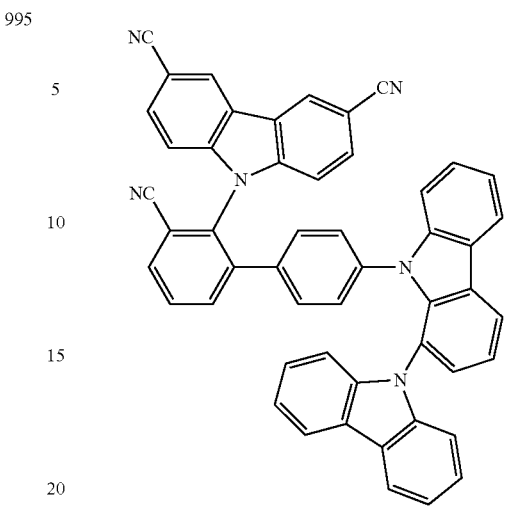
996
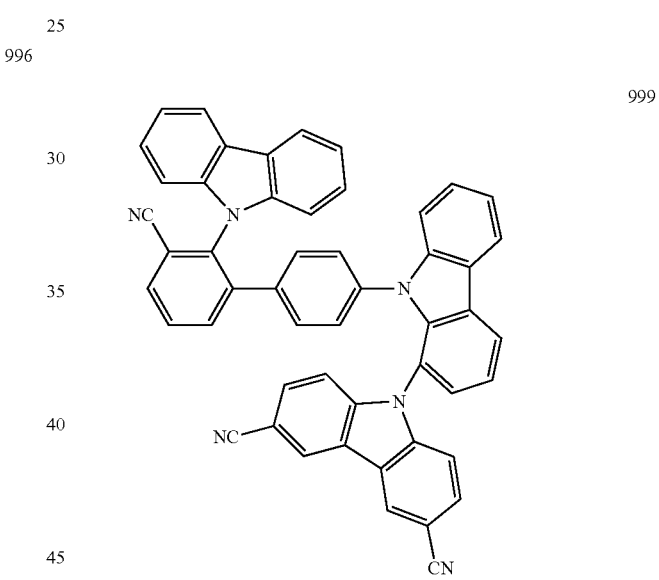
997
998
999
1000

-continued
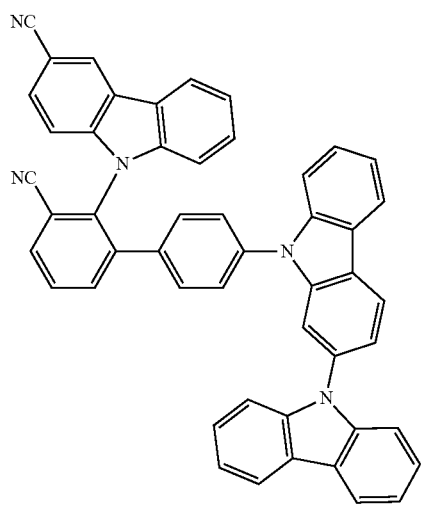
1001
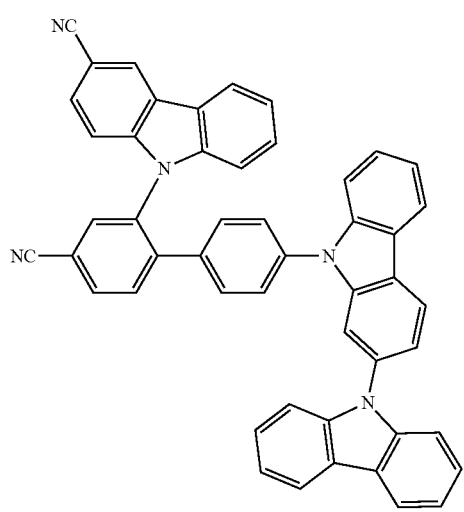
1002
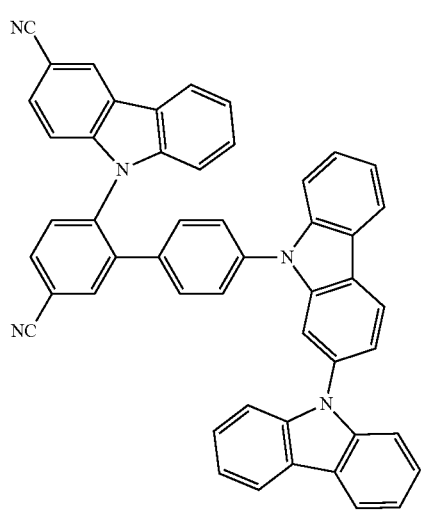
1003
-continued
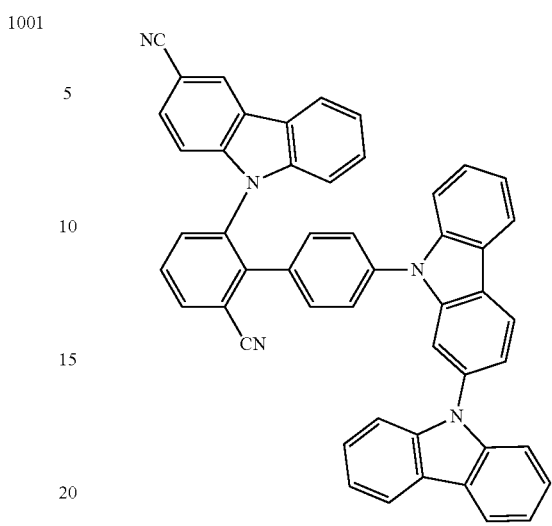
1004
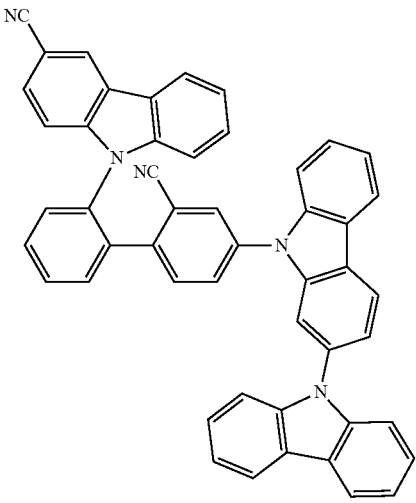
1005
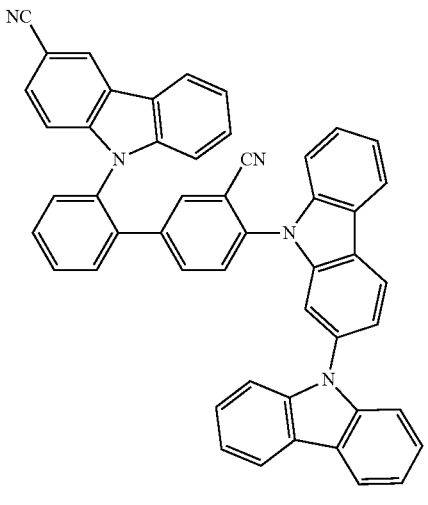
1006

1007
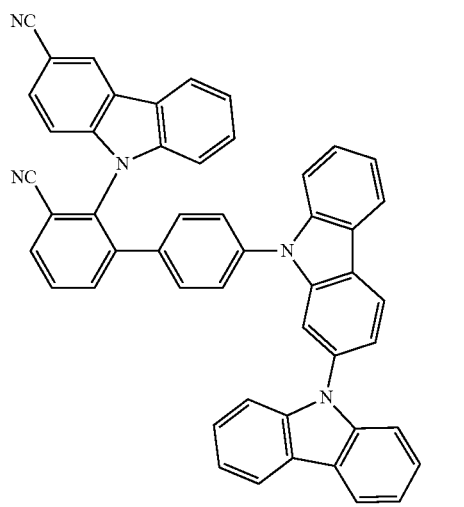
1008
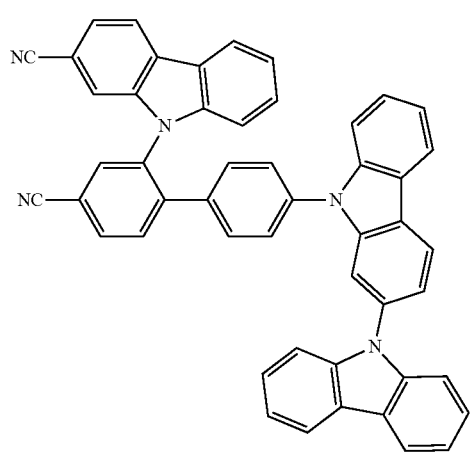
1009
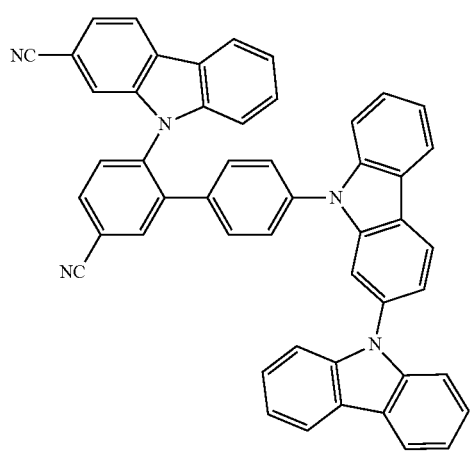
1010
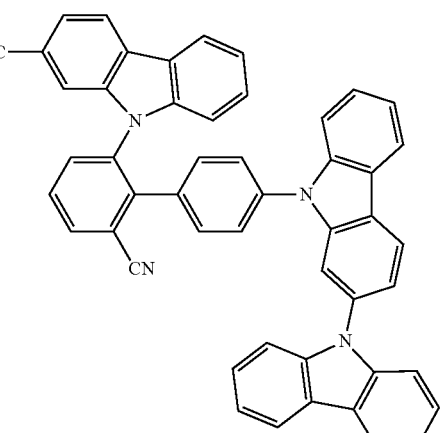
1011
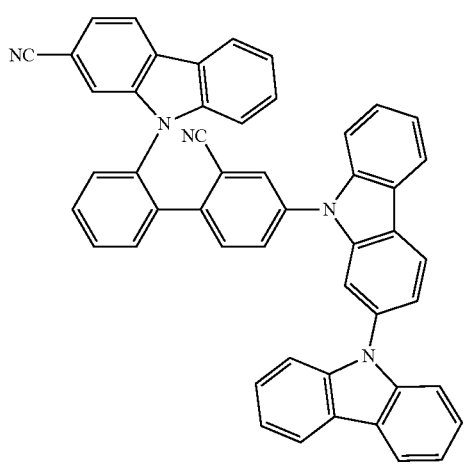
1012
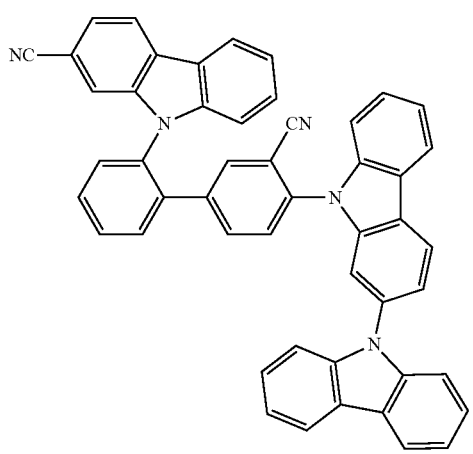

| 1013 | 1016 |
|---|---|
| 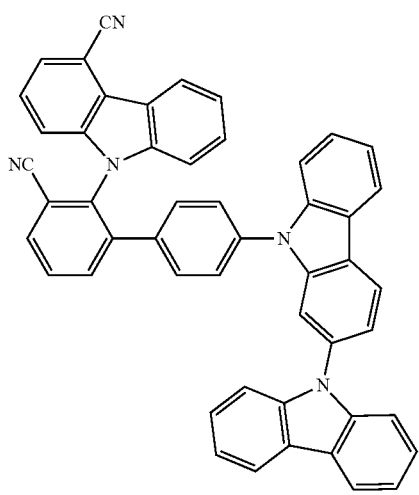 | 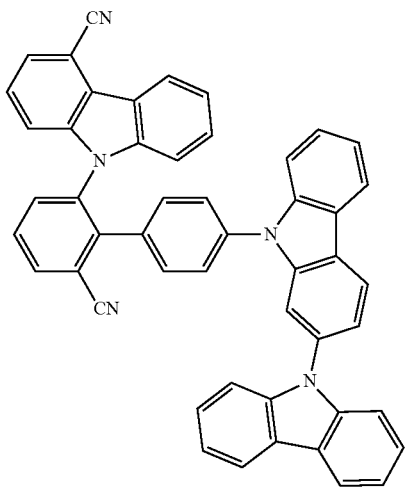 |
| 1014 | 1017 |
|---|---|
| 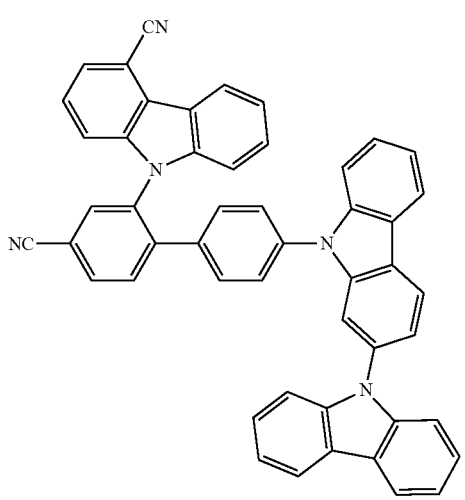 | 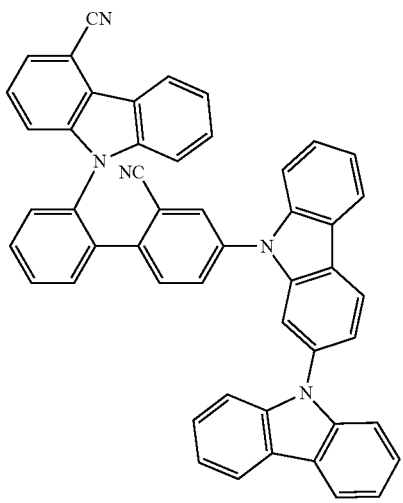 |
| 1015 | 1018 |
|---|---|
| 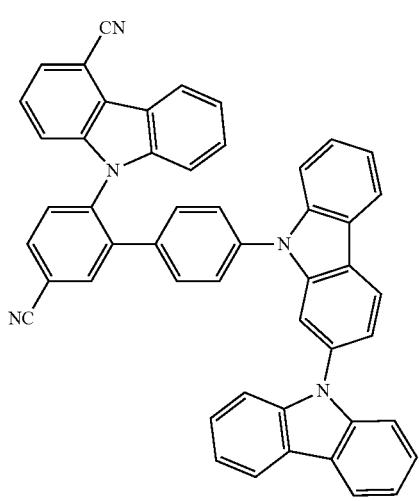 | 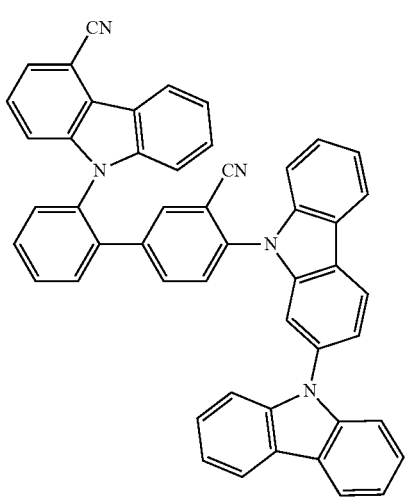 |

1019 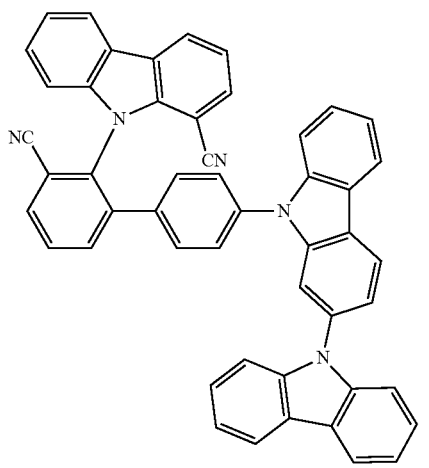
1020 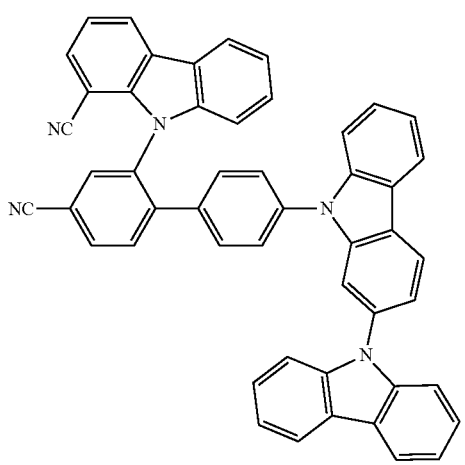
1021 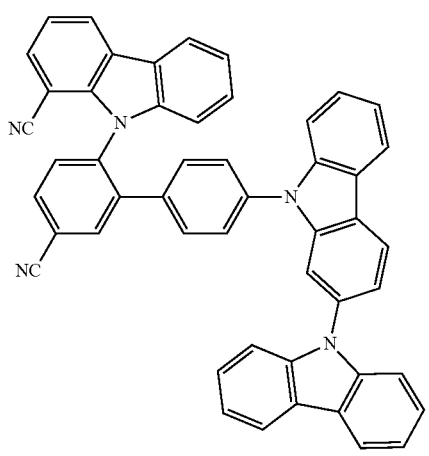
1022 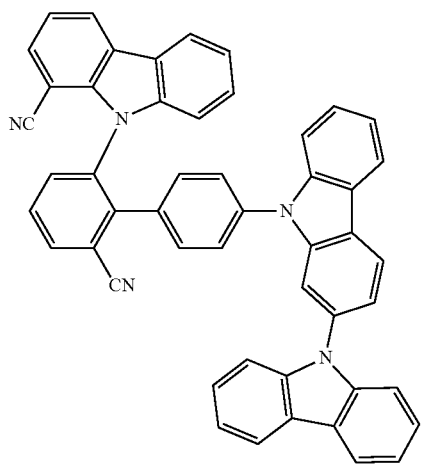
1023 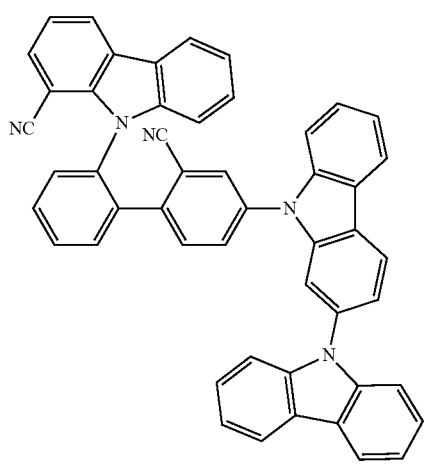
1024 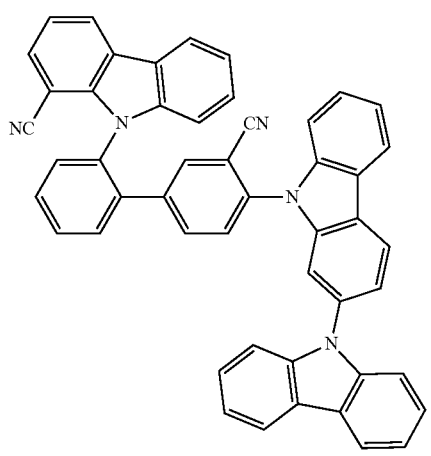

1025
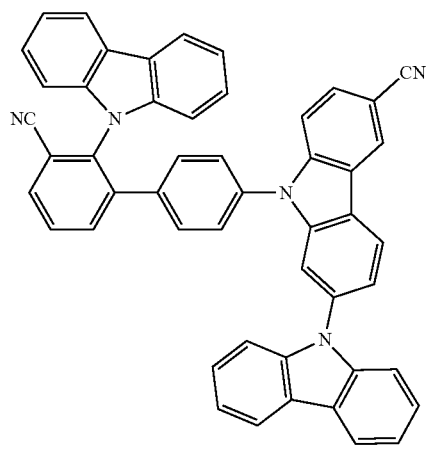
1026
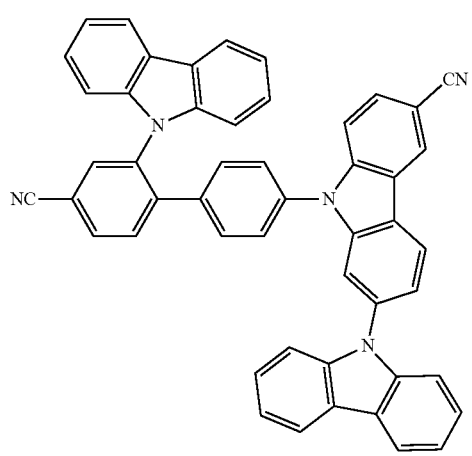
1027
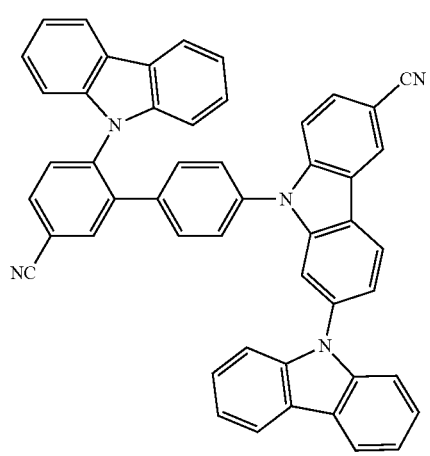
1028
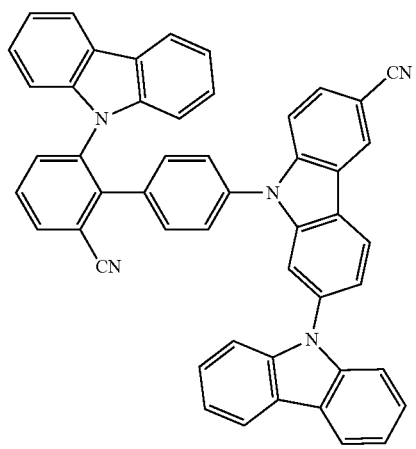
1029
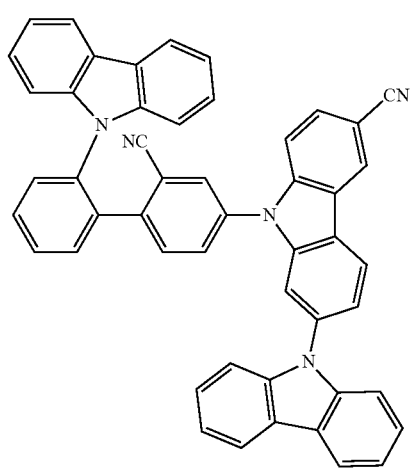
1030
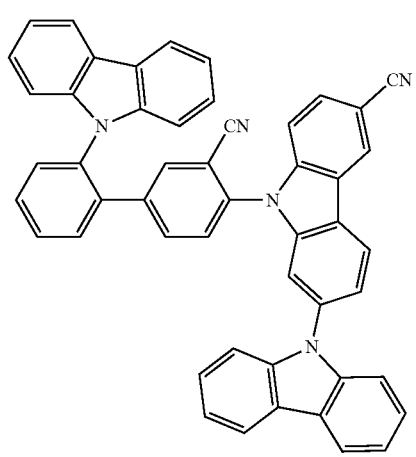

1031
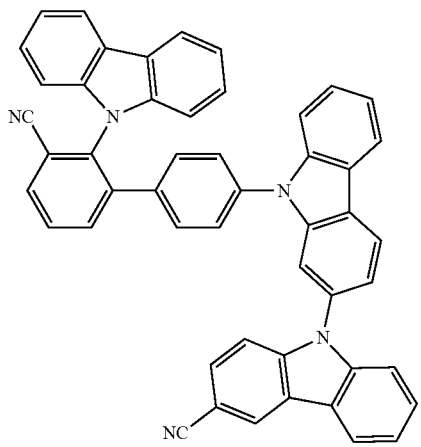
1032
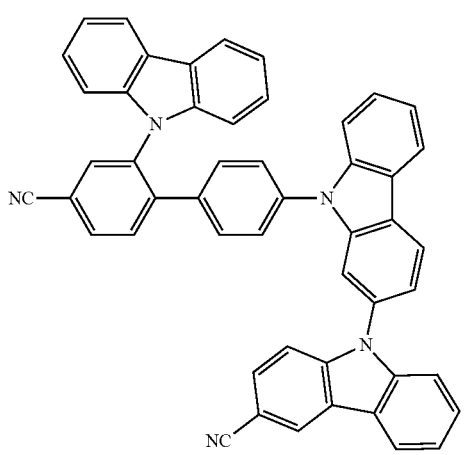
1033
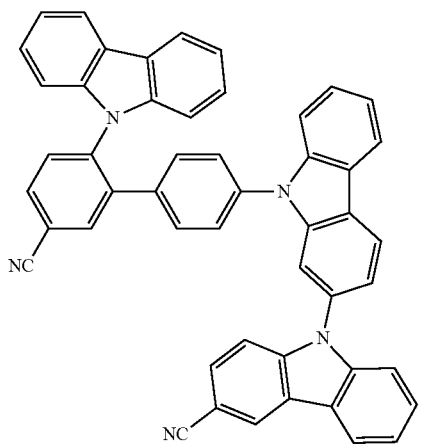
1034
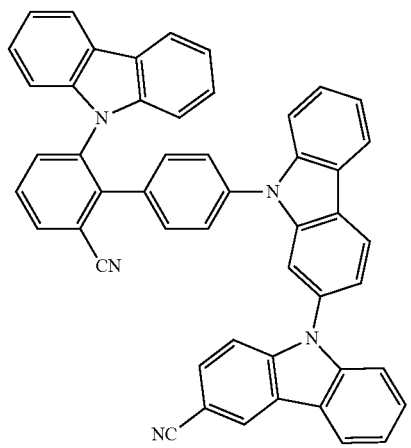
1035
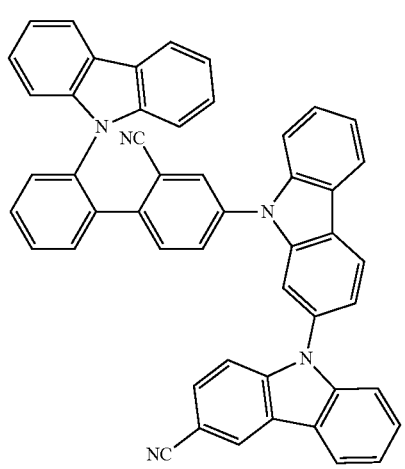
1036
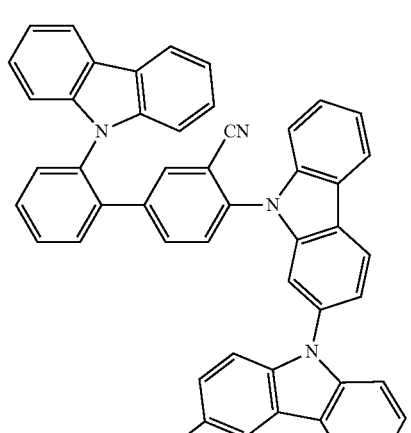

-continued
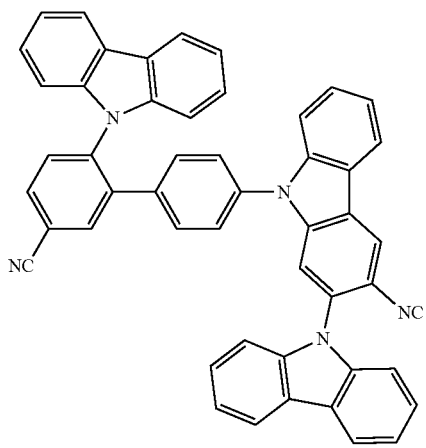
1037
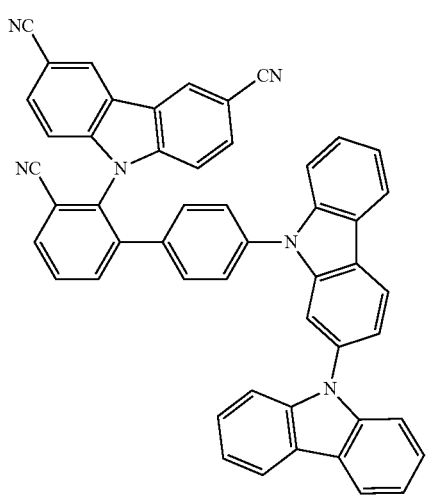
1038
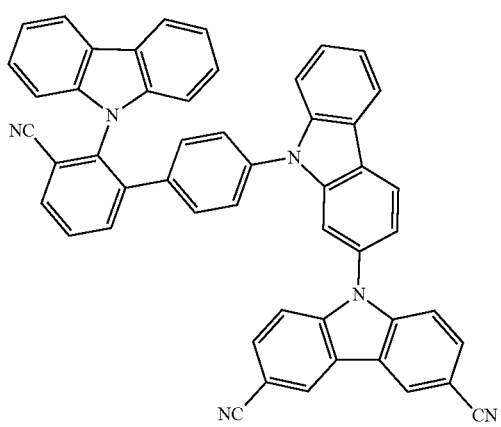
1039
-continued
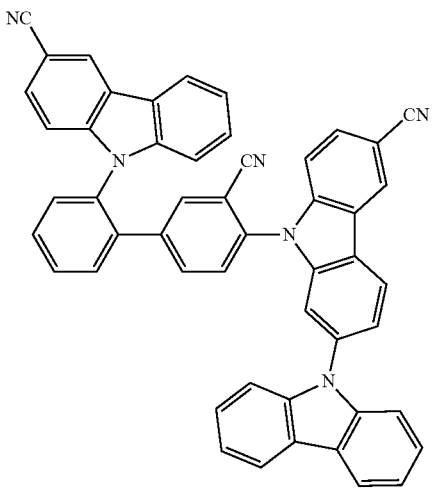
1040
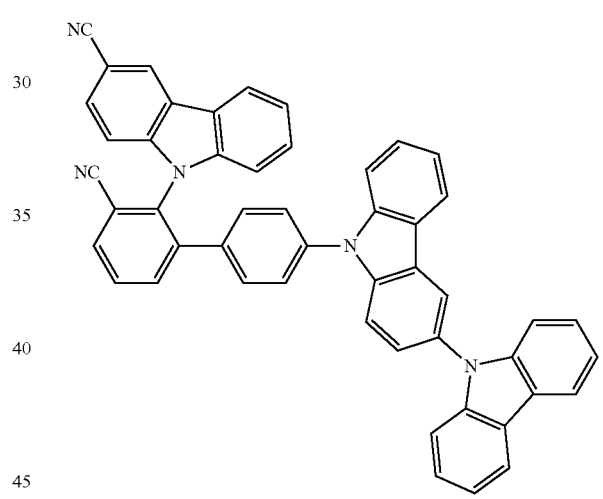
1041
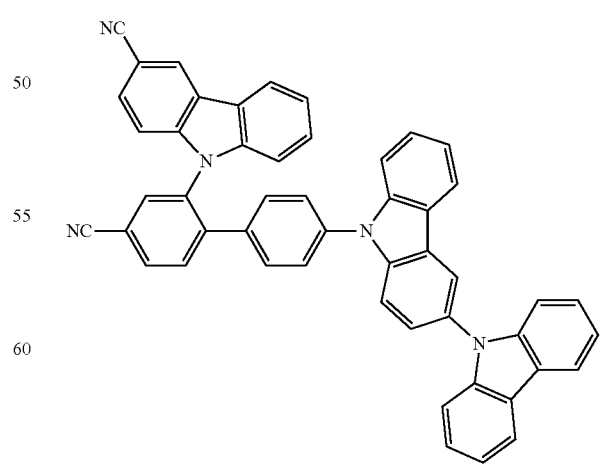
1042

1043
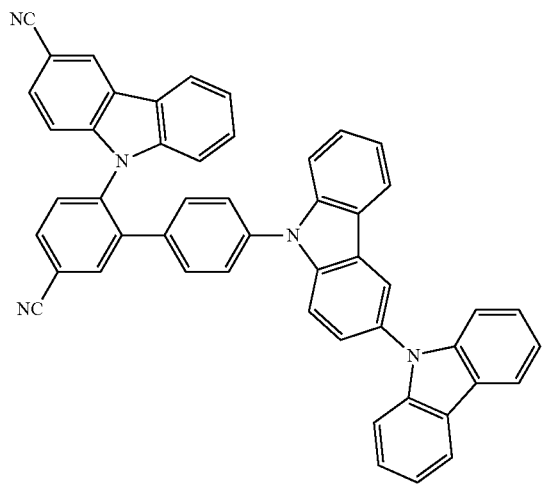
1044
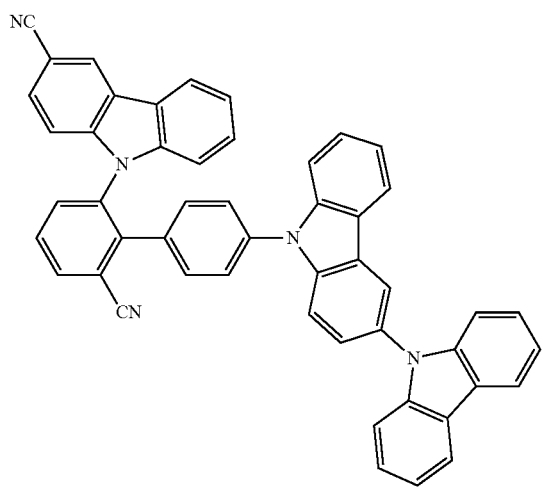
1045
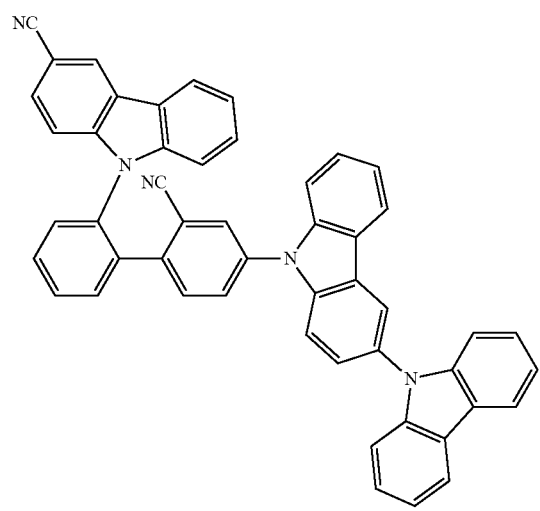
1046
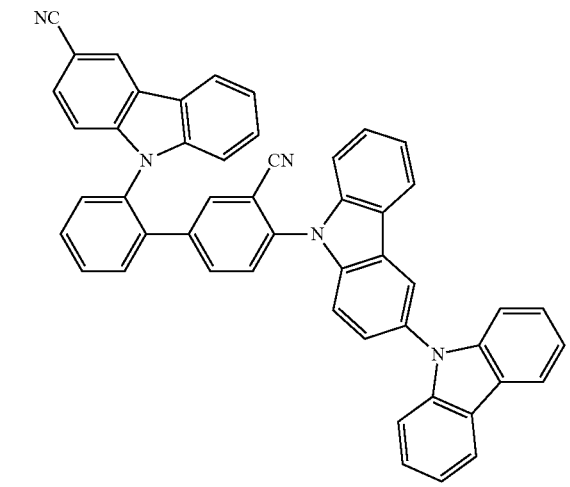
1047
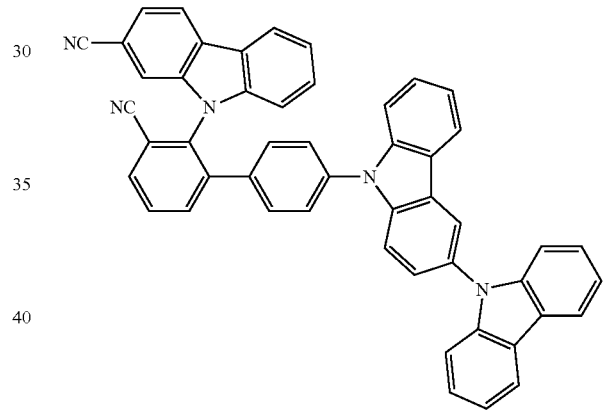
1048
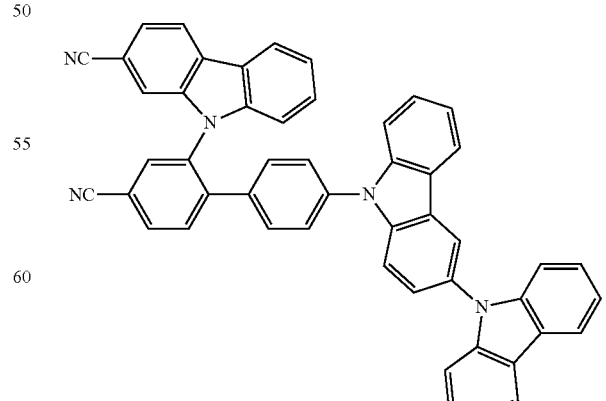

-continued
1049
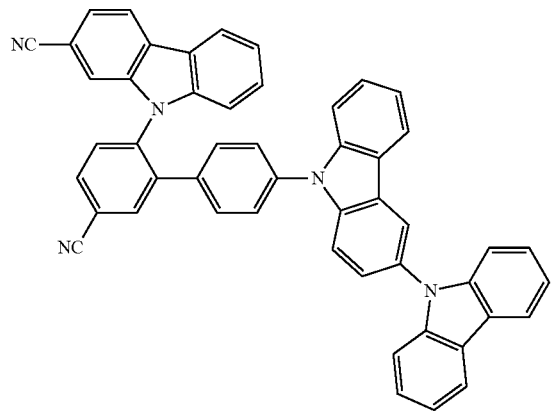
1050
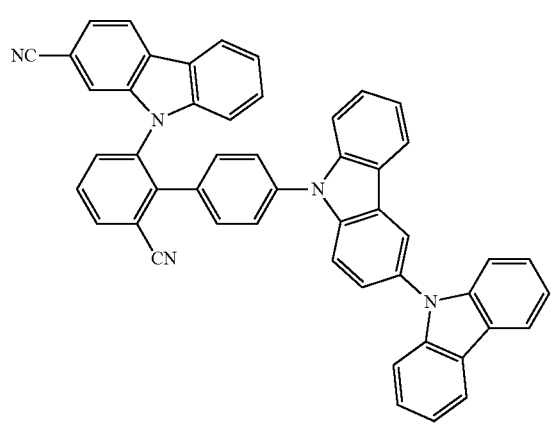
1051
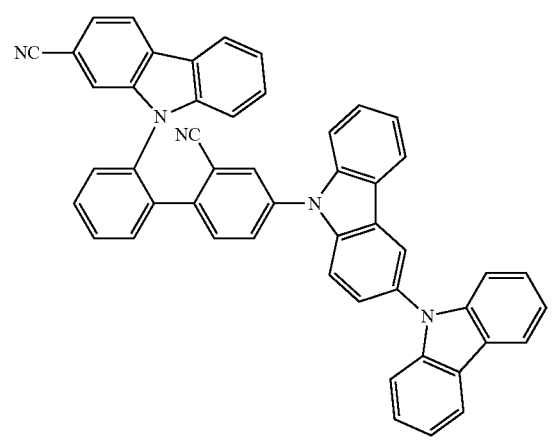
-continued
1052
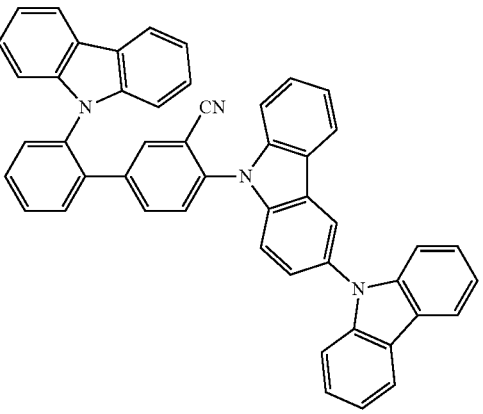
1053
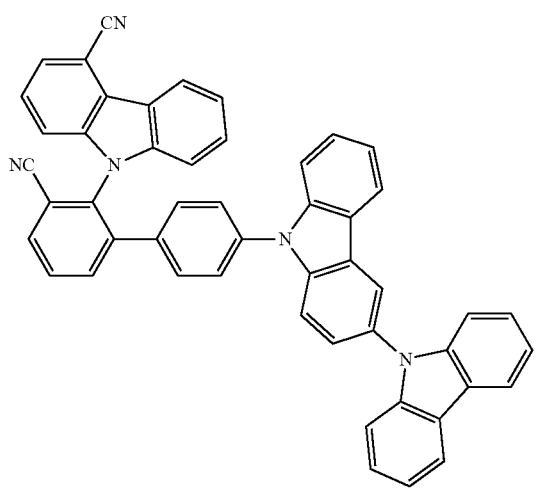
1054
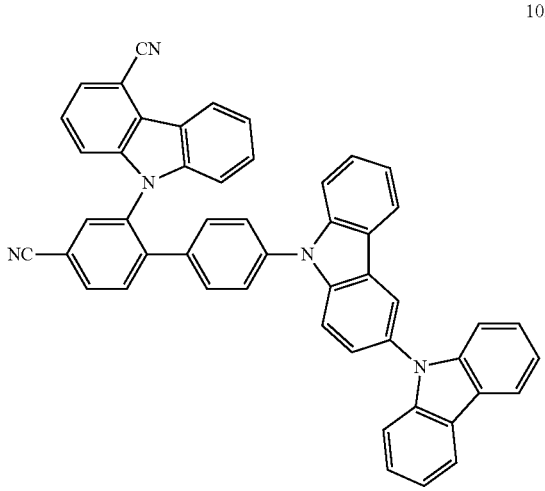

1055
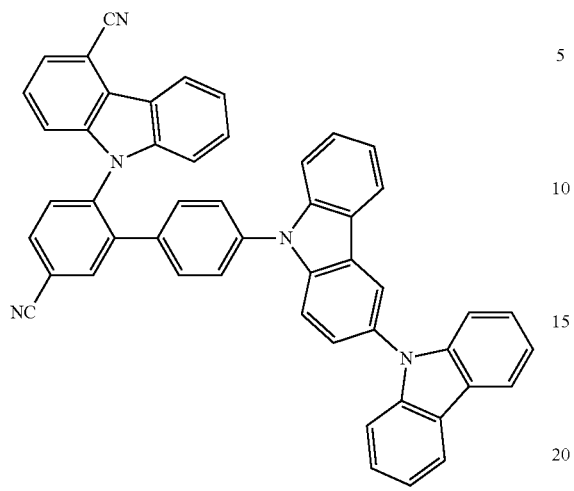
1056
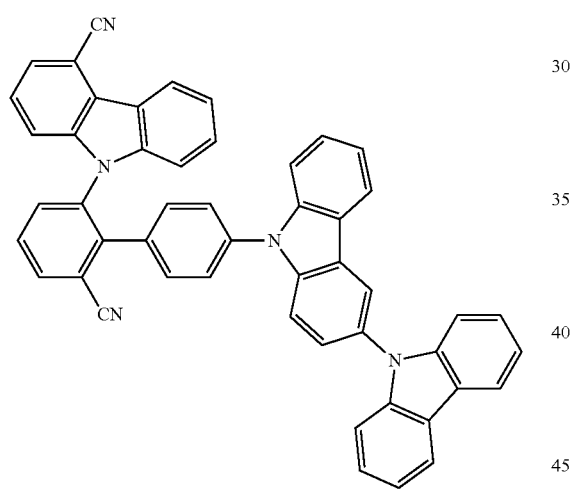
1057
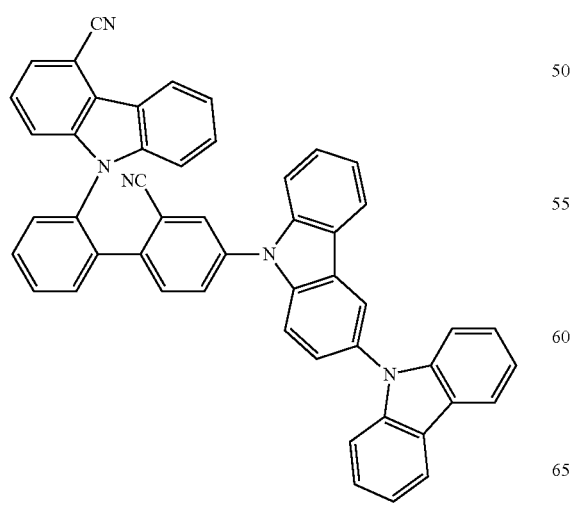
1058
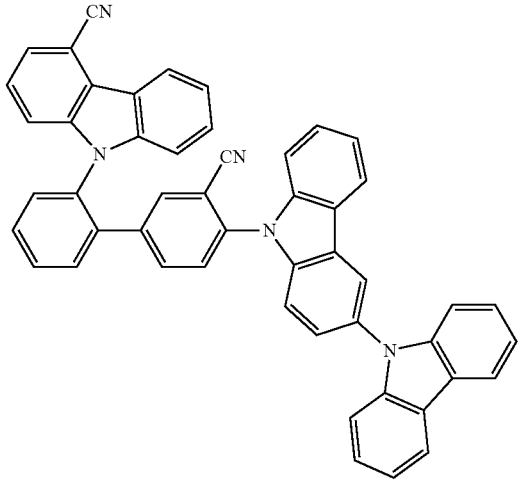
1059
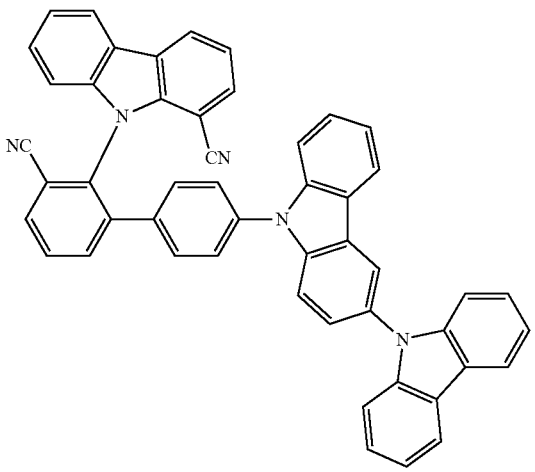
1060
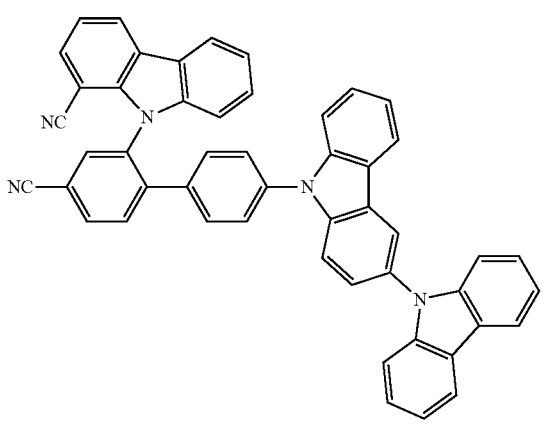

1061
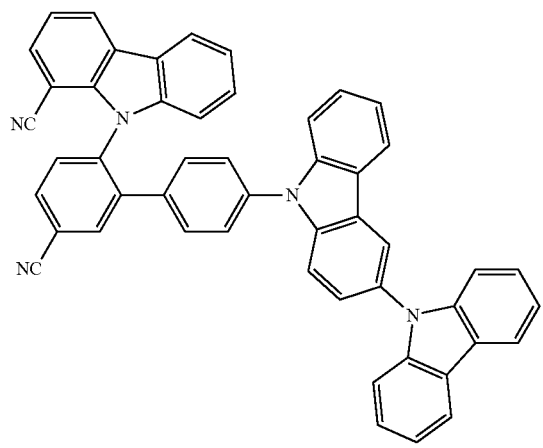
1062
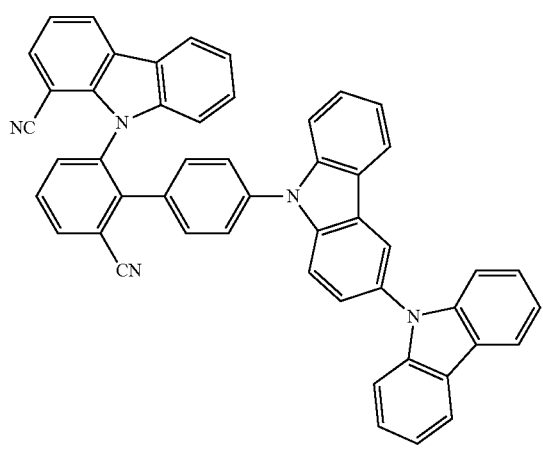
1063
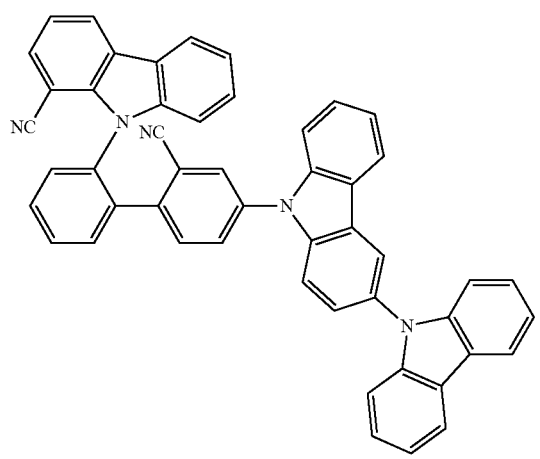
1064
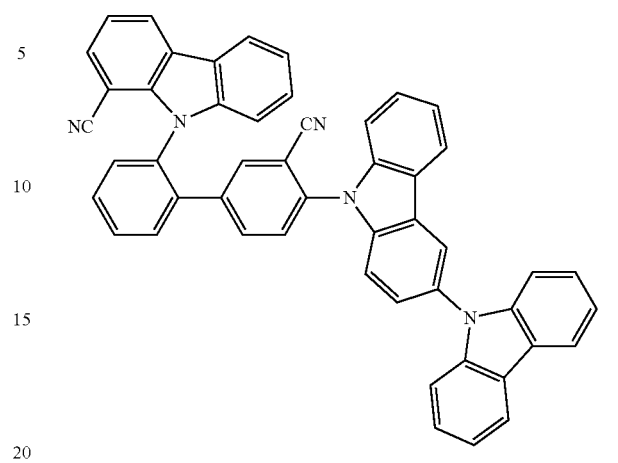
1065
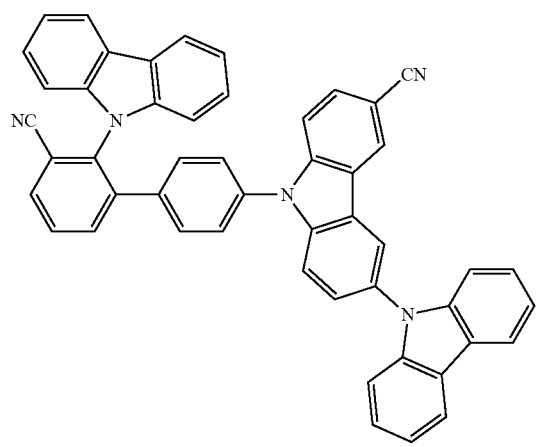
1066
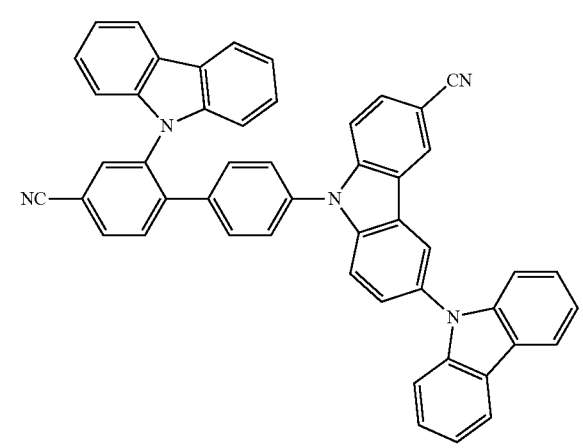

-continued
1067
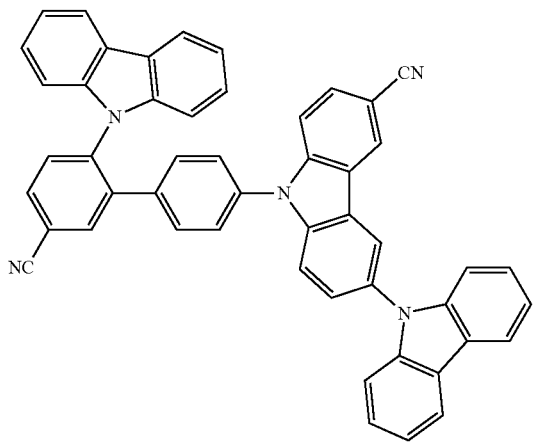
1068
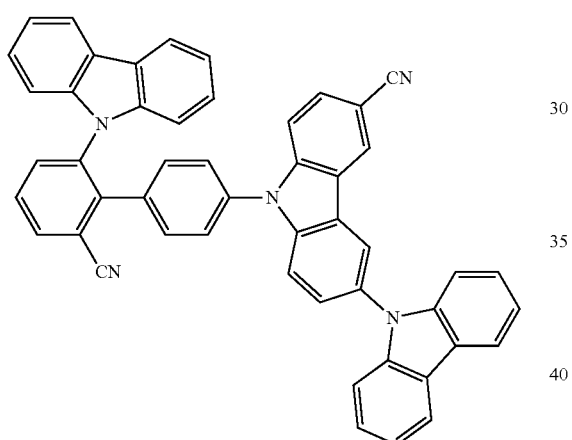
1069
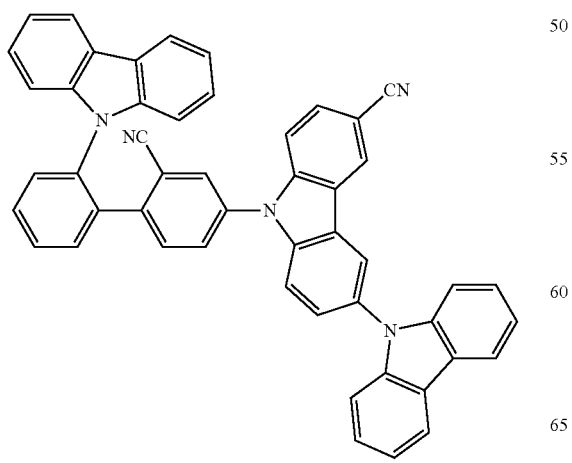
-continued
1070
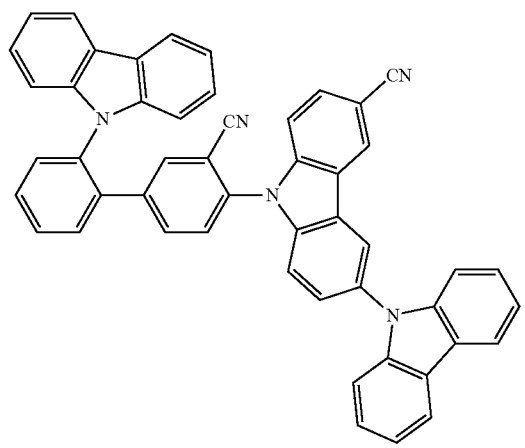
1071
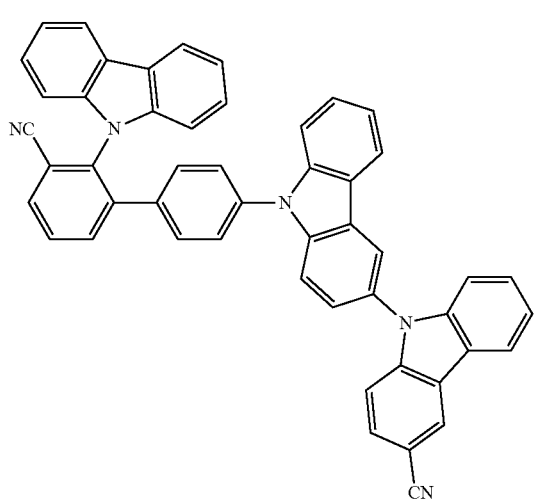
1072
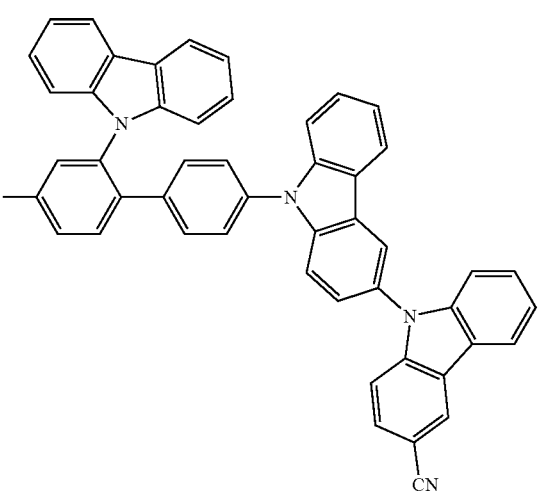

375
-continued
1073
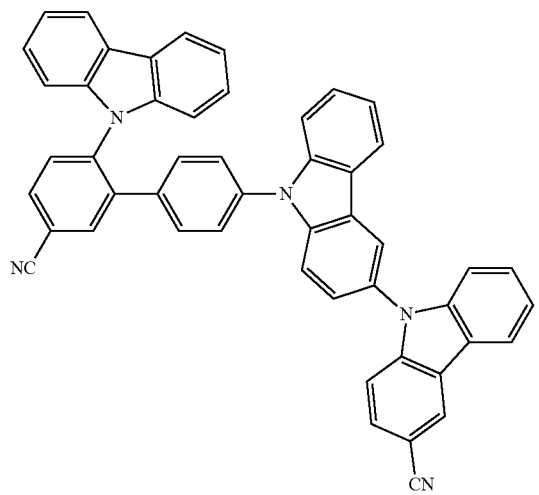
1074
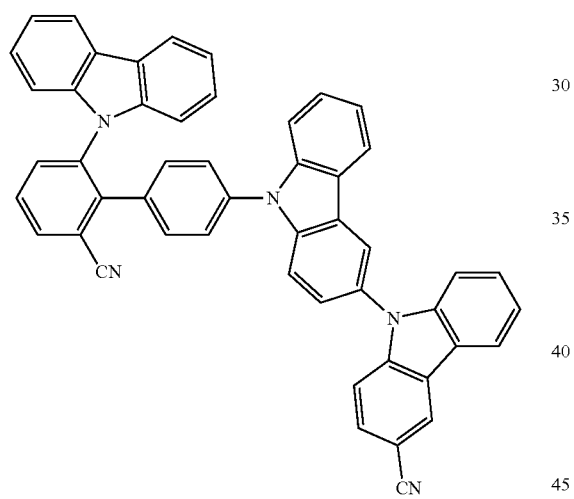
1075
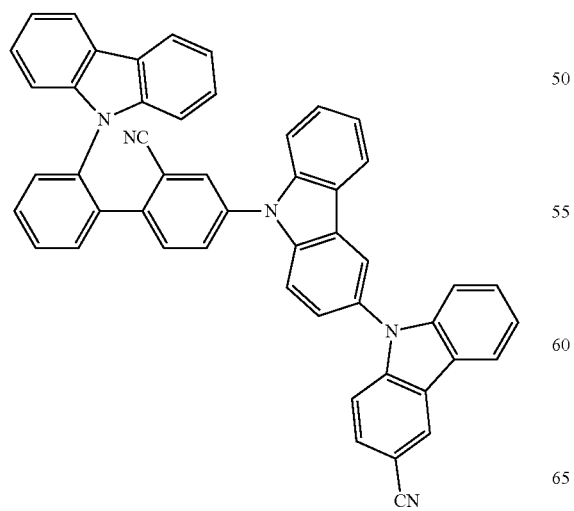
376
-continued
1076
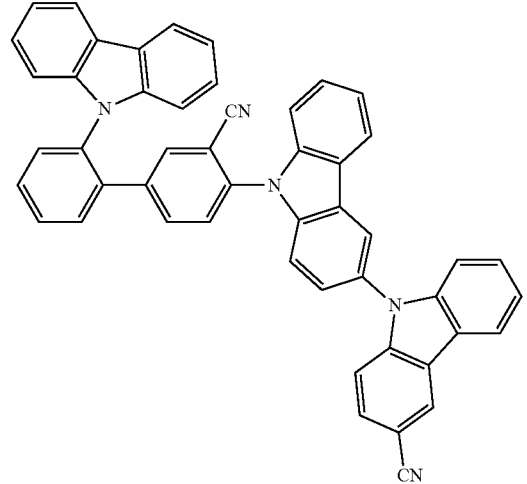
1077
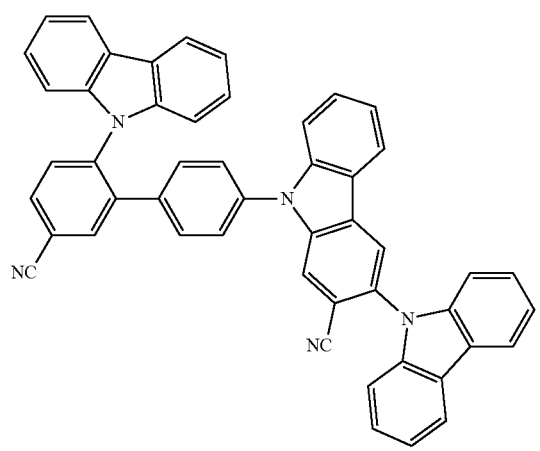
1078
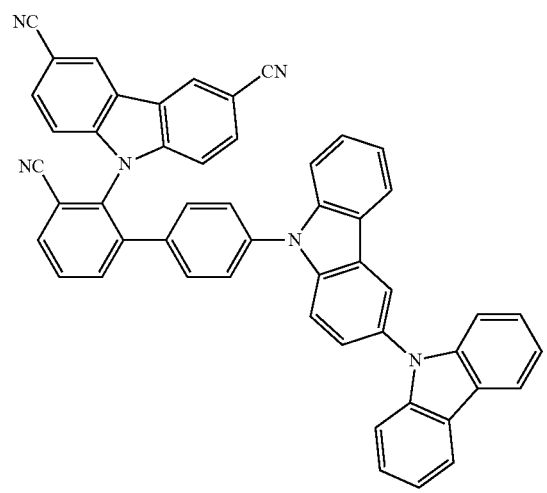

-continued
1079
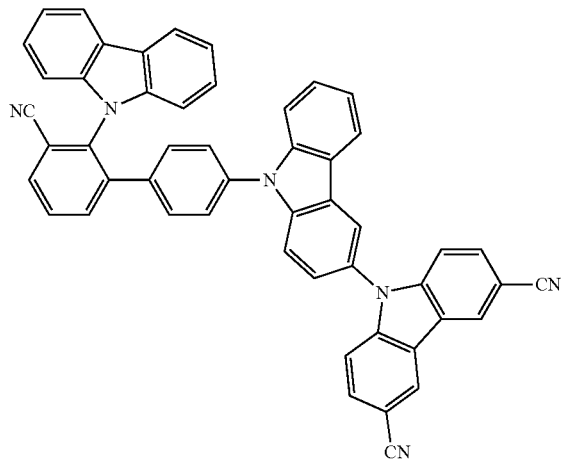
1080
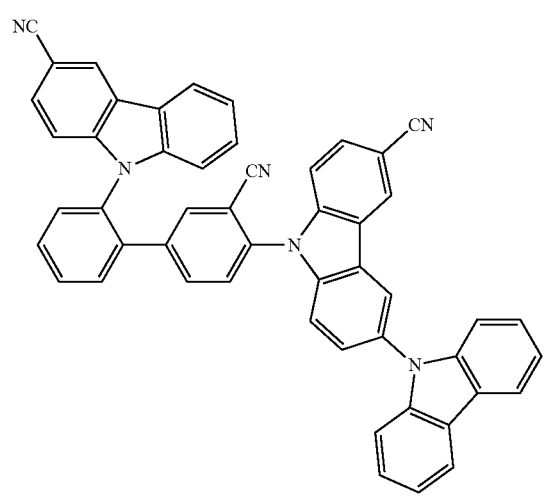
1081
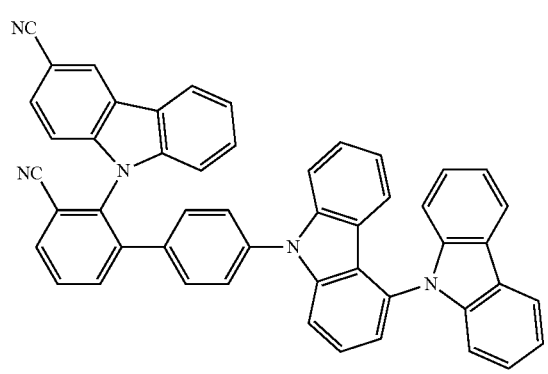
-continued
1082
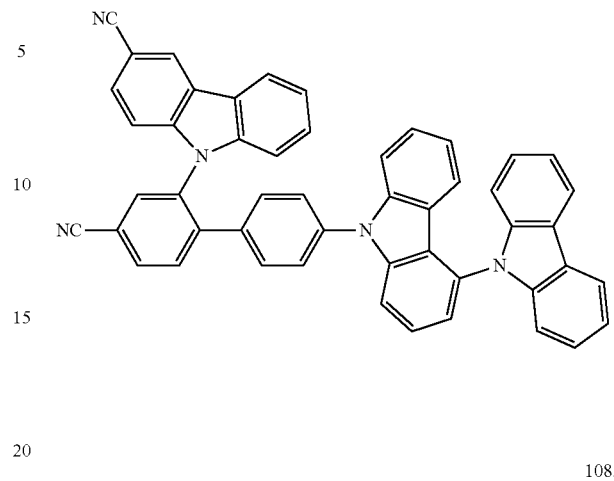
1083
1084
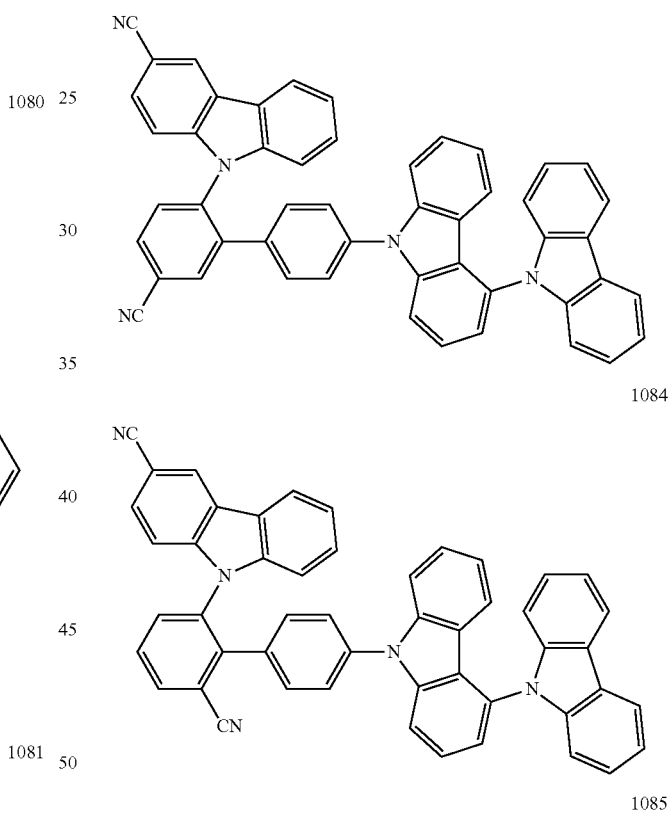
1085
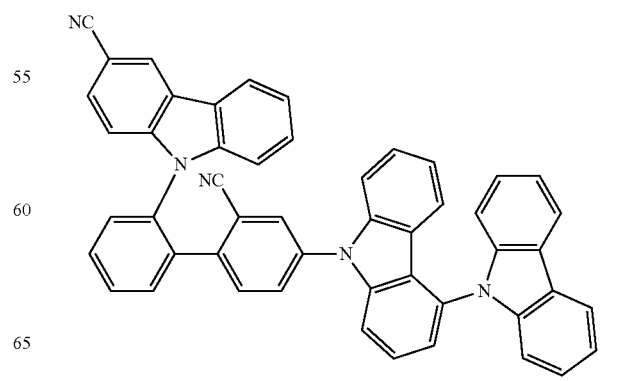

1086
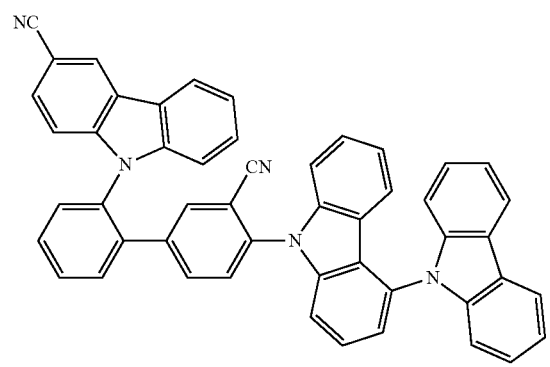
1087
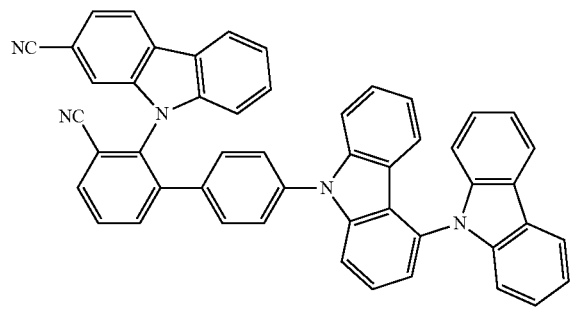
1088
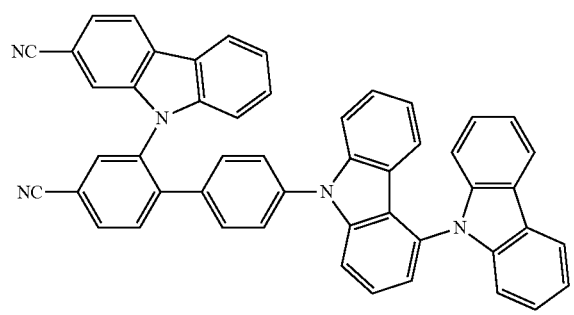
1089
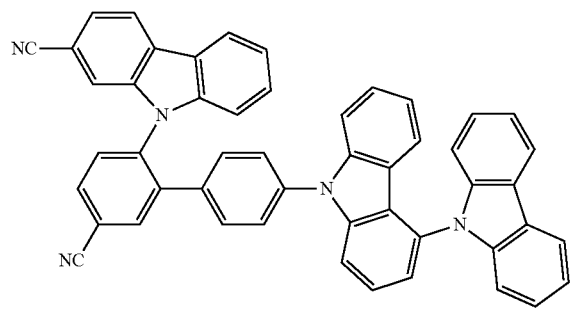
1090
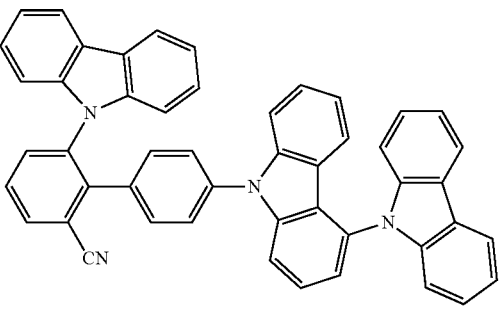
1091
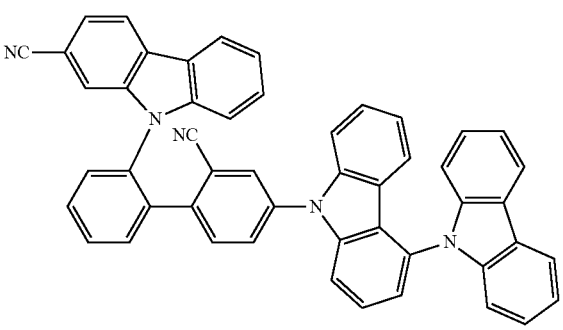
1092
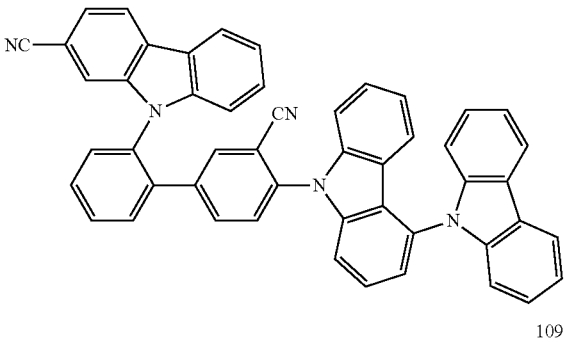
1093
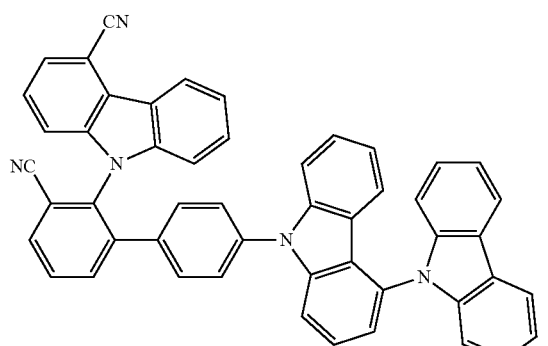

-continued
1094
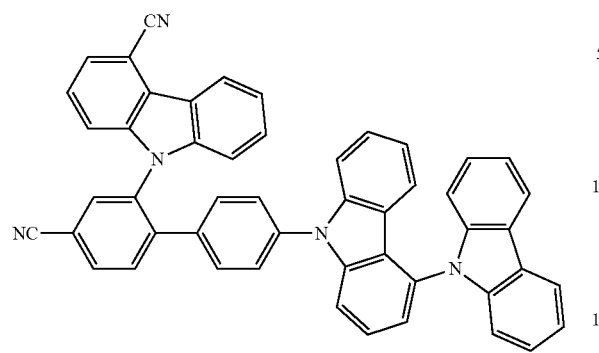
1095
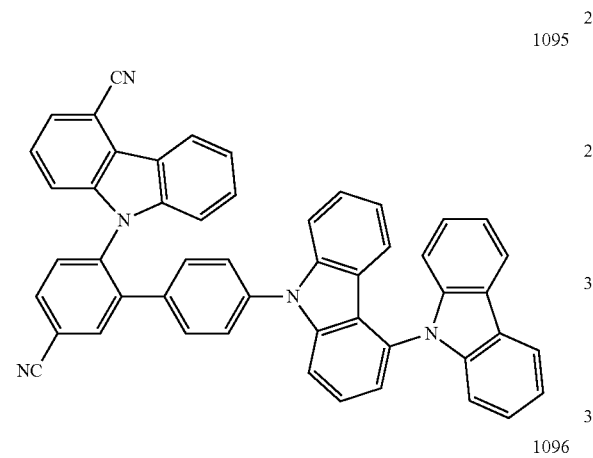
1096
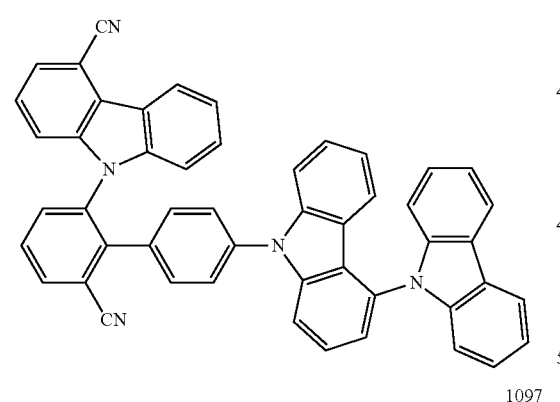
1097
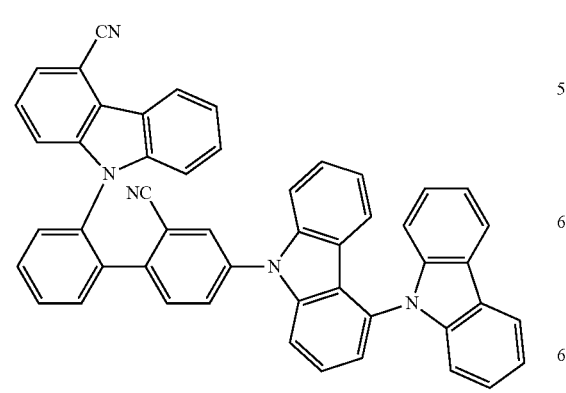
-continued
1098
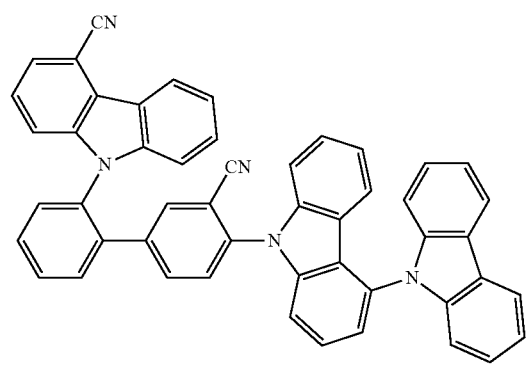
1099
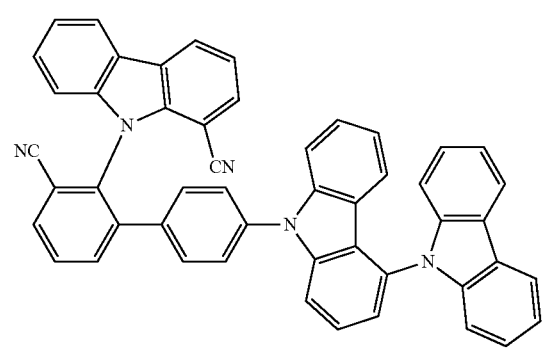
1100
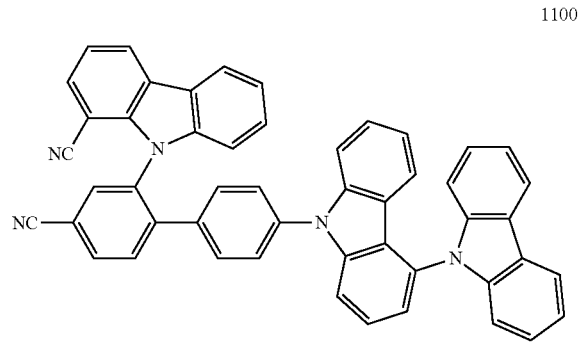
1101
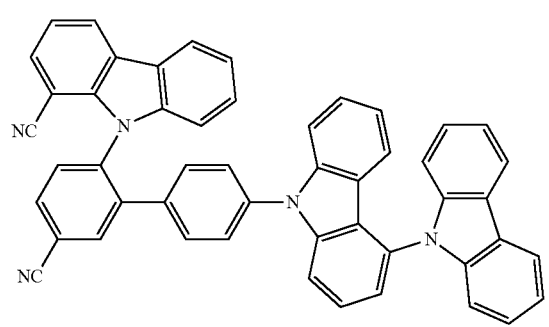

-continued
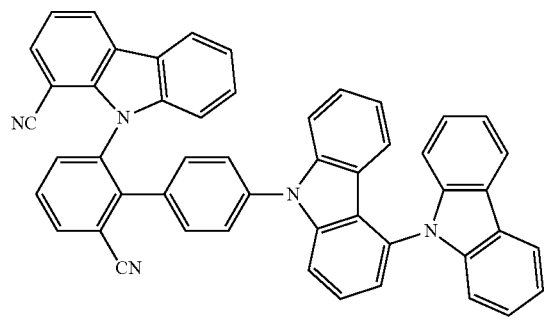
1102
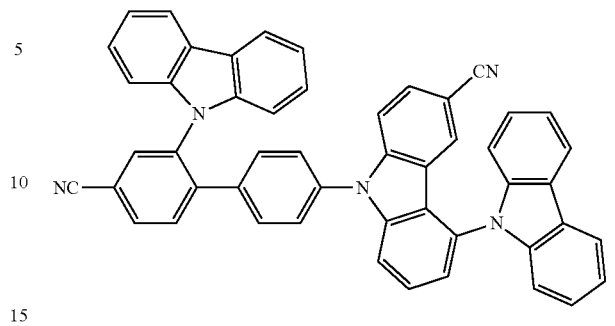
1106
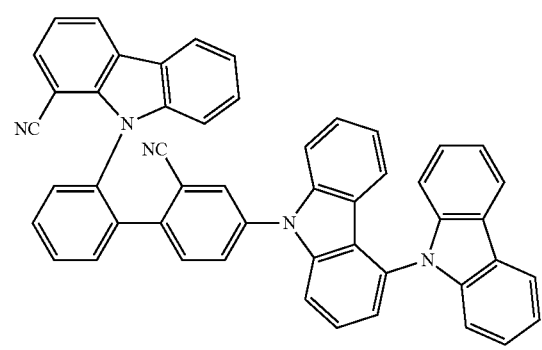
1103
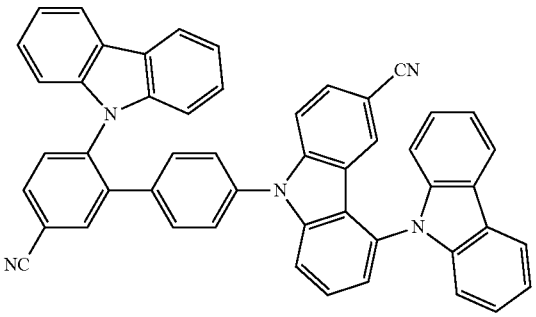
1107
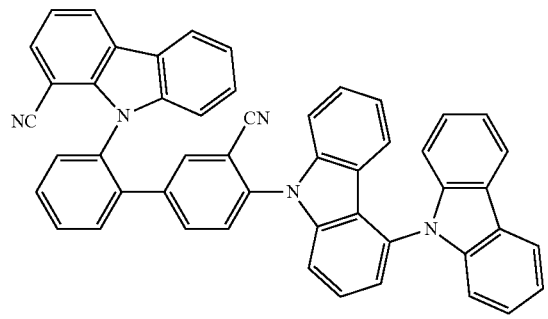
1104
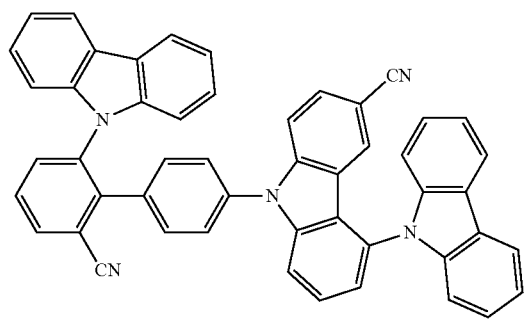
1108
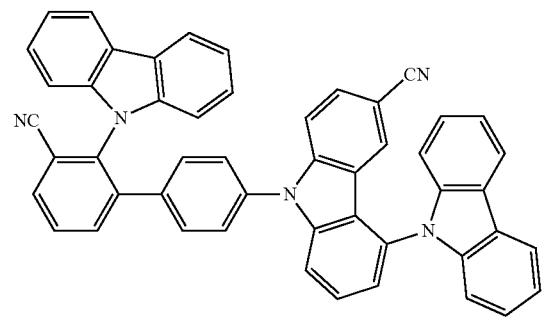
1105
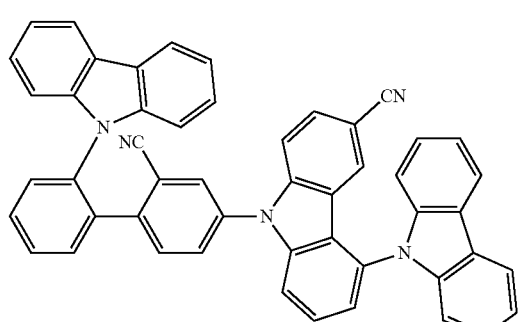
1109

-continued
1110
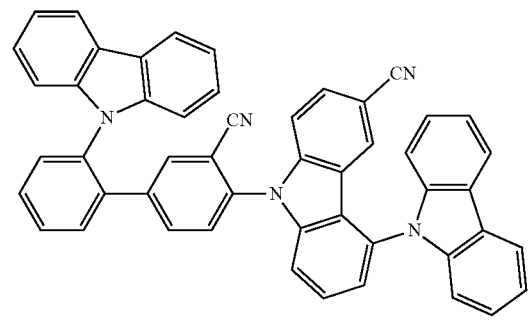
1111
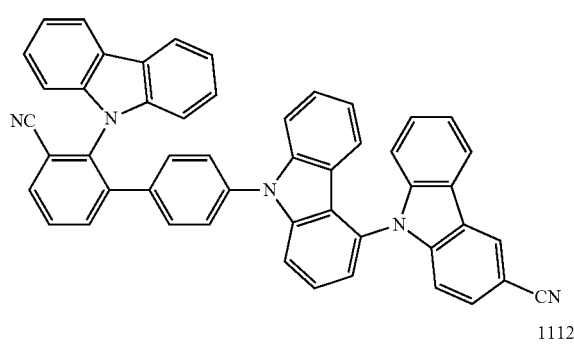
1112
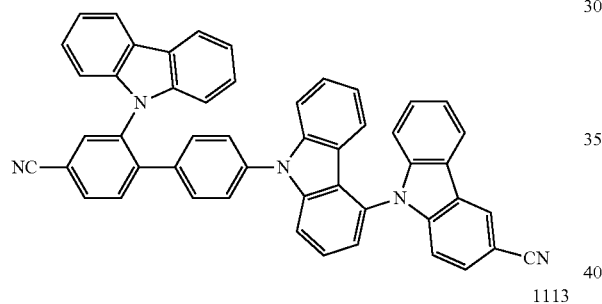
1113
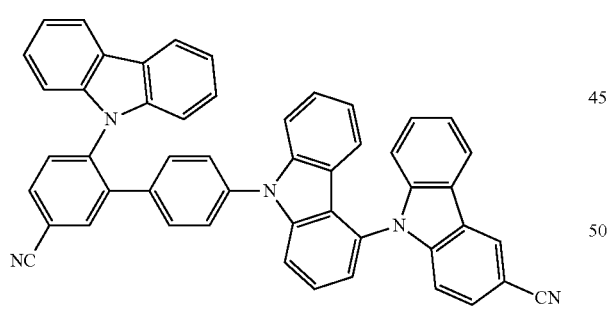
1114
-continued
1115
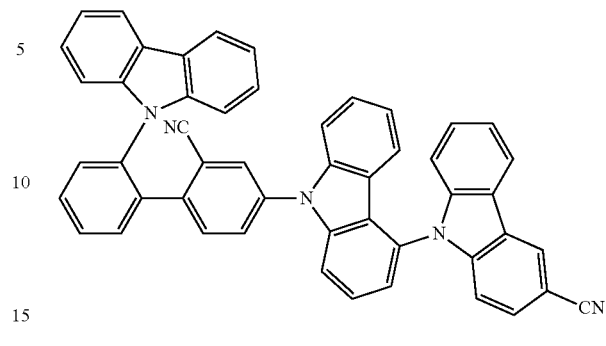
1116
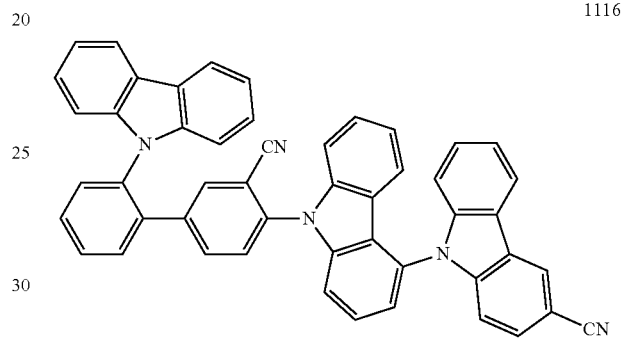
1117
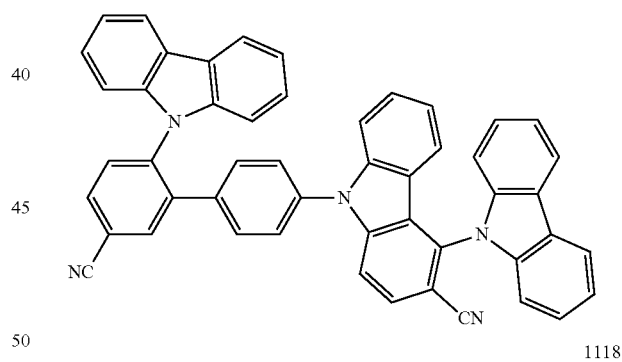
1118
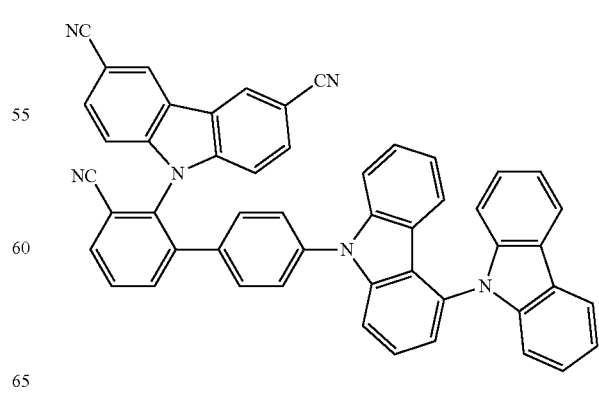

1119
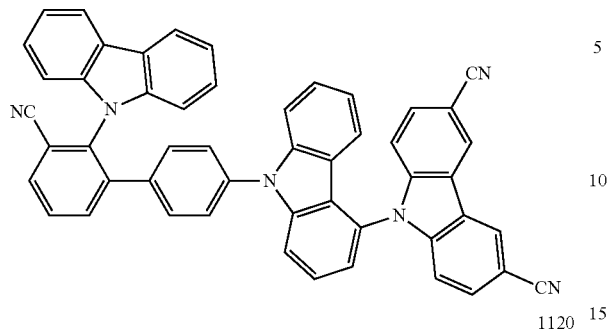
1120
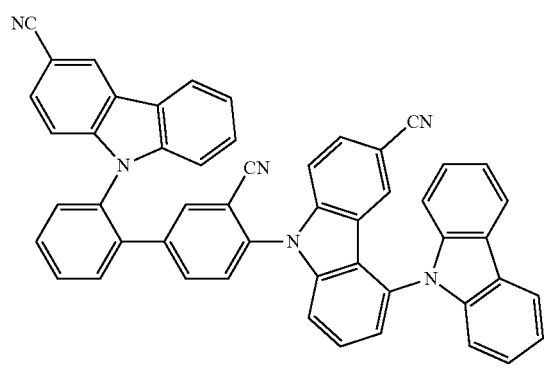
1121
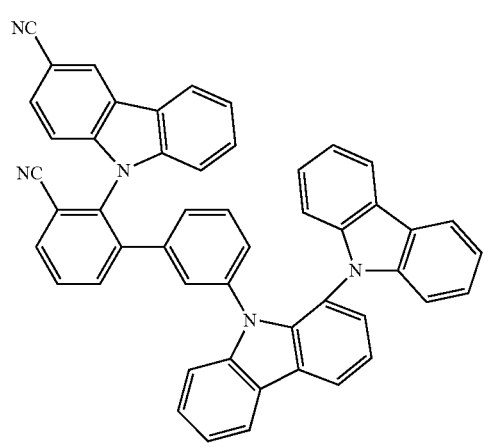
1122
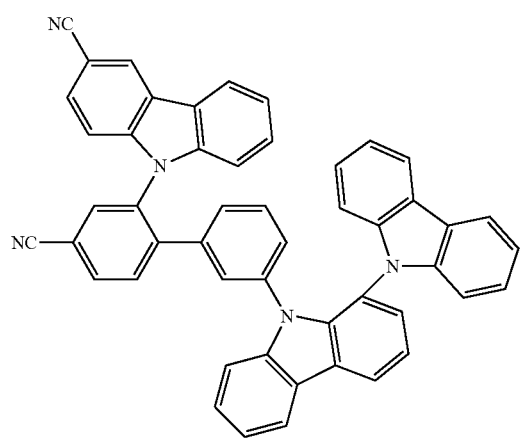
1123
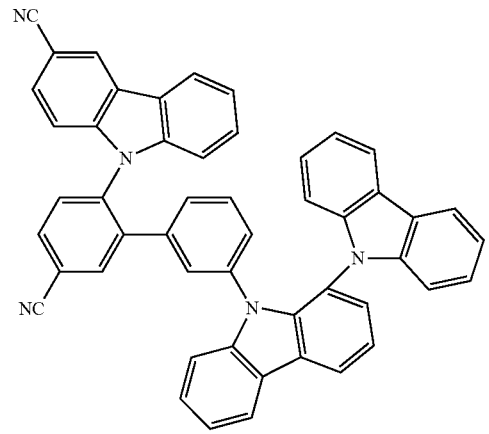
1124
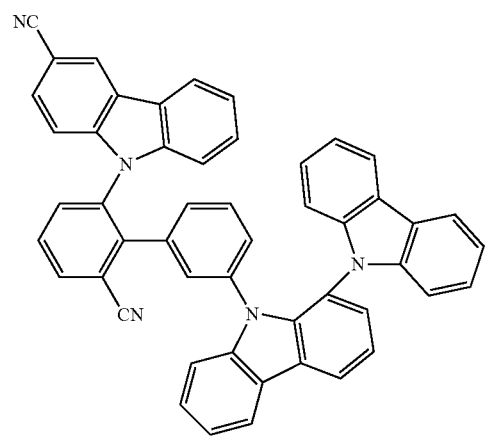
1125
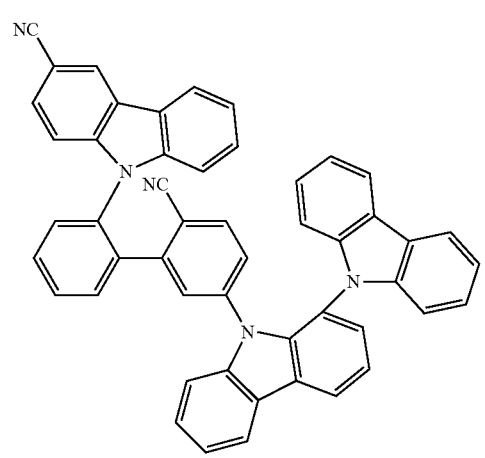

1126
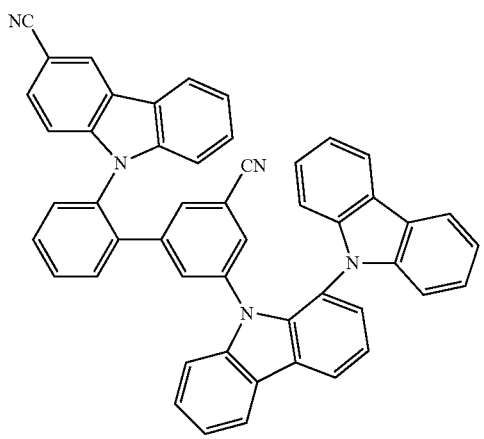
1127
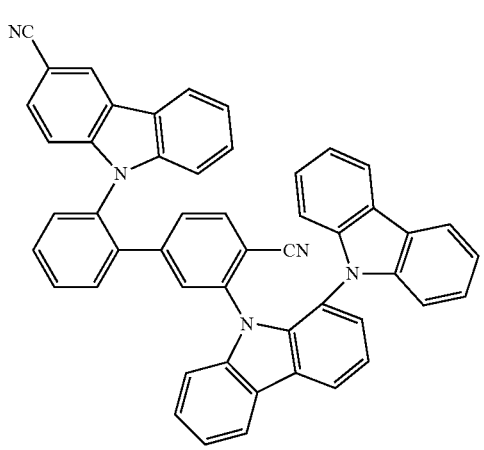
1128
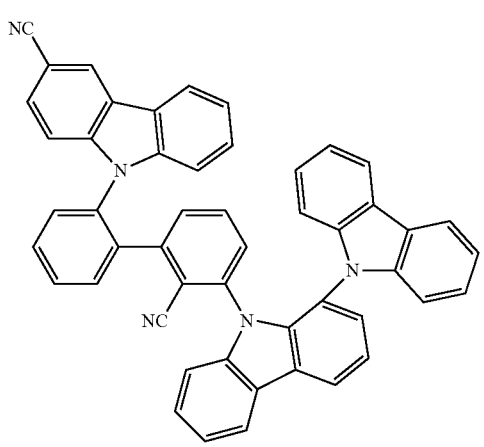
1129
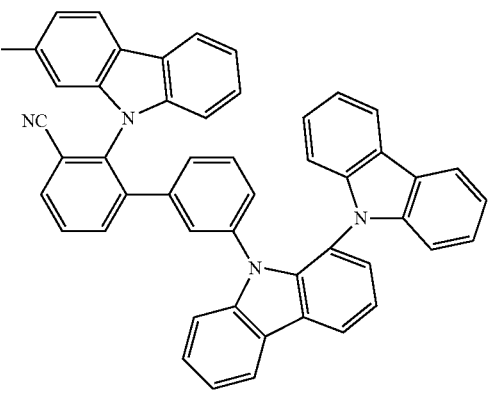
1130
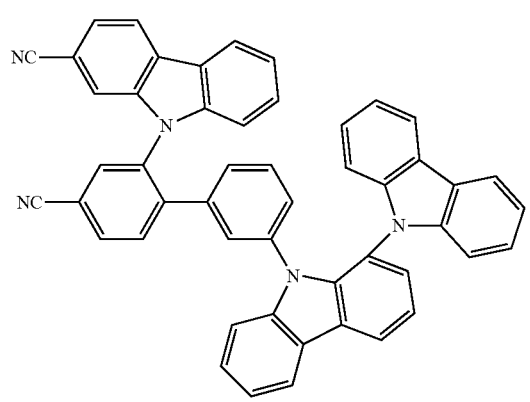
1131
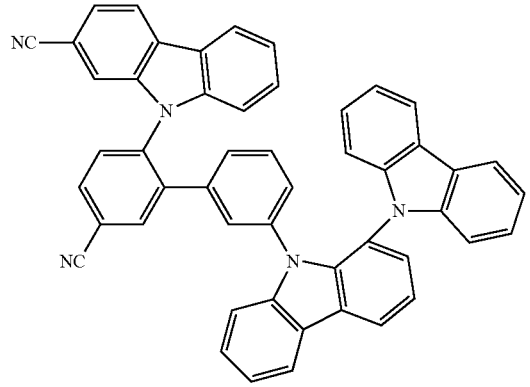
1132
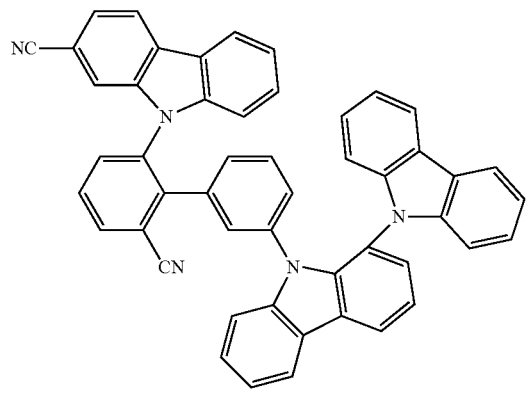

391
-continued
1133
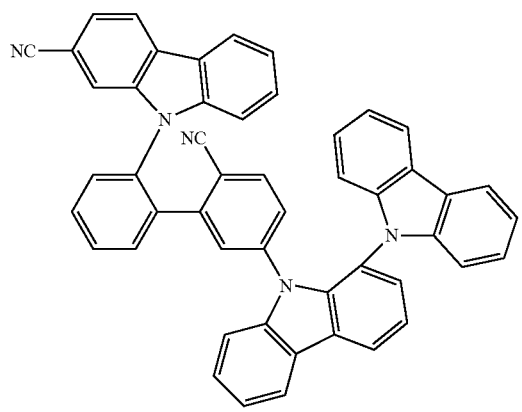
1134
1135
1136
392
-continued
1137
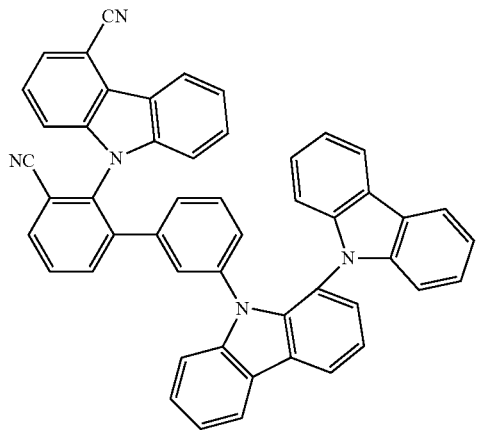
1138
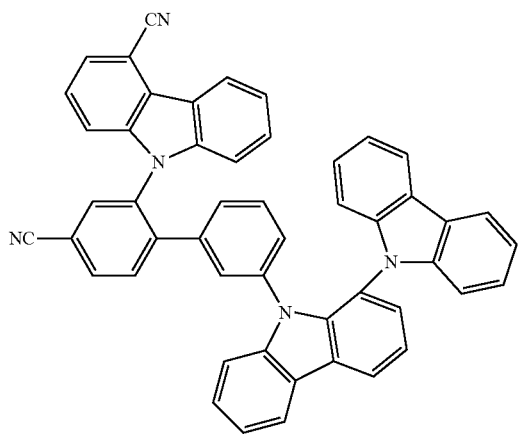
1139
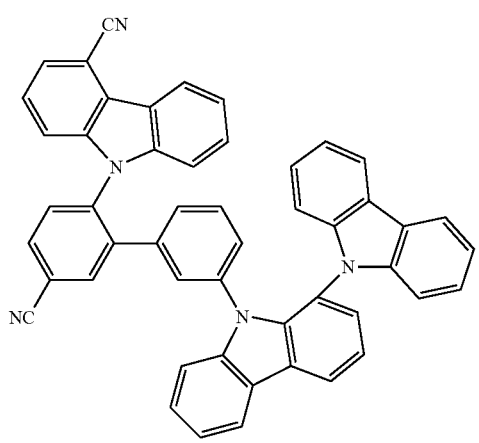

1140
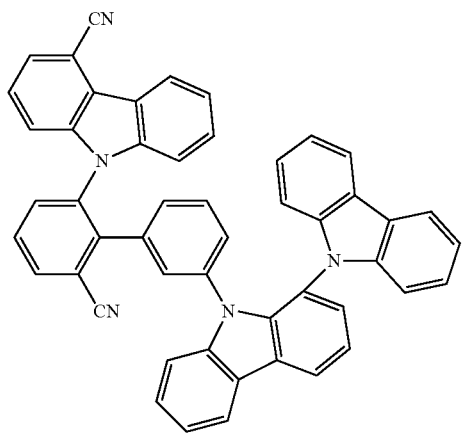
1141
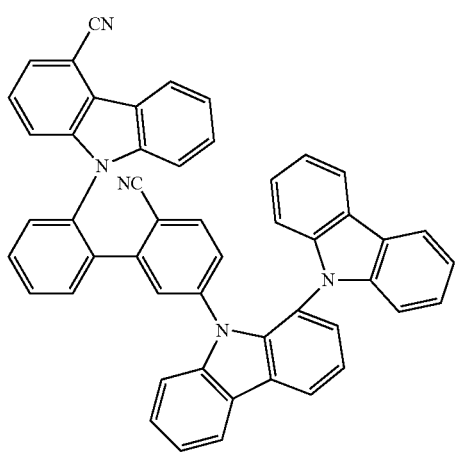
1142
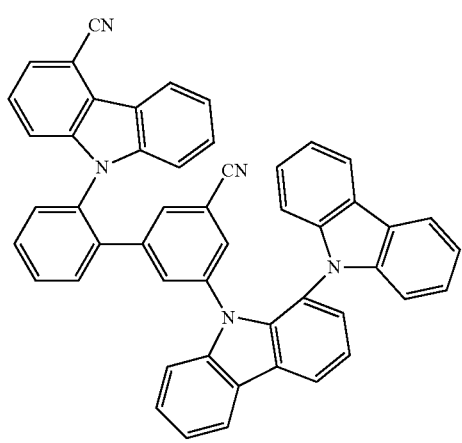
1143
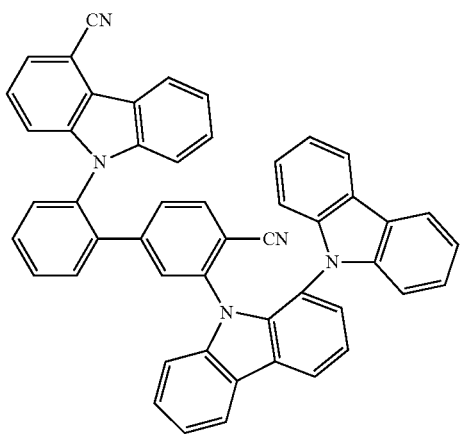
1144
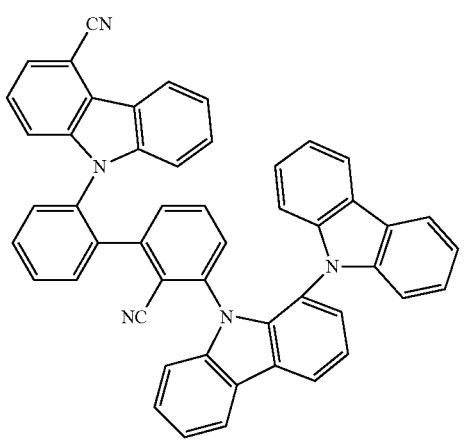
1145
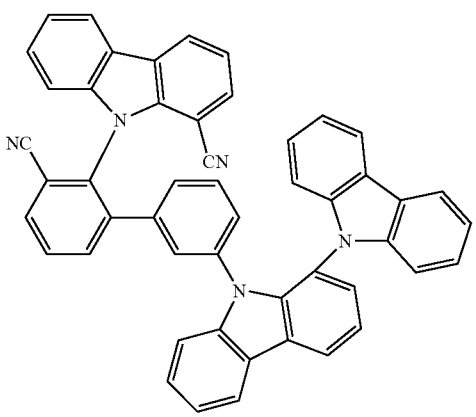

1146
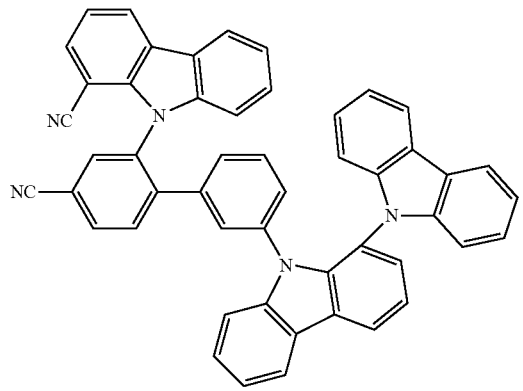
1147
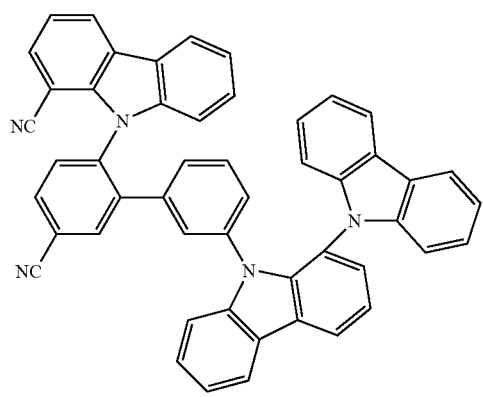
1148
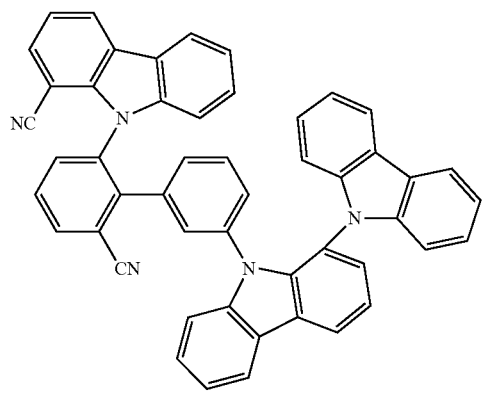
1149
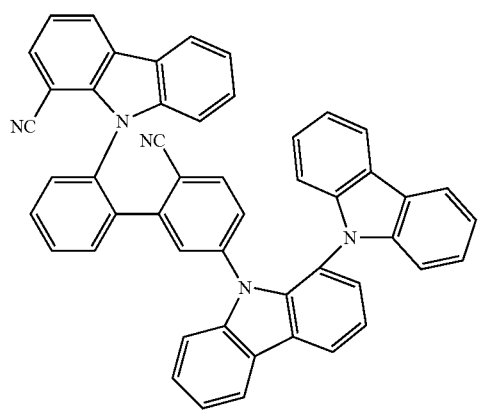
1150
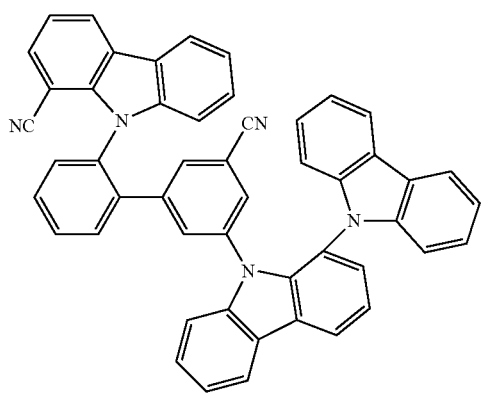
1151
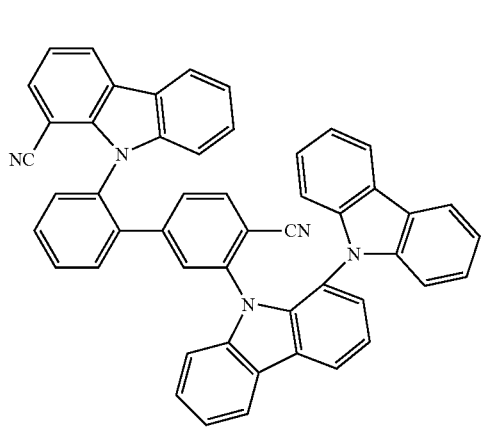
1152
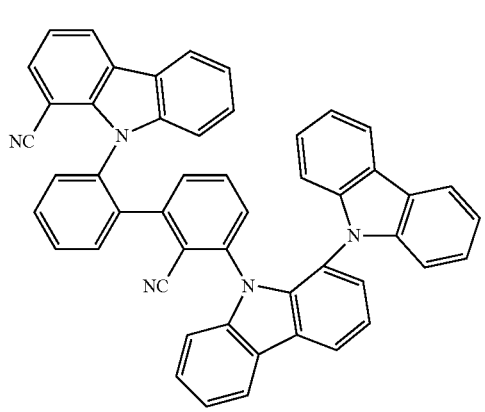

1153
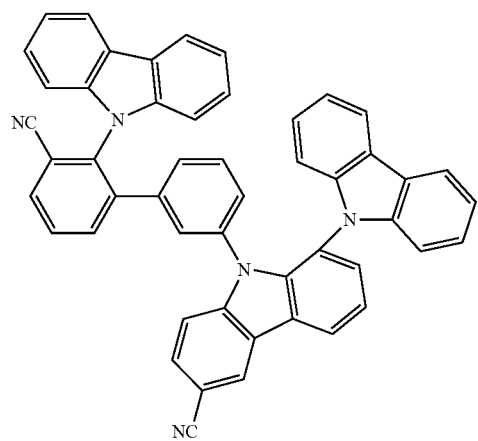
1154
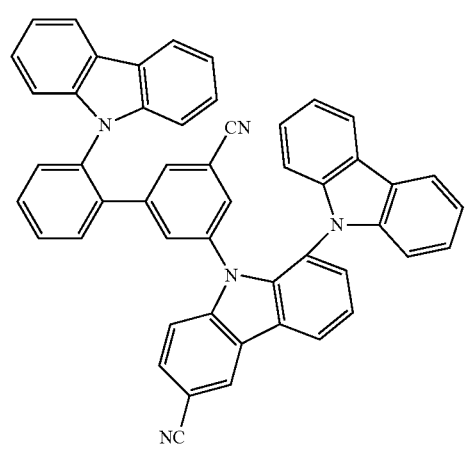
1155
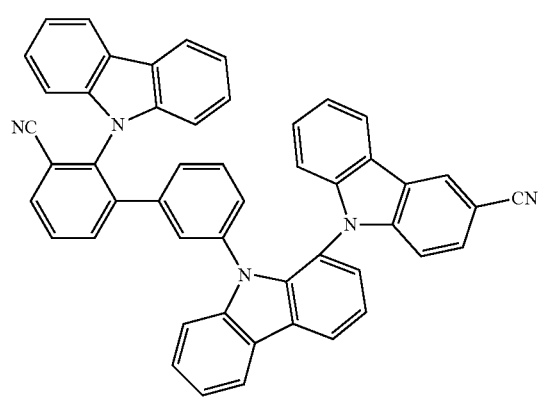
1156
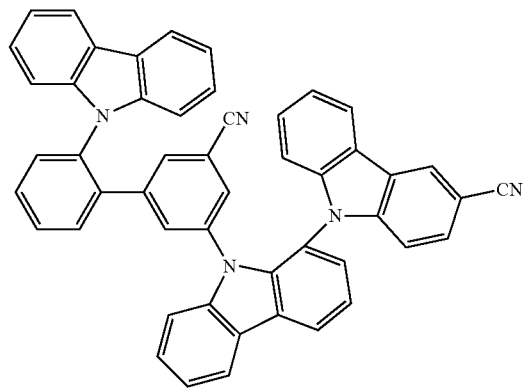
1157
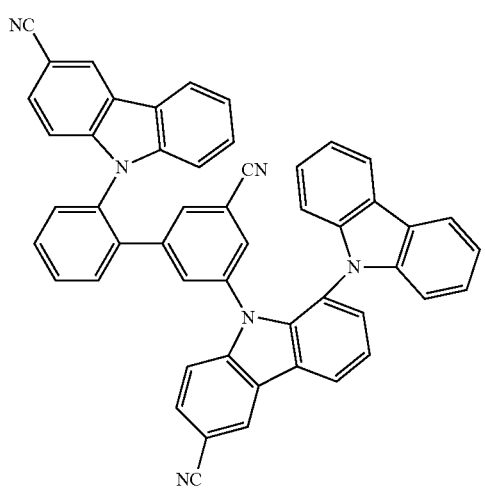
1158
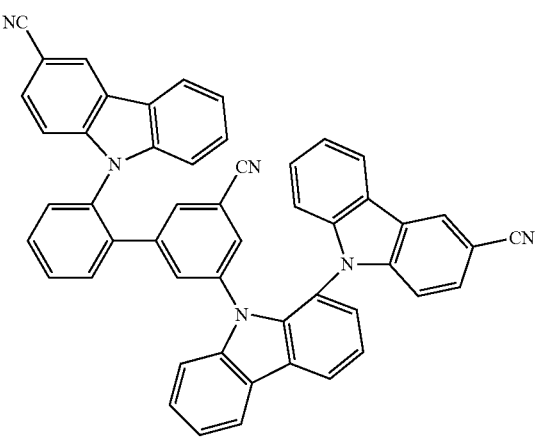

1159
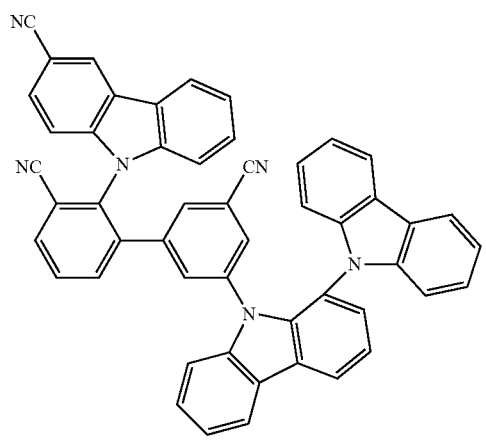
1160
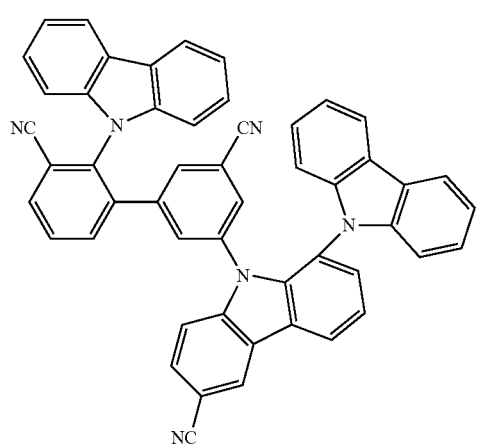
1161
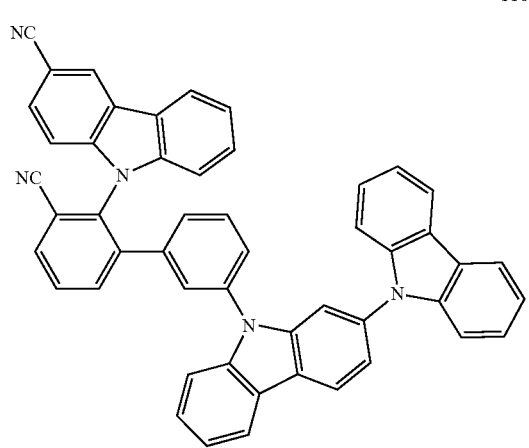
1162
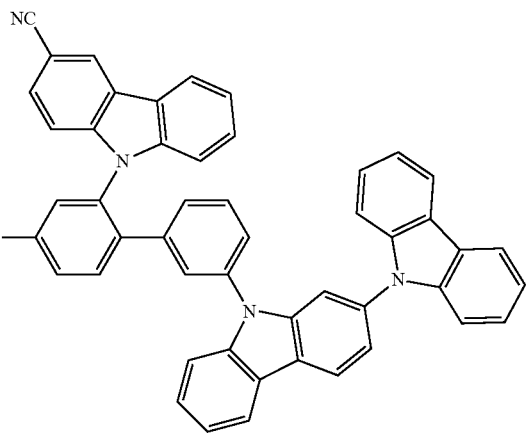
1163
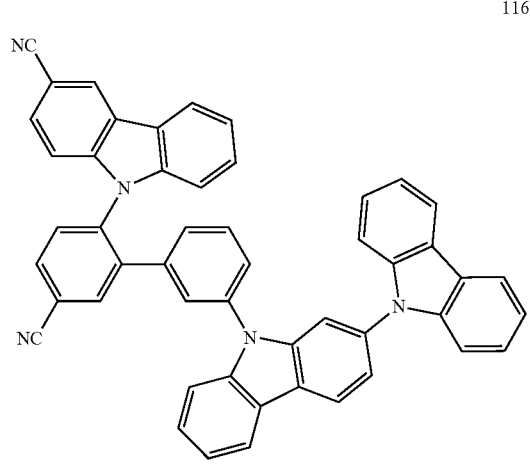
1164
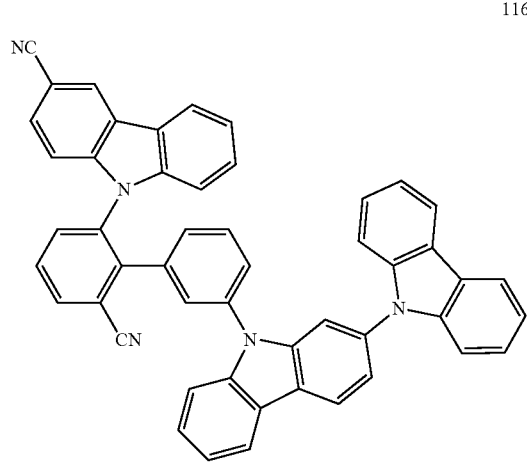

401
-continued
1165
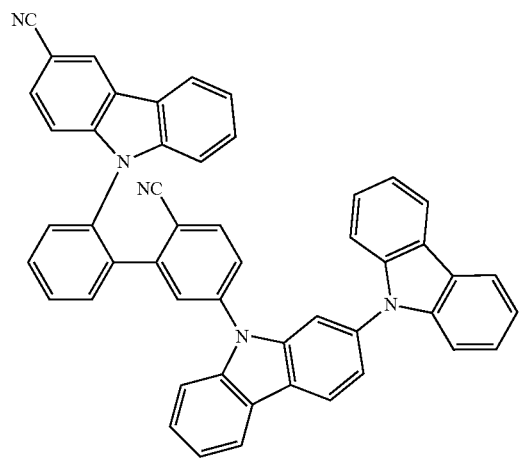
1166
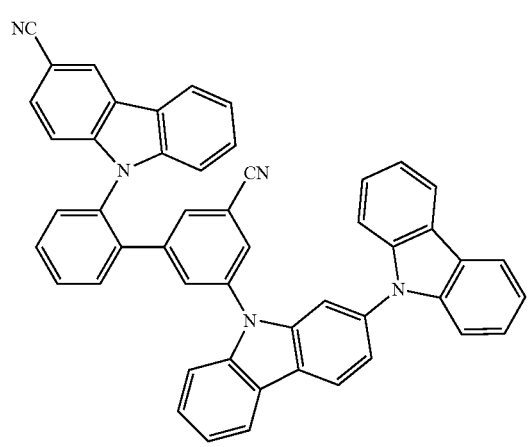
1167
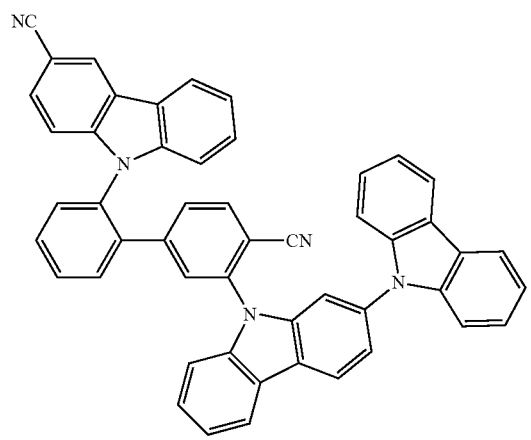
402
-continued
1168
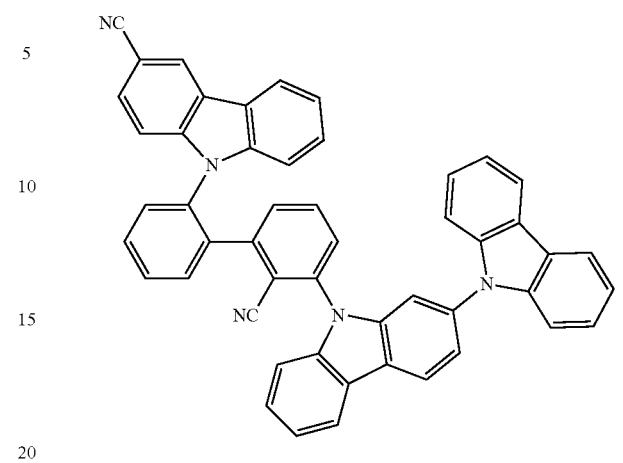
1169
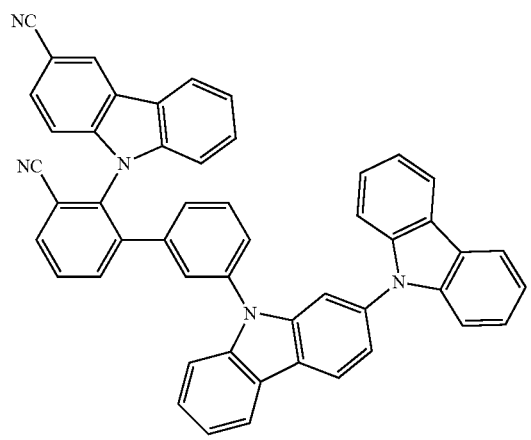
1170
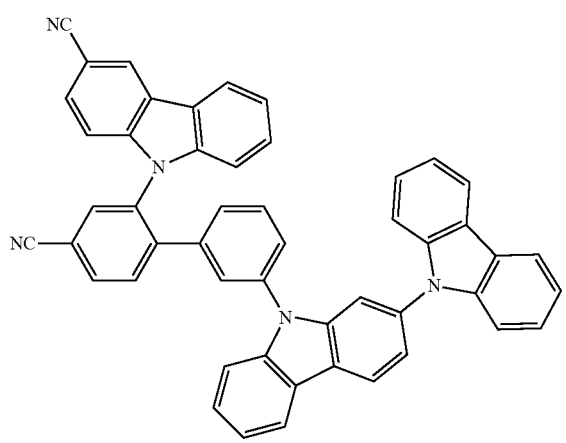

1171
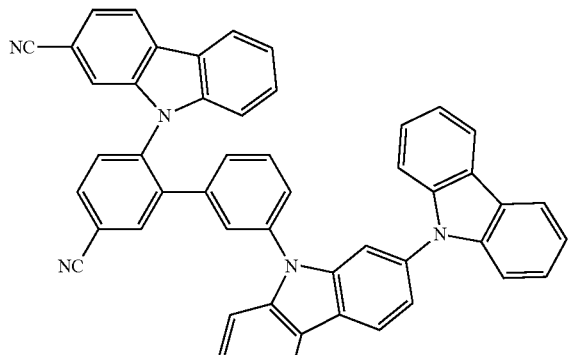
1172
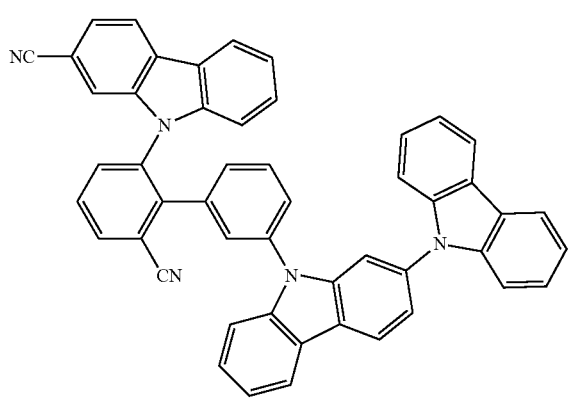
1173
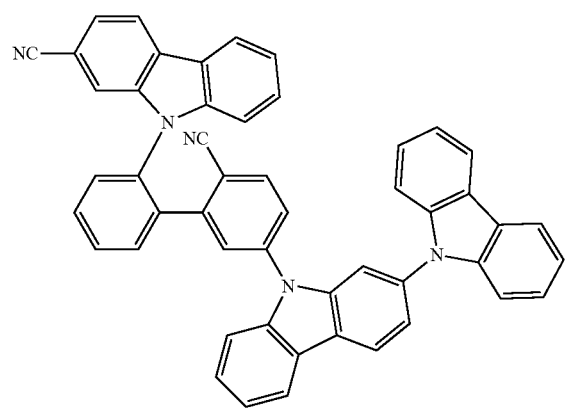
1174
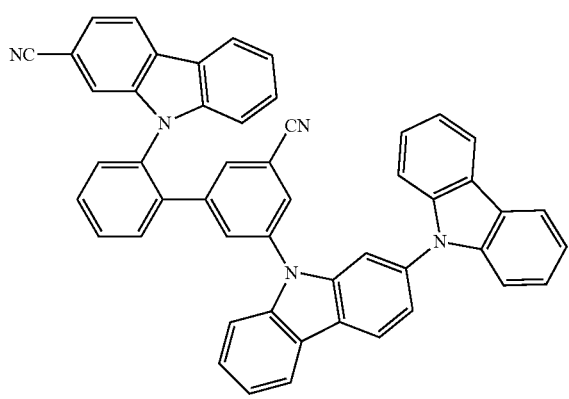
1175
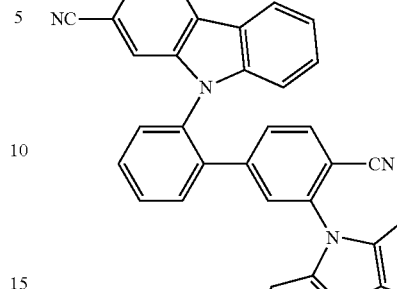
1176
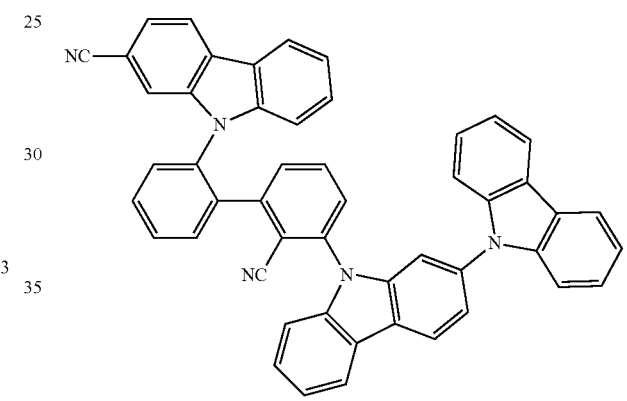
1177
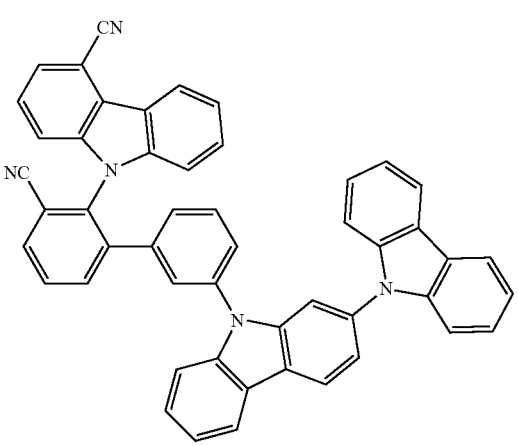

1178
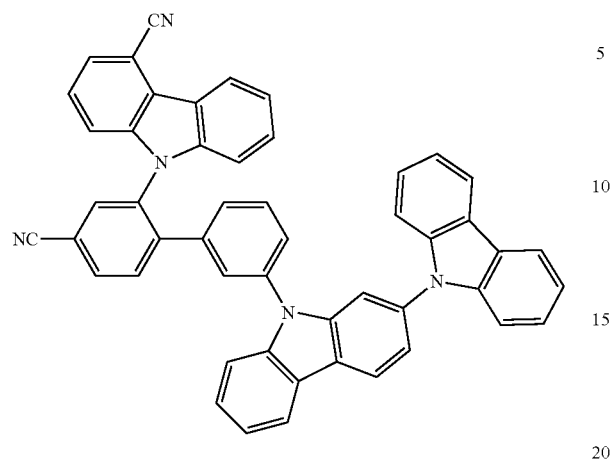
1179
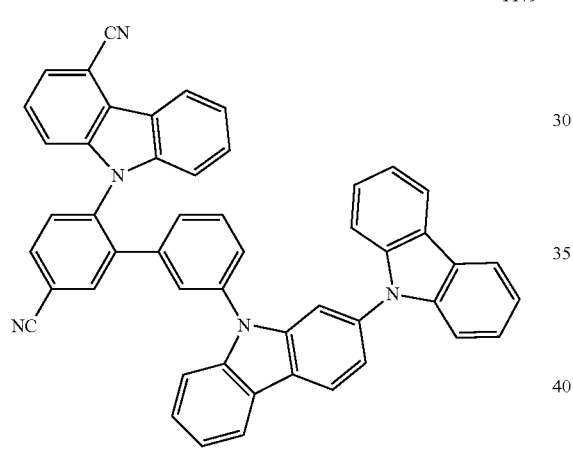
1180
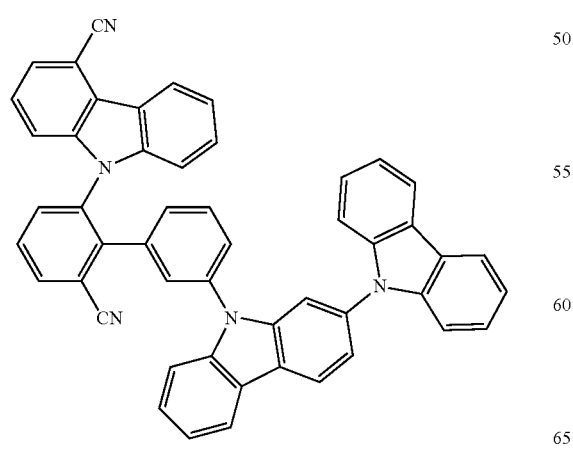
1181
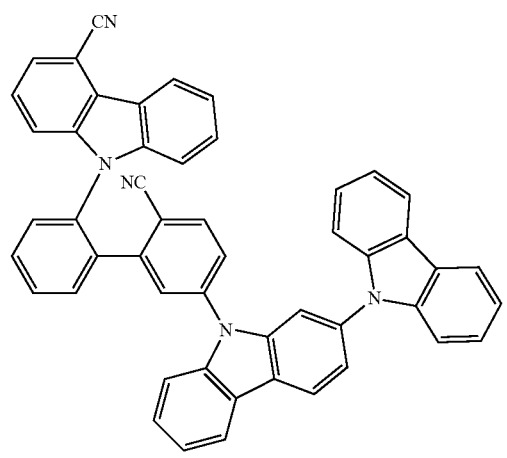
1182
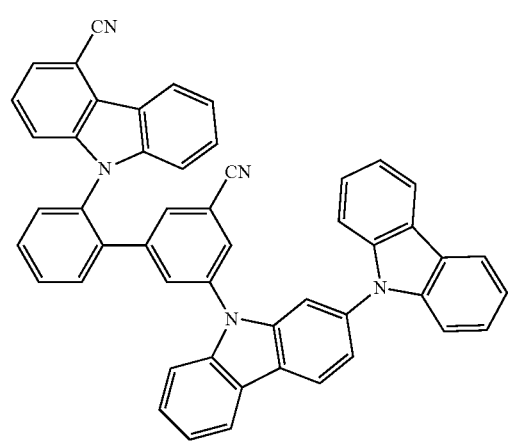
1183
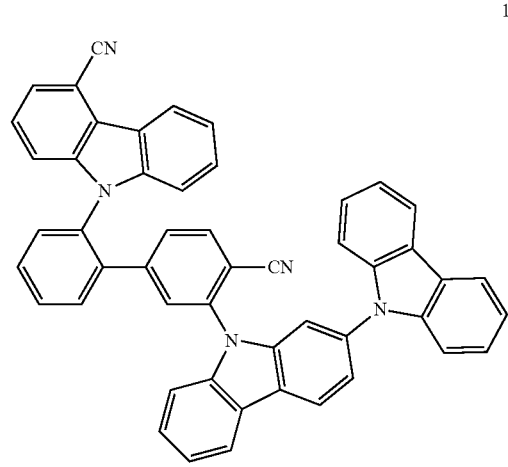

407
-continued
1184
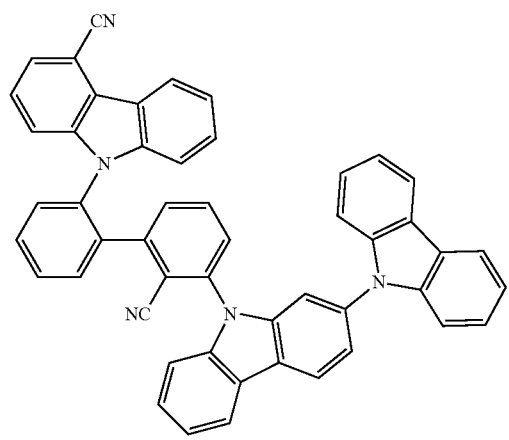
1185
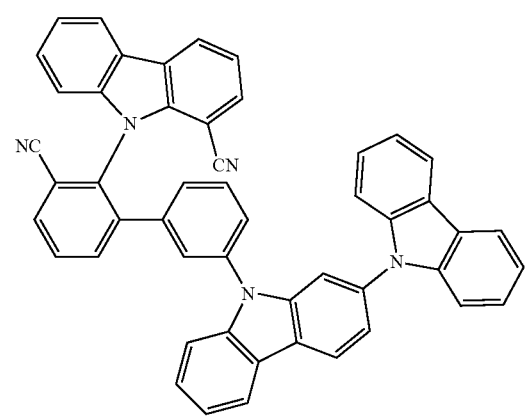
1186
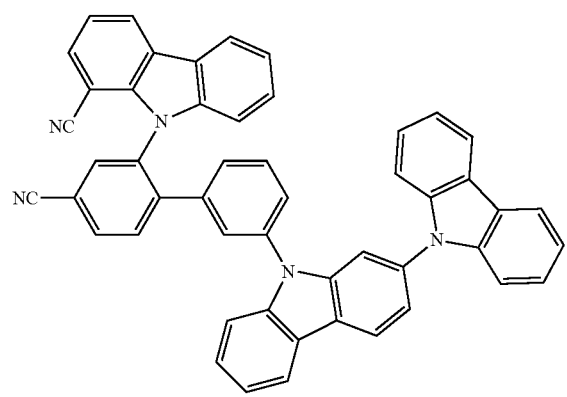
408
-continued
1187
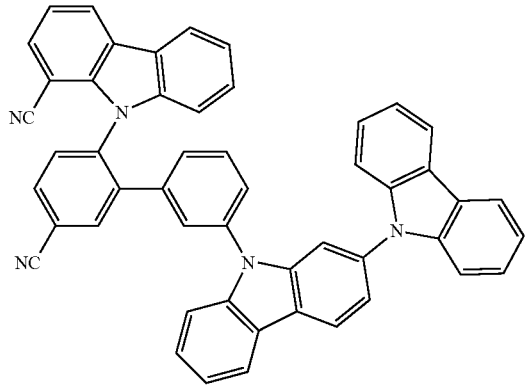
1188
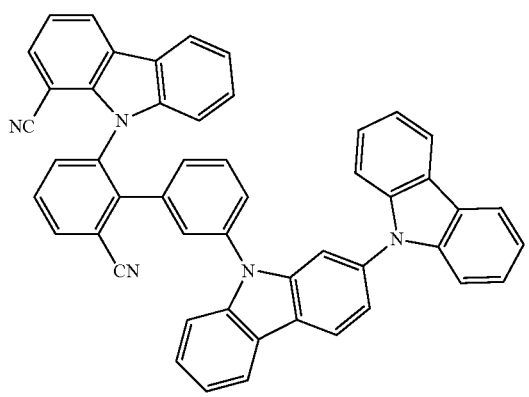
1189
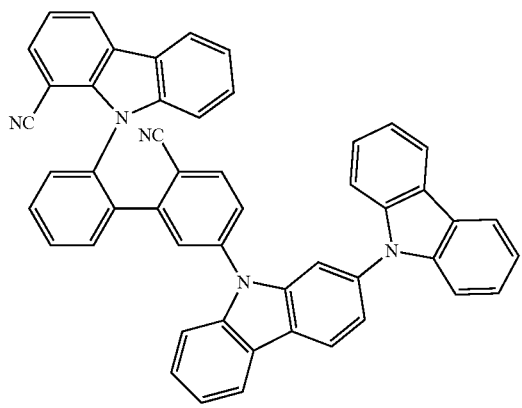
1190
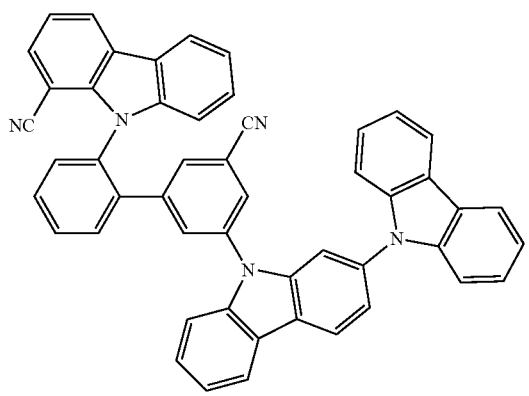

-continued
1191
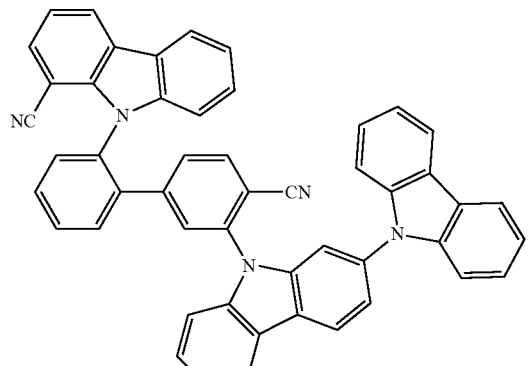
1192
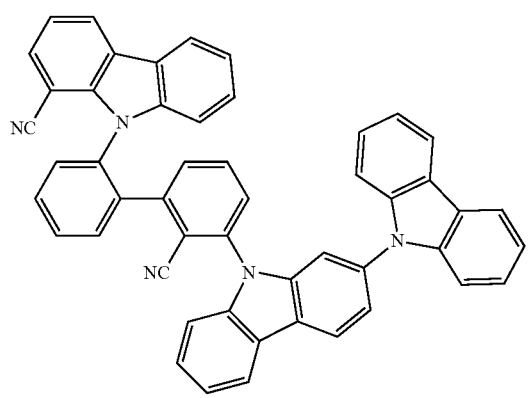
1193
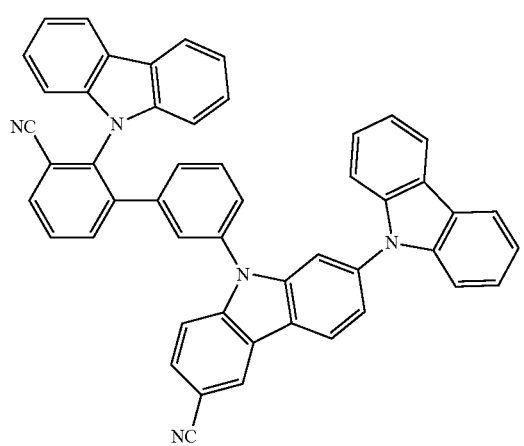
-continued
1194
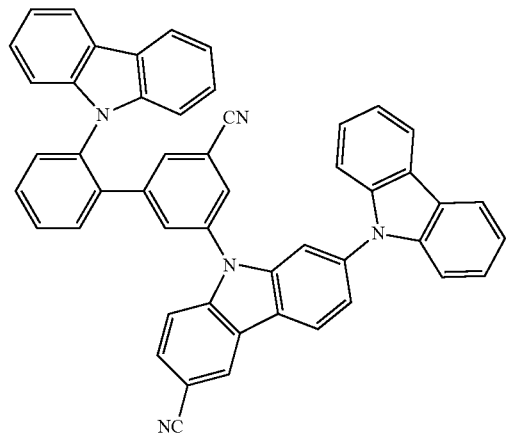
1195
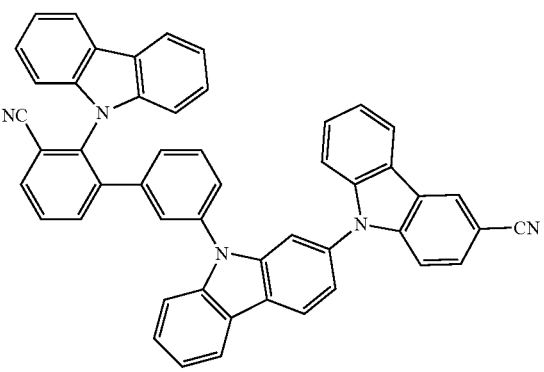
1196
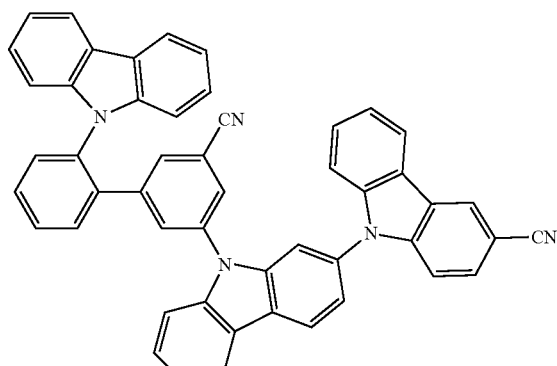

411
-continued
1197
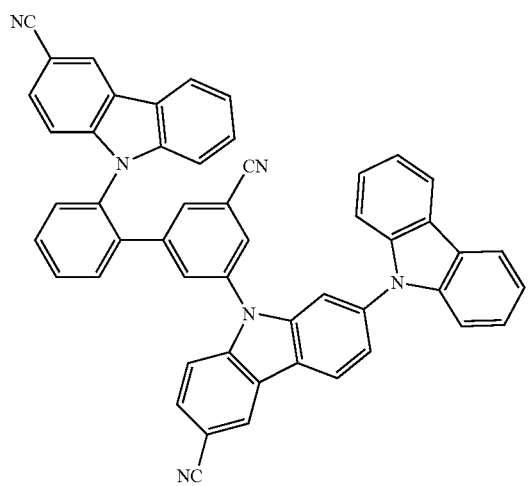
1198
412
-continued
1200
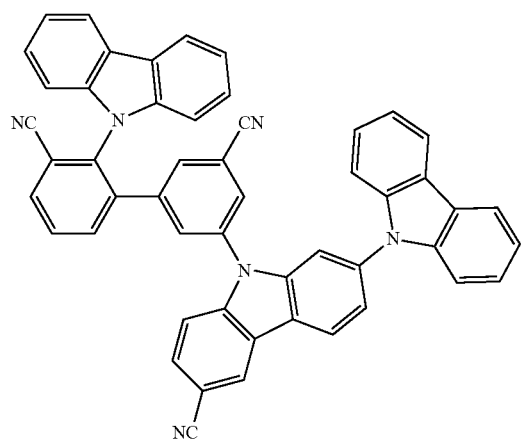
1201
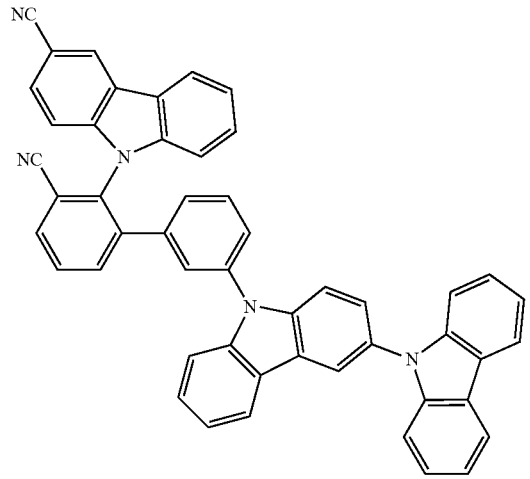
1199
1202
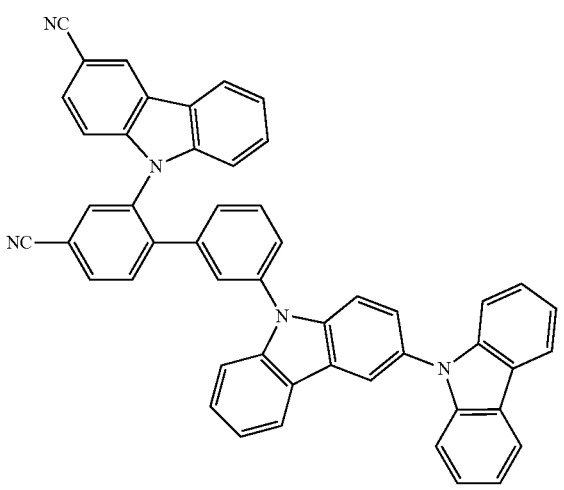

1203
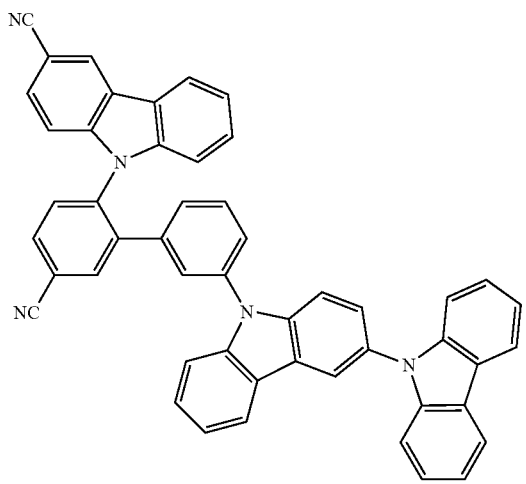
1204
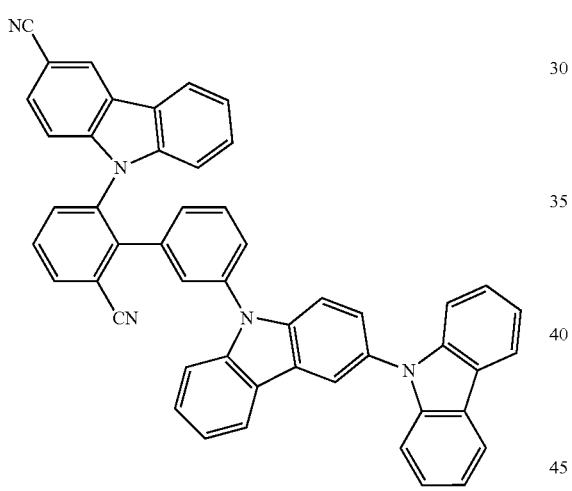
1205
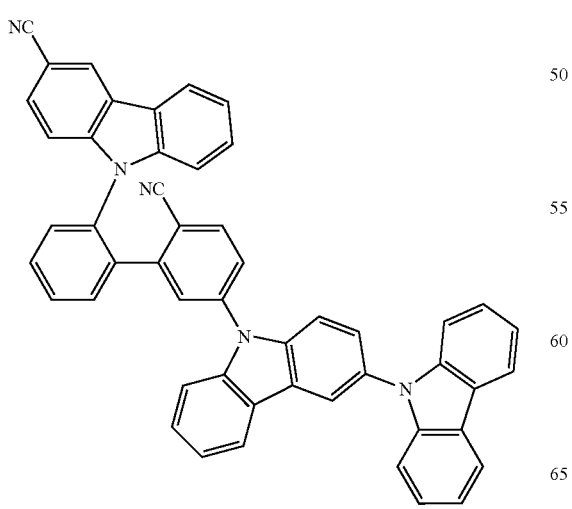
1206
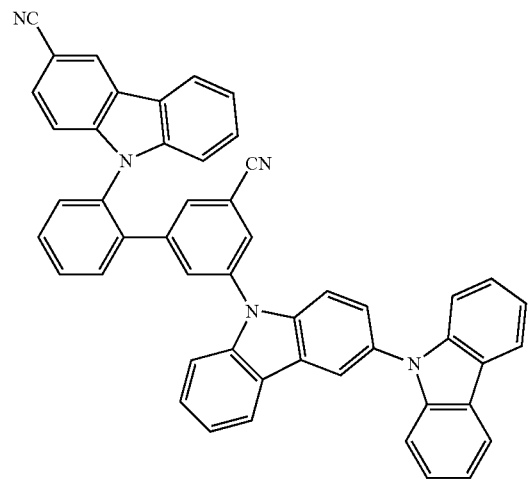
1207
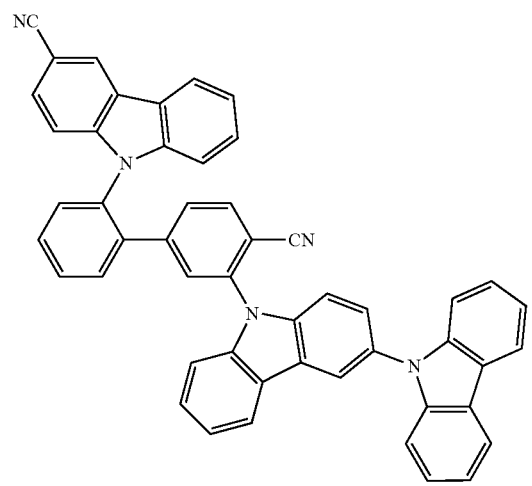
1208
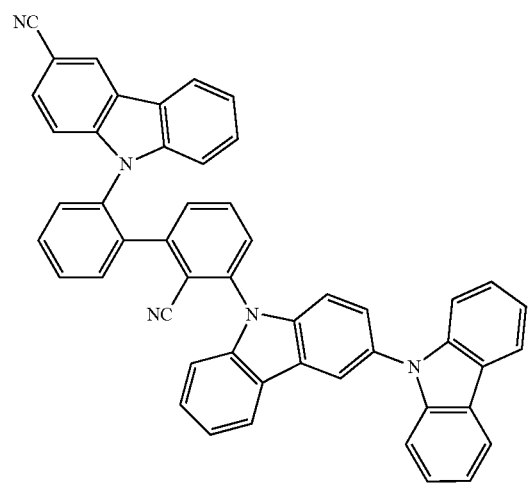

415
-continued
1209
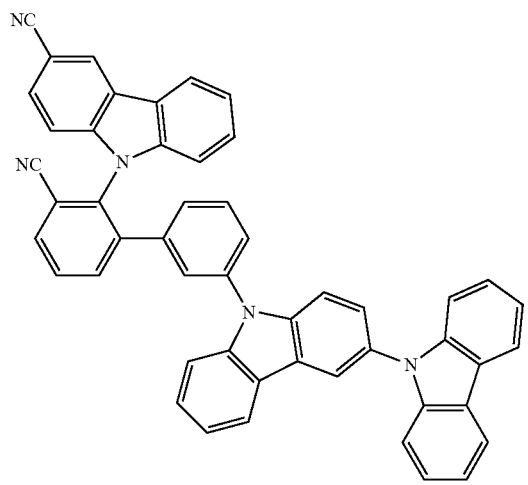
1210
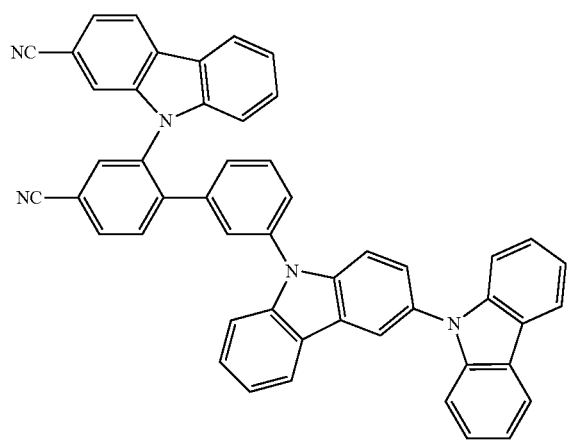
1211
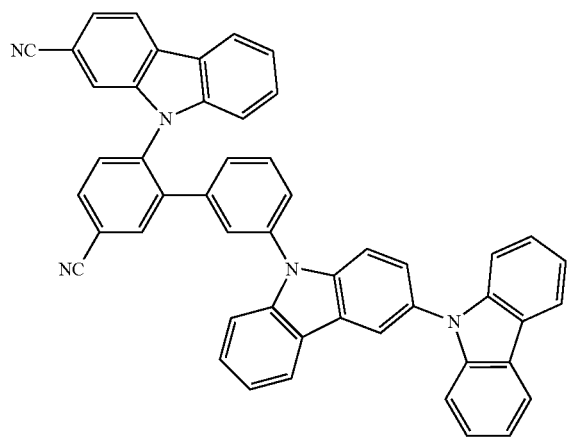
416
-continued
1212
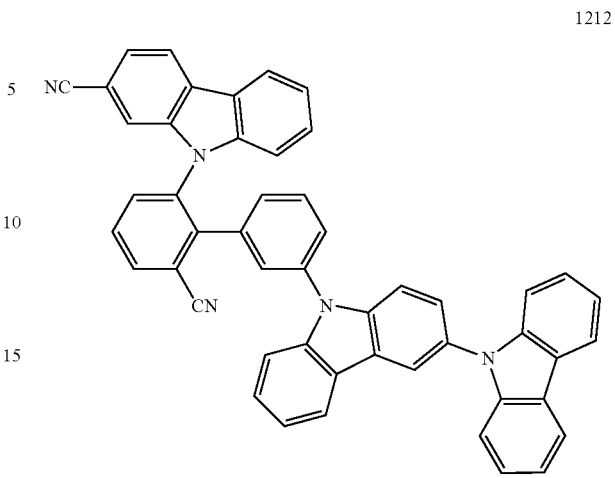
1213
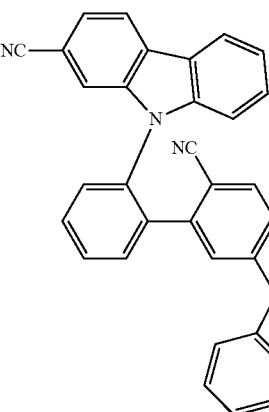
1214
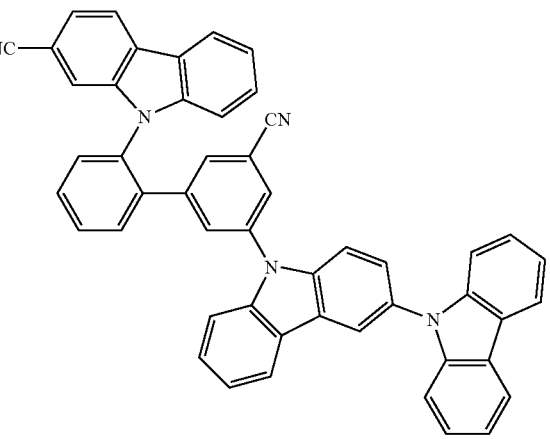

-continued
1215
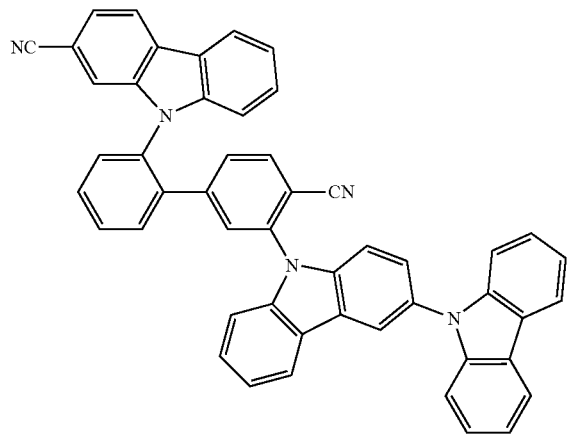
1216
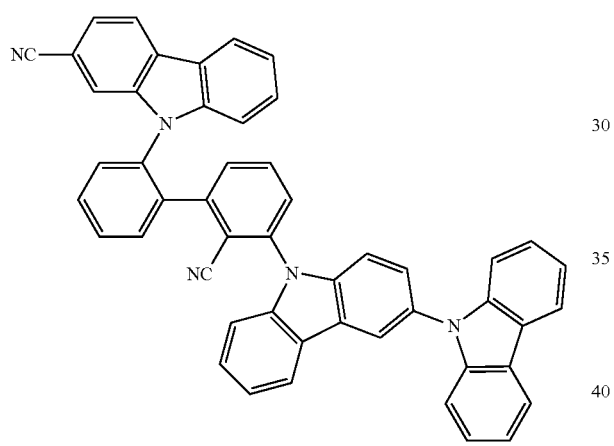
1217
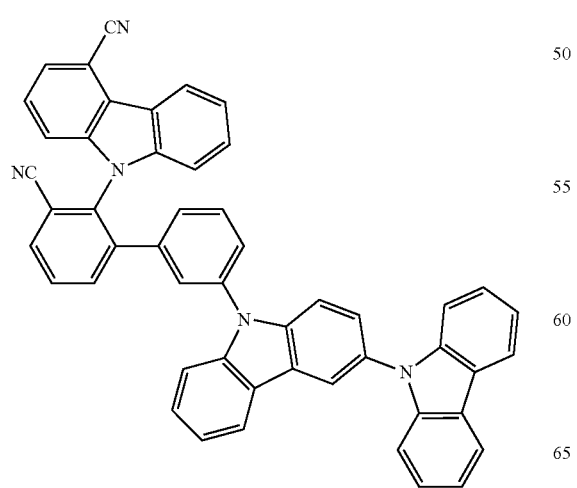
-continued
1218
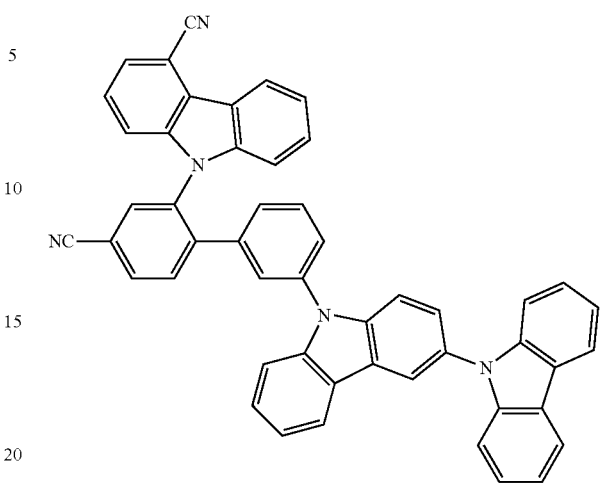
1219
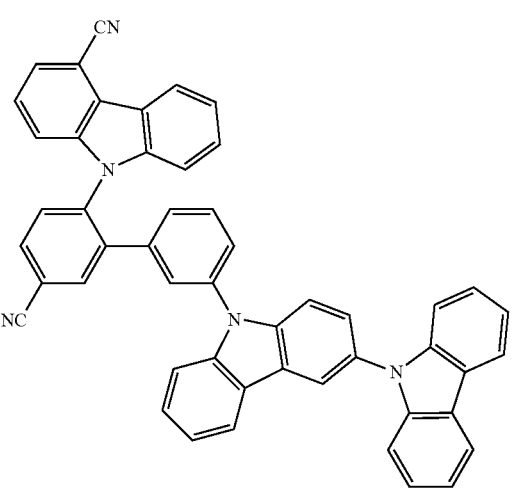
1220
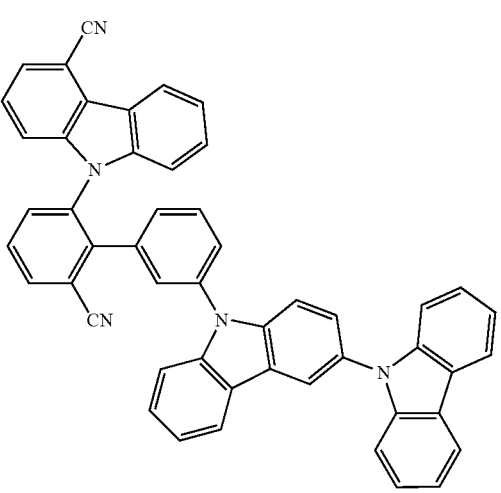

1221
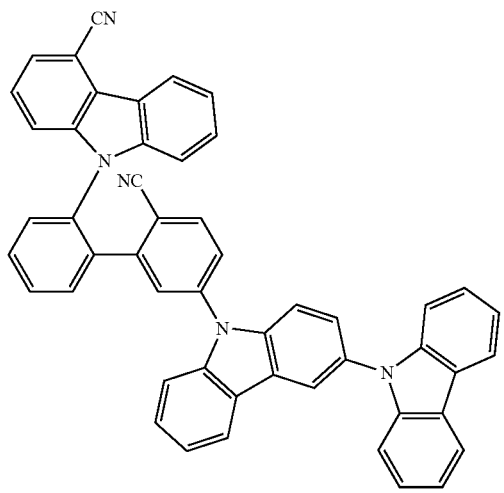
1222
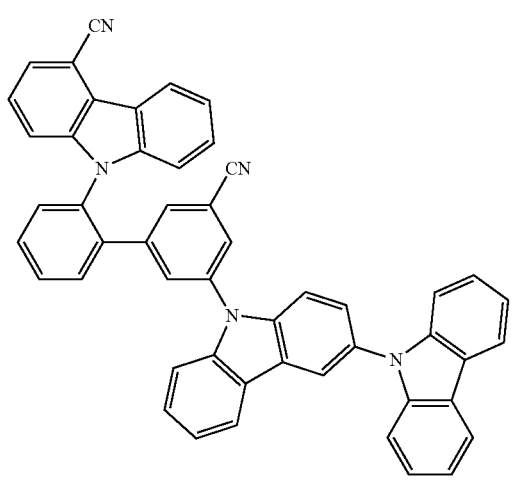
1223
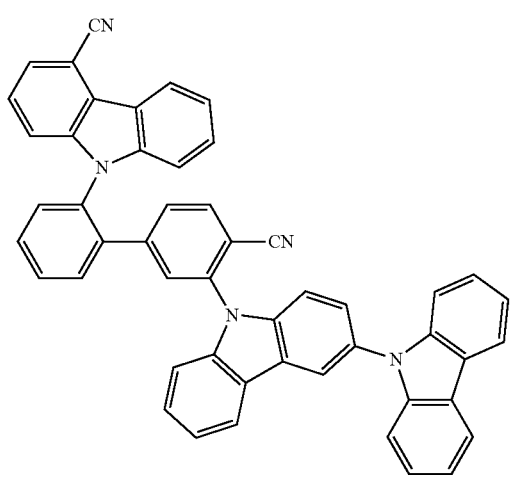
-continued
1224
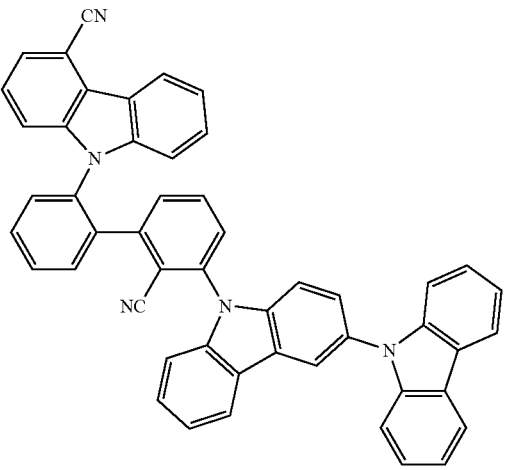
1225
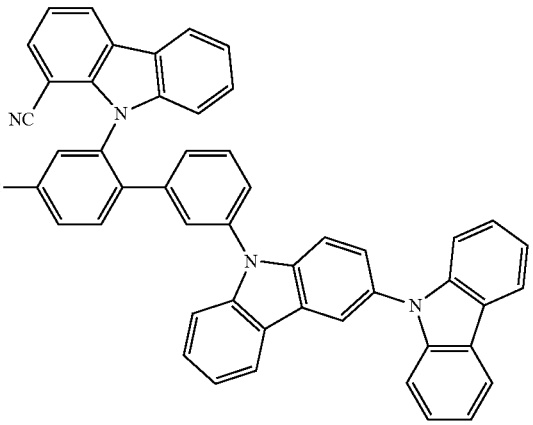
1226

-continued
1227
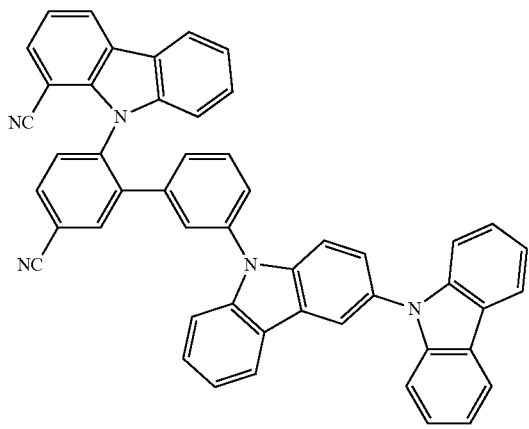
1228
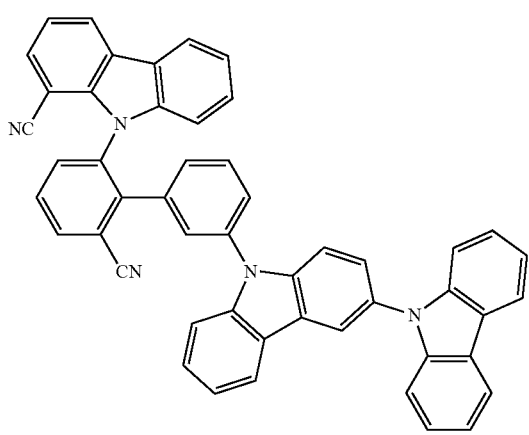
1229
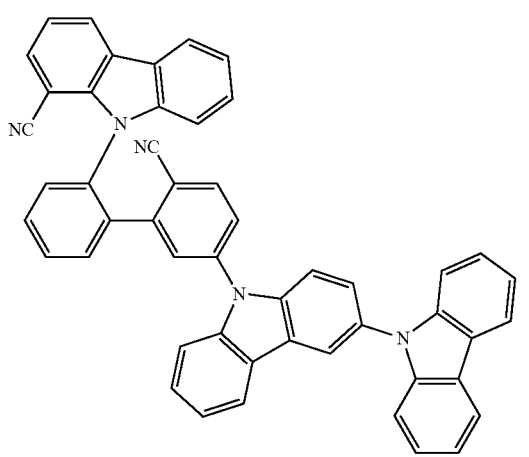
-continued
1230
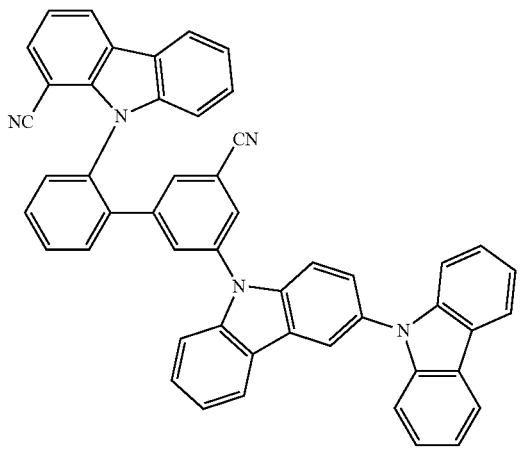
1231
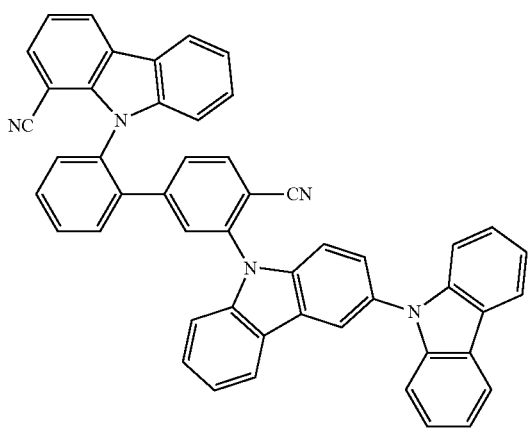
1232
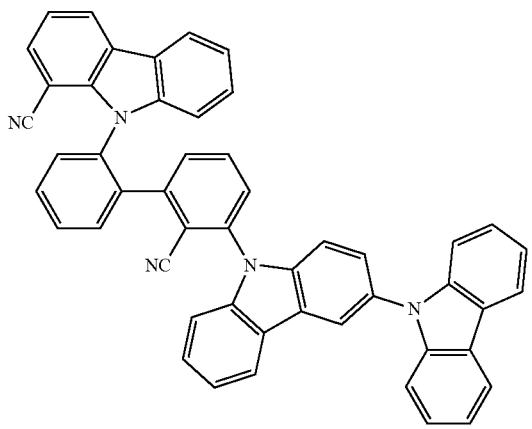

1233
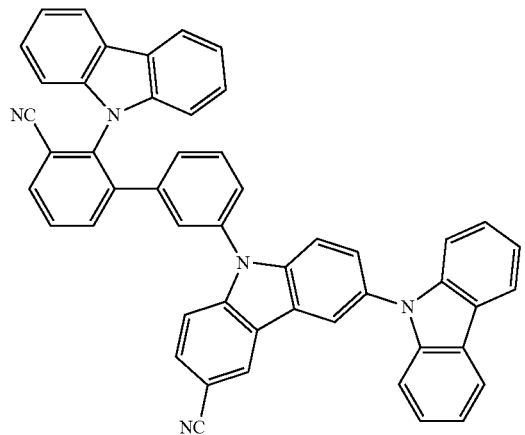
1234
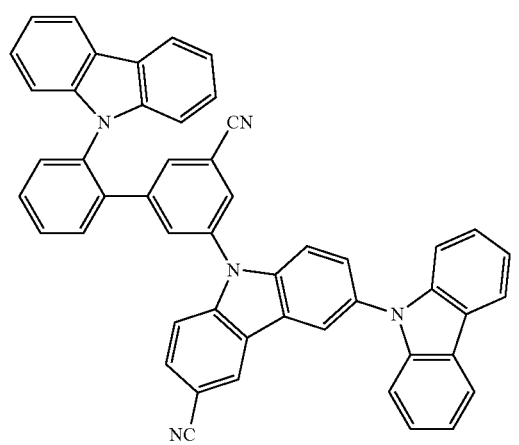
1235
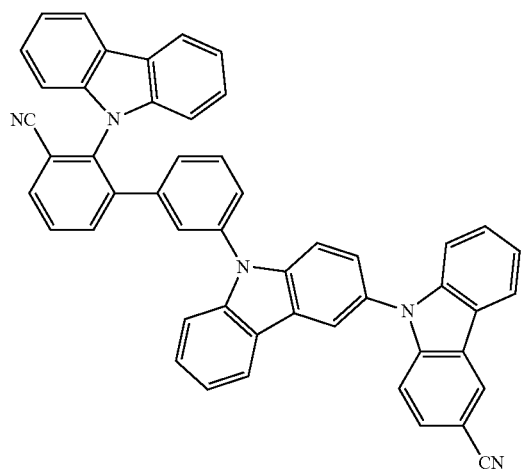
1236
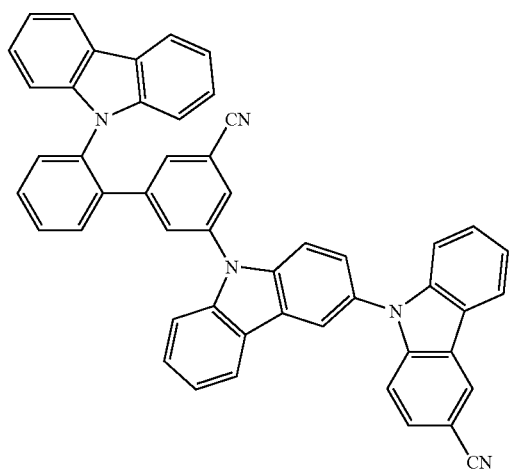
1237
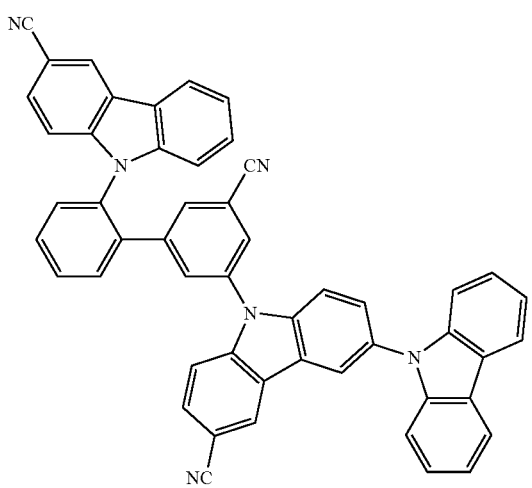
1238
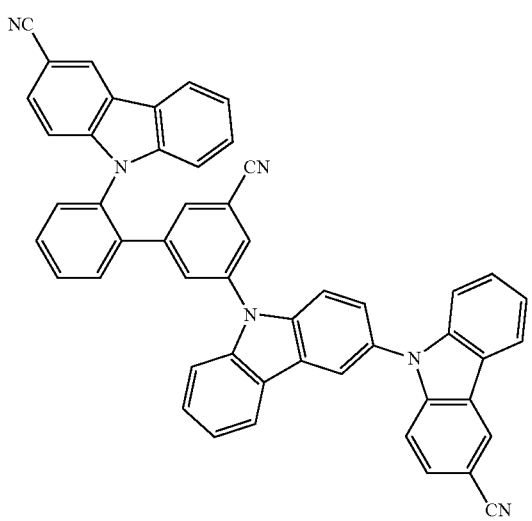

-continued
1239
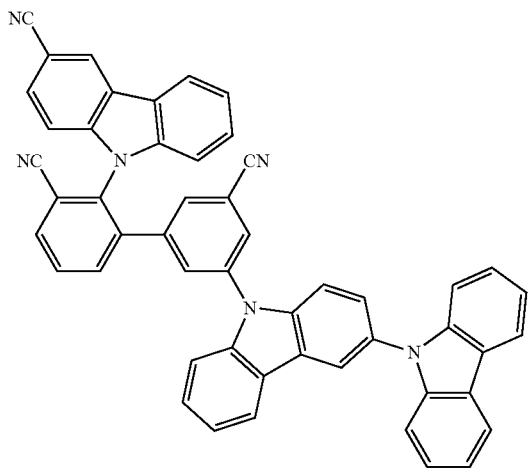
1240
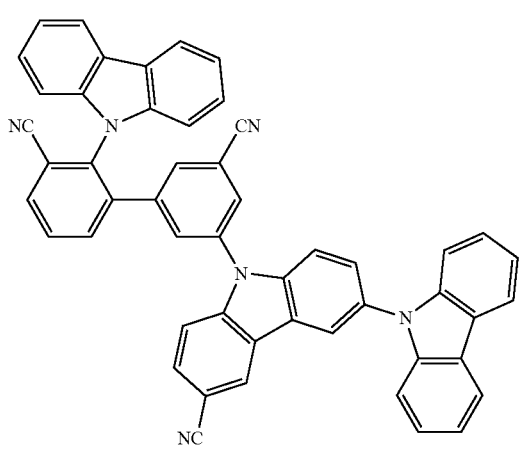
1241
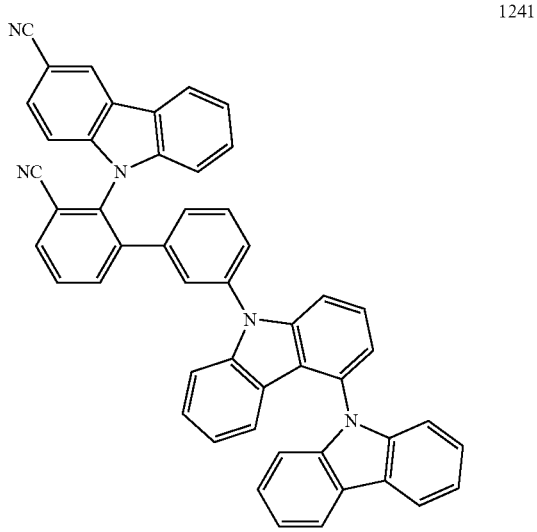
-continued
1242
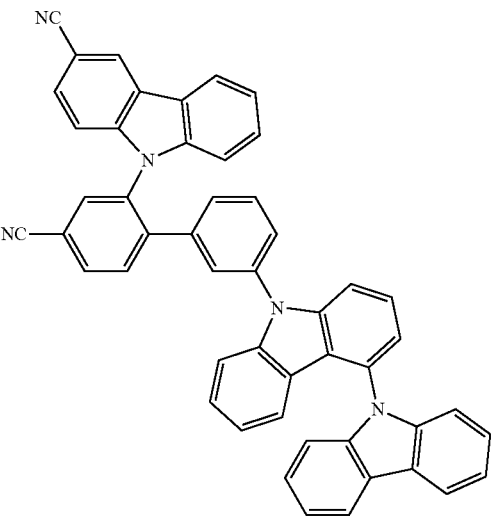
1243
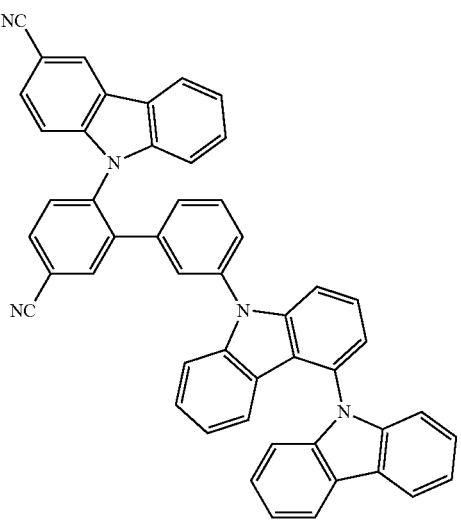
1244
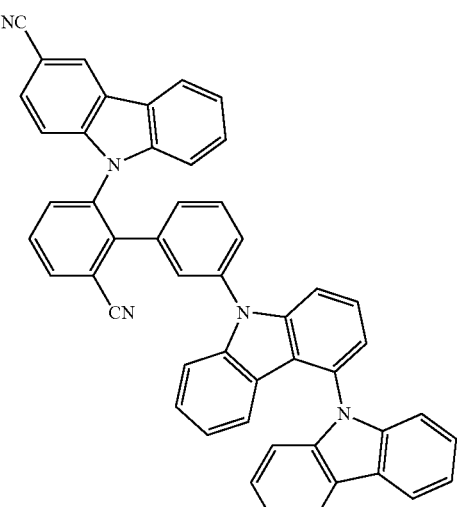

1245
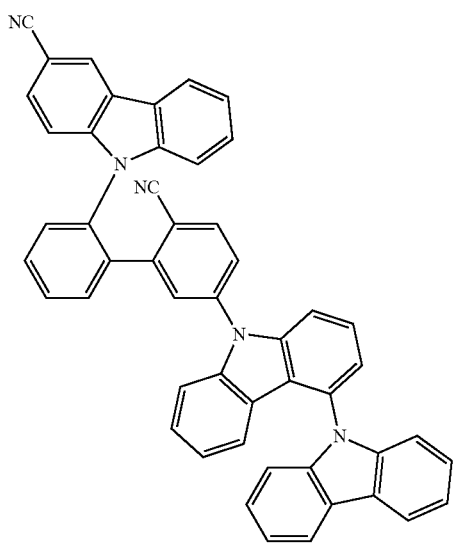
1246
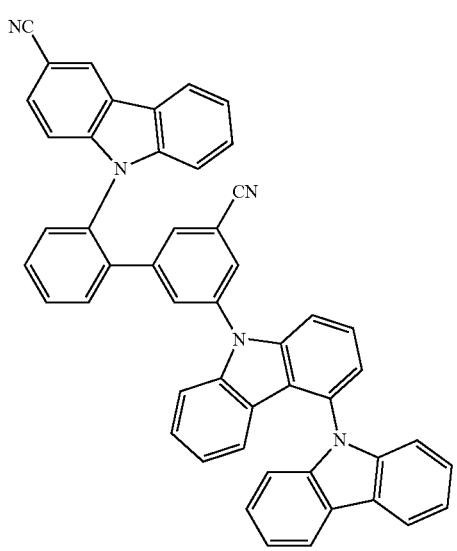
1247
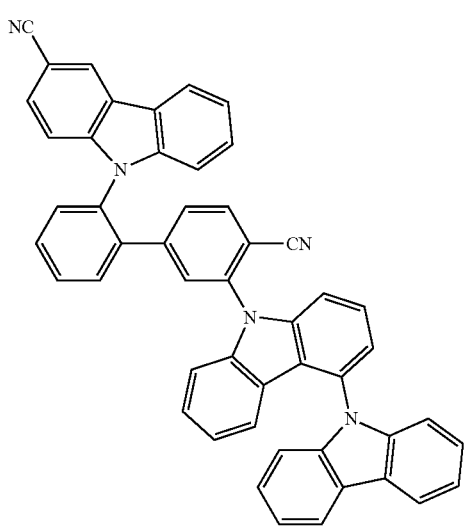
1248
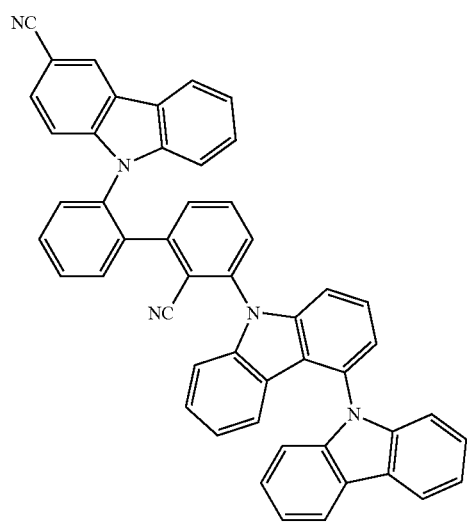
1249
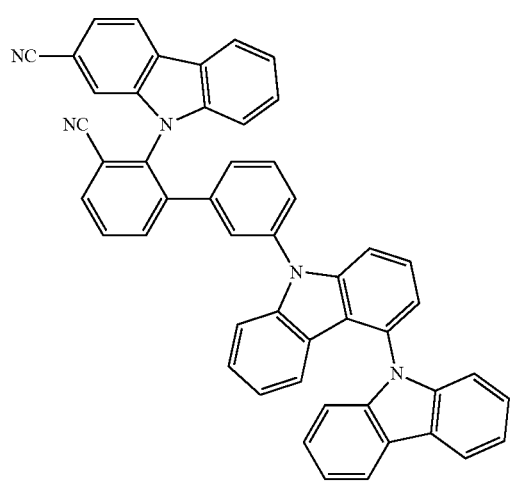
1250
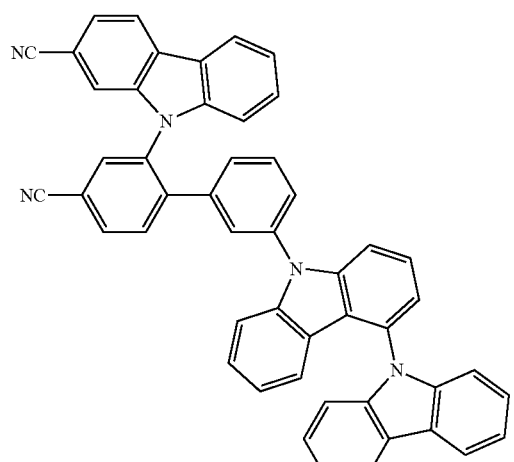

-continued
1251
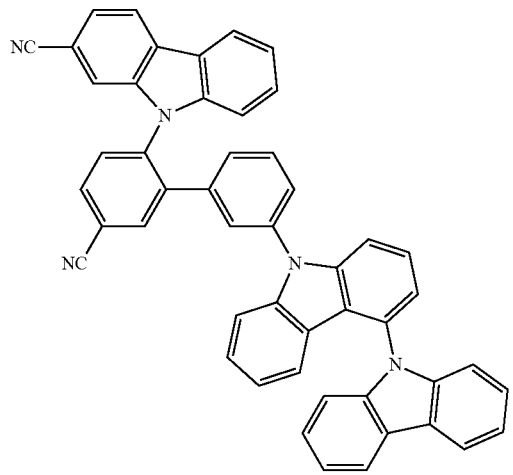
1252
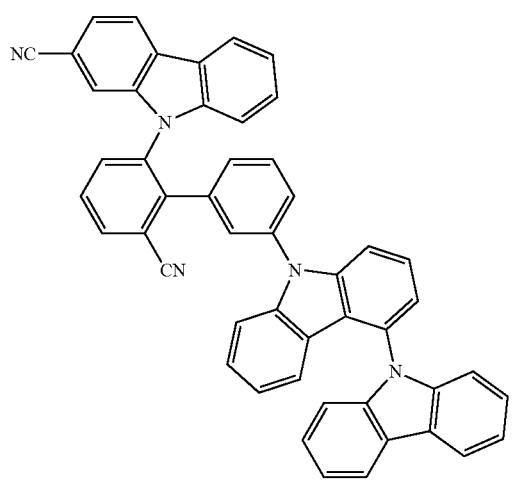
1253
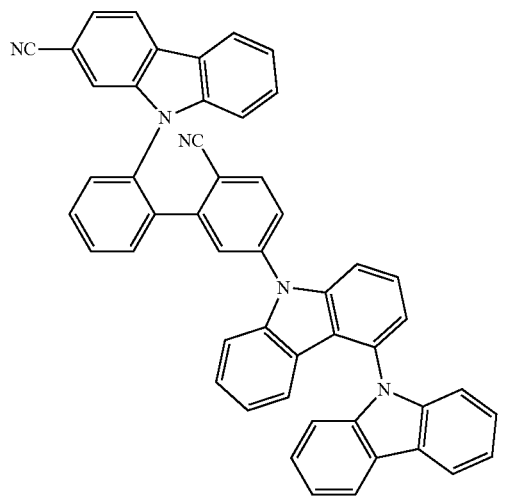
1254
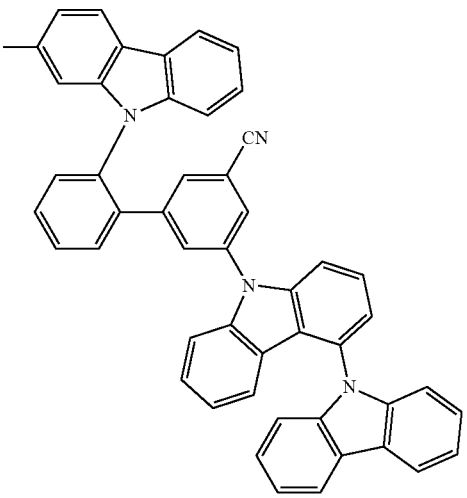
1255
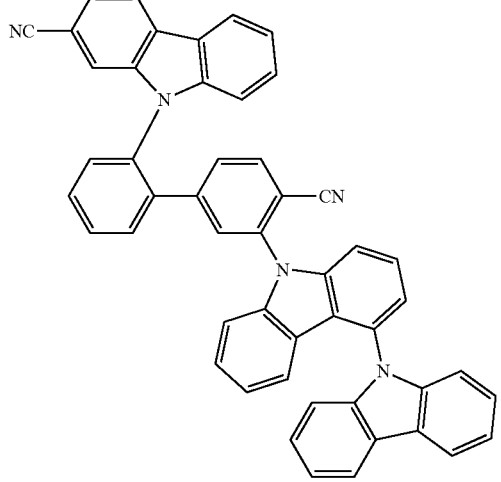
1256
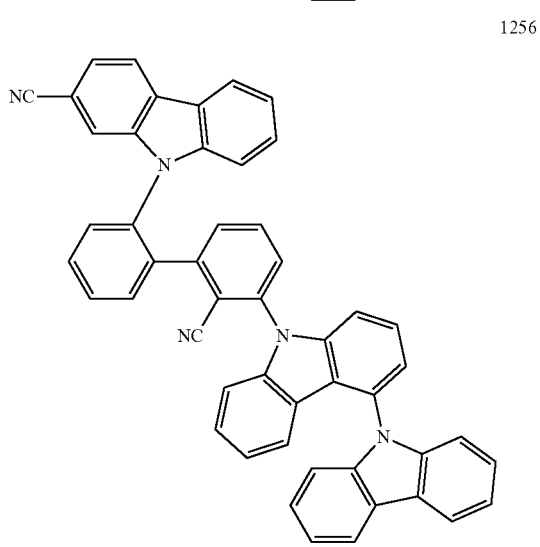

431
-continued
432
-continued
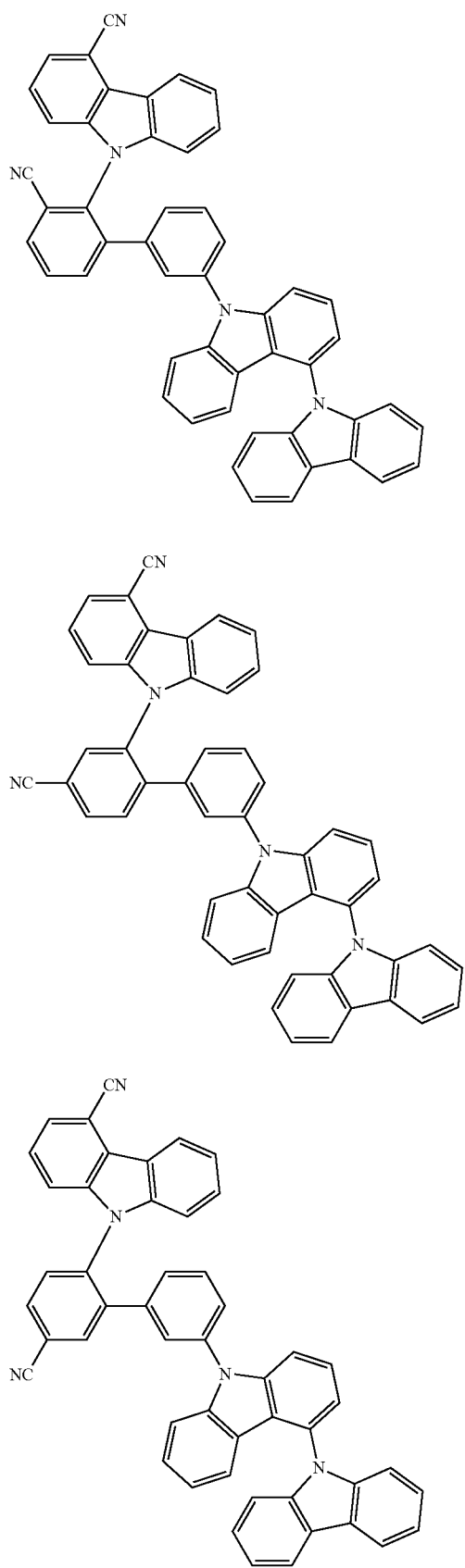
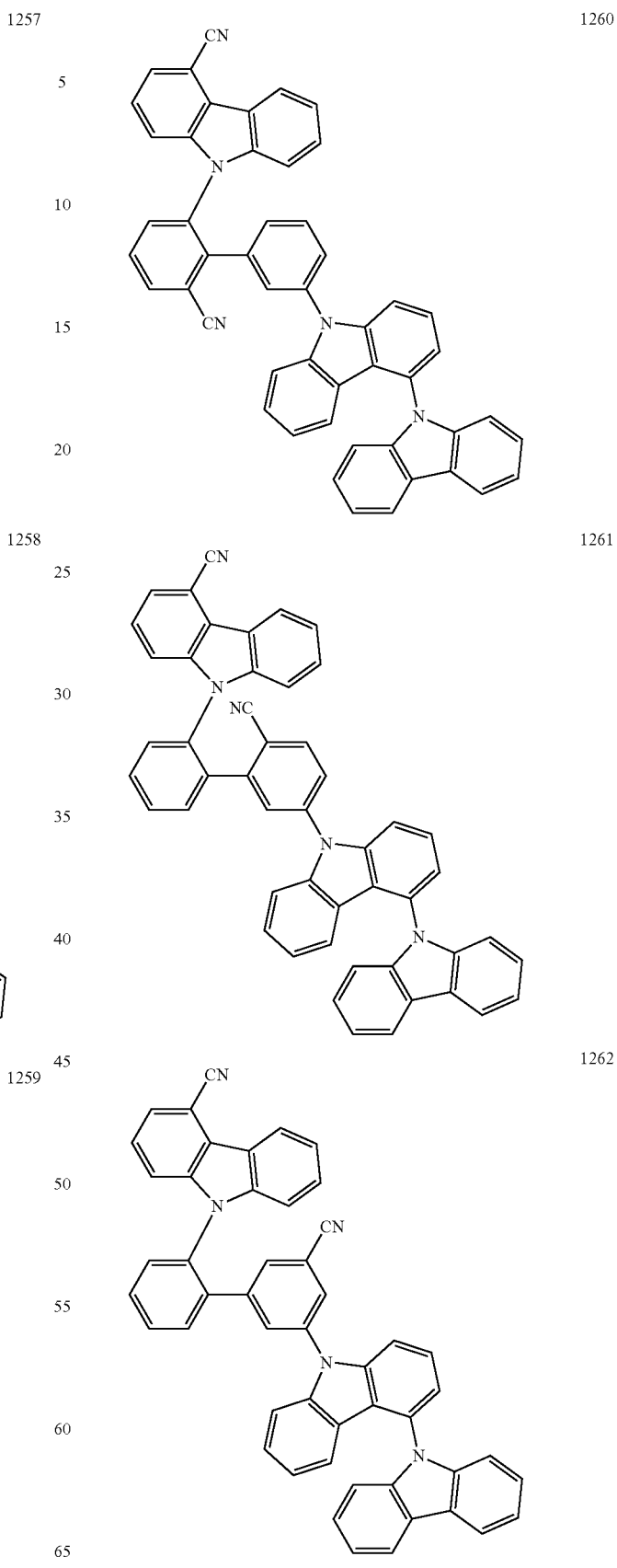

1263
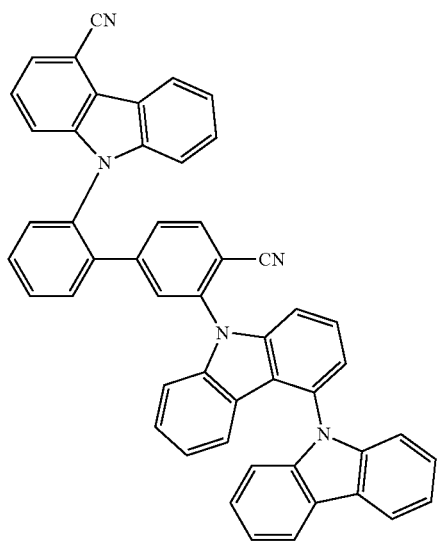
1264
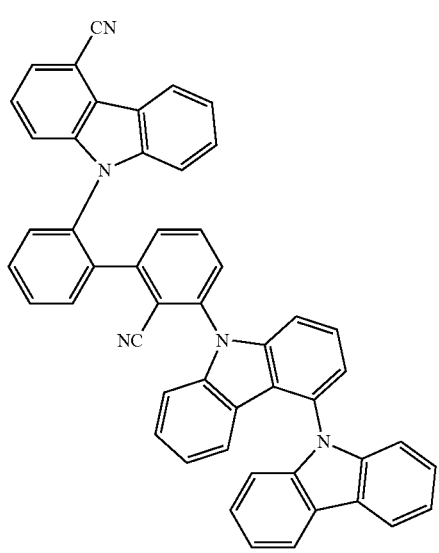
1265
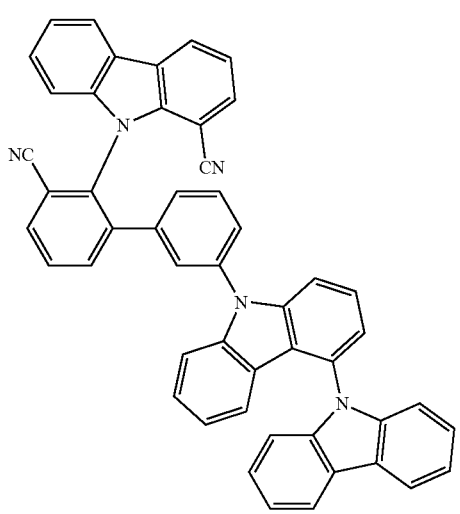
1266
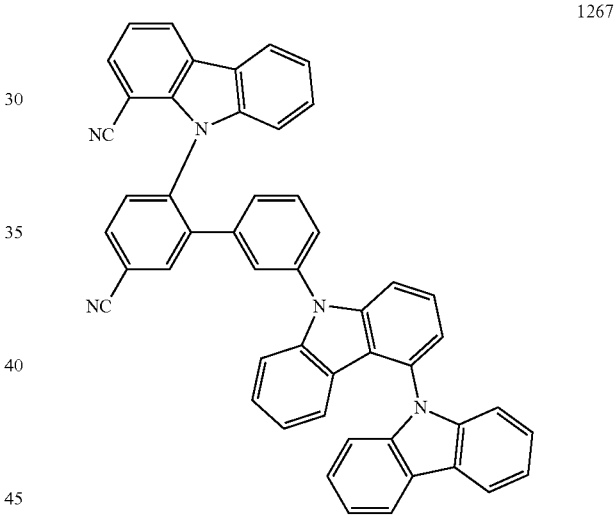
1267
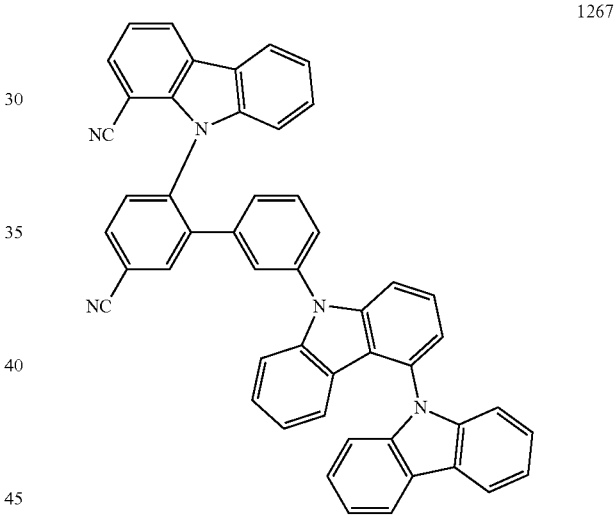
1268
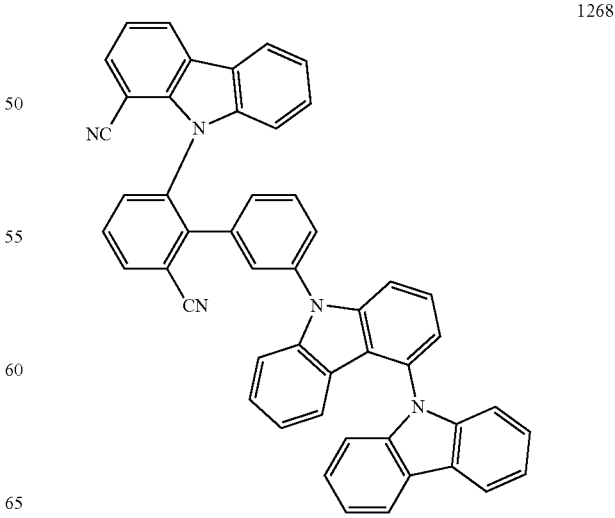

1269 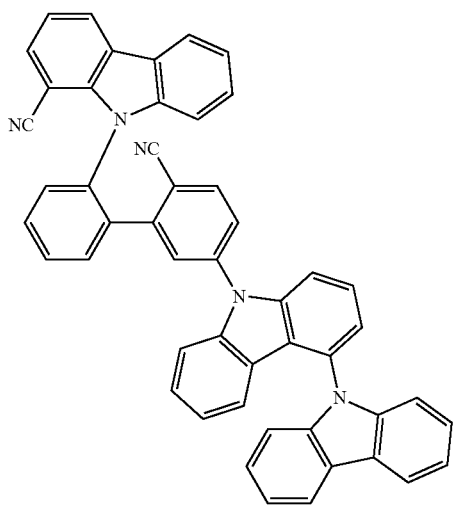
1270 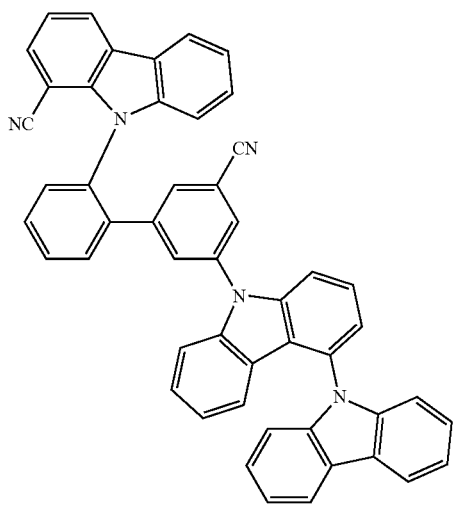
1271 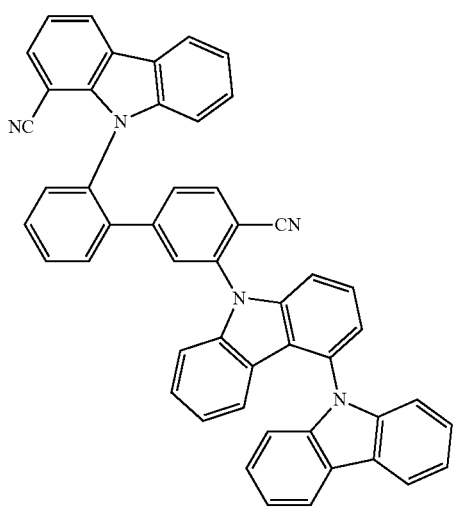
1272 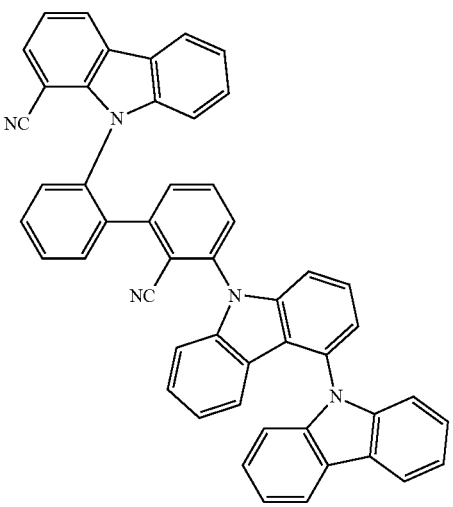
1273 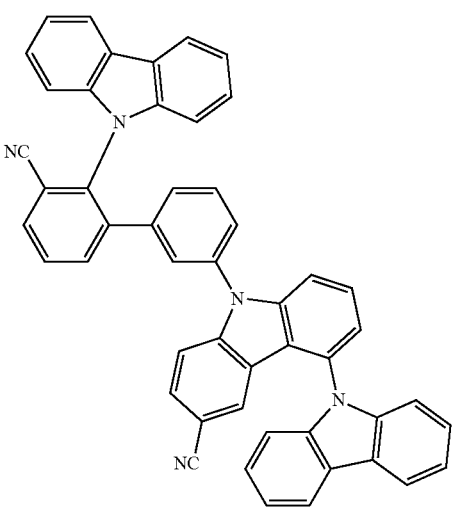
1274 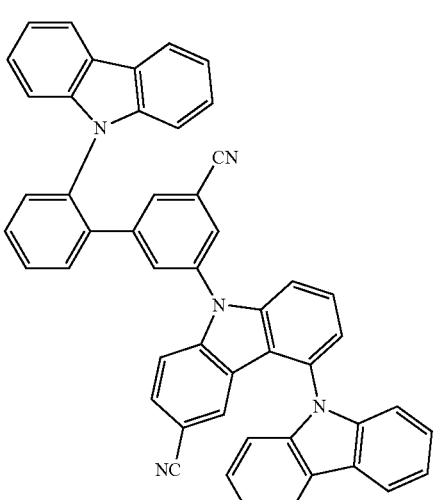

1275
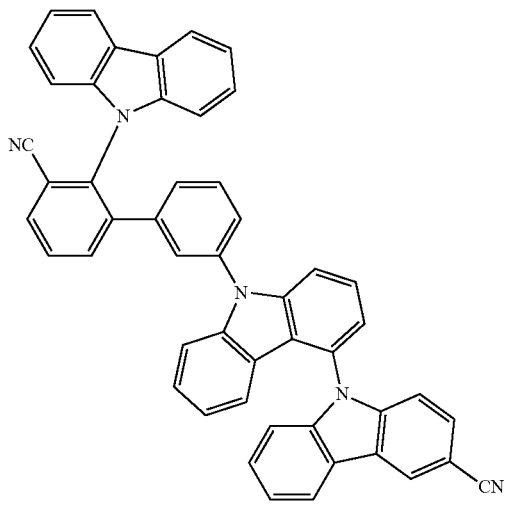
1276
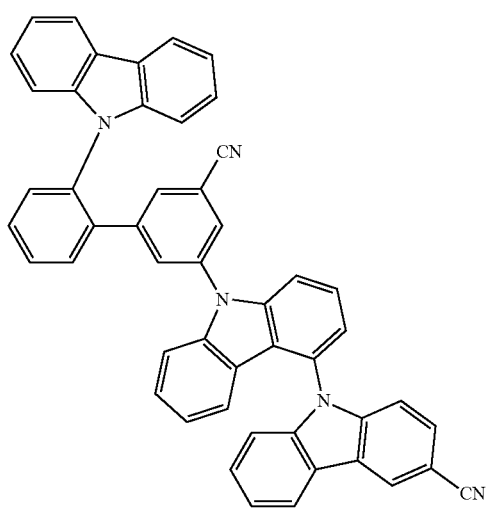
1277
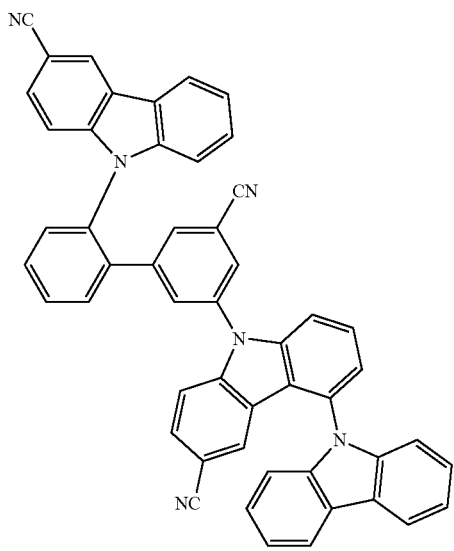
1278
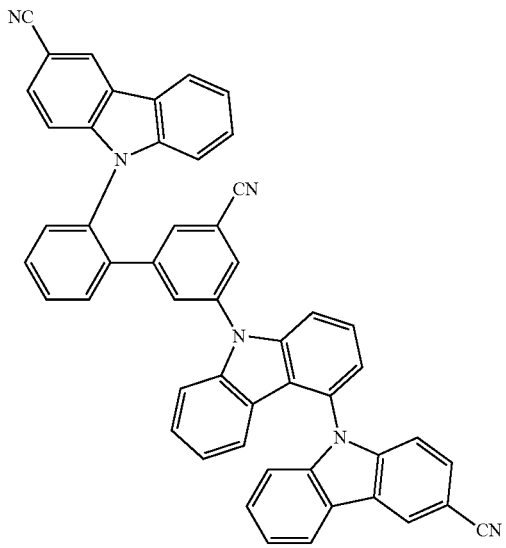
1279
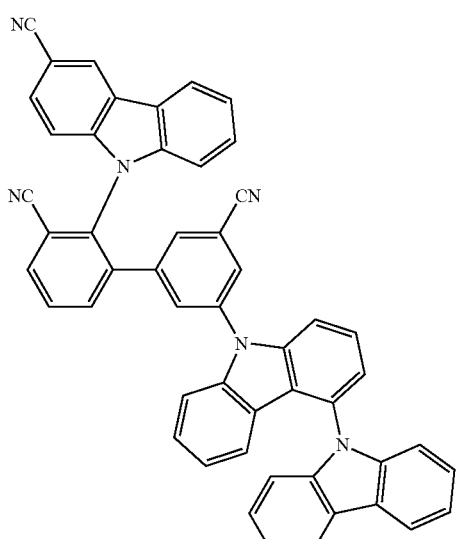
1280
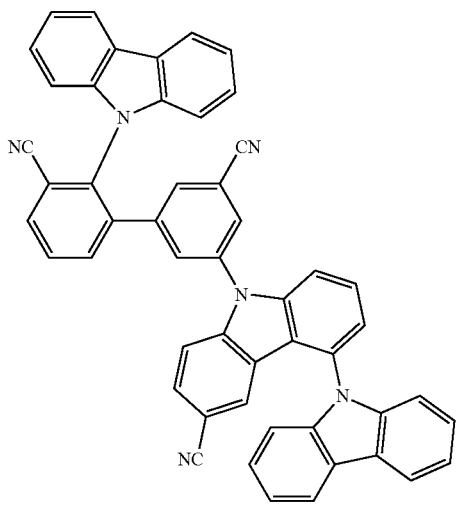

-continued
1281
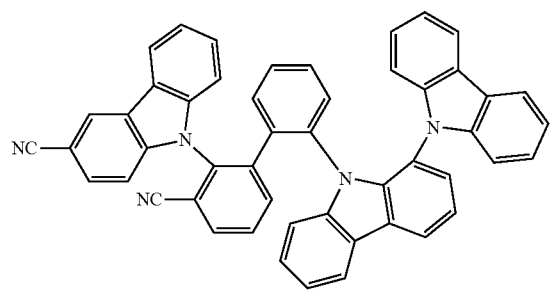
1282
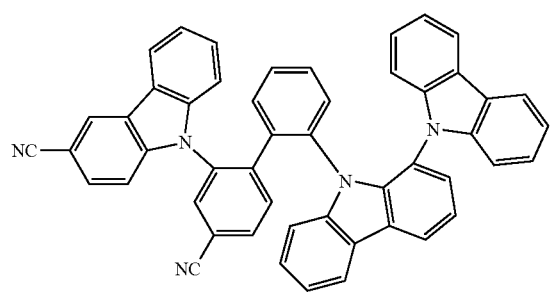
1283
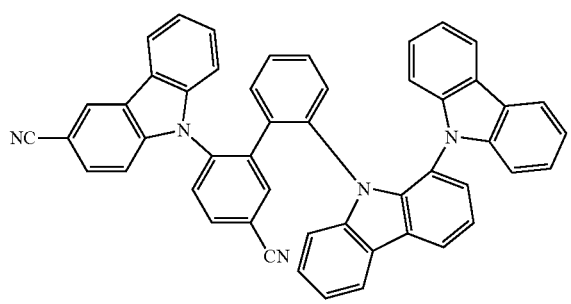
1284
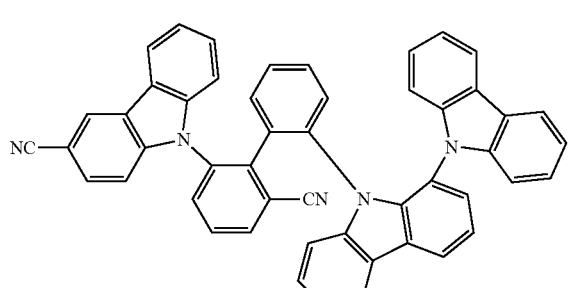
1285
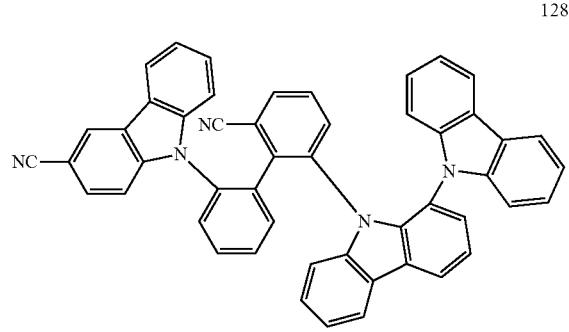
-continued
1286
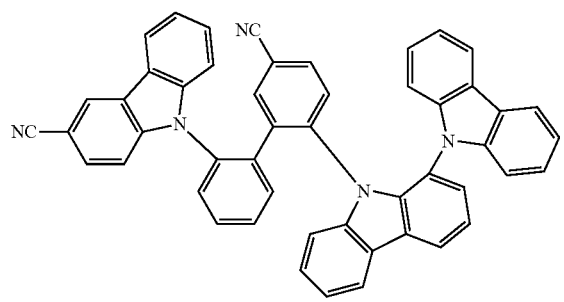
1287
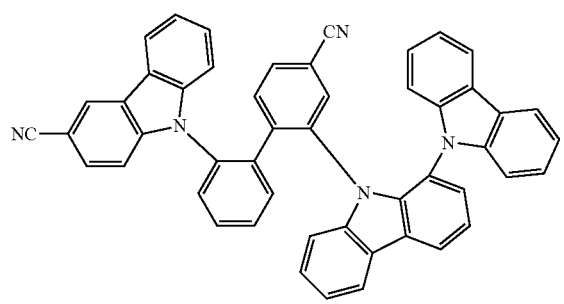
1288
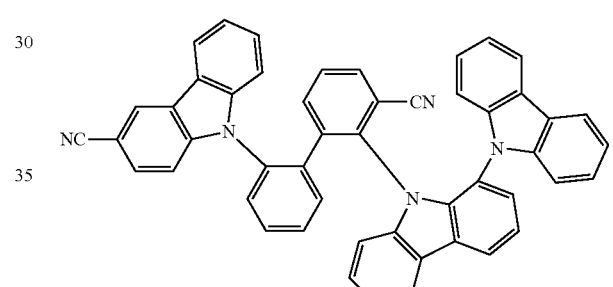
1289
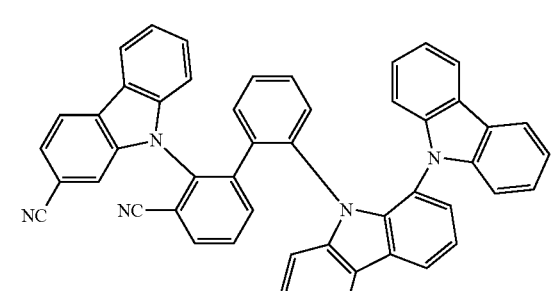
1290
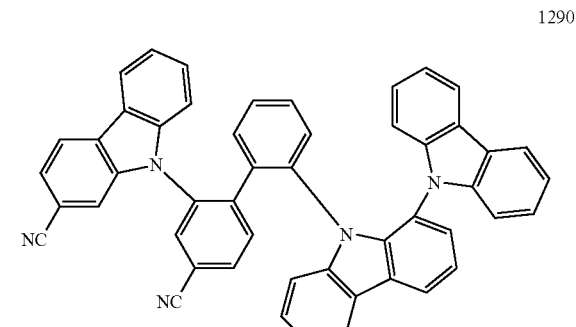

1291
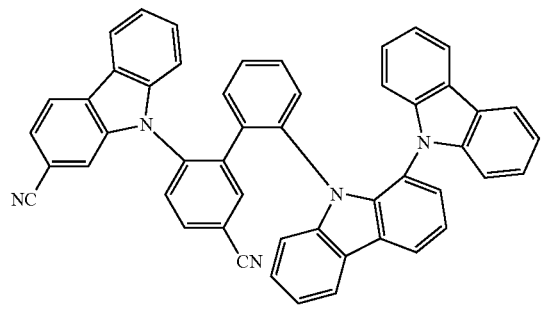
1292
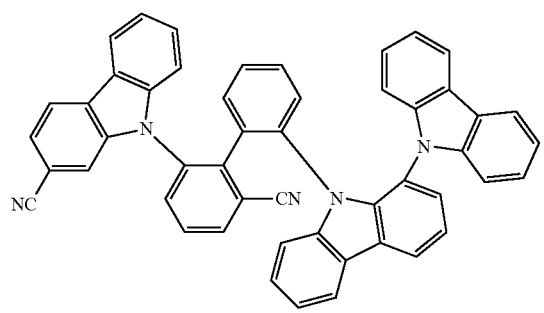
1293
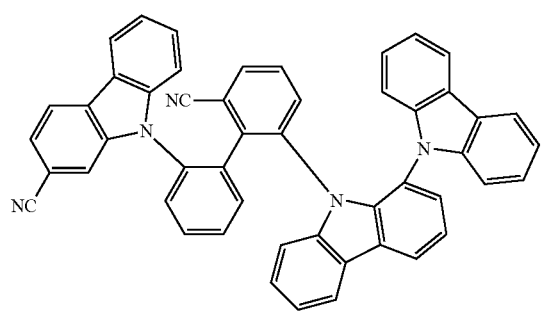
1294
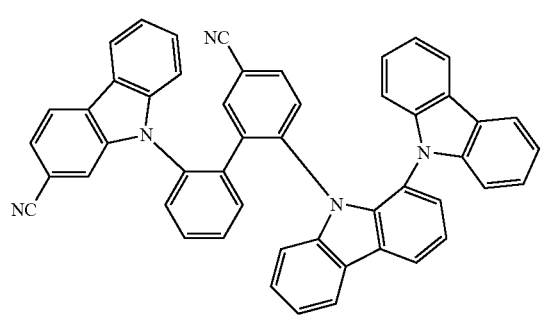
1295
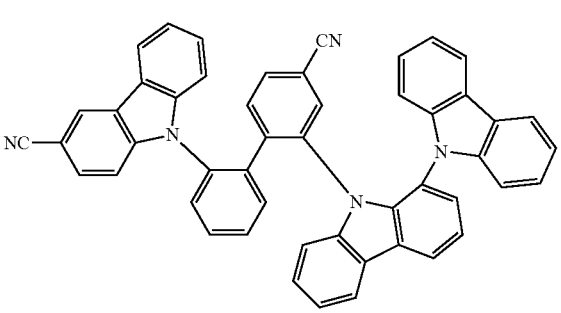
1296
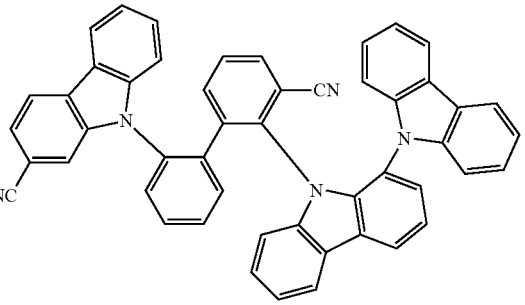
1297
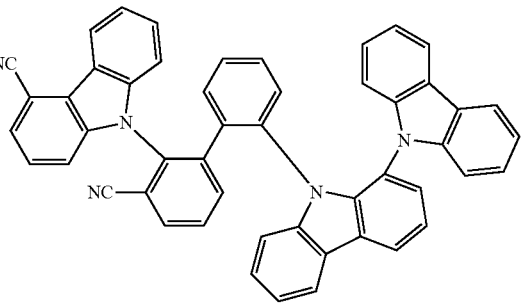
1298
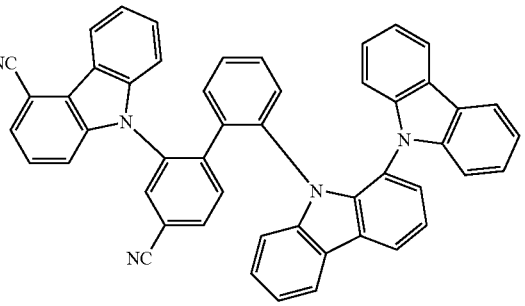
1299
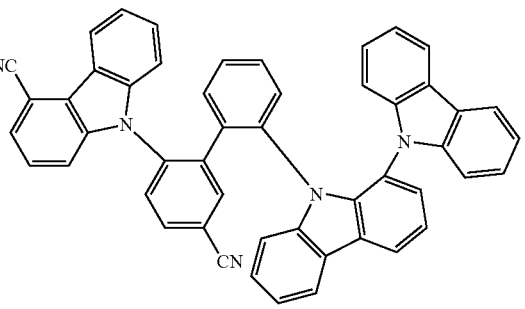
1300
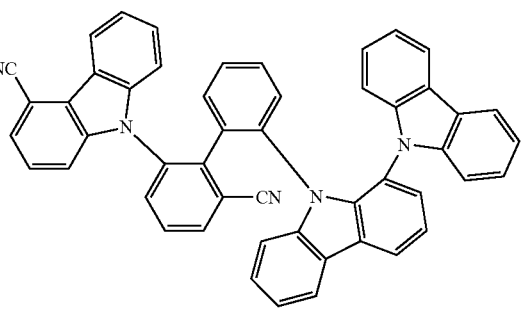

1301
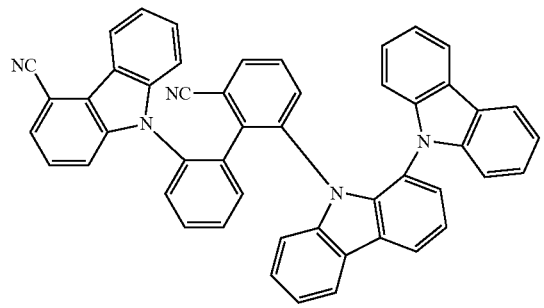
1302
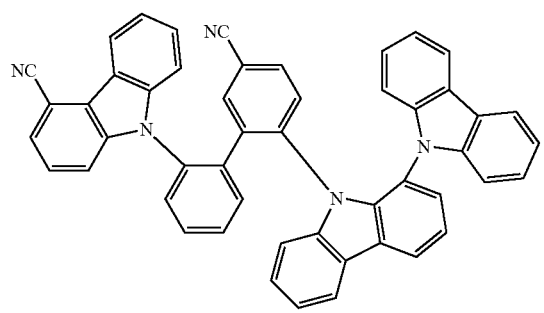
1303
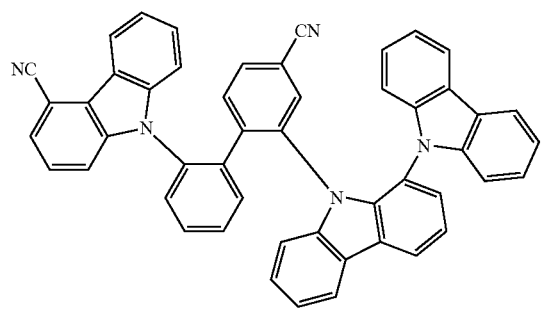
1304
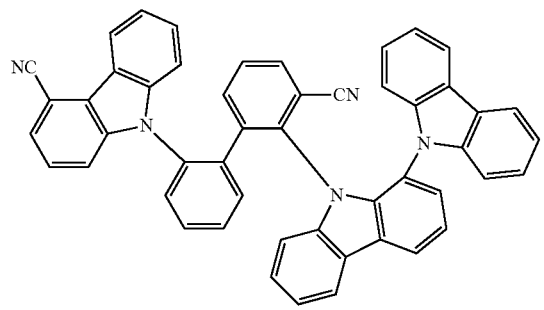
1305
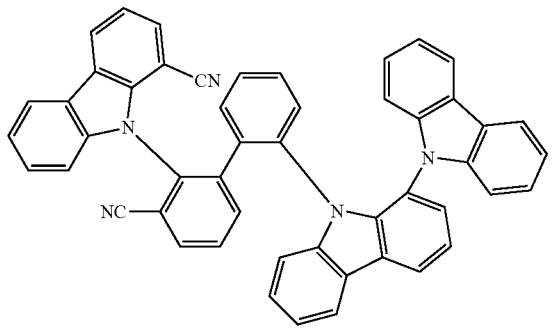
1306
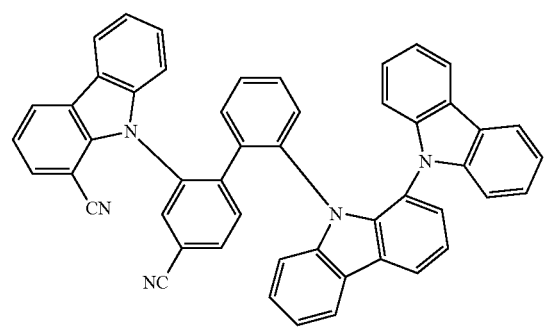
1307
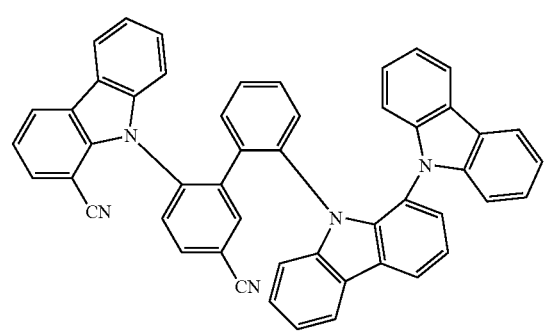
1308
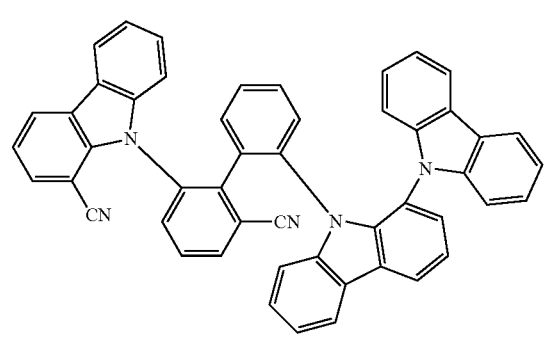

1309
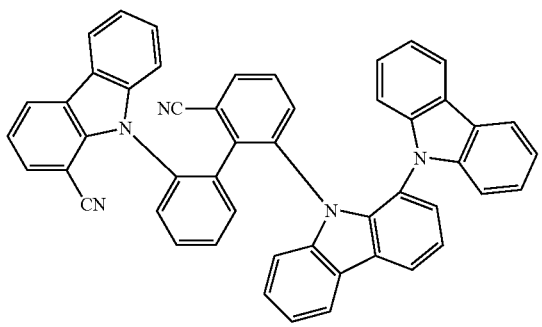
1310
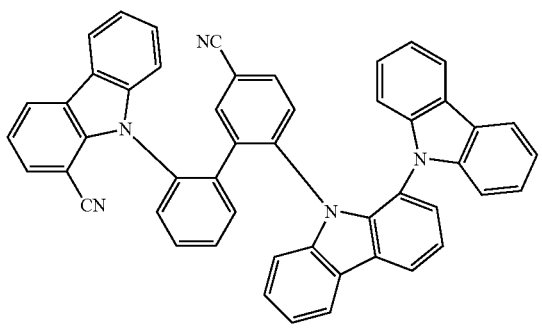
1311
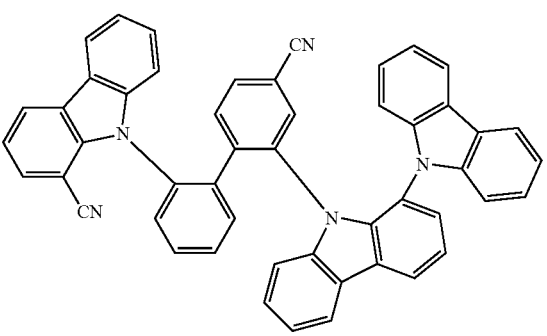
1312
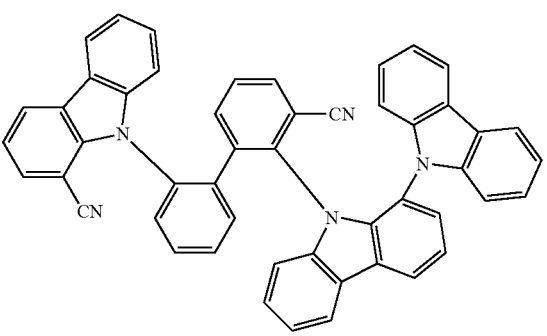
1313
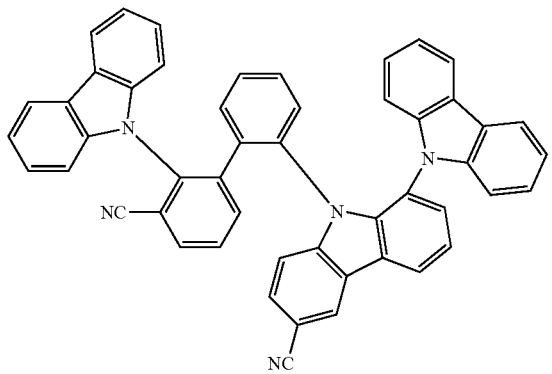
1314
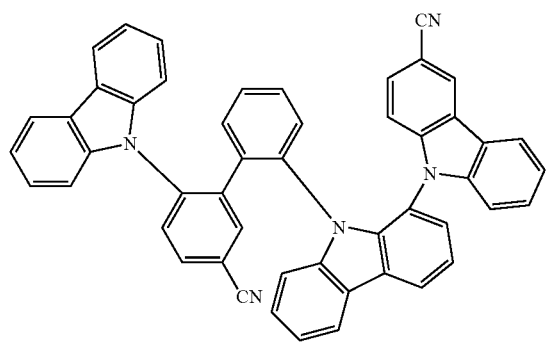
1315
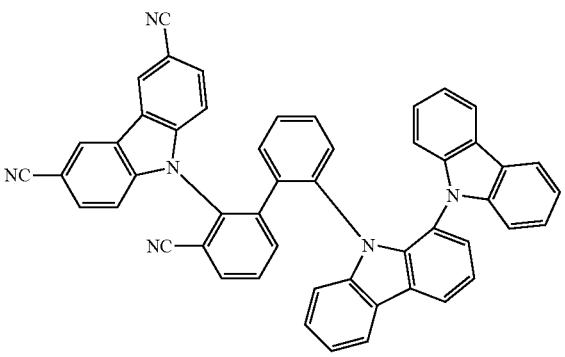
1316
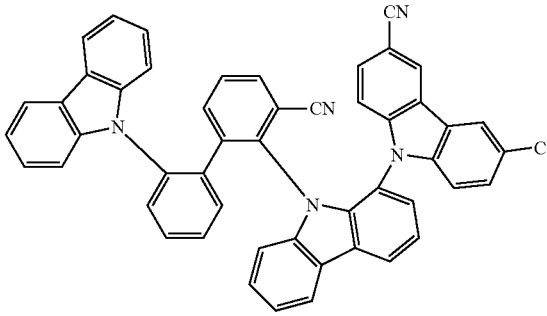

1317
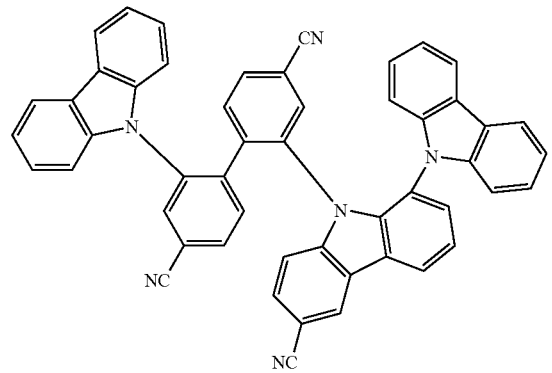
1318
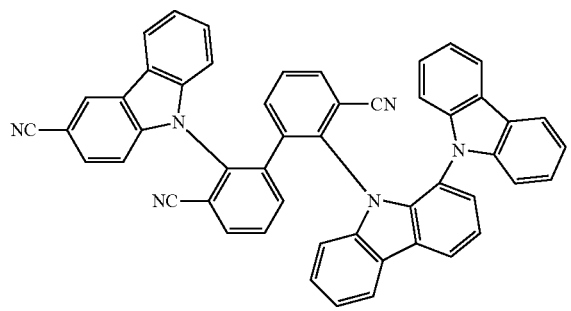
1319
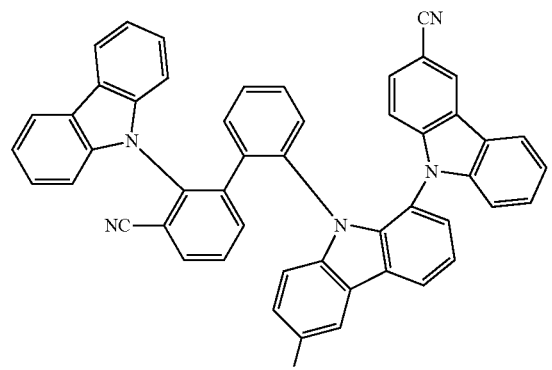
1320
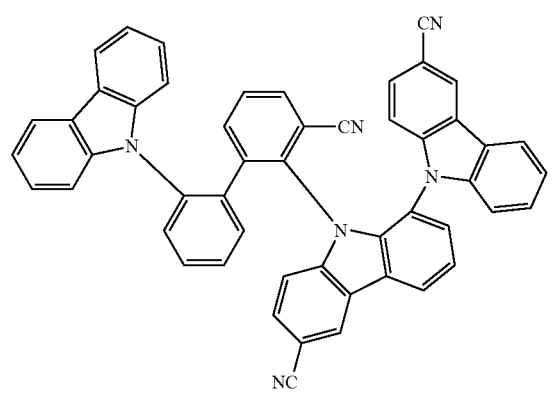
1321
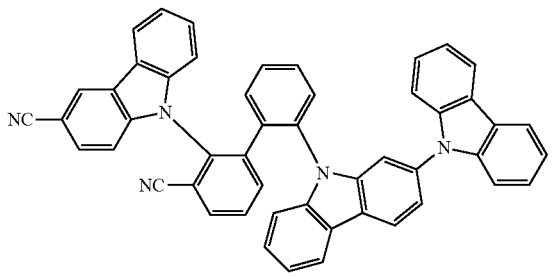
1322
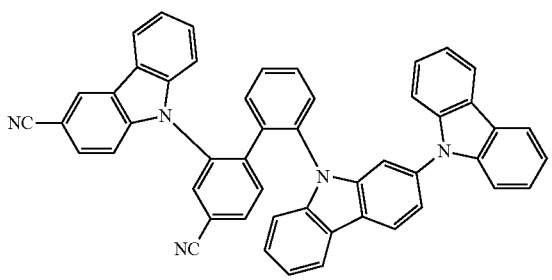
1323
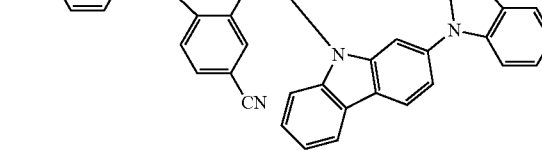
1324
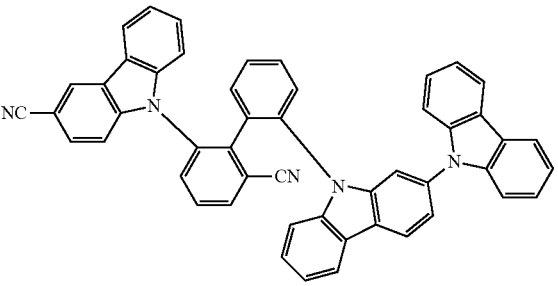
1325
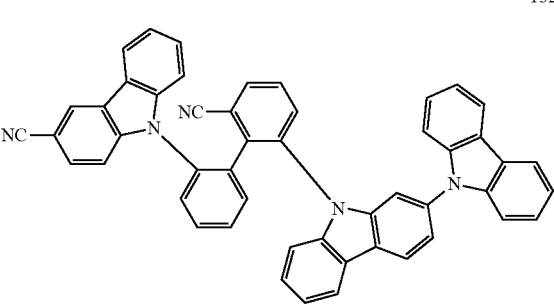

1326
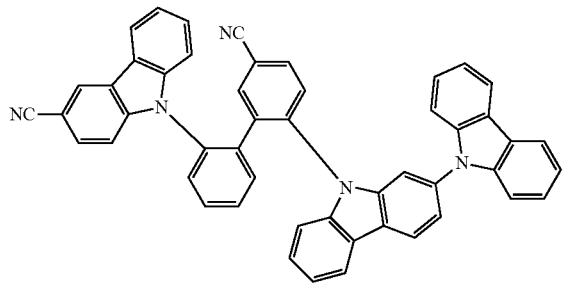
1327
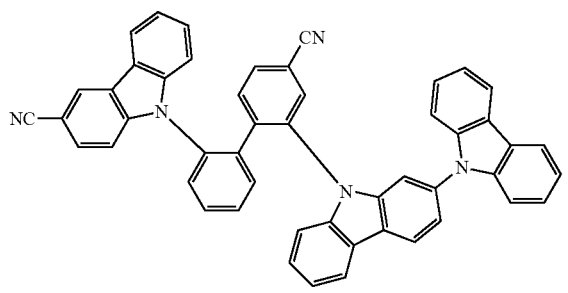
1328
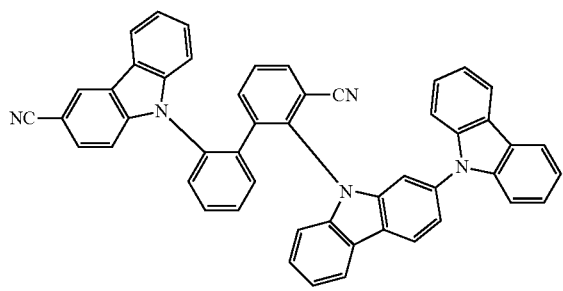
1329
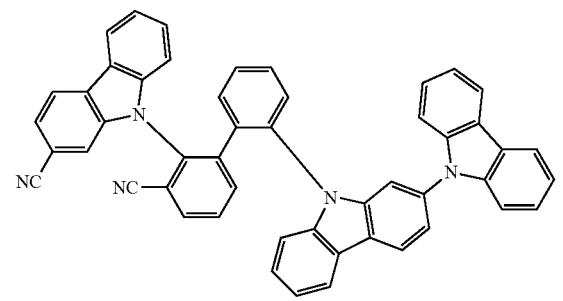
1330
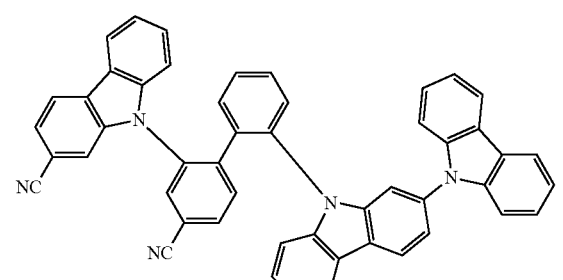
1331
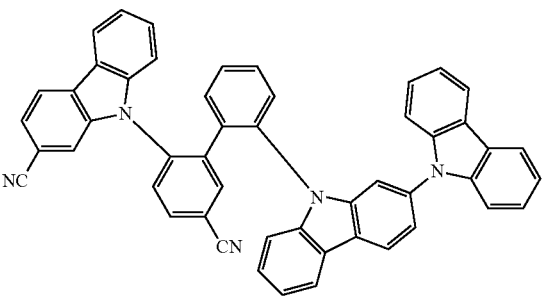
1332
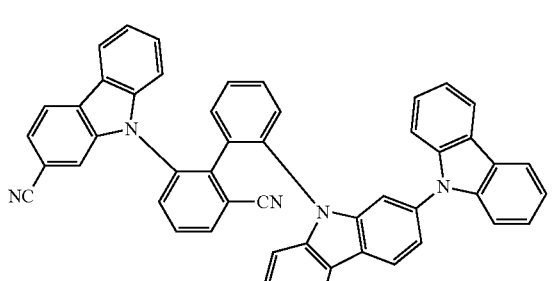
1333
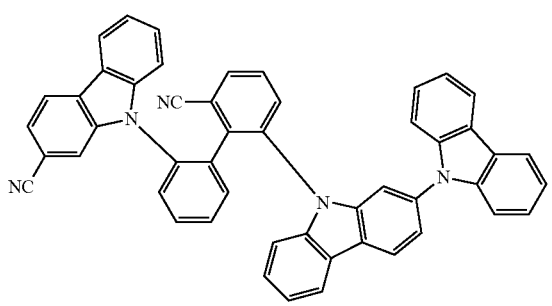
1334
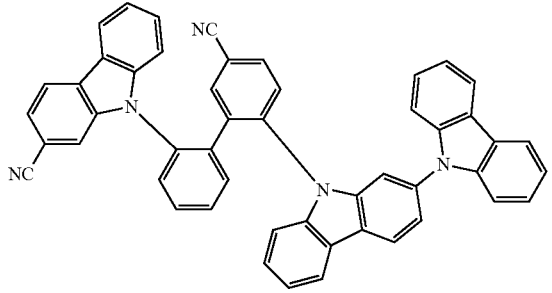
1335
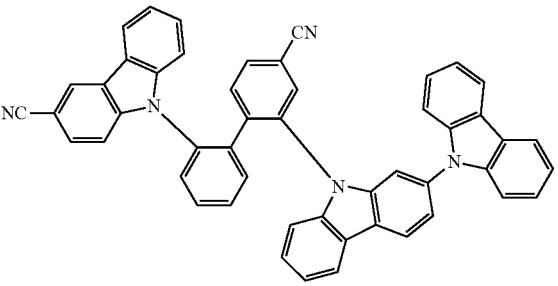

1336
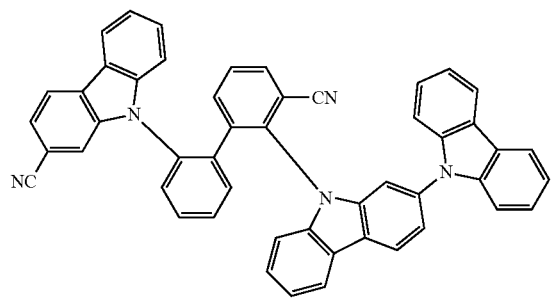
1337
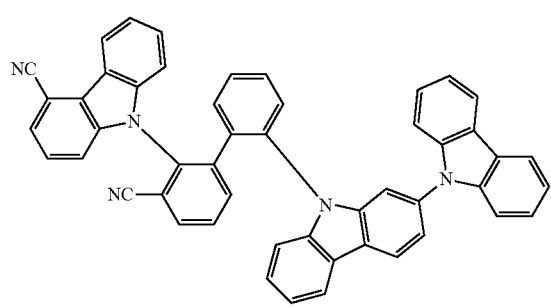
1338
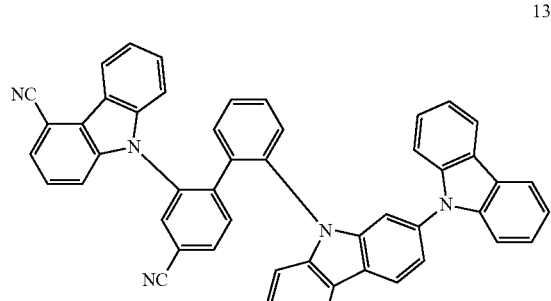
1339
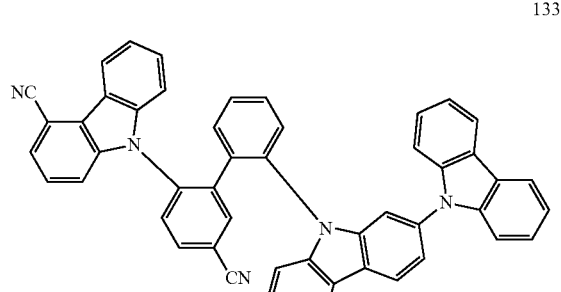
1340
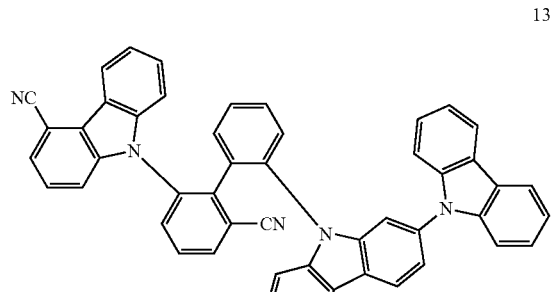
1341
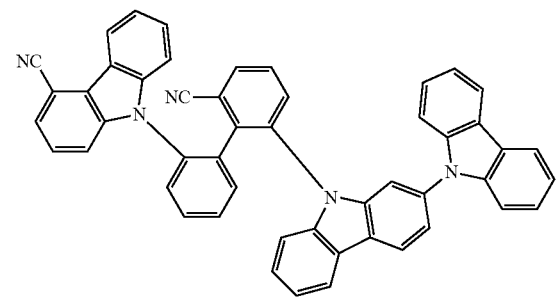
1342
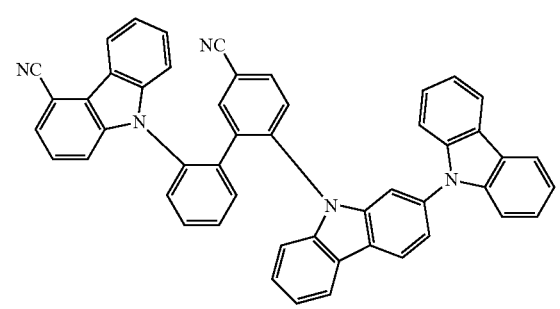
1343
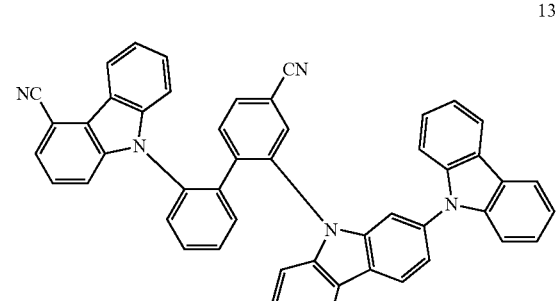
1344
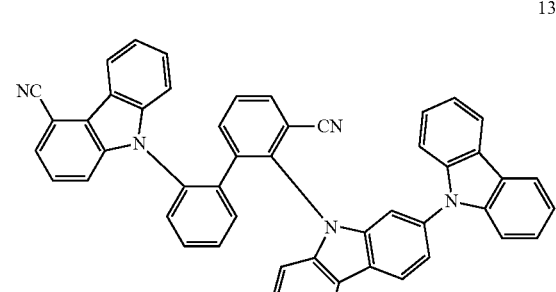
1345
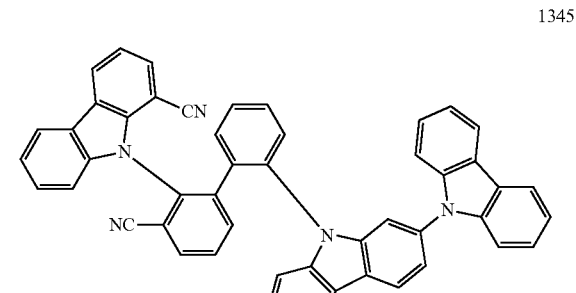

1346
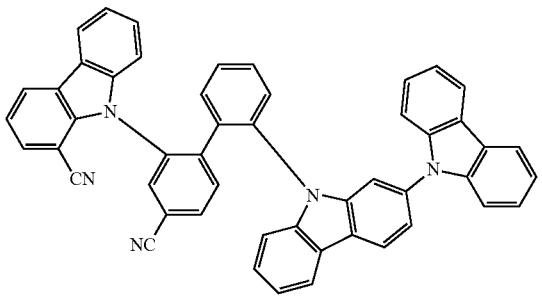
1347
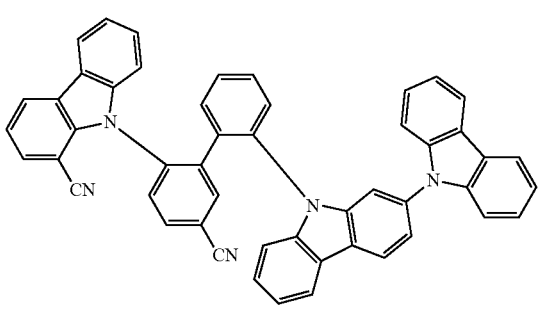
1348
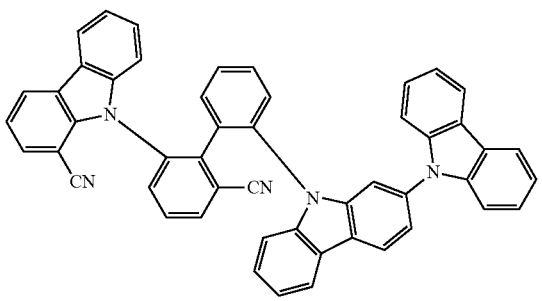
1349
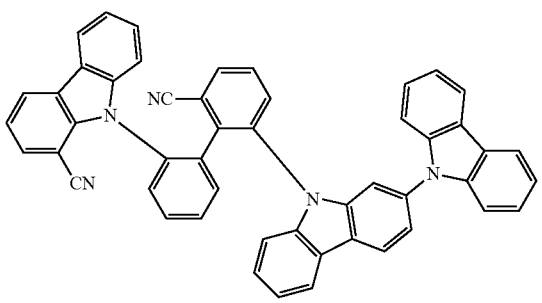
1350
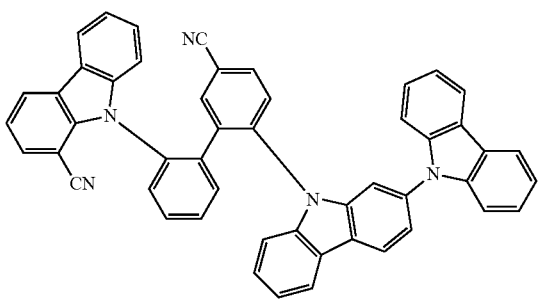
1351
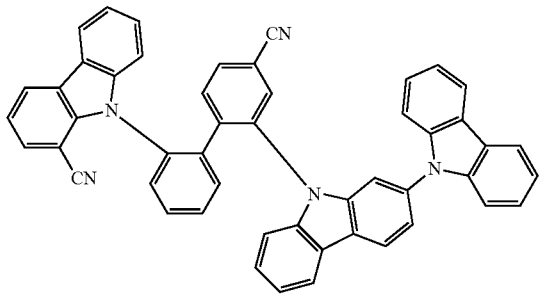
1352
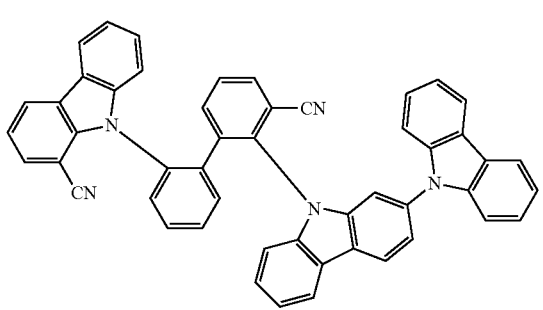
1353
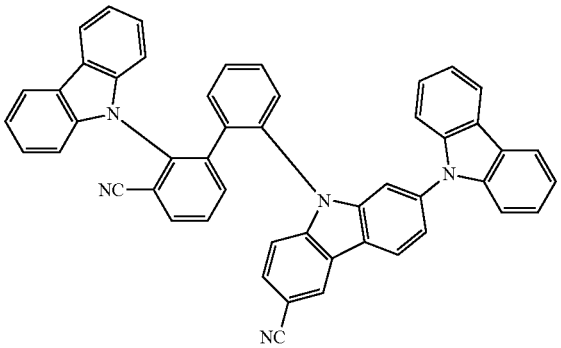
1354
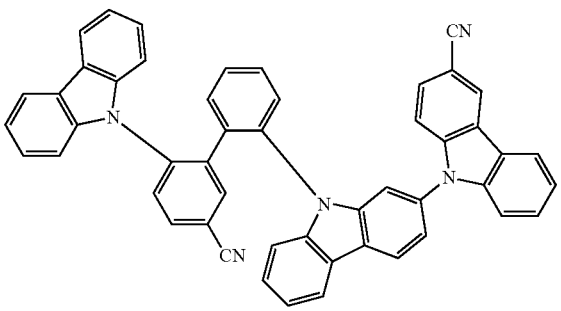

1355
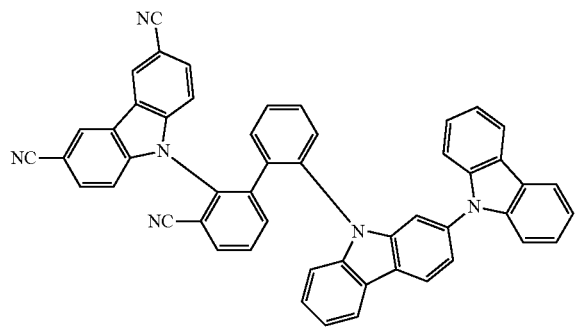
1356
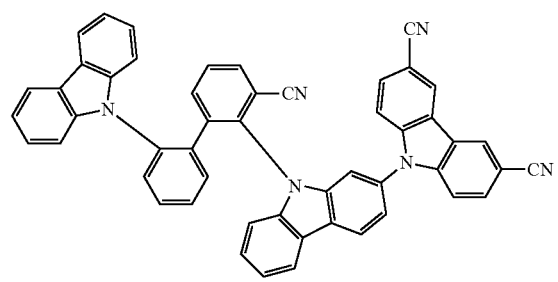
1357
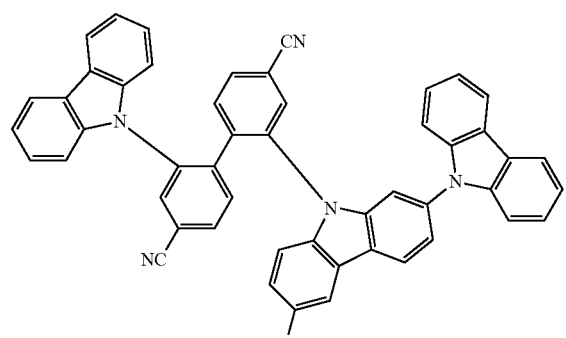
1358
1359
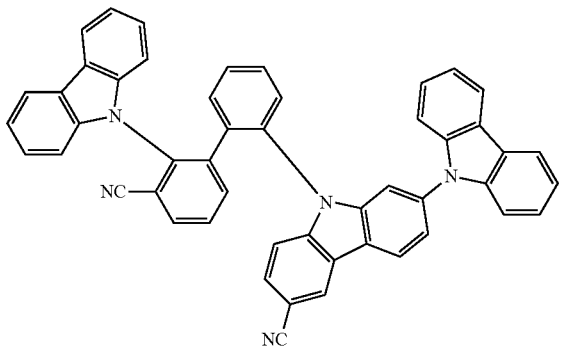
1360
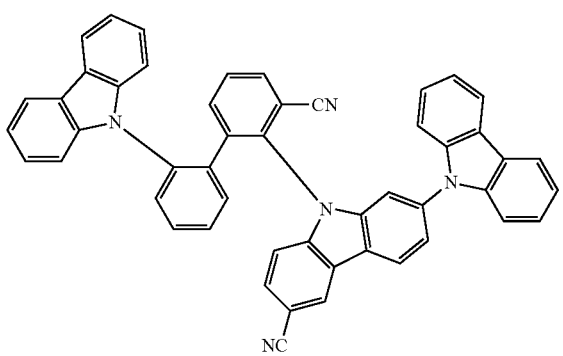
1361
1362
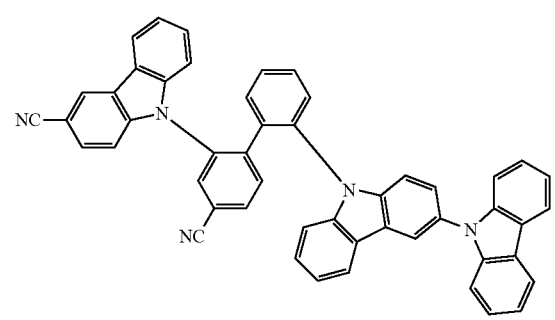

-continued
1363
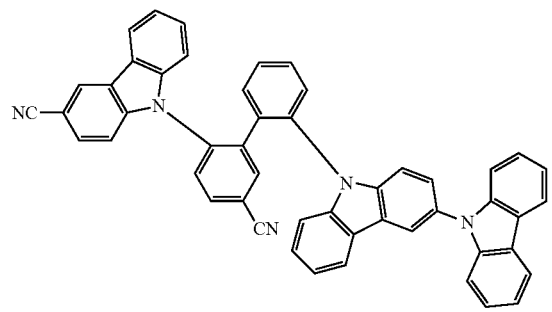
1364
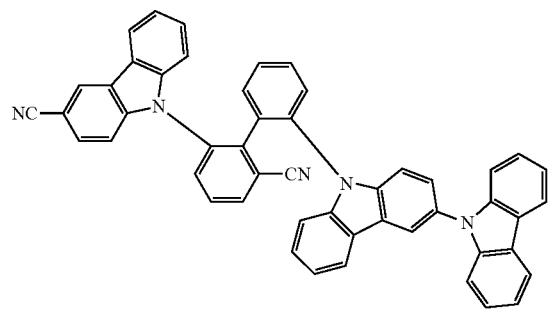
1365
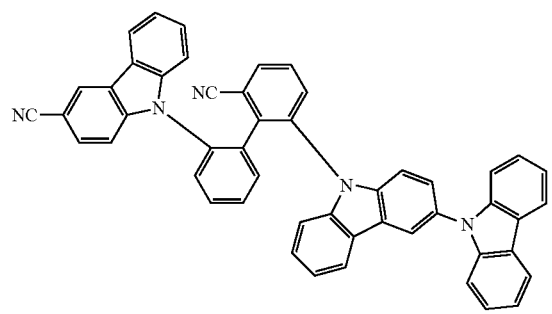
1366
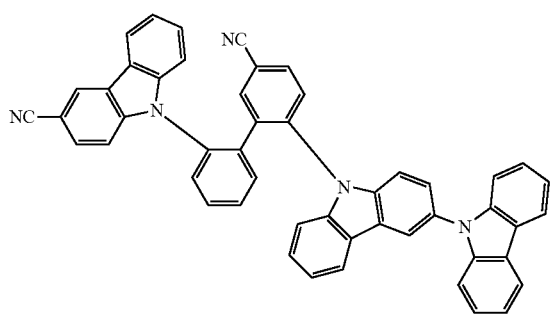
-continued
1367
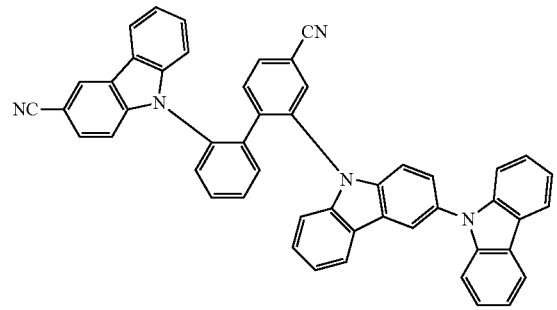
1368
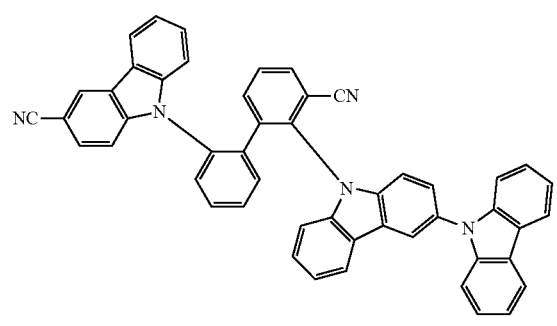
1369
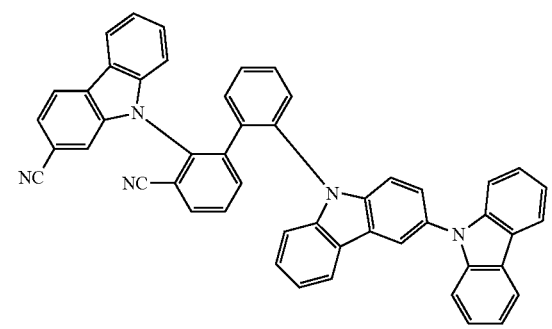
1370
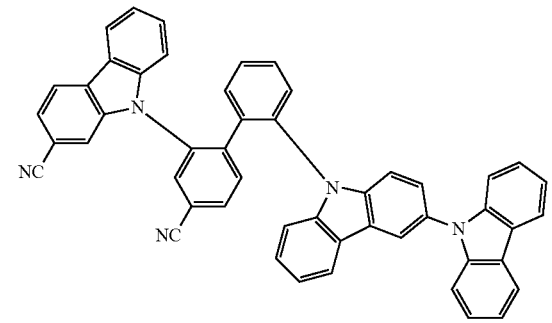

-continued
1371
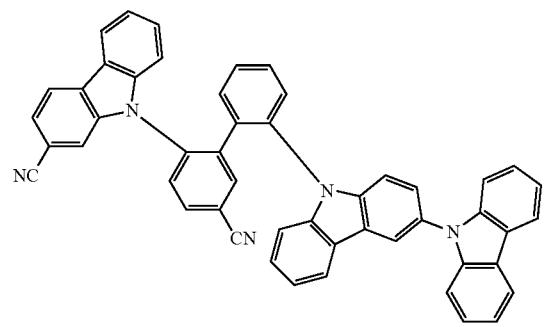
1372
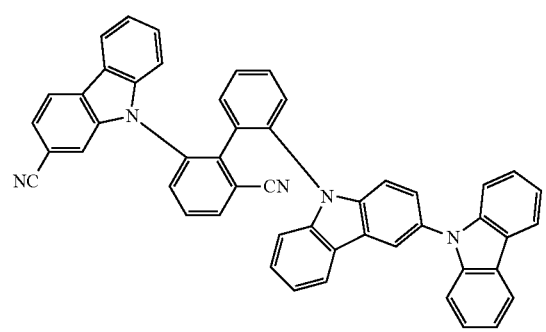
1373
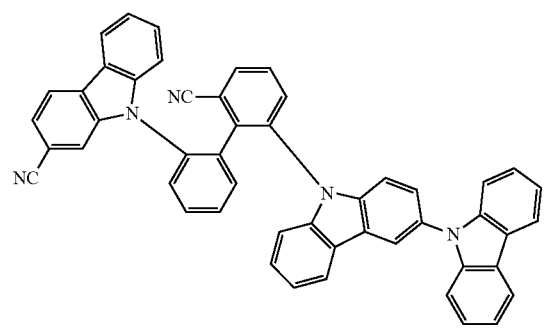
1374
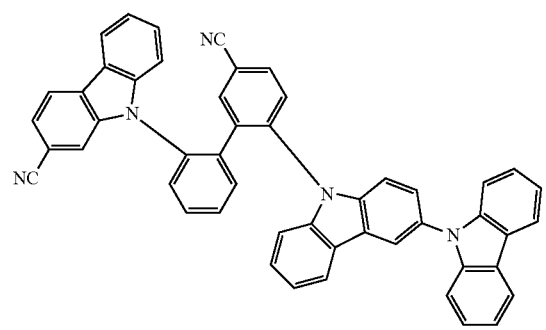
-continued
1375
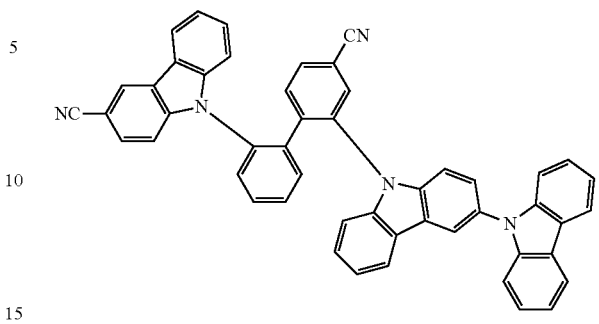
1376
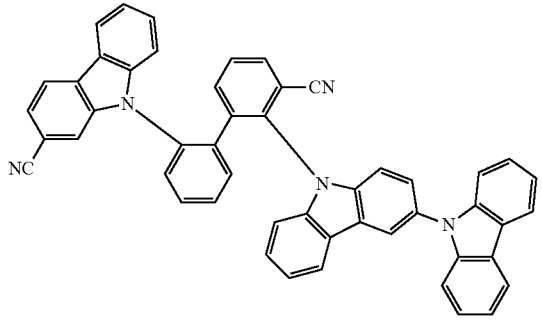
1377
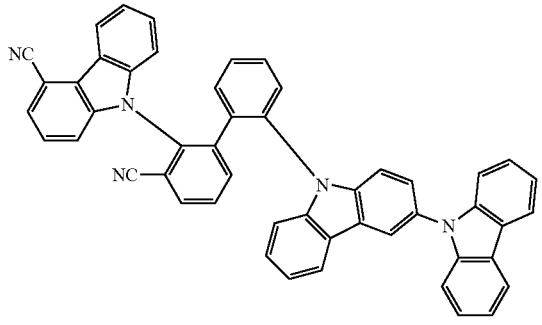
1378
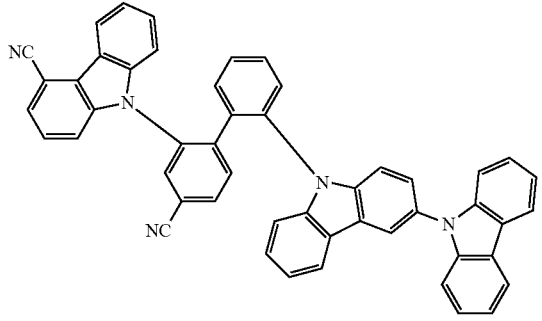

1379
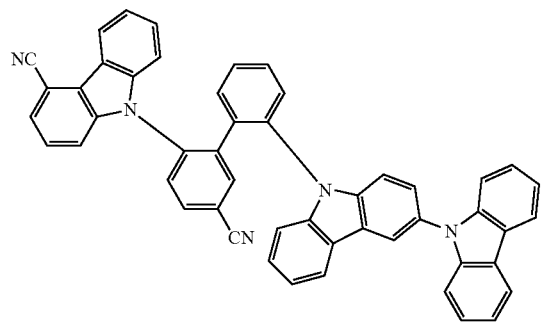
1380
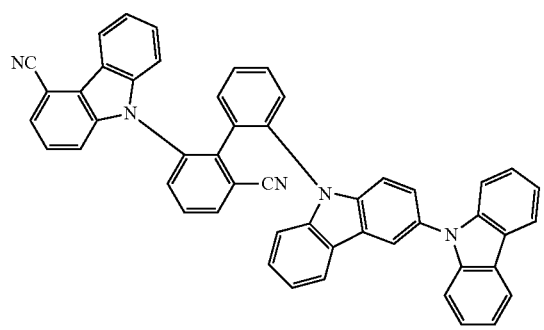
1381
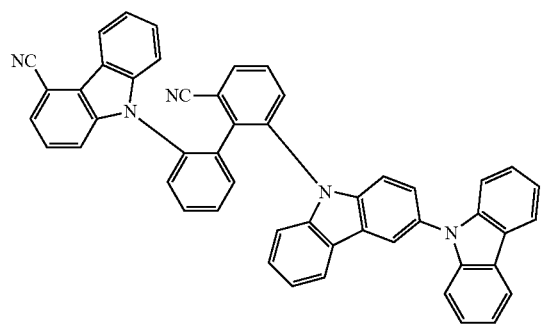
1362
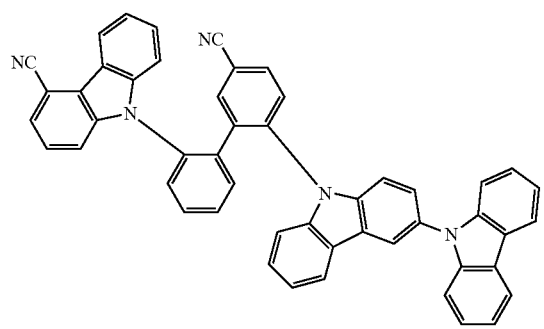
1363
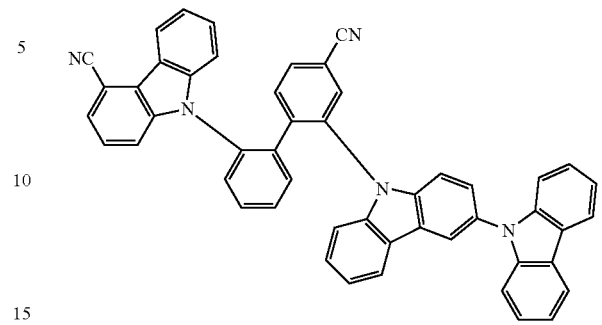
1364
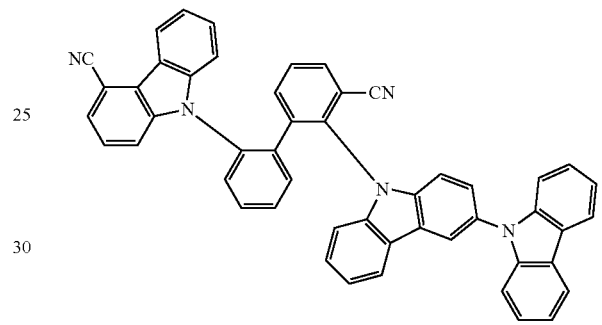
1365
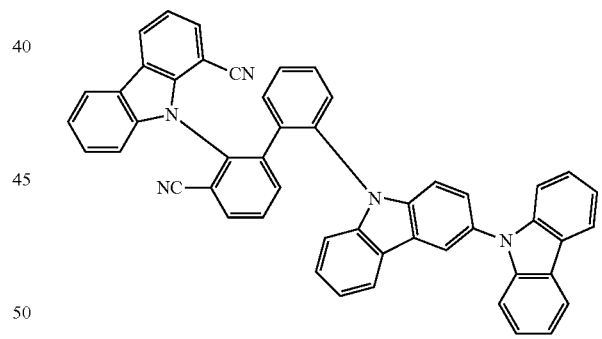
1386
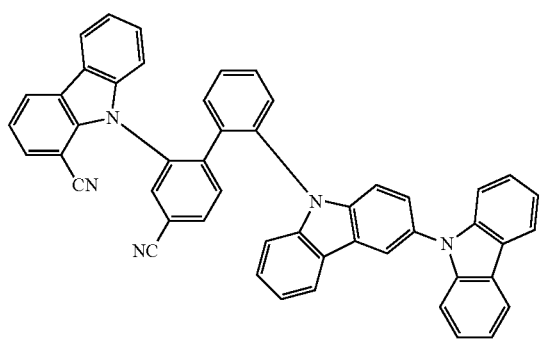

1387
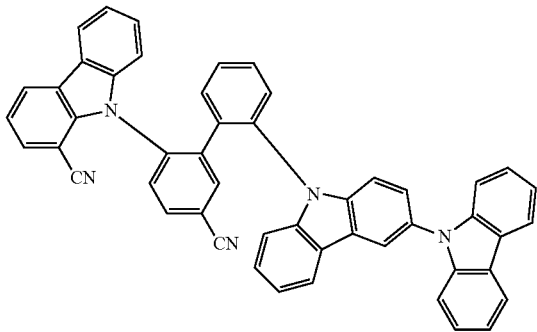
1388
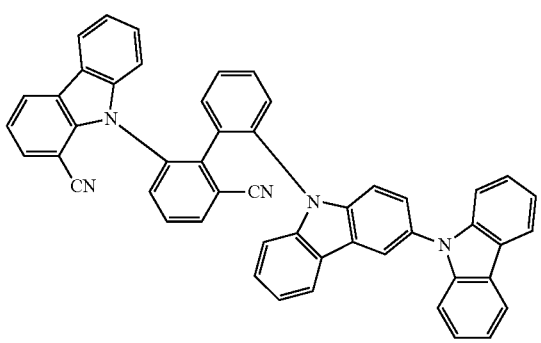
1389
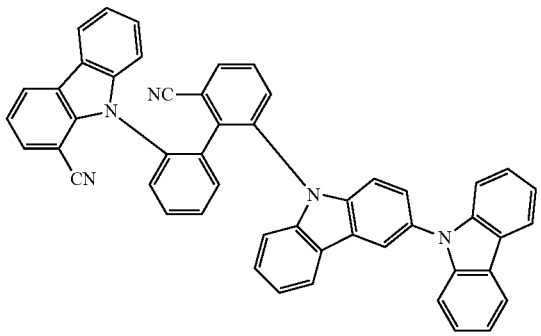
1390
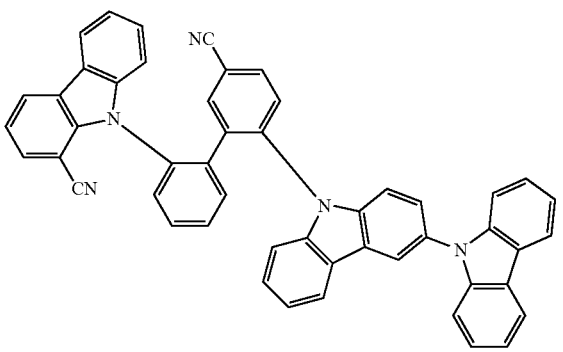
1391
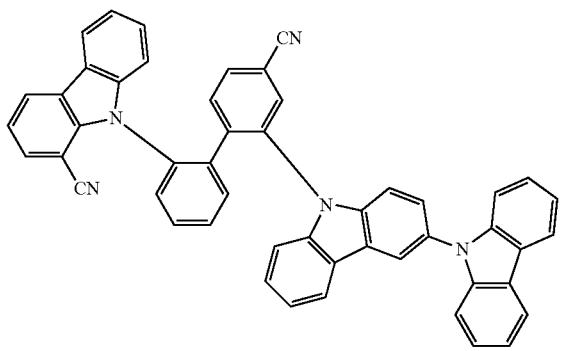
1392
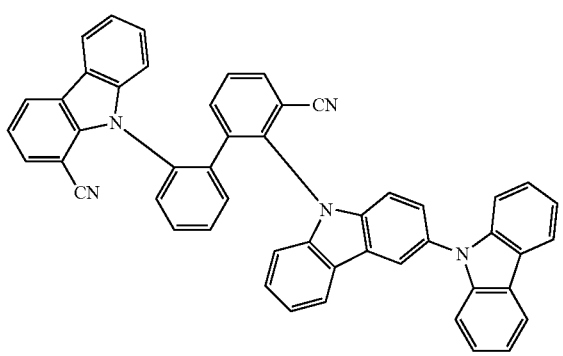
1393
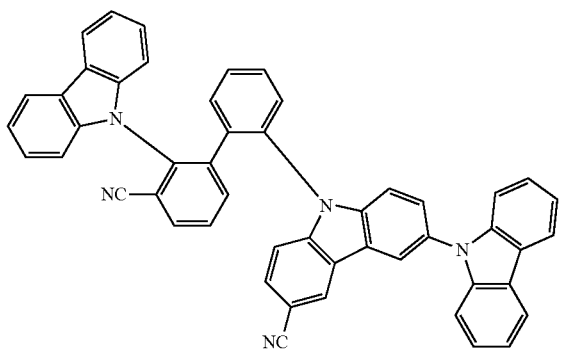
1394
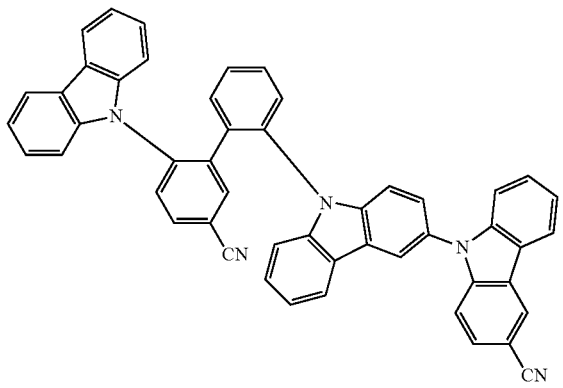

-continued
1395
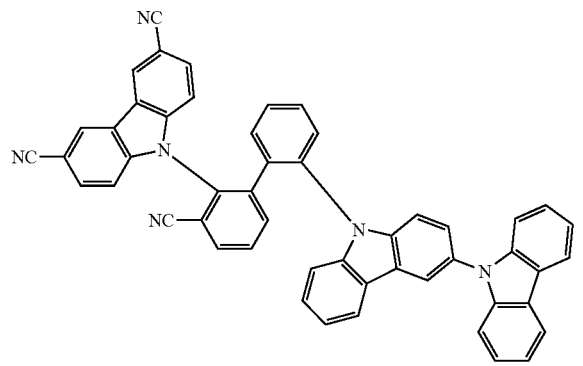
1396
1397
1398
1399
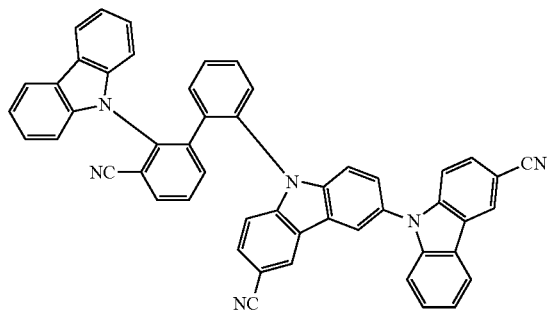
1400
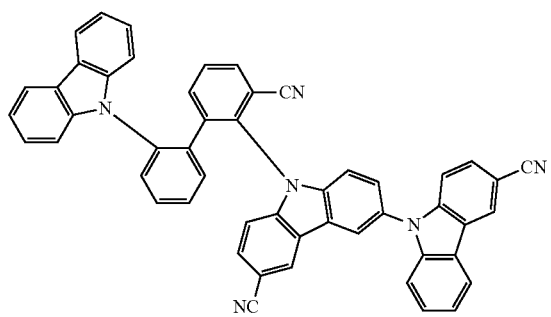
1401
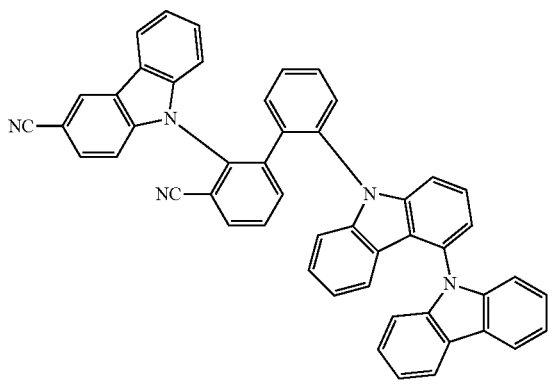
1402
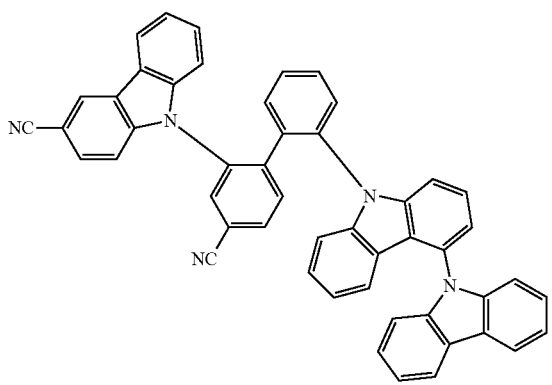

-continued
1403
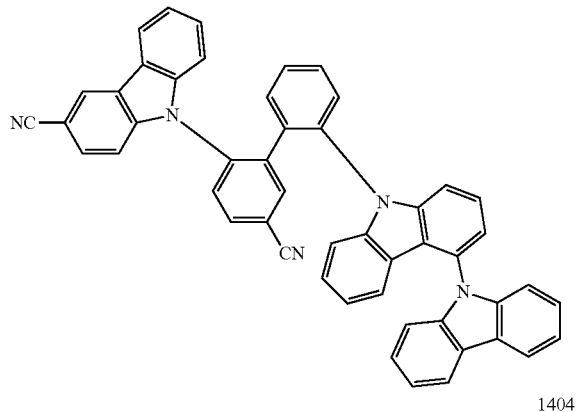
1407
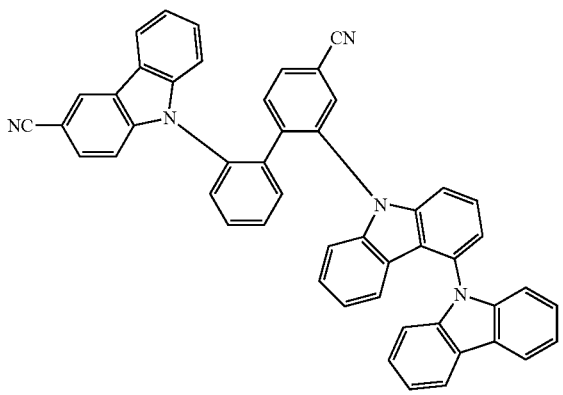
1404
1408
1405
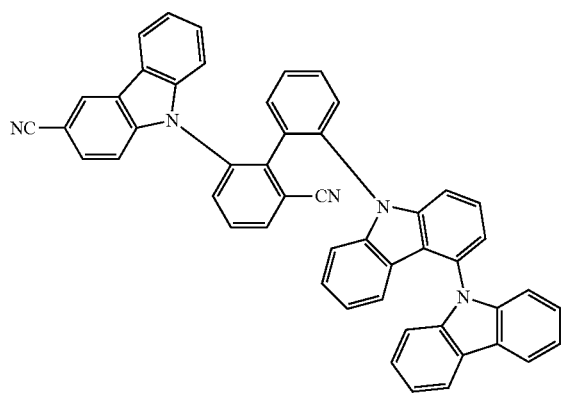
1406
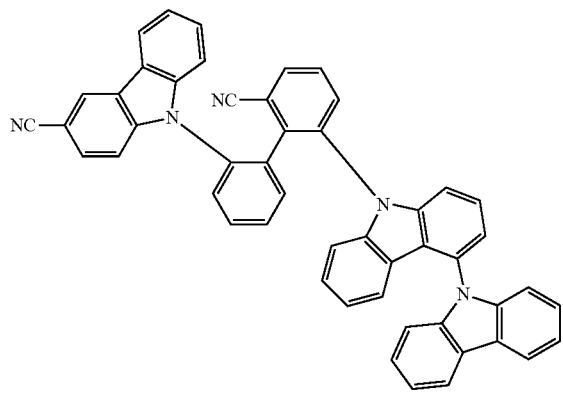
1409
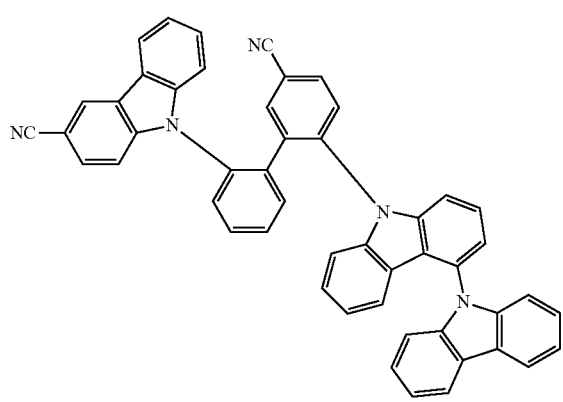

-continued
1410
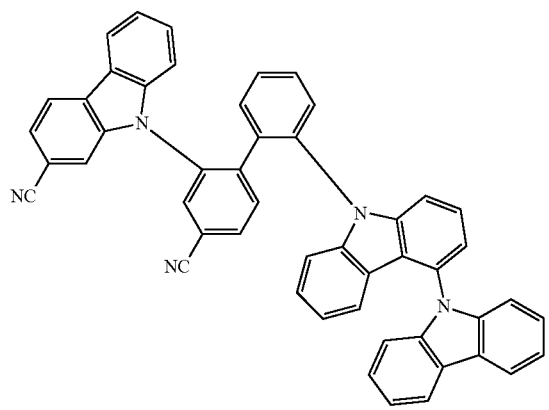
1411
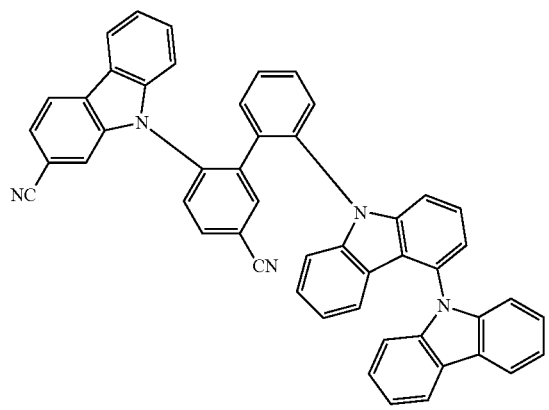
1412
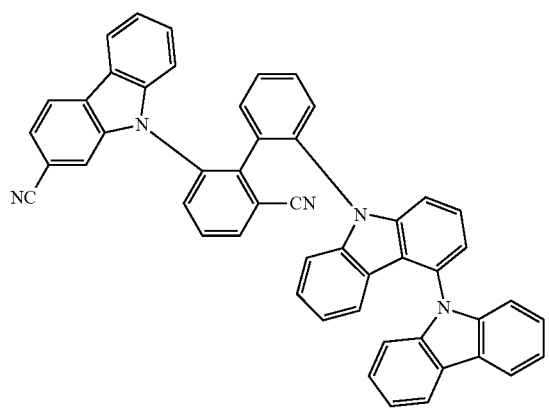
-continued
1413
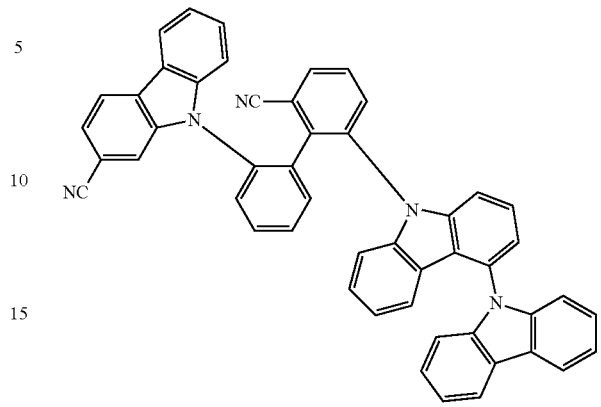
1414
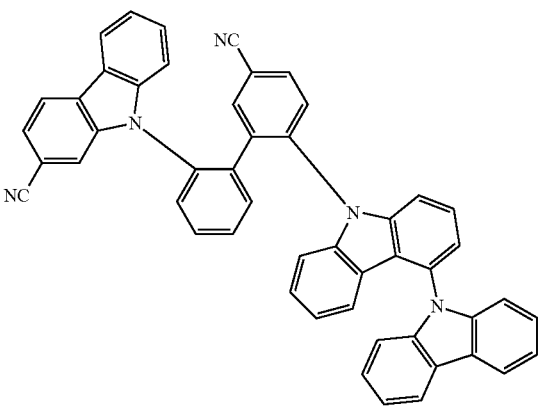
1415
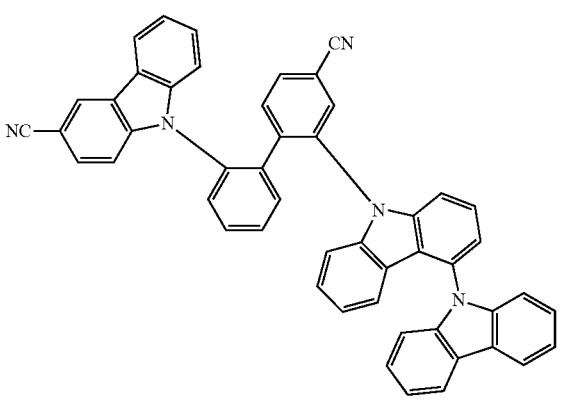

1416
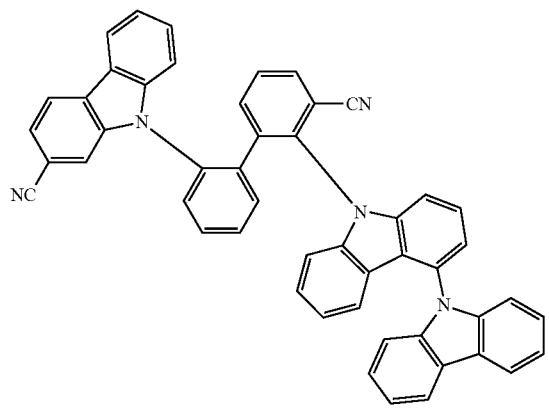
1417
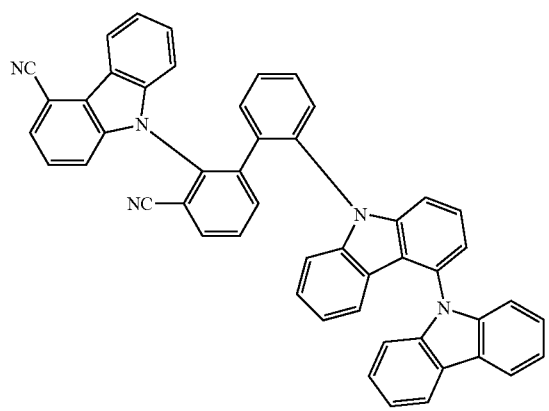
1418
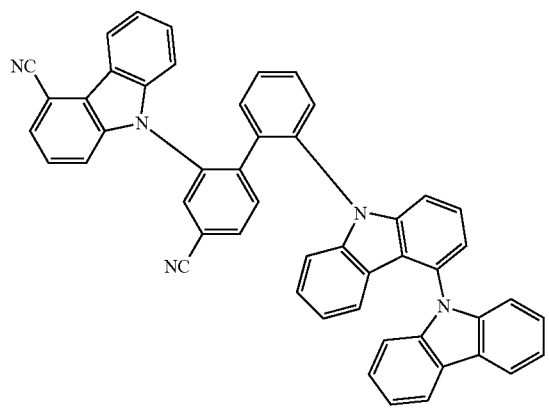
1419
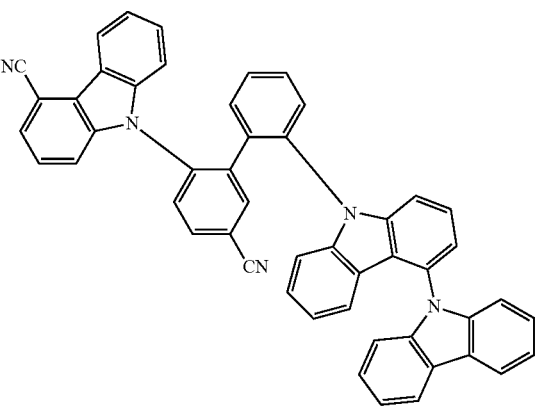
1420
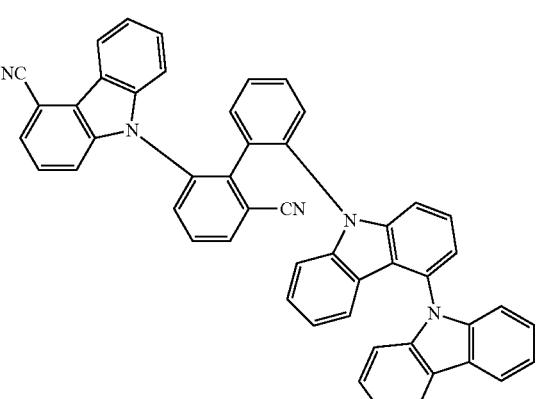
1421
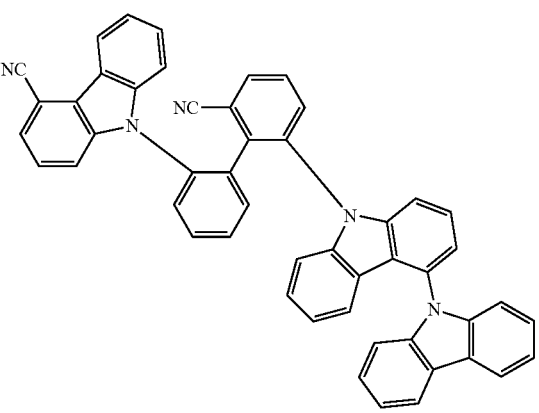

-continued
1422
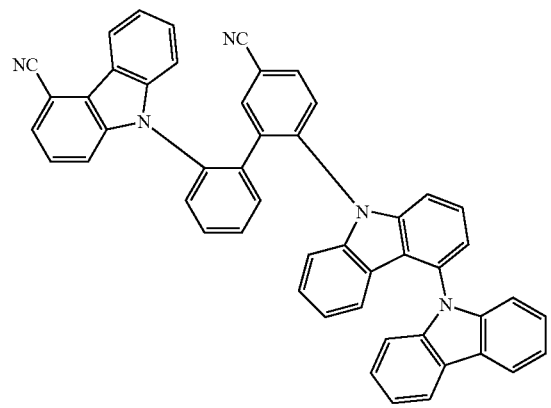
1423
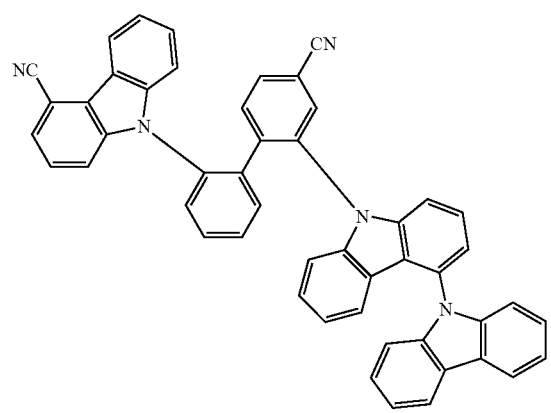
1424
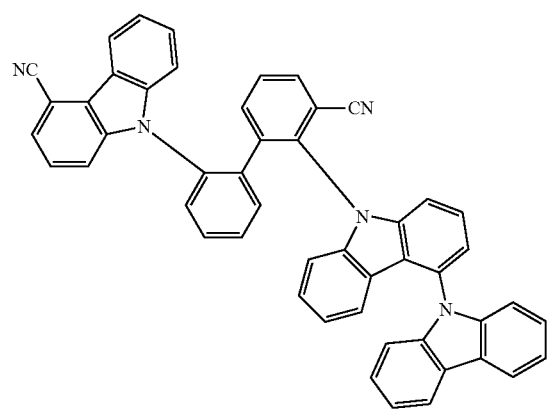
-continued
1425
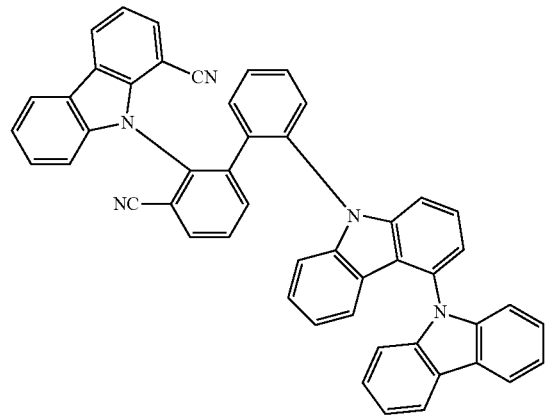
1426
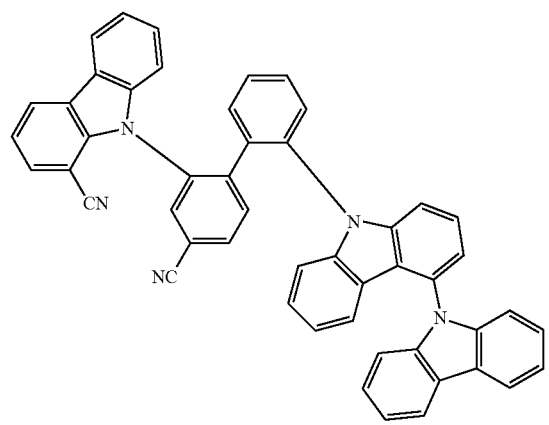
1427
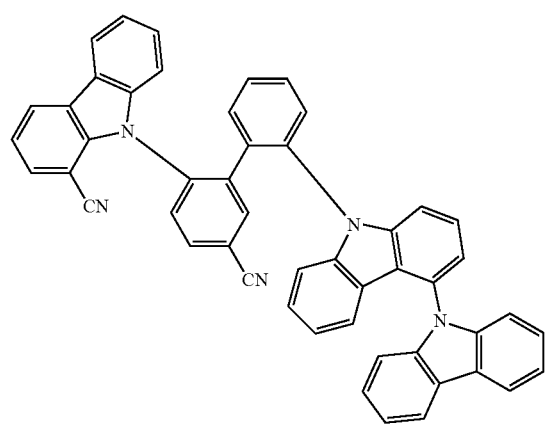

1428
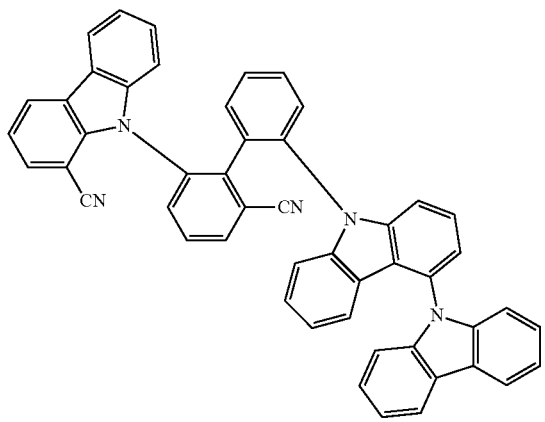
1429
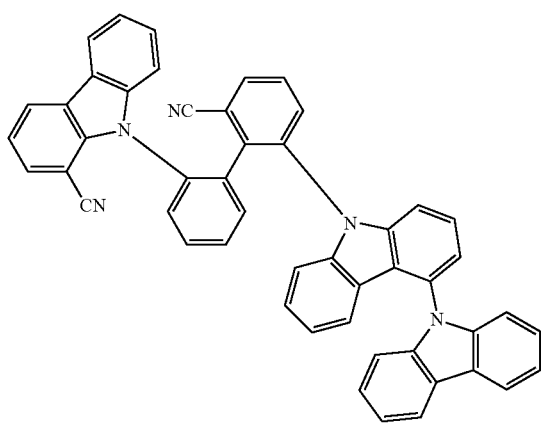
1430
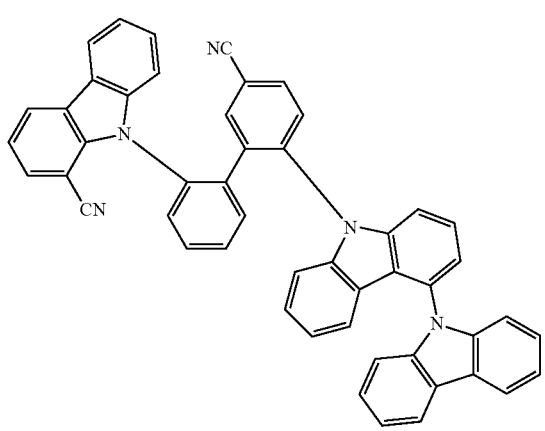
1431
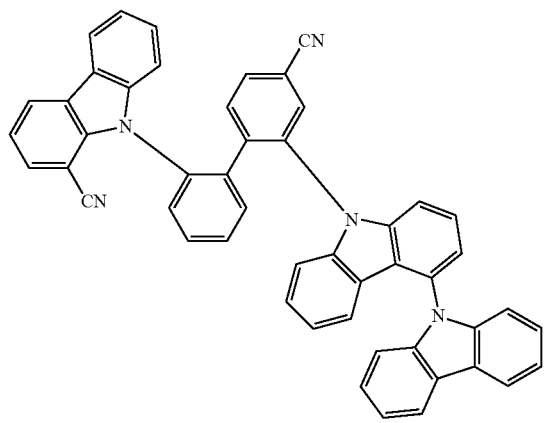
1432
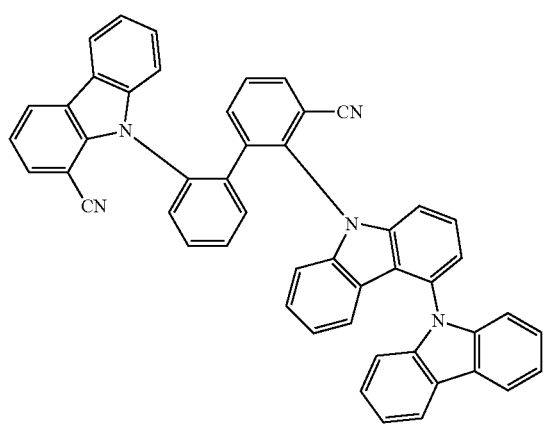
1433
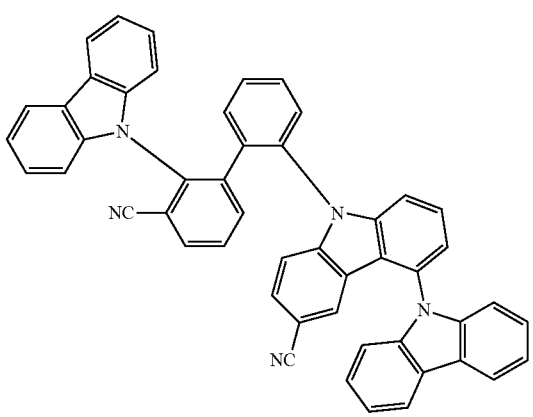

1434
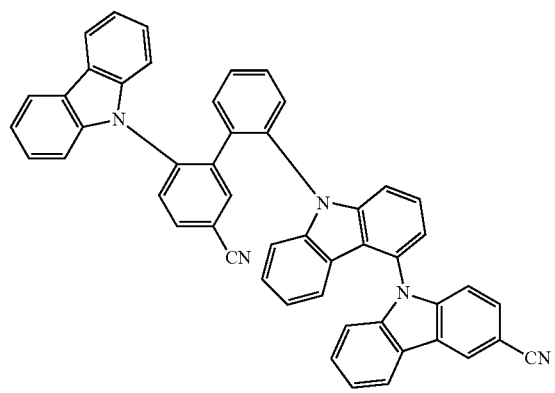
1435
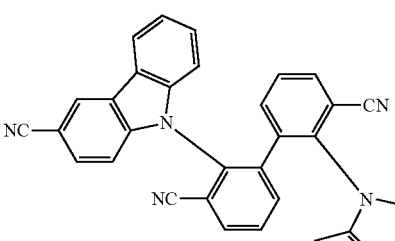
1436
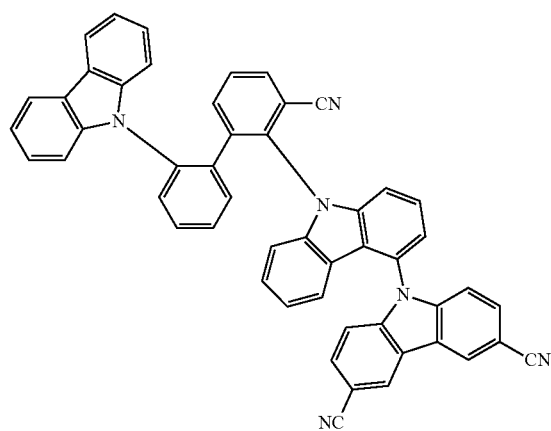
1437
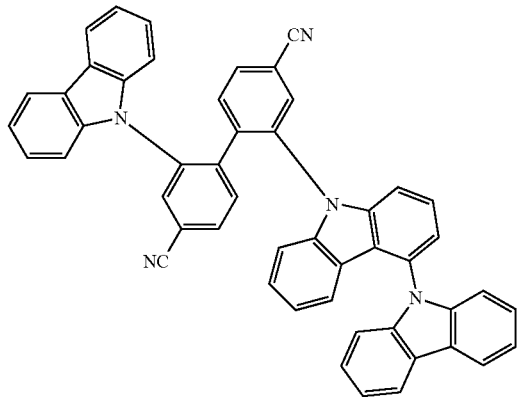
1438
1439
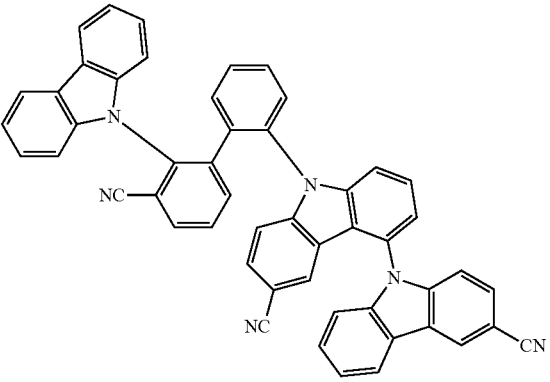
1440
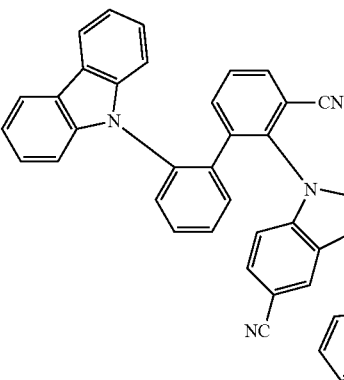

-continued
1441
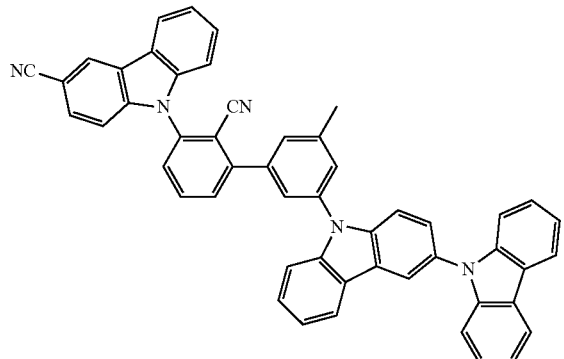
1442
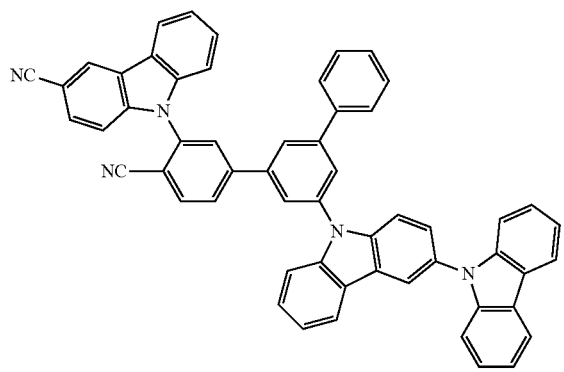
1443
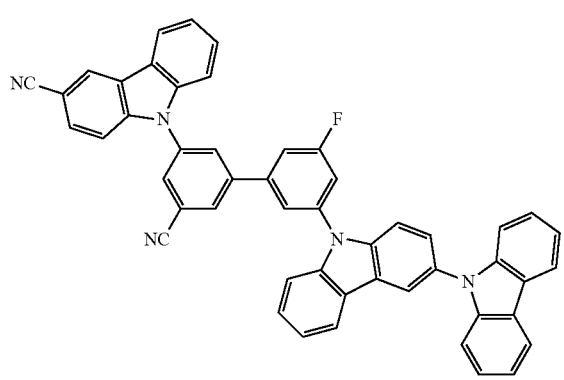
1444
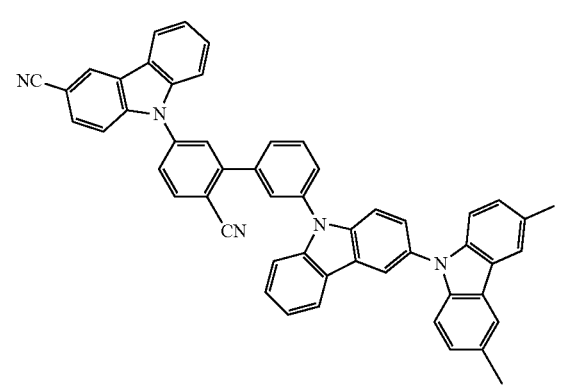
-continued
1445
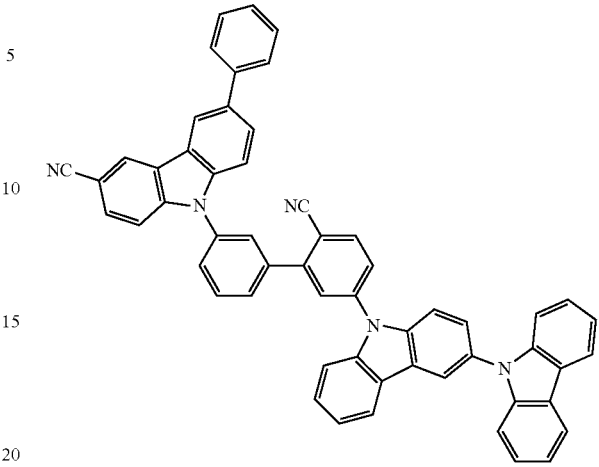
1446
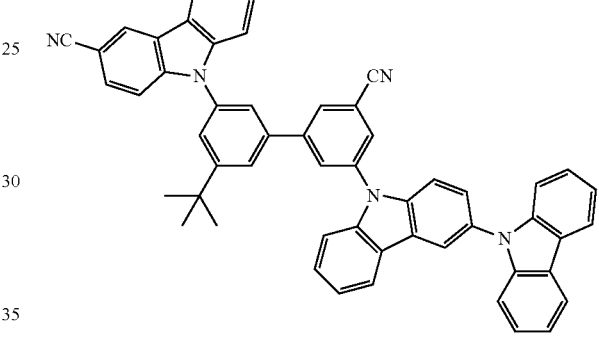
1447
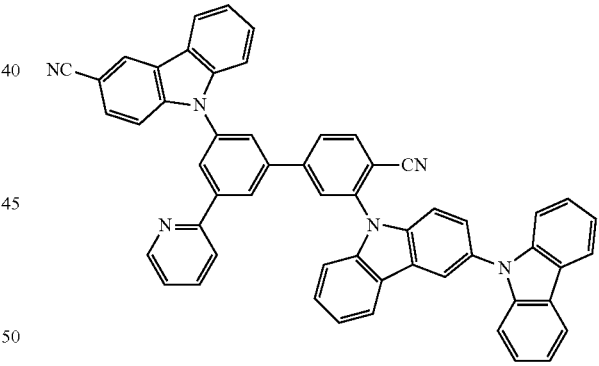
1448
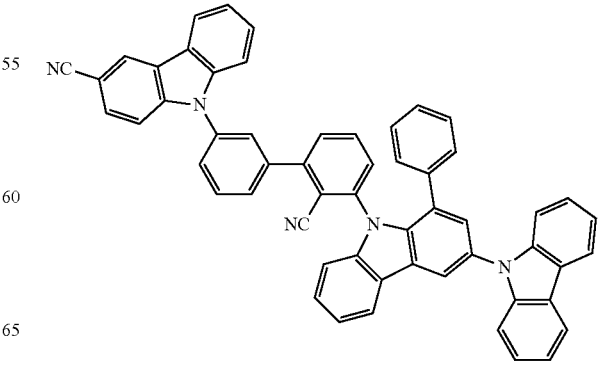

1449
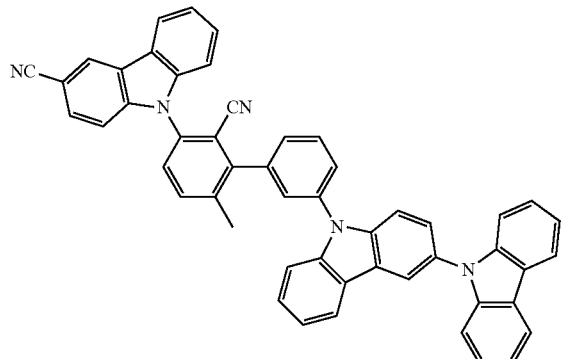
1450
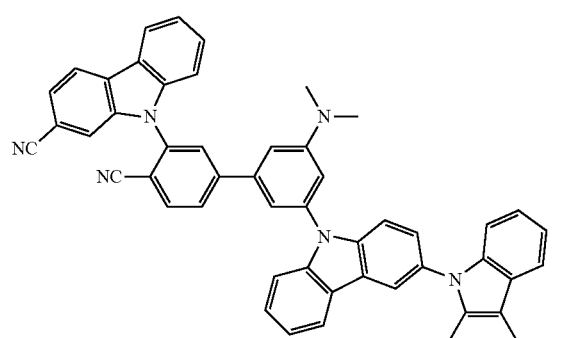
1451
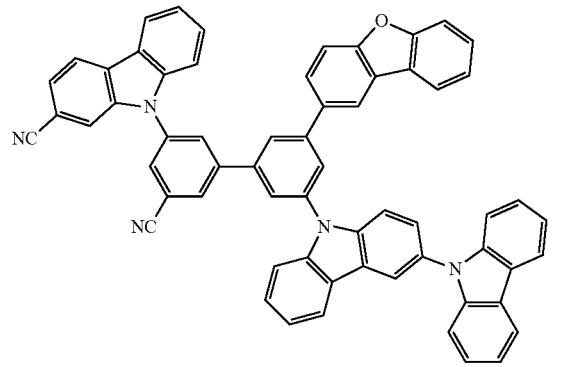
1452
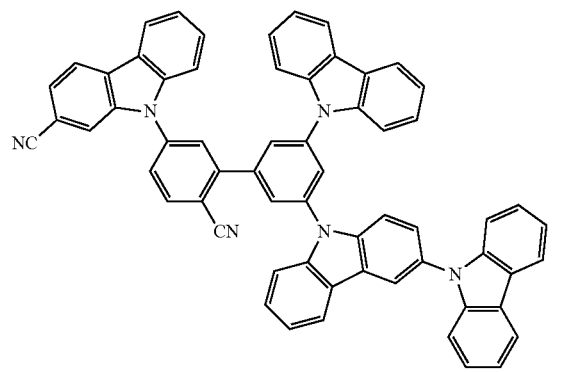
1453
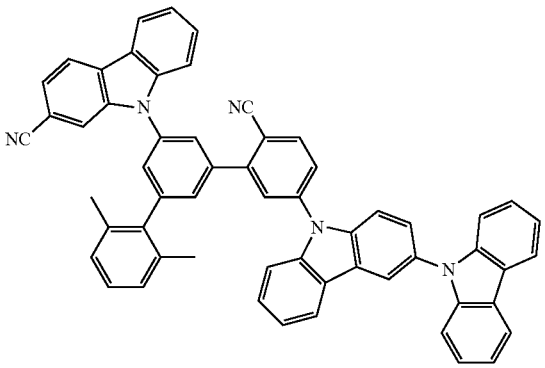
1454
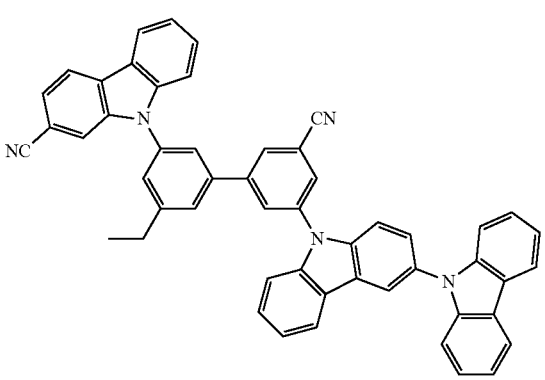
1455
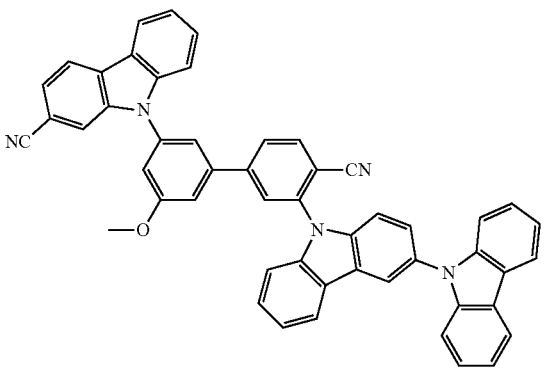
1456
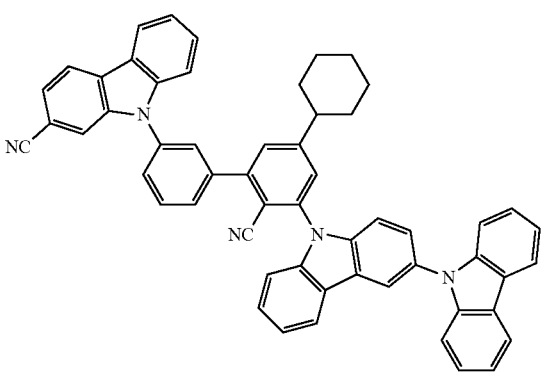

1457

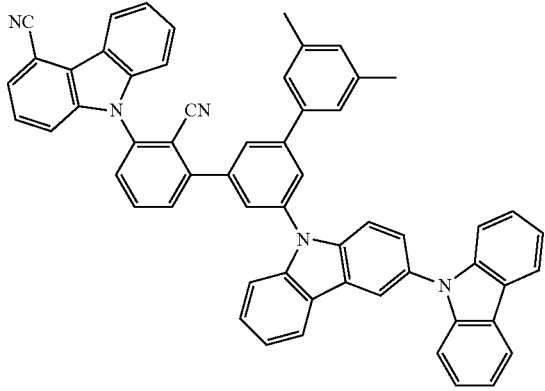

1460

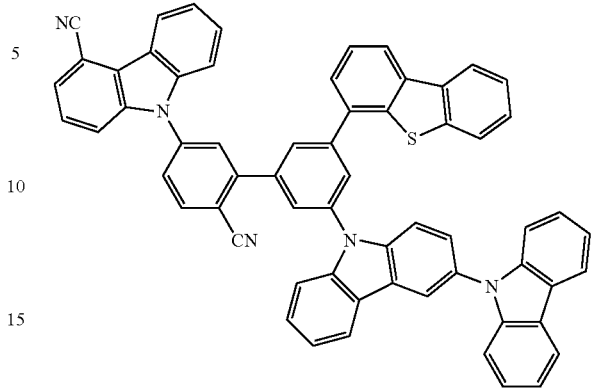

1458

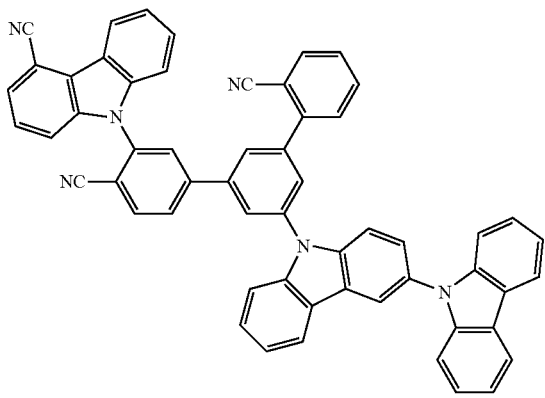

1459

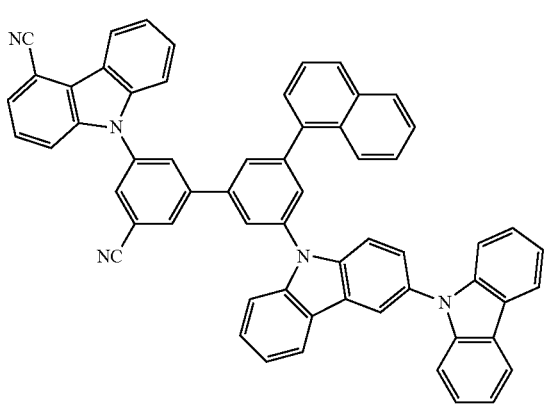

The condensed cyclic compound represented by Formula 1 includes a cyano group in $L_{11}$-$L_{12}$, and thus has a lowest unoccupied molecular orbital (LUMO) energy level and/or a highest occupied molecular orbital (HOMO) energy level suitable for use in an electronic device, for example, an organic light-emitting device (in one embodiment, an organic light-emitting device that emits blue light). In addition, the number of cyano groups included in $L_{11}$-$L_{12}$ may be adjusted so as to appropriately adjust the LUMO energy level and/or the HOMO energy level. In addition, since the condensed cyclic compound represented by Formula 1 may have a relatively high lowest excitation triplet energy ($T_1$) level and excellent electron mobility characteristics, an electronic device, for example, an organic light-emitting device (in one embodiment, an organic light-emitting device that emits blue light) may have a high luminescent efficiency and/or a long lifespan.

Since the condensed cyclic compound represented by Formula 1 includes a cyano group in $A_{11}$, $A_{12}$, or a combination thereof, the condensed cyclic compound represented by Formula 1 may have an improved glass transition temperature (Tg) and/or improved thermal decomposition temperature (Td), thereby providing improved thermal stability. In addition, the condensed cyclic compound represented by Formula 1 may have a relatively high lowest excitation triplet energy ($T_1$) level and excellent electron mobility characteristics. In the case of the compound that does not include a cyano group on $A_{11}$, $A_{12}$, or a combination thereof, it is difficult to secure electron mobility characteristics or thermal characteristics suitable for use as a host material of an electronic device, for example, an organic light-emitting device (in one embodiment, an organic light-emitting device that emits blue light).

Since the condensed cyclic compound represented by Formula 1 includes $A_{11}$ and $A_{12}$, the condensed cyclic compound represented by Formula 1 may have appropriate hole mobility characteristics and provide improved thermal stability. In addition, since the condensed cyclic compound represented by Formula 1 has an "asymmetrical" structure that includes $A_{11}$ and $A_{12}$, the condensed cyclic compound represented by Formula 1 may have relatively excellent amorphous thin film characteristics. On the other hand, since crystallinity of the compound having a "symmetrical" structure increases, a material in a thin film may forms a crystal in a process such a panel manufacturing process, thereby deteriorating device characteristics.

Since the condensed cyclic compound represented by Formula 1 includes a bicarbazole in $A_{12}$, it is possible to three-dimensionally protect $L_{11}$-$L_{12}$ and improve electric stability of $L_{11}$-$L_{12}$.

In addition, since the condensed cyclic compound represented by Formula 1 includes bicarbazole in $A_{12}$, the condensed cyclic compound represented by Formula 1 may have a relatively high lowest excitation triplet energy ($T_1$) level, a relatively low lowest singlet energy ($S_1$) level, improved optical stability, improved thermal stability, and improved electron mobility characteristics. Therefore, an electronic device, for example, an organic light-emitting device (in one embodiment, an organic light-emitting device that emits blue light), which includes the condensed cyclic compound represented by Formula 1, may have high luminescent efficiency and/or a long lifespan.

As described above, the condensed cyclic compound represented by Formula 1 may have electric characteristics suitable for use as a material for manufacturing an organic light-emitting device, for example, a host material in an emission layer, particularly, a blue light-emitting diode. Therefore, an organic light-emitting device including the condensed cyclic compound may have high efficiency and/or a long lifespan.

In an exemplary embodiment, the HOMO energy level, LUMO energy level, $T_1$ energy level, and $S_1$ energy level of some Compounds were evaluated by a density functional theory (DFT) method of Gaussian program (structurally optimized at a level of B3LYP, 6-31G(d,p)), and results thereof are shown in Table 1.

TABLE 1

| Compound No. | HOMO (eV) | LUMO (eV) | $T_1$ (eV) | $S_1$ (eV) |
| --- | --- | --- | --- | --- |
| 245 | −5.346 | −2.095 | 2.850 | 2.895 |
| 275 | −5.639 | −2.037 | 2.869 | 3.200 |
| 406 | −5.346 | −2.026 | 2.912 | 2.934 |
| 563 | −5.301 | −2.133 | 2.810 | 2.897 |
| 587 | −5.422 | −2.057 | 2.952 | 3.084 |
| 593 | −5.669 | −1.973 | 2.965 | 3.216 |
| 723 | −5.305 | −2.137 | 2.870 | 2.888 |
| 724 | −5.181 | −2.157 | 2.718 | 2.732 |
| 726 | −5.329 | −2.085 | 2.831 | 2.880 |
| 753 | −5.409 | −2.040 | 2.970 | 3.068 |
| 754 | −5.452 | −2.152 | 2.922 | 2.951 |
| 755 | −5.669 | −1.972 | 2.989 | 3.202 |
| 756 | −5.644 | −2.042 | 3.029 | 3.166 |
| 757 | −5.392 | −2.442 | 2.613 | 2.635 |
| 1041 | −5.176 | −2.055 | 2.852 | 2.874 |
| A | −5.220 | −1.515 | 3.118 | 3.362 |
| B | −5.263 | −1.919 | 2.912 | 2.973 |
| C | −5.333 | −2.141 | 2.792 | 2.834 |
| D | −5.779 | −1.977 | 2.984 | 3.200 |
| E | −5.222 | −1.888 | 2.996 | 3.045 |
| F | −5.306 | −2.227 | 2.786 | 2.802 |

TABLE 1-continued
| Compound No. | HOMO (eV) | LUMO (eV) | T₁ (eV) | S₁ (eV) |
|---|---|---|---|---|
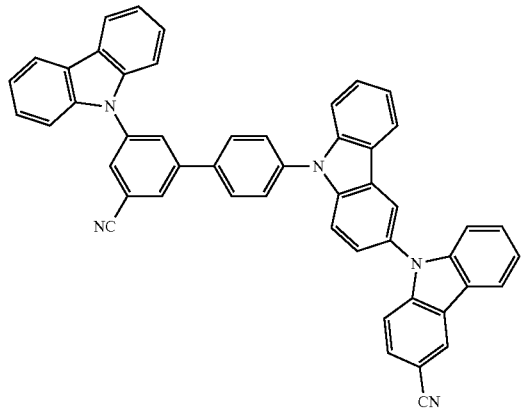
593
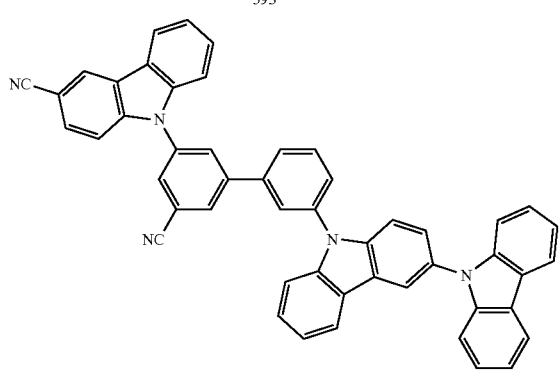
723
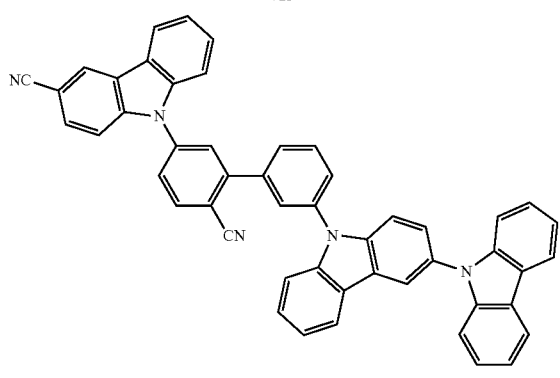
724
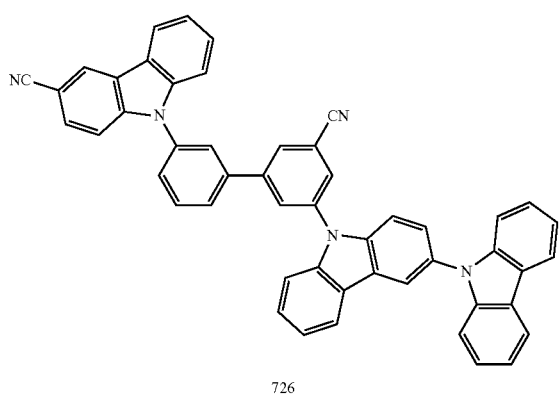 [SMILES: N#Cc1cc(-c2cccc(-n3c4ccccc4c4cc(C#N)ccc43)c2)cc(-n2c3ccccc3c3cc(-n4c5ccccc5c5ccccc54)ccc32)c1]
726
TABLE 1-continued
| Compound No. | HOMO (eV) | LUMO (eV) | T₁ (eV) | S₁ (eV) |
|---|---|---|---|---|
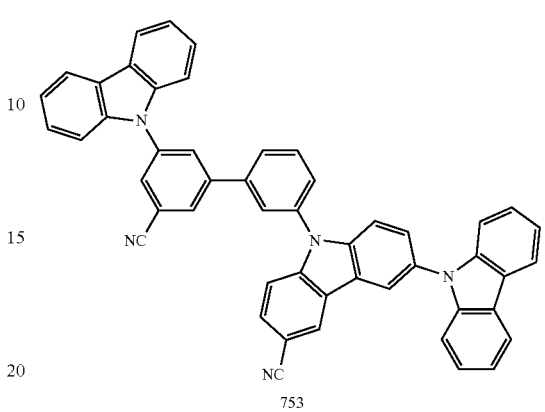
753
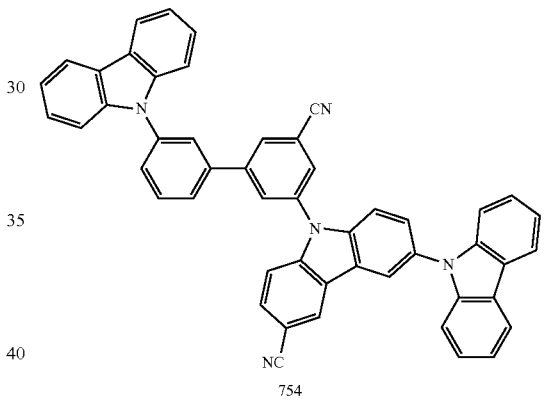
754
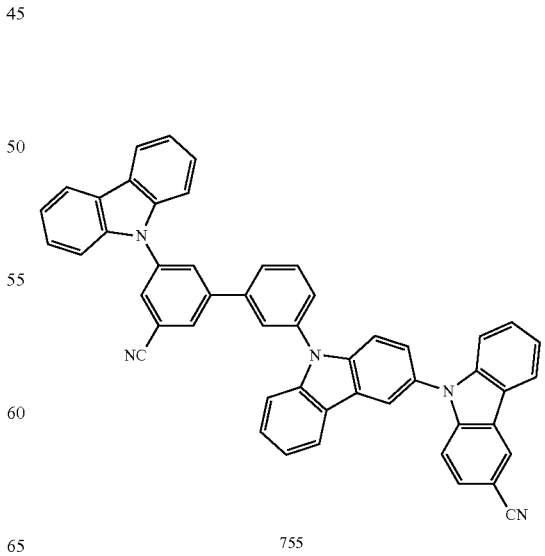
755

TABLE 1-continued
| Compound No. | HOMO (eV) | LUMO (eV) | T₁ (eV) | S₁ (eV) |
|---|---|---|---|---|
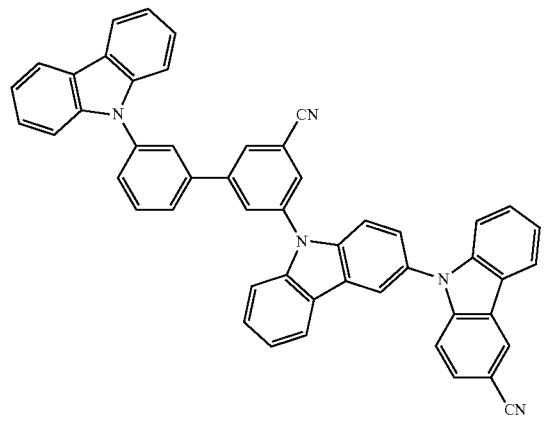
756
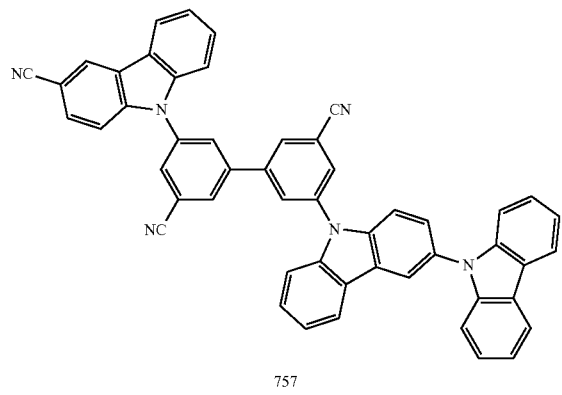 [SMILES: N#Cc1cc(-c2cc(C#N)cc(-n3c4ccccc4c4cc(-n5c6ccccc6c6ccccc65)ccc43)c2)cc(-n2c3ccccc3c3cc(C#N)ccc32)c1]
757
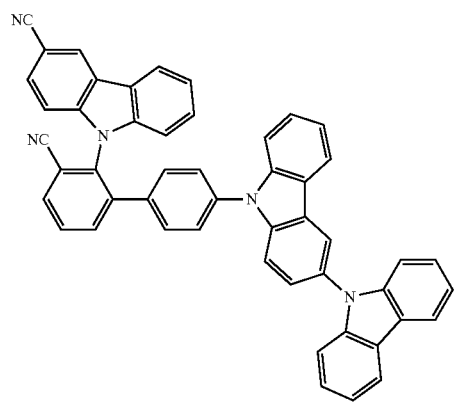
1041
TABLE 1-continued
| Compound No. | HOMO (eV) | LUMO (eV) | T₁ (eV) | S₁ (eV) |
|---|---|---|---|---|
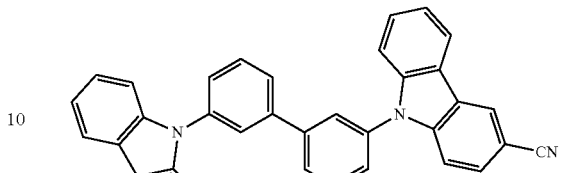
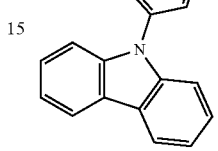
A
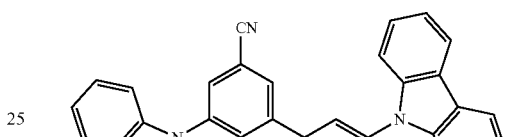
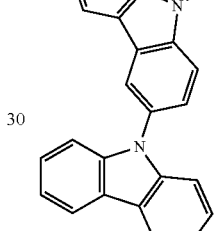
B
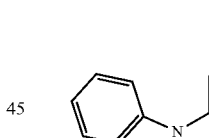
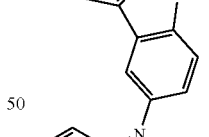
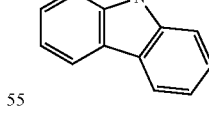
C
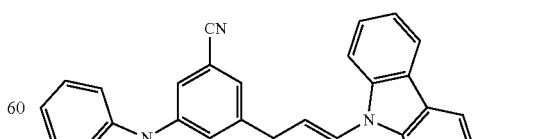
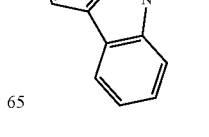
D TABLE 1-continued

| Compound No. | HOMO (eV) | LUMO (eV) | T$_1$ (eV) | S$_1$ (eV) |
|---|---|---|---|---|

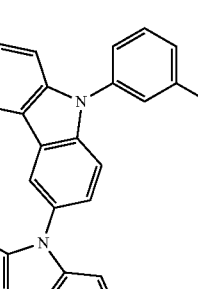

E

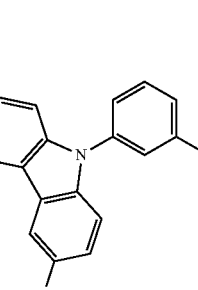

F

Referring to Table 1, it is confirmed that the compounds represented by Formula 1 have a relatively high T$_1$ energy level and a relatively low S$_1$ energy level. Therefore, it is confirmed that the electronic device, for example, the organic light-emitting device, which includes the compound represented by Formula 1, may have high luminescent efficiency.

Synthesis methods of the condensed compound resented by Formula 1 may be understood by one of ordinary skill in the art by referring to Synthesis Examples provided below.

Another aspect of the present disclosure, a composition includes:
a first compound; and
a second compound, wherein
the first compound may be a condensed cyclic compound represented by Formula 1,
the second compound may include a carbazole group, a dibenzofuran group, a dibenzothiophene group, an indenocarbazole group, an indolocarbazole group, a benzofurocarbazole group, a benzothienocarbazole group, an acridine group, a dihydroacridine group, a triindolobenzene group, or a combination thereof, but does not include an electron withdrawing group,
the electron withdrawing group may be:
—F, —CFH$_2$, —CF$_2$H, —CF$_3$, —ON, or —NO$_2$;
a C$_1$-C$_{60}$ alkyl group substituted with —F, —CFH$_2$, —CF$_2$H, —CF$_3$, —CN, —NO$_2$, or a combination thereof;
a C$_1$-C$_{60}$ heteroaryl group or a monovalent non-aromatic condensed polycyclic heterocyclic group, each of which includes *=N—*' as a ring-forming moiety; or
a C$_1$-C$_{60}$ heteroaryl group or a monovalent non-aromatic condensed polycyclic heterocyclic group, each substituted with deuterium, —F, —CFH$_2$, —CF$_2$H, —CF$_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_2$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, or a combination thereof, and each of which includes *=N—*' as a ring-forming moiety.

In an exemplary embodiment, the composition may be used in forming an organic layer of an electronic device (for example, an organic light-emitting device).

In the composition, the first compound may be an electron transport material, and the second compound may be a hole transport material.

In one embodiment, the composition is the first compound and the second compound, but embodiments of the present disclosure are not limited thereto.

In the composition, the condensed cyclic compound represented by Formula 1, which may be the first compound, may be understood by referring to the description provided herein.

In an exemplary embodiment, in the composition, the second compound may be a compound represented by Formula H-1:

Formula H-1

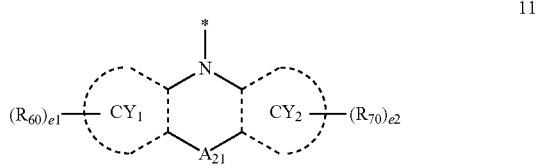

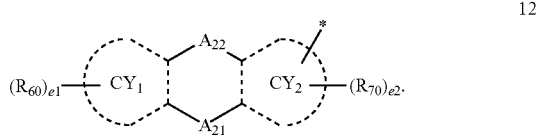

In Formulae H-1, 11 and 12, $L_1$ may be:
- a single bond, a phenylene group, a naphthylene group, a fluorenylene group, a carbazolylene group, a dibenzofuranylene group, or a dibenzothiophenylene group; or
- a phenylene group, a naphthylene group, a fluorenylene group, a carbazolylene group, a dibenzofuranylene group, and a dibenzothiophenylene group, each substituted deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a biphenyl group, or —Si$(Q_{11})(Q_{12})(Q_{13})$, d1 may be an integer from 1 to 10, wherein, when d1 is two or more, two or more $L_1$ may be identical to or different from each other, $Ar_{11}$ may be a group represented by Formulae 11 or 12,
$Ar_{12}$ may be:
- a group represented by Formulae 11 or 12, a phenyl group, or a naphthyl group; or
- a phenyl group and a naphthyl group, each substituted with deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, or a biphenyl group, $CY_1$ and $CY_2$ may each independently be a benzene group, a naphthalene group, a fluorene group, a carbazole group, a benzocarbazole group, an indolocarbazole group, a dibenzofuran group, a dibenzothiophene group, or a dibenzosilole group, $A_{21}$ may be a single bond, O, S, N($R_{51}$), C($R_{51}$)($R_{52}$), or Si($R_{51}$)($R_{52}$), $A_{22}$ may be a single bond, O, S, N($R_{53}$), C($R_{53}$)($R_{54}$), or Si($R_{53}$)($R_{54}$), $A_{21}$, $A_{22}$, or a combination thereof in Formula 12 may not be a single bond, $R_{51}$ to $R_{54}$, $R_{60}$, and $R_{70}$ may each independently be:
  hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;
  - a $C_1$-$C_{20}$ alkyl group or a $C_1$-$C_{20}$ alkoxy group, each substituted with deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, or a combination thereof;
  - a phenyl group, a naphthyl group, a fluorenyl group, a carbazolyl group, a dibenzofuranyl group, or a dibenzothiophenyl group;
  - a phenyl group, a naphthyl group, a fluorenyl group, a carbazolyl group, a dibenzofuranyl group, or a dibenzothiophenyl group, each substituted with deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, or a combination thereof; or
  —Si$(Q_1)(Q_2)(Q_3)$, e1 and e2 may each independently be an integer from 0 to 10, $Q_1$ to $Q_3$ and $Q_{11}$ to $Q_{13}$ may each independently be hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, or a biphenyl group, and

* indicates a binding site to a neighboring atom.

In an exemplary embodiment, $CY_1$, $CY_2$, or a combination thereof in Formulae 11 and 12 may be a benzene group, but embodiments of the present disclosure are not limited thereto.

In one embodiment, in Formula H-1, $Ar_{11}$ may be a group represented by Formulae 11-1 to 11-8 or 12-1 to 12-8, and $Ar_{12}$ may be:
- a group represented by Formulae 11-1 to 11-8 or 12-1 to 12-8, a phenyl group, or a naphthyl group; or
- a phenyl group or a naphthyl group, each substituted with deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, or a combination thereof, but embodiments of the present disclosure are not limited thereto:

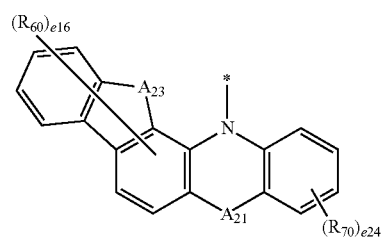

11-1

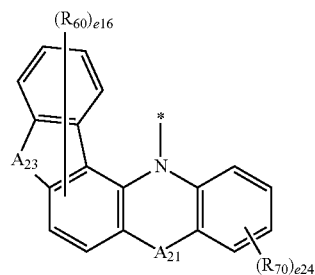

11-2

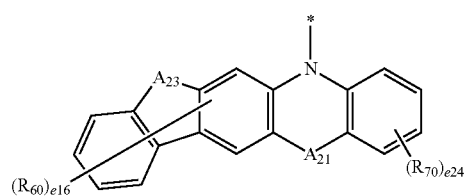

11-3

495
-continued
11-4
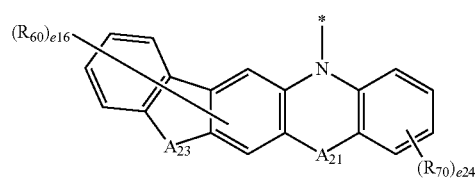
11-5
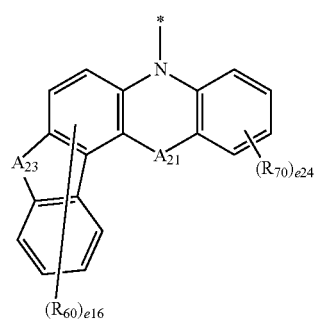
11-6
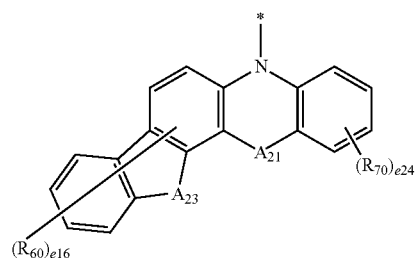
11-7
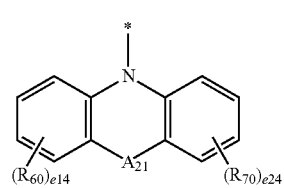
11-8
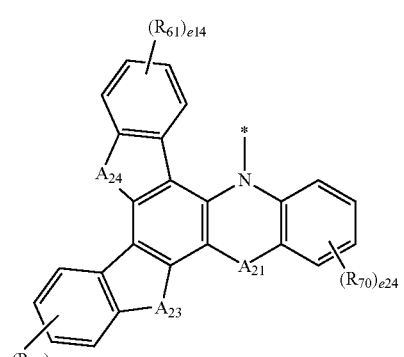
12-1
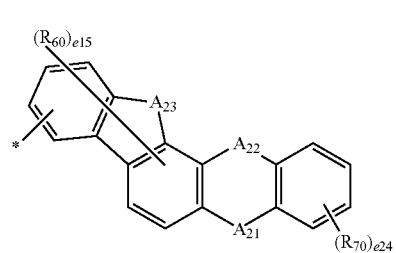
496
-continued
12-2
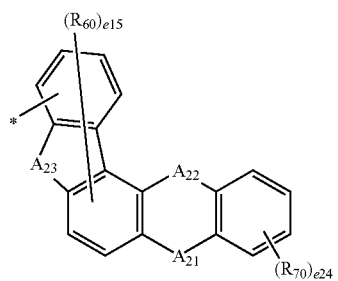
12-3
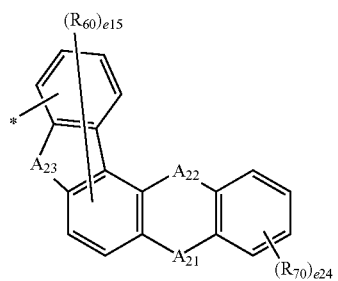
12-4
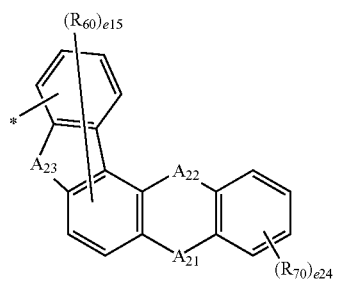
12-5
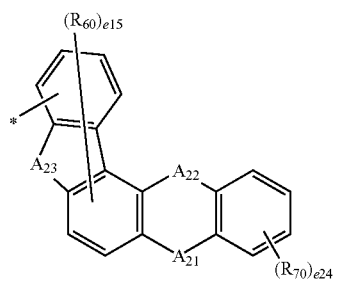
12-6
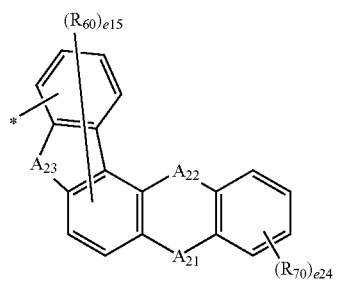
12-7
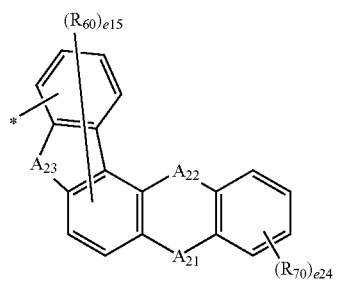

-continued

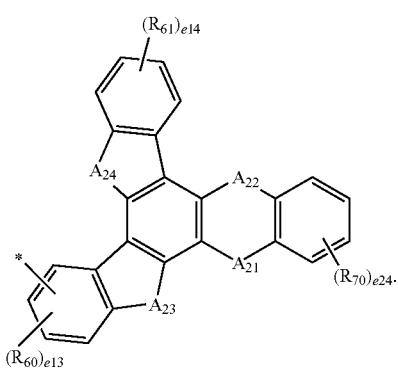
12-8

In Formulae 11-1 to 11-8 and 12-1 to 12-8, $A_{23}$ may be O, S, $N(R_{55})$, $C(R_{55})(R_{56})$, or $Si(R_{55})(R_{56})$, $A_{24}$ may be O, S, $N(R_{57})$, $C(R_{57})(R_{58})$, or $Si(R_{57})(R_{58})$, $A_{21}$, $A_{22}$, $R_{60}$, and $R_{70}$ are each independently the same as described herein, $R_{55}$ to $R_{58}$ may each independently be the same as defined in connection with $R_{51}$, e16 may be an integer from 0 to 6, e15 may be an integer from 0 to 5, e14 may be an integer from 0 to 4, e13 may be an integer from 0 to 3, e24 may be an integer from 0 to 4, and

* indicates a binding site to a neighboring atom.

In one or more embodiments, in the composition, i) the second compound may be represented by Formula H-1, wherein $L_1$ in Formula H-1 may be a single bond; or ii) the second compound may be a compound represented by Formulae H-1(1) to H-1(52), but embodiments of the present disclosure are not limited thereto:

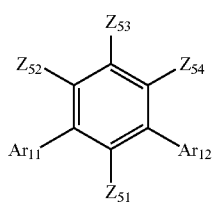
H-1(1)

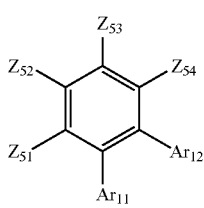
H-1(2)

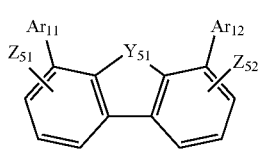
H-1(3)

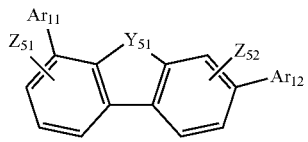
H-1(4)

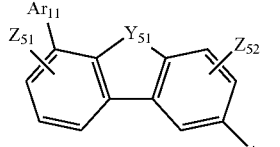
H-1(5)

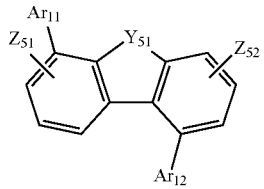
H-1(6)

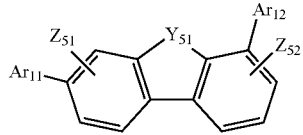
H-1(7)

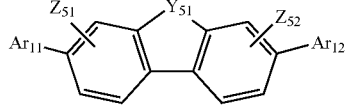
H-1(8)

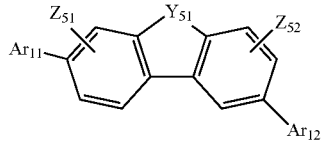
H-1(9)

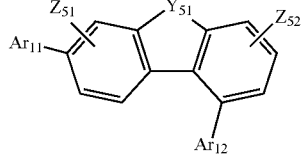
H-1(10)

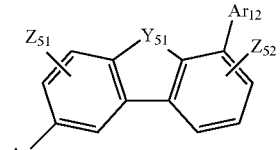
H-1(11)

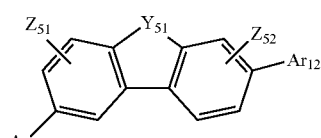
H-1(12)

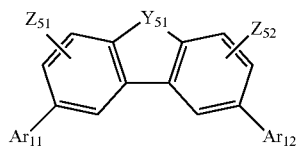
H-1(13)

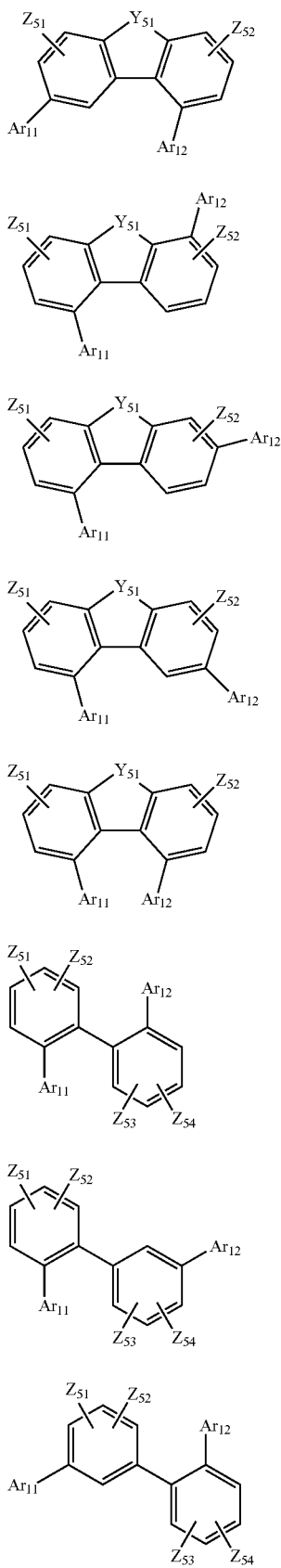
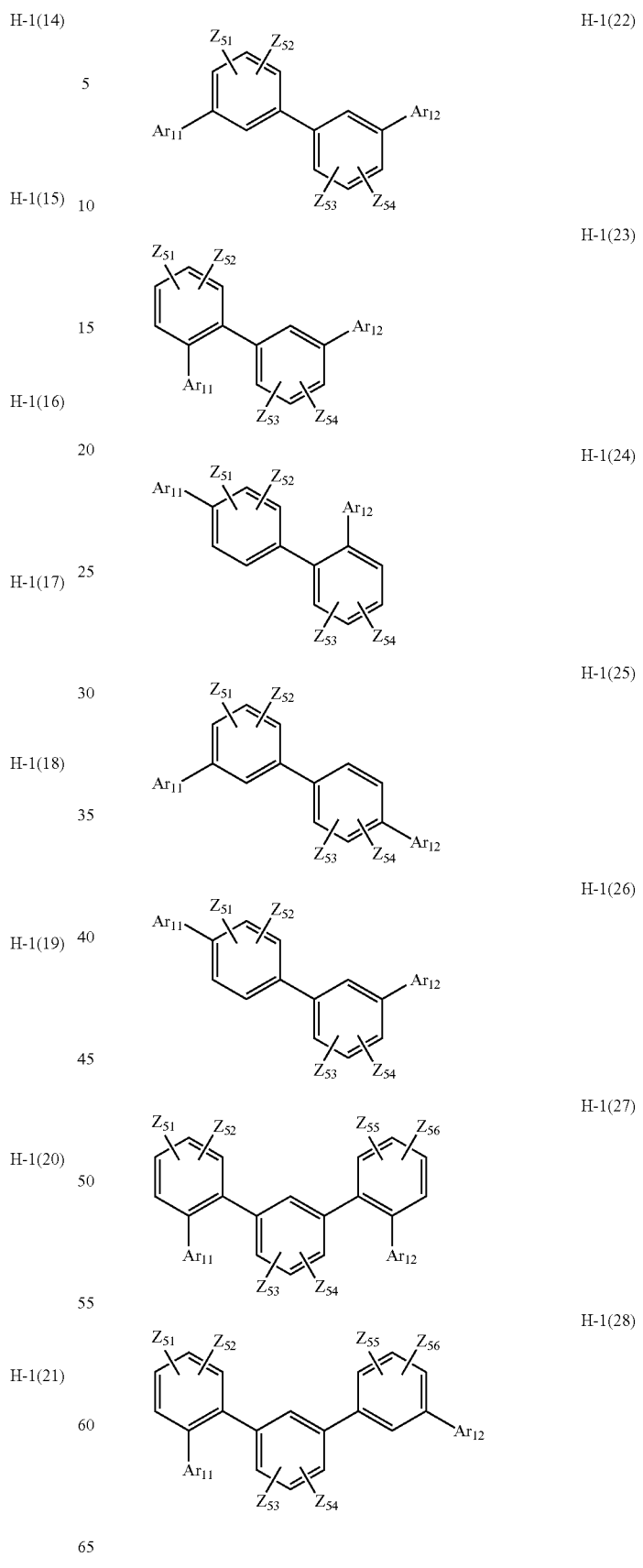

501
-continued
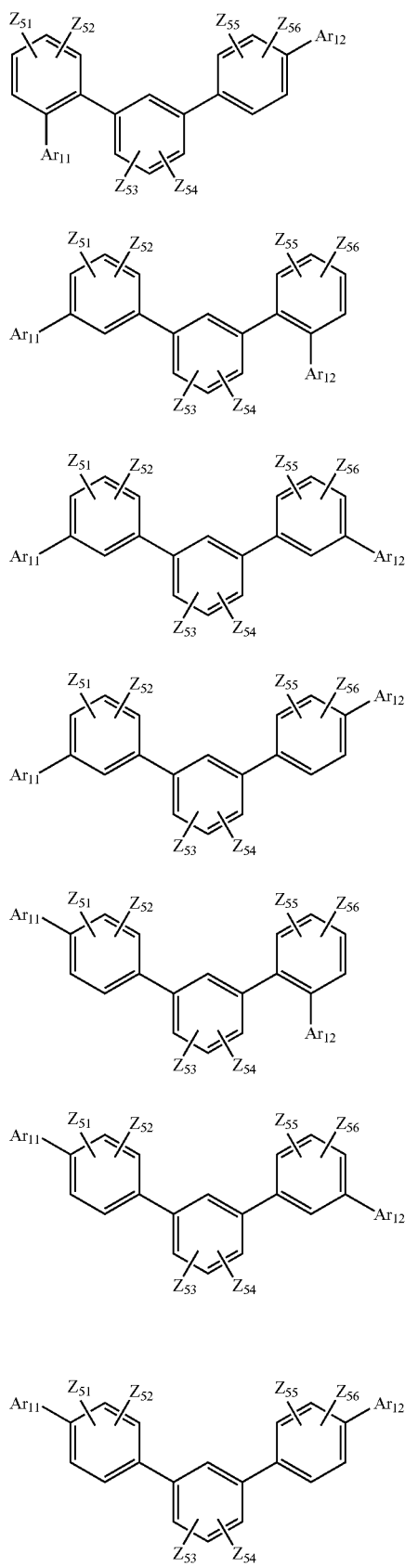
H-1(29)
H-1(30)
H-1(31)
H-1(32)
H-1(33)
H-1(34)
H-1(35)
502
-continued
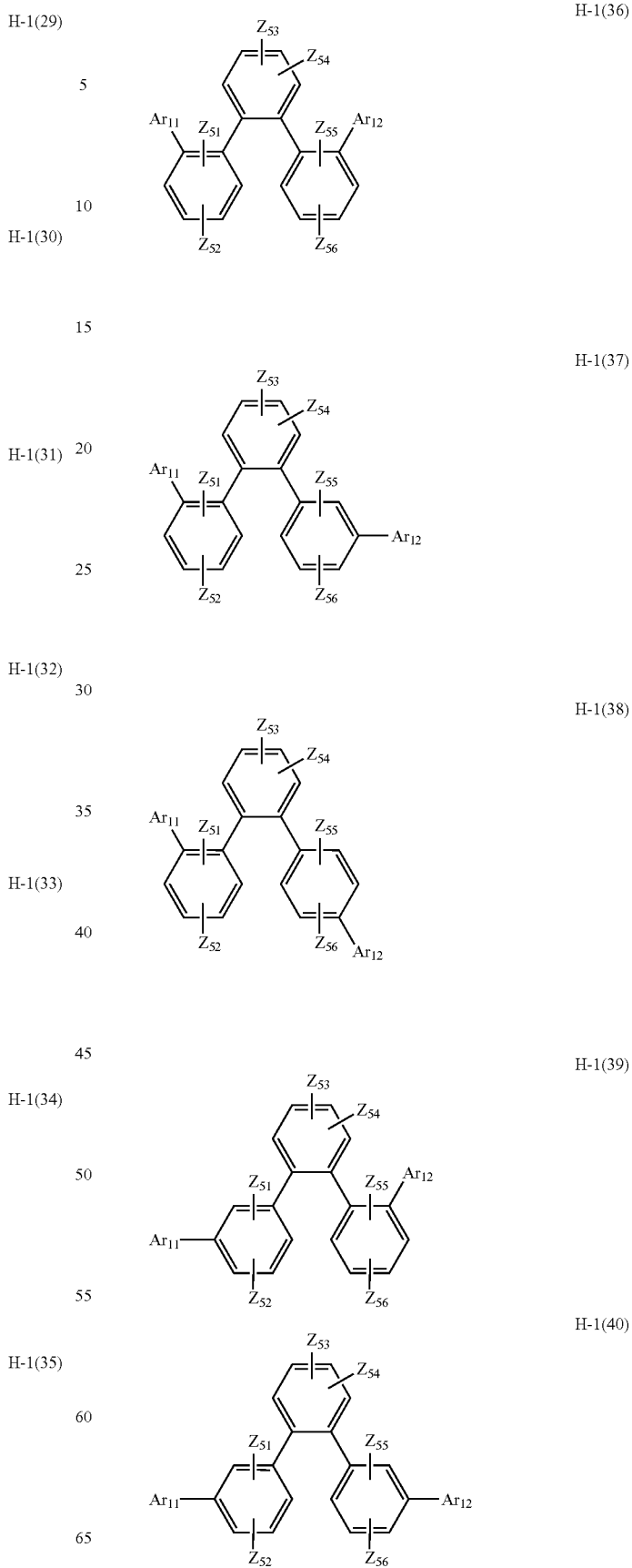
H-1(36)
H-1(37)
H-1(38)
H-1(39)
H-1(40)

H-1(41)

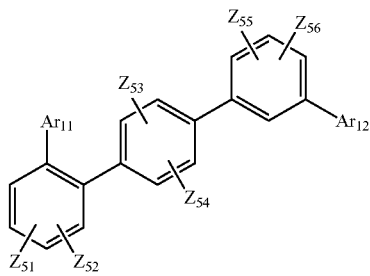

H-1(42)

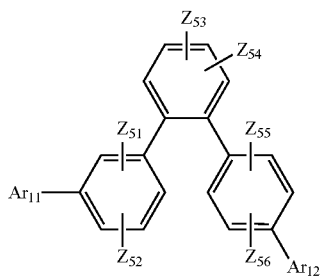

H-1(43)

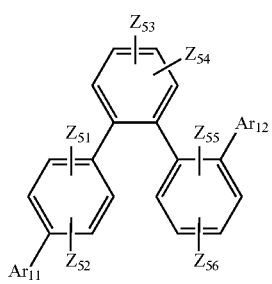

H-1(44)

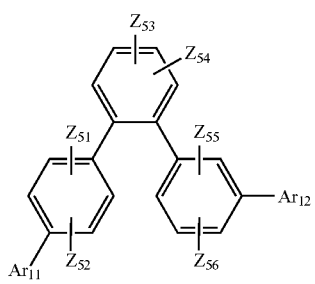

H-1(45)

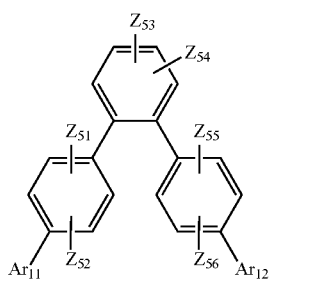

H-1(46)

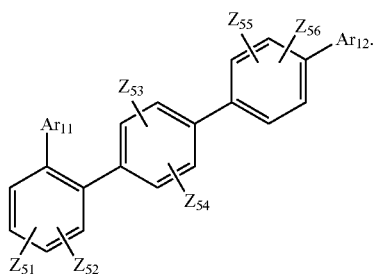

H-1(47)

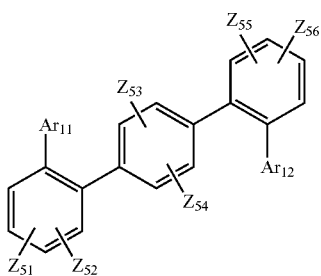

In Formulae H-1(1) to H-1(52),

Ar$_{11}$ and Ar$_{12}$ are the same as described above,

Y$_{51}$ may be C(Z$_{53}$)(Z$_{54}$), Si(Z$_{53}$)(Z$_{54}$), N(Z$_{55}$), O, or S, Z$_{51}$ to Z$_{56}$ may each independently be hydrogen, deuterium, a C$_1$-C$_{10}$ alkyl group, a C$_1$-C$_{10}$ alkoxy group, a phenyl group, a naphthyl group, a fluorenyl group, a carbazolyl group, a dibenzofuranyl group, a dibenzothiophenyl group, a biphenyl group, or —Si(Q$_{11}$)(Q$_{12}$)(Q$_{13}$), Q$_{11}$ to Q$_{13}$ may each independently be hydrogen, a C$_1$-C$_{10}$ alkyl group, a C$_1$-C$_{10}$ alkoxy group, a phenyl group, or a naphthyl group, but embodiments of the present disclosure are not limited thereto.

In one embodiment, the second compound in the composition may be one of Compounds H-1 to H-41, but embodiments of the present disclosure are not limited thereto:

H-1

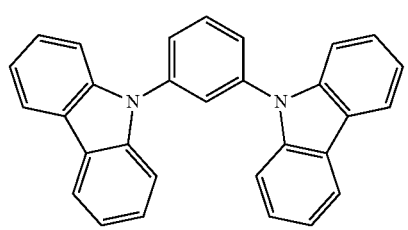

H-2

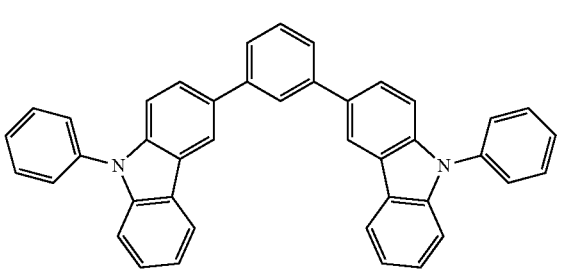

H-3
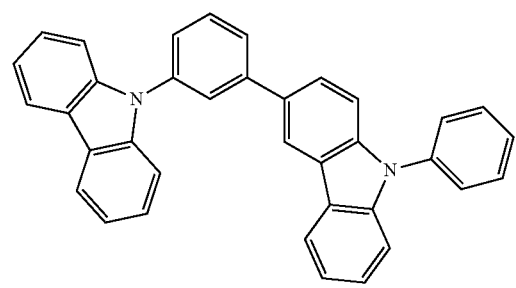
H-4
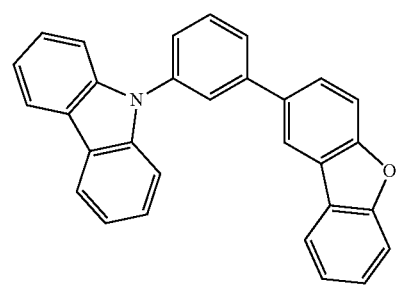
H-5
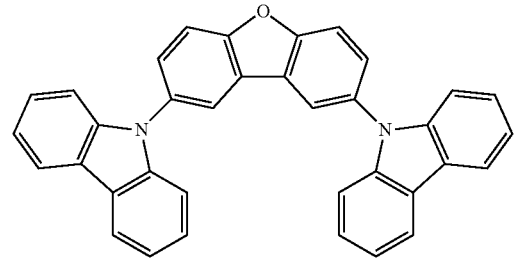
H-6
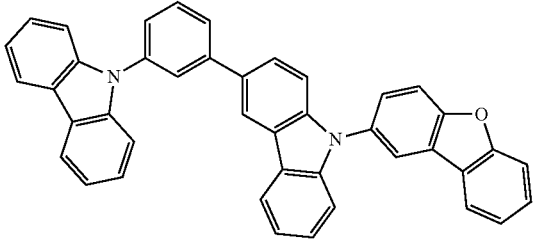
H-7
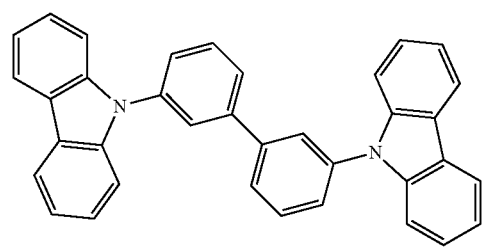
H-8
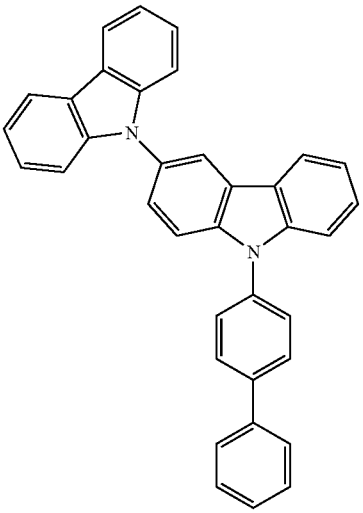
H-9
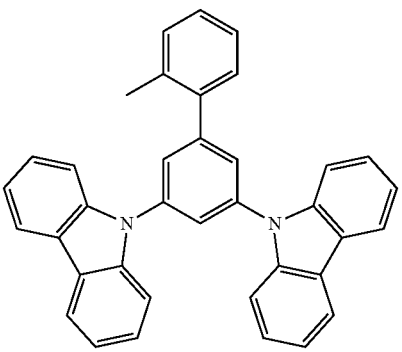
H-10
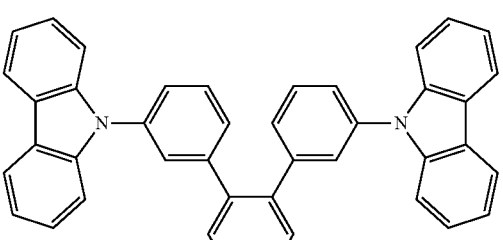
H-11
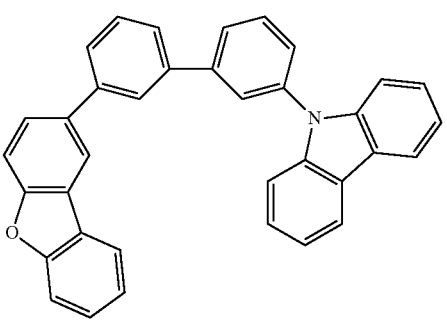

-continued
H-12
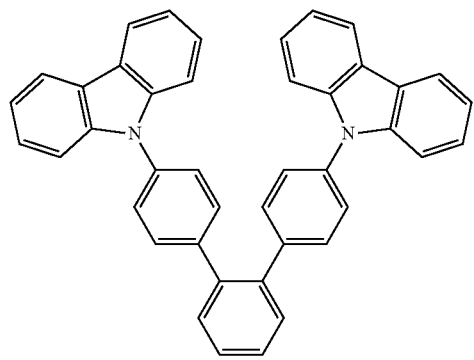
H-13
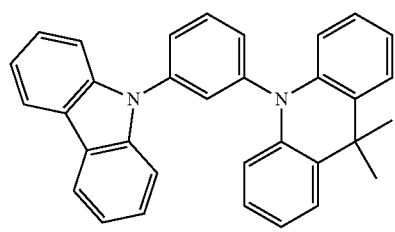
H-14
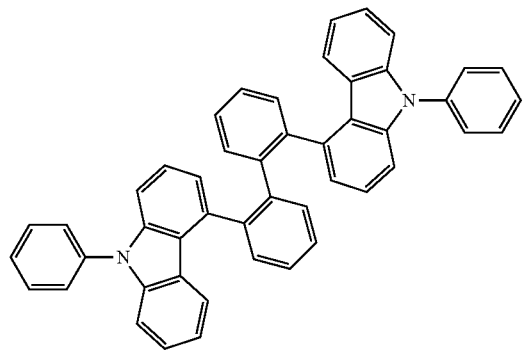
H-15
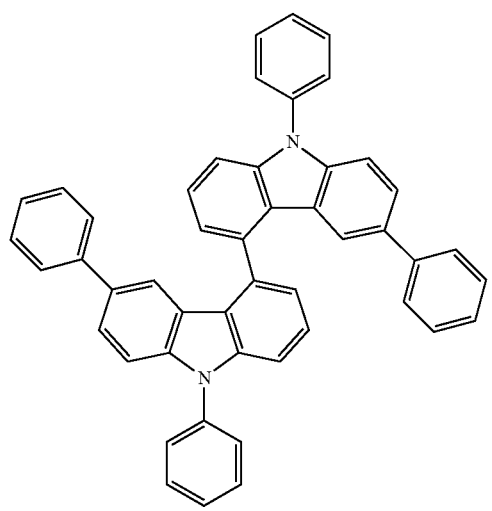
-continued
H-16
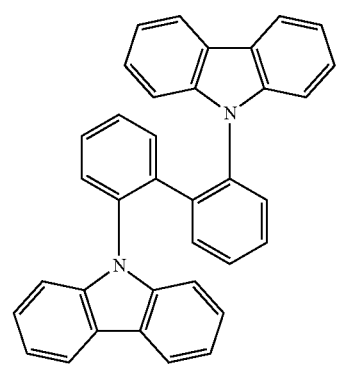
H-17
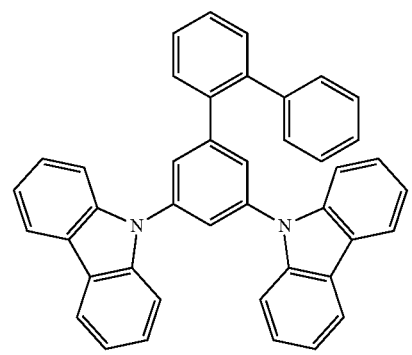
H-18
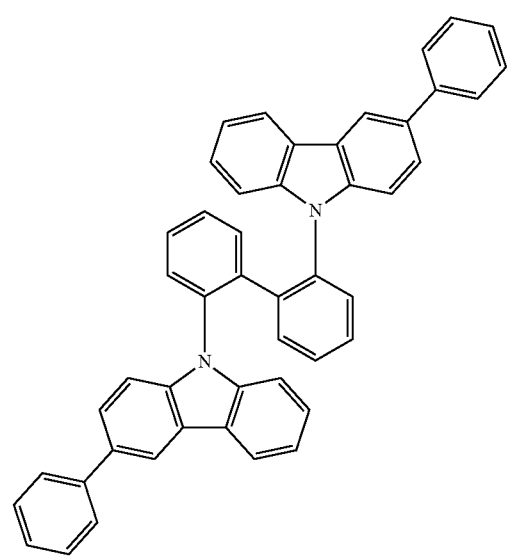
H-19
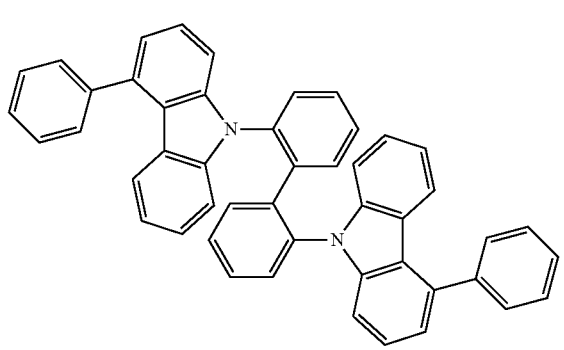

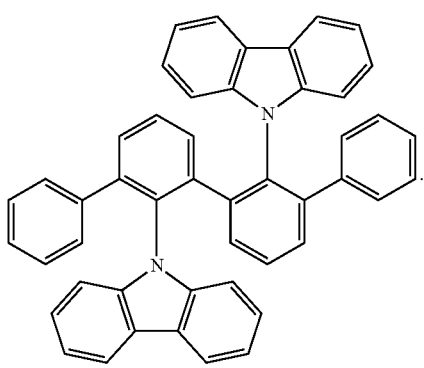

H-20

A weight ratio of the first compound to the second compound in the composition may be in a range of 1:99 to 99:1, for example, 70:30 to 30:70. In an exemplary embodiment, a weight ratio of the first compound to the second compound in the composition may be in a range of 40:60 to about 60:40, but embodiments of the present disclosure are not limited thereto. When the weight ratio of the first compound and the second compound in the composition is satisfied within the ranges above, the composition may exhibit excellent charge transfer balance.

A condensed cyclic compound represented by Formula 1 or a composition including a first compound and a second compound may be suitable for use as an organic layer of an organic light-emitting device, and for example, may be used as a material for forming an emission layer and/or a material for forming an electron transport region. Therefore, according to another aspect of the present disclosure, an organic light-emitting device includes: a first electrode, a second electrode, and an organic layer disposed between the first electrode and the second electrode, the organic layer including an emission layer and a condensed cyclic compound represented by Formula 1 described above or a composition described above.

The organic light-emitting device may have, due to the inclusion of an organic layer including a condensed cyclic compound represented by Formula 1 or a composition including a first compound and a second compound, low driving voltage, high efficiency, high brightness, high quantum emission efficiency, and a long lifespan.

In one embodiment, in the organic light-emitting device,
the first electrode may be an anode, and the second electrode may be a cathode,
the organic layer may include a hole transport region disposed between the first electrode and the emission layer and an electron transport region disposed between the emission layer and the second electrode,
the hole transport region may include a hole injection layer, a hole transport layer, an electron blocking layer, a buffer layer, or any combination thereof, and
the electron transport region may include a hole blocking layer, an electron transport layer, an electron injection layer, or any combination thereof, but embodiments of the present disclosure are not limited thereto.

In an exemplary embodiment, the emission layer in the organic light-emitting device may include a condensed cyclic compound represented by Formula 1, or may include a composition including a first compound and a second compound as described above.

In one embodiment, the emission layer in the organic light-emitting device may include a host and a dopant, wherein the host may include a condensed cyclic compound represented by Formula 1, or may include a composition including a first compound and a second compound as described above, and the dopant may include a phosphorescent dopant or a fluorescent dopant. In an exemplary embodiment, the dopant may include a phosphorescent dopant (for example, the organometallic compound represented by Formula 81). The condensed cyclic compound included in the host may transfer energy to the dopant due to a delayed fluorescence emission mechanism. An amount of the host in the emission layer may be larger than an amount of the dopant in the emission layer. The host may further include an arbitrary host in addition to a condensed cyclic compound represented by Formula 1 or a composition including a first compound and a second compound.

In one or more embodiments, the emission layer of the organic light-emitting device may include a host and a dopant, and the dopant may include a condensed cyclic compound represented by Formula 1. The condensed cyclic compound included in the dopant may act as an emitter that emits delayed fluorescence due to a delayed fluorescence emission mechanism. Alternatively, the dopant may further include a known arbitrary light-emitting dopant, and the condensed cyclic compound may act as an auxiliary dopant that transfers energy to the light-emitting dopant due to a delayed fluorescence emission mechanism. An amount of the host in the emission layer may be larger than an amount of the dopant in the emission layer. The host may include an arbitrary host.

The emission layer may emit red light, green light, or blue light. In an exemplary embodiment, the emission layer may emit blue light.

In one or more embodiments, the emission layer may be a blue light emission layer including a phosphorescent dopant.

In one embodiment, a condensed cyclic compound represented by Formula 1 may be included in the electron transport region of the organic light-emitting device electron transport region.

In an exemplary embodiment, the hole transport region may include a hole blocking layer, an electron transport layer, or a combination thereof, wherein the hole blocking layer, the electron transport layer, or the combination thereof may include a condensed cyclic compound represented by Formula 1.

In one embodiment, the electron transport region of the organic light-emitting device may include a hole blocking layer, wherein the hole blocking layer includes a compound represented by Formula 1. The hole blocking layer may be in direct contact with the emission layer.

In one or more embodiments, the electron transport region may include a hole blocking layer and an electron transport layer, wherein the hole blocking layer may be disposed between the emission layer and the electron transport layer, and the hole blocking layer may include a condensed cyclic compound represented by Formula 1.

In one or more embodiments, the organic layer of the organic light-emitting device may further include, in addition to a condensed cyclic compound represented by Formula 1,
i) a second compound described above;
ii) an organometallic compound represented by Formula 81; or
iii) any combination thereof:

$$M(L_{81})_{n81}(L_{82})_{n82}$$ Formula 81

In Formula 81,

M may be iridium (Ir), platinum (Pt), osmium (Os), titanium (Ti), zirconium (Zr), hafnium (Hf), europium (Eu), terbium (Tb), thulium (Tm), or rhodium (Rh), $L_{81}$ may be a ligand represented by Formula 81A,

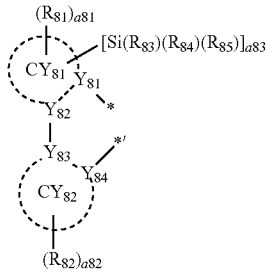

Formula 81A

In Formula 81, n81 may be an integer from 1 to 3, wherein, when n81 is two or more, two or more $L_{81}$ may be identical to or different from each other, and $L_{82}$ may be an organic ligand, and n82 may be an integer from 0 to 4, wherein, when n82 is two or more, two or more $L_{82}$ may be identical to or different from each other, In Formula 81A, $Y_{81}$ to $Y_{84}$ may each independently be carbon or nitrogen, $Y_{81}$ and $Y_{82}$ may be linked via a single bond or a double bond, and $Y_{83}$ and $Y_{84}$ may be linked via a single bond or a double bond, $CY_{81}$ and $CY_{82}$ may each independently be a $C_5$-$C_{60}$ carbocyclic group or a $C_2$-$C_{60}$ heterocyclic group, $CY_{81}$ and $CY_{82}$ may optionally be further linked via an organic linking group, $R_{81}$ to $R_{85}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_{81}$)(Q$_{82}$)(Q$_{83}$), —N(Q$_{84}$)(Q$_{85}$), —B(Q$_{86}$)(Q$_{87}$), or —P(=O)(Q$_{88}$)(Q$_{89}$), a81 to a83 may each independently be an integer from 0 to 5, wherein when a81 is two or more, two or more $R_{81}$ may be identical to or different from each other, when a82 is two or more, two or more $R_{82}$ may be identical to or different from each other, when a81 is two or more, two neighboring $R_{81}$ may optionally be linked to form a saturated or unsaturated $C_2$-$C_{30}$ ring (for example, a benzene ring, a cyclopentane ring, a cyclohexane ring, a cyclopentene ring, a cyclohexene ring, a norbornane ring, a bicyclo[2.2.1]heptane ring, a naphthalene ring, a indene ring, a indole ring, a benzofuran ring, a benzothiophene ring, a pyridine ring, a pyrimidine ring, or a pyrazine ring), or a saturated or unsaturated $C_2$-$C_{30}$ ring substituted with a $R_{88}$ (for example, a benzene ring, a cyclopentane ring, a cyclohexane ring, a cyclopentene ring, a cyclohexene ring, a norbornane ring, a bicyclo[2.2.1]heptane ring, a naphthalene ring, a indene ring, a indole ring, a benzofuran ring, a benzothiophene ring, a pyridine ring, a pyrimidine ring, or a pyrazine ring, each substituted with a $R_{88}$), when a82 is two or more, two neighboring $R_{82}$ may optionally be linked to form a saturated or unsaturated $C_2$-$C_{30}$ ring (for example, a benzene ring, a cyclopentane ring, a cyclohexane ring, a cyclopentene ring, a cyclohexene ring, a norbornane ring, a bicyclo[2.2.1]heptane ring, a naphthalene ring, a indene ring, a indole ring, a benzofuran ring, a benzothiophene ring, a pyridine ring, a pyrimidine ring, or a pyrazine ring), or a saturated or unsaturated $C_2$-$C_{30}$ ring substituted at least one $R_{89}$ (for example, a benzene ring, a cyclopentane ring, a cyclohexane ring, a cyclopentene ring, a cyclohexene ring, a norbornane ring, a bicyclo[2.2.1]heptane ring, a naphthalene ring, a indene ring, a indole ring, a benzofuran ring, a benzothiophene ring, a pyridine ring, a pyrimidine ring, or a pyrazine ring, each substituted a $R_{89}$), $R_{88}$ may be the same as defined in connection with $R_{81}$, $R_{89}$ may be the same as defined in connection with $R_{82}$, and *' in Formula 81A each indicate a binding site to M in Formula 81, a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group may be deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si(Q$_{91}$)(Q$_{92}$)(Q$_{93}$), or a combination thereof, and $Q_{81}$ to $Q_{89}$ and $Q_{91}$ to $Q_{93}$ may each independently be hydrogen, deuterium, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

In one embodiment, in Formula 81A,
a83 may be 1 or 2, and,
$R_{83}$ to $R_{85}$ may each independently be:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$;
an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group; or
an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each substituted with deuterium, a $C_1$-$C_{10}$ alkyl group, a phenyl group, or a combination thereof, but embodiments of the present disclosure are not limited thereto.

In one or more embodiments, in Formula 81A,
$Y_{81}$ may be nitrogen,
$Y_{82}$ and $Y_{83}$ may each independently be carbon,
$Y_{84}$ may be nitrogen or carbon, and
$CY_{81}$ and $CY_{82}$ may each independently be a cyclopentadiene group, a benzene group, a heptalene group, an indene group, a naphthalene group, an azulene group, a heptalene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a corogen group, an ovalene group, a pyrrole group, an isoindole group, an indole group, an indazole group, a pyrazole group, an imidazole group, a triazole group, an oxazole group, an isoxazole group, an oxadiazole group, a thiazole group, an isothiazole group, a thiadiazole group, a purine group, a furan group, a thiophene group, a pyridine group, a pyrimidine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzofuran group, a benzothiophene group, an isobenzothiazole group, a benzoxazole group, an isobenzoxazole group, a benzocarbazole group, a dibenzocarbazole group, an imidazopyridine group, an imidazopyrimidine group, a dibenzofuran group, a dibenzothiophene group, a dibenzothiophene sulfone group, a carbazole group, a dibenzosilole group, or a 2,3-dihydro-1H-imidazole group.

In one or more embodiments, in Formula 81A,
$Y_{81}$ may be nitrogen,
$Y_{82}$ to $Y_{84}$ may each independently be carbon,
$CY_{81}$ may be a 5-membered ring including two nitrogen atoms as ring-forming atoms, and
$CY_{82}$ may be a benzene group, a naphthalene group, a fluorene group, a dibenzofuran group, or a dibenzothiophene group, but embodiments of the present disclosure are not limited thereto.

In one or more embodiments, in Formula 81A,
$Y_{81}$ may be nitrogen,
$Y_{82}$ to $Y_{84}$ may each independently be carbon,
$CY_{81}$ may be an imidazole group or a 2,3-dihydro-1H-imidazole group, and
$CY_{82}$ may be a benzene group, a naphthalene group, a fluorene group, a dibenzofuran group, or a dibenzothiophene group, but embodiments of the present disclosure are not limited thereto.

In one or more embodiments, in Formula 81A,
$Y_{81}$ may be nitrogen,
$Y_{82}$ to $Y_{84}$ may each independently be carbon,
$CY_{81}$ may be a pyrrole group, a pyrazole group, an imidazole group, a triazole group, an oxazole group, an isoxazole group, an oxadiazole group, a thiazole group, an isothiazole group, a thiadiazole group, a pyridine group, a pyrimidine group, a quinoline group, an isoquinoline group, a benzoquinoline group, a phthalazine group, a naphthyridine group, a quinoxaline group, a quinazoline group, a cinnoline group, a benzimidazole group, an isobenzothiazole group, a benzoxazole group, or an isobenzoxazole group, and
$CY_{82}$ may be cyclopentadiene group, a benzene group, a naphthalene group, a fluorene group, a benzofluorene group, a dibenzofluorene group, a phenanthrene group, an anthracene group, a triphenylene group, a pyrene group, a chrysene group, a perylene group, a benzofuran group, a benzothiophene group, a benzocarbazole group, a dibenzocarbazole group, a dibenzofuran group, a dibenzothiophene group, a dibenzothiophene sulfone group, a carbazole group, or a dibenzosilole group.

In one or more embodiments, in Formula 81A,
$R_{81}$ and $R_{82}$ may each independently be:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, $C_1$-$C_{20}$ alkyl group, or a $C_1$-$C_{20}$ alkoxy group;
a $C_1$-$C_{20}$ alkyl group or a $C_1$-$C_{20}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a pyridinyl group, a pyrimidinyl group, or a combination thereof;
a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a combination thereof; or —B($Q_{86}$)($Q_{87}$) or —P(=O)($Q_{88}$)($Q_{89}$), and $Q_{86}$ to $Q_{89}$ may each independently be:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H or —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each substituted with deuterium, a $C_1$-$C_{10}$ alkyl group, a phenyl group, or a combination thereof.

In one or more embodiments, in Formula 81A, $R_{82}$ in the number of a82 may be a cyano group.

In one or more embodiments, in Formula 81A, $R_{81}$ in the number of a81 and $R_{82}$ in the number of a82 may be deuterium.

In one or more embodiments, in Formula 81, $L_{82}$ may be a ligand represented by Formulae 3-1(1) to 3-1(60), 3-1(61) to 3-1(69), 3-1(71) to 3-1(79), 3-1(81) to 3-1(88), 3-1(91) to 3-1(98), or 3-1(101) to 3-1(114):

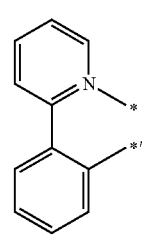

3-1(1)

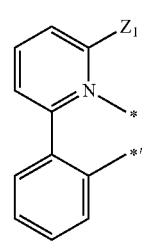

3-1(2)

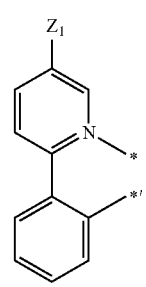

3-1(3)

3-1(4)
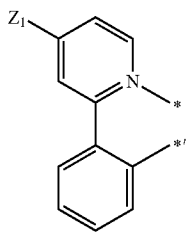
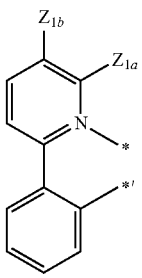
3-1(10)
3-1(5)
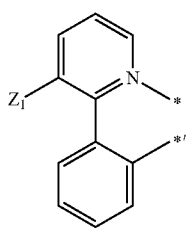
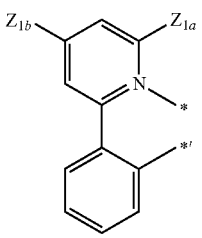
3-1(11)
3-1(6)
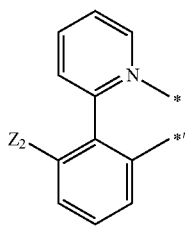
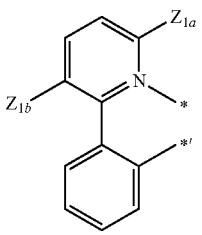
3-1(12)
3-1(7)
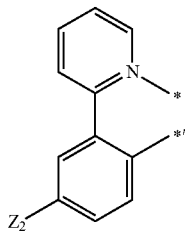
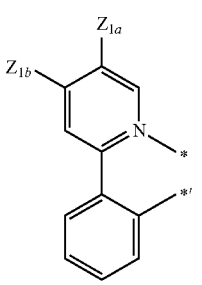
3-1(13)
3-1(8)
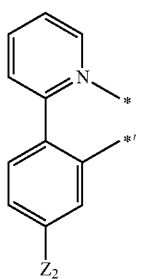
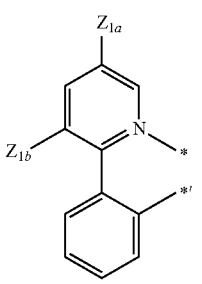
3-1(14)
3-1(9)
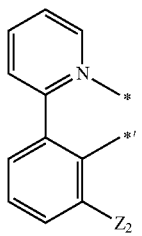
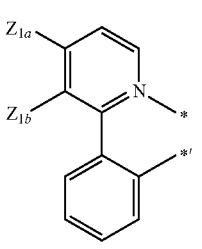
3-1(15)

519
-continued
3-1(16) 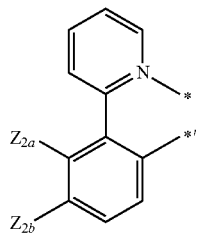
3-1(17) 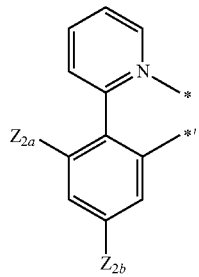
3-1(18) 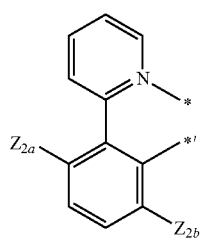
3-1(19) 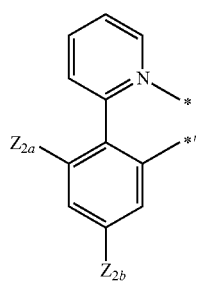
3-1(20) 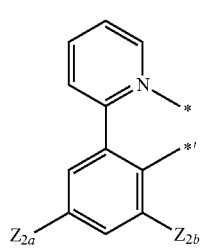
3-1(21) 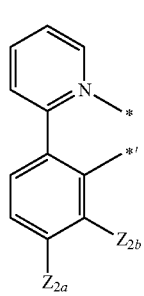
520
-continued
3-1(22) 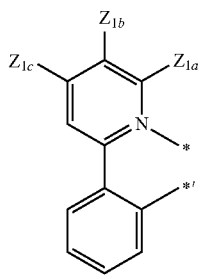
3-1(23) 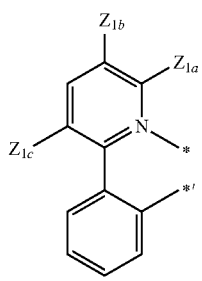
3-1(24) 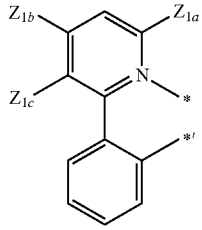
3-1(25) 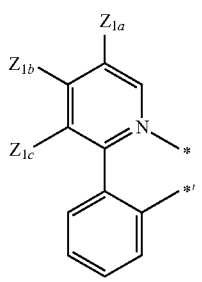
3-1(26) 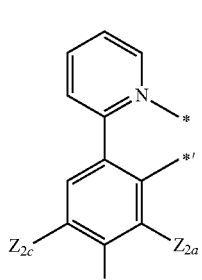
3-1(27) 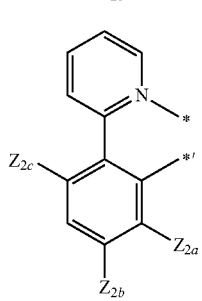

-continued
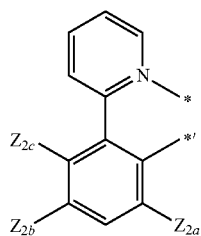
3-1(28)
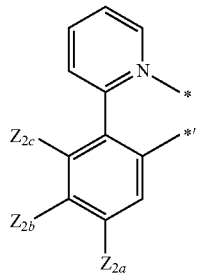
3-1(29)
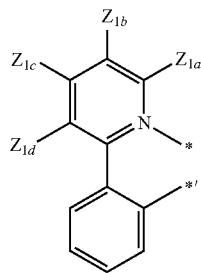
3-1(30)
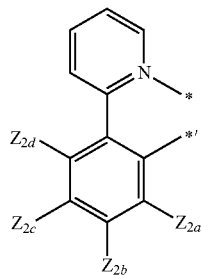
3-1(31)
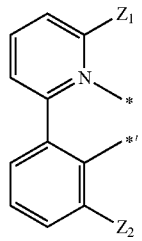
3-1(32)
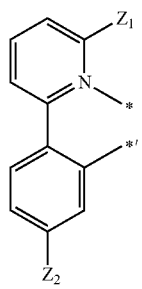
3-1(33)
-continued
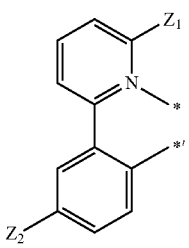
3-1(34)
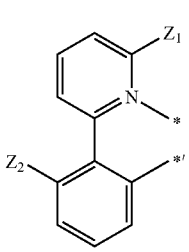
3-1(35)
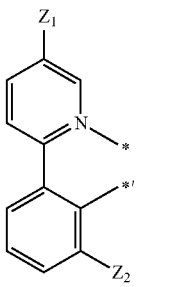
3-1(36)
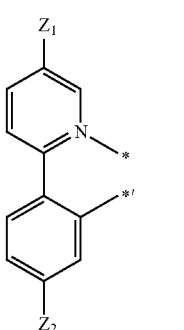
3-1(37)
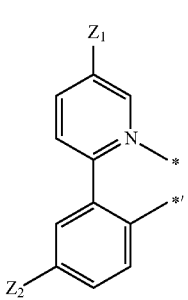
3-1(38)

-continued
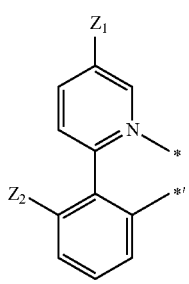
3-1(39)
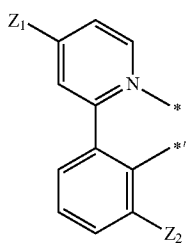
3-1(40)
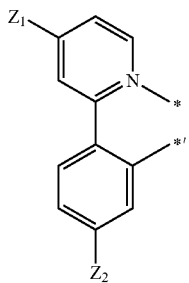
3-1(41)
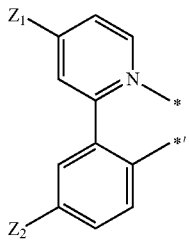
3-1(42)
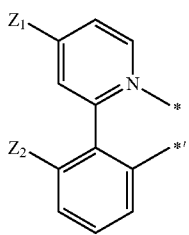
3-1(43)
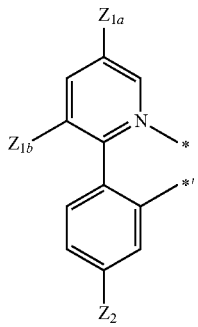
3-1(44)
-continued
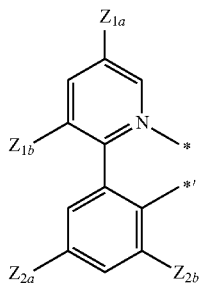
3-1(45)
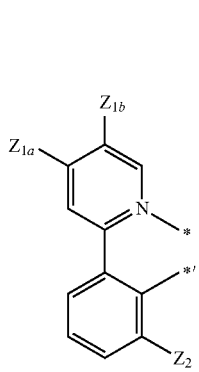
3-1(46)
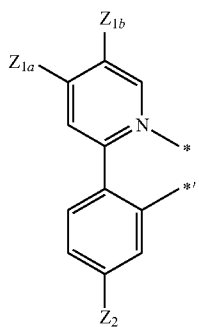
3-1(47)
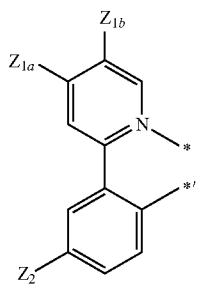
3-1(48)
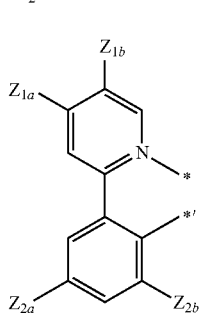
3-1(49)

-continued
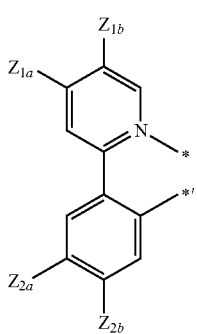
3-1(50)
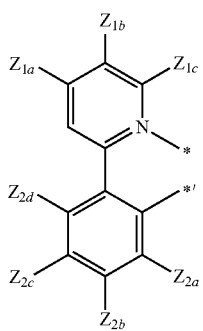
3-1(51)
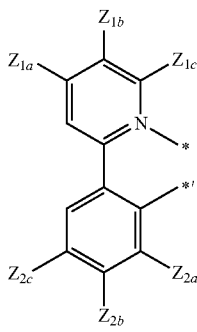
3-1(52)
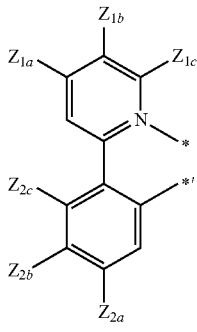
3-1(53)
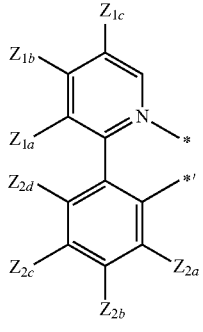
3-1(54)
-continued
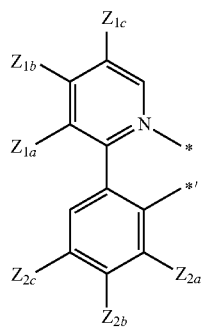
3-1(55)
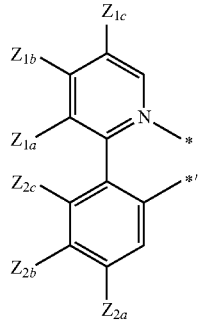
3-1(56)
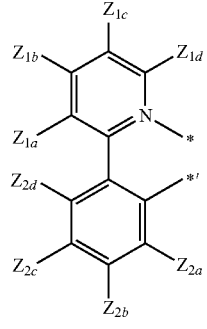
3-1(57)
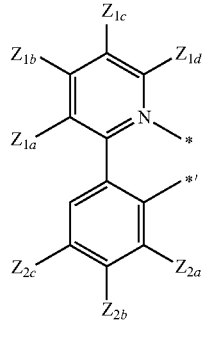
3-1(58)
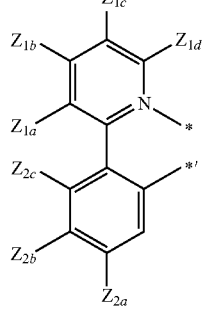
3-1(59)

527
-continued
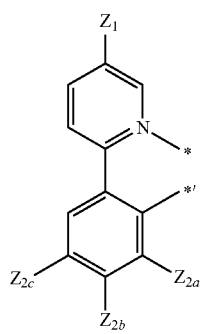
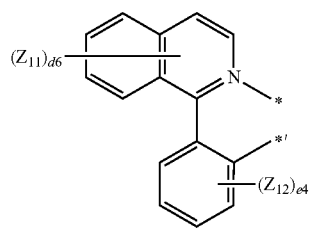
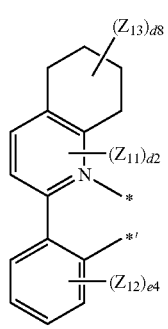
528
-continued
3-1(60)
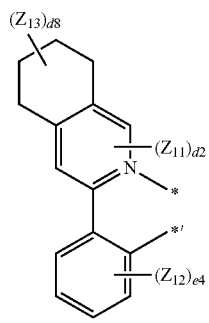
3-1(61)
3-1(62)
3-1(63)
3-1(64)
3-1(65)
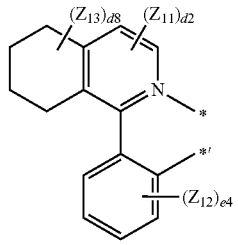
3-1(66)
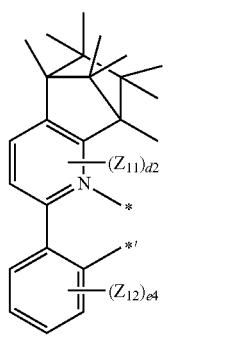
3-1(67)
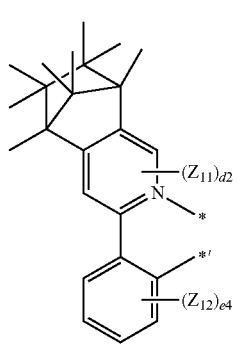
3-1(68)
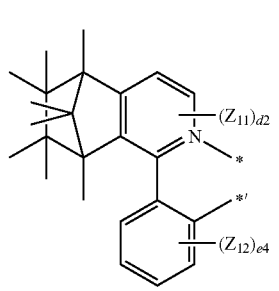
3-1(69)

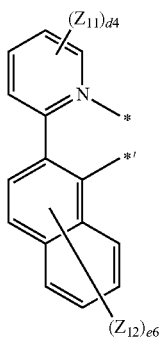
3-1(71)
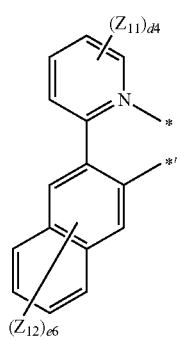
3-1(72)
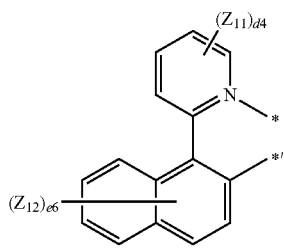
3-1(73)
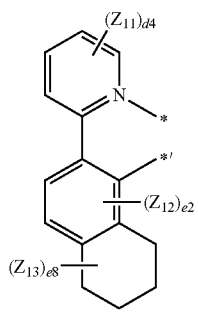
3-1(74)
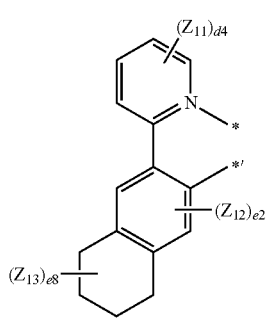
3-1(75)
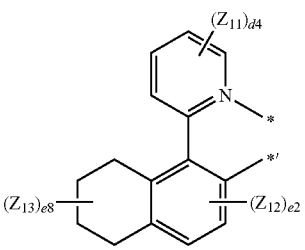
3-1(76)
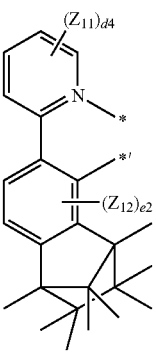
3-1(77)
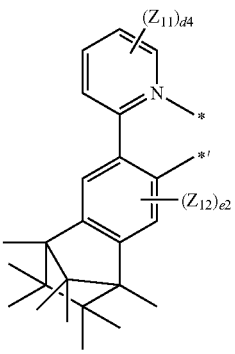
3-1(78)
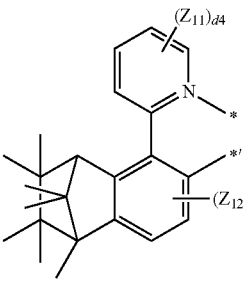
3-1(79)
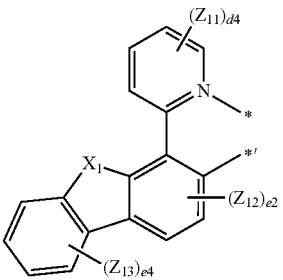
3-1(81)

531
-continued
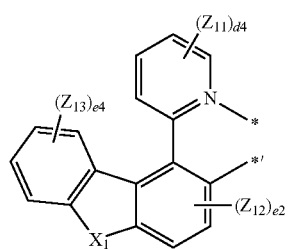
3-1(82)
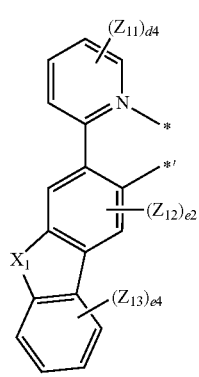
3-1(83)
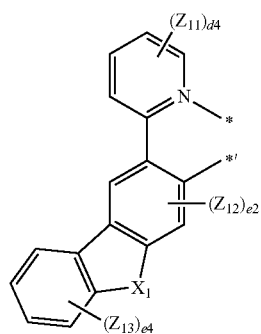
3-1(84)
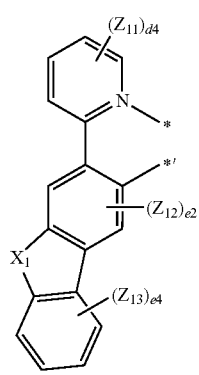
3-1(85)
532
-continued
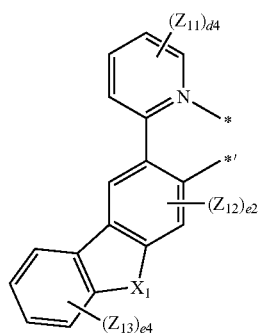
3-1(86)
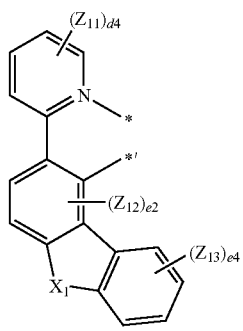
3-1(87)
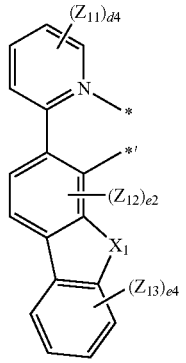
3-1(88)
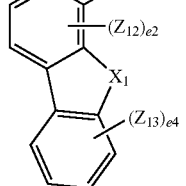
3-1(91)
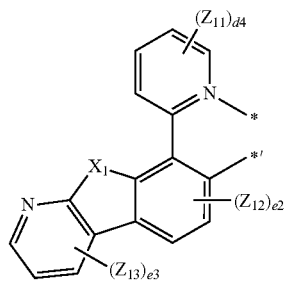
3-1(92)
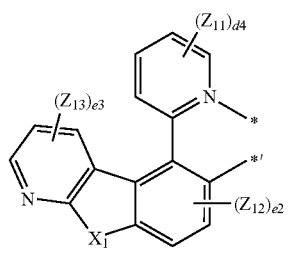

3-1(93)
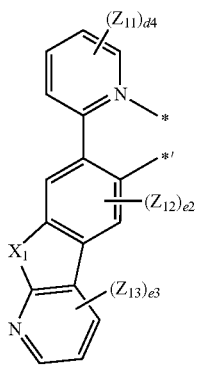
3-1(94)
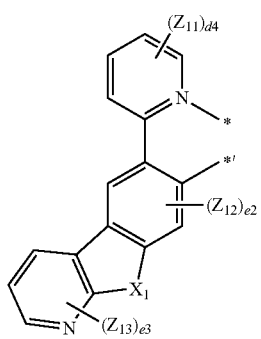
3-1(95)
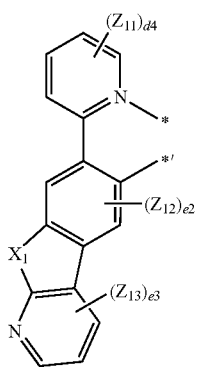
3-1(96)
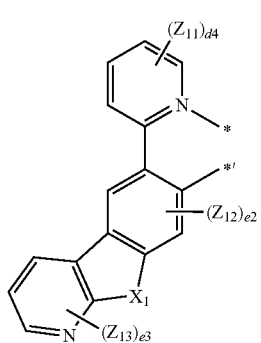
3-1(97)
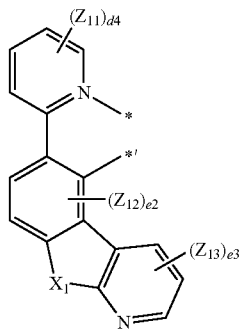
3-1(98)
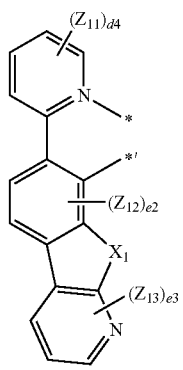
3-1(101)
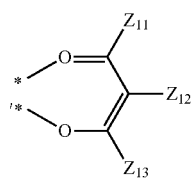
3-1(102)
3-1(103)
3-1(104)
3-1(105)
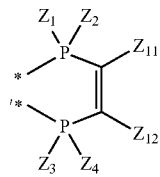

In Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114), $X_1$ may be O, S, $C(Z_{21})(Z_{22})$, or $N(Z_{23})$, $X_{31}$ may be N or $C(Z_{1a})$, $X_{32}$ may be N or $C(Z_{1b})$, $X_{41}$ may be O, S, $N(Z_{1a})$, or $C(Z_{1a})(Z_{1b})$, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, C$_1$-C$_{20}$ alkyl group, or a C$_1$-C$_{20}$ alkoxy group;

a C$_1$-C$_{20}$ alkyl group or a C$_1$-C$_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a pyridinyl group, a pyrimidinyl group, or a combination thereof;

a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a combination thereof; or —B(Q$_{86}$)(Q$_{87}$) or —P(=O)(Q$_{88}$)(Q$_{89}$), and Q$_{86}$ to Q$_{89}$ may each independently be:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, or —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each substituted with deuterium, a $C_1$-$C_{10}$ alkyl group, a phenyl group, or a combination thereof, d2 and e2 may each independently be 0 or 2, e3 may be an integer from 0 to 3, d4 and e4 may each independently be an integer from 0 to 4, d6 and e6 may each independently be an integer from 0 to 6, d8 and e8 may each independently be an integer from 0 to 8, and and *' each indicate a binding site to M in Formula 1.

In one or more embodiments, in Formula 81, M may be Ir, and n81+n82 may be 3; or M may be Pt, and n81+n82 may be 2.

In one or more embodiments, the organometallic compound represented by Formula 81 may not be a salt including a pair of a cation and an anion, but a neutral compound.

In one or more embodiments, the organometallic compound represented by Formula 81 may include Compounds PD1 to PD78 and FIr$_6$, but embodiments of the present disclosure are not limited thereto.

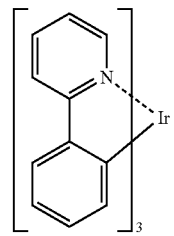

PD1

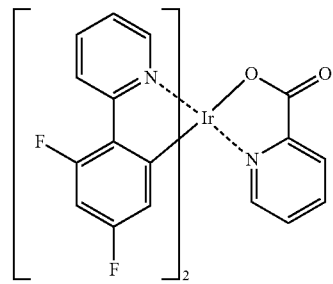

PD2

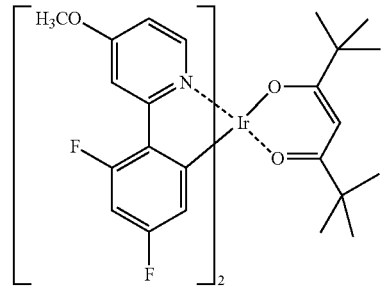

PD3

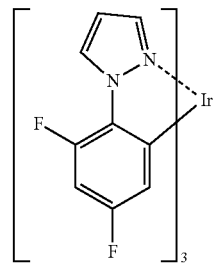

PD4

-continued
PD5
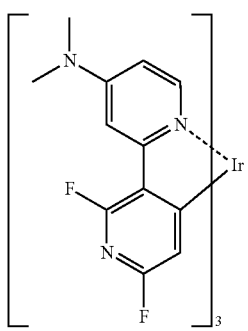
PD6
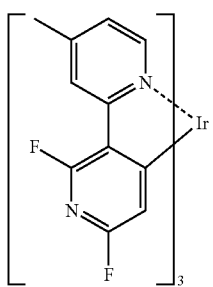
PD7
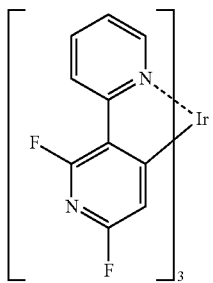
PD8
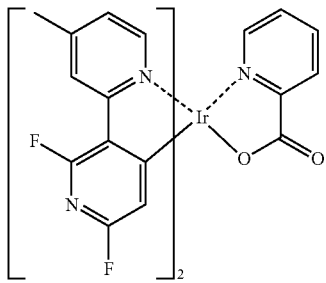
PD9
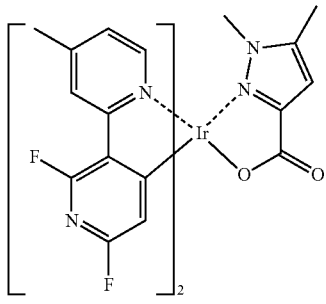
-continued
PD10
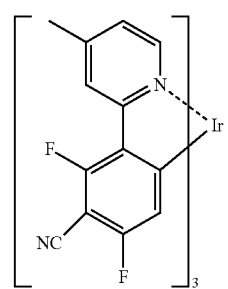
PD11
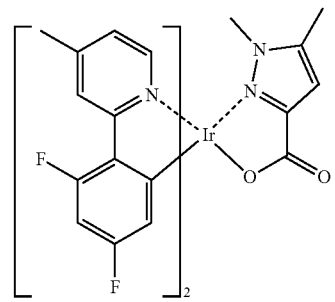
PD12
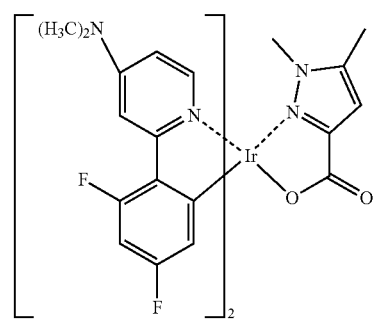
PD13
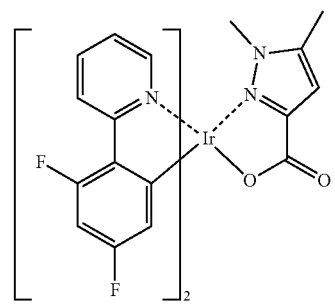
PD14
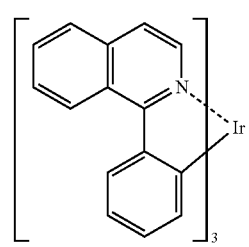

-continued
PD15
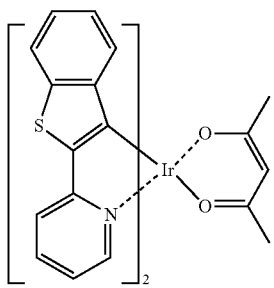
PD16
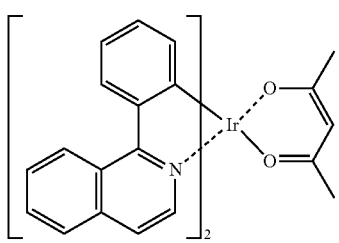
PD17
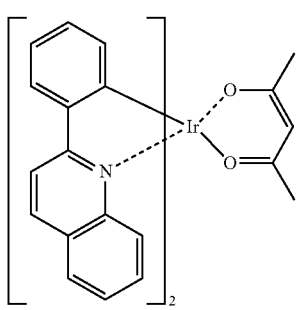
PD18
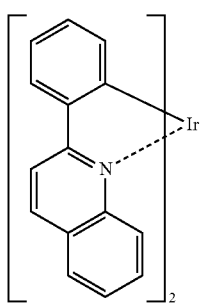
PD19
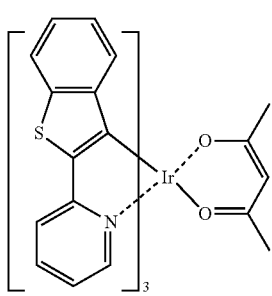
-continued
PD20
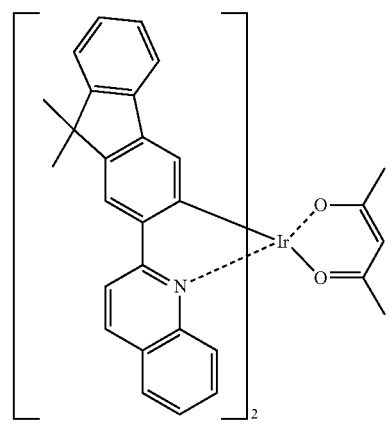
PD21
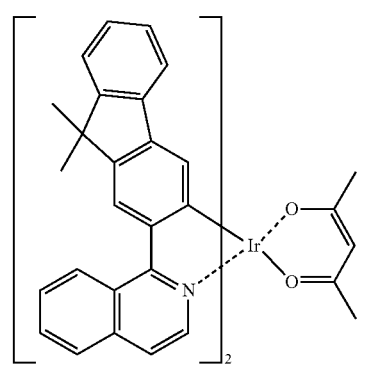
PD22
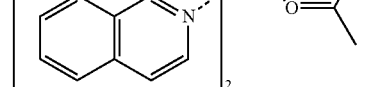
PD23
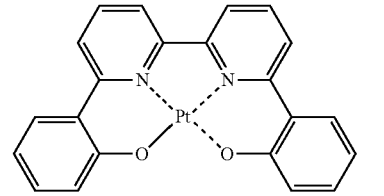
PD24
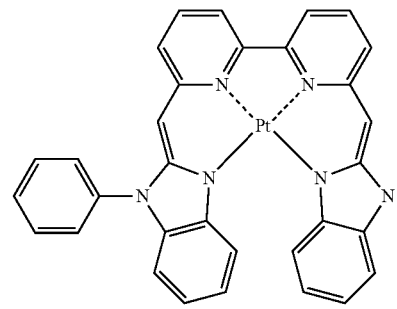

PD25 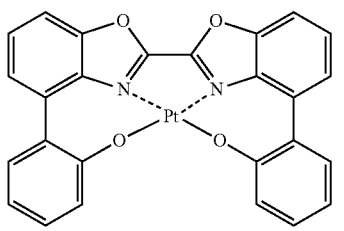
PD26 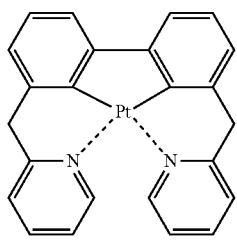
PD27 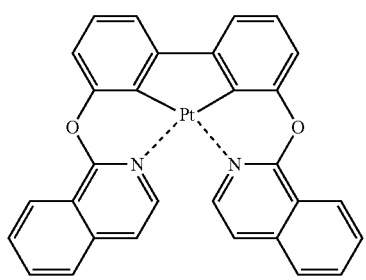
PD28 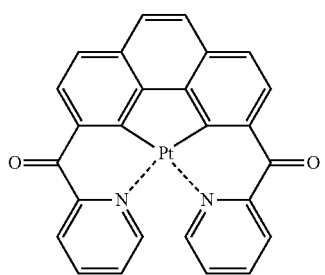
PD29 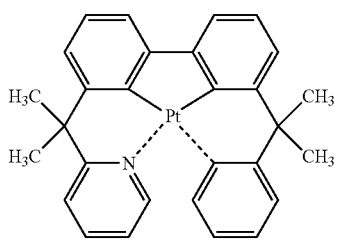
PD30 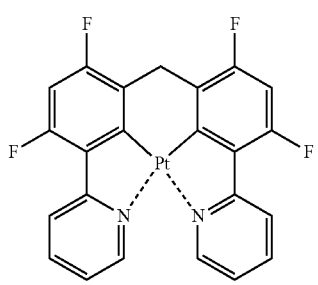
PD31 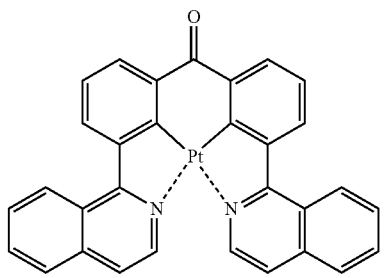
PD32 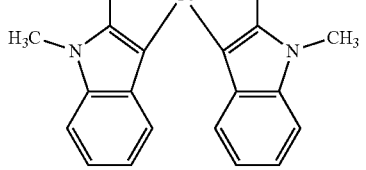
PD33 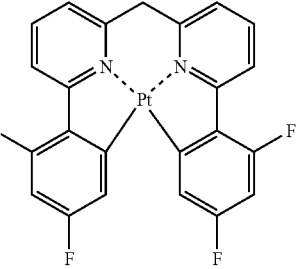
PD34 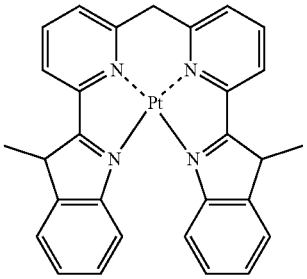
PD35 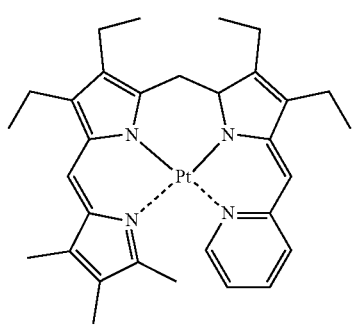

-continued
PD36 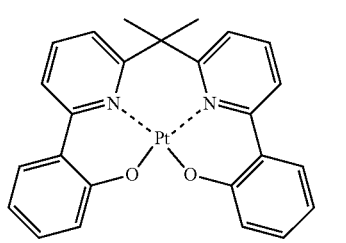
PD37 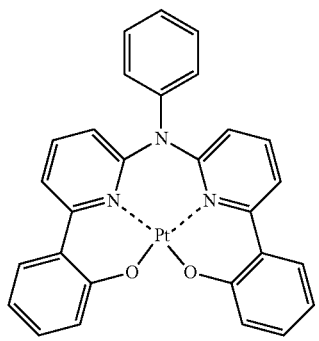
PD38 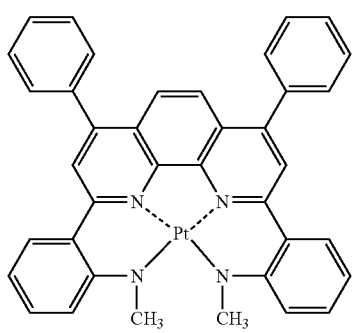
PD39 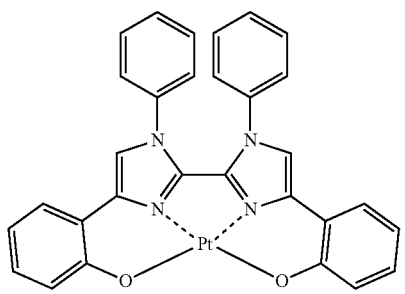
PD40 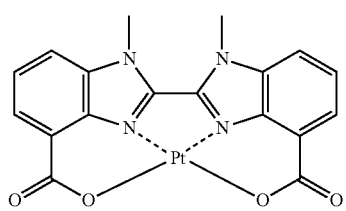
PD41 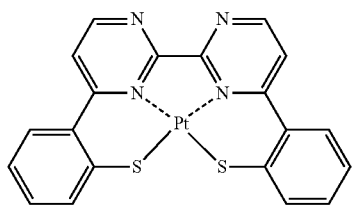
-continued
PD42 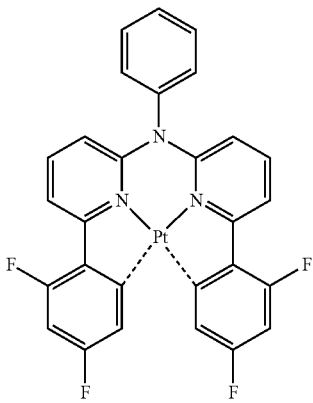
PD43 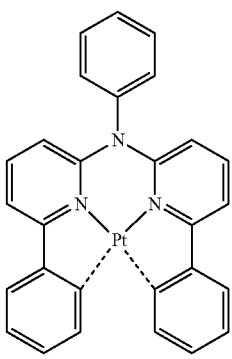
PD44 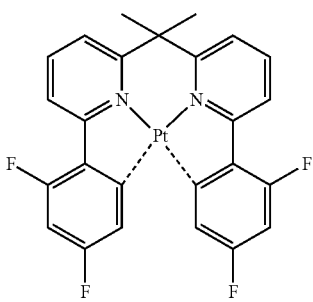
PD45 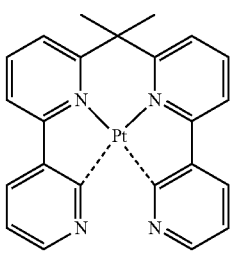
PD46 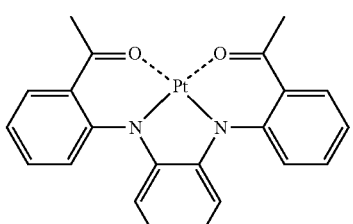

-continued
PD47 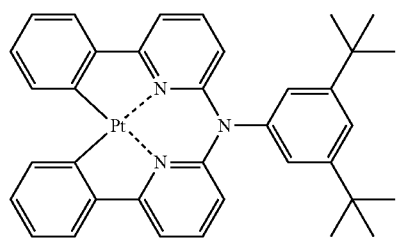
PD48 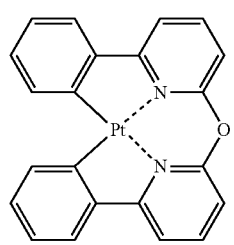
PD49 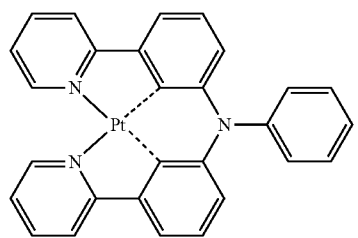
PD50 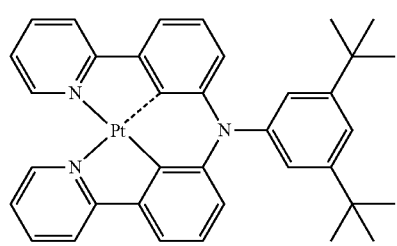
PD51 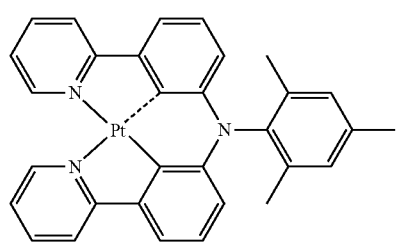
PD52 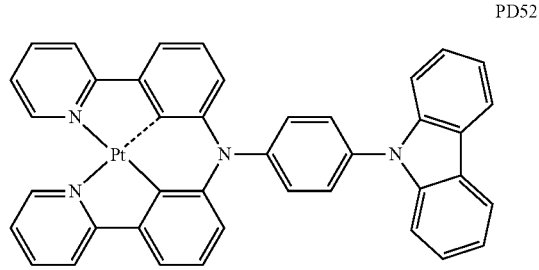
-continued
PD53 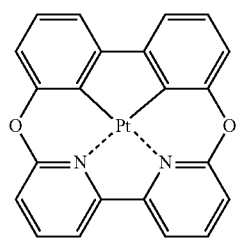
PD54 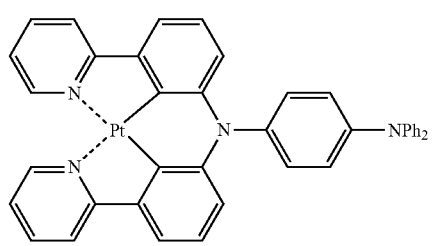
PD55 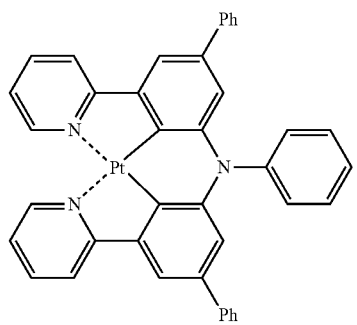
PD56 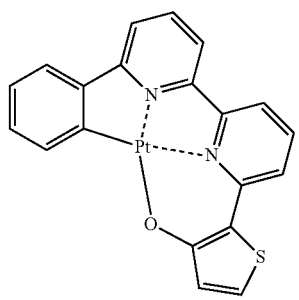
PD57 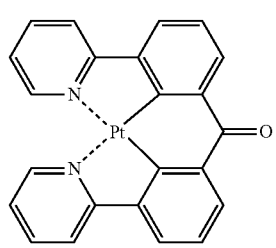

-continued
PD58
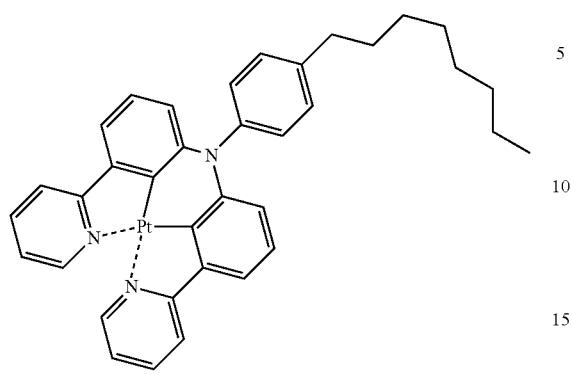
PD59
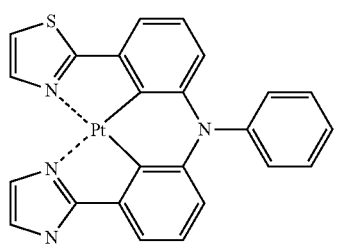
PD60
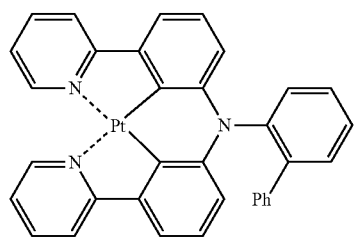
PD61
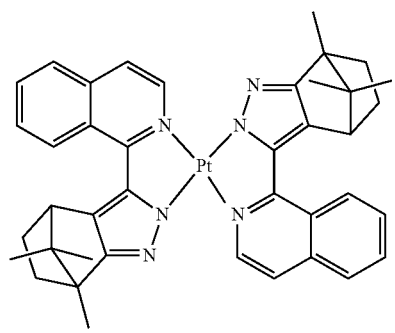
PD62
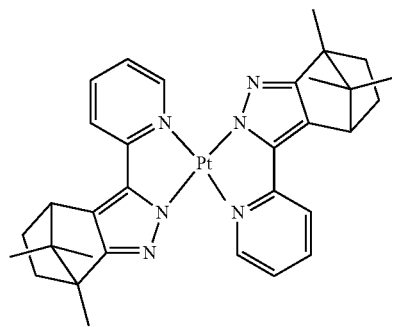
-continued
PD63
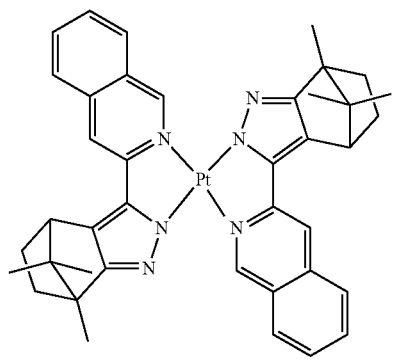
PD64
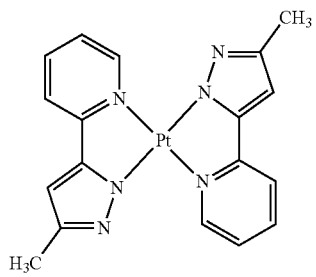
PD65
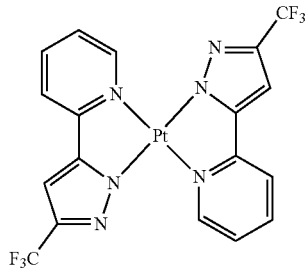
PD66
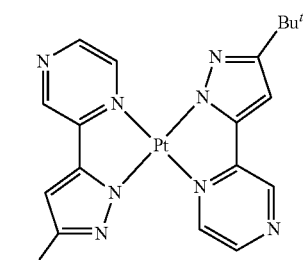
PD67
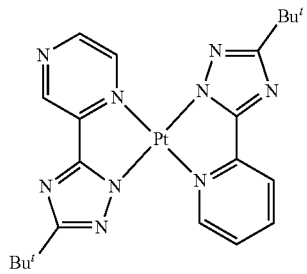

-continued
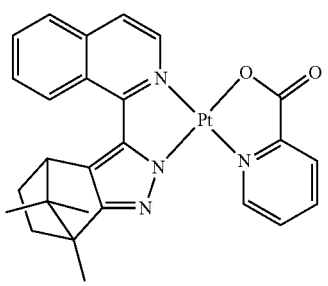
PD68
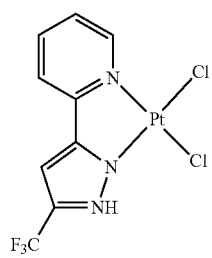
PD69
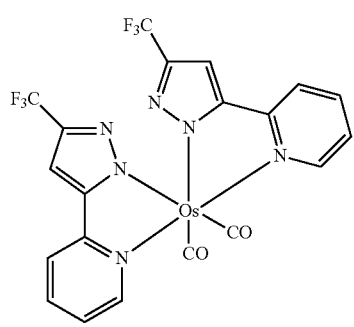
PD70
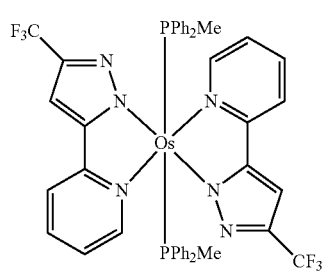
PD71
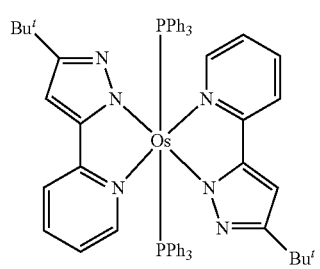
PD72
-continued
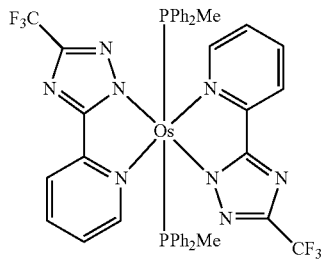
PD73
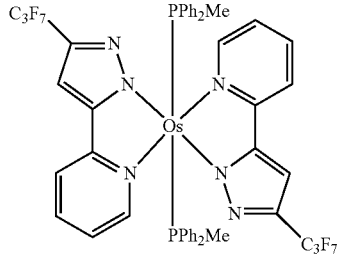
PD74
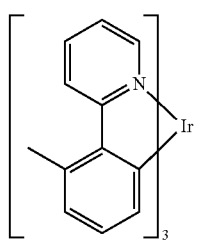
PD75
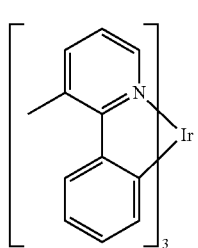
PD76
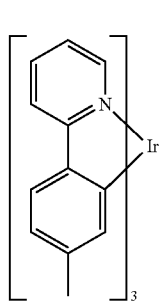
PD77
PD78

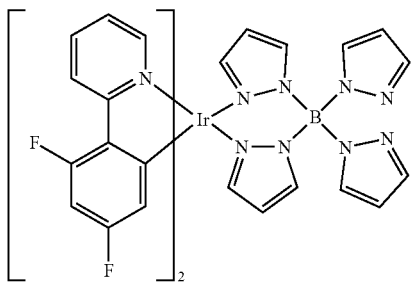
FIr6

The expression "(an organic layer) includes a condensed cyclic compound" as used herein may include a case in which (an organic layer) includes a single condensed cyclic compound represented by Formula 1, a case in which (an organic layer) includes two more identical compounds represented by Formula 1, and a case in which (an organic layer) includes two or more different condensed cyclic compounds represented by Formula 1.

In an exemplary embodiment, the organic layer may include, as the condensed cyclic compound, only Compound 1. In this regard, Compound 1 may exist in an emission layer of the organic light-emitting device. In one or more embodiments, the organic layer may include, as the condensed cyclic compound, Compound 1 and Compound 2. In this regard, Compound 1 and Compound 2 may exist in an identical layer (for example, Compound 1 and Compound 2 may both exist in an emission layer), or different layers (for example, Compound 1 may exist in an emission layer and Compound 2 may exist in a hole blocking layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

The term "organic layer" as used herein refers to a single layer and/or a plurality of layers disposed between the first electrode and the second electrode of the organic light-emitting device. The "organic layer" may include, in addition to an organic compound, an organometallic complex including metal.

FIG. is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

In one or more embodiments, the first electrode 11 may be formed by depositing or sputtering a material for forming the first electrode 11 on the substrate. The first electrode 11 may be an anode. The material for forming the first electrode 11 may be a material with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), or zinc oxide (ZnO). In one or more embodiments, the material for forming the first electrode 11 may be a metal, such as magnesium (Mg), aluminum (Al), aluminum-lithium (Al—Li), calcium (Ca), or an alloy, such as magnesium-indium (Mg—In), or magnesium-silver (Mg—Ag).

The first electrode 11 may have a single-layered structure or a multi-layered structure including two or more layers. In an exemplary embodiment, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or a combination thereof.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer, the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. In an exemplary embodiment, the deposition conditions may include a deposition temperature of about 100° C. to about 500° C., a vacuum pressure of about $10^{-8}$ to about $10^{-3}$ torr, and a deposition rate of about 0.01 Å/sec to about 100 Å/sec. However, the deposition conditions are not limited thereto.

When the hole injection layer is formed using spin coating, the coating conditions may vary according to the compound that is used to form the hole injection layer, and the desired structure and thermal properties of the hole injection layer to be formed. In an exemplary embodiment, the coating rate may be in the range of about 2,000 rpm to about 5,000 rpm, and a temperature at which heat treatment is performed to remove a solvent after coating may be in the range of about 80° C. to about 200° C. However, the coating conditions are not limited thereto.

Conditions for forming a hole transport layer and an electron blocking layer may be understood by referring to conditions for forming the hole injection layer.

The hole transport region may include m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201 below, a compound represented by Formula 202 below, or a combination thereof:

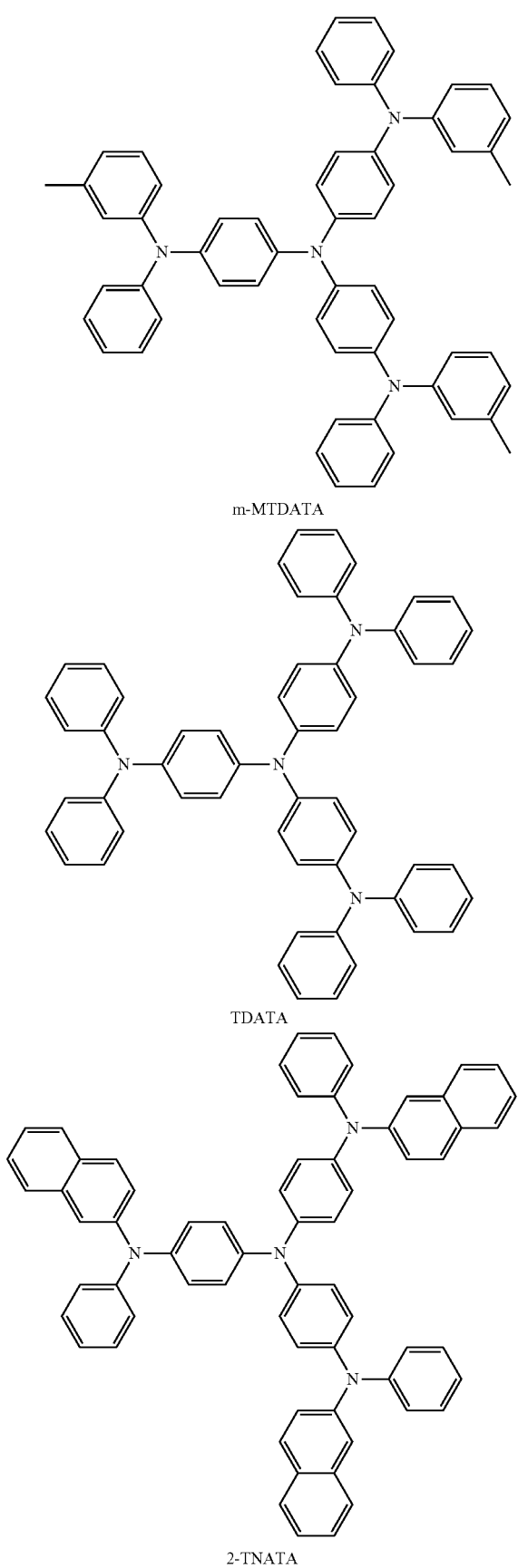
m-MTDATA
TDATA
2-TNATA
-continued
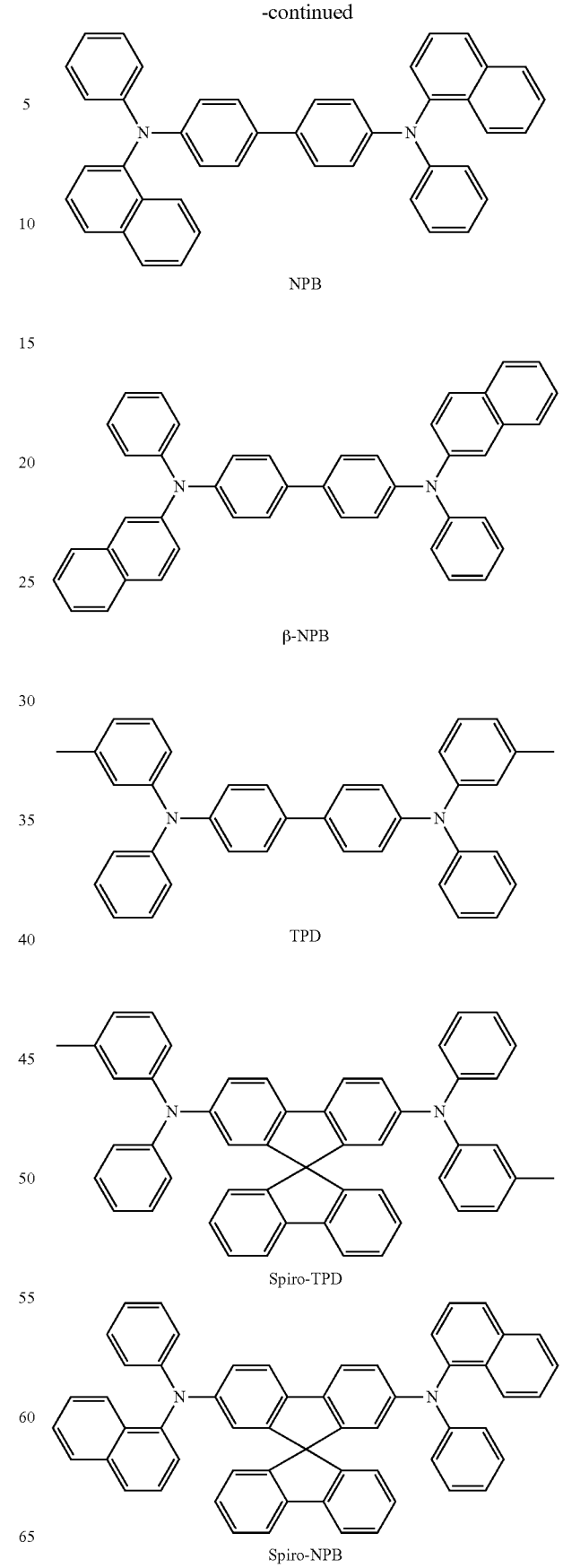
NPB
β-NPB
TPD
Spiro-TPD
Spiro-NPB -continued

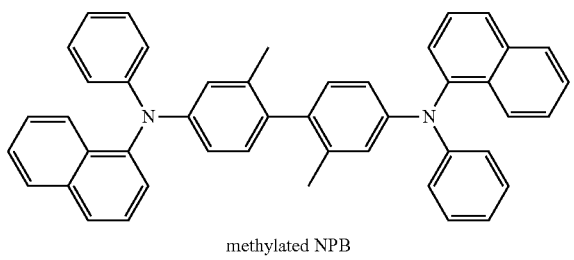

methylated NPB

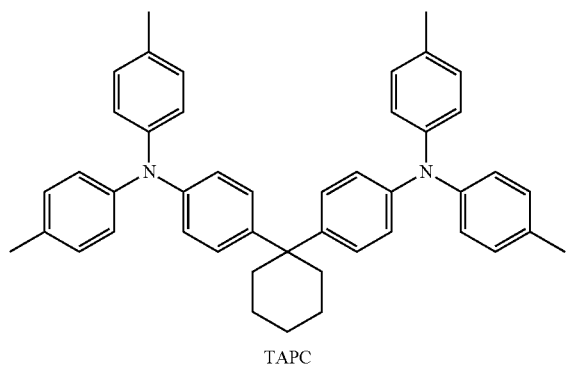

TAPC

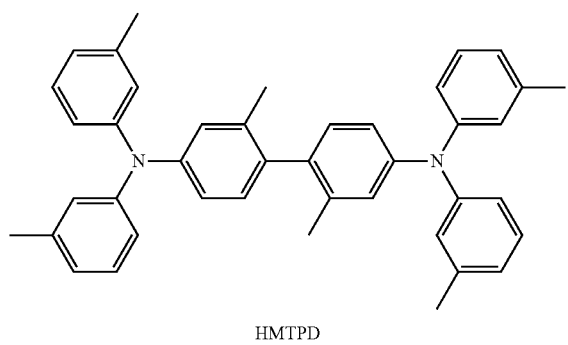

HMTPD

Formula 201

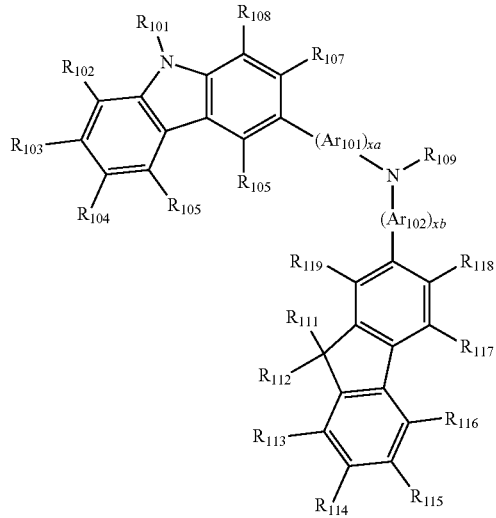

-continued

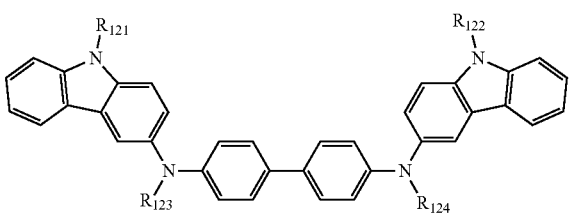

Formula 202

$Ar_{101}$ and $Ar_{102}$ in Formula 201 may each independently be:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group; or a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or a combination thereof.

xa and xb in Formula 201 may each independently be an integer from 0 to 5, or 0, 1 or 2. In an exemplary embodiment, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or a combination thereof;

a phenyl group, a naphthyl group, an anthracenyl group, a fluorenyl group, or a pyrenyl group; or a phenyl group, a naphthyl group, an anthracenyl group, a fluorenyl group, or a pyrenyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, or a combination thereof, but embodiments of the present disclosure are not limited thereto.

$R_{109}$ in Formula 201 may be:

a phenyl group, a naphthyl group, an anthracenyl group, or a pyridinyl group; or a phenyl group, a naphthyl group, an anthracenyl group, or a pyridinyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyridinyl group, or a combination thereof.

According to an embodiment, the compound represented by Formula 201 may be represented by Formula 201A below, but embodiments of the present disclosure are not limited thereto:

Formula 201A

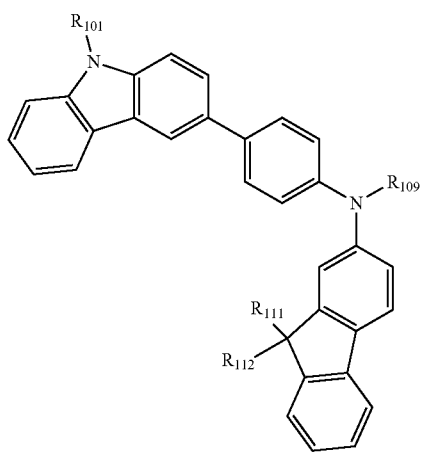

wherein $R_{101}$, $R_{111}$, $R_{112}$, and $R_{109}$ in Formula 201A are the same as described above.

In an exemplary embodiment, the compound represented by Formula 201, and the compound represented by Formula 202 may include compounds HT1 to HT20 illustrated below, but are not limited thereto:

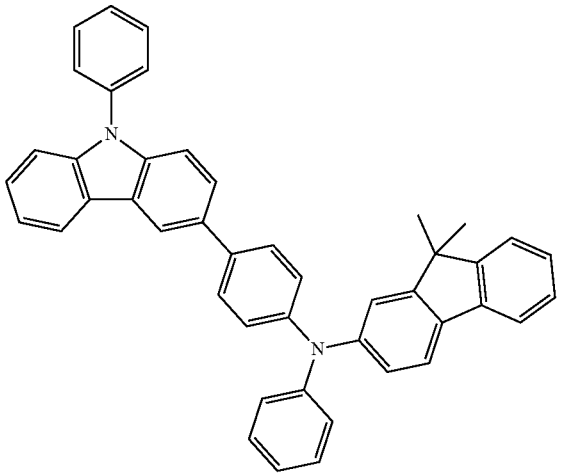

HT3
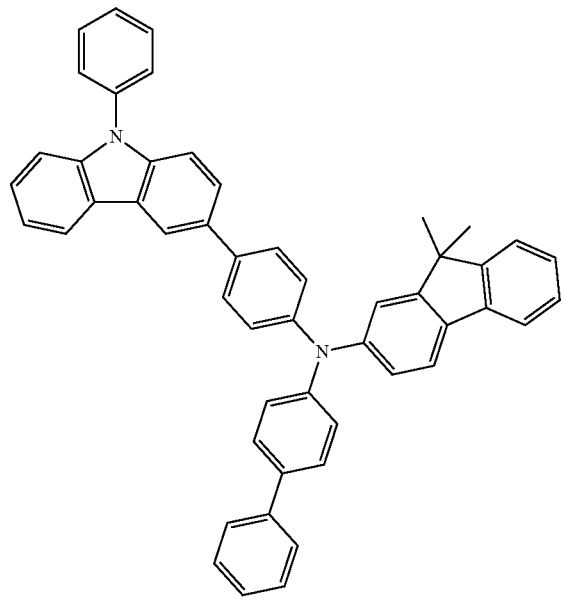
HT5
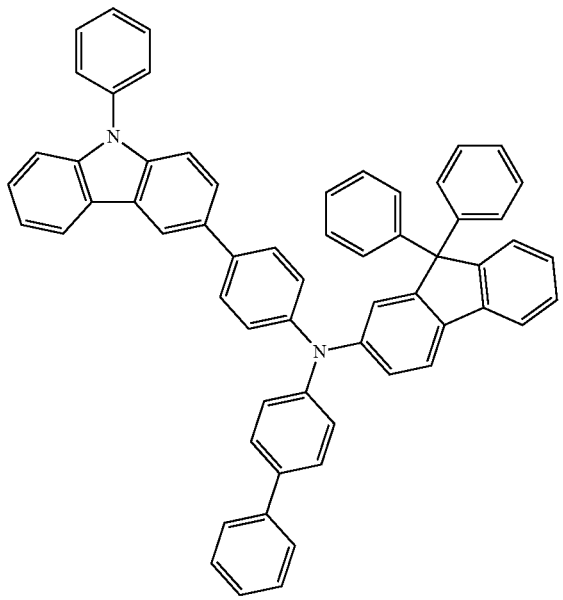
HT4
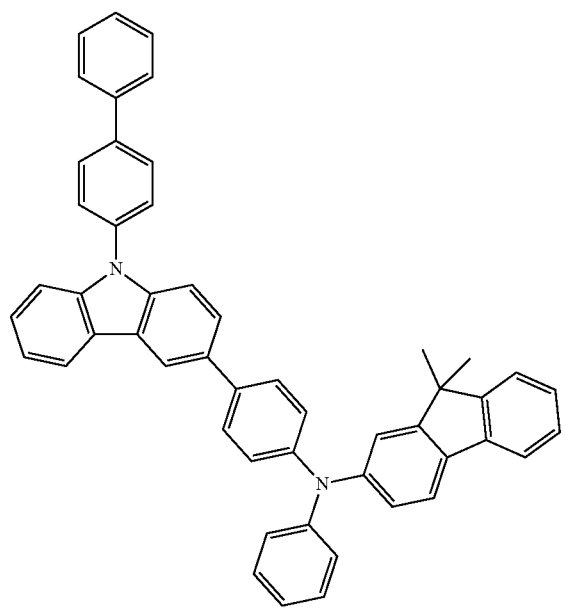
HT6
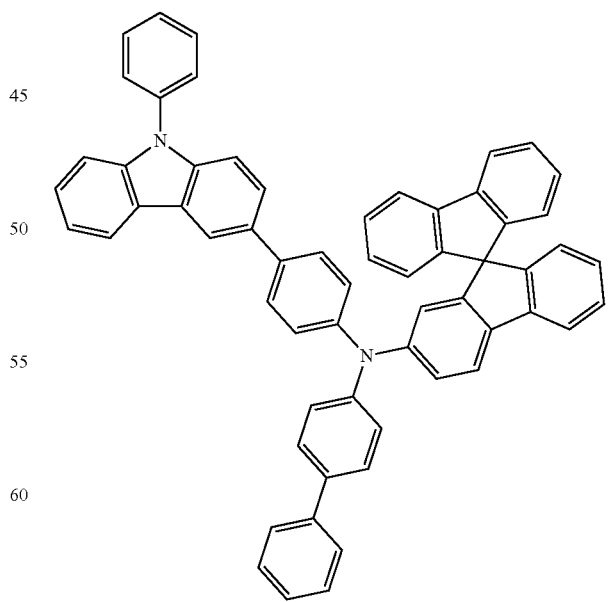

HT7
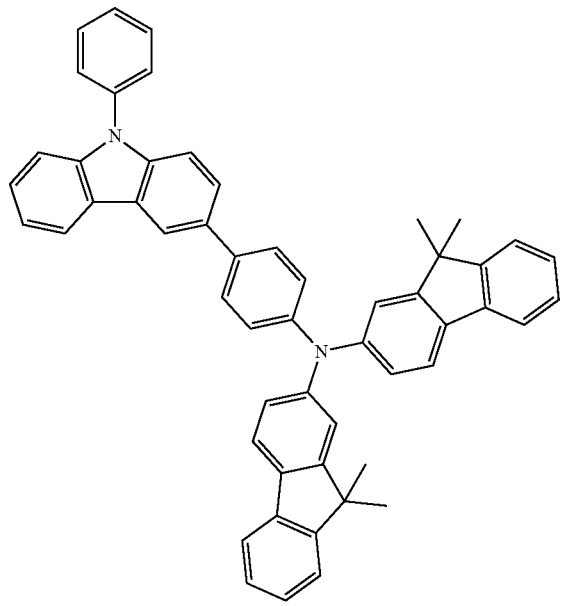
HT8
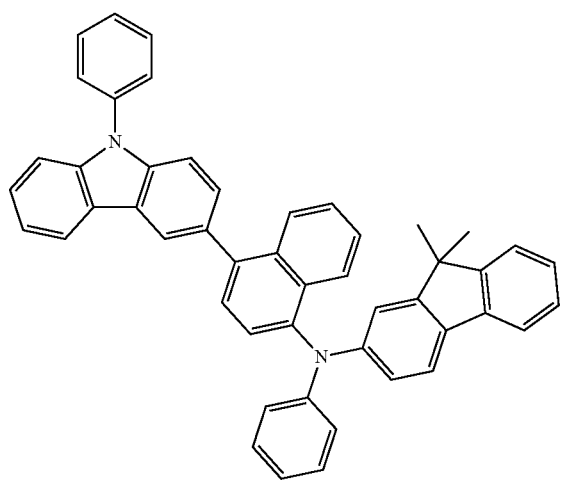
HT9
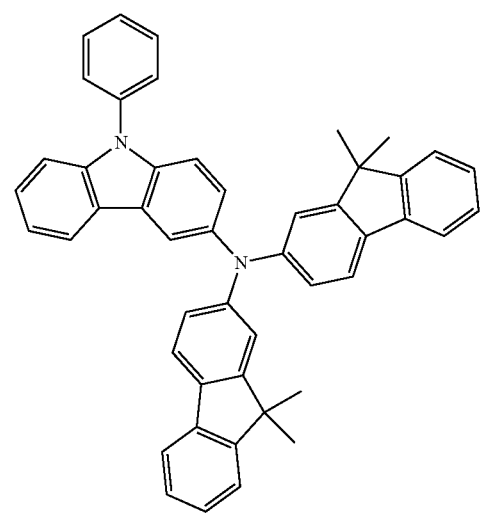
HT10
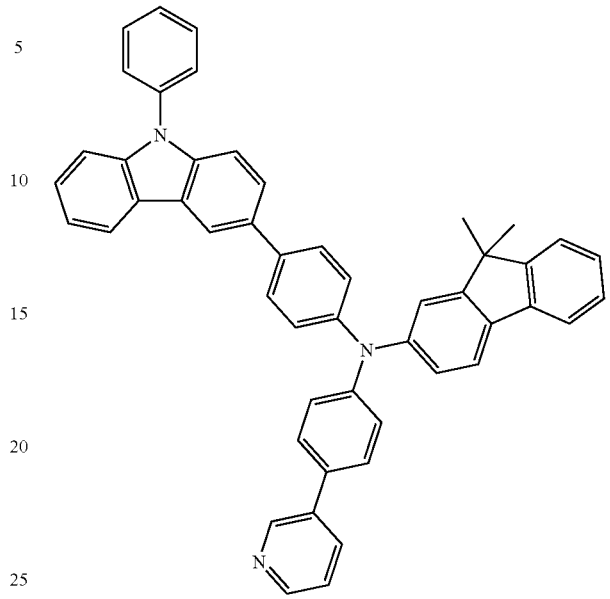
HT11
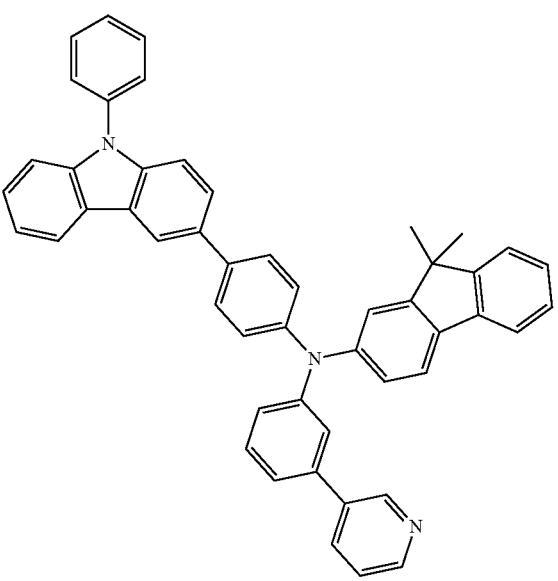

HT12 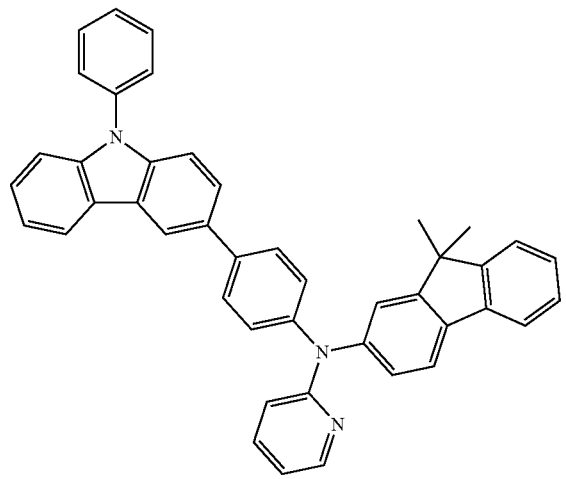
HT13 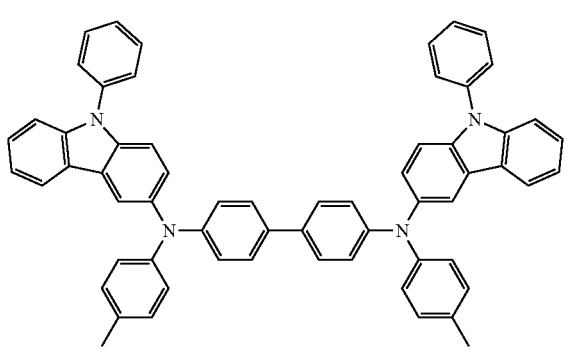
HT14 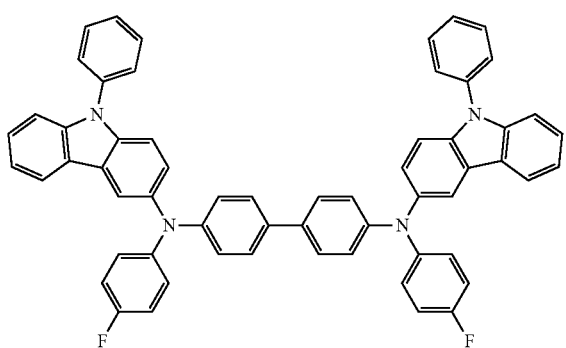
HT16 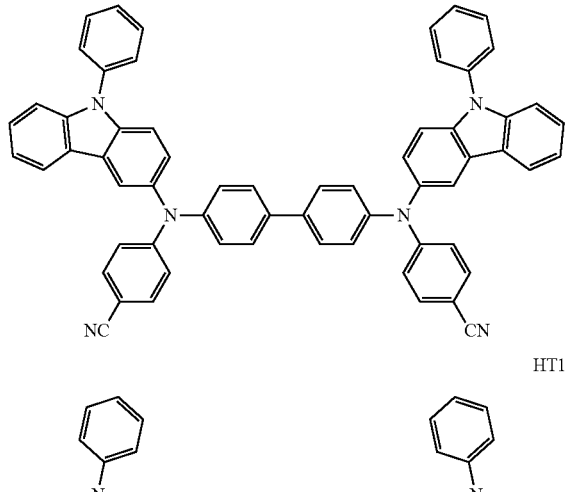
HT17 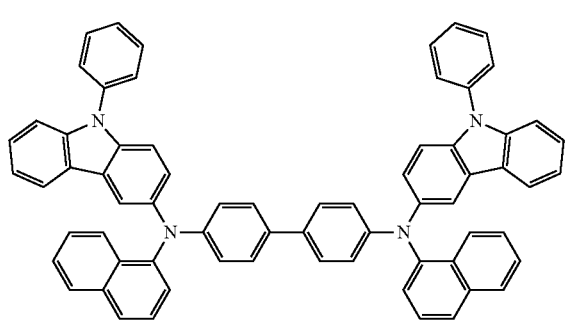
HT18 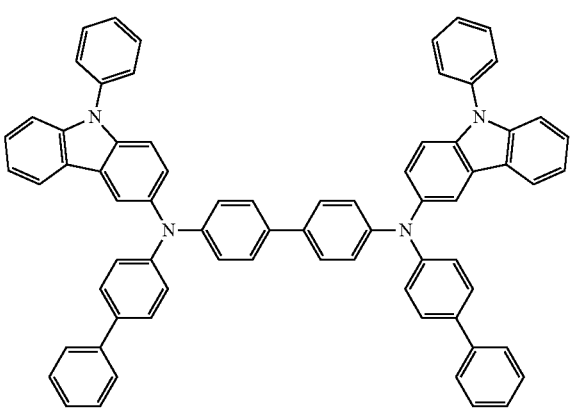

HT20

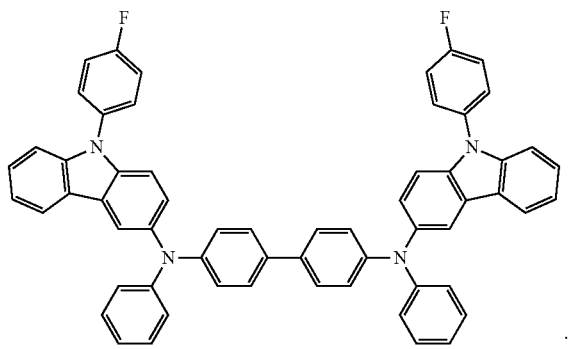

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be a quinone derivative, a metal oxide, or a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or HP-1, but are not limited thereto:

HT-D1

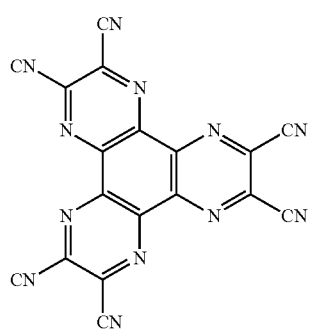

F4-TCNQ

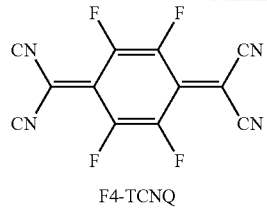

HP-1

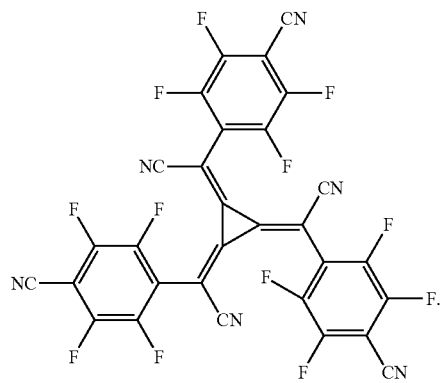

The hole transport region may include a buffer layer.

Also, the buffer layer may compensate for an optical resonance distance according to a wavelength of light emitted from the emission layer, and thus, efficiency of a formed organic light-emitting device may be improved.

The electron transport region may further include an electron blocking layer. The electron blocking layer may include, for example, mCP, but a material therefor is not limited thereto:

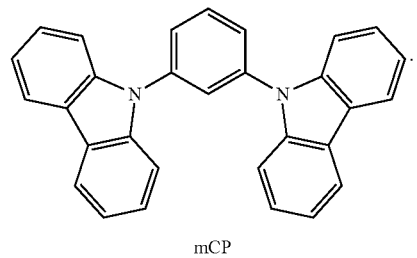 [SMILES: c1cc(-n2c3ccccc3c3ccccc32)cc(-n2c3ccccc3c3ccccc32)c1]

mCP

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

When the organic light-emitting device is a full-color organic light-emitting device, the emission layer may be patterned into a red emission layer, a green emission layer, and/or a blue emission layer. In one or more embodiments, due to a stacked structure including a red emission layer, a green emission layer, and/or a blue emission layer, the emission layer may emit white light.

The emission layer may include a condensed cyclic compound represented by Formula 1.

In an exemplary embodiment, the emission layer may include a condensed cyclic compound represented by Formula 1 alone.

In one or more embodiments, the emission layer may include a condensed cyclic compound represented by Formula 1, and may further include:

i) a second compound (for example, a compound represented by Formula H-1);

ii) an organometallic compound represented by Formula 81; or iii) any combination thereof.

The condensed cyclic compound represented by Formula 1, the second compound, and the organometallic compound represented by Formula 81 are the same as described above.

In one embodiment, when the emission layer includes a host and a dopant, an amount of the dopant may be in a range of about 0.01 parts to about 20 parts by weight based on 100 parts by weight of the host, but embodiments of the present disclosure are not limited thereto. When the amount of the dopant is satisfied within the range above, the emission without extinction phenomenon may be realized.

In one or more embodiments, when the emission layer includes a condensed cyclic compound represented by Formula 1 and a second compound, a weight ratio of the condensed cyclic compound represented by Formula 1 to the second compound may be in a range of about 1:99 to about 99:1, for example, about 70:30 to about 30:70. In one or more embodiments, a weight ratio of the condensed cyclic compound represented by Formula 1 to the second compound may be in a range of about 60:40 to about 40:60. When the weight ratio of the condensed cyclic compound represented by Formula 1 to the second compound is satisfied within the ranges above, the charge transport balance in the emission layer may be efficiently achieved.

A thickness of the emission layer may be in a range of about 100 Å to about 1,000 Å, for example, about 200 Å to about 600 Å. When the thickness of the emission layer is within these ranges, excellent light-emission characteristics may be obtained without a substantial increase in driving voltage.

An electron transport region may be disposed on the emission layer.

The electron transport region may include a hole blocking layer, an electron transport layer, an electron injection layer, or a combination thereof.

In an exemplary embodiment, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, BCP, Bphen, or a combination thereof, but may also include other materials:

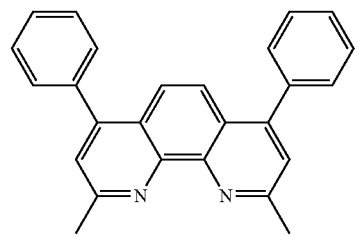

BCP

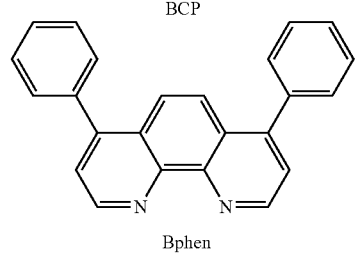

Bphen

The hole blocking layer may include a compound of the hosts described above. In an exemplary embodiment, the hole blocking layer may include Compound H19, but embodiments of the present disclosure are not limited thereto.

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include, in addition to a compound represented by Formula 1, BCP, Bphen, Alq$_3$, BAlq, TAZ, NTAZ, or a combination thereof:

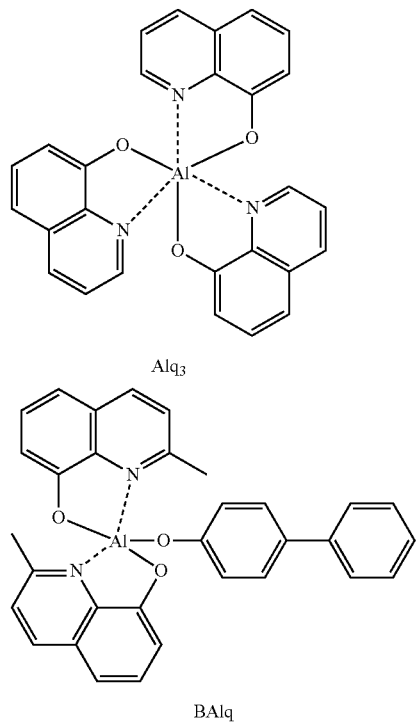

Alq$_3$

BAlq

-continued

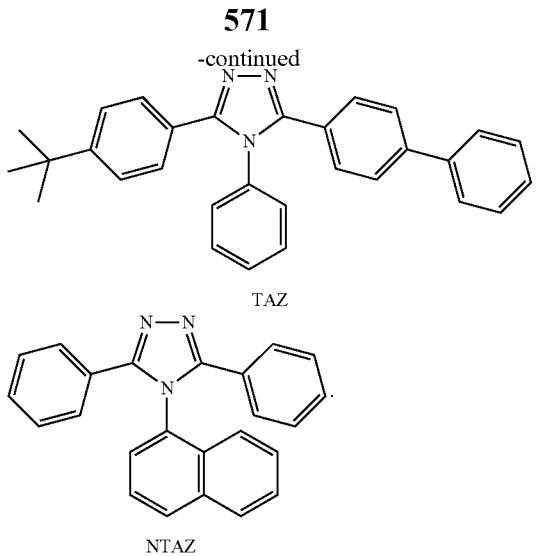

TAZ

NTAZ

In one or more embodiments, the electron transport layer may include Compounds ET1, ET2, ET3, or a combination thereof, but embodiments of the present disclosure are not limited thereto:

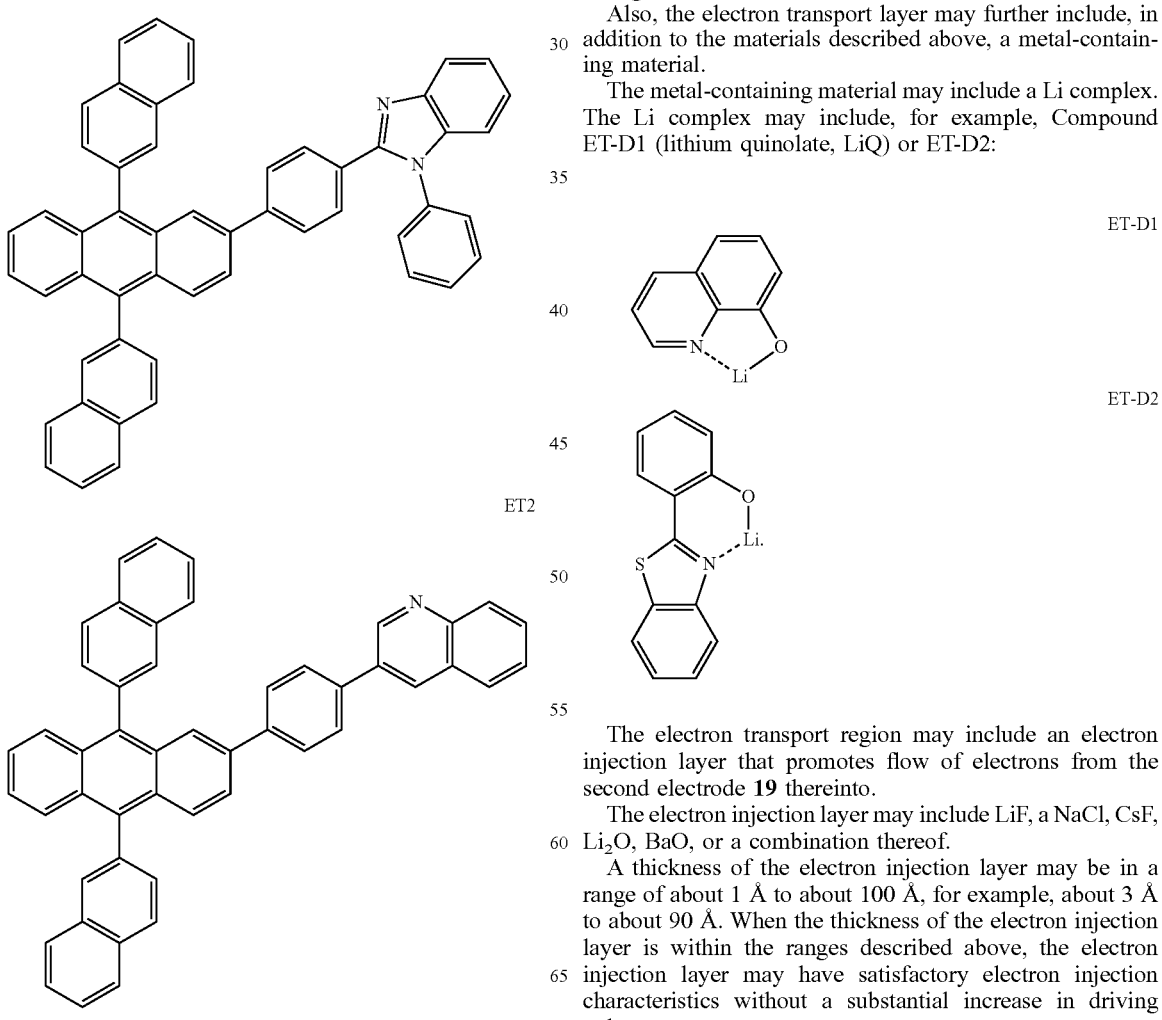

ET1

ET2

-continued

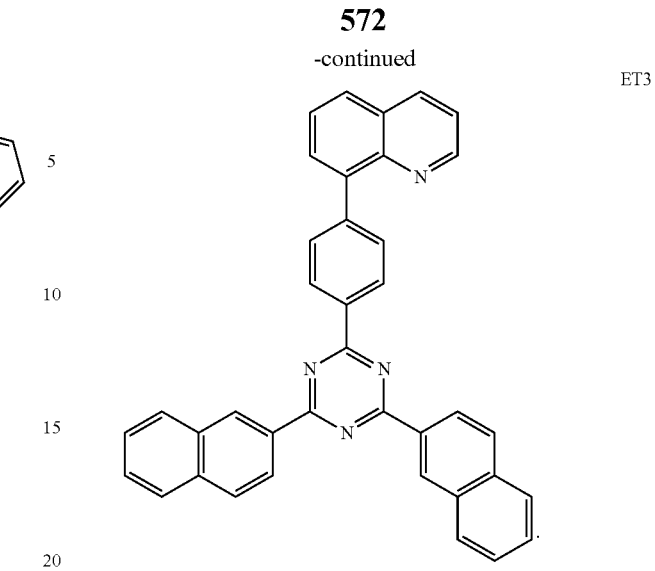

ET3

A thickness of the electron transport layer may be in a range of about 100 Å to about 1,000 Å, for example, about 150 Å to about 500 Å. When the thickness of the electron transport layer is within the ranges described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1

ET-D2

The electron transport region may include an electron injection layer that promotes flow of electrons from the second electrode 19 thereinto.

The electron injection layer may include LiF, a NaCl, CsF, $Li_2O$, BaO, or a combination thereof.

A thickness of the electron injection layer may be in a range of about 1 Å to about 100 Å, for example, about 3 Å to about 90 Å. When the thickness of the electron injection layer is within the ranges described above, the electron injection layer may have satisfactory electron injection characteristics without a substantial increase in driving voltage.

The second electrode 19 may be disposed on the organic layer 15. The second electrode 19 may be a cathode. A material for forming the second electrode 19 may be metal, an alloy, an electrically conductive compound, or a combination thereof, which have a relatively low work function. In an exemplary embodiment, lithium (Li), magnesium (Mg), aluminum (Al), aluminum-lithium (Al—Li), calcium (Ca), magnesium-indium (Mg—In), or magnesium-silver (Mg—Ag) may be the material for forming the second electrode 19. To manufacture a top-emission type light-emitting device, a transmissive electrode formed using ITO or IZO may be used as the second electrode 19.

Hereinbefore, the organic light-emitting device has been described with reference to the FIGURE, but embodiments of the present disclosure are not limited thereto.

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_2$-$C_{60}$ alkenyl group" as used herein refers to a hydrocarbon group having at least one double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_2$-$C_{10}$ heterocycloalkyl group" as used herein refers to a monovalent saturated monocyclic group that has a N, O, P, Si, S, or a combination thereof as ring-forming atoms and 2 to 10 carbon atoms, and non-limiting examples thereof include a tetrahydrofuranyl group, and a tetrahydrothiophenyl group. The term "$C_2$-$C_{10}$ heterocycloalkylene group" as used herein refers to a divalent group having the same structure as the $C_2$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group," used herein, refers to a divalent group having the same structure as the $C_3$-$C_{10}$ cycloalkenyl group.

The term "$C_2$-$C_{10}$ heterocycloalkenyl group" as used herein refers to a monovalent monocyclic group that has an N, O, P, Si, S, or a combination thereof as ring-forming atoms, 2 to 10 carbon atoms, and at least one double bond in its ring. Non-limiting examples of the $C_2$-$C_{10}$ heterocycloalkenyl group are a 2,3-dihydrofuranyl group, and a 2,3-dihydrothiophenyl group. The term "$C_2$-$C_{10}$ heterocycloalkenylene group," used herein, refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_2$-$C_{60}$ heteroaryl group" as used herein refers to a monovalent group having a heterocyclic aromatic system that has an N, O, P, Si, S, or a combination thereof as ring-forming atoms and 2 to 60 carbon atoms. The term "$C_2$-$C_{60}$ heteroarylene group" as used herein refers to a divalent group having a heterocyclic aromatic system that has N, O, P, Si, S, or a combination thereof as ring-forming atoms, in addition to 2 to 60 carbon atoms. Examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), and the term "$C_6$-$C_{60}$ arylthio group" as used herein refers to —$SA_{103}$ (wherein $A_{103}$ is the $C_6$-$C_{60}$ aryl group).

The term "monovalent non-aromatic condensed polycyclic group" as used herein refers to a monovalent group having two or more rings condensed to each other, including only carbon atoms (for example, the number of carbon atoms may be in a range of 8 to 60) as a ring-forming atom, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, including a heteroatom that is N, O, P, Si, S, or a combination thereof as ring-forming atoms, carbon atoms (for example, the number of carbon atoms may be in a range of 2 to 60) as a ring-forming atom, and no aromaticity in its entire molecular structure. A non-limiting example of a monovalent non-aromatic condensed heteropolycyclic group is a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a saturated or unsaturated cyclic group having, as a ring-forming atom, 5 to 60 carbon atoms only. The term "$C_5$-$C_{60}$ carbocyclic group" as used herein refers to a monocyclic group or a polycyclic group, and, according to its chemical structure, a monovalent, divalent, trivalent, tetravalent, pentavalent, or hexavalent group.

The term "$C_2$-$C_{60}$ heterocyclic group" as used herein refers to a saturated or unsaturated cyclic group having, as ring-forming atoms, a heteroatom that is N, O, Si, P, S, or a combination thereof other than the 2 to 60 carbon atoms. The term "$C_2$-$C_{60}$ heterocyclic group" as used herein refers to a monocyclic group or a polycyclic group, and, according to its chemical structure, a monovalent, divalent, trivalent, tetravalent, pentavalent, or hexavalent group.

A substituent of the substituted $C_5$-$C_{60}$ carbocyclic group, the substituted $C_2$-$C_{60}$ heterocyclic group, the substituted π electron-depleted nitrogen-containing $C_2$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, or a combination thereof may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), —P(=O)($Q_{18}$)($Q_{19}$), or a combination thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), —P(=O)($Q_{28}$)($Q_{29}$), or a combination thereof; or —N($Q_{31}$)($Q_{32}$), —Si($Q_{33}$)($Q_{34}$)($Q_{35}$), —B($Q_{36}$)($Q_{37}$) or —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, or a $C_6$-$C_{60}$ aryl group substituted with a $C_1$-$C_{60}$ alkyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or a combination thereof.

The term "room temperature" as used herein refers to a temperature of about 25° C.

Hereinafter, a compound and an organic light-emitting device according to embodiments are described in detail with reference to Synthesis Examples and Examples. However, the organic light-emitting device is not limited thereto. The wording "'B' was used instead of 'A'" used in describing Synthesis Examples means that a molar equivalent of 'A' was identical to a molar equivalent of 'B'.

EXAMPLES

Synthesis Example 1: Synthesis of Compound 245

Compound 245 was synthesized according to the Reaction Scheme below.

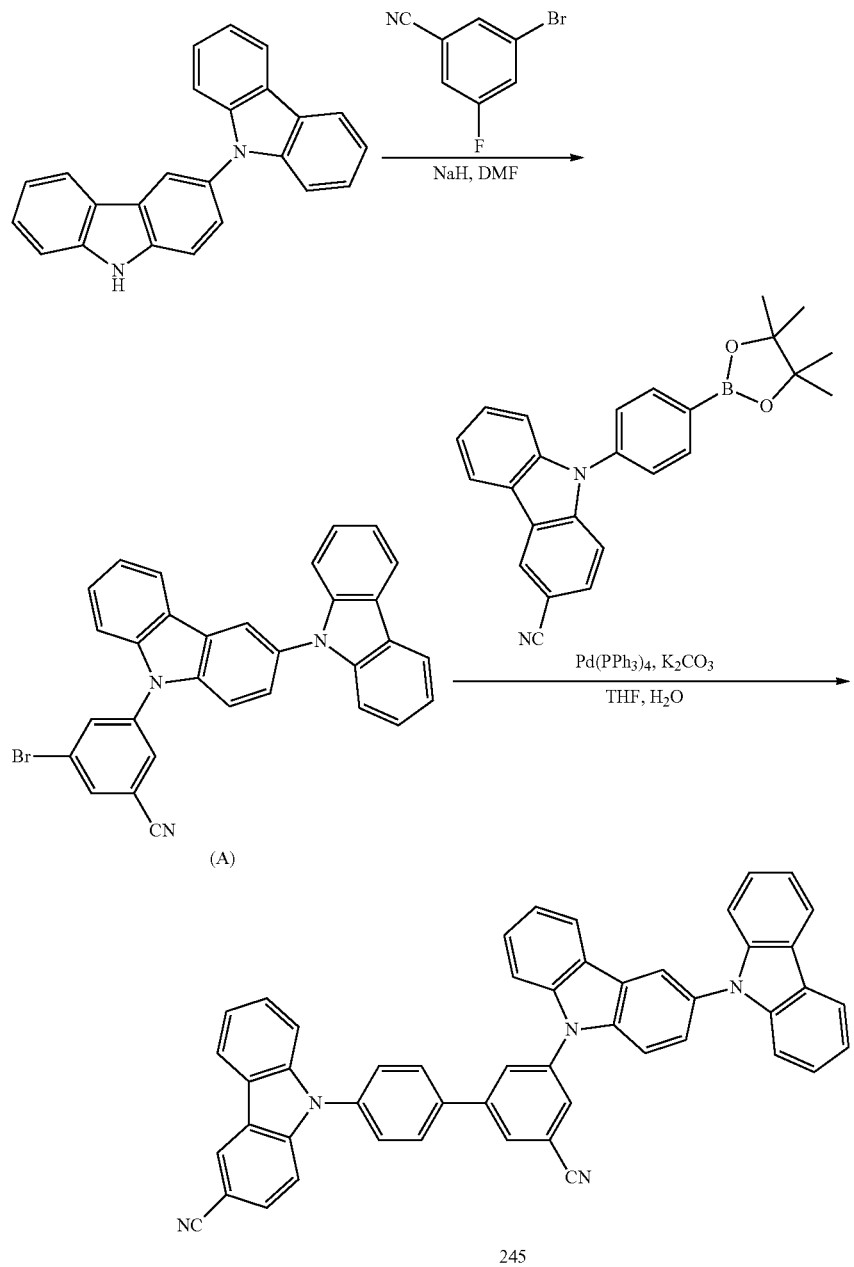

(1) Synthesis of Intermediate (A)

15.0 g (45.1 mmol) of 9H-3,9'-bicarbazole was dissolved in 100 mL of dimethylformamide (DMF) and cooled to a temperature of 0° C. 1.90 g (47.4 mmol) of NaH (60% dispersion in mineral oil) was slowly added thereto and stirred at a temperature of 0° C. for 30 minutes. A solution in which 9.93 g (49.6 mmol) of 3-bromo-5-fluorobenzonitrile was diluted in 50 mL of DMF was slowly added to the reaction mixture for 10 minutes. The reaction temperature was raised to a temperature of 150° C. and the reaction mixture was additionally stirred for 18 hours. After the reaction was completed, the reaction product was cooled to room temperature, saturated aqueous ammonium chloride ($NH_4Cl$) solution was added thereto, and an organic layer was extracted and separated therefrom by using dichloromethane (DCM). The organic layer was dried by using anhydrous magnesium sulfate ($MgSO_4$), filtered, and then concentrated under reduced pressure. Then, the product obtained therefrom was separated by silica gel column chromatography to obtain 18.3 g (yield of 79%) of Intermediate (A).

LC-Mass (calc'd.: 511.07 g/mol, found: M+1=512 g/mol).

(2) Synthesis of Compound 245

5.00 g (9.76 mmol) of Intermediate (A), 4.23 g (10.7 mmol) of 9-(4-(4,4,5,5-tetramethyl-1,3,2-dioxaborolan-2-yl)phenyl)-9H-carbazole-3-carbonitrile, 0.564 g (0.488 mmol) of tetrakis(triphenylphosphine)palladium(0) (Pd$(PPh_3)_4$), and 3.37 g (24.4 mmol) of potassium carbonate were added to a mixed solution containing 20 mL of tetrahydrofuran (THF) and 10 mL of water and stirred under reflux. After the reaction was completed, the reaction product was cooled to room temperature, and an aqueous layer was removed therefrom by extraction. The resulting organic layer was filtered under reduced pressure through silica gel, and a filtrate was concentrated under reduced pressure. Then, the product obtained therefrom was separated by silica gel column chromatography to obtain 5.74 g (yield of 84%) of Compound 245.

LC-Mass (calc'd.: 699.24 g/mol, found: M+1=700 g/mol).

Synthesis Example 2: Synthesis of Compound 275

Compound 275 was synthesized according to the Reaction Scheme below.

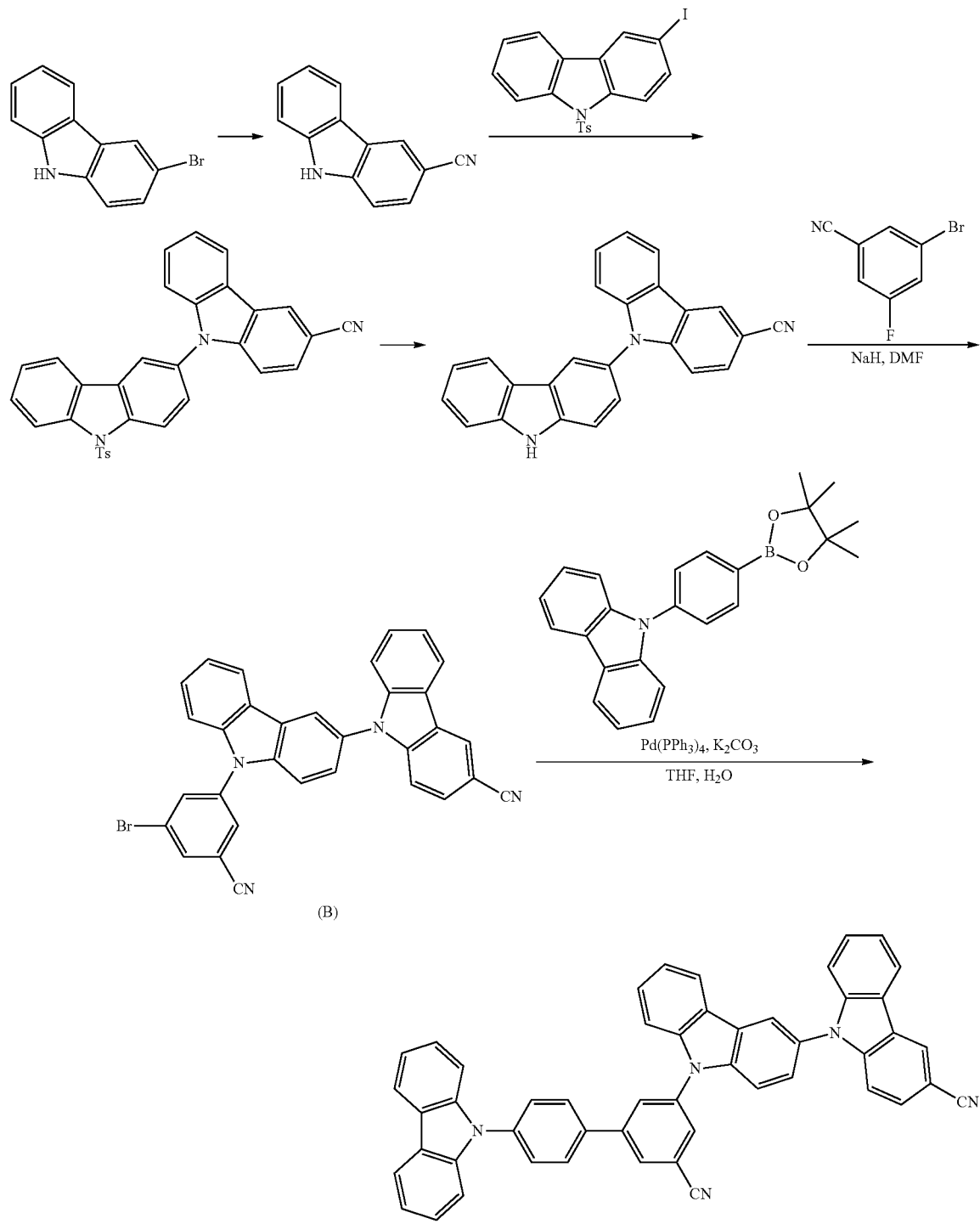

(1) Synthesis of 9H-[3,9'-bicarbazole]-3'-carbonitrile a) 100 g (0.406 mol) of 3-bromo-9H-carbazole and 58.2 g (0.650 mol) of CuCN were added to 800 mL of DMF, and the reaction mixture was stirred for 20 hours in a nitrogen atmosphere under reflux. The reaction mixture was cooled to room temperature, and 4 L of water was added thereto. The reaction mixture was filtered, and a residue obtained therefrom was washed three times by using 1 L of water. A white solid obtained therefrom was added to 1.5 L of 10% aqueous ammonia solution, stirred for 3 hours, filtered, washed three times by using 1 L of water, and then dried overnight at 80° C. and 125 mbar. The solid obtained therefrom was added to 1 L of boiling THF, 100 g of silica was added thereto, and the mixture was stirred for 1 hour and filtered in a hot state. The filtrate was concentrated to 400 mL, cooled to room temperature, the resulting solid was filtered, and the filtered solid was washed three times by using 50 mL of cold THF. Then, the product was dried overnight at 80° C. and 125 mbar to obtain 43.3 g (yield of 55.6%) of a white solid 9H-carbazole-3-carbonitrile.

$^1$H-NMR (400 MHz, CDCl$_3$): δ 8.39 (br s, 2H), 8.10 (d, J=8.0 Hz, 1H), 7.67 (dxd, J$_1$=8.4 Hz, J$_2$=1.6 Hz, 1H), 7.54-7.47 (m, 3H), 7.35-7.31 (m, 1H).

b) 58.4 g (0.131 mol) of 3-iodo-9-(p-tolylsulfonyl) carbazole, 30.0 g (0.156 mol) of 9H-carbazole-3-carbonitrile, 8.9 g (0.078 mol) of trans-1,2-diamino-cyclohexane, 173.9 g (0.822 mol) of K$_3$PO$_4$, and 13.9 g (0.073 mol) of CuI were added to 900 mL of 1,4-dioxane, and the gray mixture was stirred for 27 hours under reflux. The reaction mixture was filtered in a hot state and washed three times by using 200 mL of 1,4-dioxane. The filtrate was concentrated and dissolved in 750 mL of ethyl acetate (EtOAc). 50 g of silica was added thereto, stirred for 1 hour, filtered, and then washed three times by using 100 mL of EtOAc. The filtrate was concentrated to 140 g, cooled to a temperature of 0° C., and then filtered. The residue was washed once by using 20 mL of cold EtOAc, washed twice by using 20 mL of cold MeOH, and then dried overnight at 80° C. and 125 mbar to obtain 36.8 g of a crude product. 250 mL of MeOH was added to the crude product, and the mixture was stirred for 3 hours under reflux, cooled to room temperature, and then filtered. The residue was washed three times by using 25 mL of MeOH and dried overnight at 80° C. and 125 mbar to obtain 35.6 g of an ivory solid 9-[9-(p-tolylsulfonyl)carbazol-3-yl]carbazole-3-carbonitrile.

$^1$H-NMR (400 MHz, CDCl$_3$): δ 8.58 (d, J=8.8 Hz, 1H), 8.48 (s, 1H), 8.40 (d, J=8.8 Hz, 1H), 8.18 (d, J=7.2 Hz, 2H), 8.05 (d, J=2.0 Hz, 1H), 7.90 (d, J=7.6 Hz, 1H), 7.83 (d, J=8.4 Hz, 2H), 7.66-7.56 (m, 3H), 7.50 (t, J=8.4 Hz, 1H), 7.43-7.36 (m, 4H), 7.22 (d, J=8.0 Hz, 2H), 2.35 (s, 3H).

c) 9.2 g (139.3 mmol) of 85% KOH was dissolved in 290 mL of EtOH, 35.6 g (69.6 mmol) of 9-[9-(p-tolylsulfonyl)carbazol-3-yl]carbazole-3-carbonitrile dissolved in 590 mL of THF was added thereto and stirred for 6 hours, and 500 mL of H$_2$O was added dropwise thereto. 4 N HCl was added thereto to adjust pH to 8, and an organic solvent was distilled under reduced pressure. A residue was extracted therefrom three times by using 250 mL of EtOAc, and a collected organic layer was washed once by using 100 mL of H$_2$O and washed once by using 100 mL of brine, dried by using Na$_2$SO$_4$, filtered, and then concentrated to obtain 40.6 g of a crude product as a gray solid. 250 mL of MeOH was added to the crude product, and the mixture was stirred for 3 hours under reflux, cooled to room temperature, and then filtered. A residue was washed three times by using 20 mL of MeOH and dried overnight at 80° C. and 125 mbar. The above procedure was performed once again to obtain 18.2 g (yield of 73.0%) of a white solid 9-(9H-carbazol-3-yl)carbazole-3-carbonitrile.

$^1$H-NMR (400 MHz, CDCl$_3$): δ 8.48 (s, 1H), 8.41 (br s, 1H), 8.20-8.16 (m, 2H), 8.04 (d, J=8.0 Hz, 1H), 7.66-7.28 (m, 10H).

(2) Synthesis of Intermediate (B)

15.1 g (yield of 67%) of Intermediate (B) was obtained in the same manner as in Synthesis of Intermediate (A), except that 15.0 g (42.0 mmol) of 9H-[3,9'-bicarbazole]-3'-carbonitrile was used instead of 9H-3,9'-bicarbazole during synthesis.

LC-Mass (calc'd.: 536.06 g/mol, found: M+1=537 g/mol).

(3) Synthesis of Compound 275

5.27 g (yield of 81%) of Compound 275 was obtained in the same manner as in Synthesis of Compound 245, except that 5.00 g (9.30 mmol) of Intermediate (B) was used instead of Intermediate (A), and 3.78 g (10.2 mmol) of 9-(4-(4,4,5,5-tetramethyl-1,3,2-dioxaborolan-2-yl)phenyl)-9H-carbazole was used instead of 9-(4-(4,4,5,5-tetramethyl-1,3,2-dioxaborolan-2-yl)phenyl)-9H-carbazole-3-carbonitrile during synthesis.

LC-Mass (calc'd.: 699.24 g/mol, found: M+1=700 g/mol).

Synthesis Example 3: Synthesis of Compound 406

Compound 406 was synthesized according to the Reaction Scheme below.

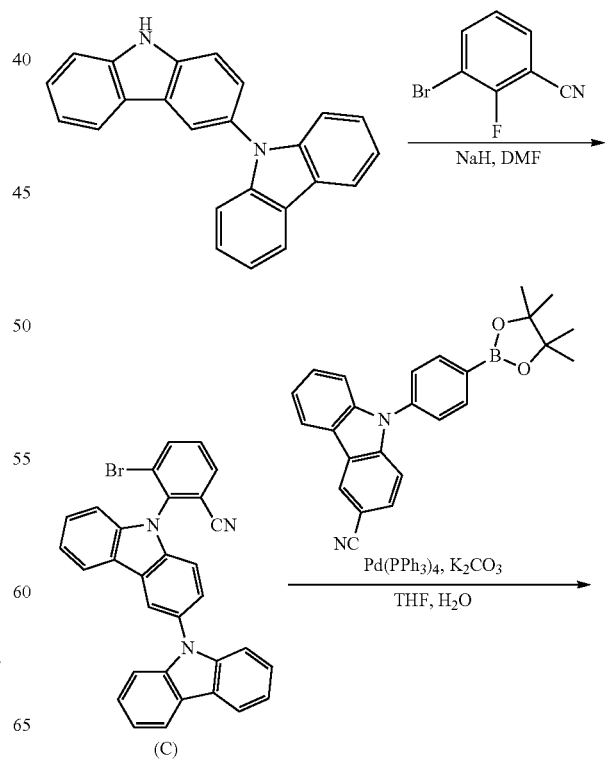

-continued

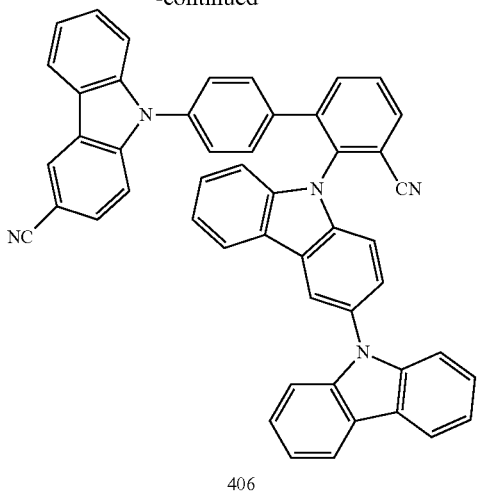

406

(1) Synthesis of Intermediate (C)

15.0 g (yield of 65%) of Intermediate (C) was obtained in the same manner as in Synthesis of Intermediate (A), except that 9.94 g (49.7 mmol) of 3-bromo-2-fluorobenzonitrile was used instead of 3-bromo-5-fluorobenzonitrile during synthesis.

LC-Mass (calc'd.: 511.07 g/mol, found: M+1=512 g/mol)

(2) Synthesis of Compound 406

3.69 g (yield of 54%) of Compound 406 was obtained in the same manner as in Synthesis of Compound 245, except that 5.00 g (9.76 mmol) of Intermediate (C) was used instead of Intermediate (A) during synthesis.

LC-Mass (calc'd.: 699.24 g/mol, found: M+1=700 g/mol).

Synthesis Example 4: Synthesis of Compound 563

Compound 563 was synthesized according to the Reaction Scheme below.

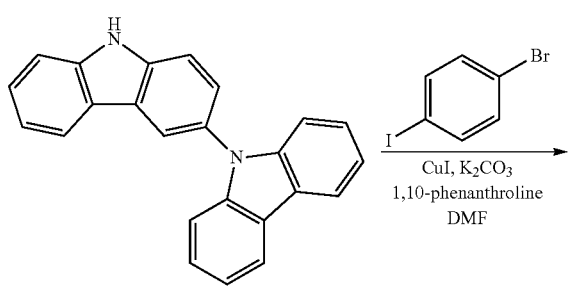

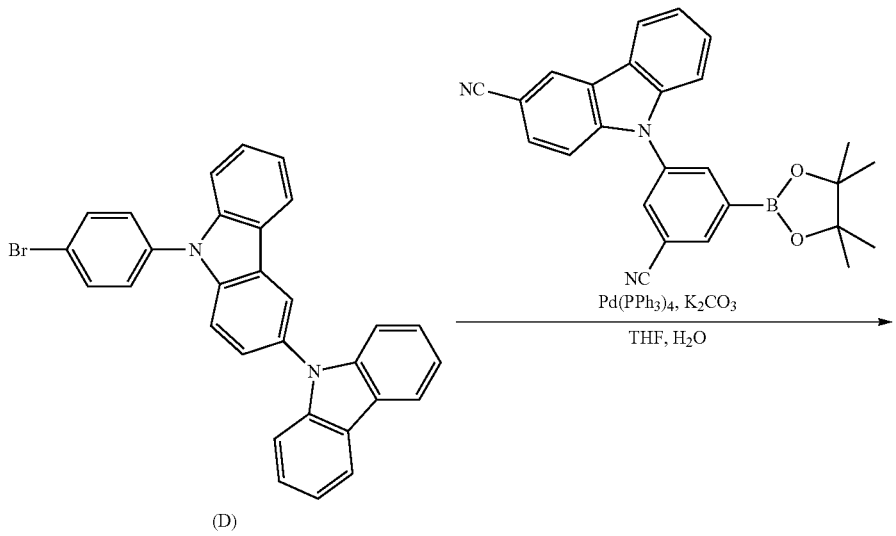

(D)

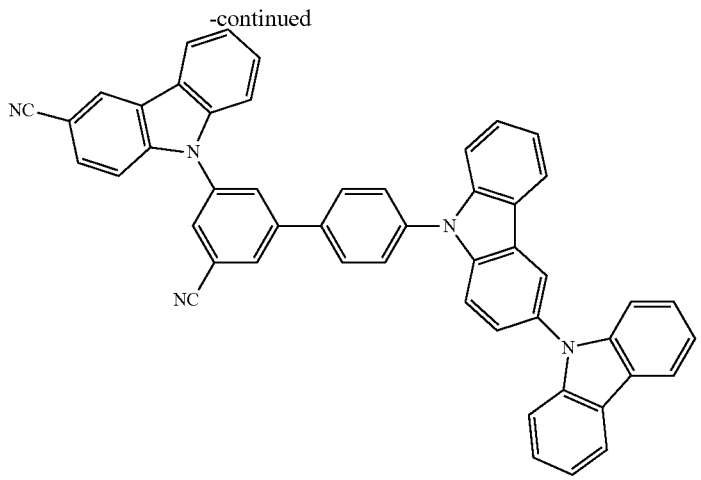

563

(1) Synthesis of 9-(3-cyano-5-(4,4,5,5-tetramethyl-1,3,2-dioxaborolan-2-yl)penyl)-9H-carbazole-3-carbonitrile a) 10.0 g (52.0 mmol) of 9H-carbazole-3-carbonitrile, 15.6 g (78.0 mmol) of 3-bromo-5-fluorobenzonitrile, 1.98 g (10.4 mmol) of copper iodide (CuI), 28.8 g (208 mmol) of potassium carbonate ($K_2CO_3$), and 3.75 g (20.8 mmol) of 1,10-phenanthroline were dissolved in 175 mL of DMF and stirred for 24 hours under reflux. After the reaction was completed, the reaction product was cooled to room temperature and then filtered under reduced pressure through silica gel, and a filtrate was concentrated under reduced pressure. A crude product obtained therefrom was separated by silica gel column chromatography to obtain 14.3 g (yield of 74%) of 9-(3-bromo-5-cyanophenyl)-9H-carbazole-3-carbonitrile.

LC-Mass (calc'd.: 371.01 g/mol, found: M+1=372 g/mol).

b) 13.9 g (43.2 mmol) of 9-(3-bromo-5-cyanophenyl)-9H-carbazole-3-carbonitrile, 13.2 g (51.8 mmol) of bis(pinacolato)diboron, 1.76 g (2.16 mmol) of $PdCl_2$(dppf).$CH_2Cl_2$, and 12.7 g (130 mmol) of potassium acetate were dissolved in 145 mL of DMF and stirred at a temperature of 100° C. for 20 hours. After the reaction was completed, the reaction product was cooled to room temperature and then filtered under reduced pressure through silica gel, and the filtrate was concentrated. The product obtained therefrom was separated by silica gel column chromatography. The crude product was recrystallized from dichloromethane (DCM)/n-hexane to obtain 12.7 g (yield of 70%) of 9-(3-cyano-5-(4,4,5,5-tetramethyl-1,3,2-dioxaborolan-2-yl)phenyl)-9H-carbazole-3-carbonitrile.

LC-Mass (calc'd: 419.18 g/mol, found: M+1=420 g/mol).

(2) Synthesis of Intermediate (D)

10.0 g (30.1 mmol) of 9H-3,9'-bicarbazole, 12.8 g (45.1 mmol) of 1-bromo-4-iodobenzene, 1.15 g (6.02 mmol) of copper iodine (CuI), 16.6 g (120 mmol) of potassium carbonate ($K_2CO_3$), and 2.17 g (12.0 mmol) of 1,10-phenanthroline were dissolved in 100 mL of DMF and stirred for 24 hours under reflux. After the reaction was completed, the reaction product was cooled to room temperature and filtered under reduced pressure through silica gel, and the filtrate was concentrated under reduced pressure. The product obtained therefrom was separated by silica gel column chromatography to obtain 11.3 g (yield of 77%) of Intermediate (D).

LC-Mass (calc'd.: 486.07 g/mol, found: M+1=487 g/mol).

(3) Synthesis of Compound 563

5.74 g (yield of 80%) of Compound 563 was obtained in the same manner as in the Synthesis of Compound 245, except that 5.00 g (10.3 mmol) of Intermediate (D) was used instead of Intermediate (A), and 4.73 g (11.3 mmol) of 9-(3-cyano-5-(4,4,5,5-tetramethyl-1,3,2-dioxaborolan-2-yl)phenyl)-9H-carbazole-3-carbonitrile was used instead of 9-(4-(4,4,5,5-tetramethyl-1,3,2-dioxaborolan-2-yl)phenyl)-9H-carbazole-3-carbonitrile during synthesis.

LC-Mass (calc'd.: 699.24 g/mol, found: M+1=700 g/mol).

Synthesis Example 5: Synthesis of Compound 593

Compound 593 was synthesized according to the Reaction Scheme below.

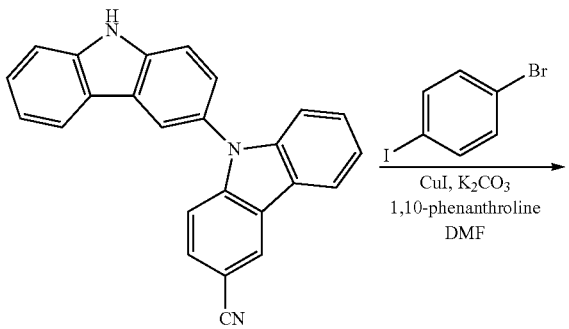

-continued

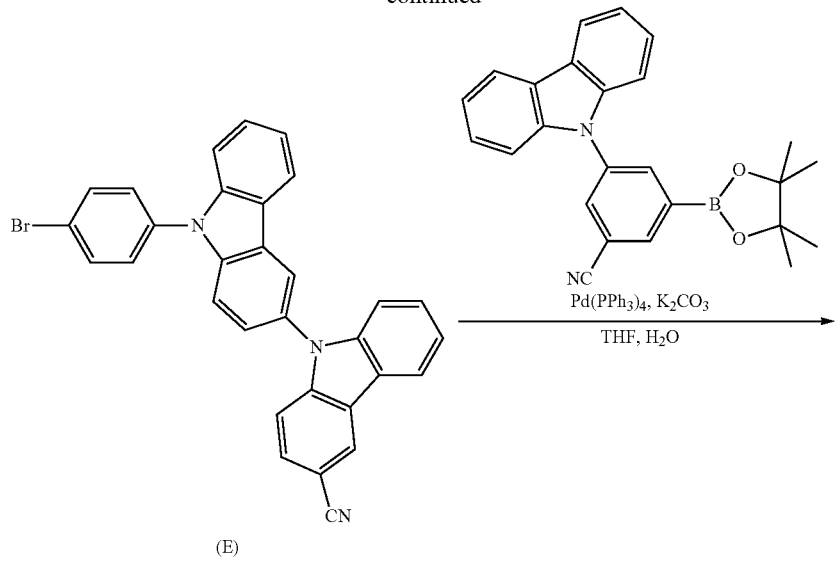

(E)

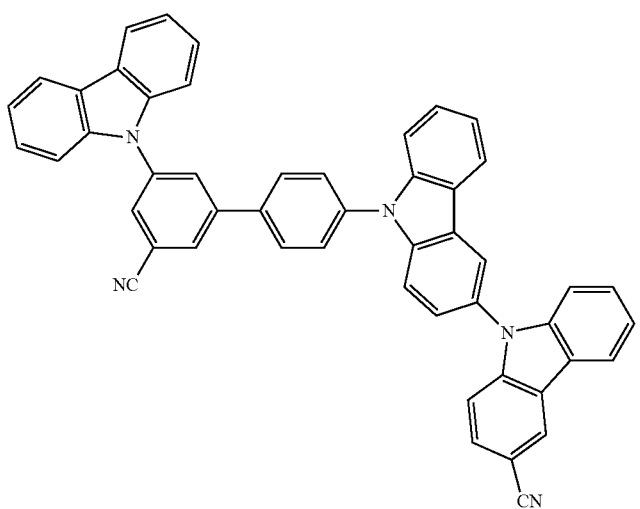

593

(1) Synthesis of 3-(9H-carbazole-9-yl)-5-(4,4,5,5-tetramethyl-1,3,2-dioxaborolan-2-yl)benzonitrile 3-(9H-carbazole-9-yl)-5-(4,4,5,5-tetramethyl-1,3,2-dioxaborolan-2-yl)benzonitrile was synthesized in the same manner as in the Synthesis of 9-(3-cyano-5-(4,4,5,5-tetramethyl-1,3,2-dioxaborolan-2-yl)phenyl)-9H-carbazole-3-carbonitrile, except that carbazole was used instead of 9H-carbazole-3-carbonitrile during synthesis.

(2) Synthesis of Intermediate (E)

9.89 g (yield of 69%) of Intermediate (E) was obtained in the same manner as in the Synthesis of Intermediate (D), except that 10.0 g (30.0 mmol) of 9H-[3,9'-bicarbazole]-3'-carbonitrile was used instead of 9H-3,9'-bicarbazole during synthesis.

LC-Mass (calc'd.: 511.07 g/mol, found: M+1=512 g/mol).

(3) Synthesis of Compound 593

5.19 g (yield of 76%) of Compound 593 was obtained in the same manner as in the Synthesis of Compound 245, except that 5.00 g (9.79 mmol) of Intermediate (E) was used instead of Intermediate (A), and 4.23 g (10.7 mmol) of 3-(9H-carbazol-9-yl)-5-(4,4,5,5-tetramethyl-1,3,2-dioxaborolan-2-yl)benzonitrile was used instead of 9-(4-(4,4,5,5-tetramethyl-1,3,2-dioxaborolan-2-yl)phenyl)-9H-carbazole-3-carbonitrile during synthesis.

LC-Mass (calc'd.: 699.24 g/mol, found: M+1=700 g/mol).

Synthesis Example 6: Synthesis of Compound 723

Compound 723 was synthesized according to the Reaction Scheme below.

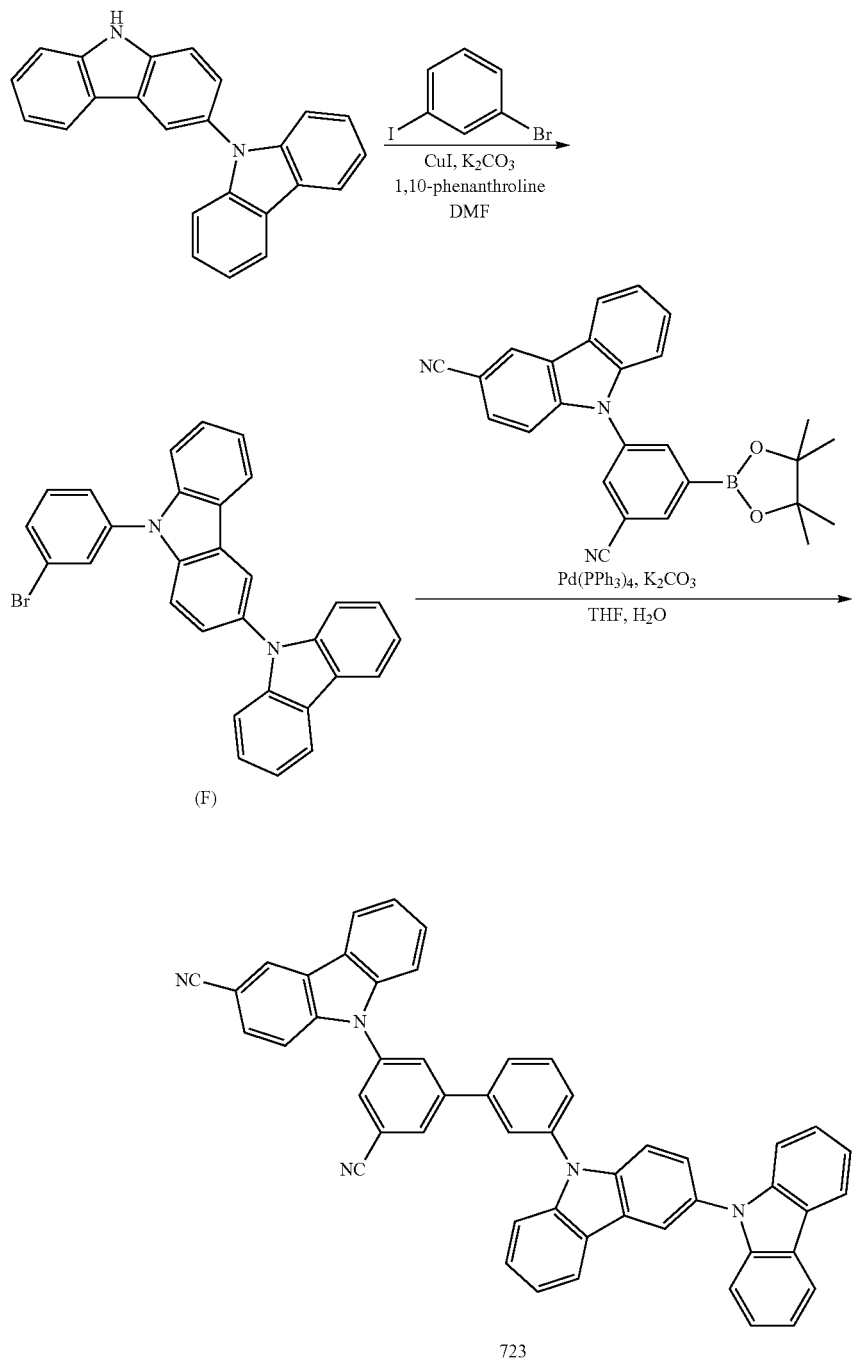

(1) Synthesis of Intermediate (F)

12.8 g (yield of 87%) of Intermediate (F) was obtained in the same manner as in the Synthesis of Intermediate (D), except that 12.8 g (45.1 mmol) of 1-bromo-4-iodobenzene was used instead of 1-bromo-4-iodobenzene during synthesis.

LC-Mass (calc'd.: 486.07 g/mol, found: M+1=487 g/mol).

(2) Synthesis of Compound 723

6.10 g (yield of 85%) of Compound 723 was obtained in the same manner as in the Synthesis of Compound 245, except that 5.00 g (10.3 mmol) of Intermediate (F) was used instead of Intermediate (A), and 4.73 g (11.3 mmol) of 9-(3-cyano-5-(4,4,5,5-tetramethyl-1,3,2-dioxaborolan-2-yl)phenyl)-9H-carbazole-3-carbonitrile was used instead of 9-(4-(4,4,5,5-tetramethyl-1,3,2-dioxaborolan-2-yl)phenyl)-9H-carbazole-3-carbonitrile during synthesis.

LC-Mass (calc'd.: 699.24 g/mol, found: M+1=700 g/mol).

Synthesis Example 7: Synthesis of Compound 724

Compound 724 was synthesized according to the Reaction Scheme below.

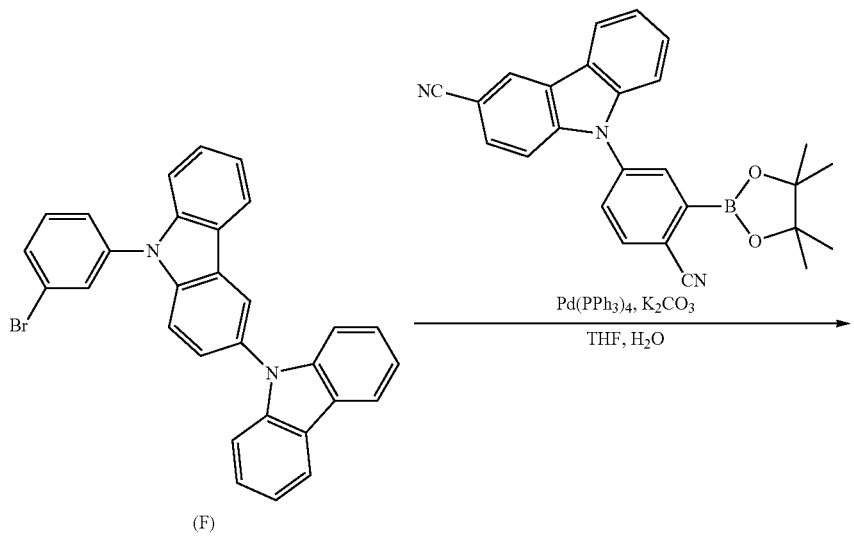

(F)

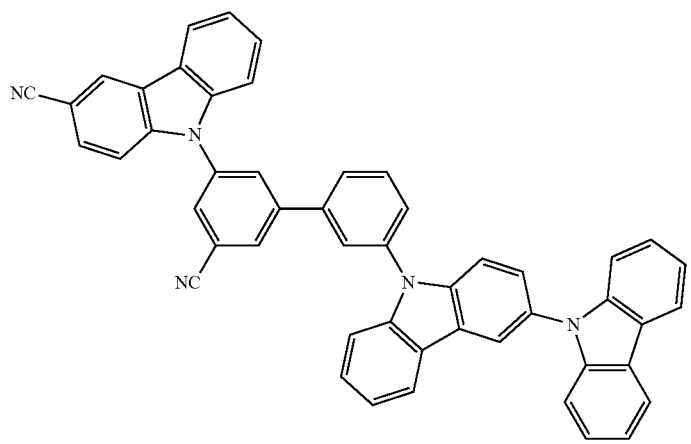

724

(1) Synthesis of 9-(4-cyano-3-(4,4,5,5-tetramethyl-1,3,2-dioxaborolan-2-yl)penyl)-9H-carbazole-3-carbonitrile 9-(4-cyano-3-(4,4,5,5-tetramethyl-1,3,2-dioxaborolan-2-yl)penyl)-9H-carbazole-3-carbonitrile was obtained in the same manner as in the Synthesis of 9-(3-cyano-5-(4,4,5,5-tetramethyl-1,3,2-dioxaborolan-2-yl)penyl)-9H-carbazole-3-carbonitrile, except that 4-bromo-2-fluorobenzonitrile was used instead of 3-bromo-5-fluorobenzonitrile during synthesis.

(2) Synthesis of Compound 724

4.59 g (yield of 64%) of Compound 724 was obtained in the same manner as in the Synthesis of Compound 245, except that 5.00 g (10.3 mmol) of Intermediate (F) was used instead of Intermediate (A), and 4.73 g (11.3 mmol) of 9-(4-cyano-3-(4,4,5,5-tetramethyl-1,3,2-dioxaborolan-2-yl)phenyl)-9H-carbazole-3-carbonitrile was used instead of 9-(4-(4,4,5,5-tetramethyl-1,3,2-dioxaborolan-2-yl)phenyl)-9H-carbazole-3-carbonitrile during synthesis.

LC-Mass (calc'd.: 699.24 g/mol, found: M+1=700 g/mol).

Regarding the Synthesis of 9-(4-cyano-3-(4,4,5,5-tetramethyl-1,3,2-dioxaborolan-2-yl)phenyl)-9H-carbazole-3-carbonitrile, a synthesis method disclosed in US 20170358755 was referred to.

Synthesis Example 8: Synthesis of Compound 726

Compound 726 was synthesized according to the Reaction Scheme below.

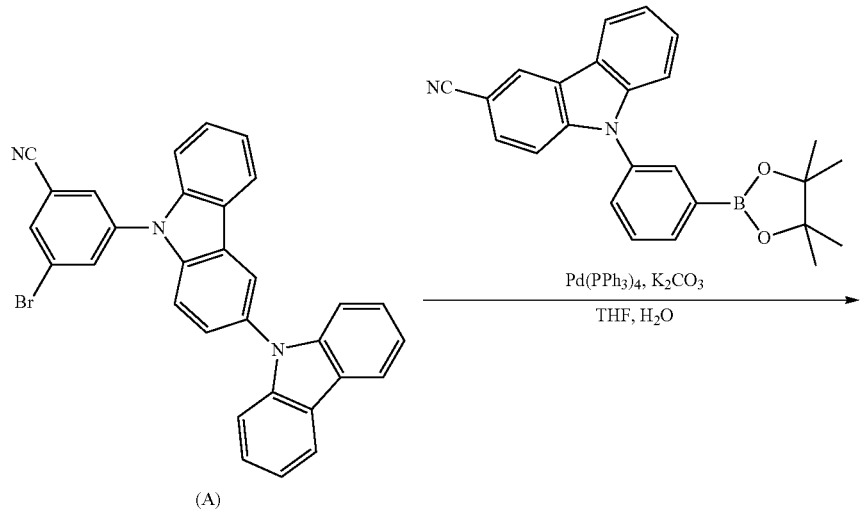

(A)

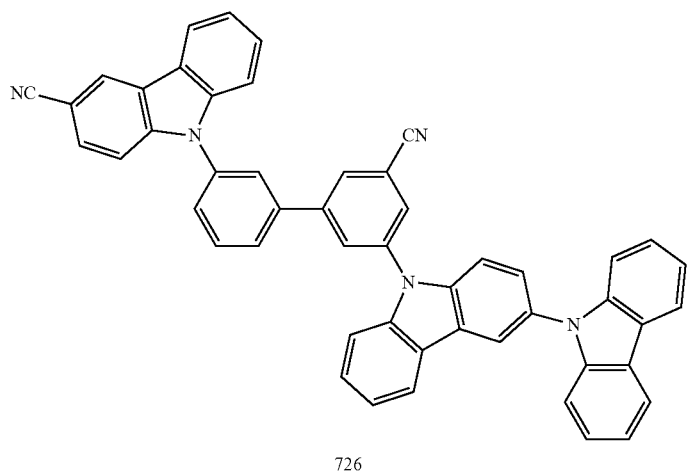

726

(1) Synthesis of Compound 726

5.82 g (yield of 81%) of Compound 726 was obtained in the same manner as in the Synthesis of Compound 245, except that 4.73 g (11.3 mmol) of 9-(3-(4,4,5,5-tetramethyl-1,3,2-dioxaborolan-2-yl)phenyl)-9H-carbazole-3-carbonitrile was used instead of 9-(4-(4,4,5,5-tetramethyl-1,3,2-dioxaborolan-2-yl)phenyl)-9H-carbazole-3-carbonitrile during synthesis.

LC-Mass (calc'd.: 699.24 g/mol, found: M+1=700 g/mol).

Synthesis Example 9: Synthesis of Compound 755

Compound 755 was synthesized according to the Reaction Scheme below.

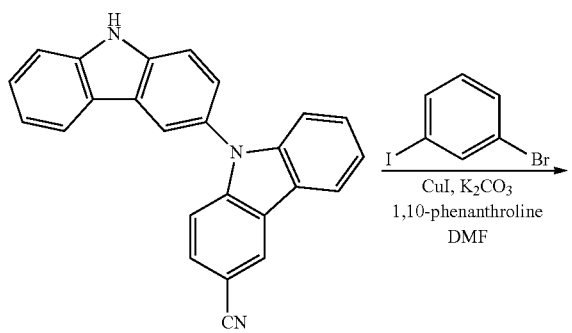

-continued

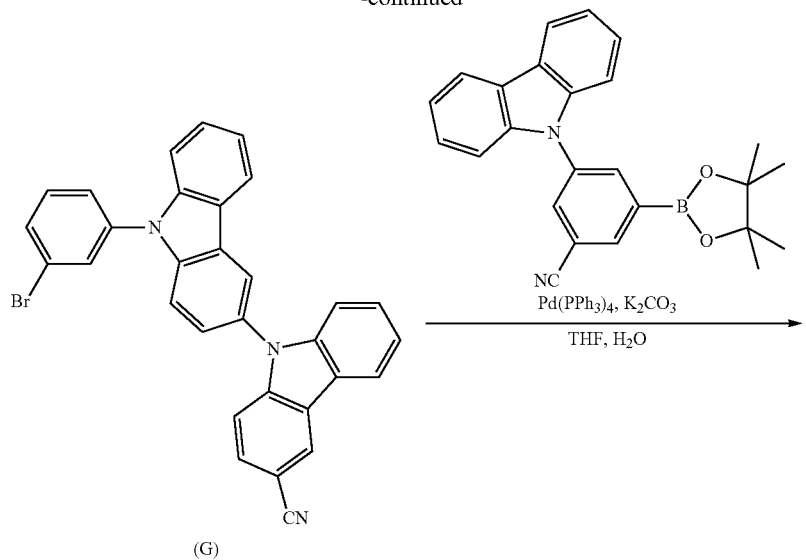

(G)

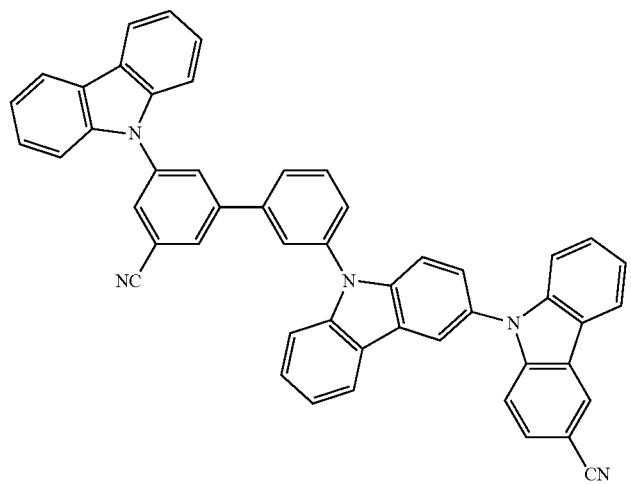

755

(1) Synthesis of Intermediate (G)

10.0 g (yield of 70%) of intermediate (G) was obtained in the same manner as in the Synthesis of Intermediate (F), except that 10.0 g (30.0 mmol) of 9H-[3,9'-bicarbazole]-3'-carbonitrile was used instead of 9H-3,9'-bicarbazole during synthesis.

LC-Mass (calc'd.: 511.07 g/mol, found: M+1=512 g/mol).

(2) Synthesis of Compound 755

6.01 g (yield of 88%) of Compound 755 was obtained in the same manner as in the Synthesis of Compound 245, except that 5.00 g (9.79 mmol) of Intermediate (G) was used instead of Intermediate (A), and 4.23 g (10.7 mmol) of 3-(9H-carbazol-9-yl)-5-(4,4,5,5-tetramethyl-1,3,2-dioxaborolan-2-yl)benzonitrile was used instead of 9-(4-(4,4,5,5-tetramethyl-1,3,2-dioxaborolan-2-yl)phenyl)-9H-carbazole-3-carbonitrile during synthesis.

LC-Mass (calc'd.: 699.24 g/mol, found: M+1=700 g/mol).

Synthesis Example 10: Synthesis of Compound 756

Compound 756 was synthesized according to the Reaction Scheme below.

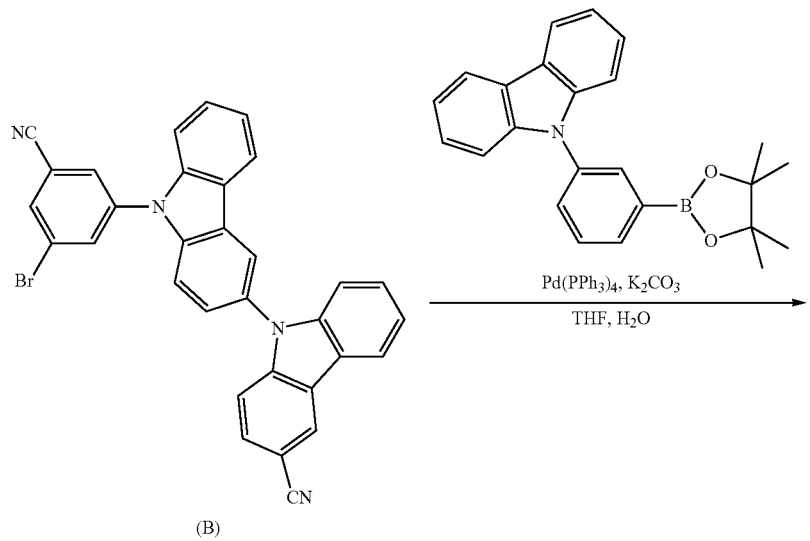

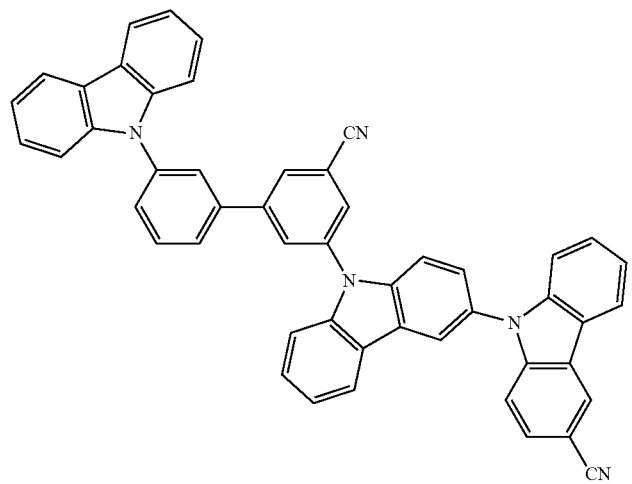

756

(1) Synthesis of Compound 756

5.40 g (yield of 83%) of Compound 756 was obtained in the same manner as in the Synthesis of Compound 245, except that 5.00 g (9.30 mmol) of Intermediate (B) was used instead of Instead of (A), and 3.78 g (10.2 mmol) of 9-(3-(4,4,5,5-tetramethyl-1,3,2-dioxaborolan-2-yl)phenyl)-9H-carbazole was used instead of 9-(4-(4,4,5,5-tetramethyl-1,3,2-dioxaborolan-2-yl)phenyl)-9H-carbazole-3-carbonitrile during synthesis.

LC-Mass (calc'd.: 699.24 g/mol, found: M+1=700 g/mol).

Synthesis Example 11: Synthesis of Compound 757

Compound 757 was synthesized according to the Reaction Scheme below.

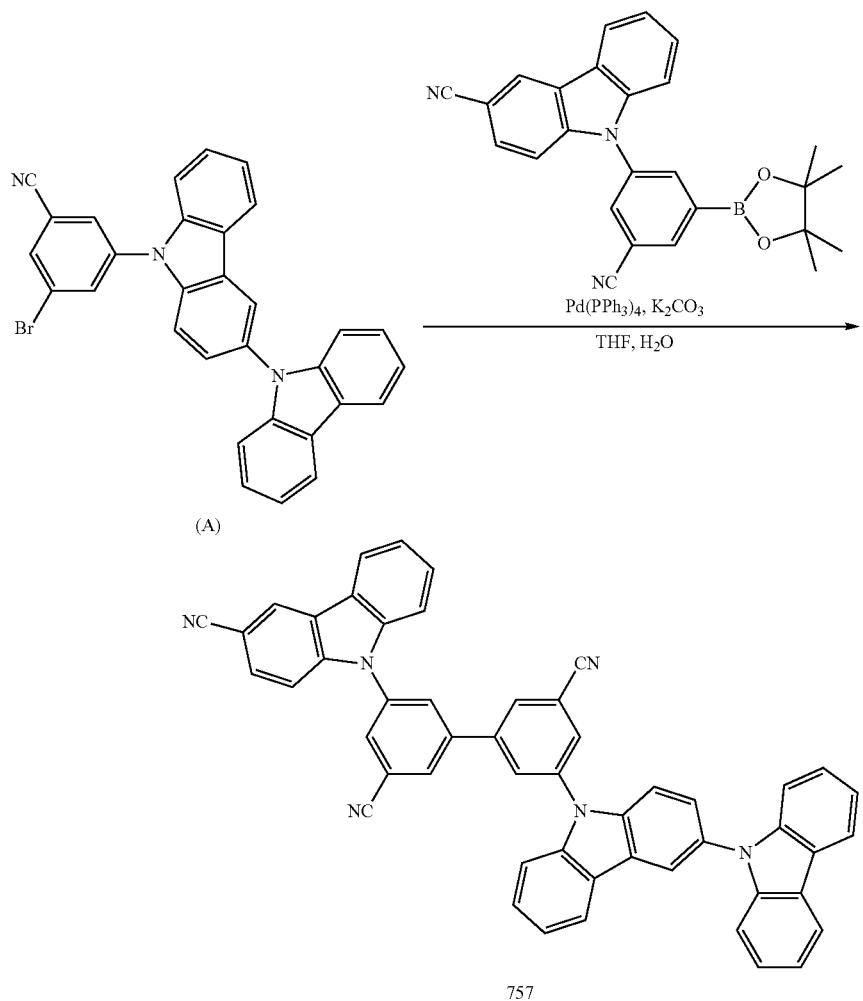

(1) Synthesis of Compound 757

4.17 g (Yield of 59%) of Compound 757 was obtained in the same manner as in the Synthesis of Compound 245, except that 4.50 g (10.7 mmol) of 9-(3-cyano-5-(4,4,5,5-tetramethyl-1,3,2-dioxaborolan-2-yl)phenyl)-9H-carbazole-3-carbonitrile was used instead of 9-(4-(4,4,5,5-tetramethyl-1,3,2-dioxaborolan-2-yl)phenyl)-9H-carbazole-3-carbonitrile during synthesis.

LC-Mass (calc'd.: 724.24 g/mol, found: M+1=725 g/mol).

Example 1

A glass substrate, on which a 1,500 Å ITO electrode (first electrode, anode) was formed, was cleaned by distilled water ultrasonic rays. After distilled water cleaning was completed, the glass substrate was cleaned with ultrasonic rays by using a solvent such as isopropyl alcohol, acetone, and methanol, dried, provided to a plasma cleaner. The glass substrate was cleaned for 5 minutes by oxygen plasma, and subjected to a vacuum deposition apparatus.

Compound HT3 and Compound HT-D2 were co-deposited on the ITO electrode of the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 100 Å, thereby forming a hole transport region.

Compound 1 (host) and FIr6 (dopant, 10 wt %) were co-deposited on the hole transport region to form an emission layer having a thickness of 400 Å.

BCP was vacuum-deposited on the emission layer to form a hole blocking layer having a thickness of 100 Å, Compound ET3 and LiQ were vacuum-deposited on the hole blocking layer to form an electron transport layer having a thickness of 300 Å, LiQ was deposited on the electron transport layer to form an electron injection layer having a thickness of 10 Å, and Al was deposited on the electron injection layer to form a second electrode (cathode) having a thickness of 1,200 Å, thereby completing the manufacture of an organic light-emitting device.

601

HT3
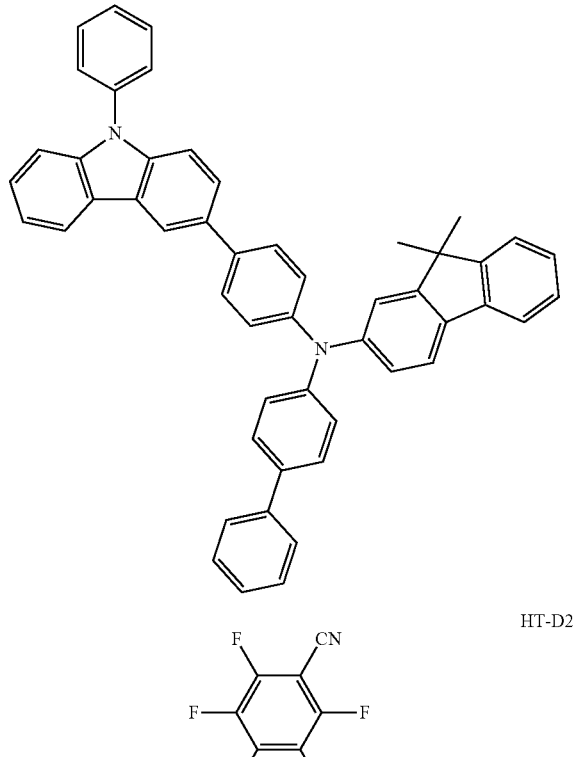

HT-D2
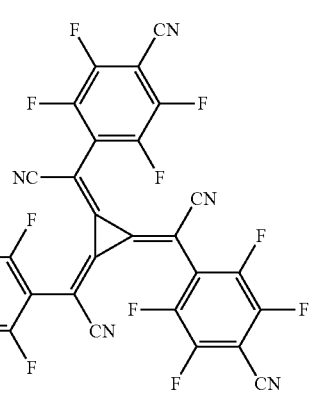

mCP
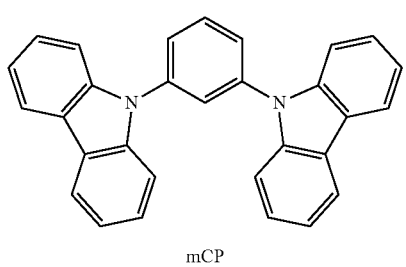

Fir6
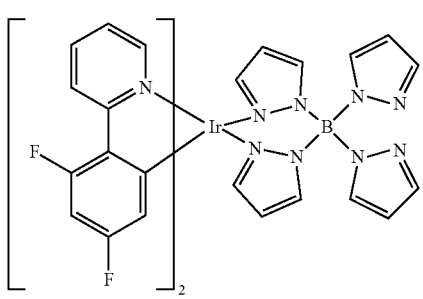

602

-continued

BCP
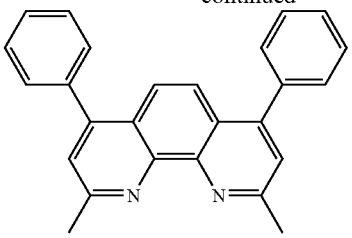

ET3
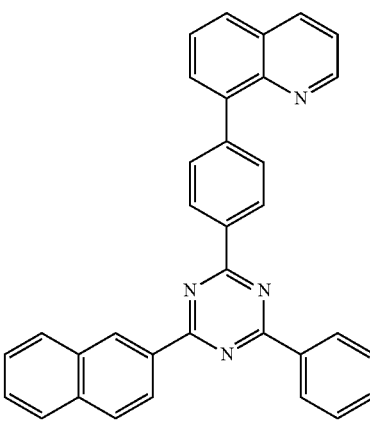

Examples 2 to 11 and Comparative Examples 1 to 7

Organic light-emitting devices were manufactured in the same manner as in Example 1, except that Compounds shown in Table 2 were each used instead of Compound 1 as a host in forming an emission layer.

Evaluation Example 3: Evaluation of Characteristics of Organic Light-Emitting Device The current density change, luminance change, and luminescent efficiency of the organic light-emitting devices manufactured according to Examples 1 to 11 and Comparative Examples 1 to 7 were measured. Detailed measurement methods are as follows, and results thereof are shown in Table 2. The driving voltage, current efficiency, and durability are expressed by relative values when the driving voltage, current efficiency, and durability of the organic light-emitting device manufactured according to Comparative Example 1 was 100%.

(1) Measurement of Current Density Change According to Voltage Change

A current-voltage meter (KEITHLEY 2400) was used to measure a value of a current flowing through a unit element with respect to the manufactured organic light-emitting devices while increasing a voltage from 0 volts (V) to 10 V, and the measured current value was divided by an area to thereby obtain the current density change.

(2) Measurement of Luminance Change According to Voltage Change

A luminance meter (MINOLTA Cs-1000A) was used to measure luminance with respect to the manufactured organic light-emitting devices while increasing a voltage from 0 V to 10 V to thereby obtain the luminance change.

(3) Measurement of Luminescent Efficiency

The current efficiency (cd/A) at the same current density (10 mA/cm$^2$) was calculated by using the luminance and the current density calculated in the above (1) and (2) and the voltage.

(4) Measurement of Durability

The time that lapsed when luminance was 95% of initial luminance (100%) was evaluated.

TABLE 2

| | No. of Host compound | Driving voltage (relative value) | Current efficiency (relative value) | Durability (relative value) | Emission color |
|---|---|---|---|---|---|
| Example 1 | 245 | 83 | 134 | 145 | Blue |
| Example 2 | 275 | 82 | 141 | 135 | Blue |
| Example 3 | 406 | 95 | 124 | 121 | Blue |
| Example 4 | 563 | 79 | 154 | 172 | Blue |
| Example 5 | 593 | 78 | 143 | 180 | Blue |
| Example 6 | 723 | 72 | 163 | 186 | Blue |
| Example 7 | 724 | 75 | 157 | 198 | Blue |
| Example 8 | 726 | 77 | 152 | 179 | Blue |
| Example 9 | 755 | 74 | 139 | 141 | Blue |
| Example 10 | 756 | 74 | 128 | 152 | Blue |
| Example 11 | 757 | 85 | 145 | 177 | Blue |
| Comparative Example 1 | A | 100 | 100 | 100 | Blue |
| Comparative Example 2 | B | 124 | 85 | 77 | Blue |
| Comparative Example 3 | C | 154 | 73 | 82 | Blue |
| Comparative Example 4 | D | 95 | 119 | 115 | Blue |
| Comparative Example 5 | E | 105 | 97 | 108 | Blue |
| Comparative Example 6 | F | 165 | 78 | 54 | Blue |
| Comparative Example 7 | G | 92 | 121 | 131 | Blue |

245

275

406

563

587

TABLE 2-continued
| No. of Host compound | Driving voltage (relative value) | Current efficiency (relative value) | Durability (relative value) | Emission color |
|---|---|---|---|---|
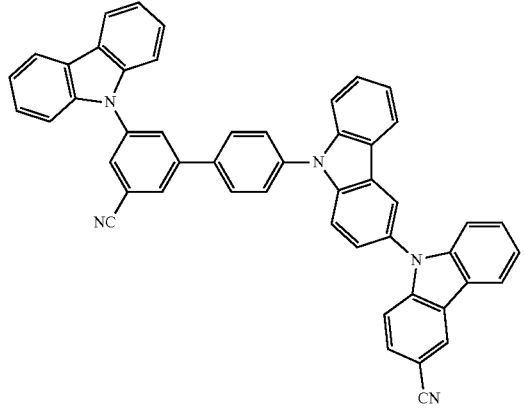
593
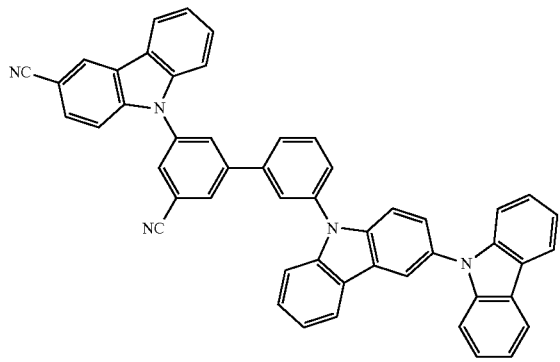
723
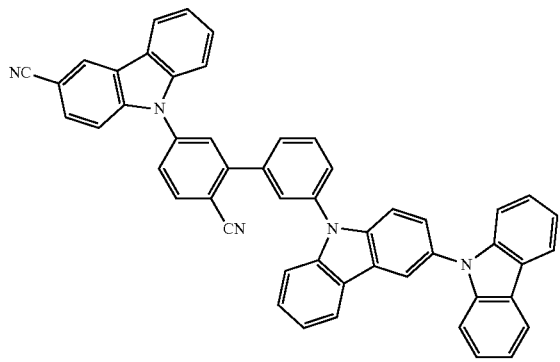
724
TABLE 2-continued
| No. of Host compound | Driving voltage (relative value) | Current efficiency (relative value) | Durability (relative value) | Emission color |
|---|---|---|---|---|
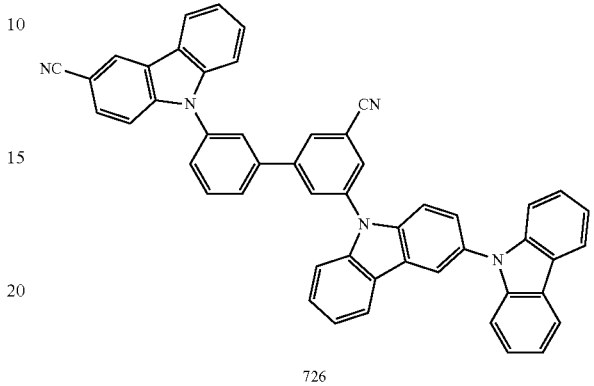
726
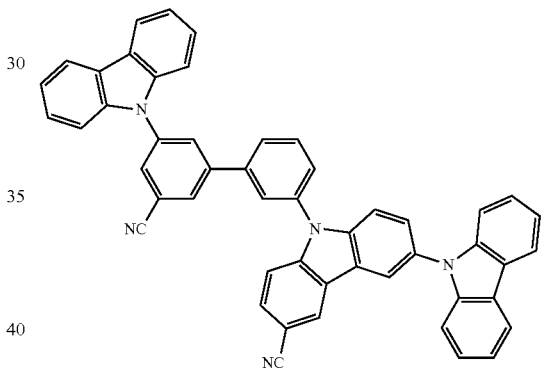
753
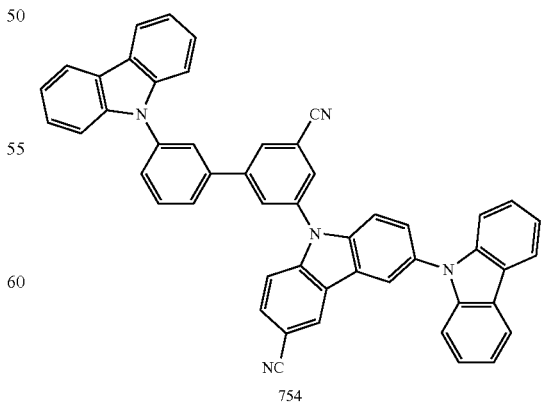
754

TABLE 2-continued
| No. of Host compound | Driving voltage (relative value) | Current efficiency (relative value) | Durability (relative value) | Emission color |
|---|---|---|---|---|
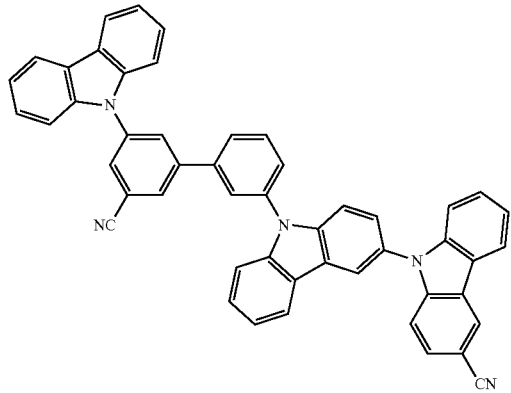
755
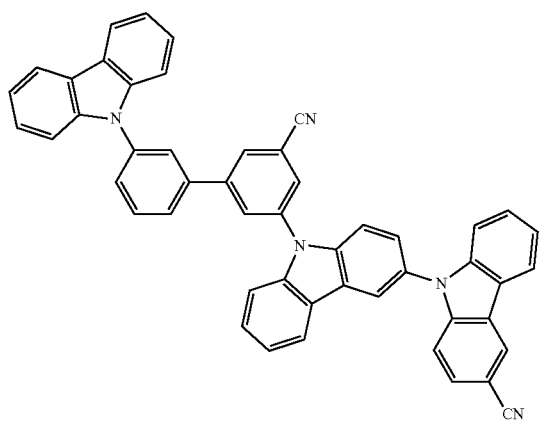
756
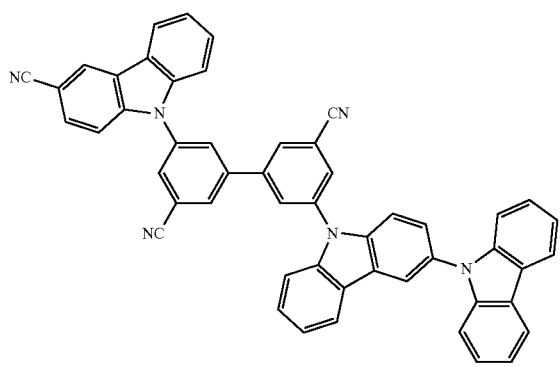
757
TABLE 2-continued
| No. of Host compound | Driving voltage (relative value) | Current efficiency (relative value) | Durability (relative value) | Emission color |
|---|---|---|---|---|
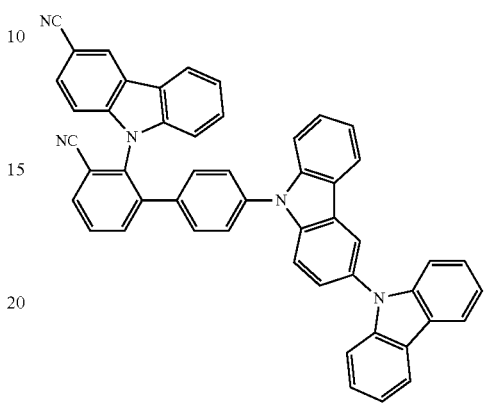
1041
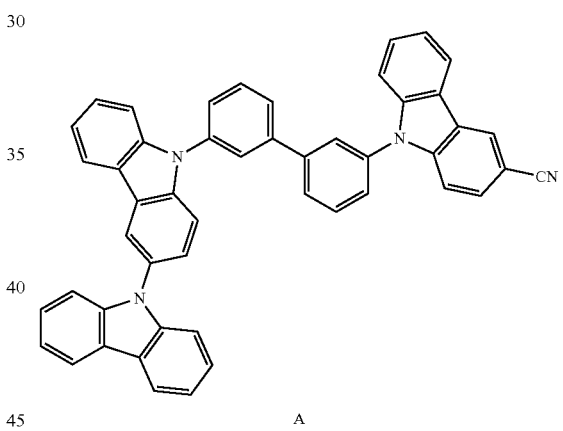
A
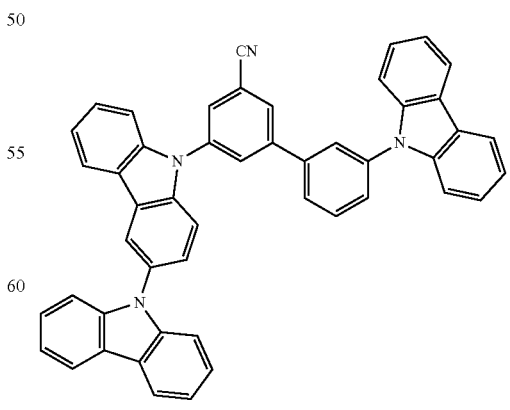
B TABLE 2-continued

| No. of Host compound | Driving voltage (relative value) | Current efficiency (relative value) | Durability (relative value) | Emission color |
| --- | --- | --- | --- | --- |

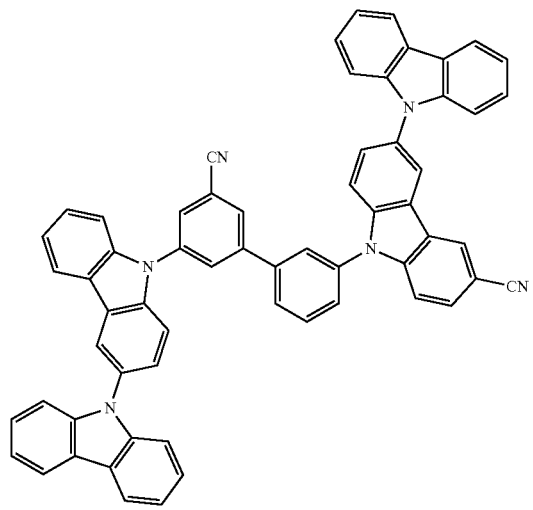

C

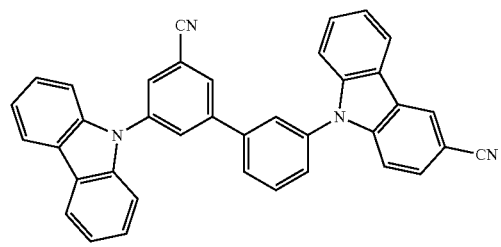

D

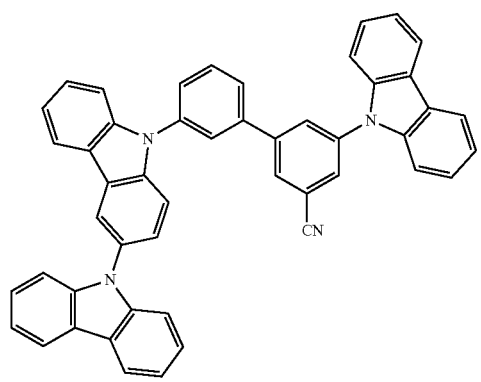

E

TABLE 2-continued

| No. of Host compound | Driving voltage (relative value) | Current efficiency (relative value) | Durability (relative value) | Emission color |
| --- | --- | --- | --- | --- |

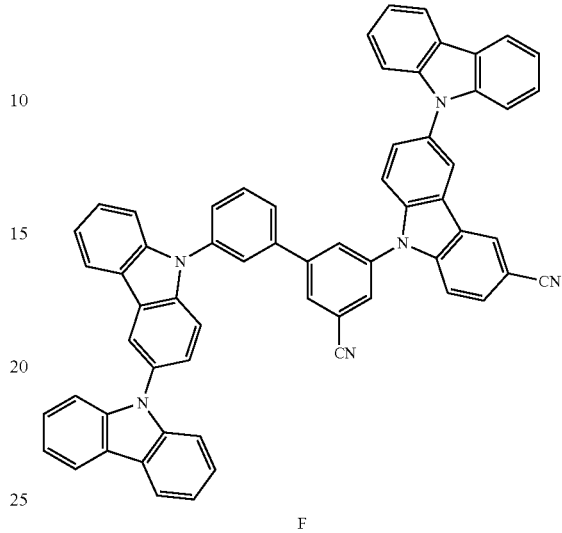

F

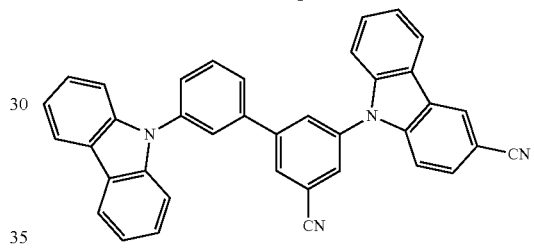

G

Referring to Table 2, it is confirmed that the organic light-emitting devices of Examples 1 to 11 have a low driving voltage, high efficiency, high power, and a long lifespan, as compared with those of the organic light-emitting devices of Comparative Examples 1 to 7.

Since the condensed cyclic compound has excellent electric characteristics and thermal stability, an organic light-emitting device including the condensed cyclic compound may have low driving voltage, high efficiency, high power, high quantum efficiency, and long lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:

1. An organic light-emitting device comprising:
   a first electrode;
   a second electrode; and
   an organic layer disposed between the first electrode and the second electrode and comprising an emission layer,
   wherein the emission layer comprises a condensed cyclic compound represented by Formula 1 and FIr6, wherein the emission layer emits blue light:

$$A_{11}\text{-}L_{11}\text{-}L_{12}\text{-}A_{12},\quad \text{Formula 1}$$

wherein, in Formula 1, i) $A_{11}$ is a group represented by Formula 4-3, and $A_{12}$ is a group represented by one of Formulae 5-3, 5-6, 5-10, 5-17, 5-21, 5-25, 5-32, 5-36, 5-40, 5-43, or 5-101 to 5-104; or ii) $A_{11}$ is a group represented by Formula 4-101, and $A_{12}$ is a group represented by one of Formulae 5-3, 5-6, 5-10, 5-17, 5-21, 5-25, 5-32, 5-36, 5-40, or 5-43, $L_{11}$ is a group represented by one of Formulae 2-15, 2-22, 2-23, or 2-102, and $L_{12}$ is a group represented by one of Formulae 3-15, 3-22, or 3-23, or $L_{11}$ is a group represented by one of Formulae 2-15, 2-22, or 2-23, and $L_{12}$ is a group represented by one of Formulae 3-15, 3-22, 3-23, or 3-102, and wherein the condensed cyclic compound comprises two or three cyano groups:

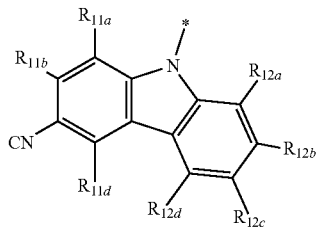

4-3

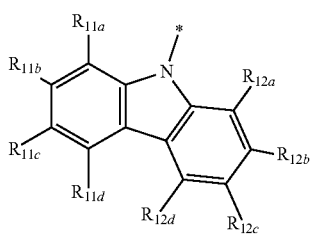

4-101

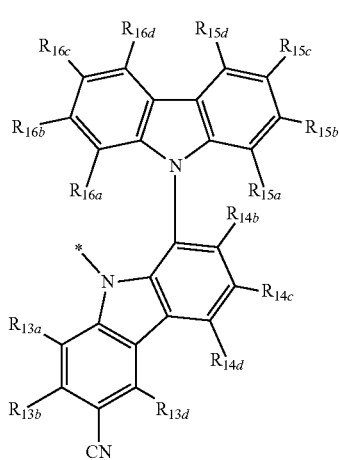

5-3

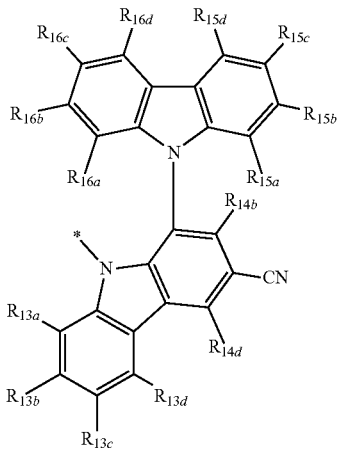

5-6

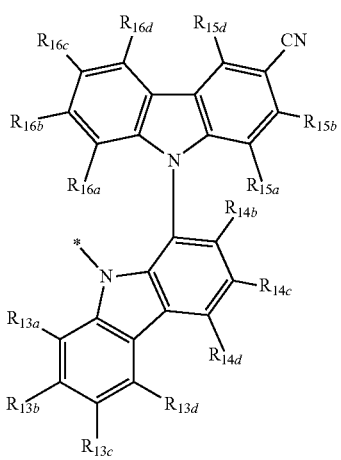

5-10

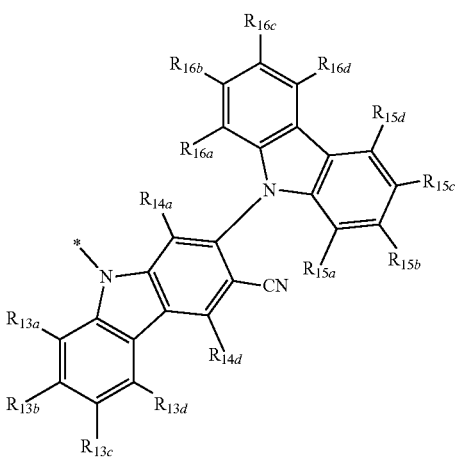

5-17

-continued
5-21
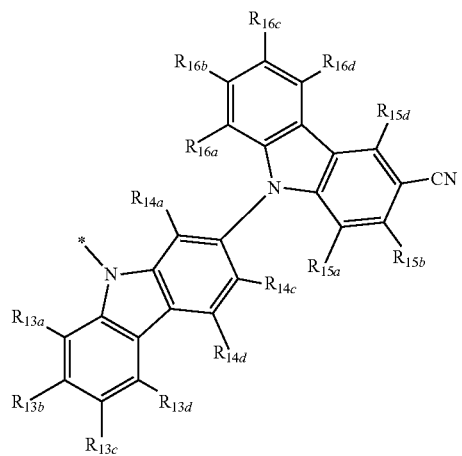
5-25
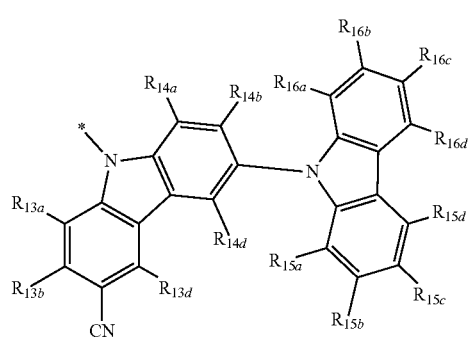
5-32
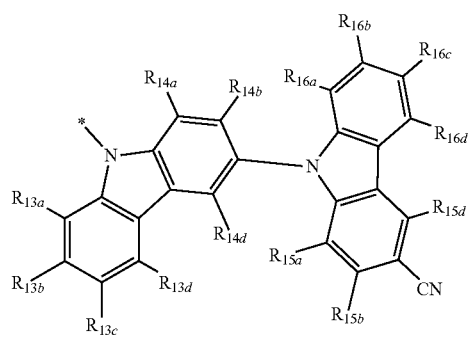
5-36
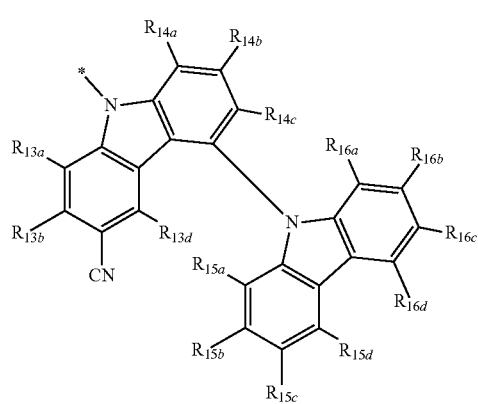
5-40
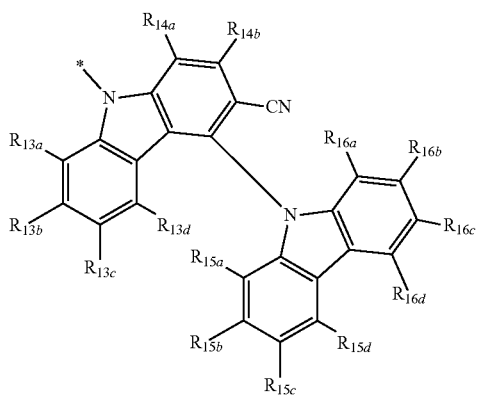
5-43
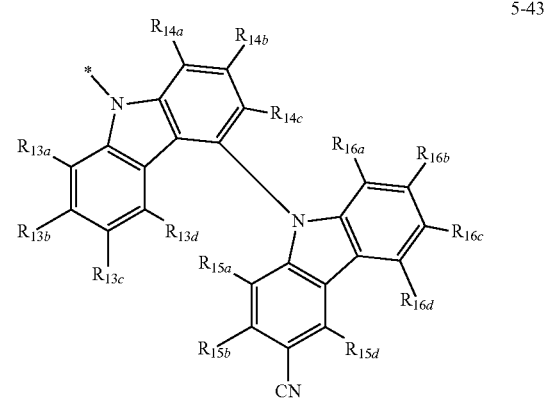
5-101
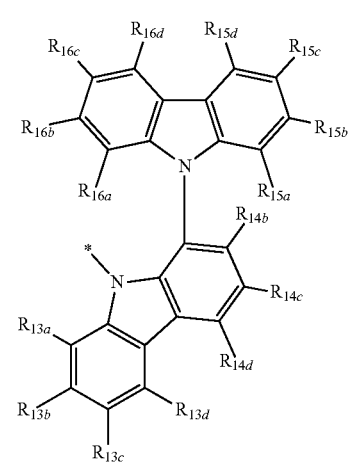

-continued
5-102
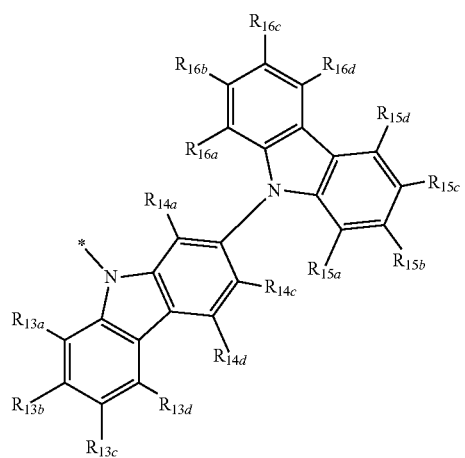
5-103
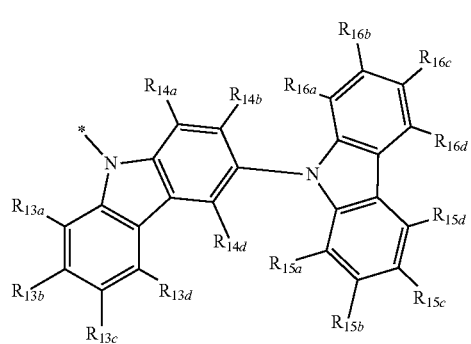
5-104
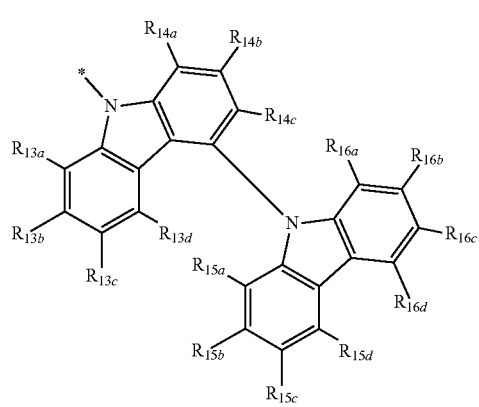
2-15
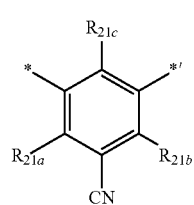
-continued
2-22
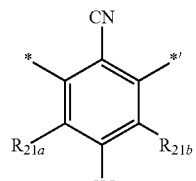
2-23
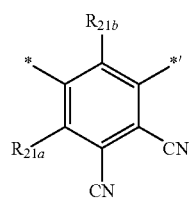
2-102
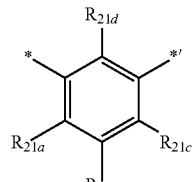
3-15
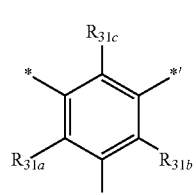
3-22
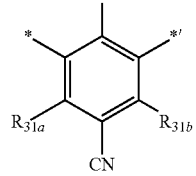
3-23
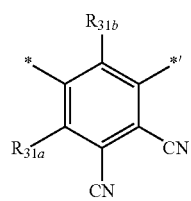
3-102
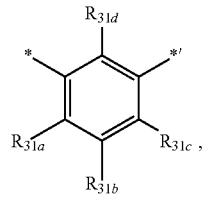
wherein:
$R_{11a}$ to $R_{11d}$ and $R_{12a}$ to $R_{12d}$, $R_{13a}$ to $R_{13d}$, $R_{14a}$ to $R_{14d}$, $R_{15a}$ to $R_{15d}$, and $R_{16a}$ to $R_{16d}$, $R_{21a}$ to $R_{21d}$, $R_{31a}$ to $R_{31d}$ are each independently hydrogen or deuterium, and
* and *' each indicate a binding site to a neighboring atom.

2. The organic light-emitting device of claim 1, wherein in the condensed cyclic compound,
  i) $A_{11}$ is a group represented by Formulae 4-3 or 4-101, and $A_{12}$ is a group represented by Formulae 5-3, 5-6, 5-10, 5-17, 5-21, 5-25, 5-32, 5-36, 5-40, or 5-43; or
  ii) $A_{11}$ is a group represented by Formula 4-3, and $A_{12}$ is a group represented by Formulae 5-3, 5-6, 5-10, 5-17, 5-21, 5-25, 5-32, 5-36, 5-40, 5-43, or 5-101 to 5-104.

3. The organic light-emitting device of claim 1, wherein in the condensed cyclic compound,
  i) $A_{11}$ is a group represented by Formula 4-3, and $A_{12}$ is a group represented by Formulae 5-3, 5-6, 5-10, 5-14, 5-17, 5-21, 5-25, 5-32, 5-36, 5-40, 5-43, or 5-101 to 5-104; or
  ii) $A_{11}$ is a group represented by Formula 4-101, and $A_{12}$ is a group represented by Formulae 5-3, 5-6, 5-10, 5-17, 5-21, 5-25, 5-32, 5-36, 5-40, or 5-43.

4. The organic light-emitting device of claim 1, wherein in the condensed cyclic compound,
  i) $L_{11}$ is a group represented by Formula 2-15, and $L_{12}$ is a group represented by Formula 3-102;
  ii) $L_{11}$ is a group represented by Formula 2-102, and $L_{12}$ is represented by Formula 3-15;
  iii) $L_{11}$ is a group represented by Formula 2-15, and $L_{12}$ is a group represented by Formula 3-15;
  iv) $L_{11}$ is a group represented by Formulae 2-22 to 2-23, and $L_{12}$ is a group represented by Formula 3-102; or
  v) $L_{11}$ is a group represented by Formula 2-102, and $L_{12}$ is a group represented by Formulae 3-22 to 2-23.

5. The organic light-emitting device of claim 1, wherein the condensed cyclic compound is one of Compounds 641-713 and 715-800 Group I Group I

641

642

-continued

643

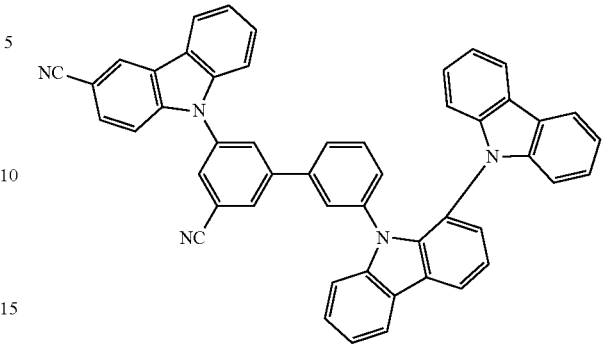

644

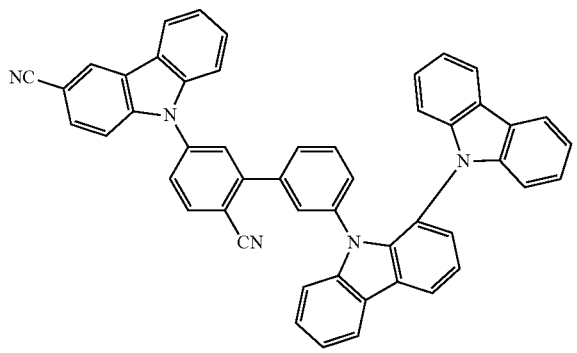

645

646

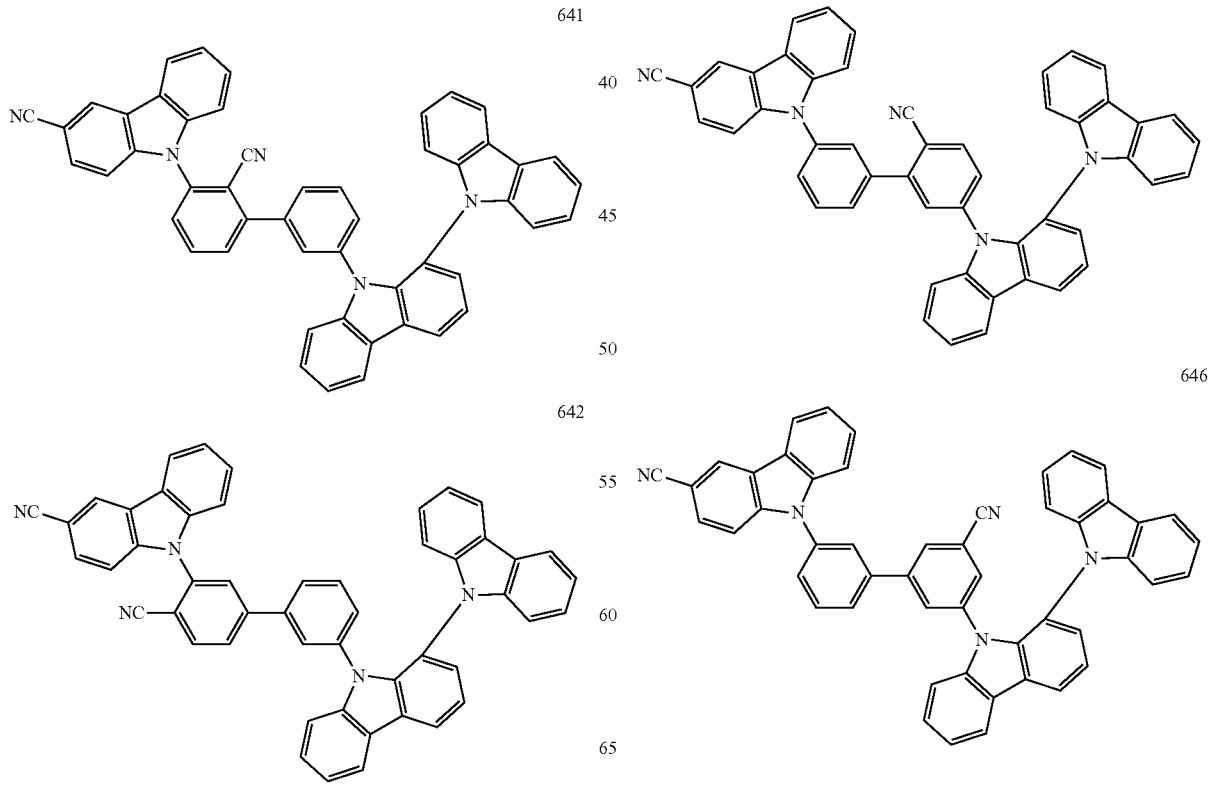

647
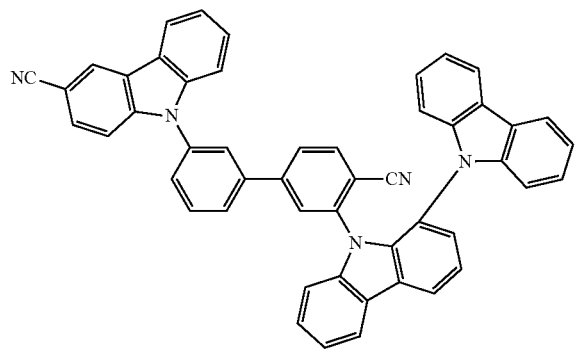
648
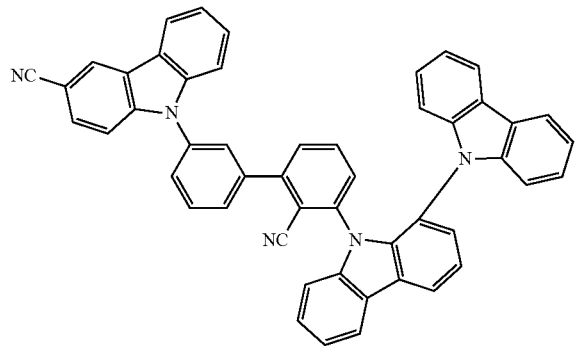
649
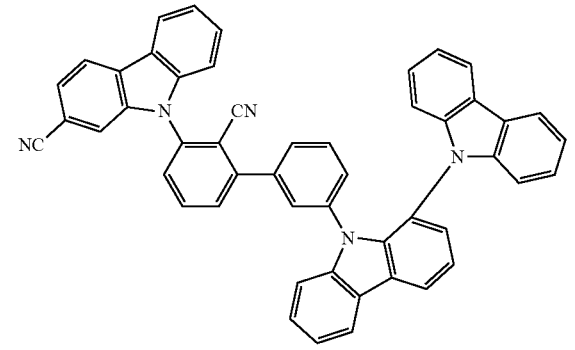
650
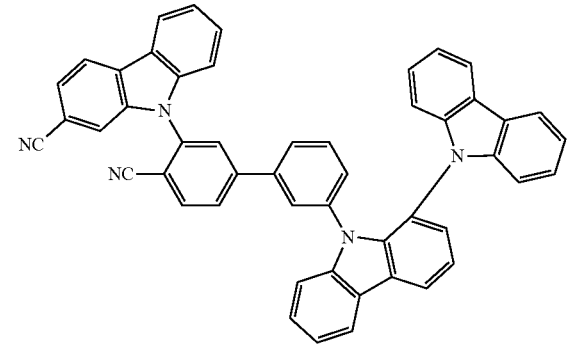
651
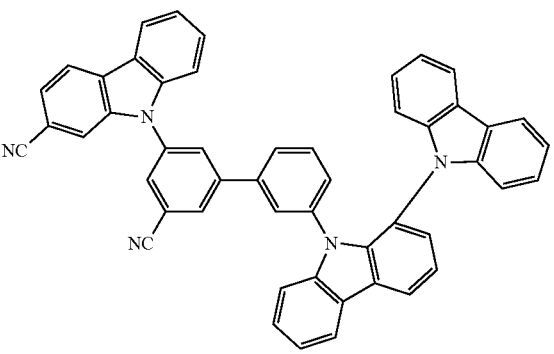
652
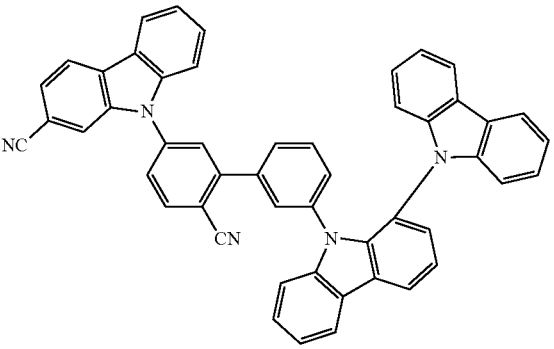
653
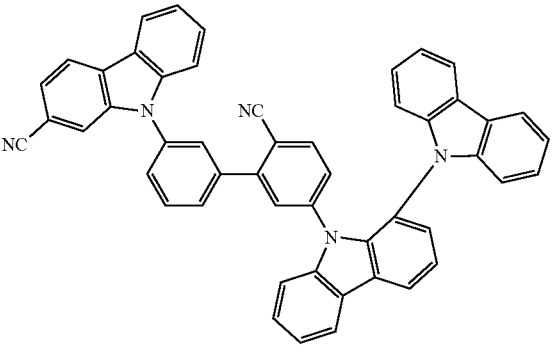
654
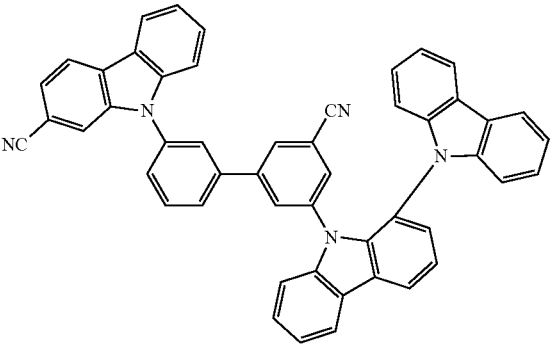

655
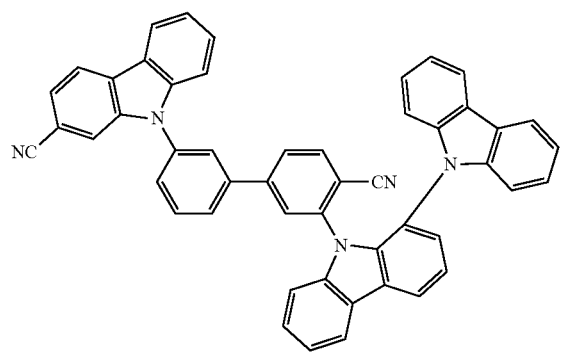
659
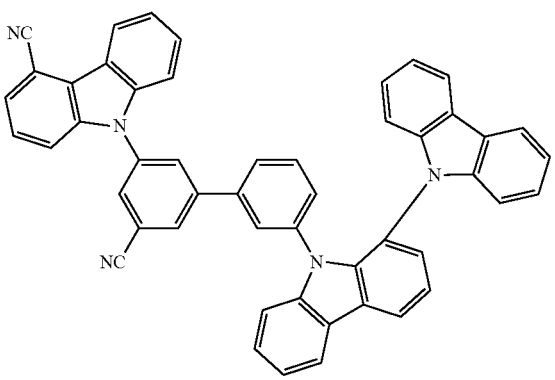
656
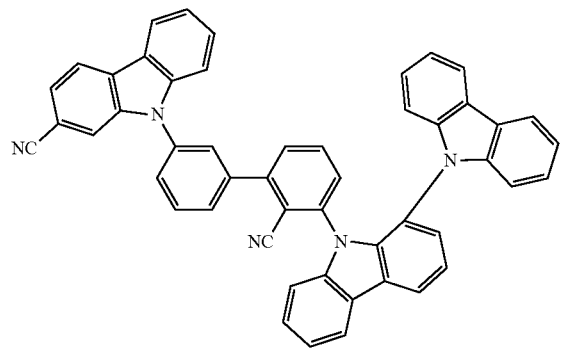
660
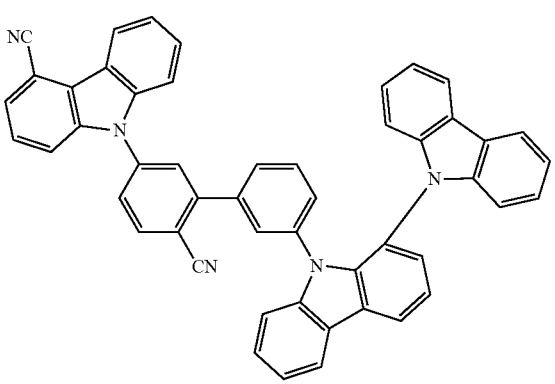
657
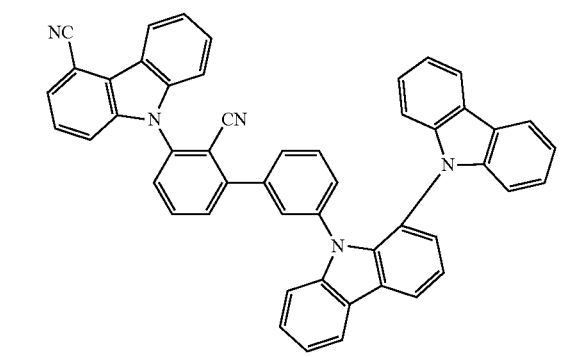
661
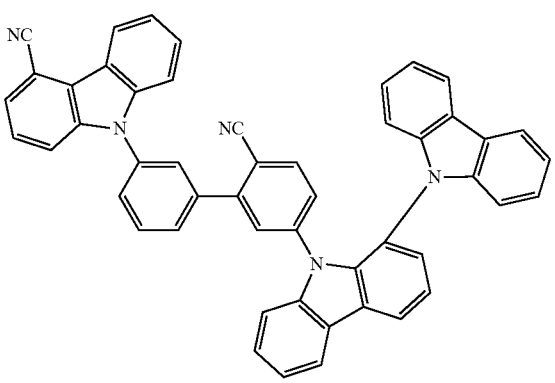
658
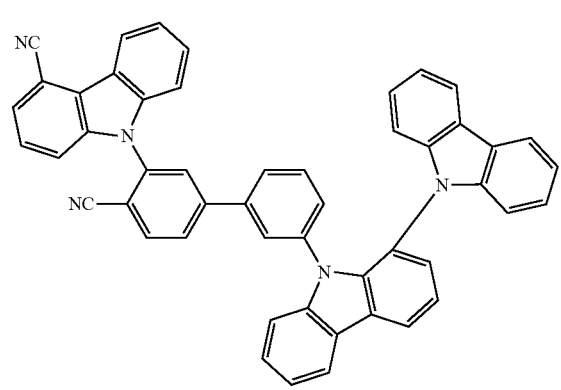
662
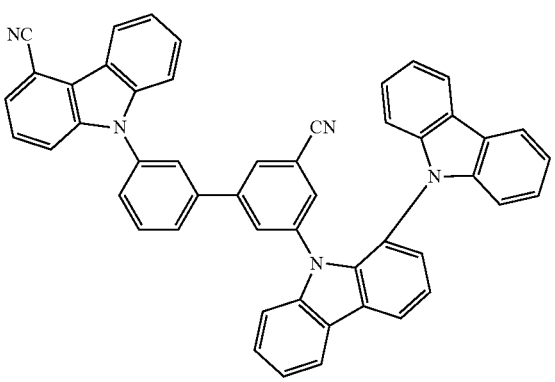

663
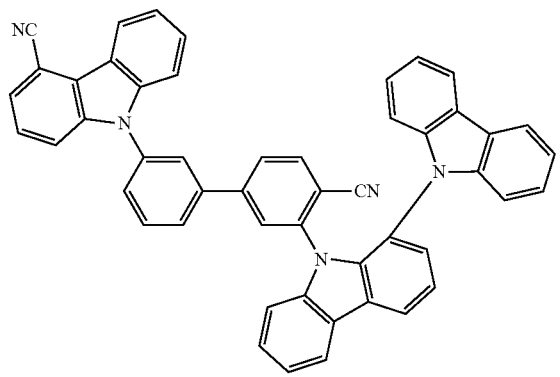
664
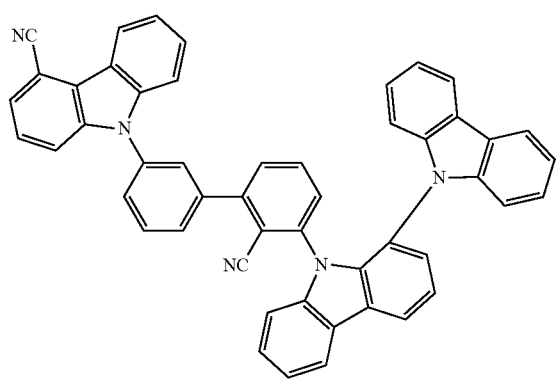
665
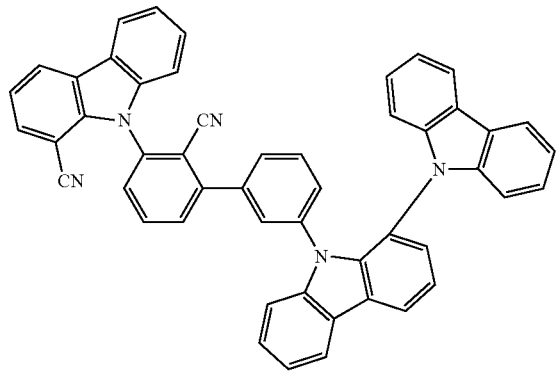
666
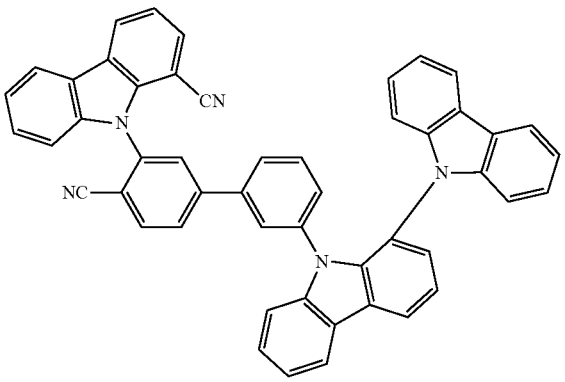
667
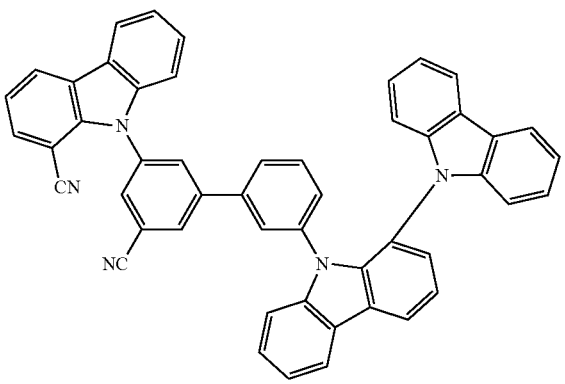
668
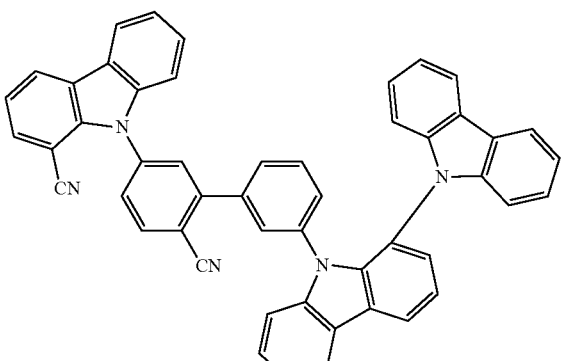
669
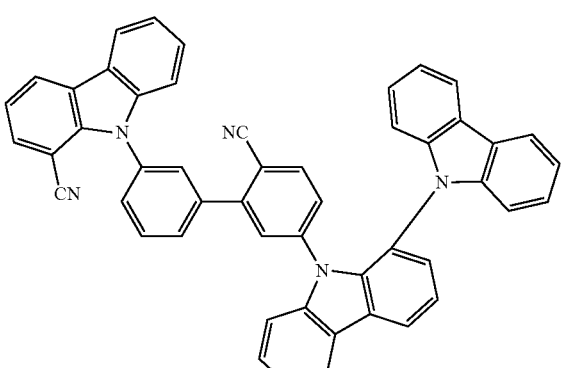
670
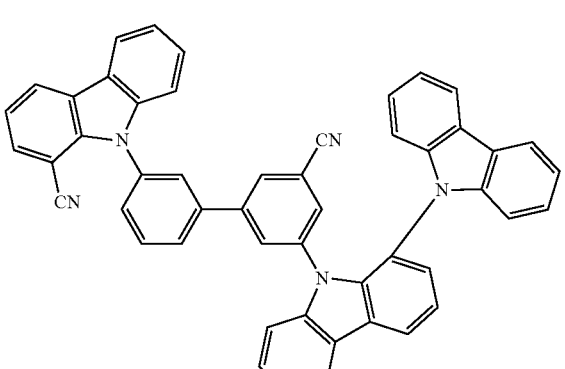

671
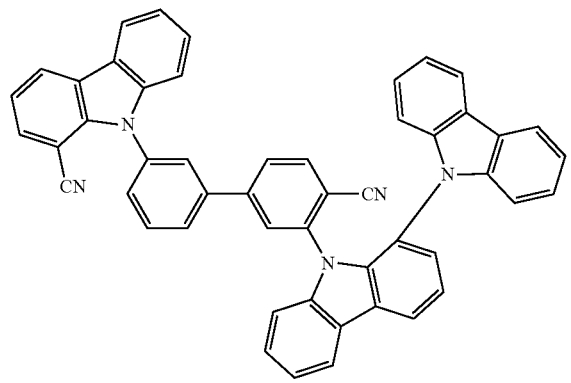
672
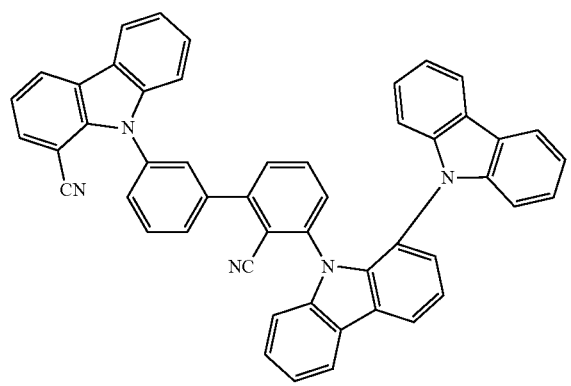
673
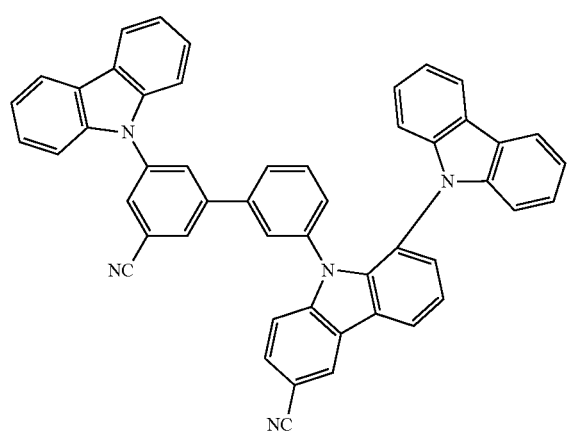
674
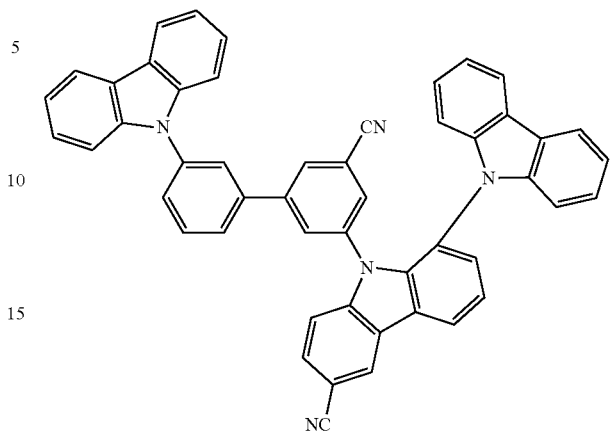
675
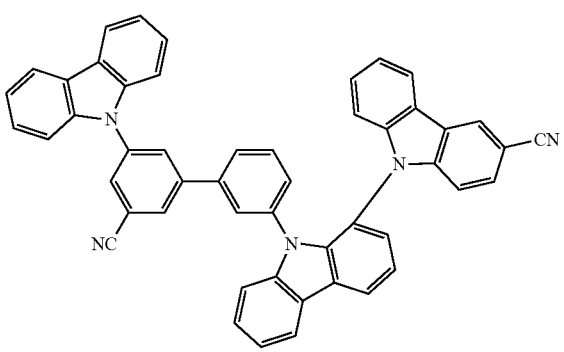
676
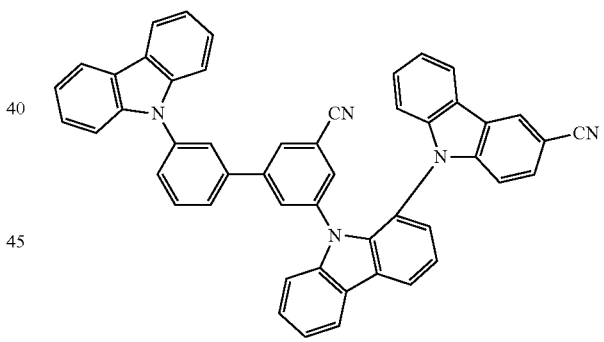
677
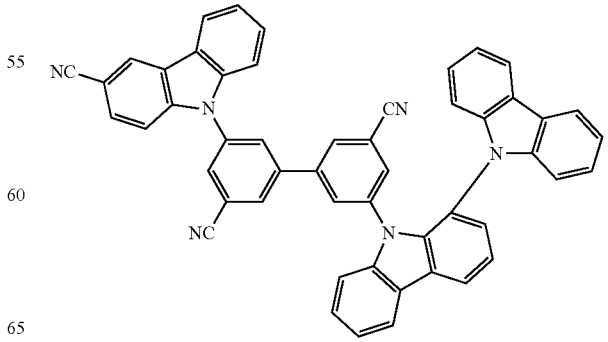

678
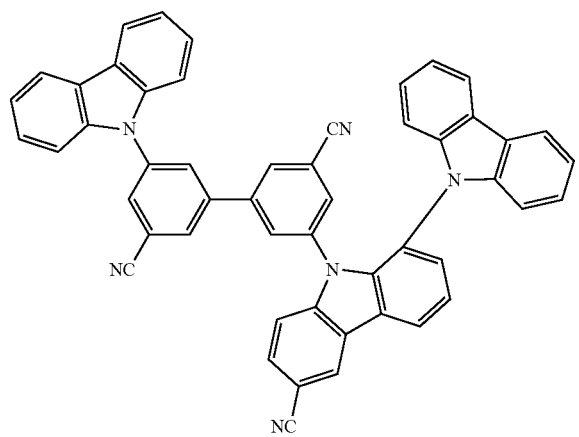
679
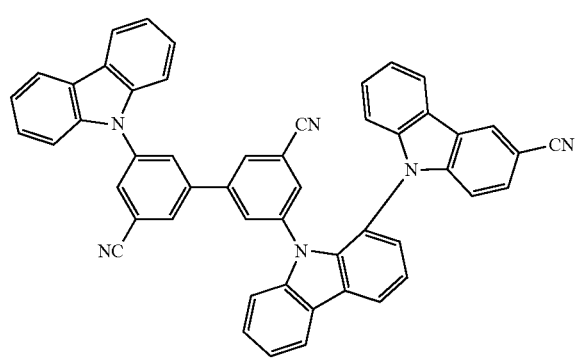
680
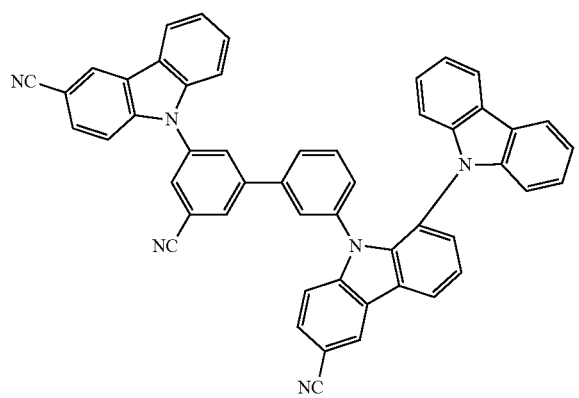
681
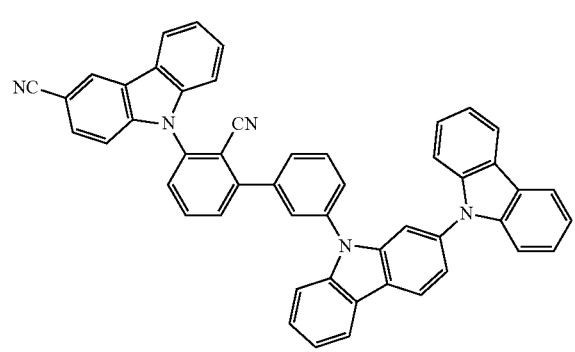
682
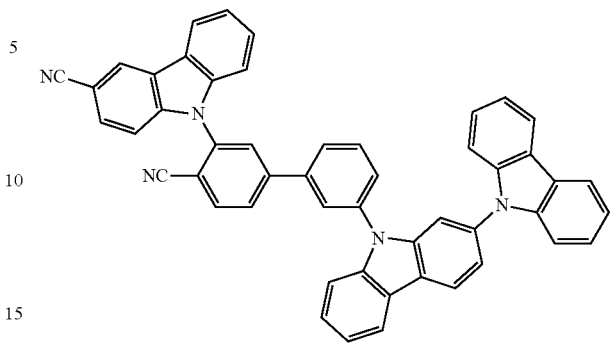
683
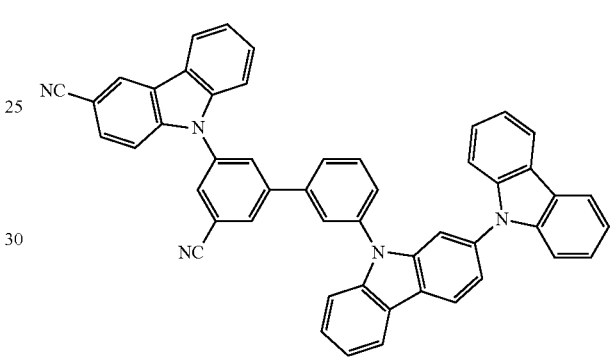
684
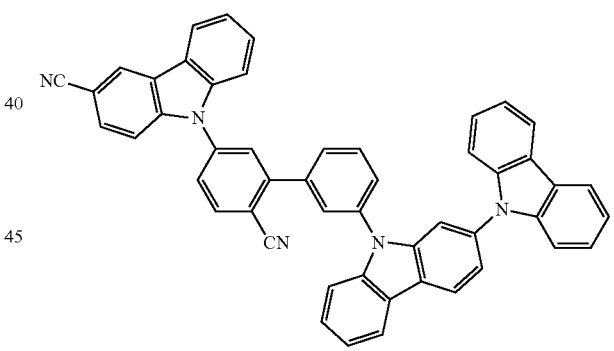
685
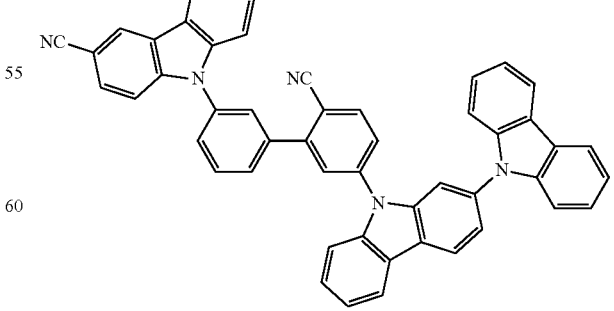

686
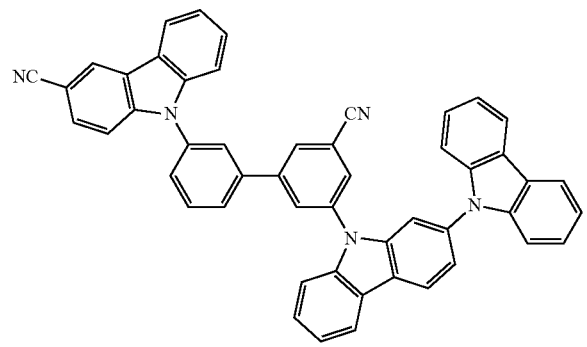
687
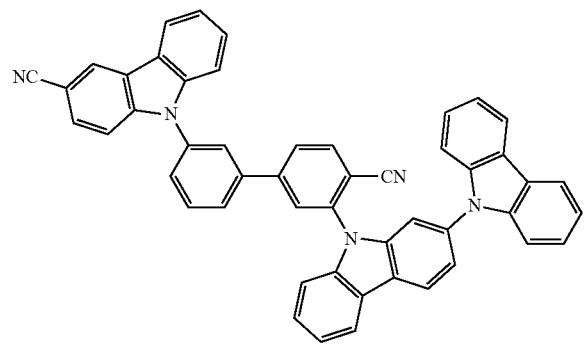
688
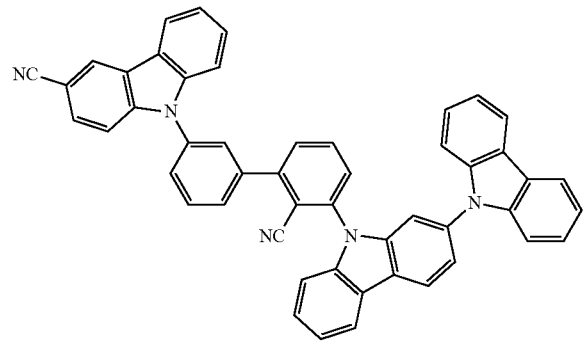
689
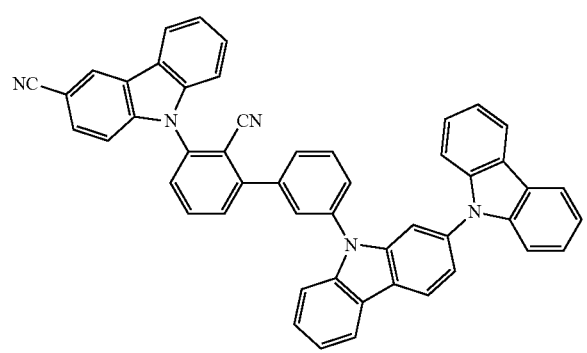
690
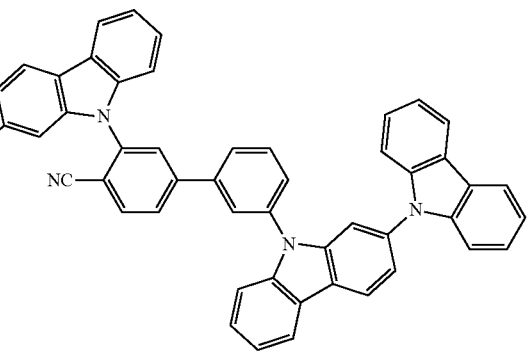
691
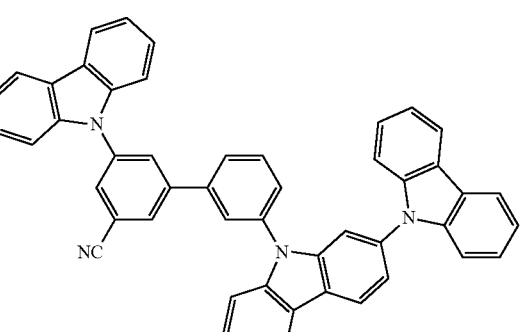
692
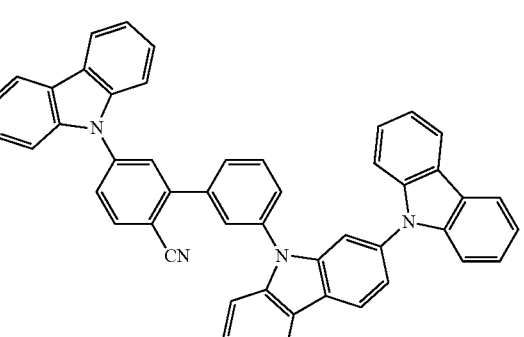
693
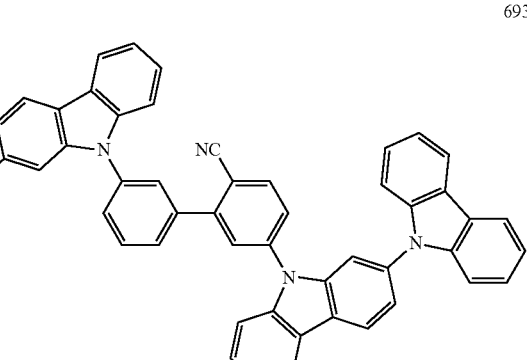

694
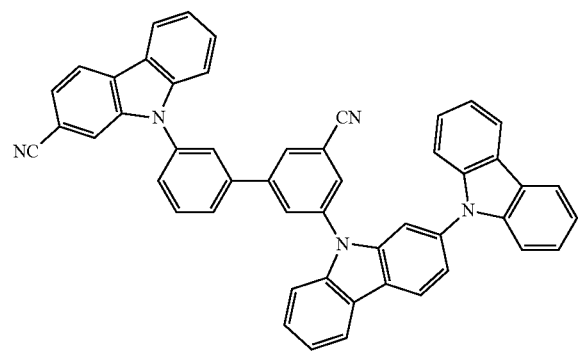
698
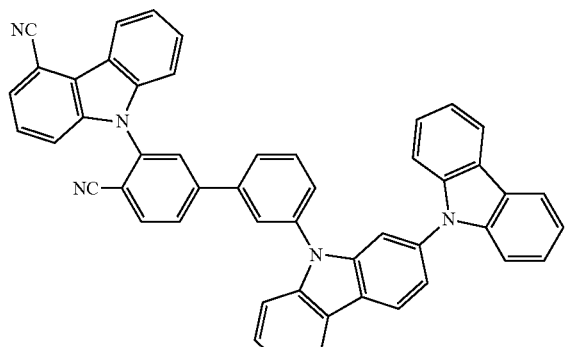
695
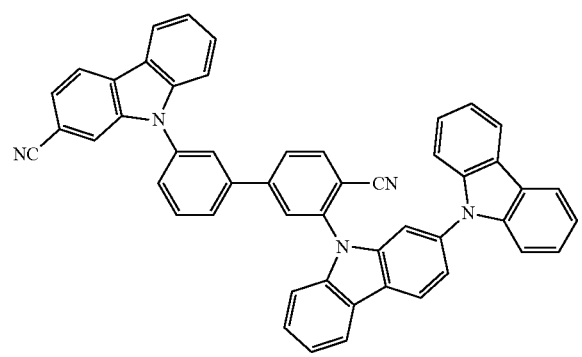
699
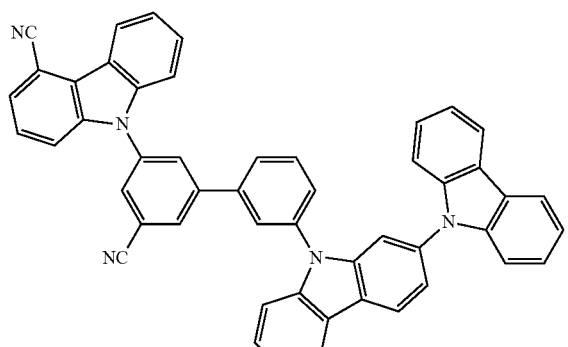
696
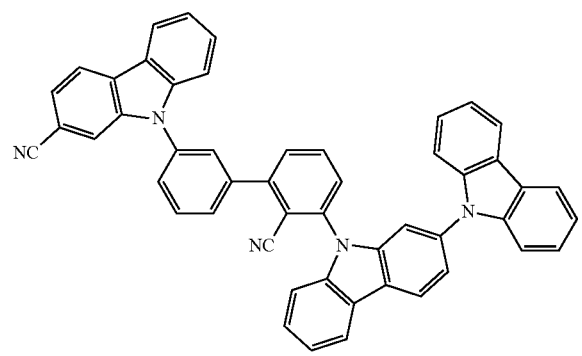
700
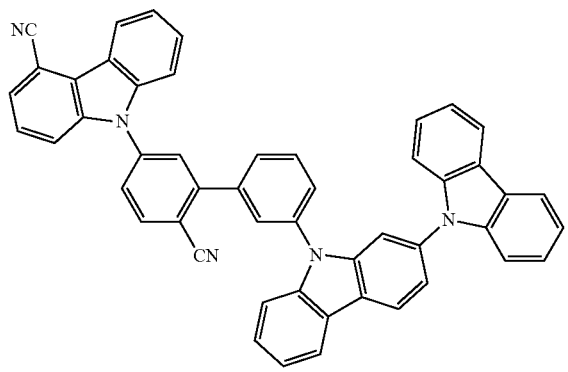
697
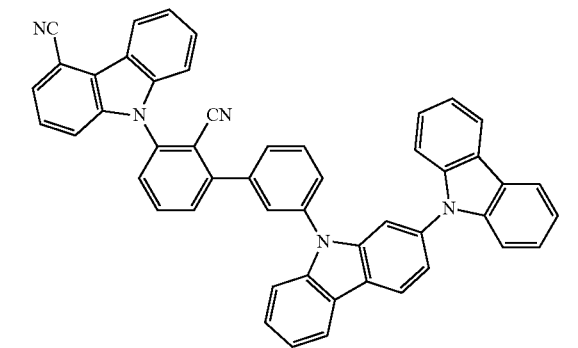
701
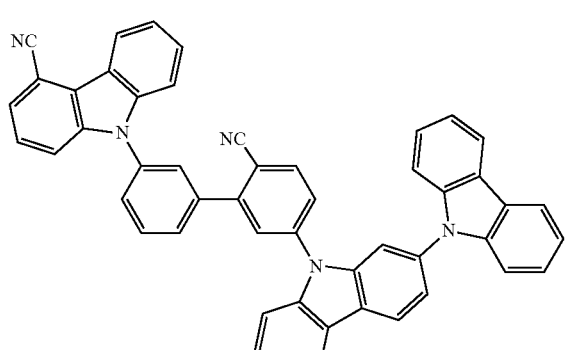

702
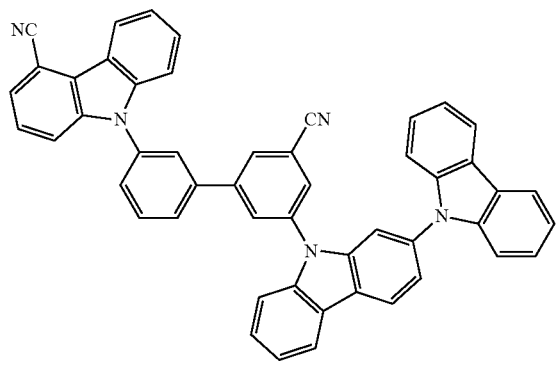
703
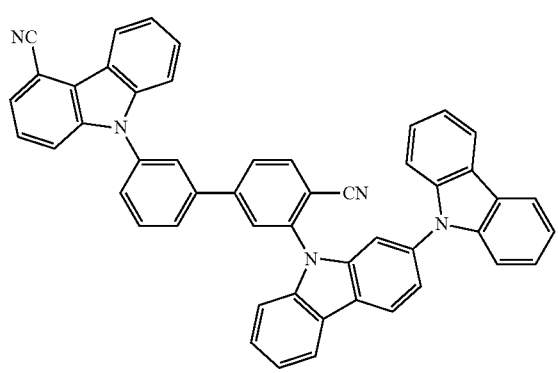
704
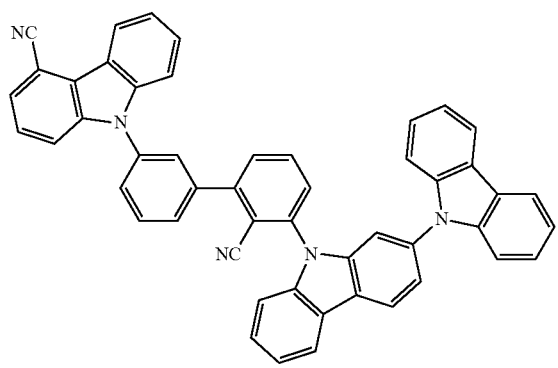
705
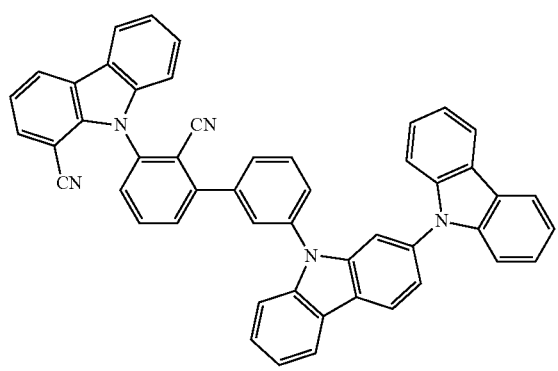
706
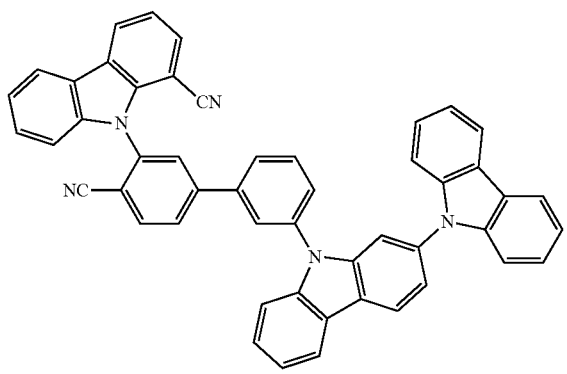
707
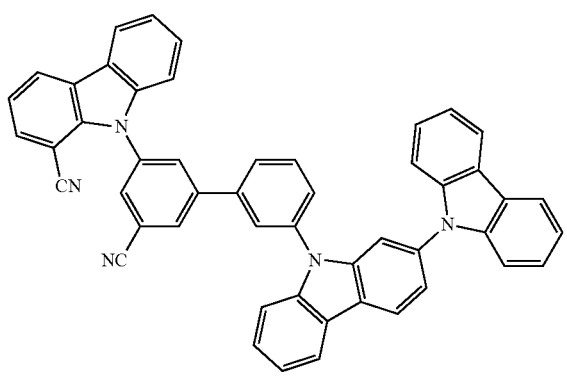
708
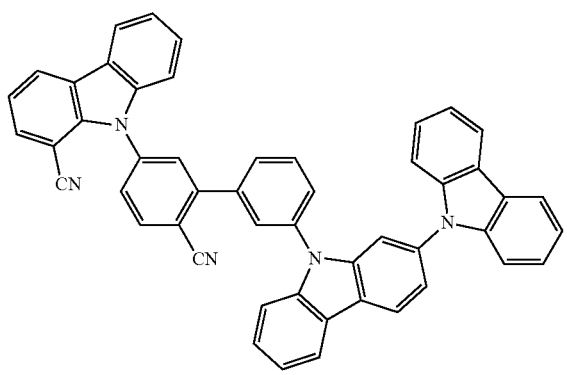
709
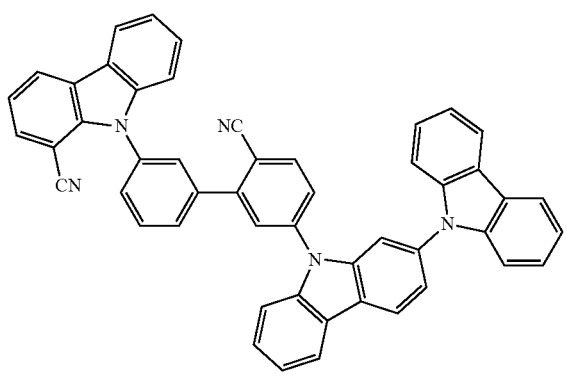

-continued
710
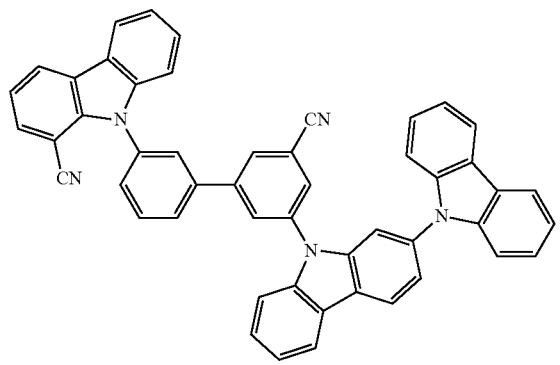
711
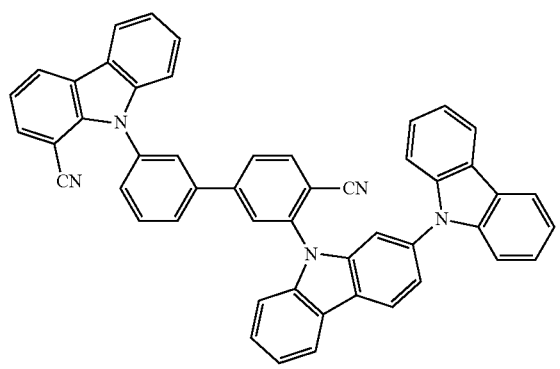
712
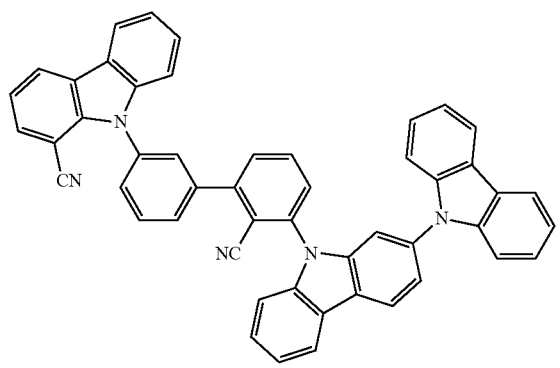
713
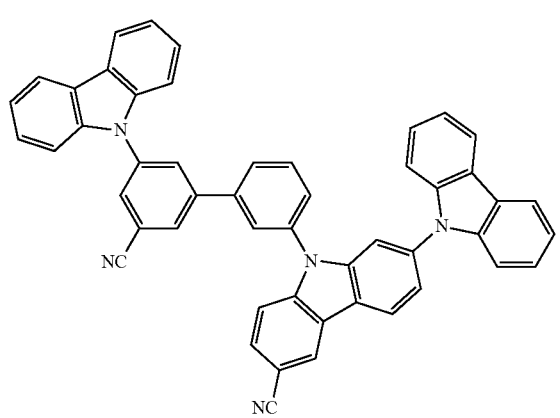
-continued
715
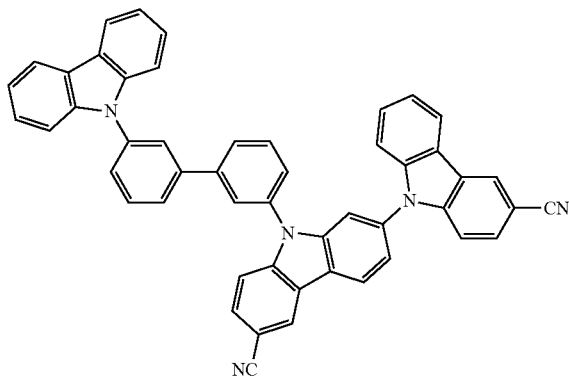
716
717
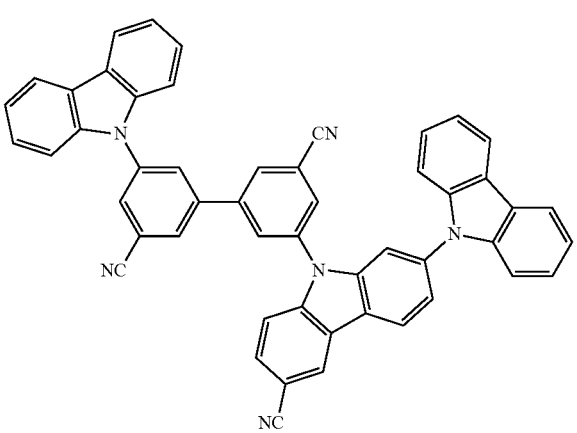
718

719
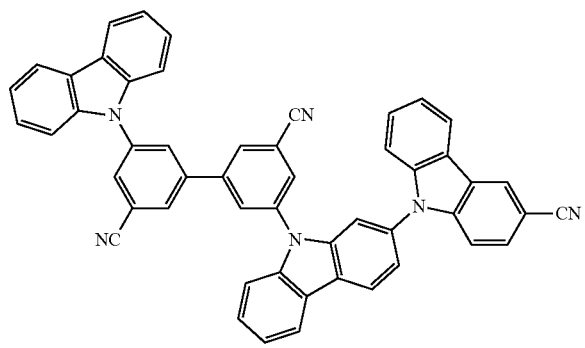
720
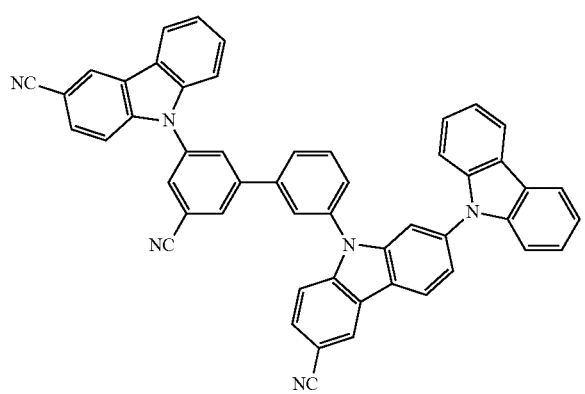
721
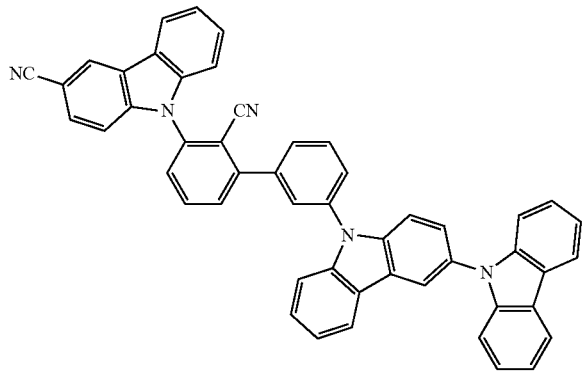
722
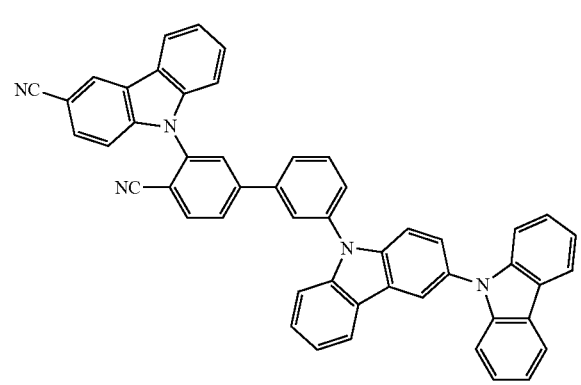
723
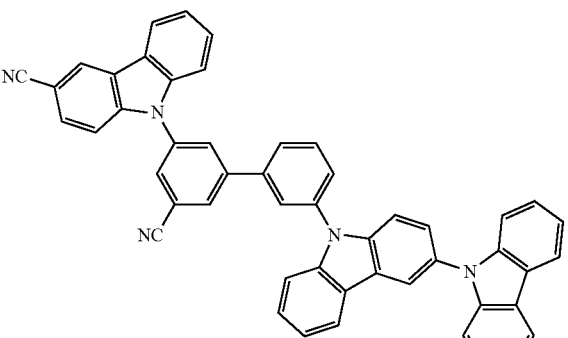
724
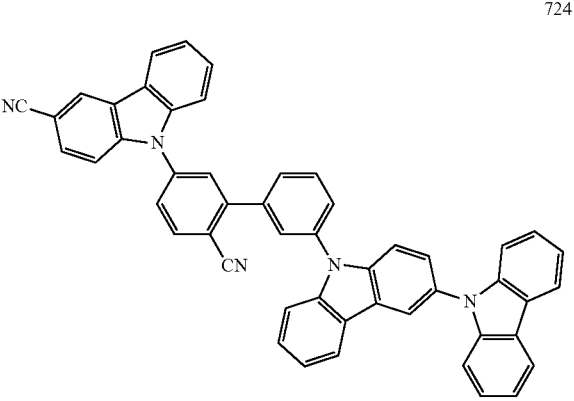
725
726
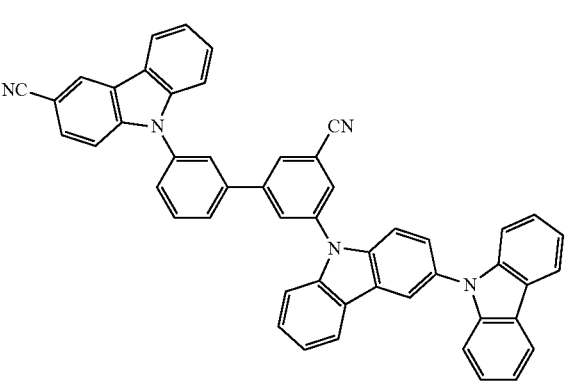

727
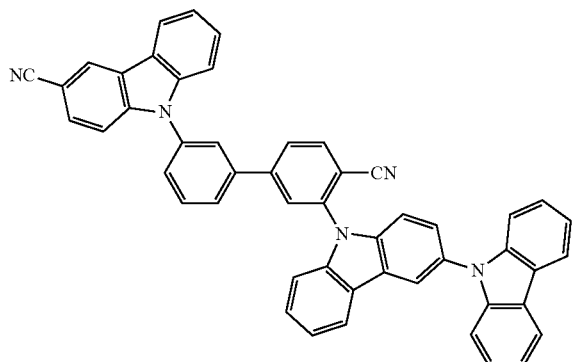
728
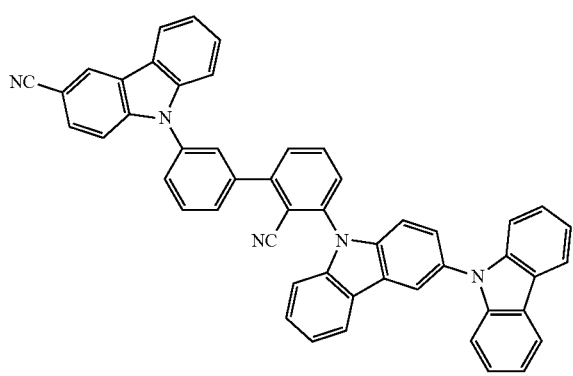
729
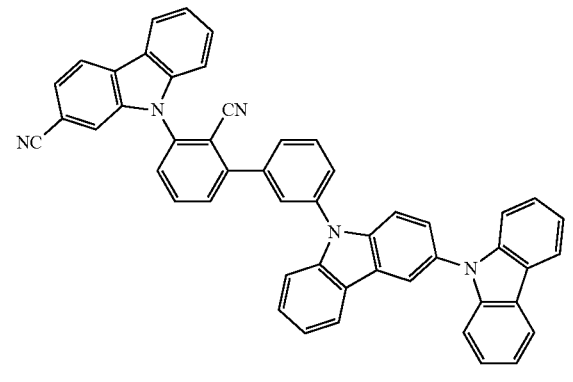
730
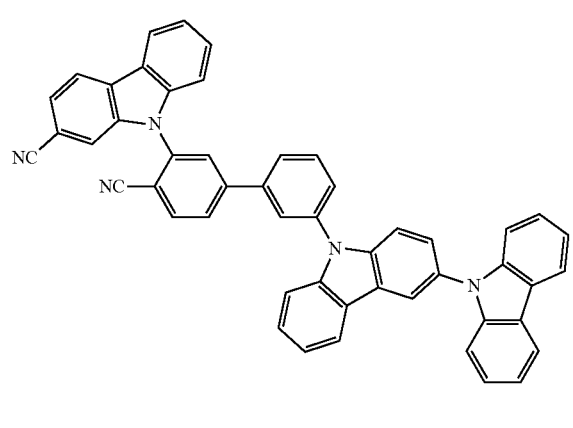
731
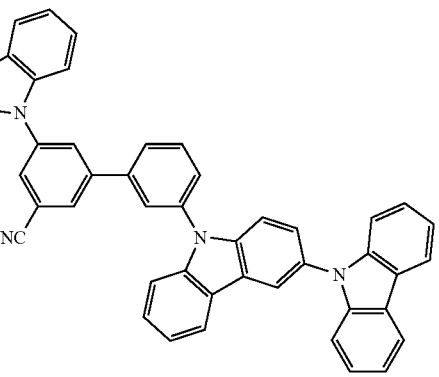
732
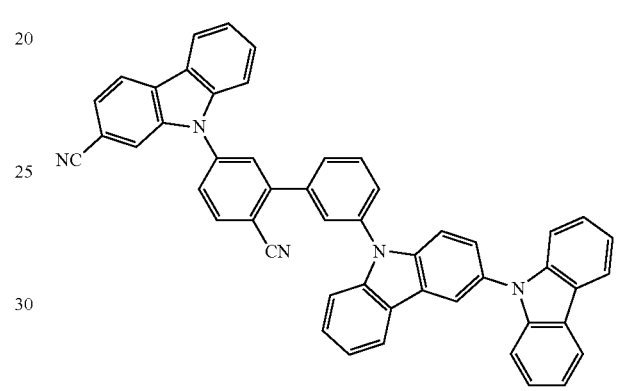
733
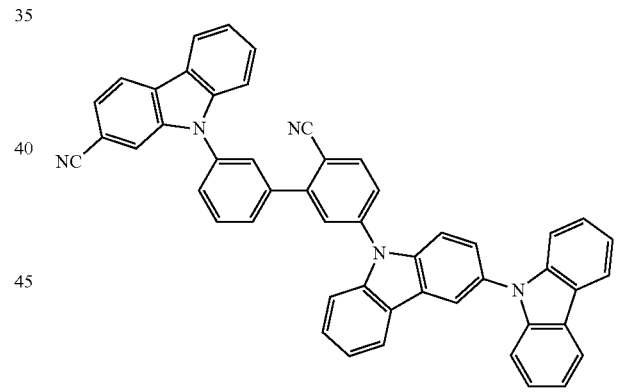
734

735
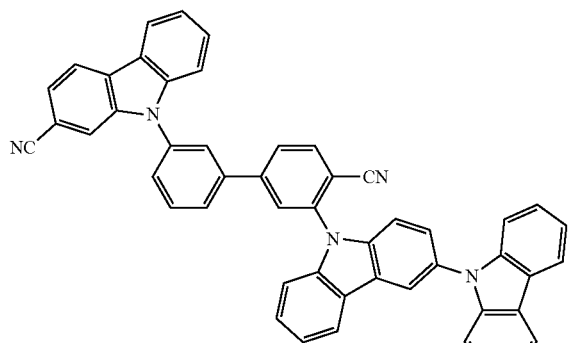
736
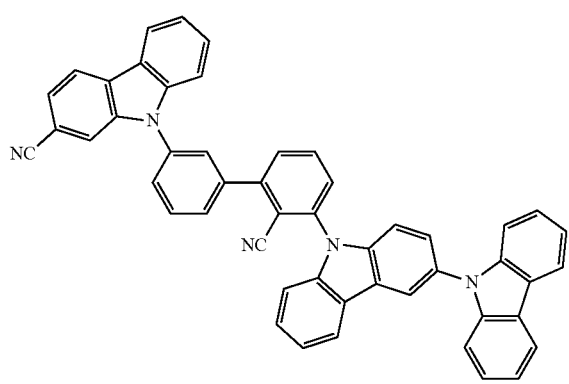
737
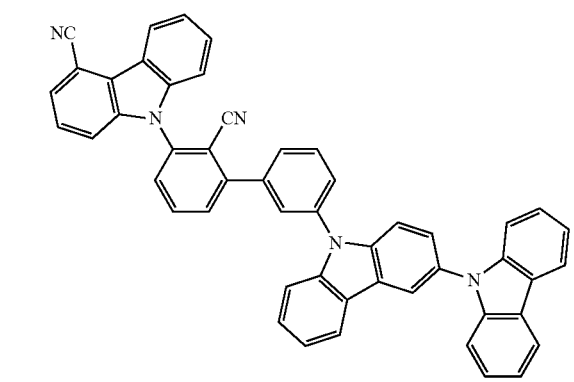
738
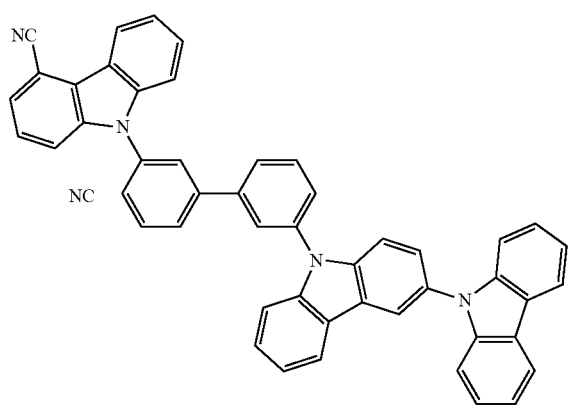
739
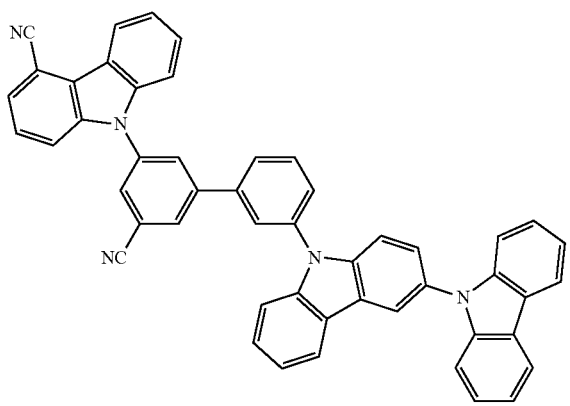
740
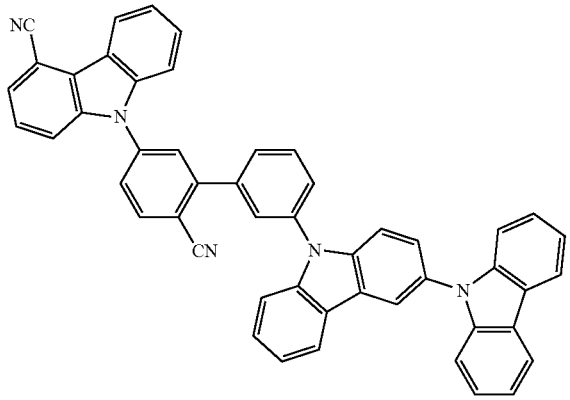
741
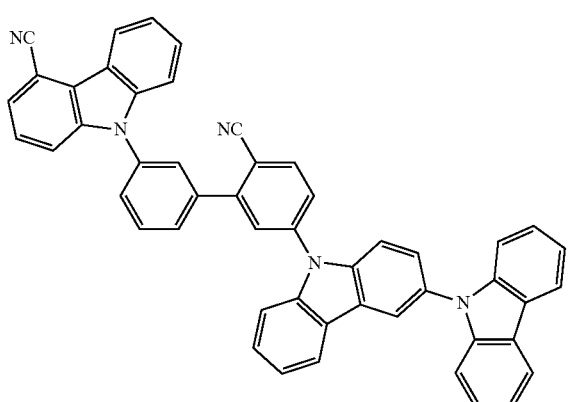

742
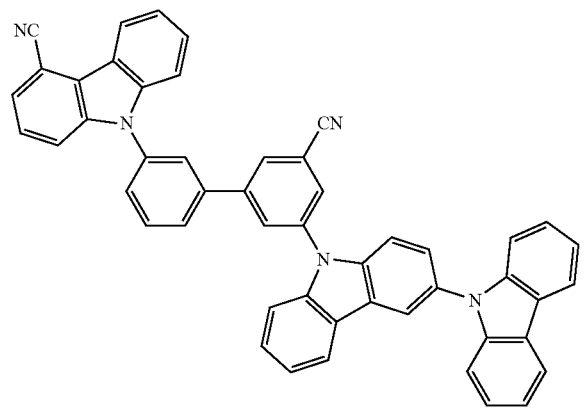
745
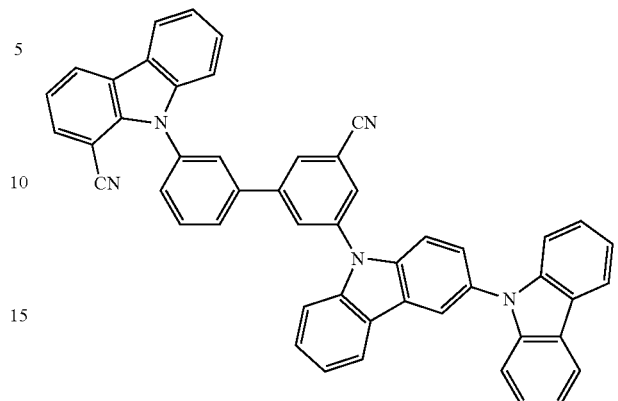
743
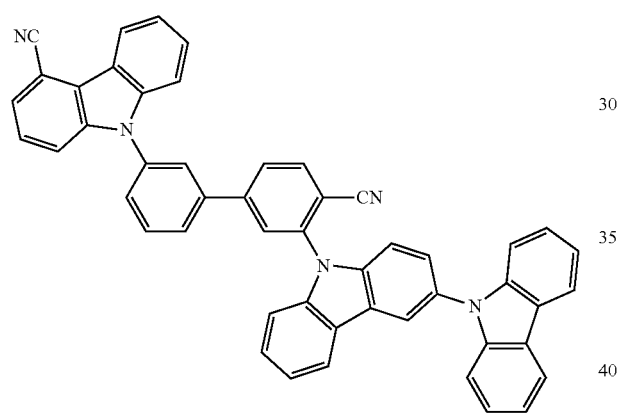
746
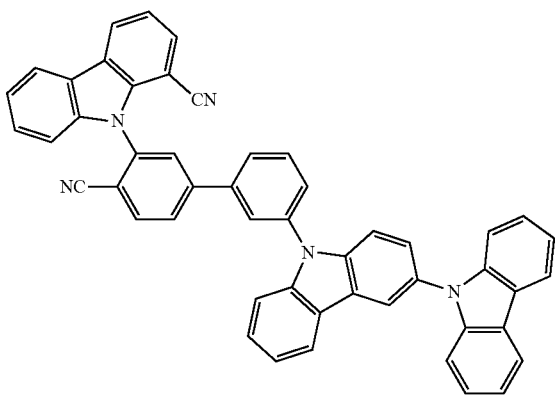
744
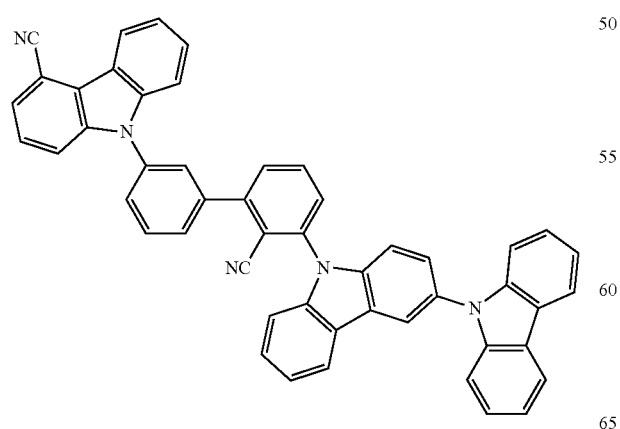
747
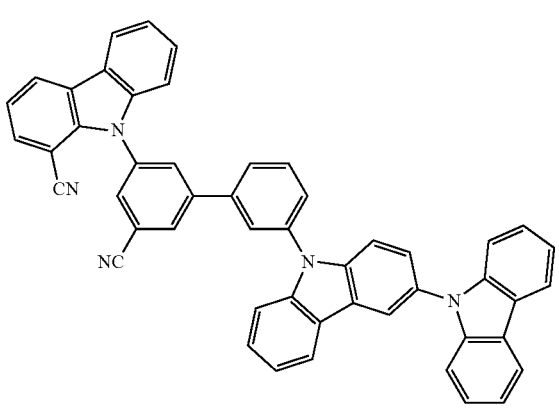

748
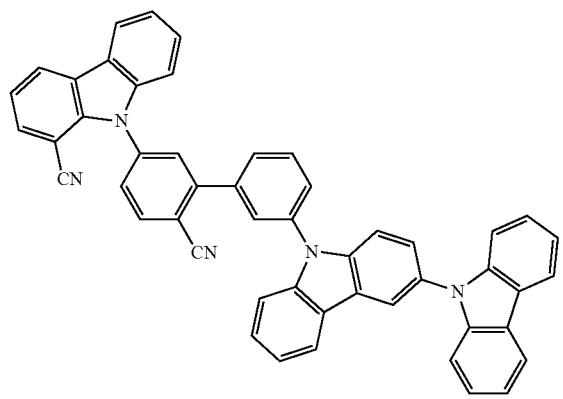
749
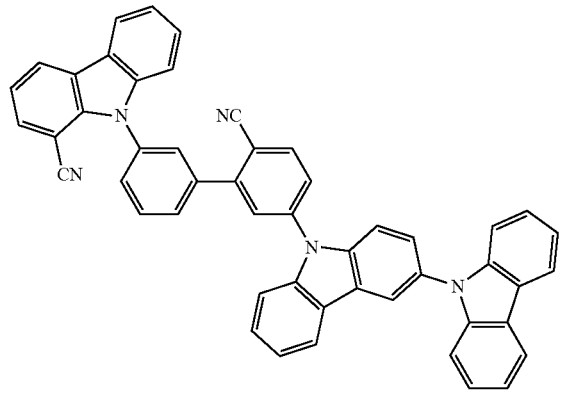
750
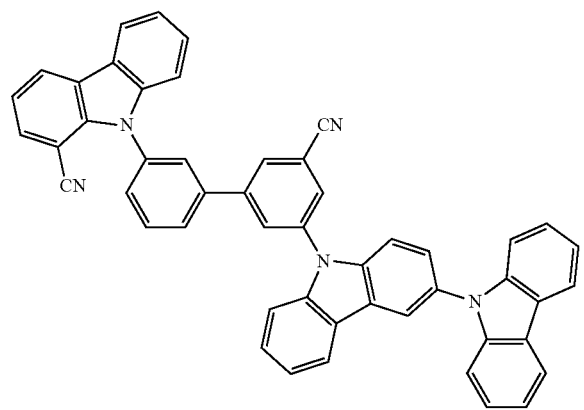
751
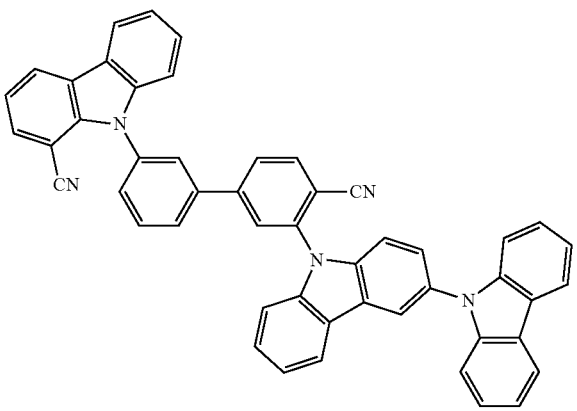
752
753
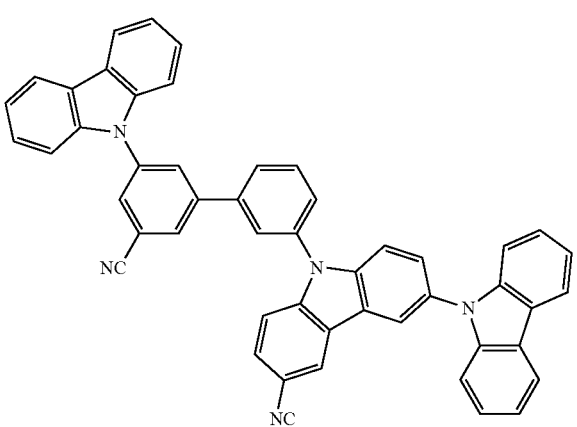

754
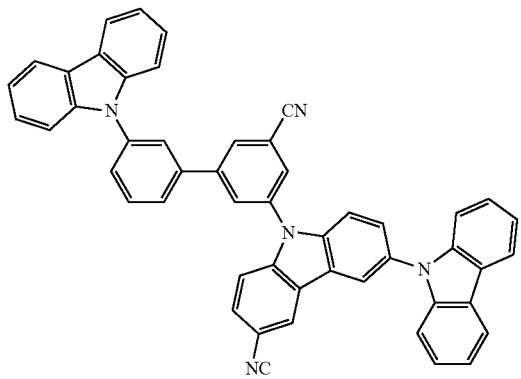
755
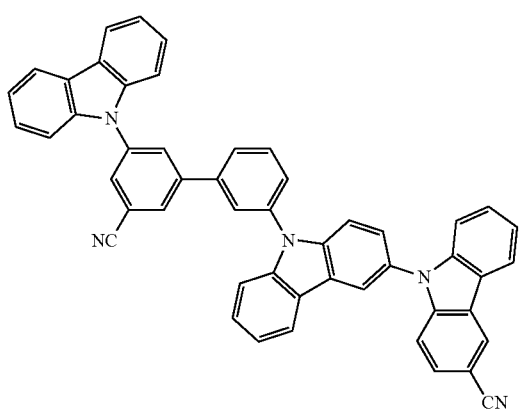 [SMILES: N#Cc1cc(-c2cccc(-n3c4ccc(C#N)cc4c4cc(-n5c6ccccc6c6ccccc65)ccc43)c2)cc(-n2c3ccccc3c3ccccc32)c1]
756
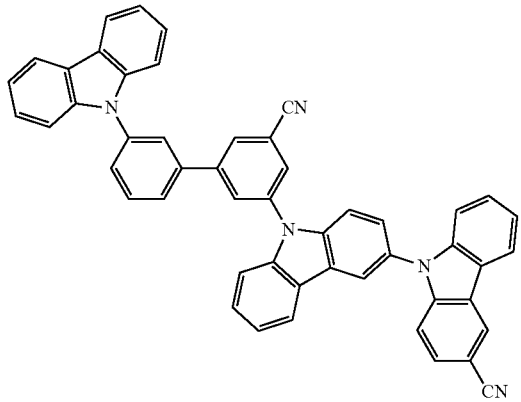 [SMILES: N#Cc1cc(-c2cccc(-n3c4ccccc4c4ccccc43)c2)cc(-n2c3ccc(C#N)cc3c3cc(-n4c5ccccc5c5ccccc54)ccc32)c1]
757
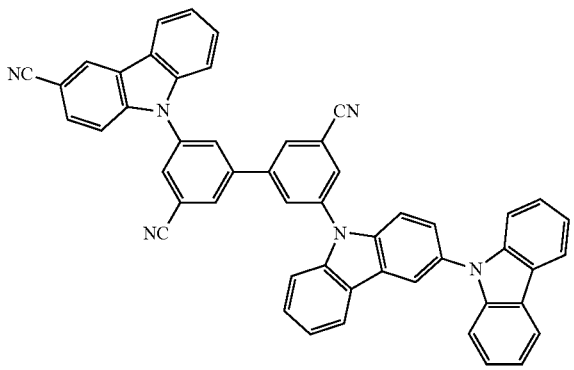
758
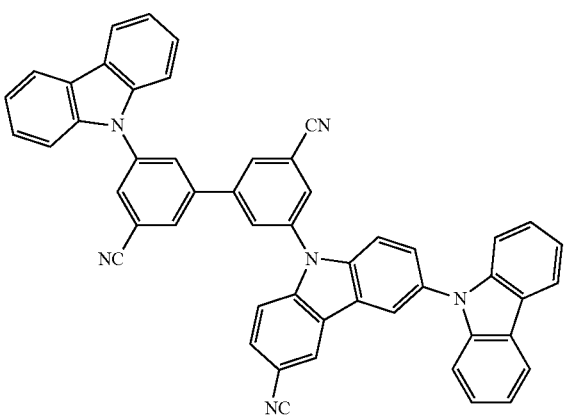
759
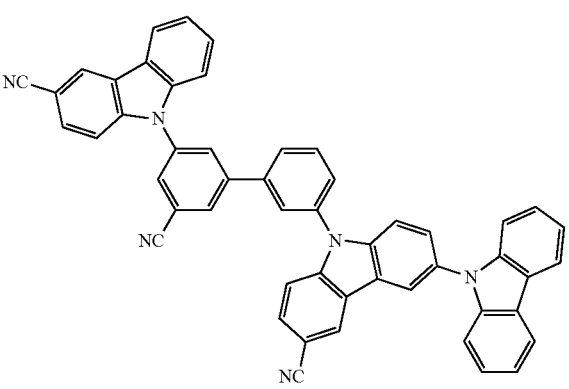
760

761
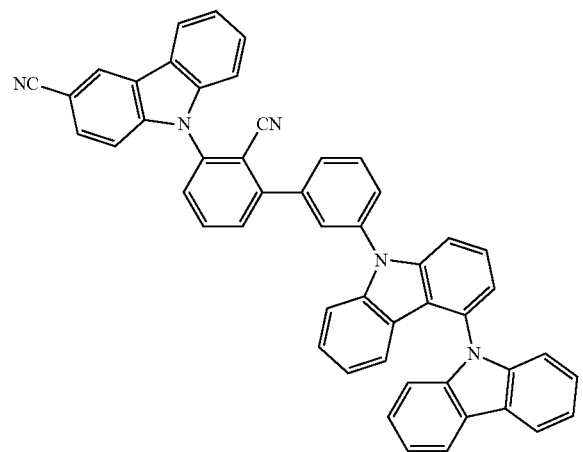
764
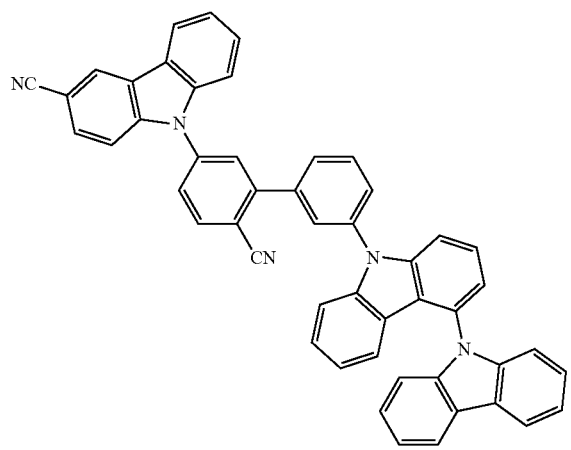
762
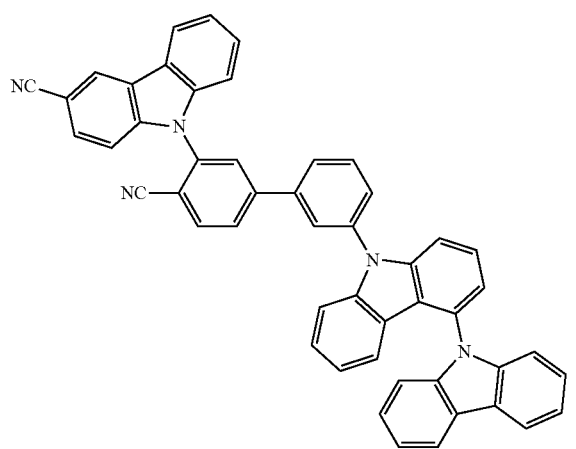
765
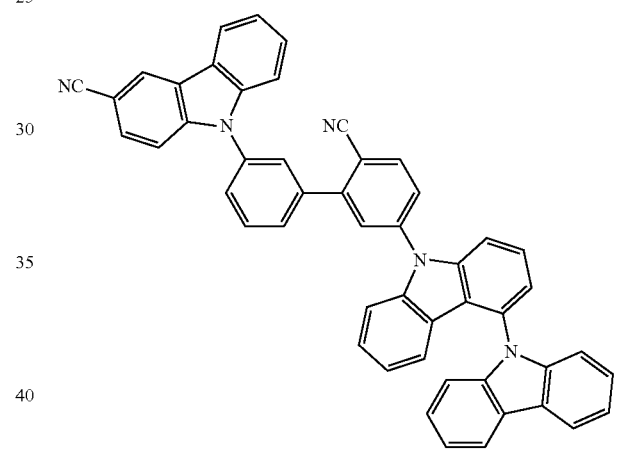
763
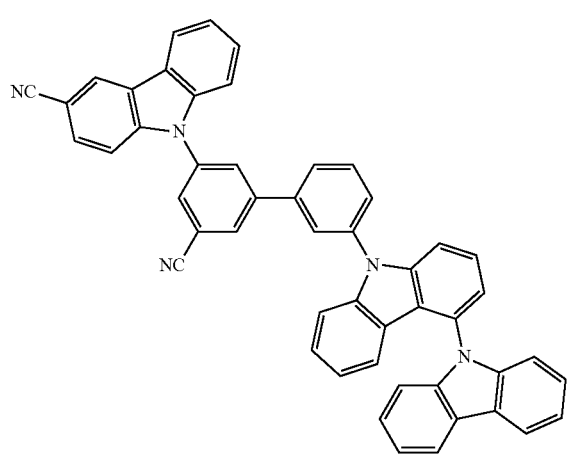
766
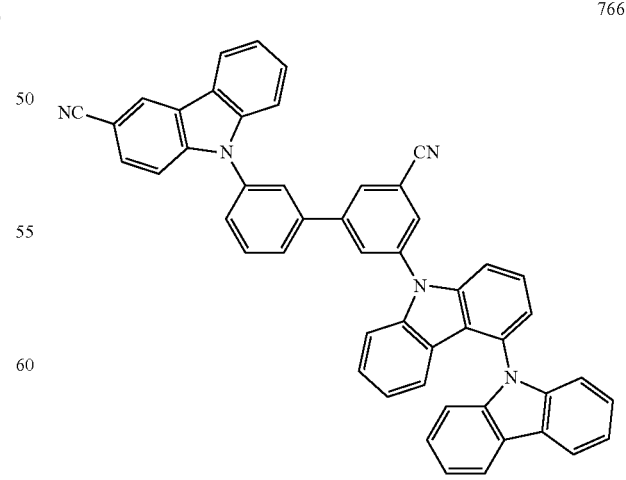

767
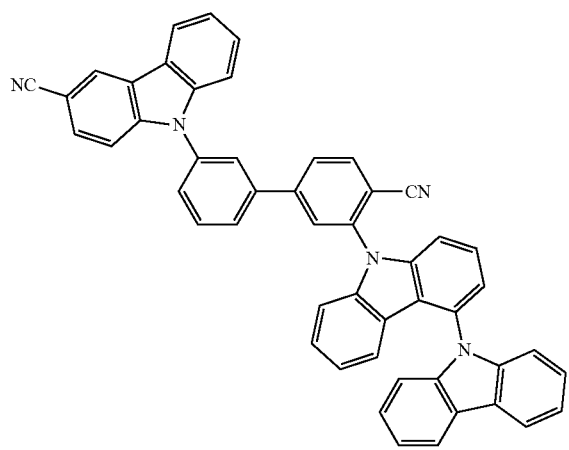
768
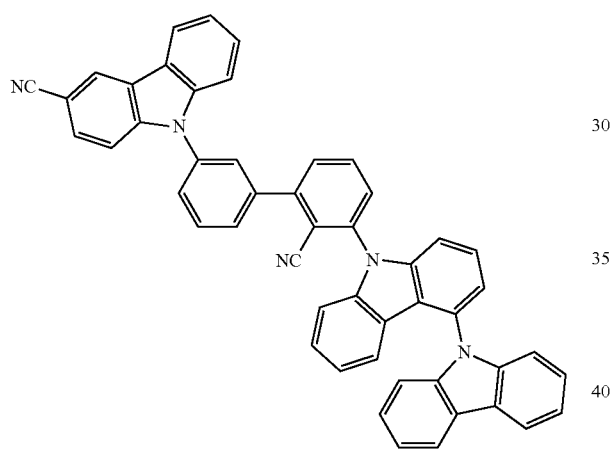
769
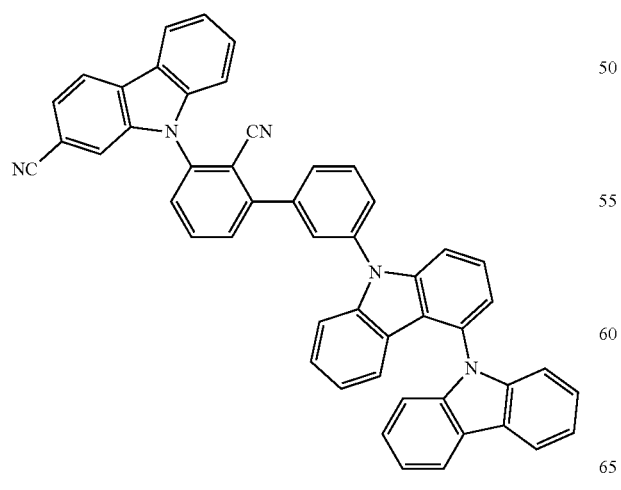
770
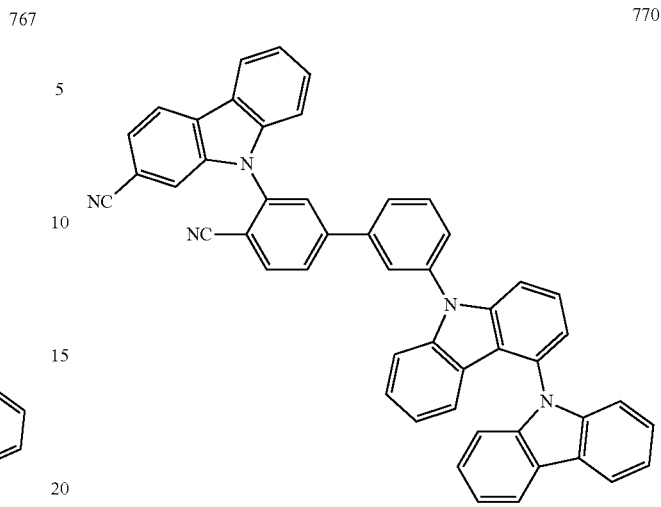
771
772

773 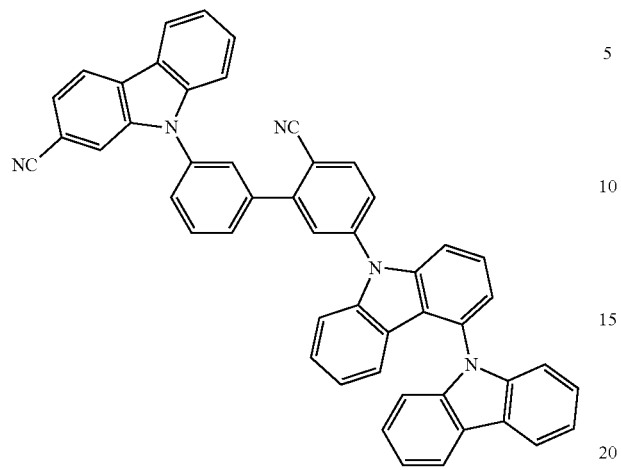
776 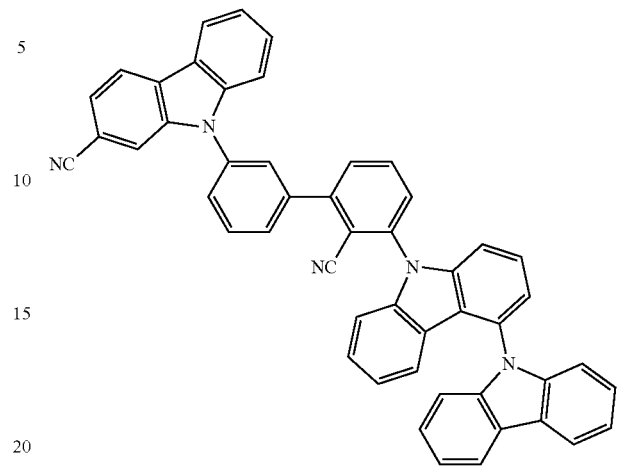
774 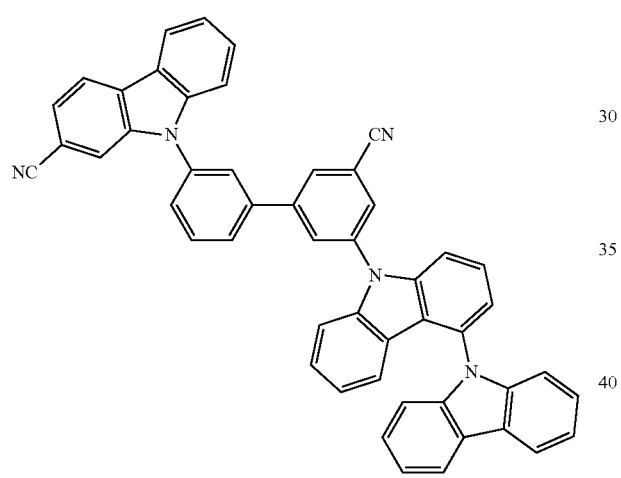
777 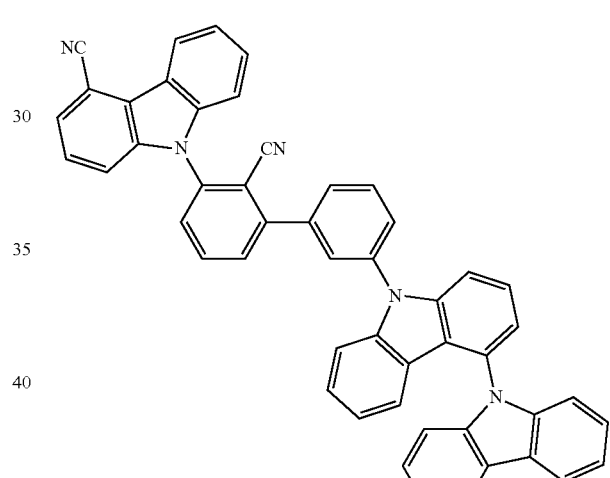
775 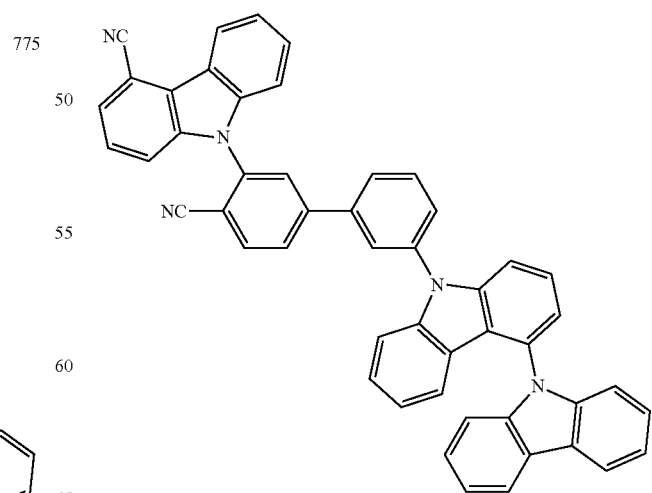
778

-continued

779

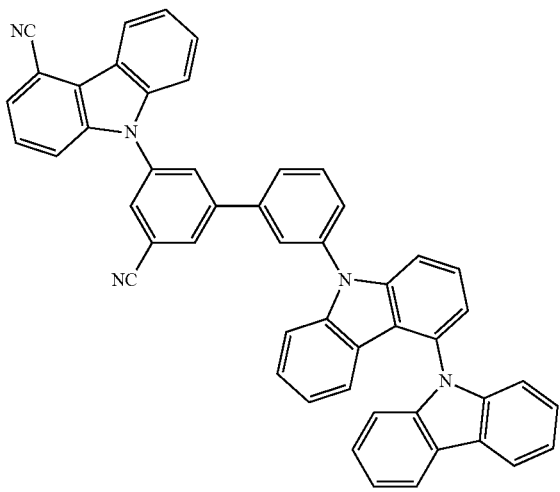

780

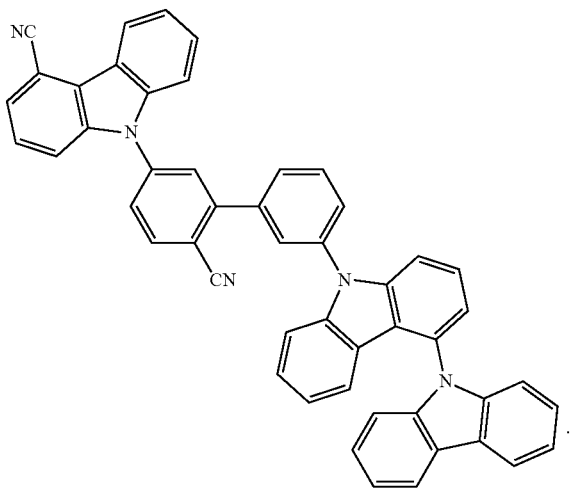

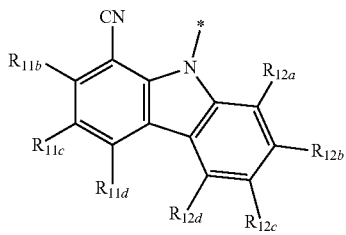

4-1

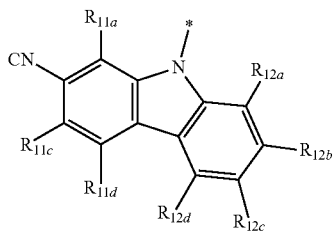

4-2

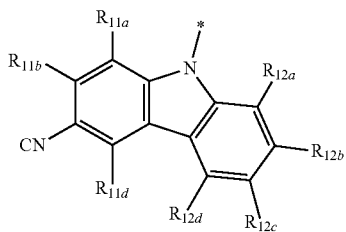

4-3

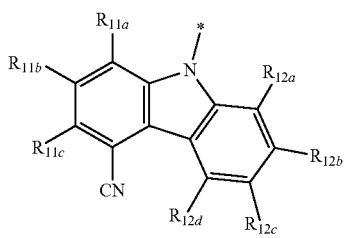

4-4

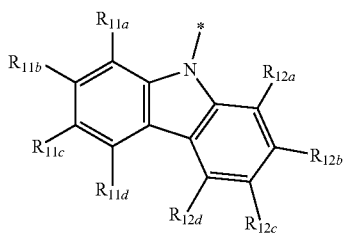

4-101

6. A condensed cyclic compound represented by Formula 1:

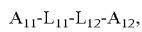
Formula 1 wherein, in Formula 1,
i) $A_{11}$ is a group represented by one of Formulae 4-1 to 4-4, and $A_{12}$ is a group represented by one of Formulae 5-1 to 5-11, 5-23 to 5-44, 5-101, 5-103 and 5-104; or
ii) $A_{11}$ is a group represented by Formula 4-101, and $A_{12}$ is a group represented by one of Formulae 5-1 to 5-11 and 5-23 to 5-44,
$L_{11}$ is a group represented by one of Formulae 2-2 to 2-3,
$L_{12}$ is a group represented by one of Formulae 3-2 to 3-3, and:

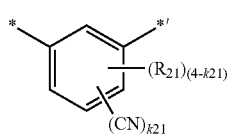
Formula 2-2

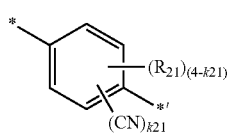
Formula 2-3

-continued
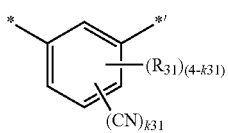
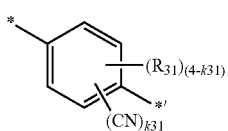
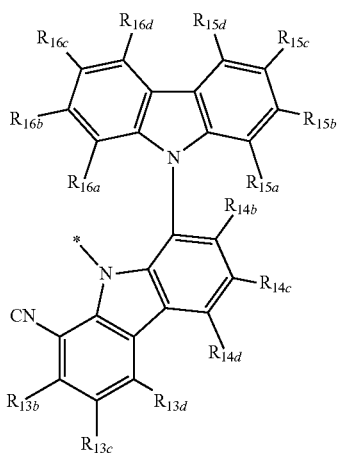
5-1
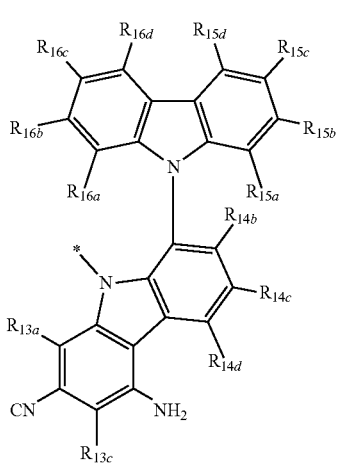
5-2
-continued
Formula 3-2
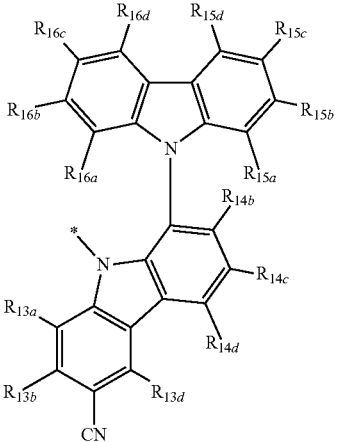
5-3
Formula 3-3
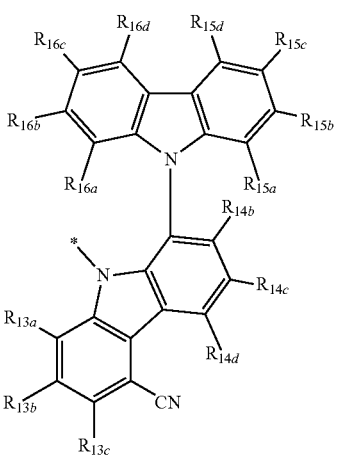
5-4
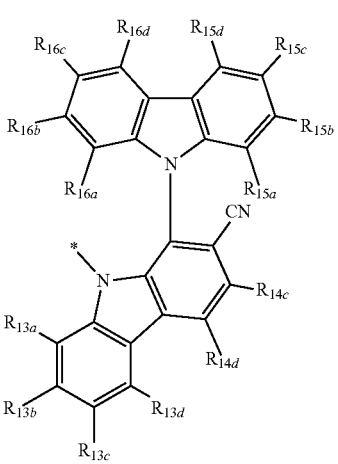
5-5

5-6
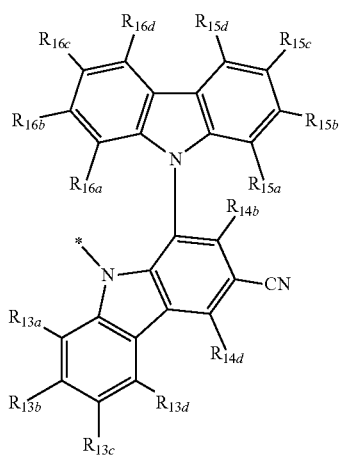
5-7
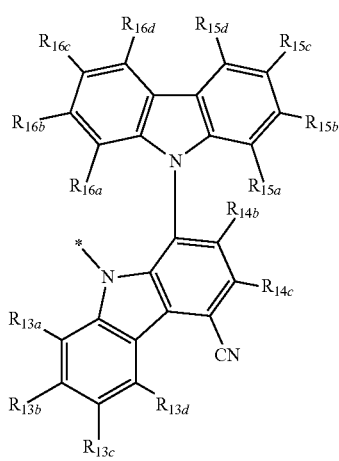
5-8
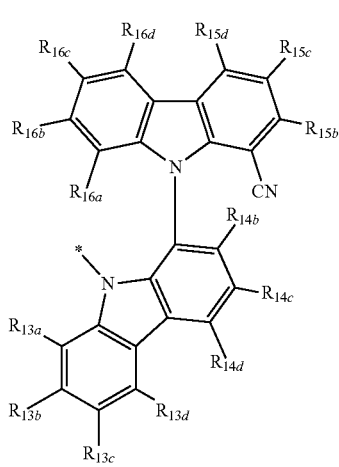
5-9
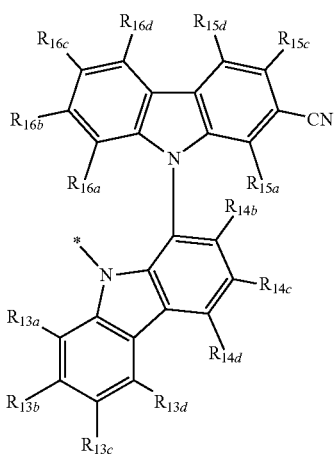
5-10
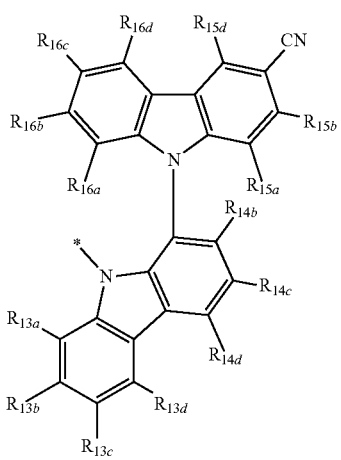
5-11
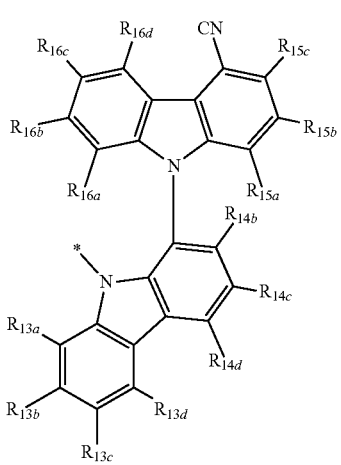

5-23
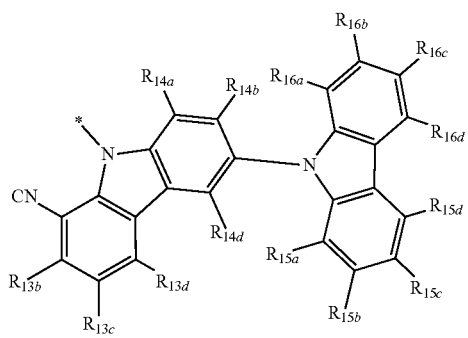
5-27
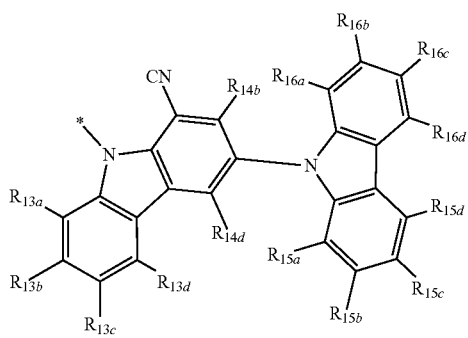
5-24
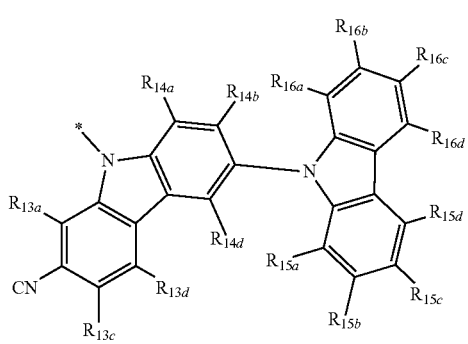
5-28
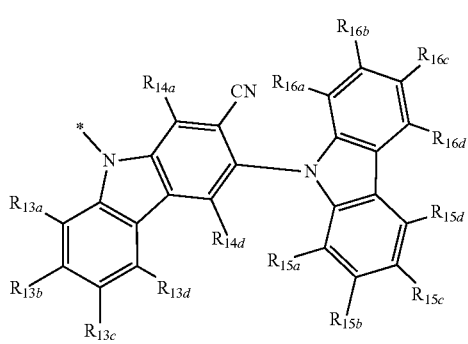
5-25
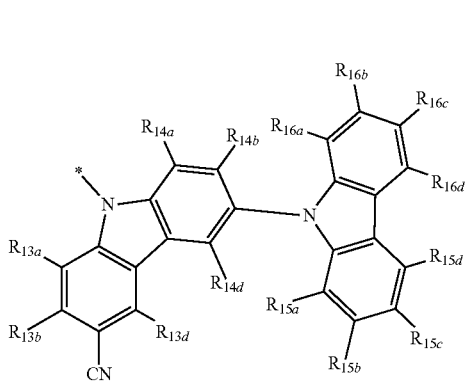
5-29
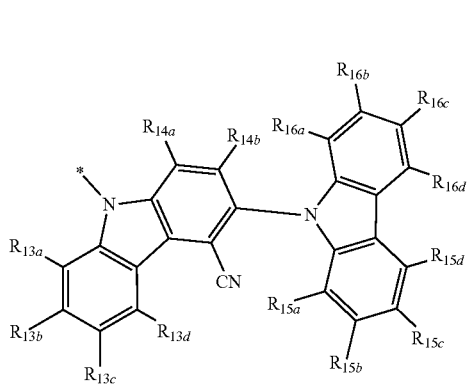
5-26
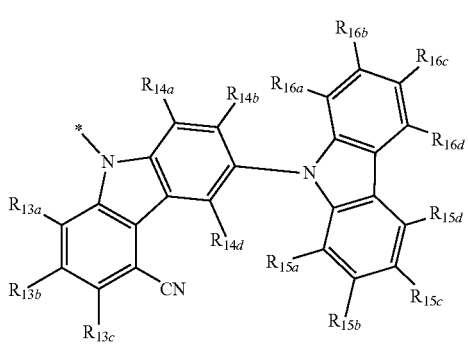
5-30
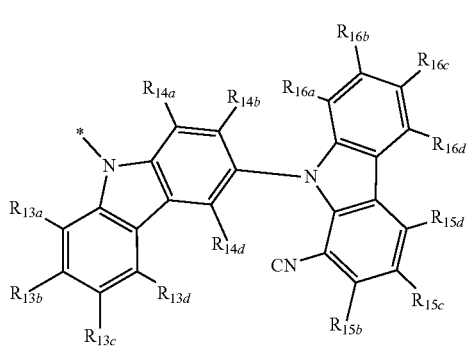

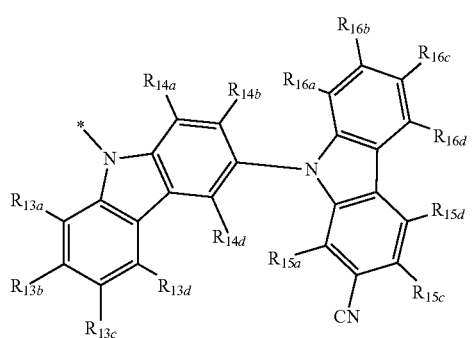
5-31
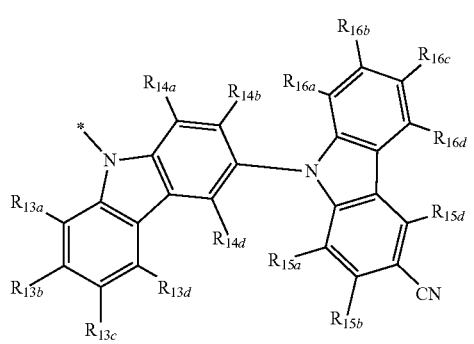
5-32
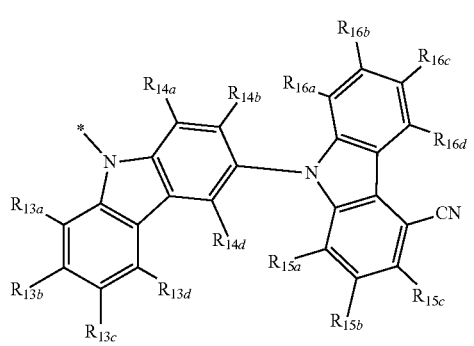
5-33
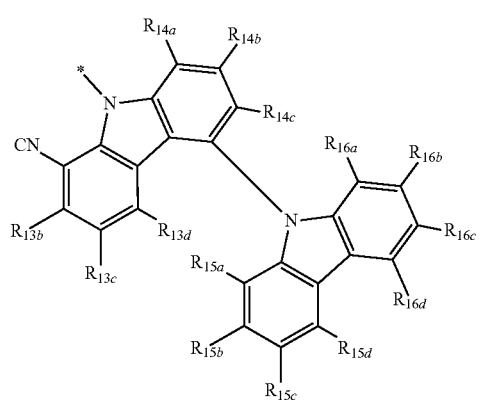
5-34
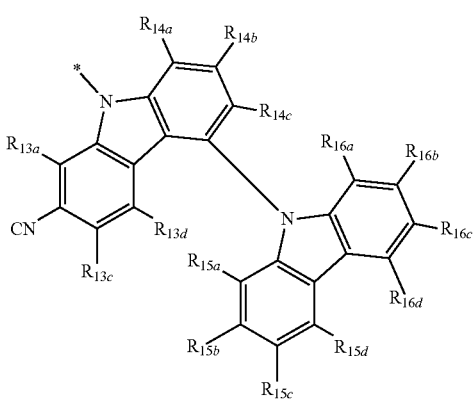
5-35
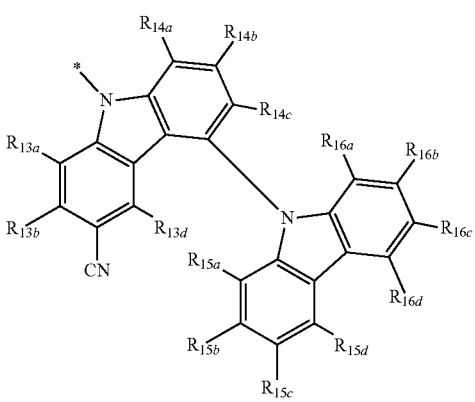
5-36
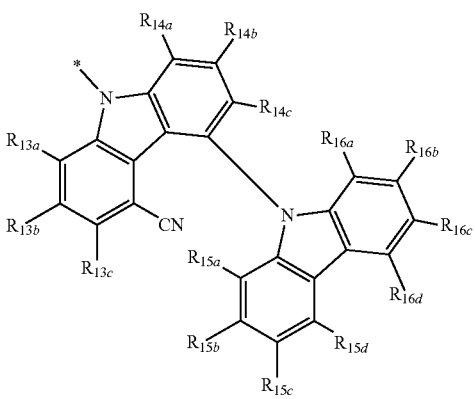
5-37
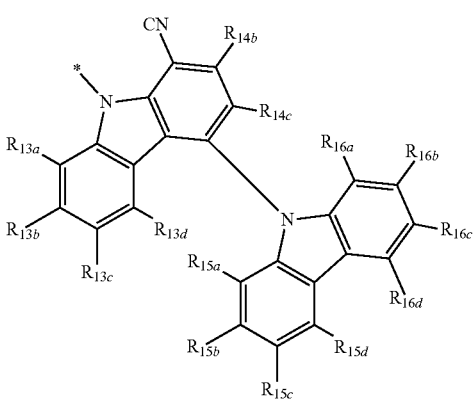
5-38

-continued
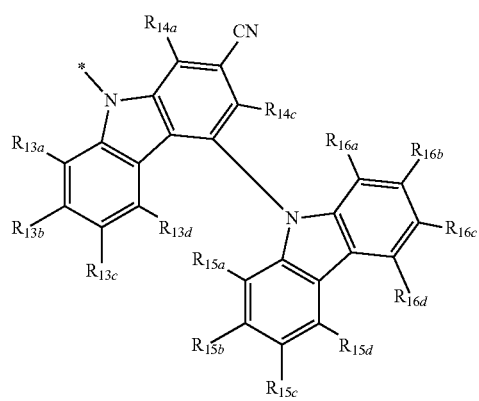
5-39
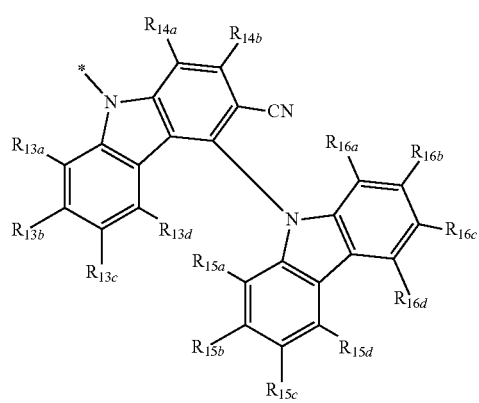
5-40
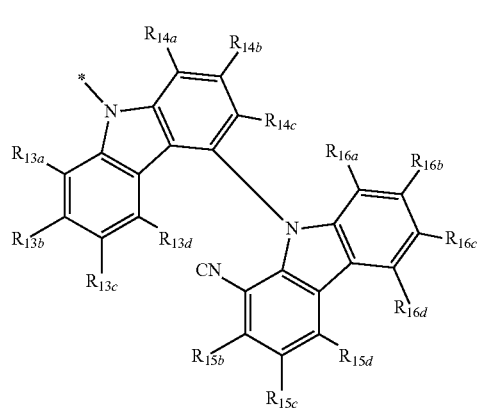
5-41
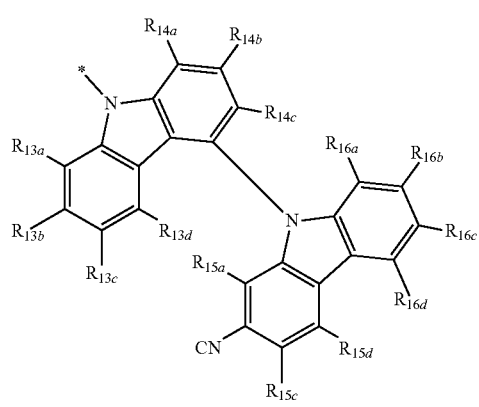
5-42
-continued
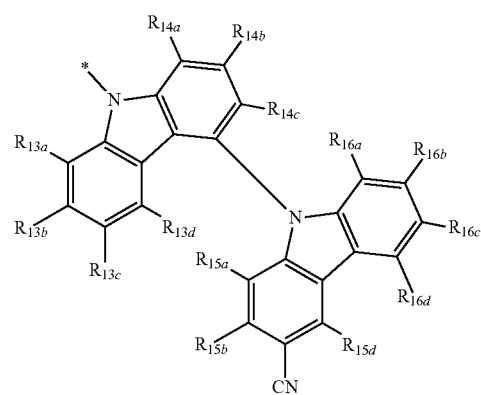
5-43
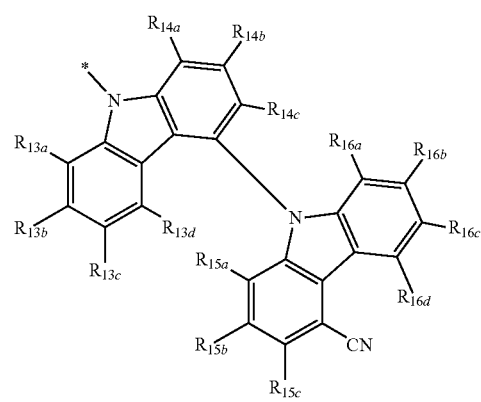
5-44
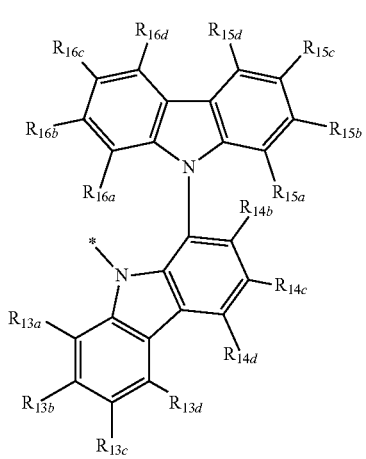
5-101

-continued

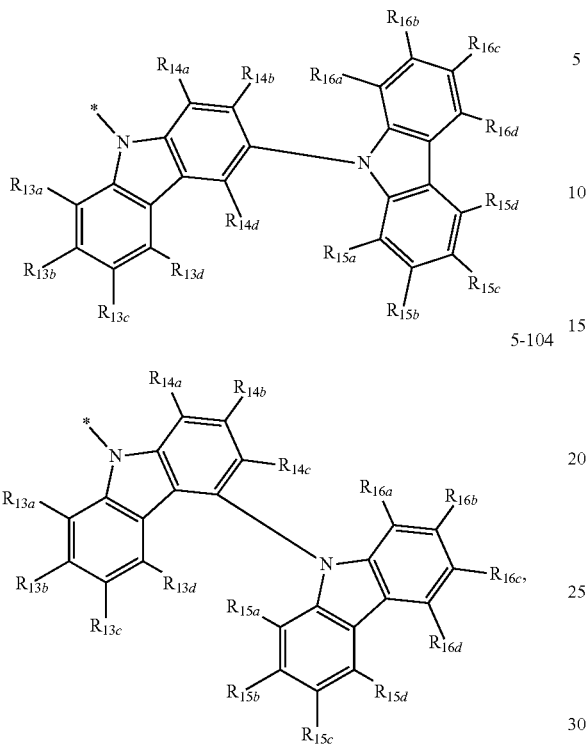

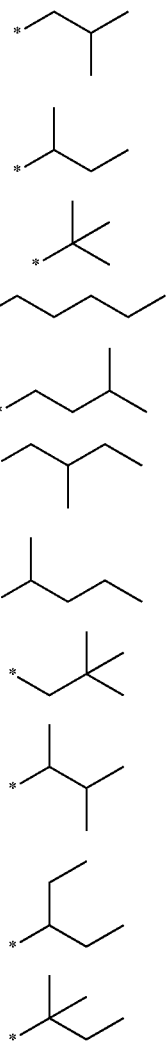

$R_{11a}$ to $R_{11a}$, $R_{12a}$ to $R_{12d}$, $R_{13a}$ to $R_{13a}$, $R_{14a}$ to $R_{14a}$, $R_{15a}$ to $R_{15}$, and $R_{16a}$ to $R_{16a}$, $R_{21}$ and $R_{31}$ are each independently hydrogen, deuterium, —F, a nitro group, —CH$_3$, —CD$_3$, —CD$_2$H, —CDH$_2$, —CF$_3$, —CF$_2$H, —CFH$_2$, groups represented by Formulae 9-1 to 9-15, or groups represented by Formulae 9-1 to 9-15 of which a hydrogen is substituted with deuterium, in Formulae 2-2 to 2-3 and 3-2 to 3-3, k21 and k31 are each independently 0, 1, 2, 3, or 4, the sum of k21 and k31 is 1 or more, and

* and *' each indicate a binding site to a neighboring atom.

* * * * *